United States Patent
Scott et al.

(10) Patent No.: US 9,314,467 B2
(45) Date of Patent: Apr. 19, 2016

(54) STYRENYL DERIVATIVE COMPOUNDS FOR TREATING OPHTHALMIC DISEASES AND DISORDERS

(71) Applicant: Acucela Inc., Seattle, WA (US)

(72) Inventors: Ian Leslie Scott, Monroe, WA (US); Vladimir Aleksandrovich Kuska, Seattle, WA (US); Anna Gall, Woodinville, WA (US); Mark W. Orme, Seattle, WA (US); Jennifer Gage, Kenmore, WA (US); Thomas L. Little, Jr., Redmond, WA (US); Qin Jiang, Latham, NY (US); Lana Michele Rossiter, Clifton Park, NY (US); Kevin F. McGee, Jr., Niskayuna, NY (US); Ryo Kubota, Seattle, WA (US)

(73) Assignee: ACUCELA INC., Seattle, WA (US)

( * ) Notice: Subject to any disclaimer, the term of this patent is extended or adjusted under 35 U.S.C. 154(b) by 0 days.

(21) Appl. No.: 14/630,889

(22) Filed: Feb. 25, 2015

(65) Prior Publication Data

US 2015/0166494 A1 Jun. 18, 2015

Related U.S. Application Data

(62) Division of application No. 12/107,040, filed on Apr. 21, 2008, now abandoned.

(60) Provisional application No. 60/937,002, filed on Jun. 22, 2007, provisional application No. 60/913,241, filed on Apr. 20, 2007.

(51) Int. Cl.

| | |
|---|---|
| C07C 211/27 | (2006.01) |
| A61K 31/137 | (2006.01) |
| A61K 31/5375 | (2006.01) |
| C07C 211/28 | (2006.01) |
| C07C 211/29 | (2006.01) |
| C07C 215/08 | (2006.01) |
| C07C 215/30 | (2006.01) |
| C07C 215/42 | (2006.01) |
| C07C 215/46 | (2006.01) |
| C07C 217/16 | (2006.01) |
| C07C 217/48 | (2006.01) |
| C07C 217/54 | (2006.01) |
| C07C 217/62 | (2006.01) |
| C07C 217/72 | (2006.01) |
| C07C 225/18 | (2006.01) |
| C07C 233/05 | (2006.01) |
| C07C 237/04 | (2006.01) |
| C07C 317/28 | (2006.01) |
| C07C 323/25 | (2006.01) |
| C07C 323/32 | (2006.01) |
| C07D 295/03 | (2006.01) |
| C07C 217/10 | (2006.01) |
| C07C 225/06 | (2006.01) |

(Continued)

(52) U.S. Cl.
CPC ........... *A61K 31/5375* (2013.01); *A61K 31/137* (2013.01); *A61K 31/145* (2013.01); *A61K 31/167* (2013.01); *A61K 31/40* (2013.01); *A61K 31/4453* (2013.01); *A61K 31/495* (2013.01); *C07C 211/27* (2013.01); *C07C 211/28* (2013.01); *C07C 211/29* (2013.01); *C07C 215/08* (2013.01); *C07C 215/30* (2013.01); *C07C 215/42* (2013.01); *C07C 215/46* (2013.01); *C07C 217/10* (2013.01); *C07C 217/16* (2013.01); *C07C 217/48* (2013.01); *C07C 217/54* (2013.01); *C07C 217/62* (2013.01); *C07C 217/72* (2013.01); *C07C 225/06* (2013.01); *C07C 225/18* (2013.01); *C07C 233/05* (2013.01); *C07C 237/04* (2013.01); *C07C 317/28* (2013.01); *C07C 323/25* (2013.01); *C07C 323/32* (2013.01); *C07C 323/33* (2013.01); *C07D 207/06* (2013.01); *C07D 211/14* (2013.01); *C07D 295/03* (2013.01); *C07C 2102/14* (2013.01); *C07C 2102/16* (2013.01)

(58) Field of Classification Search
CPC ............................. C07C 211/27; A61K 31/137
See application file for complete search history.

(56) References Cited

U.S. PATENT DOCUMENTS

| | | | |
|---|---|---|---|
| 2,566,360 | A | 9/1951 | Papa et al. |
| 3,095,449 | A | 6/1963 | Wirth et al. |

(Continued)

FOREIGN PATENT DOCUMENTS

| | | |
|---|---|---|
| CA | 2406392 A1 | 11/2001 |
| CH | 368181 A | 3/1963 |

(Continued)

OTHER PUBLICATIONS

Ahmed et al. Oxygen distribution in the macaque retina. Invest. Ophthalmol. Vis. Sci. 34(3):516-521 (1993).

(Continued)

*Primary Examiner* — Robert Havlin
(74) *Attorney, Agent, or Firm* — Wilson Sonsini Goodrich & Rosati

(57) ABSTRACT

The present invention relates generally to compositions and methods for treating neurodegenerative diseases and disorders, particularly ophthalmic diseases and disorders. Provided herein are styrenyl derivative compounds, including but not limited to stilbene derivative compounds, and compositions comprising these compounds, that are useful for treating and preventing ophthalmic diseases and disorders, including age-related macular degeneration (AMD) and Stargardt's Disease.

11 Claims, 2 Drawing Sheets

(51) Int. Cl.

| | | |
|---|---|---|
| C07C 323/33 | (2006.01) | |
| C07D 207/06 | (2006.01) | |
| C07D 211/14 | (2006.01) | |
| A61K 31/145 | (2006.01) | |
| A61K 31/167 | (2006.01) | |
| A61K 31/40 | (2006.01) | |
| A61K 31/4453 | (2006.01) | |
| A61K 31/495 | (2006.01) | |

(56) References Cited

U.S. PATENT DOCUMENTS

| 3,746,768 | A | 7/1973 | Johnson et al. |
|---|---|---|---|
| 4,569,354 | A | 2/1986 | Shapiro et al. |
| 4,861,897 | A | 8/1989 | Press et al. |
| 5,736,516 | A | 4/1998 | Louis |
| 5,929,117 | A | 7/1999 | Muller et al. |
| 6,090,624 | A | 7/2000 | Greenwood et al. |
| 6,117,675 | A | 9/2000 | van der Kooy et al. |
| 6,183,735 | B1 | 2/2001 | Greenwood et al. |
| 6,406,840 | B1 | 6/2002 | Li et al. |
| 6,713,300 | B1 | 3/2004 | Allikmets et al. |
| RE38,761 | E | 7/2005 | Levitzki et al. |
| 8,420,863 | B2 | 4/2013 | Scott et al. |
| 8,653,142 | B2 | 2/2014 | Scott et al. |
| 2002/0009713 | A1 | 1/2002 | Miller et al. |
| 2003/0032078 | A1 | 2/2003 | Travis |
| 2003/0050283 | A1 | 3/2003 | Richter et al. |
| 2004/0116403 | A1 | 6/2004 | Klimko et al. |
| 2004/0147019 | A1 | 7/2004 | Kubota et al. |
| 2005/0059148 | A1 | 3/2005 | Kubota |
| 2005/0074497 | A1 | 4/2005 | Schultz |
| 2005/0159662 | A1 | 7/2005 | Imanishi et al. |
| 2006/0069078 | A1 | 3/2006 | Rando |
| 2006/0128662 | A1 | 6/2006 | Tagmose et al. |
| 2007/0002275 | A1 | 1/2007 | Yan et al. |
| 2009/0170841 | A1 | 7/2009 | Scott et al. |

FOREIGN PATENT DOCUMENTS

| CN | 1844304 A | 10/2006 |
|---|---|---|
| EP | 0731085 A1 | 9/1996 |
| EP | 1698618 A1 | 9/2006 |
| GB | 815211 A | 6/1959 |
| GB | 962461 A | 7/1964 |
| JP | S4992034 A | 9/1974 |
| JP | S5251352 A | 4/1977 |
| JP | S60158170 A | 8/1985 |
| JP | H08301831 A | 11/1996 |
| JP | 2004270261 A | 9/2004 |
| JP | 2007525496 A | 9/2007 |
| JP | 2008531586 A | 8/2008 |
| RU | 2006133300 A | 3/2008 |
| WO | WO-9812303 A1 | 3/1998 |
| WO | WO-9929279 A2 | 6/1999 |
| WO | WO-0040699 A2 | 7/2000 |
| WO | WO-0040699 A3 | 11/2000 |
| WO | WO-0109327 A2 | 2/2001 |
| WO | WO-0142784 A2 | 6/2001 |
| WO | WO-0109327 A3 | 8/2001 |
| WO | WO-0174810 A2 | 10/2001 |
| WO | WO-0181551 A2 | 11/2001 |
| WO | WO-0183714 A2 | 11/2001 |
| WO | WO-0142784 A3 | 12/2001 |
| WO | WO-0183714 A3 | 4/2002 |
| WO | WO-0250007 A2 | 6/2002 |
| WO | WO-0181551 A3 | 10/2002 |
| WO | WO-03035008 A2 | 5/2003 |
| WO | WO-04000302 A1 | 12/2003 |
| WO | WO-2004056806 A1 | 7/2004 |
| WO | WO-2005025498 A2 | 3/2005 |
| WO | WO-2006002097 A2 | 1/2006 |
| WO | WO-2006063128 A2 | 6/2006 |
| WO | WO-2007089673 A2 | 8/2007 |

OTHER PUBLICATIONS

Akula et al. Rod photoreceptor function predicts blood vessel abnormality in retinopathy of prematurity. Invest. Ophthalmol. Vis. Sci. 48(9):4351-4359 (2007).

Allikmets et al. A photoreceptor cell-specific ATP-binding transporter gene (ABCR) is mutated in recessive Stargardt macular dystrophy. Nat. Genet. 15:236-246 (1997).

Ambati et al. An animal model of age-related macular degeneration in senescent Ccl-2- or Ccr-2-deficient mice. Nat. Med. 9(11):1390-1397 (2003); Epub Oct. 19, 2003.

Asi et al. Relationships between the electroretinogram a-wave, b-wave and oscillatory potentials and their application to clinical diagnosis. Documenta Ophthalmologica 79(2):125-139 (1992).

Baker et al. CAPLUS Abstract of EP 134111. published Mar. 13, 1985.

Beniot et al. Synthesis and therapeutic properties of amino and hydroxy derivatives of stilbene. Bulletin of the Chemical Society of France 193:829-832 (1950).

Berge et al. Pharmaceutical Salts. Journal of Pharmaceutical Sciences 66(1):1-19 (Jan. 1977).

Braun et al. Retinal oxygen tension and the electroretinogram during arterial occlusion in the cat. Invest Ophthalmol Vis Sci. 1995; 36(3):523-41.

Bron et al. (Eds). Eye and Orbit, 8th Ed. Chapman and Hall. 1997.

Bundgard et al. Design of Prodrugs pp. 7-9, 21-24 (1985).

Chemistry of Functional Groups. In 73 volumes. John Wiley & Sons.

Co-pending U.S. Appl. No. 14/630,897, filed Feb. 25, 2015.

Co-pending U.S. Appl. No. 14/631,711, filed Feb. 25, 2015.

Crabb et al. Cloning of the cDNAs encoding the cellular retinaldehyde-binding protein from bovine and human retina and comparison of the protein structures. J Biol Chem. 1988; 263(35):18688-92.

Crabb et al. Structural and functional characterization of recombinant human cellular retinaldehyde-binding protein. Protein Sci. 7(3):746-57 (1998).

Cringle et al. Intraretinal oxygen consumption in the rat in vivo. Invest. Ophthalmol. Vis Sci. 43(6):1922-1927 (2002).

De Gooyer et al. Rod photoreceptor loss in Rho-31 /− mice reduces retinal hypoxia and hypoxia-regulated gene expression. Invest. Ophthalmol. Vis Sci. 47(12):5553-5560 (2006).

De Laey et al. Hyperlipofuscinosis and subretinal fibrosis in Stargardt's disease. Retina 15(5):399-406 (1995).

Deigner et al. Membranes as the energy source in the endergonic transformation of vitamin A to 11-cis-retinol. Science 244(4907):968-971 (1989).

Dembinska et al. Evidence for a brief period of enhanced oxygen susceptibility in the rat model of oxygen-induced retinopathy. Invest. Ophthalmol. Vis. Sci. 43(7):2481-2490 (2002).

Dentchev et al. Amyloid-beta is found in drusen from some age-related macular degeneration retinas, but not in drusen from normal retinas. Mol. Vis. 9:184-190 (2003).

Einhorn et al. CAPLUS Abstract of: Berichte der Deutschen Chemischen Gesellschaft 42:4837-50 (1910).

Eldred et al. Retinal age pigments generated by self-assembling lysosomotropic detergents. Nature 361(6414):724-726 (1993).

Filipek et al. G protein-coupled receptor rhodopsin: a prospectus. Annu. Rev. Physiol. 65:851-879 (2003).

Finneman et al. The lipofuscin component A2E selectively inhibits phagolysosomal degradation of photoreceptor phospholipid by the retinal pigment epithelium. Proc. Natl. Acad. Sci. USA 99:3842-3847 (2002).

Fuhrhop et al. Organic Sythesis: Concepts, Mehods, Starting Materials. Second, Revised and Enlarged Edition. John Wiley & Sons. 1994.

Gennaro. Remington: The Science and Practice of Pharmacy. 21st Ed. Mack Pub. Co., Easton, PA. (2005).

Giasson et al. The relationship between oxidative/nitrative stress and pathological inclusions in Alzheimer's and Parkinson's diseases. Free Radic. Biol. Med. 32(12):1264-1275 (2002).

Gilchrist. Heterocyclic Chemistry, 2nd Ed., John Wiley & Sons, New York, 1992.

(56) References Cited

OTHER PUBLICATIONS

Glazer et al. Understanding the etiology of Stargardt's disease. Ophthalmol. Clin. North Am. 15(1):93-100, viii (2002).
Golczak et al. Positively charged retinoids are potent and selective inhibitors of the trans-cis isomerization in the retinoid (visual) cycle. PNAS 102(23):8162-8167 (2005).
Gollapalli et al. The specific binding of retinoic acid to RPE65 and approaches to the treatment of macular degeneration. Proc Natl Acad Sci U S A. 2004; 101(27):10030-5.
Gollapalli et al. Specific inactivation of isomerohydrolase activity by 11-cis-retinoids, Biochim Biophys Acta. 1651(1-2):93-101 (2003).
Gorin et al. The genetics of age-related macular degeneration, Mol. Vis. 5:29 (1999).
Groenendijk et al. Quantitative Determination of Retinals with Complete Retention of Their Geometric Configuration, Biochim. Biophys. Acta. 617:430-438 (1980).
Gwiazda et al. Myopia and ambient night-time lighting. Nature 404(6774):144 (2000).
Haeseleer et al. Essential role of Ca2+-binding protein 4, a Cav1.4 channel regulator, in photoreceptor synaptic function. Nat. Neurosci. 7(10):1079-1087 (2004).
Hancock et al. Oscillatory potential analysis and ERGs of normal and diabetic rats. Invest. Ophthalmol. Vis. Sci. 45(3):1002-1008 (2004).
Haugh et al. Mathematical models of the spatial distribution of retinal oxygen tension and consumption, including changes upon illumination. Ann Biomed Eng. 1990; 18(1):19-36.
Higuchi et al. Pro-drugs as Novel Delivery Systems. A.C.S. Symposium Series, 1975, vol. 14.
Hoffman. Organic Chemistry, An Intermediate Text. (1996) Oxford University Press, ISBN 0-19-509618-5.
Hogan. Retina. Histology of the Human Eye: an Atlas and Text Book. Hogan et al. (eds). WB Saunders; Philadelphia, PA. 1971.
Holz et al. Inhibition of Lysosomal Degradative Functions in RPE Cells by a Retinoid Component of Lipofuscin. Investigative Ophthalmology & Visual Science 40(3):737-743 Mar. 1999.
House et al. Modern Synthetic Reactions. 2nd Ed., W.A. Benjamin, Inc., Menlo Park, CA (1972).
Imanishi et al Noninvasive two-photon imaging reveals retinyl ester storage structures in the eye. J Cell Biol. 164(3):373-383 (2004).
Industrial Organic Chemicals: Starting Materials and Intermediates: An Ullmann's Encyclopedia (1999) John Wiley & Sons, ISBN: 3-527-29645-X, in 8 volumes.
Intres et al. Molecular cloning and structural analysis of the human gene encoding cellular retinaldehyde-binding protein. J. Biol. Chem. 269(41):25411-25418 (1994).
Iyengar et al. Dissection of genomewide-scan data in extended families reveals a major locus and oligogenic susceptibility for age-related macular degeneration. Am. J. Hum. Genet. 74(1):20-39 (2004); Epub Dec. 19, 2003.
Jaakson et al. Genotyping microarray (gene chip) for the ABCR (ABCA4) gene. Hum. Mutat. 22(5):395-403 (2003).
Johnson et al. The Alzheimer's amyloid beta-peptide is deposited at sites of complement activation in pathologic deposits associated with aging and age-related macular degeneration, Proc. Natl. Acad. Sci. USA 99(18):11830-11835 (2002).
Keating et al. Technical aspects of multifocal ERG recording. Doc Ophthalmol. 2000; 100(2-3):77-98.
Kenealy et al. Linkage analysis for age-related macular degeneration supports a gene on chromosome 10q26, Mol. Vis. 10:57-61 (2004).
Kljavin et al. Müller cells are a preferred substrate for in vitro neurite extension by rod photoreceptor cells. J. Neurosci. 11(10):2985-9294 (1991).
Kubiniy.3D QSAR in Drug Design: Ligand-Protein Interactions and Molecular Similarity, vol. 2-3, Springer, 1998, 800 pages. TOC & pp. 243-244 provided.
Lamb et al. Dark adaptation and the retinoid cycle of vision. Prog. Retin. Eye Res. 23(3):307-380 (2004).
Larock. Comprehensive Organic Transformations: A Guide to Functional Group Preparations. 2nd Edition (1999) Wiley-VCH, ISBN: 0-471-19031-4.
Law et al. The molecular basis of retinoic acid induced night blindness. Biochem. Biophys. Res. Commun. 161(2):825-829 (1989).
Lewis et al. Formation and Behavior of Flurescent Lewis Acid—Base Exciplexes and Triplexes between 3-Aminostilbenes and Aliphatic Amines. Journal of Physical Chemistry A 108:1425-1434 (2004).
Li, et al. Integrin alpha(1) beta(1)-mediated activation of cyclin-dependent kinase 5 activity is involved in neurite outgrowth and human neurofilament protein H Lys-Ser-Pro tail domain phosphorylation. J Neurosci. 2000; 20(16):6055-62.
Liang et al. Rhodopsin signaling and organization in heterozygote rhodopsin knockout mice. J. Biol. Chem. 279: 48189-48196 (2004).
Linsenmeier et al. Oxygen distribution and consumption in the cat retina during normoxia and hypoxemia. J Gen Physiol. 1992; 99(2):177-97.
Linsenmeier et al. Improved fabrication of double-barreled recessed cathode O2 microelectrodes. Journal of Applied Physiology. 1987; 63(6): 2554-2557.
Liu et al. Development of the electroretinographic oscillatory potentials in normal and ROP rats. Invest Ophthalmol Vis Sci. 2006; 47(12):5447-52.
Liu et al. The retinal vasculature and function of the neural retina in a rat model of retinopathy of prematurity. Invest Ophthalmol Vis Sci. 2006; 47(6):2639-47.
Luan et al. Retinal thickness and subnormal retinal oxygenation response in experimental diabetic retinopathy. Invest Ophthalmol Vis Sci. 2006; 47(1):320-8.
Maeda et al. Evaluation of the role of the retinal G protein-coupled receptor (RGR) in the vertebrate retina in vivo. J Neurochem. 85(4):944-56 (2003).
Maiti et al. Small Molecule RPE65 Antagonists Limit the Visual Cycle and Prevent Lipofuscin Formation. Biochemistry 45:852-860 (2006).
March. Advanced Organic Chemistry: Reactions, Mechanisms, and Structure 4th Edition (1992) John Wiley & Sons, ISBN: 0-471-60180-2.
Mata et al. Delayed dark-adaptation and lipofuscin accumulation in abcr+/− mice: implications for involvement of ABCR in age-related macular degeneration. Invest Ophthalmol Vis Sci. 2001; 42(8):1685-90.
Mata et al. Isomerization and oxidation of vitamin a in cone-dominant retinas: a novel pathway for visual-pigment regeneration in daylight. Neuron. 2002; 36(1):69-80.
Mata et al. Biosynthesis of a major lipofuscin fluorophore in mice and humans with ABCR-mediated retinal and macular degeneration. Proc.Natl. Acad. Sci. USA, 97(13):7154-7159, Jun. 20, 2000.
McBee et al. Confronting complexity: the interlink of phototransduction and retinoid metabolism in the vertebrate retina. Prog. Retin. Eye Res. 20(4):469-529 (2001).
Moiseyev et al. Inhibition of the visual cycle by A2E through direct interaction with RPE65 and implications in Stargardt disease. PNAS 107(41):17551-17556 (2010).
Oglivie et al., Growth Factors in Combination, but Not Individually, Rescue rd Mouse Photoreceptors in Organ Culture. Exp. Neurol. 161:675-685 (2000).
Okajima et al. Retinol kinetics in the isolated retina determined by retinoid extraction and HPLC. Exp. Eye Res. 65(3):331-340 (1997).
Organ et al. Combining the use of solid-supported transition metal catalysis with microwave irradiation in solution-phase parallel library synthesis. Molecular Diversity 7:211-227 (2003).
Organic Reactions (1942-2000) John Wiley & Sons, in over 55 volumes.
Otera. (editor) Modern Carbonyl Chemistry (2000) Wiley VCH, ISBN: 3-527-29871-1.
Papa et al. Pyridyl-aryloxy Alkamine Ethers as Histamine Antagonists. Journal of the American Chemical Society 73:1279-1280 (1951).
Parish et al. Isolation and one-step preparation of A2E and iso-A2E, fluorophores from human retinal pigment epithelium, Proc. Natl. Acad. Sci. USA 95(25):14609-14613 (1998).
Patai, S. Patai's 1992 Guide to the Chemistry of Functional Groups. (1992) Interscience ISBN: 0-471-93022-9.
PCT/US2008/61073 International Preliminary Report on Patentability dated Oct. 20, 2009.

(56) References Cited

OTHER PUBLICATIONS

PCT/US2008/61073 International Search Report dated Oct. 6, 2008.
Penn et al. Oxygen-induced retinopathy in the rat: relationship of retinal nonperfusion to subsequent neovascularization. Invest. Ophthalmol. Vis. Sci. 35(9):3429-3435 (1994).
Pettit et al. Antineoplastic Agents. 445. Synthesis and Evaluation of Structural Modifications of (Z)- and (E)-Combretastatin A-4. Journal of Medicinal Chemistry 48:4087-4099 (2005).
Phipps et al. Rod photoreceptor dysfunction in diabetes: activation, deactivation, and dark adaptation. Invest. Ophthalmol. Vis. Sci. 47(7):3187-3194 (2006).
Quin et al. A Guide to Organophosphorus Chemistry. (2000) Wiley-Interscience, ISBN: 0-471-31824-8.
Quinn et al. Myopia and ambient lighting at night. Nature 399(6732):113-114 (1999).
Radu et al. Light exposure stimulates formation of A2E oxiranes in a mouse model of Stargardt's macular degeneration. Proc Natl Acad Sci U S A. 2004; 101(16):5928-33.
Radu et al. Treatment with isotretinoin inhibits lipofuscin accumulation in a mouse model of recessive Stargardt's macular degeneration. Proc Natl Acad Sci Usa. 100(8):4742-4747 (2003).
Rammler. Biological Actions of Dimethyl Sulfoxide. Annals fo the New York Academy of Sciences 141:291-299 (Mar. 1967).
Ramsey et al. An electrophysiological study of retinal function in the diabetic female rat, Invest. Ophthalmol. Vis. Sci. 47(11):5116-5124 (2006).
Roche et al. Bioreversible Carriers in Drug Design. American Pharmaceutical Association and Pergamon Press, 1987.
Sandler et al., Organic Functional Group Preparations, 2nd Ed., Academic Press, New York, 1983.
Seddon et al. Assessment of mutations in the Best macular dystrophy (VMD2) gene in patients with adult-onset foveomacular vitelliform dystrophy, age-related maculopathy, and bull's-eye maculopathy. Ophthalmology 108(11):2060-2067 (2001).
Sharma et al. Identification of substrate binding site of cyclin-dependent kinase 5, J. Biol. Chem. 274(14):9600-9606 (1999).
Solomons. Organic Chemistry 7th Edition (2000) John Wiley & Sons, ISBN: 0-471-19095-0.
Spaeth. Ed. Ophthalmic Surgery: Principles of Practice. W. B. Sanders Co. Philadelphia, Pa 1990; 85-87.
Sparrow et al. A2E-epoxides damage DNA in retinal pigment epithelial cells. Vitamin E and other antioxidants inhibit A2E-epoxide formation. J. Biol. Chem. 278(20):18207-18213 (2003).
Sparrow et al. A2E, a Lipofuscin Fluorophore, in Human Retinal Pigmented Epithelial Cells in Culture. Investigative Ophthalmology & Visual Science, 40(12):2988-2995, Nov. 1995.
Sparrow et al. Involvement of Oxidative Mechanisms in Blue-Light Induced Damage to A2E-Laden RPE. Investigative Ophthalmology & Visual Science, 43(4):1222-1227, Apr. 2002.
Sparrow. Therapy for macular degeneration: Insights from acne. Proc. Natl. Acad. Sci., USA, 100(8):4353-4354, Apr. 15, 2003.
Stahl et al. Handbook of Pharmaceutical Salts. Verlag Helvetica Chimica Acta. Zurich. 2002.
Stecher et al. Preferential release of 11-cis-retinol from retinal pigment epithelial cells in the presence of cellular retinaldehyde-binding protein, J. Biol. Chem. 274(13):8577-8585 (1999).
Stowell. Intermediate Organic Chemistry 2nd Edition (1993) Wiley-Interscience, Isbn: 0-471-57456-2.
Sugitomo et al. A procedure for electroretinogram (ERG) recording in mice—effect of monoiodoacetic acid on the ERG in pigmented mice, J. Toxicol. Sci. 22 Suppl 2:315-325 (1997).
Suter et al. Age-related macular degeneration. The lipofusion component N-retinyl-N-retinylidene ethanolamine detaches proapoptotic proteins from mitochondria and induces apoptosis in mammalian retinal pigment epithelial cells. J. Biol. Chem. 275(50):39625-39630 (2000).
Suzuki et al. Retinyl and 3-dehydroretinyl esters in the crayfish retina. Vision Res. 28(10):1061-1070 (1988).
Trevino et al. Retinoid cycles in the cone-dominated chicken retina. J. Exp. Biol. 208:4151-57 (2005).
U.S. Appl No. 12/107,040 Office Action dated Aug. 28, 2014.
U.S. Appl No. 12/107,040 Office Action dated Dec. 11, 2012.
U.S. Appl No. 12/107,040 Office Action dated Jan. 24, 2014.
U.S. Appl No. 12/107,040 Office Action dated Jan. 26, 2011.
U.S. Appl No. 12/107,040 Office Action dated May 23, 2013.
U.S. Appl No. 12/107,040 Office Action dated May 4, 2012.
U.S. Appl No. 12/107,040 Office Action dated Sep. 22, 2011.
U.S. Appl No. 13/360,285 Office Action dated Jul. 18, 2012.
Van Hooser et al. Recovery of visual functions in a mouse model of Leber congenital amaurosis, J. Biol. Chem. 277(21):19173-19182 (2002).
Wagner et al. Synthetic Organic Chemistry. John Wiley & Sons Inc. New York, NY. 1953.
Wang, et al. Hyperoxia improves oxygen consumption in the detached feline retina. Invest Ophthalmol Vis Sci. 2007; 48(3):1335-41.
Weng et al. Insights into the function of Rim protein in photoreceptors and etiology of Stargardt's disease from the phenotype in abcr knockout mice.Cell 98(1):13-23 (1999).
Werdich et al. Variable oxygen and retinal VEGF levels: correlation with incidence and severity of pathology in a rat model of oxygen-induced retinopathy.Exp. Eye Res. 79(5):623-630 (2004).
Wermuth. The Practice of Medicinal Chemistry, 2d ed. 768 pages, chapters 9-10 provided (2003).
Wermuth. Strategies in the search for new lead compounds or original working hypotheses, Chapter 5 in The Practice of Medicinal Chemistry, 2003, pp. 69-89.
Woodruff et al. Spontaneous activity of opsin apoprotein is a cause of Leber congenital amaurosis. Nat. Genet. 35(2):158-164 (2003).
Wright et al. Local Anesthetics. V. 4-Morpholinylalkyl Aryl Ether. Journal of the American Chemical Society 76:4396-4398 (1954).
Yates et al. Genetic susceptibility to age related macular degeneration. J. Med. Genet. 37(2):83-87 (2000).
Zadnik et al. Myopia and ambient night-time lighting. CLEERE Study Group. Collaborative Longitudinal Evaluation of Ethnicity and Refractive Error. Nature. 2000; 404(6774):143-4.
Garratt et al. Mapping the melatonin receptor. 4. Comparison of the binding affinities of a series of substituted phenylalkyl amides. J Med Chem 39(9):1797-1805 (1996) (CAPLUS Abstract).
Sikazwe et al. Binding of sulfonyl-containing arylalkylamines at human 5-HT6 serotonin receptors. J Med Chem 49(17):5217-5225 (2006) (CAPLUS Abstract).
U.S. Appl. No. 12/107,040 Office Action dated Apr. 14, 2015.

STYRENYL DERIVATIVE COMPOUNDS FOR TREATING OPHTHALMIC DISEASES AND DISORDERS

CROSS-REFERENCE

This application is a divisional application of patent application Ser. No. 12/107,040, filed Apr. 21, 2008, which claims the benefit of U.S. Provisional Application Nos. 60/937,002 and 60/913,241, filed on Jun. 22, 2007 and Apr. 20, 2007, respectively, all of which applications are incorporated herein by reference in their entirety.

BACKGROUND OF THE INVENTION

Neurodegenerative diseases, such as glaucoma, macular degeneration, and Alzheimer's disease, affect millions of patients throughout the world. Because the loss of quality of life associated with these diseases is considerable, drug research and development in this area is of great importance.

Macular degeneration affects between ten and fifteen million patients in the United States, and it is the leading cause of blindness in aging populations worldwide. Age-related macular degeneration affects central vision and causes the loss of photoreceptor cells in the central part of the retina called the macula. Macular degeneration can be classified into two types: dry-type and wet-type. The dry-form is more common than the wet, with about 90% of age-related macular degeneration (AMD) patients diagnosed with the dry-form. The wet-form of the disease and geographic atrophy, which is the end-stage phenotype of dry AMD, causes the most serious vision loss. All patients who develop wet-form AMD are believed to previously have been developing dry-form AMD for a prolonged period of time. The exact causes of age-related macular degeneration are still unknown. The dry-form of AMD may result from the senescence and thinning of macular tissues associated with the deposition of pigment in the macular retinal pigment epithelium. In wet AMD, new blood vessels grow beneath the retina, form scar tissue, bleed, and leak fluid. The overlying retina can be severely damaged, creating "blind" areas in the central vision.

For the vast majority of patients who have the dry-form of macular degeneration, no effective treatment is yet available. Because the dry-form precedes development of the wet-form of macular degeneration, therapeutic intervention to prevent or delay disease progression in the dry-form AMD would benefit patients with dry-form AMD and might reduce the incidence of the wet-form.

Decline of vision noticed by the patient or characteristic features detected by an ophthalmologist during a routine eye exam may be the first indicator of age-related macular degeneration. The formation of "drusen," or membranous debris beneath the retinal pigment epithelium of the macula is often the first physical sign that AMD is developing. Late symptoms include the perceived distortion of straight lines and, in advanced cases, a dark, blurry area or area with absent vision appears in the center of vision; and/or there may be color perception changes.

Different forms of genetically-linked macular degenerations may also occur in younger patients. In other maculopathies, there are hereditary, nutritional, traumatic, infection, or other ecologic factors.

Glaucoma is a broad term used to describe a group of diseases that causes a slowly progressive visual field loss, usually asymptomatically. The lack of symptoms may lead to a delayed diagnosis of glaucoma until the terminal stages of the disease. The prevalence of glaucoma is estimated to be 2.2 million in the United States, with about 120,000 cases of blindness attributable to the condition. The disease is particularly prevalent in Japan, which has four million reported cases. In many parts of the world, treatment is less accessible than in the United States and Japan, thus glaucoma ranks as a leading cause of blindness worldwide. Even if subjects afflicted with glaucoma do not become blind, their vision is often severely impaired.

The progressive loss of peripheral visual field in glaucoma is caused by the death of ganglion cells in the retina. Ganglion cells are a specific type of projection neuron that connects the eye to the brain. Glaucoma is usually accompanied by an increase in intraocular pressure. Current treatment includes use of drugs that lower the intraocular pressure; however, contemporary methods to lower the intraocular pressure are often insufficient to completely stop disease progression. Ganglion cells are believed to be susceptible to pressure and may suffer permanent degeneration prior to the lowering of intraocular pressure. An increasing number of cases of normal-tension glaucoma are observed in which ganglion cells degenerate without an observed increase in the intraocular pressure. Because current glaucoma drugs only treat intraocular pressure, a need exists to identify new therapeutic agents that will prevent or reverse the degeneration of ganglion cells.

Recent reports suggest that glaucoma is a neurodegenerative disease, similar to Alzheimer's disease and Parkinson's disease in the brain, except that it specifically affects retinal neurons. The retinal neurons of the eye originate from diencephalon neurons of the brain. Though retinal neurons are often mistakenly thought not to be part of the brain, retinal cells are key components of the central nervous system, interpreting the signals from the light-sensing cells.

Alzheimer's disease (AD) is the most common form of dementia among the elderly. Dementia is a brain disorder that seriously affects a person's ability to carry out daily activities. Alzheimer's is a disease that affects four million people in the United States alone. It is characterized by a loss of nerve cells in areas of the brain that are vital to memory and other mental functions. Currently available drugs can ameliorate AD symptoms for a relatively period of time, but no drugs are available that treat the disease or completely stop the progressive decline in mental function. Recent research suggests that glial cells that support the neurons or nerve cells may have defects in AD sufferers, but the cause of AD remains unknown. Individuals with AD seem to have a higher incidence of glaucoma and age-related macular degeneration, indicating that similar pathogenesis may underlie these neurodegenerative diseases of the eye and brain. (See Giasson et al., *Free Radic. Biol. Med.* 32:1264-75 (2002); Johnson et al., *Proc. Natl. Acad. Sci. USA* 99:11830-35 (2002); Dentchev et al., *Mol. Vis.* 9:184-90 (2003)).

Neuronal cell death underlies the pathology of these diseases. Unfortunately, very few compositions and methods that enhance retinal neuronal cell survival, particularly photoreceptor cell survival, have been discovered. A need therefore exists to identify and develop compositions that can be used for treatment and prophylaxis of a number of retinal diseases and disorders that have neuronal cell death as a primary, or associated, element in their pathogenesis.

In vertebrate photoreceptor cells, the irradiance of a photon causes isomerization of 11-cis-retinylidene chromophore to all-trans-retinylidene and uncoupling from the visual opsin receptors. This photoisomerization triggers conformational changes of opsins, which, in turn, initiate the biochemical chain of reactions termed phototransduction (Filipek et al., *Annu. Rev. Physiol.* 65:851-79 (2003)). Regeneration of the visual pigments requires that the chromophore be converted back to the 11-cis-configuration in the processes collectively called the retinoid (visual) cycle (see, e.g., McBee et al., *Prog. Retin. Eye Res.* 20:469-52 (2001)). First, the chromophore is released from the opsin and reduced in the photoreceptor by retinol dehydrogenases. The product, all-trans-retinol, is trapped in the adjacent retinal pigment epithelium (RPE) in the form of insoluble fatty acid esters in subcellular structures known as retinosomes (Imanishi et al., *J. Cell Biol.* 164:373-87 (2004)).

In Stargardt's disease (Allikmets et al., *Nat. Genet.* 15:236-46 (1997)), a disease associated with mutations in the ABCR transporter that acts as a flippase, the accumulation of all-trans-retinal may be responsible for the formation of a lipofuscin pigment, A2E, which is toxic towards retinal pigment epithelial cells and causes progressive retinal degeneration and, consequently, loss of vision (Mata et al., *Proc. Natl. Acad. Sci. USA* 97:7154-59 (2000); Weng et al., *Cell* 98:13-23 (1999)). Treating patients with an inhibitor of retinol dehydrogenases, 13-cis-RA (Isotretinoin, Accutane®, Roche), has been considered as a therapy that might prevent or slow the formation of A2E and might have protective properties to maintain normal vision (Radu et al., *Proc. Natl. Acad. Sci. USA* 100:4742-47 (2003)). 13-cis-RA has been used to slow the synthesis of 11-cis-retinal by inhibiting 11-cis-RDH (Law et al., *Biochem. Biophys. Res. Commun.* 161:825-9 (1989)), but its use can also be associated with significant night blindness. Others have proposed that 13-cis-RA works to prevent chromophore regeneration by binding RPE65, a protein essential for the isomerization process in the eye (Gollapalli et al., *Proc. Natl. Acad. Sci. USA* 101:10030-35 (2004)). Gollapalli et al. reported that 13-cis-RA blocked the formation of A2E and suggested that this treatment may inhibit lipofuscin accumulation and, thus, delay either the onset of visual loss in Stargardt's disease or age-related macular degeneration, which are both associated with retinal pigment-associated lipofuscin accumulation. However, blocking the retinoid cycle and forming unliganded opsin may result in more severe consequences and worsening of the patient's prognosis (see, e.g., Van Hooser et al., J. Biol. Chem. 277:19173-82 (2002); Woodruff et al., *Nat. Genet.* 35:158-164 (2003)). Failure of the chromophore to form may lead to progressive retinal degeneration and may produce a phenotype similar to Leber Congenital Amaurosis (LCA), is a very rare genetic condition affecting children shortly after birth.

A need exists in the art for an effective treatment for treating ophthalmic diseases or disorders resulting in ophthalmic disfunction including those described above. In particular, there exists a pressing need for compositions and methods for treating Stargardt's disease and age-related macular degeneration (AMD) without causing further unwanted side effects such as progressive retinal degeneration, LCA-like conditions, night blindness, or systemic vitamin A deficiency. A need also exists in the art for effective treatments for other ophthalmic diseases and disorders that adversely affect the retina.

SUMMARY OF THE INVENTION

The present invention relates to styrenyl derivative compounds, which can be inhibitors of an isomerization step of the retinoid cycle and are useful for treating ophthalmic diseases and disorders. Also provided are pharmaceutical compositions comprising the styrenyl derivative compounds and methods for treating various ophthalmic diseases using these compounds.

In one embodiment is a compound having a structure of Formula (A):

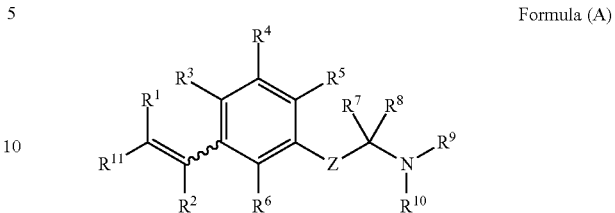

Formula (A)

as an isolated E or Z geometric isomer or a mixture of E and Z geometric isomers, as a tautomer or a mixture of tautomers, as a stereoisomer or as a pharmaceutically acceptable salt, hydrate, solvate, N-oxide or prodrug thereof, wherein: R1 and R2 are each the same or different and independently hydrogen or alkyl; R3, R4, R5 and R6 are each the same or different and independently hydrogen, halogen, nitro, —NH2, —NHR13, —N(R13)2, —OR12, alkyl or fluoroalkyl;

R7 and R8 are each the same or different and independently hydrogen or alkyl; or R7 and R8 together with the carbon atom to which they are attached, form a carbocyclyl or heterocyclyl; or R7 and R8 together form an imino;

R9 is hydrogen, alkyl, carbocyclyl, heterocyclyl, —C(=O)R13, —SO2R13, —CO2R13, —CONH2, —CON(R13)2 or —CON(H)R13;

R10 is hydrogen or alkyl; or R9 and R10, together with the nitrogen atom to which they are attached, form an N-heterocyclyl;

R11 is alkyl, alkenyl, aryl, carbocyclyl, heteroaryl or heterocyclyl; each R12 is independently selected from hydrogen or alkyl; each R13 is independently selected from alkyl, carbocyclyl, heterocyclyl, aryl or heteroaryl;

Z is a bond, Y or W—Y, wherein W is —C(R14)(R15)-, —O—, —S—, —S(=O)—, —S(=O)2- or —N(R12)-; Y is —C(R16)(R17)- or C(R16)(R17)-C(R21)(R22)-; R14 and R15 are each the same or different and independently hydrogen, halogen, alkyl, fluoroalkyl, —OR12, —NR18R19, carbocyclyl or heterocyclyl; or R14 and R15 together form an oxo, an imino, an oximo, or a hydrazino; R16 and R17 are each the same or different and independently hydrogen, halogen, alkyl, fluoroalkyl, —OR12, —NR18R19, carbocyclyl or heterocyclyl; or R16 and R17 together form an oxo; or optionally, R14 and R16 together form a direct bond to provide a double bond connecting W and Y; or optionally, R14 and R16 together form a direct bond, and R15 and R17 together form a direct bond to provide a triple bond connecting W and Y; each R18 and R19 is independently selected from hydrogen, alkyl, carbocyclyl, or —C(=O)R13, —SO2R13, —CO2R13, —CONH2, —CON(R13)2 or —CON(H)R13; or R18 and R19, together with the nitrogen atom to which they are attached, form an N-heterocyclyl; R21 and R22 are each the same or different and independently hydrogen, halogen, alkyl, fluoroalkyl, —OR12, —NR18R19, carbocyclyl or heterocyclyl;

provided that when R11 is phenyl, the compound of Formula (A) is not:

2-amino-N-[2-methoxy-5-[(1Z)-2-(3,4,5-trimethoxyphenyl)ethenyl]phenyl]acetamide;

(2S,3R)-amino-3-hydroxy-N-[2-methoxy-5-[(1Z)-2-(3,4,5-trimethoxyphenyl)-ethenyl]phenyl]-butanamide;

L-glutamic acid, 1-[2-methoxy-5-[(1Z)-2-(3,4,5-trimethoxyphenyl)ethenyl]phenyl]ester;

glycine, 3-hydroxy-5-[(1E)-2-(4-hydroxyphenyl)ethenyl]phenyl ester;

(2S)-2-amino-N-[2-methoxy-5-[(1Z)-2-(3,4,5-trimethoxyphenyl)ethenyl]phenyl]propanamide;

(2S)-2-amino-3-hydroxy-N-[2-methoxy-5-[(1Z)-2-(3,4,5-trimethoxyphenyl)ethenyl]phenyl]propanamide;

(2S)-2-amino-N-[2-methoxy-5-[(1Z)-2-(3,4,5-trimethoxyphenyl)ethenyl]phenyl]-4-methyl-pentanamide;

(2S)-2-amino-N-[2-methoxy-5-[(1Z)-2-(3,4,5-trimethoxyphenyl)ethenyl]phenyl]-3-methyl-butanamide; or 2-amino-N-[2-methoxy-5-[(1Z)-2-(3,4,5-trimethoxyphenyl)ethenyl]phenyl]butanamide.

In another embodiment is the compound wherein each of R1 and R8 is hydrogen, and the compound has a structure of Formula (B):

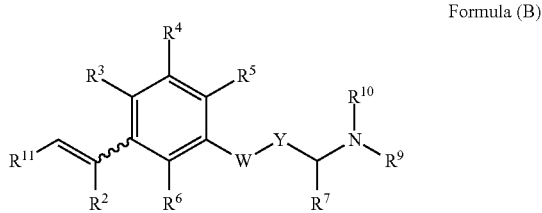

Formula (B)

wherein
R2 is H or C1-C6 alkyl;
each of R3, R4, R5, and R6 is the same or different and independently hydrogen, halo, C1-C6 alkyl, or —OR12;
R7 is H or C1-C6 alkyl;
R9 is hydrogen, C1-C6 alkyl, —(CH2)nOH wherein n is 2-6, or —C(=O)R13;
R10 is hydrogen or C1-C6 alkyl; or R9 and R10, together with the nitrogen atom to which they are attached, form an N-heterocyclyl;
W is —C(R14)(R15)-, —O—, —S—, —S(=O)—, —S(=O)2- or —N(H)—;
Y is —C(R16)(R17)-; each R12 is independently hydrogen or C1-C6 alkyl;
each R13 is independently a C1-C6 alkyl; R14 and R15 are each the same or different and independently selected from hydrogen, halogen, C1-C6 alkyl, fluoroalkyl, —OR12, or —NH2; or R14 and R15 together form an oxo, an imino, an oximo, or a hydrazino; R16 and R17 are each the same or different and independently hydrogen, halogen, C1-C6 alkyl, or —OR12; or R16 and R17 together form an oxo; or optionally, R14 and R16 together form a direct bond to provide a double bond connecting W and Y; or optionally, R14 and R16 together form a direct bond, and R15 and R17 together form a direct bond to provide a triple bond connecting W and Y; and R11 is selected from:
a) alkyl;
b) phenyl substituted with alkyl, —OR12, —O(CH2)mOCH3 wherein m is 1-6, alkenyl, alkynyl, halogen, fluoroalkyl, phenyl, —SCH3, or aralkyl;
c) naphthenyl optionally substituted with alkyl, halogen, or —OR12;
d) carbocyclyl; or
e) cyclohexenyl optionally substituted with alkyl,
provided that R11 is not 3,4,5-tri-methoxyphenyl.

In a further embodiment is the compound of Formula (A) or (B) wherein R2 is hydrogen or n-butyl. In an additional embodiment is the compound of Formula (A) or (B) wherein halogen is fluoro or chloro.

In yet another embodiment is the compound of either Formula (A) or (B) wherein each of R3, R4, R5, and R6 is the same or different and independently hydrogen, halogen, methyl, or methoxy.

In an additional embodiment is the compound of Formula (A) or (B), wherein at least two of R3, R4, R5, and R6 are hydrogen.

In a further embodiment is the compound of Formula (A) or (B), wherein W is —C(R14)(R15)-, and wherein R14 and R15 are each the same or different and independently hydrogen, fluoro, methyl, ethyl, trifluoromethyl, —OH, —OCH3, or —NH2.

In another embodiment is the compound of Formula (A) or (B), wherein each of R14 and R15 is hydrogen.

In an additional embodiment is the compound of Formula (A) or (B), wherein Y is CH2-, —CH(CH3)-, —C(CH3)2-, —C(H)OH—, —C(H)F—, —CF2-, or C(=O)—.

In yet another embodiment is the compound of Formula (A) or (B), wherein R11 is phenyl substituted with alkyl, —OR12, —O(CH2)nOCH3 wherein n is 2-6, alkenyl, alkynyl, halogen, fluoroalkyl, phenyl, or —SCH3.

In one embodiment is the compound of Formula (A) or (B), wherein R11 is naphthenyl substituted with —OR12, wherein R12 is hydrogen or C1-C6 alkyl.

In an additional embodiment is the compound of Formula (A) or (B), wherein R11 is cyclohexenyl optionally substituted with C1-C6 alkyl. In some embodiments R11 is trimethyl-cyclohexenyl.

In additional embodiments is the compound of Formula (A) or (B), wherein R11 is alkyl optionally substituted with —OR12 wherein R12 is hydrogen or C1-C6 alkyl.

In an additional embodiment is the compound of Formula (A), wherein R11 is aryl or carbocyclyl.

In an alternative embodiment is the compound of Formula (C), wherein R11 is aryl:

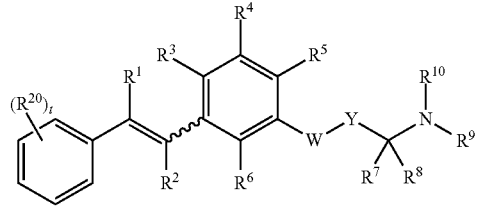

Formula (C) as an isolated E or Z geometric isomer or a mixture of E and Z geometric isomers, as a tautomer or a mixture of tautomers, as a stereoisomer, or as a pharmaceutically acceptable salt, hydrate, solvate, N-oxide or prodrug thereof, wherein:
R1 and R2 are each the same or different and independently hydrogen or alkyl;
R3, R4, R5 and R6 are each the same or different and independently hydrogen, halogen, nitro, —NH2, —NHR13, —N(R13)2, —OR12, alkyl or fluoroalkyl;
R7 and R8 are each the same or different and independently hydrogen or alkyl;
R9 is hydrogen, alkyl, carbocyclyl or —C(=O)R13;
R10 is hydrogen or alkyl; or R9 and R10, together with the nitrogen atom to which they are attached, form an N-heterocyclyl;
each R12 is independently selected from hydrogen or alkyl;
R13 is alkyl, carbocyclyl or aryl;
W is —C(R14)(R15)-, —O—, —S—, —S(=O)—, —S(=O)2- or —N(R12)-;
Y is —C(R16)(R17)-;

R14 and R15 are each the same or different and independently hydrogen, halogen, alkyl, fluoroalkyl, —OR12, —NR18R19 or carbocyclyl; or R14 and R15 together form an oxo, an imino, an oximo, or a hydrazino;

R16 and R17 are each the same or different and independently hydrogen, halogen, alkyl, fluoroalkyl, —OR12, —NR18R19 or carbocyclyl; or R16 and R17 together form an oxo;

optionally, R14 and R16 together form a direct bond to provide a double bond connecting W and Y; or optionally, R14 and R16 together form a direct bond, and R15 and R17 together form a direct bond to provide a triple bond connecting W and Y;

each R18 and R19 is independently selected from hydrogen, alkyl, carbocyclyl, or —C(═O)R13;

t is 0, 1, 2, 3, 4 or 5; and each R20 is the same or different and independently selected from alkyl, —OR12, —SR12, alkenyl, alkynyl, halo, fluoroalkyl, aryl or aralkyl; or two adjacent R20 groups, together with the two carbon atoms to which they are attached, form a fused phenyl ring.

In an additional embodiment is the compound wherein each of R9 and R10 is hydrogen and the compound has a structure of Formula (D):

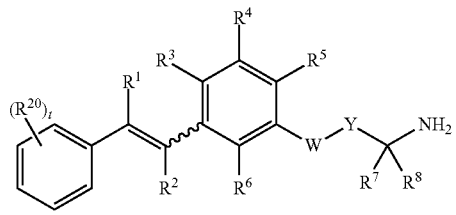

Formula (D)

In a further embodiment is the compound of Formula (E) wherein W is —C(R14)(R15)-:

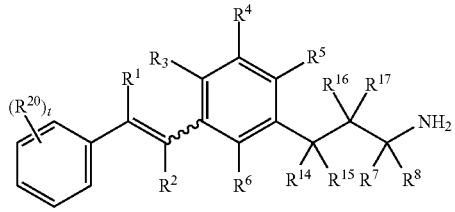

Formula (E)

as an isolated E or Z geometric isomer or a mixture of E and Z geometric isomers, as a tautomer or a mixture of tautomers, as a stereoisomer, or as a pharmaceutically acceptable salt, hydrate, solvate, N-oxide or prodrug thereof, wherein:

R1 and R2 are each the same or different and independently hydrogen or alkyl;

R3, R4, R5 and R6 are each the same or different and independently hydrogen, halogen, nitro, —NH2, —NHR13, —N(R13)2, —OR12, alkyl or fluoroalkyl;

R7 and R8 are each the same or different and independently hydrogen or alkyl;

each R12 is independently selected from hydrogen or alkyl;

R13 is alkyl, carbocyclyl or aryl;

R14 and R15 are each the same or different and independently hydrogen, halogen, alkyl, fluoroalkyl, —OR12, —NR18R19 or carbocyclyl; or R14 and R15 form an oxo, an imino, an oximo, or a hydrazino;

R16 and R17 are each the same or different and independently hydrogen, halogen, alkyl, fluoroalkyl, —OR12, —NR18R19 or carbocyclyl; or R16 and R17 form an oxo;

each R18 and R19 are each the same or different and independently hydrogen, alkyl, carbocyclyl, or —C(═O)R13;

t is 0, 1, 2, 3, 4 or 5; and each R20 is the same or different and independently alkyl, —OR12, —SR12, alkenyl, alkynyl, halo, fluoroalkyl, aryl or aralkyl, or two adjacent R20, together with the two carbon atoms to which they are attached, form a fused phenyl ring.

In a additional embodiment is the compound of Formula (E) wherein t is 0, 1, 2 or 3;

each R20 is independently alkyl, —OR12, —SR12, alkynyl, phenyl, halo or fluoroalkyl; and R3, R4, R5 and R6 are each independently hydrogen, alkyl, —OR12, halo or fluoroalkyl.

In a further embodiment is the compound of Formula (E), wherein R7, R8, R14, R15, R16 and R17 are each independently hydrogen, halogen, alkyl or —OR12, wherein each R12 is independently selected from hydrogen or alkyl.

In an additional embodiment is the compound of Formula (E), wherein:

t is 2 or 3; two adjacent R20, together with the two carbon atoms to which they are attached, form a fused phenyl ring; and R3, R4, R5 and R6 are each independently hydrogen, alkyl, halo or fluoroalkyl.

In another embodiment is the compound of Formula (E), wherein R7, R8, R14, R15, R16 and R17 are each independently hydrogen, halogen, alkyl or —OR12.

In an additional embodiment is the compound of Formula (E), wherein W is —O—, —S—, —S(═O)—, —S(═O)2- or —N(R12)-.

In yet another embodiment is the compound of Formula (E), wherein: t is 0, 1, 2 or 3; each R20 is independently alkyl, —OR12 or halo; and R3, R4, R5 and R6 are each independently hydrogen, alkyl or halo.

In a specific embodiment is the compound of Formula (E) wherein W and Y are connected by a double bond.

In an additional embodiment is the compound of Formula (E), wherein R9 and R10 together with the nitrogen to which they are attached form a N-heterocyclyl.

In an additional embodiment is the compound of Formula (E), wherein the N-heterocyclyl is morpholinyl, pyrrolidinyl, piperidinyl or piperazinyl.

In an additional embodiment is the compound of Formula (E), wherein: each of R1 and R2 is hydrogen; t is 0, 1, 2 or 3; each R20 is independently alkyl or halo; and R3, R4, R5 and R6 are each independently hydrogen, alkyl or halo.

In another embodiment is the compound of Formula (E), wherein W is —C(R14)(R15)-.

In an additional embodiment is the compound of Formula (E), wherein R9 is alkyl or —C(═O)R13, wherein R13 is alkyl, and R10 is hydrogen or alkyl.

In an additional embodiment is the compound of Formula (E), wherein: each of R1 and R2 is hydrogen; t is 0, 1, 2 or 3; each R20 is independently alkyl or halo; and R3, R4, R5 and R6 are each independently hydrogen, alkyl or halo.

In an additional embodiment is the compound of Formula (E), wherein W is —C(R14)(R15)-.

In an additional embodiment is the compound of Formula (A), wherein R11 is 3-, 4-, 5-, 6-, 7- or 8-member cycloalkyl. In some embodiments R11 is cyclohexyl.

In an additional embodiment is the compound of Formula (A), wherein R11 is 5-, 6-, or 7-member cycloalkenyl.

In an additional embodiment is the compound of Formula (F), wherein R11 is cyclohexenyl:

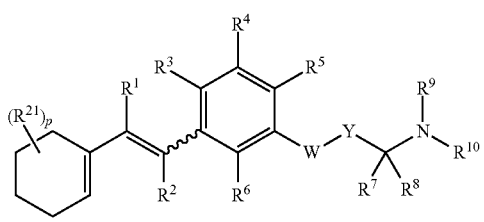

Formula (F)

as an isolated E or Z geometric isomer or a mixture of E and Z geometric isomers, as a tautomer or a mixture of tautomers, as a stereoisomer, or as a pharmaceutically acceptable salt, hydrate, solvate, N-oxide or prodrug thereof, wherein:

R1 and R2 are each the same or different and independently hydrogen or alkyl;

R3, R4, R5 and R6 are each the same or different and independently hydrogen, halogen, nitro, —NH2, —NHR13, —N(R13)2, —OR12, alkyl or fluoroalkyl;

R7 and R8 are each the same or different and independently hydrogen or alkyl;

R9 is hydrogen, alkyl, carbocyclyl or —C(=O)R13;

R10 is hydrogen or alkyl; or R9 and R10, together with the nitrogen atom to which they are attached, form an N-heterocyclyl;

each R12 is independently selected from hydrogen or alkyl;

each R13 is independently selected from alkyl, carbocyclyl or aryl;

W is —C(R14)(R15)-, —O—, —S—, —S(=O)—, —S(=O)2- or —N(R12)-;

Y is —C(R16)(R17)-;

R14 and R15 are each the same or different and independently hydrogen, halogen, alkyl, fluoroalkyl, —OR12, —NR18R19 or carbocyclyl; or R14 and R15 together form an oxo, an imino, an oximo, or a hydrazino;

R16 and R17 are each the same or different and independently hydrogen, halogen, alkyl, fluoroalkyl, —OR12, —NR18R19 or carbocyclyl; or R16 and R17 together form an oxo;

optionally, R14 and R16 together form a direct bond to provide a double bond connecting W and Y; or R14 and R16 together form a direct bond, and R15 and R17 together form a direct bond to provide a triple bond connecting W and Y;

each R18 and R19 is independently selected from hydrogen, alkyl, carbocyclyl, or —C(=O)R13;

p is 0, 1, 2, 3, 4, 5, 7, 8 or 9; and each R21 is the same or different and independently selected from alkyl, —OR12, alkenyl, alkynyl, halo, fluoroalkyl or aralkyl.

In an additional embodiment is the compound wherein W is —C(R14)(R15)-, and the compound has a structure of Formula (G):

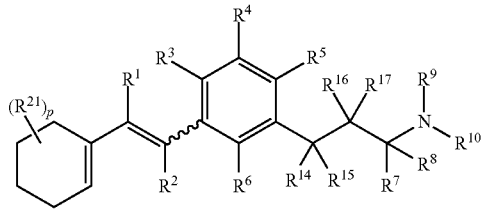

Formula (G)

as an isolated E or Z geometric isomer or a mixture of E and Z geometric isomers, as a tautomer or a mixture of tautomers, as a stereoisomer, or as a pharmaceutically acceptable salt, hydrate, solvate, N-oxide or prodrug thereof, wherein:

R1 and R2 are each the same or different and independently hydrogen or alkyl;

R3, R4, R5 and R6 are each the same or different and independently hydrogen, halogen, nitro, —NH2, —NHR13, —N(R13)2, —OR12, alkyl or fluoroalkyl;

R7 and R8 are each the same or different and independently hydrogen or alkyl;

R9 is hydrogen, alkyl, carbocyclyl or —C(=O)R13;

R10 is hydrogen or alkyl; or R9 and R10, together with the nitrogen atom to which they are attached, form an N-heterocyclyl;

each R12 is independently selected from hydrogen or alkyl;

each R13 is independently alkyl, carbocyclyl or aryl;

R14 and R15 are each the same or different and independently hydrogen, halogen, alkyl, fluoroalkyl, —OR12, —NR18R19 or carbocyclyl; or R14 and R15 together form an oxo, an imino, an oximo, or a hydrazino;

R16 and R17 are each the same or different and independently hydrogen, halogen, alkyl, fluoroalkyl, —OR12, —NR18R19 or carbocyclyl; or R16 and R17 together form an oxo;

optionally, R14 and R16 together form a direct bond to provide a double bond connecting W and Y; or R14 and R16 together form a direct bond, and R15 and R17 together form a direct bond to provide a triple bond connecting W and Y;

each R18 and R19 is independently selected from hydrogen, alkyl, carbocyclyl, or —C(=O)R13;

p is 0, 1, 2, 3, 4, 5, 7, 8 or 9; and each R21 is the same or different and independently alkyl, —OR12, alkenyl, alkynyl, halo, fluoroalkyl or aralkyl.

In an additional embodiment is the compound of Formula (G), wherein each of R9 and R10 is hydrogen.

In an additional embodiment is the compound of Formula (G), wherein: each of R1 and R2 is hydrogen; p is 0, 1, 2 or 3; each R21 is independently alkyl, halo or fluoroalkyl; and each of R3, R4, R5 and R6 is independently hydrogen, alkyl, halo, fluoroalkyl or —OR12.

In an additional embodiment is the compound of Formula (G), wherein: R7, R8, R14, R15, R16 and R17 are each independently hydrogen, halogen, alkyl, fluoroalkyl, —OR12 or —NR18R19, wherein each R12 is independently hydrogen or alkyl; and each R18 and R19 are independently hydrogen or alkyl.

In an additional embodiment is the compound of Formula (G), wherein R9 is alkyl and R10 is hydrogen.

In an additional embodiment is the compound of Formula (G), wherein: each of R1 and R2 is hydrogen; p is 0, 1, 2 or 3; each R21 is independently alkyl, halo or fluoroalkyl; and each of R3, R4, R5 and R6 is independently hydrogen, alkyl, halo, fluoroalkyl or —OR12.

In an additional embodiment is the compound of Formula (G), wherein R7, R8, R14, R15, R16 and R17 are each independently hydrogen, halogen, alkyl, fluoroalkyl or —OR12, wherein each R12 is independently hydrogen or alkyl.

In an additional embodiment is the compound of Formula (G), wherein: R7, R8, R16 and R17 are each independently hydrogen, halogen, alkyl, fluoroalkyl or —OR12, wherein R12 is hydrogen or alkyl; and R14 and R15 together form oxo.

In an additional embodiment is the compound of Formula (G), wherein W is —NH— or —O—.

In an additional embodiment is the compound of Formula (G), wherein each of R1, R2, R9 and R10 is hydrogen.

In an additional embodiment is the compound of Formula (G), wherein: p is 0, 1, 2 or 3; each R21 is independently alkyl or halo; and R3, R4, R5 and R6 are each independently hydrogen, alkyl, halo or fluoroalkyl.

In an additional embodiment is the compound of Formula (G), wherein W and Y are connected by a double or triple bond.

In an additional embodiment is the compound of Formula (G), wherein each of R1, R2, R9 and R10 is hydrogen.

In an additional embodiment is the compound of Formula (G), wherein: p is 0, 1, 2 or 3; each R21 is independently alkyl or halo; R3, R4, R5 and R6 are each independently hydrogen, alkyl, halo or fluoroalkyl; and R15 and R17 are each independently hydrogen, alkyl or halogen.

In an additional embodiment is the compound of Formula (A), wherein R11 is alkyl. In an additional embodiment W is —C(R14)(R15)-. In a further embodiment, R1, R2, R3, R4, R5 and R6 are each independently hydrogen or alkyl.

In an additional embodiment, Z is —C(R16)(R17)- and the compound has the structure of Formula (H):

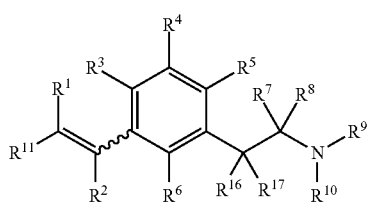

Formula (H)

as an isolated E or Z geometric isomer or a mixture of E and Z geometric isomers, as a tautomer or a mixture of tautomers, as
a stereoisomer or as a pharmaceutically acceptable salt, hydrate, solvate, N-oxide or prodrug thereof, wherein:
R1 and R2 are each the same or different and independently hydrogen or alkyl;
R3, R4, R5 and R6 are each the same or different and independently hydrogen, halogen, nitro, —NH2, —NHR13, —N(R13)2, —OR12, alkyl or fluoroalkyl;
R7 and R8 are each the same or different and independently hydrogen or alkyl; or R7 and R8 together with the carbon atom to which they are attached, form a carbocyclyl or heterocyclyl; or R7 and R8 together form an imino;
R9 is hydrogen, alkyl, carbocyclyl, heterocyclyl, —C(=O)R13, —SO2R13, —CO2R13, —CONH2, —CON(R13)2 or —CON(H)R13;
R10 is hydrogen or alkyl; or R9 and R10, together with the nitrogen atom to which they are attached, form an N-heterocyclyl;
R11 is alkyl, alkenyl, aryl, carbocyclyl, heteroaryl or heterocyclyl;
each R12 is independently selected from hydrogen or alkyl;
each R13 is independently selected from alkyl, carbocyclyl, heterocyclyl, aryl or heteroaryl;
R16 and R17 are each the same or different and independently hydrogen, halogen, alkyl, fluoroalkyl, —OR12, —NR18R19, carbocyclyl or heterocyclyl;
each R18 and R19 is independently selected from hydrogen, alkyl, carbocyclyl, or —C(=O)R13, —SO2R13, —CO2R13, —CONH2, —CON(R13)2 or —CON(H)R13; or R18 and R19, together with the nitrogen atom to which they are attached, form an N-heterocyclyl.

In a further embodiment is the compound of Formula (H), wherein R1, R2, R3, R4, R5 and R6 are all hydrogen; R11 is aryl or carbocyclyl; and R16 and R17 are each the same or different and independently hydrogen, halogen, alkyl, fluoroalkyl or —OR12.

In a further embodiment is the compound of Formula (A), wherein Z is a bond and the compound has the structure of Formula (J):

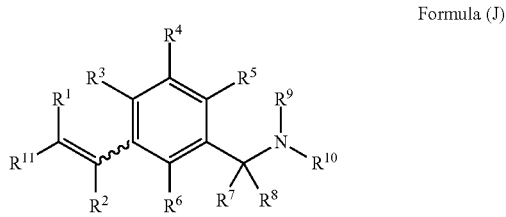

Formula (J)

as an isolated E or Z geometric isomer or a mixture of E and Z geometric isomers, as a tautomer or a mixture of tautomers, as a stereoisomer or as a pharmaceutically acceptable salt, hydrate, solvate, N-oxide or prodrug thereof, wherein:
R1 and R2 are each the same or different and independently hydrogen or alkyl;
R3, R4, R5 and R6 are each the same or different and independently hydrogen, halogen, nitro, —NH2, —NHR13, —N(R13)2, —OR12, alkyl or fluoroalkyl;
R7 and R8 are each the same or different and independently hydrogen or alkyl; or R7 and R8 together with the carbon atom to which they are attached, form a carbocyclyl or heterocyclyl; or R7 and R8 together form an imino;
R9 is hydrogen, alkyl, carbocyclyl, heterocyclyl, —C(=O)R13, —SO2R13, —CO2R13, —CONH2, —CON(R13)2 or CON(H)R13;
R10 is hydrogen or alkyl; or R9 and R10, together with the nitrogen atom to which they are attached, form an N-heterocyclyl;
R11 is alkyl, alkenyl, aryl, carbocyclyl, heteroaryl or heterocyclyl;
each R12 is independently selected from hydrogen or alkyl; and
each R13 is independently selected from alkyl, carbocyclyl, heterocyclyl, aryl or heteroaryl.

In a further embodiment is the compound of Formula (J), wherein
R1, R2, R3, R4, R5 and R6 are hydrogen; and
R11 is aryl or carbocyclyl.

In a further embodiment is the compound of Formula (A), wherein Z is —C(R14)(R15)-C(R16)(R17)-(R21)(R22)- and the compound has the structure of Formula (K):

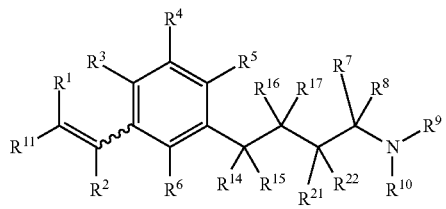

Formula (K)

as an isolated E or Z geometric isomer or a mixture of E and Z geometric isomers, as a tautomer or a mixture of tautomers, as a stereoisomer or as a pharmaceutically acceptable salt, hydrate, solvate, N-oxide or prodrug thereof, wherein:

R1 and R2 are each the same or different and independently hydrogen or alkyl;

R3, R4, R5 and R6 are each the same or different and independently hydrogen, halogen, nitro, —NH2, —NHR13, —N(R13)2, —OR12, alkyl or fluoroalkyl;

R7 and R8 are each the same or different and independently hydrogen or alkyl; or R7 and R8 together with the carbon atom to which they are attached, form a carbocyclyl or heterocyclyl; or R7 and R8 together form an imino;

R9 is hydrogen, alkyl, carbocyclyl, heterocyclyl, —C(═O)R13, —SO2R13, —CO2R13, —CONH2, —CON(R13)2 or —CON(H)R13;

R10 is hydrogen or alkyl; or R9 and R10, together with the nitrogen atom to which they are attached, form an N-heterocyclyl;

R11 is alkyl, alkenyl, aryl, carbocyclyl, heteroaryl or heterocyclyl;

each R12 is independently selected from hydrogen or alkyl;

each R13 is independently selected from alkyl, carbocyclyl, heterocyclyl, aryl or heteroaryl;

R14 and R15 are each the same or different and independently hydrogen, halogen, alkyl, fluoroalkyl, —OR12, —NR18R19, carbocyclyl or heterocyclyl; or R14 and R15 together form an oxo, an imino, an oximo, or a hydrazino;

R16 and R17 are each the same or different and independently hydrogen, halogen, alkyl, fluoroalkyl, —OR12, —NR18R19, carbocyclyl or heterocyclyl; or R16 and R17 together form an oxo;

each R18 and R19 is independently selected from hydrogen, alkyl, carbocyclyl, or —C(═O)R13, —SO2R13, —CO2R13, —CONH2, —CON(R13)2 or —CON(H)R13; or R18 and R19, together with the nitrogen atom to which they are attached, form an N-heterocyclyl; and R21 and R22 are each the same or different and independently hydrogen, halogen, alkyl, fluoroalkyl, —OR12, —NR18R19, carbocyclyl or heterocyclyl.

In a further embodiment is the compound of Formula (K), wherein

R1, R2, R3, R4, R5 and R6 are hydrogen;

R11 is aryl or carbocyclyl;

14 and R15 are each the same or different and independently hydrogen, halogen, alkyl, fluoroalkyl or —OR12; and R16, R17, R21 and R22 are each independently hydrogen or alkyl.

In a specific embodiment is the compound selected from:
(E)-3-(3-(2,6-dimethylstyryl)phenyl)propan-1-amine;
(Z)-3-(3-(2,6-dimethylstyryl)phenyl)propan-1-amine;
(E)-3-(3-(2-methylstyryl)phenyl)propan-1-amine;
(Z)-3-(3-(2-methylstyryl)phenyl)propan-1-amine;
(E)-3-(3-(2,6-dimethylstyryl)-2-methylphenyl)propan-1-amine;
(Z)-3-(3-(2,6-dimethylstyryl)-2-methylphenyl)propan-1-amine;
(E/Z)-3-(3-(2-ethyl-6-methylstyryl)phenyl)propan-1-amine;
(E/Z)-3-(3-(2,5-dimethylstyryl)phenyl)propan-1-amine;
(E/Z)-3-(3-(2,4-dimethylstyryl)phenyl)propan-1-amine;
(E)-3-(3-(2,4,6-trimethylstyryl)phenyl)propan-1-amine;
(E/Z)-3-(3-(2-ethylstyryl)phenyl)propan-1-amine;
(E/Z)-3-(3-(2-ethynylstyryl)phenyl)propan-1-amine;
(E/Z)-3-(3-(3,4-dimethylstyryl)phenyl)propan-1-amine;
(E/Z)-3-(3-(2-isopropylstyryl)phenyl)propan-1-amine;
(E/Z)-4-(3-(3,5-dimethylstyryl)phenyl)propan-1-amine;
(E/Z)-4-(3-(2-methoxystyryl)phenyl)propan-1-amine;
(E)-3-(3-(2,6-dichlorostyryl)phenyl)propan-1-amine;
(E/Z)-3-(3-(2,3-dimethylstyryl)phenyl)propan-1-amine;
(E)-3-(3-(2,6-dimethylstyryl)-4-fluorophenyl)propan-1-amine;
(E/Z)-3-(3-(2-(trifluoromethyl)styryl)phenyl)propan-1-amine;
(E)-3-(3-(2,6-dimethoxystyryl)phenyl)propan-1-amine;
(E)-3-(3-(2,6-bis(trifluoromethyl) styryl)phenyl)propan-1-amine;
(E)-3-amino-1-(3-(2,6-dichlorostyryl)phenyl)propan-1-ol;
(E)-3-amino-1-(3-(2-chloro-6-methylstyryl)phenyl)propan-1-ol;
(E)-2-(3-(3-aminopropyl)styryl)phenol;
(E)-3-(5-(2,6-dichlorostyryl)-2-methoxyphenyl)propan-1-amine;
(R,E)-1-amino-3-(3-(2,6-dichlorostyryl)phenyl)propan-2-ol;
(S,E)-1-amino-3-(3-(2,6-dichlorostyryl)phenyl)propan-2-ol;
(E/Z)-(3-(3-(2,6-diethoxystyryl)phenyl)propan-1-amine;
(E)-3-(3-(2-ethoxystyryl)phenyl)propan-1-amine;
(E/Z)-3-(3-(2-isopropoxystyryl)phenyl)propan-1-amine;
(E)-3-amino-1-(3-(2,6-dichlorostyryl)phenyl)propan-1-one;
(E)-1-amino-3-(3-(2,6-dichlorostyryl)phenyl)propan-2-one;
(R,E)-3-amino-1-(3-(2,6-dichlorostyryl)phenyl)propan-1-ol;
(S,E)-3-amino-1-(3-(2,6-dichlorostyryl)phenyl)propan-1-ol;
(S,E)-3-(3-(2,6-dichlorostyryl)phenyl)-2-fluoropropan-1-amine;
(E)-3-(3-(2,6-dichlorostyryl)phenyl)-2,2-difluoropropan-1-amine;
(Z)-3-(3-(2-(2-methoxyethoxy)styryl)phenyl)-propan-1-amine;
(E)-3-(3-(3-methoxystyryl)phenyl)propan-1-amine;
(Z)-3-(3-(4-chlorostyryl)phenyl)propan-1-amine;
(E)-3-(3-(2-(biphenyl-2-yl)vinyl)phenyl)propan-1-amine;
(E)-3-(3-(3-chlorostyryl)phenyl)propan-1-amine;
(E)-3-(3-(2-butoxystyryl)phenyl)propan-1-amine;
(E)-3-(3-(4-methoxystyryl)phenyl)propan-1-amine;
(Z)-3-(3-(2-Propoxystyryl)phenyl)propan-1-amine;
(E)-3-(5-(2-Chloro-6-(methylthio)styryl)-2-methoxyphenyl)propan-1-amine;
(E)-3-(3-(2-(1-methoxynaphthalen-2-yl)vinyl)phenyl)propan-1-amine;
(Z)-3-(3-(2-(naphthalen-1-yl)vinyl)phenyl)propan-1-amine;
(Z)-3-(3-(2-(3-methoxynaphthalen-2-yl)vinyl)phenyl)propan-1-amine;
(E/Z)-3-(3-(2-(2-methoxynaphthalen-1-yl)vinyl)phenyl)propan-1-amine;
(E)-2-amino-N-(3-(2,6-dimethylstyryl)phenyl)acetamide;
(E)-2-(3-(2,6-dimethylstyryl)phenylthio)ethanamine;
(E)-2-(3-(2,6-dimethylstyryl)phenylsulfinyl)ethanamine;
(E)-2-(3-(2,6-dimethylstyryl)phenylsulfonyl)ethanamine;
(E)-3-(3-(2,6-dimethylstyryl)phenyl)prop-2-en-1-amine;
(E)-4-(3-(3-(2,6-dimethylstyryl)phenyl)propyl)morpholine;
(Z)-4-(3-(3-(2,6-dimethylstyryl)phenyl)propyl)morpholine;

(E)-1-(3-(3-(2,6-dimethylstyryl)phenyl)propyl)pyrrolidine;
(Z)-1-(3-(3-(2,6-dimethylstyryl)phenyl)propyl)pyrrolidine;
(E)-1-(3-(3-(2,6-dimethylstyryl)phenyl)propyl)piperidine;
(Z)-1-(3-(3-(2,6-dimethylstyryl)phenyl)propyl)piperidine;
(E)-3-(3-(2,6-dimethylstyryl)phenyl)-N-methylpropan-1-amine;
(Z)-3-(3-(2,6-dimethylstyryl)phenyl)-N-methylpropan-1-amine;
(E)-3-(3-(2,6-dimethylstyryl)phenyl)-N,N-dimethylpropan-1-amine;
(Z)-3-(3-(2,6-dimethylstyryl)phenyl)-N,N-dimethylpropan-1-amine;
(E/Z)—N-(3-(3-(2,6-dimethylstyryl)phenyl)propyl)acetamide;
(E)-1-(3-(3-aminopropyl)styryl)cyclohexanol;
(E)-1-(3-(3-aminopropyl)styrypcyclopentanol;
(E)-1-(3-(3-aminopropyl)styryl)cycloheptanol;
(E)-3-(3-(2-cyclohexylvinyl)phenyl)propan-1-amine;
(E)-3-(3-(2-cyclopentylvinyl)phenyl)propan-1-amine;
(E)-3-(3-(2-cycloheptylvinyl)phenyl)propan-1-amine;
(E)-3-(3-(2-(2,6,6-trimethylcyclohex-1-enyl)vinyl)phenyl)propan-1-amine;
(E)-3-amino-1-(3-(2-(2,6,6-trimethylcyclohex-1-enyl)vinyl)phenyl)propan-1-ol;
(S,E)-3-amino-1-(3-(2-(2,6,6-trimethylcyclohex-1-enyl)vinyl)phenyl)propan-1-ol;
(R,E)-3-Amino-1-(3-(2-(2,6,6-trimethylcyclohex-1-enyl)vinyl)phenyl)propan-1-ol;
(E)-2-methyl-3-(3-(2-(2,6,6-trimethylcyclohex-1-enyl)vinyl)phenyl)propan-1-amine;
(E)-3-(3-(2-(2,6,6-trimethylcyclohex-1-enyl)vinyl)phenyl)butan-1-amine;
(E)-3-(2-methyl-5-(2-(2,6,6-trimethylcyclohex-1-enyl)vinyl)phenyl)propan-1-amine;
(E/Z)-4-amino-2-(3-(2-(2,6,6-trimethylcyclohex-1-enyl)vinyl)phenyl)butan-2-ol;
(E)-3-fluoro-3-(3-(2-(2,6,6-trimethylcyclohex-1-enyl)vinyl)phenyl)propan-1-amine;
(E)-4-amino-1,1,1-trifluoro-2-(3-(2-(2,6,6-trimethylcyclohex-1-enyl)vinyl)phenyl)butan-2-ol;
(E)-3-amino-2,2-dimethyl-1-(3-(2-(2,6,6-trimethylcyclohex-1-enyl)vinyl)phenyl)propan-1-ol;
(E)-3-amino-2-methyl-1-(3-(2-(2,6,6-trimethylcyclohex-1-enyl)vinyl)phenyl)propan-1-ol;
(E)-1-(3-(2-(2,6,6-trimethylcyclohex-1-enyl)vinyl)phenyl)propane-1,3-diamine;
(E)-4,4,4-trifluoro-3-(3-(2-(2,6,6-trimethylcyclohex-1-enyl)vinyl)phenyl)butan-1-amine;
(E)-3-methoxy-3-(3-(2-(2,6,6-trimethylcyclohex-1-enyl)vinyl)phenyl)propan-1-amine;
(E)-4-(3-(2-(2,6,6-trimethylcyclohex-1-enyl)vinyl)phenyl)butan-2-amine;
(E)-1-amino-3-(3-(2-(2,6,6-trimethylcyclohex-1-enyl)vinyl)phenyl)propan-2-ol;
(E)-2-(3-(3-(2-(2,6,6-trimethylcyclohex-1-enyl)vinyl)phenyl)propylamino)ethanol;
(E)-3-methoxy-N-methyl-3-(3-(2-(2,6,6-trimethylcyclohex-1-enyl)vinyl)phenyl)propan-1-amine;
(E)-3-amino-1-(3-(2-(2,6,6-trimethylcyclohex-1-enyl)vinyl)phenyl)propan-1-one;
(E)-3-amino-2,2-dimethyl-1-(3-(2-(2,6,6-trimethylcyclohex-1-enyl)vinyl)phenyl)propan-1-one;
(E)-3-amino-2-methyl-1-(3-(2-(2,6,6-trimethylcyclohex-1-enyl)vinyl)phenyl)propan-1-one;
(E)-3-amino-2-fluoro-1-(3-(2-(2,6,6-trimethylcyclohex-1-enyl)vinyl)phenyl)propan-1-one;
(E)-2-(3-(2-(2,6,6-trimethylcyclohex-1-enyl)vinyl)phenoxy)ethanamine;
(E)-2-amino-N-(3-(2-(2,6,6-trimethylcyclohex-1-enyl)vinyl)phenyl)acetamide;
(E)-3-(3-(2-(2,6,6-trimethylcyclohex-1-enyl)vinyl)phenyl)prop-2-yn-1-amine;
(E)-2-fluoro-3-(3-((E)-2-(2,6,6-trimethylcyclohex-1-enyl)vinyl)phenyl)prop-2-en-1-amine;
(E)-3-(3-(2-(2,6,6-trimethylcyclohex-1-enyl)vinyl)phenyl)prop-2-yn-1-amine;
(E)-2-fluoro-3-(34E)-2-(2,6,6-trimethylcyclohex-1-enyl)vinyl)phenyl)prop-2-en-1-amine;
(E)-3-(3-(pent-1-enyl)phenyl)propan-1-amine;
(E)-3-(3-(hept-1-enyl)phenyl)propan-1-amine;
(E)-3-(3-(non-4-en-5-yl)phenyl)propan-1-amine;
(E)-4-(3-(3-aminopropyl)phenyl)-2-methylbut-3-en-2-ol;
(E)-4-(3-(3-aminopropyl)styryl)heptan-4-ol;
(E)-1-(3-(3-aminopropyl)phenyl)hex-1-en-3-ol;
(E)-4-(3-(2-aminoethoxy)styryl)heptan-4-ol;
(E)-1-(3-(3-aminopropyl)phenyl)-3-ethylpent-1-en-3-ol;
(E)-3-(3-(3-aminopropyl)phenyl)prop-2-en-1-ol;
(E)-3-(3-(3-methoxyprop-1-enyl)phenyl)propan-1-amine;
(E)-(3-(2-(2,6,6-trimethylcyclohex-1-enyl)vinyl)phenyl)methanamine;
(E)-1-(3-(2,6-dimethylstyryl)phenyl)-N,N-dimethylmethanamine;
(E)-4-(3-(2,6-dimethylstyryl)phenyl)butan-1-amine;
(E)-2-(3-(2,6-dimethylstyryl)phenyl)ethanamine;
(E)-2-(3-(2,6-dimethylstyryl)benzylamino)ethanol;
(E)-3-(3-(2,6-dimethylstyryl)phenyl)-3-hydroxypropanimidamide;
(E)-3-hydroxy-3-(3-(2-(2,6,6-trimethylcyclohex-1-enyl)vinyl)phenyl)propanimidamide;
(Z)-3-amino-1-(3-(2,6-dimethylstyryl)phenyl)propan-1-one oxime;
(Z)-3-amino-1-(3-((E)-2-(2,6,6-trimethylcyclohex-1-enyl)vinyl)phenyl)propan-1-one oxime;
(Z)-3-(3-(2,6-dimethylstyryl)phenyl)-3-hydrazonopropan-1-amine;
(Z)-3-hydrazono-3-(3-((E)-2-(2,6,6-trimethylcyclohex-1-enyl)vinyl)phenyl)propan-1-amine;
(E)-2-(3-(2,6-dimethylstyryl)phenyl)ethanamine;
(E)-2-(3-(2-(2,6,6-trimethylcyclohex-1-enyl)vinyl)phenyl)ethanamine;
(E)-2-amino-1-(3-(2,6-dimethylstyryl)phenyl)ethanol;
(E)-2-amino-1-(3-(2-(2,6,6-trimethylcyclohex-1-enyl)vinyl)phenyl)ethanol;
(E)-1-(3-(3-aminopropyl)phenyl)-3-methylhex-1-en-3-ol; and
(E)-1-(3-(3-aminopropyl)phenyl)-3-ethylhex-1-en-3-ol.

In an additional embodiment is a pharmaceutical composition comprising a pharmaceutically acceptable carrier and a compound disclosed herein, including compound of Formula (A)-(K).

In yet another embodiment is a compound that inhibits 11-cis-retinol production with an IC50 of about 1 uM or less when assayed in vitro, utilizing extract of cells that express RPE65 and LRAT, wherein the extract further comprises CRALBP, wherein the compound is stable in solution for at least about 1 week at room temperature. In a specific embodiment, the compound inhibits 11-cis-retinol production with an IC50 of about 100 nM or less when assayed in vitro, utilizing extract of cells that express RPE65 and LRAT, wherein the extract further comprises CRALBP, wherein the compound is stable in solution for at least about 1 week at room temperature. In a further embodiment, the compound inhibits 11-cis-retinol production with an IC50 of about 10 nM or less when assayed in vitro, utilizing extract of cells that express RPE65 and LRAT, wherein the extract further comprises CRALBP, wherein the compound is stable in solution for at least about 1 week at room temperature.

In an additional embodiment is a non-retinoid compound that inhibits an isomerase reaction resulting in production of 11-cis retinol, wherein said isomerase reaction occurs in RPE, and wherein said compound has an ED50 value of 1 mg/kg or less when administered to a subject. In a further embodiment is a non-retinoid compound of wherein the ED50 value is measured after administering a single dose of the compound to said subject for about 2 hours or longer. In an additional embodiment the compound is a styrenyl compound. In a further embodiment the compound is a non-retinoid compound.

In a further embodiment is a pharmaceutical composition comprising a pharmaceutically acceptable carrier and a compound that inhibits 11-cis-retinol production with an IC50 of about 1 uM or less when assayed in vitro, utilizing extract of cells that express RPE65 and LRAT, wherein the extract further comprises CRALBP, wherein the compound is stable in solution for at least about 1 week at room temperature. In an additional embodiment is a pharmaceutical composition comprising a pharmaceutically acceptable carrier and a non-retinoid compound that inhibits an isomerase reaction resulting in production of 11-cis retinol, wherein said isomerase reaction occurs in RPE, and wherein said compound has an ED50 value of 1 mg/kg or less when administered to a subject.

In another embodiment, the present invention provides a method of modulating chromophore flux in a retinoid cycle comprising introducing into a subject a compound disclosed herein, including a compound of any one of Formula (A)-(K). In a further embodiment the method results in a reduction of lipofuscin pigment accumulated in an eye of the subject. In yet another embodiment the lipofuscin pigment is N-retinylidene-N-retinyl-ethanolamine (A2E).

In yet another embodiment is a method for treating an ophthalmic disease or disorder in a subject, comprising administering to the subject compounds or the pharmaceutical composition described herein. In a further embodiment, the ophthalmic disease or disorder is age-related macular degeneration or Stargardt's macular dystrophy. In yet another embodiment the method results in a reduction of lipofuscin pigment accumulated in an eye of the subject. In yet another embodiment the lipofuscin pigment is N-retinylidene-N-retinyl-ethanolamine (A2E).

In additional embodiments, the ophthalmic disease or disorder is selected from retinal detachment, hemorrhagic retinopathy, retinitis pigmentosa, cone-rod dystrophy, Sorsby's fundus dystrophy, optic neuropathy, inflammatory retinal disease, diabetic retinopathy, diabetic maculopathy, retinal blood vessel occlusion, retinopathy of prematurity, or ischemia reperfusion related retinal injury, proliferative vitreoretinopathy, retinal dystrophy, hereditary optic neuropathy, Sorsby's fundus dystrophy, uveitis, a retinal injury, a retinal disorder associated with Alzheimer's disease, a retinal disorder associated with multiple sclerosis, a retinal disorder associated with Parkinson's, disease, a retinal disorder associated with viral infection, a retinal disorder related to light overexposure, myopia, and a retinal disorder associated with AIDS.

In a further embodiment is a method of inhibiting dark adaptation of a rod photoreceptor cell of the retina comprising contacting the retina with a compound disclosed herein, including a compound of any one of Formula (A)-(K).

In an additional embodiment is a method of inhibiting regeneration of rhodopsin in a rod photoreceptor cell of the retina comprising contacting the retina with the compound of Formula (A), a compound that inhibits 11-cis-retinol production with an IC50 of about 1 uM or less when assayed in vitro, utilizing extract of cells that express RPE65 and LRAT, wherein the extract further comprises CRALBP, wherein the compound is stable in solution for at least about 1 week at room temperature, or a A non-retinoid compound that inhibits an isomerase reaction resulting in production of 11-cis retinol, wherein said isomerase reaction occurs in RPE, and wherein said compound has an ED50 value of 1 mg/kg or less when administered to a subject.

In a further embodiment is a method of reducing ischemia in an eye of a subject comprising administering to the subject the pharmaceutical composition of the compound of Formula (A), a compound that inhibits 11-cis-retinol production with an IC50 of about 1 uM or less when assayed in vitro, utilizing extract of cells that express RPE65 and LRAT, wherein the extract further comprises CRALBP, wherein the compound is stable in solution for at least about 1 week at room temperature, or a A non-retinoid compound that inhibits an isomerase reaction resulting in production of 11-cis retinol, wherein said isomerase reaction occurs in RPE, and wherein said compound has an ED50 value of 1 mg/kg or less when administered to a subject. In a further embodiment, the pharmaceutical composition is administered under conditions and at a time sufficient to inhibit dark adaptation of a rod photoreceptor cell, thereby reducing ischemia in the eye.

In a further embodiment is a method of inhibiting neovascularization in the retina of an eye of a subject comprising administering to the subject the pharmaceutical composition of a compound of Formula (A). In a specific embodiment, the pharmaceutical composition is administered under conditions and at a time sufficient to inhibit dark adaptation of a rod photoreceptor cell, thereby inhibiting neovascularization in the retina.

In a further embodiment is a method of inhibiting degeneration of a retinal cell in a retina comprising contacting the retina with the compound of the compound of Formula (A), a compound that inhibits 11-cis-retinol production with an IC50 of about 1 uM or less when assayed in vitro, utilizing extract of cells that express RPE65 and LRAT, wherein the extract further comprises CRALBP, wherein the compound is stable in solution for at least about 1 week at room temperature, or a a non-retinoid compound that inhibits an isomerase reaction resulting in production of 11-cis retinol, wherein said isomerase reaction occurs in RPE, and wherein said compound has an ED50 value of 1 mg/kg or less when administered to a subject. In a further embodiment, the pharmaceutical composition is administered under conditions and at a time sufficient to inhibit dark adaptation of a rod photoreceptor cell, thereby reducing ischemia in the eye. In a specific embodiment is the method wherein the retinal cell is a retinal neuronal cell. In a certain embodiment, the retinal neuronal cell is a photoreceptor cell.

Accordingly, in one embodiment, a compound is provided that has a structure of Formula (I):

Formula (I)

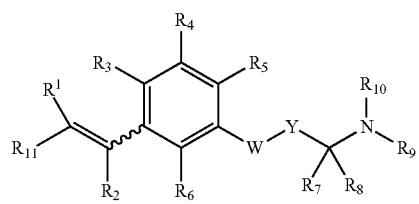

as an isolated E or Z stereoisomer or a mixture of E and Z stereoisomers, as a tautomer or a mixture of tautomers, or as a pharmaceutically acceptable salt, hydrate, solvate, N-oxide or prodrug thereof, wherein:

$R_1$ and $R_2$ are each the same or different and independently hydrogen or alkyl;

$R_3$, $R_4$, $R_5$ and $R_6$ are each the same or different and independently hydrogen, halogen, —$OR_{12}$, alkyl or fluoroalkyl;

$R_7$ and $R_8$ are each the same or different and independently hydrogen or alkyl;

$R_9$ is hydrogen, alkyl, carbocyclyl or —C(=O)$R_{13}$;

$R_{10}$ is hydrogen or alkyl; or $R_9$ and $R_{10}$, together with the nitrogen atom to which they are attached, form an N-heterocyclyl;

$R_{11}$ is alkyl, alkenyl, aryl, carbocyclyl, heteroaryl or heterocyclyl;

$R_{12}$ is hydrogen or alkyl;

$R_{13}$ is alkyl, carbocyclyl or aryl;

W is —C($R_{14}$)($R_{15}$)—, —O—, —S—, —S(=O)—, —S(=O)$_2$— or —N($R_{12}$)—;

Y is —C($R_{16}$)($R_{17}$)—;

$R_{14}$ and $R_{15}$ are each the same or different and independently hydrogen, halogen, alkyl, fluoroalkyl, —$OR_{12}$, —$NR_{18}R_{19}$ or carbocyclyl; or $R_{14}$ and $R_{15}$ form an oxo;

$R_{16}$ and $R_{17}$ are each the same or different and independently hydrogen, halogen, alkyl, fluoroalkyl, —$OR_{12}$, —$NR_{18}R_{19}$ or carbocyclyl; or $R_{16}$ and $R_{17}$ form an oxo; or $R_{14}$ and $R_{16}$ together form a direct bond to provide a double bond connecting W and Y; or $R_{14}$ and $R_{16}$ together form a direct bond, and $R_{15}$ and $R_{17}$ together form a direct bond to provide a triple bond connecting W and Y;

$R_{18}$ and $R_{19}$ are each the same or different and independently hydrogen, alkyl, carbocyclyl, or —C(=O)$R_{13}$, provided that when $R_{11}$ is phenyl, the compound of Formula (I) is not:

2-amino-N-[2-methoxy-5-[(1Z)-2-(3,4,5-trimethoxyphenyl)ethenyl]phenyl]acetamide;

(2S,3R)-amino-3-hydroxy-N-[2-methoxy-5-[(1Z)-2-(3,4,5-trimethoxyphenyl)-ethenyl]phenyl]-butanamide;

L-glutamic acid, 1-[2-methoxy-5-[(1Z)-2-(3,4,5-trimethoxyphenyl)ethenyl]phenyl]ester;

glycine, 3-hydroxy-5-[(1E)-2-(4-hydroxyphenyl)ethenyl]phenyl ester;

(2S)-2-amino-N-[2-methoxy-5-[(1Z)-2-(3,4,5-trimethoxyphenyl)ethenyl]phenyl]propanamide;

(2S)-2-amino-3-hydroxy-N-[2-methoxy-5-[(1Z)-2-(3,4,5-trimethoxyphenyl)ethenyl]phenyl]propanamide;

(2S)-2-amino-N-[2-methoxy-5-[(1Z)-2-(3,4,5-trimethoxyphenyl)ethenyl]phenyl]-4-methyl-pentanamide;

(2S)-2-amino-N-[2-methoxy-5-[(1Z)-2-(3,4,5-trimethoxyphenyl)ethenyl]phenyl]-3-methyl-butanamide; or 2-amino-N-[2-methoxy-5-[(1Z)-2-(3,4,5-trimethoxyphenyl)ethenyl]phenylbutanamide.

Also provided are compounds having structures of Formulae (II), (IIa), (IIb), (III) and (IIIc):

Formula (II)

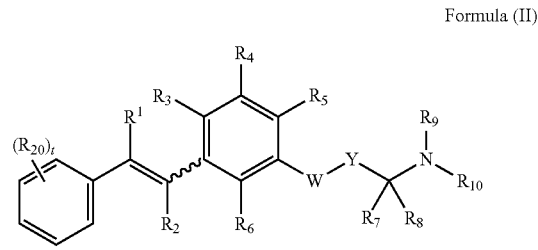

Formula (IIa)

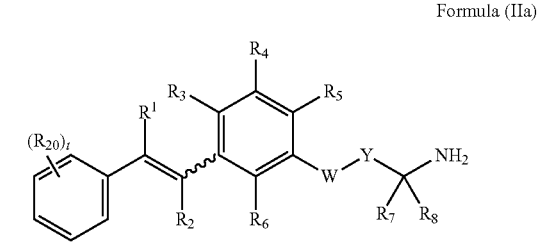

Formula (IIb)

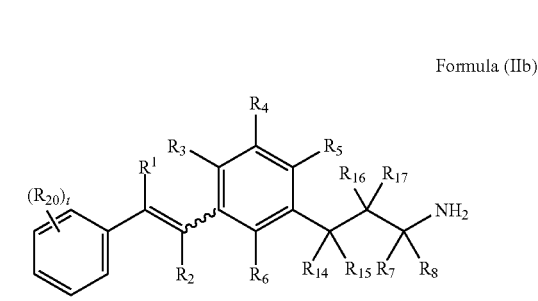

Formula (III)

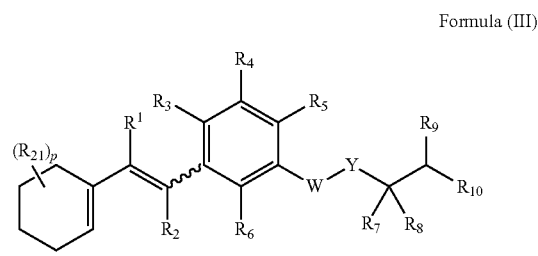

Formula (IIIa)

wherein, t, p, $R_1$, $R_2$, $R_3$, $R_4$, $R_5$, $R_6$, $R_7$, $R_8$, $R_9$, $R_{10}$, $R_{14}$, $R_{15}$, $R_{16}$, $R_{17}$, $R_{20}$, $R_{21}$, W and Y are as defined above and herein.

Another embodiment provides a pharmaceutical composition comprising a pharmaceutically acceptable carrier and a compound having a structure of Formula (I):

Formula (I)

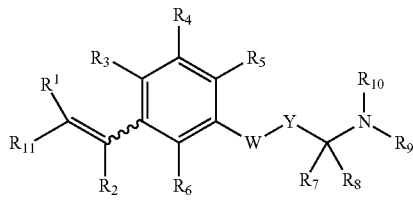

as an isolated E or Z stereoisomer or a mixture of E and Z stereoisomers, as a tautomer or a mixture of tautomers, or as a pharmaceutically acceptable salt, hydrate, solvate, N-oxide or prodrug thereof, wherein, $R_1$, $R_2$, $R_3$, $R_4$, $R_5$, $R_6$, $R_7$, $R_8$, $R_9$, $R_{10}$, $R_{11}$, W and Y are as defined herein.

Also provided are pharmaceutical compositions comprising a compound having a structure of any of Formulae (II), (IIa), (IIb), (III) and (IIIa):

Formula (II)

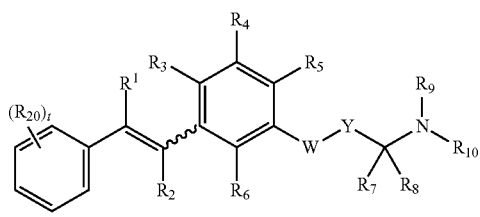

Formula (IIa)

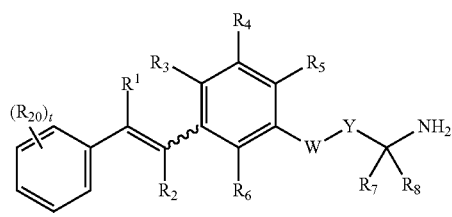

Formula (IIb)

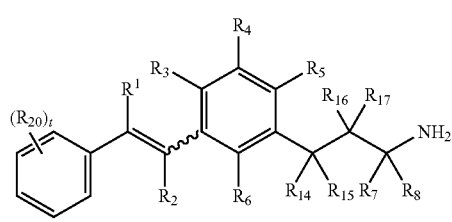

Formula (III)

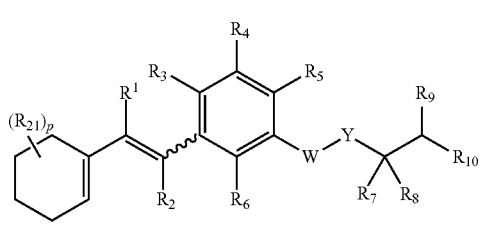

Formula (IIIa)

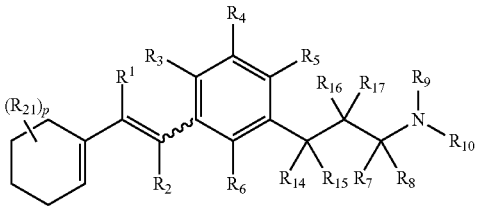

wherein, t, p, $R_1$, $R_2$, $R_3$, $R_4$, $R_5$, $R_6$, $R_7$, $R_8$, $R_9$, $R_{10}$, $R_{14}$, $R_{15}$, $R_{16}$, $R_{17}$, $R_{20}$, $R_{21}$, W and Y are as defined above and herein.

Also provided is a method for treating an ophthalmic disease or disorder in a subject comprising administering to the subject the pharmaceutical composition comprising a pharmaceutically acceptable carrier and a compound having a structure of any of Formulae (I), (II), (IIa), (IIb), (III) and (IIIa). In certain embodiments, the ophthalmic disease or disorder is macular degeneration (i.e., age-related macular degeneration) or Stargardt's disease. In other certain embodiments, the ophthalmic disease or disorder is retinal detachment, hemorrhagic retinopathy, retinitis pigmentosa, optic neuropathy, inflammatory retinal disease, proliferative vitreoretinopathy, retinal dystrophy, hereditary optic neuropathy, Sorsby's fundus dystrophy, uveitis, a retinal injury, a retinal disorder associated with Alzheimer's disease, a retinal disorder associated with multiple sclerosis, a retinal disorder associated with Parkinson's disease, a retinal disorder associated with viral infection, a retinal disorder related to light overexposure, and a retinal disorder associated with AIDS.

Also provided is a method of inhibiting at least one visual cycle trans-cis isomerase (also including trans-cis isomerohydrolase) in a subject comprising administering to the subject a pharmaceutical composition comprising a pharmaceutically acceptable carrier and a compound having a structure of any of Formulae (I), (II), (IIa), (IIb), (III) and (IIIa).

In certain particular embodiments of the aforementioned methods, the subject is human. In other particular embodiments, accumulation of lipofuscin pigment is inhibited in an eye of the subject, wherein in certain embodiments the lipofuscin pigment is N-retinylidene-N-retinyl-ethanolamine (A2E). In another embodiment, degeneration of a retinal cell is inhibited. In particular embodiments, the retinal cell is a retinal neuronal cell, and other particular embodiments, the retinal neuronal cell is any one of an amacrine cell, a photoreceptor cell, a horizontal cell, a ganglion cell, or a bipolar cell.

Also provided is a method of inhibiting at least one visual cycle trans-cis isomerase (also including trans-cis isomerohydrolase) in a cell comprising contacting the cell with a compound having a structure of any of Formulae (I), (II), (IIa), (IIb), (III) and (IIIa), thereby inhibiting the at least one visual cycle trans-cis isomerase. In another embodiment, degeneration of a retinal cell is inhibited. In particular embodiments, the retinal cell is a retinal neuronal cell, and other particular embodiments, the retinal neuronal cell is any one of an amacrine cell, a photoreceptor cell, a horizontal cell, a ganglion cell, or a bipolar cell.

In another embodiment, a method is provided for treating an ophthalmic disease or disorder in a subject, comprising administering to the subject the pharmaceutical composition described above and herein comprising at least one of the compounds having a structure of any of Formulae (I), (II), (IIa), (IIb), (III) and (IIIa), wherein the ophthalmic disease or disorder is selected from diabetic retinopathy, diabetic maculopathy, retinal blood vessel occlusion, retinopathy of prematurity, or ischemia reperfusion related retinal injury.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Figure 1:
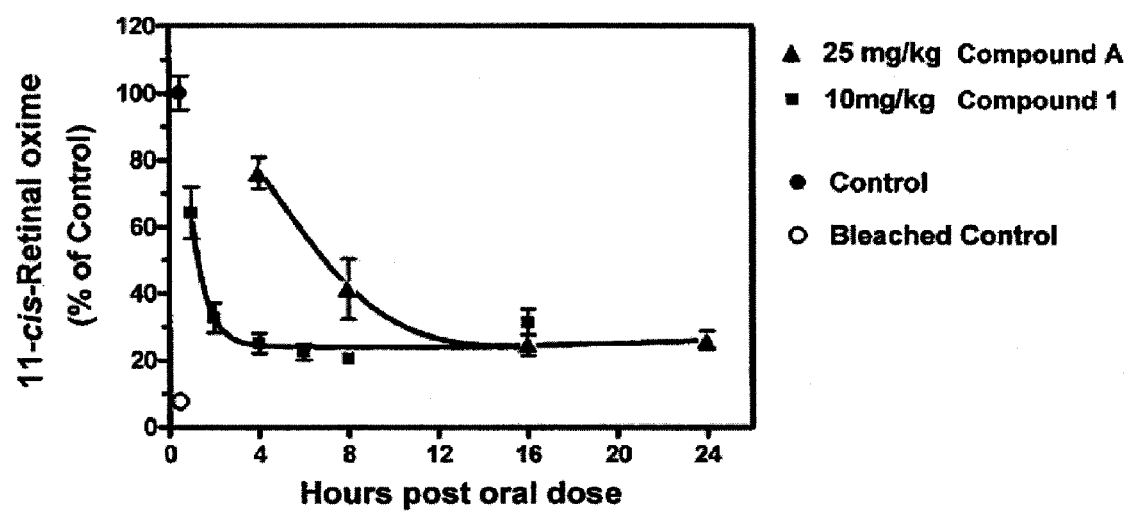
FIG. 1 presents inhibition of isomerase activity by Compound A and Compound 1 over time in an in vivo mouse model. Five animals were included in each treatment group. The error bars correspond to standard error.

Styrenyl derivative compounds are described herein that inhibit an isomerization step of the retinoid cycle. These compounds and compositions comprising these compounds may be useful for inhibiting degeneration of retinal cells or for enhancing retinal cell survival. The compounds described herein may, therefore, be useful for treating ophthalmic diseases and disorders, such as age-related macular degeneration and Stargardt's disease.

Styrenyl Derivative Compounds

In certain embodiments, styrenyl (i.e., vinyl benzene) derivative compounds comprising a meta-substituted linkage terminating in a nitrogen-containing moiety are provided. The nitrogen-containing moiety can be, for example, an amine, an amide or an N-heterocyclyl. The linking atoms form a combination of linearly constructed stable chemical bonds, including single, double or triple carbon-carbon bonds, carbon-nitrogen bonds, nitrogen-nitrogen bonds, carbon-oxygen bonds, carbon-sulfur bonds, and the like.

In one embodiment is a compound having a structure of Formula (A):

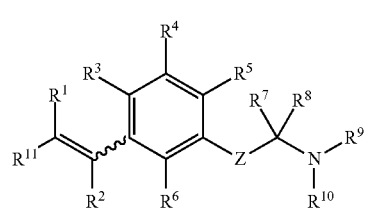

Formula (A)

as an isolated E or Z geometric isomer or a mixture of E and Z geometric isomers, as a tautomer or a mixture of tautomers, as a stereoisomer or as a pharmaceutically acceptable salt, hydrate, solvate, N-oxide or prodrug thereof, wherein: R1 and R2 are each the same or different and independently hydrogen or alkyl; R3, R4, R5 and R6 are each the same or different and independently hydrogen, halogen, nitro, —NH2, —NHR13, —N(R13)2, —OR12, alkyl or fluoroalkyl;

R7 and R8 are each the same or different and independently hydrogen or alkyl; or R7 and R8 together with the carbon atom to which they are attached, form a carbocyclyl or heterocyclyl; or R7 and R8 together form an imino;

R9 is hydrogen, alkyl, carbocyclyl, heterocyclyl, —C(=O)R13, —SO2R13, —CO2R13, —CONH2, —CON(R13)2 or —CON(H)R13;

R10 is hydrogen or alkyl; or R9 and R10, together with the nitrogen atom to which they are attached, form an N-heterocyclyl;

R11 is alkyl, alkenyl, aryl, carbocyclyl, heteroaryl or heterocyclyl; each R12 is independently selected from hydrogen or alkyl; each R13 is independently selected from alkyl, carbocyclyl, heterocyclyl, aryl or heteroaryl;

Z is a bond, Y or W—Y, wherein W is —C(R14)(R15)-, —O—, —S—, —S(=O)—, —S(=O)2- or —N(R12)-; Y is —C(R16)(R17)- or —C(R16)(R17)-C(R21)(R22)-; R14 and R15 are each the same or different and independently hydrogen, halogen, alkyl, fluoroalkyl, —OR12, —NR18R19, carbocyclyl or heterocyclyl; or R14 and R15 together form an oxo, an imino, an oximo, or a hydrazino; R16 and R17 are each the same or different and independently hydrogen, halogen, alkyl, fluoroalkyl, —OR12, —NR18R19, carbocyclyl or heterocyclyl; or R16 and R17 together form an oxo; or optionally, R14 and R16 together form a direct bond to provide a double bond connecting W and Y; or optionally, R14 and R16 together form a direct bond, and R15 and R17 together form a direct bond to provide a triple bond connecting W and Y;

each R18 and R19 is independently selected from hydrogen, alkyl, carbocyclyl, or —C(=O)R13, —SO2R13, —CO2R13, —CONH2, —CON(R13)2 or —CON(H)R13; or R18 and R19, together with the nitrogen atom to which they are attached, form an N-heterocyclyl; R21 and R22 are each the same or different and independently hydrogen, halogen, alkyl, fluoroalkyl, —OR12, —NR18R19, carbocyclyl or heterocyclyl;

provided that when R11 is phenyl, the compound of Formula (A) is not:

2-amino-N-[2-methoxy-5-[(1Z)-2-(3,4,5-trimethoxyphenyl)ethenyl]phenyl]acetamide;

(2S,3R)-amino-3-hydroxy-N-[2-methoxy-5-[(1Z)-2-(3,4,5-trimethoxyphenyl)-ethenyl]phenyl]-butanamide;

L-glutamic acid, 1-[2-methoxy-5-[(1Z)-2-(3,4,5-trimethoxyphenyl)ethenyl]phenyl]ester;

glycine, 3-hydroxy-5-[(1E)-2-(4-hydroxyphenyl)ethenyl]phenyl ester;

(2S)-2-amino-N-[2-methoxy-5-[(1Z)-2-(3,4,5-trimethoxyphenyl)ethenyl]phenyl]propanamide;

(2S)-2-amino-3-hydroxy-N-[2-methoxy-5-[(1Z)-2-(3,4,5-trimethoxyphenyl)ethenyl]phenyl]propanamide;

(2S)-2-amino-N-[2-methoxy-5-[(1Z)-2-(3,4,5-trimethoxyphenyl)ethenyl]phenyl]-4-methyl-pentanamide;

(2S)-2-amino-N-[2-methoxy-5-[(1Z)-2-(3,4,5-trimethoxyphenyl)ethenyl]phenyl]-3-methyl-butanamide; or 2-amino-N-[2-methoxy-5-[(1Z)-2-(3,4,5-trimethoxyphenyl)ethenyl]phenylbutanamide.

In another embodiment is the compound wherein each of R1 and R8 is hydrogen, and the compound has a structure of Formula (B):

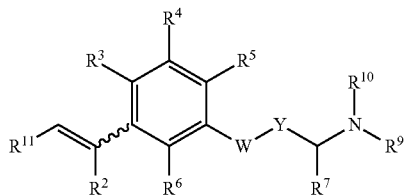

Formula (B)

wherein
R2 is H or C1-C6 alkyl;
each of R3, R4, R5, and R6 is the same or different and independently hydrogen, halo, C1-C6 alkyl, or —OR12;
R7 is H or C1-C6 alkyl;
R9 is hydrogen, C1-C6 alkyl, —(CH2)nOH wherein n is 2-6, or —C(=O)R13;
R10 is hydrogen or C1-C6 alkyl; or R9 and R10, together with the nitrogen atom to which they are attached, form an N-heterocyclyl;
W is —C(R14)(R15)-, —O—, —S—, —S(=O)—, —S(=O)2- or —N(H)—;
Y is —C(R16)(R17)-; each R12 is independently hydrogen or C1-C6 alkyl;
each R13 is independently a C1-C6 alkyl; R14 and R15 are each the same or different and independently selected from hydrogen, halogen, C1-C6 alkyl, fluoroalkyl, —OR12, or —NH2; or R14 and R15 together form an oxo, an imino, an oximo, or a hydrazino; R16 and R17 are each the same or different and independently hydrogen, halogen, C1-C6 alkyl, or —OR12; or
R16 and R17 together form an oxo; or optionally, R14 and R16 together form a direct bond to provide a double bond connecting W and Y; or optionally, R14 and R16 together form a direct bond, and R15 and R17 together form a direct bond to provide a triple bond connecting W and Y; and R11 is selected from:
a) alkyl;
b) phenyl substituted with alkyl, —OR12, —O(CH2)mOCH3 wherein m is 1-6, alkenyl, alkynyl, halogen, fluoroalkyl, phenyl, —SCH3, or aralkyl;
c) naphthenyl optionally substituted with alkyl, halogen, or —OR12;
d) carbocyclyl; or
e) cyclohexenyl optionally substituted with alkyl,
provided that R11 is not 3,4,5-tri-methoxyphenyl.

In a further embodiment is the compound of Formula (A) or (B) wherein R2 is hydrogen or n-butyl. In an additional embodiment is the compound of Formula (A) or (B) wherein halogen is fluoro or chloro.

In yet another embodiment is the compound of either Formula (A) or (B) wherein each of R3, R4, R5, and R6 is the same or different and independently hydrogen, halogen, methyl, or methoxy.

In an additional embodiment is the compound of Formula (A) or (B), wherein at least two of R3, R4, R5, and R6 are hydrogen.

In a further embodiment is the compound of Formula (A) or (B), wherein W is —C(R14)(R15)-, and wherein R14 and R15 are each the same or different and independently hydrogen, fluoro, methyl, ethyl, trifluoromethyl, —OH, —OCH3, or —NH2.

In another embodiment is the compound of Formula (A) or (B), wherein each of R14 and R15 is hydrogen.

In an additional embodiment is the compound of Formula (A) or (B), wherein Y is CH2-, —CH(CH3)-, —C(CH3)2-, —C(H)OH—, —C(H)F—, —CF2-, or C(=O)—.

In yet another embodiment is the compound of Formula (A) or (B), wherein R11 is phenyl substituted with alkyl, —OR12, —O(CH2)nOCH3 wherein n is 2-6, alkenyl, alkynyl, halogen, fluoroalkyl, phenyl, or —SCH3.

In one embodiment is the compound of Formula (A) or (B), wherein R11 is naphthenyl substituted with —OR12, wherein R12 is hydrogen or C1-C6 alkyl.

In an additional embodiment is the compound of Formula (A) or (B), wherein R11 is cyclohexenyl optionally substituted with C1-C6 alkyl. In some embodiments R11 is tri-methyl-cyclohexenyl.

In additional embodiments is the compound of Formula (A) or (B), wherein R11 is alkyl optionally substituted with —OR12 wherein R12 is hydrogen or C1-C6 alkyl.

In an additional embodiment is the compound of Formula (A), wherein R11 is aryl or carbocyclyl.

In an alternative embodiment is the compound of Formula (C), wherein R11 is aryl:

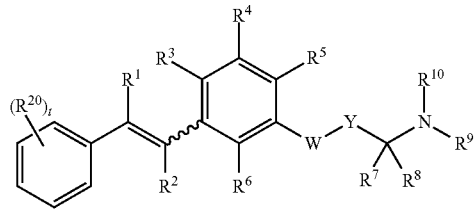

Formula (C) as an isolated E or Z geometric isomer or a mixture of E and Z geometric isomers, as a tautomer or a mixture of tautomers, as a stereoisomer, or as a pharmaceutically acceptable salt, hydrate, solvate, N-oxide or prodrug thereof, wherein:
R1 and R2 are each the same or different and independently hydrogen or alkyl;
R3, R4, R5 and R6 are each the same or different and independently hydrogen, halogen, nitro, —NH2, —NHR13, —N(R13)2, —OR12, alkyl or fluoroalkyl;
R7 and R8 are each the same or different and independently hydrogen or alkyl;
R9 is hydrogen, alkyl, carbocyclyl or —C(=O)R13;
R10 is hydrogen or alkyl; or R9 and R10, together with the nitrogen atom to which they are attached, form an N-heterocyclyl; each R12 is independently selected from hydrogen or alkyl;
R13 is alkyl, carbocyclyl or aryl;
W is —C(R14)(R15)-, —O—, —S—, —S(=O)—, —S(=O)2- or —N(R12)-;
Y is —C(R16)(R17)-;
R14 and R15 are each the same or different and independently hydrogen, halogen, alkyl, fluoroalkyl, —OR12, —NR18R19 or carbocyclyl; or R14 and R15 together form an oxo, an imino, an oximo, or a hydrazino;
R16 and R17 are each the same or different and independently hydrogen, halogen, alkyl, fluoroalkyl, —OR12, —NR18R19 or carbocyclyl; or R16 and R17 together form an oxo;
optionally, R14 and R16 together form a direct bond to provide a double bond connecting W and Y; or
optionally, R14 and R16 together form a direct bond, and R15 and R17 together form a direct bond to provide a triple bond connecting W and Y;

each R18 and R19 is independently selected from hydrogen, alkyl, carbocyclyl, or —C(═O)R13;
t is 0, 1, 2, 3, 4 or 5; and
each R20 is the same or different and independently selected from alkyl, —OR12, —SR12, alkenyl, alkynyl, halo, fluoroalkyl, aryl or aralkyl; or two adjacent R20 groups, together with the two carbon atoms to which they are attached, form a fused phenyl ring.

In an additional embodiment is the compound wherein each of R9 and R10 is hydrogen and the compound has a structure of Formula (D):

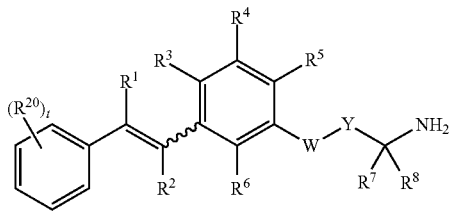

Formula (D)

In a further embodiment is the compound of Formula (E) wherein W is —C(R14)(R15)-:

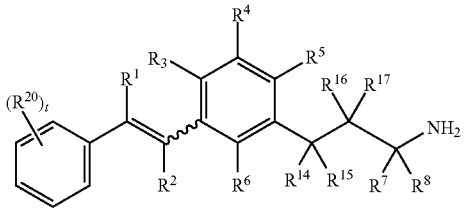

Formula (E)

as an isolated E or Z geometric isomer or a mixture of E and Z geometric isomers, as a tautomer or a mixture of tautomers, as a stereoisomer, or as a pharmaceutically acceptable salt, hydrate, solvate, N-oxide or prodrug thereof, wherein:
R1 and R2 are each the same or different and independently hydrogen or alkyl;
R3, R4, R5 and R6 are each the same or different and independently hydrogen, halogen, nitro, —NH2, —NHR13, —N(R13)2, —OR12, alkyl or fluoroalkyl;
R7 and R8 are each the same or different and independently hydrogen or alkyl;
each R12 is independently selected from hydrogen or alkyl;
R13 is alkyl, carbocyclyl or aryl;
R14 and R15 are each the same or different and independently hydrogen, halogen, alkyl, fluoroalkyl, —OR12, —NR18R19 or carbocyclyl; or R14 and R15 form an oxo, an imino, an oximo, or a hydrazino;
R16 and R17 are each the same or different and independently hydrogen, halogen, alkyl, fluoroalkyl, —OR12, —NR18R19 or carbocyclyl; or R16 and R17 form an oxo;
each R18 and R19 are each the same or different and independently hydrogen, alkyl, carbocyclyl, or —C(═O)R13;
t is 0, 1, 2, 3, 4 or 5; and
each R20 is the same or different and independently alkyl, —OR12, —SR12, alkenyl, alkynyl, halo, fluoroalkyl, aryl or aralkyl, or two adjacent R20, together with the two carbon atoms to which they are attached, form a fused phenyl ring.

In a additional embodiment is the compound of Formula (E) wherein t is 0, 1, 2 or 3;
each R20 is independently alkyl, —OR12, —SR12, alkynyl, phenyl, halo or fluoroalkyl; and
R3, R4, R5 and R6 are each independently hydrogen, alkyl, —OR12, halo or fluoroalkyl.

In a further embodiment is the compound of Formula (E), wherein R7, R8, R14, R15, R16 and R17 are each independently hydrogen, halogen, alkyl or —OR12, wherein each R12 is independently selected from hydrogen or alkyl.

In an additional embodiment is the compound of Formula (E), wherein:
t is 2 or 3; two adjacent R20, together with the two carbon atoms to which they are attached, form a fused phenyl ring; and
R3, R4, R5 and R6 are each independently hydrogen, alkyl, halo or fluoroalkyl.

In another embodiment is the compound of Formula (E), wherein R7, R8, R14, R15, R16 and R17 are each independently hydrogen, halogen, alkyl or —OR12.

In an additional embodiment is the compound of Formula (E), wherein W is —O—, —S—, —S(═O)—, —S(═O)2- or —N(R12)-.

In yet another embodiment is the compound of Formula (E), wherein:
t is 0, 1, 2 or 3;
each R20 is independently alkyl, —OR12 or halo; and
R3, R4, R5 and R6 are each independently hydrogen, alkyl or halo.

In a specific embodiment is the compound of Formula (E) wherein W and Y are connected by a double bond.

In an additional embodiment is the compound of Formula (E), wherein R9 and R10 together with the nitrogen to which they are attached form a N-heterocyclyl.

In an additional embodiment is the compound of Formula (E), wherein the N-heterocyclyl is morpholinyl, pyrrolidinyl, piperidinyl or piperazinyl.

In an additional embodiment is the compound of Formula (E), wherein:
each of R1 and R2 is hydrogen;
t is 0, 1, 2 or 3;
each R20 is independently alkyl or halo; and
R3, R4, R5 and R6 are each independently hydrogen, alkyl or halo.

In another embodiment is the compound of Formula (E), wherein W is —C(R14)(R15)-.

In an additional embodiment is the compound of Formula (E), wherein R9 is alkyl or —C(═O)R13, wherein R13 is alkyl, and R10 is hydrogen or alkyl.

In an additional embodiment is the compound of Formula (E), wherein:
each of R1 and R2 is hydrogen;
t is 0, 1, 2 or 3;
each R20 is independently alkyl or halo; and
R3, R4, R5 and R6 are each independently hydrogen, alkyl or halo.

In an additional embodiment is the compound of Formula (E), wherein W is —C(R14)(R15)-.

In an additional embodiment is the compound of Formula (A), wherein R11 is 3-, 4-, 5-, 6-, 7- or 8-member cycloalkyl. In some embodiments R11 is cyclohexyl.

In an additional embodiment is the compound of Formula (A), wherein R11 is 5-, 6-, or 7-member cycloalkenyl.

In an additional embodiment is the compound of Formula (F), wherein R11 is cyclohexenyl:

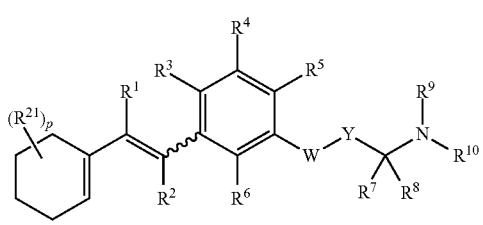

Formula (F)

as an isolated E or Z geometric isomer or a mixture of E and Z geometric isomers, as a tautomer or a mixture of tautomers, as a stereoisomer, or as a pharmaceutically acceptable salt, hydrate, solvate, N-oxide or prodrug thereof, wherein:
R1 and R2 are each the same or different and independently hydrogen or alkyl;
R3, R4, R5 and R6 are each the same or different and independently hydrogen, halogen, nitro, —NH2, —NHR13, —N(R13)2, —OR12, alkyl or fluoroalkyl;
R7 and R8 are each the same or different and independently hydrogen or alkyl;
R9 is hydrogen, alkyl, carbocyclyl or —C(=O)R13;
R10 is hydrogen or alkyl; or R9 and R10, together with the nitrogen atom to which they are attached, form an N-heterocyclyl;
each R12 is independently selected from hydrogen or alkyl;
each R13 is independently selected from alkyl, carbocyclyl or aryl;
W is —C(R14)(R15)-, —O—, —S—, —S(=O)—, —S(=O)2- or —N(R12)-;
Y is —C(R16)(R17)-;
R14 and R15 are each the same or different and independently hydrogen, halogen, alkyl, fluoroalkyl, —OR12, —NR18R19 or carbocyclyl; or R14 and R15 together form an oxo, an imino, an oximo, or a hydrazino;
R16 and R17 are each the same or different and independently hydrogen, halogen, alkyl, fluoroalkyl, —OR12, —NR18R19 or carbocyclyl; or R16 and R17 together form an oxo;
optionally, R14 and R16 together form a direct bond to provide a double bond connecting W and Y; or R14 and R16 together form a direct bond, and R15 and R17 together form a direct bond to provide a triple bond connecting W and Y;
each R18 and R19 is independently selected from hydrogen, alkyl, carbocyclyl, or —C(=O)R13;
p is 0, 1, 2, 3, 4, 5, 7, 8 or 9; and
each R21 is the same or different and independently selected from alkyl, —OR12, alkenyl, alkynyl, halo, fluoroalkyl or aralkyl.

In an additional embodiment is the compound wherein W is —C(R14)(R15)-, and the compound has a structure of Formula (G):

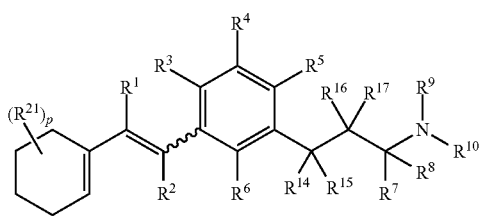

Formula (G)

as an isolated E or Z geometric isomer or a mixture of E and Z geometric isomers, as a tautomer or a mixture of tautomers, as a stereoisomer, or as a pharmaceutically acceptable salt, hydrate, solvate, N-oxide or prodrug thereof, wherein:
R1 and R2 are each the same or different and independently hydrogen or alkyl;
R3, R4, R5 and R6 are each the same or different and independently hydrogen, halogen, nitro, —NH2, —NHR13, —N(R13)2, —OR12, alkyl or fluoroalkyl;
R7 and R8 are each the same or different and independently hydrogen or alkyl;
R9 is hydrogen, alkyl, carbocyclyl or —C(=O)R13;
R10 is hydrogen or alkyl; or R9 and R10, together with the nitrogen atom to which they are attached, form an N-heterocyclyl;
each R12 is independently selected from hydrogen or alkyl;
each R13 is independently alkyl, carbocyclyl or aryl;
R14 and R15 are each the same or different and independently hydrogen, halogen, alkyl, fluoroalkyl, —OR12, —NR18R19 or carbocyclyl; or R14 and R15 together form an oxo, an imino, an oximo, or a hydrazino;
R16 and R17 are each the same or different and independently hydrogen, halogen, alkyl, fluoroalkyl, —OR12, —NR18R19 or carbocyclyl; or R16 and R17 together form an oxo;
optionally, R14 and R16 together form a direct bond to provide a double bond connecting W and Y; or R14 and R16 together form a direct bond, and R15 and R17 together form a direct bond to provide a triple bond connecting W and Y;
each R18 and R19 is independently selected from hydrogen, alkyl, carbocyclyl, or —C(=O)R13;
p is 0, 1, 2, 3, 4, 5, 7, 8 or 9; and
each R21 is the same or different and independently alkyl, —OR12, alkenyl, alkynyl, halo, fluoroalkyl or aralkyl.

In an additional embodiment is the compound of Formula (G), wherein each of R9 and R10 is hydrogen.

In an additional embodiment is the compound of Formula (G), wherein:
each of R1 and R2 is hydrogen;
p is 0, 1, 2 or 3;
each R21 is independently alkyl, halo or fluoroalkyl; and
each of R3, R4, R5 and R6 is independently hydrogen, alkyl, halo, fluoroalkyl or —OR12.

In an additional embodiment is the compound of Formula (G) wherein:
R7, R8, R14, R15, R16 and R17 are each independently hydrogen, halogen, alkyl, fluoroalkyl, —OR12 or —NR18R19, wherein each R12 is independently hydrogen or alkyl; and each R18 and R19 are independently hydrogen or alkyl.

In an additional embodiment is the compound of Formula (G), wherein R9 is alkyl and R10 is hydrogen.

In an additional embodiment is the compound of Formula (G), wherein:
each of R1 and R2 is hydrogen;
p is 0, 1, 2 or 3;
each R21 is independently alkyl, halo or fluoroalkyl; and
each of R3, R4, R5 and R6 is independently hydrogen, alkyl, halo, fluoroalkyl or —OR12.

In an additional embodiment is the compound of Formula (G), wherein R7, R8, R14, R15, R16 and R17 are each independently hydrogen, halogen, alkyl, fluoroalkyl or —OR12, wherein each R12 is independently hydrogen or alkyl.

In an additional embodiment is the compound of Formula (G), wherein:
R7, R8, R16 and R17 are each independently hydrogen, halogen, alkyl, fluoroalkyl or —OR12, wherein R12 is hydrogen or alkyl; and
R14 and R15 together form oxo.

In an additional embodiment is the compound of Formula (G), wherein W is —NH— or —O—.

In an additional embodiment is the compound of Formula (G), wherein each of R1, R2, R9 and R10 is hydrogen.

In an additional embodiment is the compound of Formula (G), wherein:
p is 0, 1, 2 or 3;
each R21 is independently alkyl or halo; and
R3, R4, R5 and R6 are each independently hydrogen, alkyl, halo or fluoroalkyl.

In an additional embodiment is the compound of Formula (G), wherein W and Y are connected by a double or triple bond.

In an additional embodiment is the compound of Formula (G), wherein each of R1, R2, R9 and R10 is hydrogen.

In an additional embodiment is the compound of Formula (G), wherein:
p is 0, 1, 2 or 3;
each R21 is independently alkyl or halo;
R3, R4, R5 and R6 are each independently hydrogen, alkyl, halo or fluoroalkyl; and
R15 and R17 are each independently hydrogen, alkyl or halogen.

In an additional embodiment is the compound of Formula (A), wherein R11 is alkyl. In an additional embodiment W is —C(R14)(R15)-. In a further embodiment, R1, R2, R3, R4, R5 and R6 are each independently hydrogen or alkyl.

In an additional embodiment, Z is —C(R16)(R17)- and the compound has the structure of Formula (H):

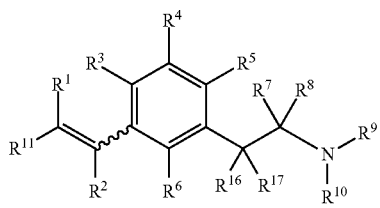

Formula (H)

as an isolated E or Z geometric isomer or a mixture of E and Z geometric isomers, as a tautomer or a mixture of tautomers, as a stereoisomer or as a pharmaceutically acceptable salt, hydrate, solvate, N-oxide or prodrug thereof, wherein:
R1 and R2 are each the same or different and independently hydrogen or alkyl;
R3, R4, R5 and R6 are each the same or different and independently hydrogen, halogen, nitro, —NH2, —NHR13, —N(R13)2, —OR12, alkyl or fluoroalkyl;
R7 and R8 are each the same or different and independently hydrogen or alkyl; or R7 and R8 together with the carbon atom to which they are attached, form a carbocyclyl or heterocyclyl; or R7 and R8 together form an imino;
R9 is hydrogen, alkyl, carbocyclyl, heterocyclyl, —C(=O)R13, —SO2R13, —CO2R13, —CONH2, —CON(R13)2 or —CON(H)R13;
R10 is hydrogen or alkyl; or R9 and R10, together with the nitrogen atom to which they are attached, form an N-heterocyclyl;
R11 is alkyl, alkenyl, aryl, carbocyclyl, heteroaryl or heterocyclyl;
each R12 is independently selected from hydrogen or alkyl;
each R13 is independently selected from alkyl, carbocyclyl, heterocyclyl, aryl or heteroaryl;
R16 and R17 are each the same or different and independently hydrogen, halogen, alkyl, fluoroalkyl, —OR12, —NR18R19, carbocyclyl or heterocyclyl;
each R18 and R19 is independently selected from hydrogen, alkyl, carbocyclyl, or —C(=O)R13, —SO2R13, —CO2R13, —CONH2, —CON(R13)2 or —CON(H)R13; or R18 and R19, together with the nitrogen atom to which they are attached, form an N-heterocyclyl.

In a further embodiment is the compound of Formula (H), wherein
R1, R2, R3, R4, R5 and R6 are all hydrogen;
R11 is aryl or carbocyclyl; and
R16 and R17 are each the same or different and independently hydrogen, halogen, alkyl, fluoroalkyl or —OR12.

In a further embodiment is the compound of Formula (A), wherein Z is a bond and the compound has the structure of Formula (J):

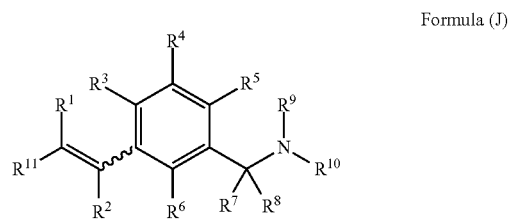

Formula (J)

as an isolated E or Z geometric isomer or a mixture of E and Z geometric isomers, as a tautomer or a mixture of tautomers, as a stereoisomer or as a pharmaceutically acceptable salt, hydrate, solvate, N-oxide or prodrug thereof, wherein:
R1 and R2 are each the same or different and independently hydrogen or alkyl;
R3, R4, R5 and R6 are each the same or different and independently hydrogen, halogen, nitro, —NH2, —NHR13, —N(R13)2, —OR12, alkyl or fluoroalkyl;
R7 and R8 are each the same or different and independently hydrogen or alkyl; or R7 and R8 together with the carbon atom to which they are attached, form a carbocyclyl or heterocyclyl; or R7 and R8 together form an imino;
R9 is hydrogen, alkyl, carbocyclyl, heterocyclyl, —C(=O) R13, —SO2R13, —CO2R13, —CONH2, —CON(R13)2 or —CON(H)R13;
R10 is hydrogen or alkyl; or R9 and R10, together with the nitrogen atom to which they are attached, form an N-heterocyclyl;
R11 is alkyl, alkenyl, aryl, carbocyclyl, heteroaryl or heterocyclyl;
each R12 is independently selected from hydrogen or alkyl; and
each R13 is independently selected from alkyl, carbocyclyl, heterocyclyl, aryl or heteroaryl.

In a further embodiment is the compound of Formula (J), wherein
R1, R2, R3, R4, R5 and R6 are hydrogen; and
R11 is aryl or carbocyclyl.

In a further embodiment is the compound of Formula (A), wherein Z is —C(R14)(R15)-C(R16)(R17)-C(R21)(R22)- and the compound has the structure of Formula (K):

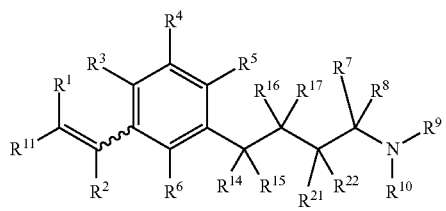

Formula (K)

as an isolated E or Z geometric isomer or a mixture of E and Z geometric isomers, as a tautomer or a mixture of tautomers, as a stereoisomer or as a pharmaceutically acceptable salt, hydrate, solvate, N-oxide or prodrug thereof, wherein:

R1 and R2 are each the same or different and independently hydrogen or alkyl;

R3, R4, R5 and R6 are each the same or different and independently hydrogen, halogen, nitro, —NH2, —NHR13, —N(R13)2, —OR12, alkyl or fluoroalkyl;

R7 and R8 are each the same or different and independently hydrogen or alkyl; or R7 and R8 together with the carbon atom to which they are attached, form a carbocyclyl or heterocyclyl; or R7 and R8 together form an imino;

R9 is hydrogen, alkyl, carbocyclyl, heterocyclyl, —C(=O)R13, —SO2R13, —CO2R13, —CONH2, —CON(R13)2 or CON(H)R13;

R10 is hydrogen or alkyl; or R9 and R10, together with the nitrogen atom to which they are attached, form an N-heterocyclyl;

R11 is alkyl, alkenyl, aryl, carbocyclyl, heteroaryl or heterocyclyl;

each R12 is independently selected from hydrogen or alkyl;

each R13 is independently selected from alkyl, carbocyclyl, heterocyclyl, aryl or heteroaryl;

R14 and R15 are each the same or different and independently hydrogen, halogen, alkyl, fluoroalkyl, —OR12, —NR18R19, carbocyclyl or heterocyclyl; or R14 and R15 together form an oxo, an imino, an oximo, or a hydrazino;

R16 and R17 are each the same or different and independently hydrogen, halogen, alkyl, fluoroalkyl, —OR12, —NR18R19, carbocyclyl or heterocyclyl; or R16 and R17 together form an oxo;

each R18 and R19 is independently selected from hydrogen, alkyl, carbocyclyl, or —C(=O)R13, —SO2R13, —CO2R13, —CONH2, —CON(R13)2 or —CON(H)R13; or R18 and R19, together with the nitrogen atom to which they are attached, form an N-heterocyclyl; and R21 and R22 are each the same or different and independently hydrogen, halogen, alkyl, fluoroalkyl, —OR12, —NR18R19, carbocyclyl or heterocyclyl.

In a further embodiment is the compound of Formula (K), wherein

R1, R2, R3, R4, R5 and R6 are hydrogen;

R11 is aryl or carbocyclyl;

14 and R15 are each the same or different and independently hydrogen, halogen, alkyl, fluoroalkyl or —OR12; and R16, R17, R21 and R22 are each independently hydrogen or alkyl.

In a specific embodiment is the compound selected from:
(E)-3-(3-(2,6-dimethylstyryl)phenyl)propan-1-amine;
(Z)-3-(3-(2,6-dimethylstyryl)phenyl)propan-1-amine;
(E)-3-(3-(2-methylstyryl)phenyl)propan-1-amine;
(Z)-3-(3-(2-methylstyryl)phenyl)propan-1-amine;
(E)-3-(3-(2,6-dimethylstyryl)-2-methylphenyl)propan-1-amine;
(Z)-3-(3-(2,6-dimethylstyryl)-2-methylphenyl)propan-1-amine;
(E/Z)-3-(3-(2-ethyl-6-methylstyryl)phenyl)propan-1-amine;
(E/Z)-3-(3-(2,5-dimethylstyryl)phenyl)propan-1-amine;
(E/Z)-3-(3-(2,4-dimethylstyryl)phenyl)propan-1-amine;
(E)-3-(3-(2,4,6-trimethylstyryl)phenyl)propan-1-amine;
(E/Z)-3-(3-(2-ethylstyryl)phenyl)propan-1-amine;
(E/Z)-3-(3-(2-ethynylstyryl)phenyl)propan-1-amine;
(E/Z)-3-(3-(3,4-dimethylstyryl)phenyl)propan-1-amine;
(E/Z)-3-(3-(2-isopropylstyryl)phenyl)propan-1-amine;
(E/Z)-4-(3-(3,5-dimethylstyryl)phenyl)propan-1-amine;
(E/Z)-4-(3-(2-methoxystyryl)phenyl)propan-1-amine;
(E)-3-(3-(2,6-dichlorostyryl)phenyl)propan-1-amine;
(E/Z)-3-(3-(2,3-dimethylstyryl)phenyl)propan-1-amine;
(E)-3-(3-(2,6-dimethylstyryl)-4-fluorophenyl)propan-1-amine;
(E/Z)-3-(3-(2-(trifluoromethyl)styryl)phenyl)propan-1-amine;
(E)-3-(3-(2,6-dimethoxystyryl)phenyl)propan-1-amine;
(E)-3-(3-(2,6-bis(trifluoromethyl)styryl)phenyl)propan-1-amine;
(E)-3-amino-1-(3-(2,6-dichlorostyryl)phenyl)propan-1-ol;
(E)-3-amino-1-(3-(2-chloro-6-methylstyryl)phenyl)propan-1-ol;
(E)-2-(3-(3-aminopropyl)styryl)phenol;
(E)-3-(5-(2,6-dichlorostyryl)-2-methoxyphenyl)propan-1-amine;
(R,E)-1-amino-3-(3-(2,6-dichlorostyryl)phenyl)propan-2-ol;
(S,E)-1-amino-3-(3-(2,6-dichlorostyryl)phenyl)propan-2-ol;
(E/Z)-(3-(3-(2,6-diethoxystyryl)phenyl)propan-1-amine;
(E)-3-(3-(2-ethoxystyryl)phenyl)propan-1-amine;
(E/Z)-3-(3-(2-isopropoxystyryl)phenyl)propan-1-amine;
(E)-3-amino-1-(3-(2,6-dichlorostyryl)phenyl)propan-1-one;
(E)-1-amino-3-(3-(2,6-dichlorostyryl)phenyl)propan-2-one;
(R,E)-3-amino-1-(3-(2,6-dichlorostyryl)phenyl)propan-1-ol;
(S,E)-3-amino-1-(3-(2,6-dichlorostyryl)phenyl)propan-1-ol;
(S,E)-3-(3-(2,6-dichlorostyryl)phenyl)-2-fluoropropan-1-amine;
(E)-3-(3-(2,6-dichlorostyryl)phenyl)-2,2-difluoropropan-1-amine;
(Z)-3-(3-(2-(2-methoxyethoxy)styryl)phenyl)-propan-1-amine;
(E)-3-(3-(3-methoxystyryl)phenyl)propan-1-amine;
(Z)-3-(3-(4-chlorostyryl)phenyl)propan-1-amine;
(E)-3-(3-(2-(biphenyl-2-yl)vinyl)phenyl)propan-1-amine;
(E)-3-(3-(3-chlorostyryl)phenyl)propan-1-amine;
(E)-3-(3-(2-butoxystyryl)phenyl)propan-1-amine;
(E)-3-(3-(4-methoxystyryl)phenyl)propan-1-amine;
(Z)-3-(3-(2-Propoxystyryl)phenyl)propan-1-amine;
(E)-3-(5-(2-Chloro-6-(methylthio)styryl)-2-methoxyphenyl)propan-1-amine;
(E)-3-(3-(2-(1-methoxynaphthalen-2-yl)vinyl)phenyl)propan-1-amine;
(Z)-3-(3-(2-(naphthalen-1-yl)vinyl)phenyl)propan-1-amine;
(Z)-3-(3-(2-(3-methoxynaphthalen-2-yl)vinyl)phenyl)propan-1-amine;
(E/Z)-3-(3-(2-(2-methoxynaphthalen-1-yl)vinyl)phenyl)propan-1-amine;
(E)-2-amino-N-(3-(2,6-dimethylstyryl)phenyl)acetamide;
(E)-2-(3-(2,6-dimethylstyryl)phenylthio)ethanamine;
(E)-2-(3-(2,6-dimethylstyryl)phenylsulfinyl)ethanamine;
(E)-2-(3-(2,6-dimethylstyryl)phenylsulfonyl)ethanamine;
(E)-3-(3-(2,6-dimethylstyryl)phenyl)prop-2-en-1-amine;
(E)-4-(3-(3-(2,6-dimethylstyryl)phenyl)propyl)morpholine;
(Z)-4-(3-(3-(2,6-dimethylstyryl)phenyl)propyl)morpholine;

(E)-1-(3-(3-(2,6-dimethylstyryl)phenyl)propyl)pyrrolidine;
(Z)-1-(3-(3-(2,6-dimethylstyryl)phenyl)propyl)pyrrolidine;
(E)-1-(3-(3-(2,6-dimethylstyryl)phenyl)propyl)piperidine;
(Z)-1-(3-(3-(2,6-dimethylstyryl)phenyl)propyl)piperidine;
(E)-3-(3-(2,6-dimethylstyryl)phenyl)-N-methylpropan-1-amine;
(Z)-3-(3-(2,6-dimethylstyryl)phenyl)-N-methylpropan-1-amine;
(E)-3-(3-(2,6-dimethylstyryl)phenyl)-N,N-dimethylpropan-1-amine;
(Z)-3-(3-(2,6-dimethylstyryl)phenyl)-N,N-dimethylpropan-1-amine;
(E/Z)—N-(3-(3-(2,6-dimethylstyryl)phenyl)propyl)acetamide;
(E)-1-(3-(3-aminopropyl)styryl)cyclohexanol;
(E)-1-(3-(3-aminopropyl)styryl)cyclopentanol;
(E)-1-(3-(3-aminopropyl)styryl)cycloheptanol;
(E)-3-(3-(2-cyclohexylvinyl)phenyl)propan-1-amine;
(E)-3-(3-(2-cyclopentylvinyl)phenyl)propan-1-amine;
(E)-3-(3-(2-cycloheptylvinyl)phenyl)propan-1-amine;
(E)-3-(3-(2-(2,6,6-trimethylcyclohex-1-enyl)vinyl)phenyl)propan-1-amine;
(E)-3-amino-1-(3-(2-(2,6,6-trimethylcyclohex-1-enyl)vinyl)phenyl)propan-1-ol;
(S,E)-3-amino-1-(3-(2-(2,6,6-trimethylcyclohex-1-enyl)vinyl)phenyl)propan-1-ol;
(R,E)-3-Amino-1-(3-(2-(2,6,6-trimethylcyclohex-1-enyl)vinyl)phenyl)propan-1-ol;
(E)-2-methyl-3-(3-(2-(2,6,6-trimethylcyclohex-1-enyl)vinyl)phenyl)propan-1-amine;
(E)-3-(3-(2-(2,6,6-trimethylcyclohex-1-enyl)vinyl)phenyl)butan-1-amine;
(E)-3-(2-methyl-5-(2-(2,6,6-trimethylcyclohex-1-enyl)vinyl)phenyl)propan-1-amine;
(E/Z)-4-amino-2-(3-(2-(2,6,6-trimethylcyclohex-1-enyl)vinyl)phenyl)butan-2-ol;
(E)-3-fluoro-3-(3-(2-(2,6,6-trimethylcyclohex-1-enyl)vinyl)phenyl)propan-1-amine;
(E)-4-amino-1,1,1-trifluoro-2-(3-(2-(2,6,6-trimethylcyclohex-1-enyl)vinyl)phenyl)butan-2-ol;
(E)-3-amino-2,2-dimethyl-1-(3-(2-(2,6,6-trimethylcyclohex-1-enyl)vinyl)phenyl)propan-1-ol;
(E)-3-amino-2-methyl-1-(3-(2-(2,6,6-trimethylcyclohex-1-enyl)vinyl)phenyl)propan-1-ol;
(E)-1-(3-(2-(2,6,6-trimethylcyclohex-1-enyl)vinyl)phenyl)propane-1,3-diamine;
(E)-4,4,4-trifluoro-3-(3-(2-(2,6,6-trimethylcyclohex-1-enyl)vinyl)phenyl)butan-1-amine;
(E)-3-methoxy-3-(3-(2-(2,6,6-trimethylcyclohex-1-enyl)vinyl)phenyl)propan-1-amine;
(E)-4-(3-(2-(2,6,6-trimethylcyclohex-1-enyl)vinyl)phenyl)butan-2-amine;
(E)-1-amino-3-(3-(2-(2,6,6-trimethylcyclohex-1-enyl)vinyl)phenyl)propan-2-ol;
(E)-2-(3-(3-(2-(2,6,6-trimethylcyclohex-1-enyl)vinyl)phenyl)propylamino) ethanol;
(E)-3-methoxy-N-methyl-3-(3-(2-(2,6,6-trimethylcyclohex-1-enyl)vinyl)phenyl)propan-1-amine;
(E)-3-amino-1-(3-(2-(2,6,6-trimethylcyclohex-1-enyl)vinyl)phenyl)propan-1-one;
(E)-3-amino-2,2-dimethyl-1-(3-(2-(2,6,6-trimethylcyclohex-1-enyl)vinyl)phenyl)propan-1-one;
(E)-3-amino-2-methyl-1-(3-(2-(2,6,6-trimethylcyclohex-1-enyl)vinyl)phenyl)propan-1-one;
(E)-3-amino-2-fluoro-1-(3-(2-(2,6,6-trimethylcyclohex-1-enyl)vinyl)phenyl)propan-1-one;
(E)-2-(3-(2-(2,6,6-timethylcyclohex-1-enyl)vinyl)phenoxy)ethanamine;
(E)-2-amino-N-(3-(2-(2,6,6-trimethylcyclohex-1-enyl)vinyl)phenyl)acetamide;
(E)-3-(3-(2-(2,6,6-trimethylcyclohex-1-enyl)vinyl)phenyl)prop-2-yn-1-amine;
(E)-2-fluoro-3-(3-((E)-2-(2,6,6-trimethylcyclohex-1-enyl)vinyl)phenyl)prop-2-en-1-amine;
(E)-3-(3-(2-(2,6,6-trimethylcyclohex-1-enyl)vinyl)phenyl)prop-2-yn-1-amine;
(E)-2-fluoro-3-(3-((E)-2-(2,6,6-trimethylcyclohex-1-enyl)vinyl)phenyl)prop-2-en-1-amine;
(E)-3-(3-(pent-1-enyl)phenyl)propan-1-amine;
(E)-3-(3-(hept-1-enyl)phenyl)propan-1-amine;
(E)-3-(3-(non-4-en-5-yl)phenyl)propan-1-amine;
(E)-4-(3-(3-aminopropyl)phenyl)-2-methylbut-3-en-2-ol;
(E)-4-(3-(3-aminopropyl)styryl)heptan-4-ol;
(E)-1-(3-(3-aminopropyl)phenyl)hex-1-en-3-ol;
(E)-4-(3-(2-aminoethoxy)styryl)heptan-4-ol;
(E)-1-(3-(3-aminopropyl)phenyl)-3-ethylpent-1-en-3-ol;
(E)-3-(3-(3-aminopropyl)phenyl)prop-2-en-1-ol;
(E)-3-(3-(3-methoxyprop-1-enyl)phenyl)propan-1-amine;
(E)-(3-(2-(2,6,6-trimethylcyclohex-1-enyl)vinyl)phenyl)methanamine;
(E)-1-(3-(2,6-dimethylstyryl)phenyl)-N,N-dimethylmethanamine;
(E)-4-(3-(2,6-dimethylstyryl)phenyl)butan-1-amine;
(E)-2-(3-(2,6-dimethylstyryl)phenyl)ethanamine;
(E)-2-(3-(2,6-dimethylstyryl)benzylamino)ethanol;
(E)-3-(3-(2,6-dimethylstyryl)phenyl)-3-hydroxypropanimidamide;
(E)-3-hydroxy-3-(3-(2-(2,6,6-trimethylcyclohex-1-enyl)vinyl)phenyl)propanimidamide;
(Z)-3-amino-1-(3-(2,6-dimethylstyryl)phenyl)propan-1-one oxime;
(Z)-3-amino-1-(3-4E)-2-(2,6,6-trimethylcyclohex-1-enyl)vinyl)phenyl)propan-1-one oxime;
(Z)-3-(3-(2,6-dimethylstyryl)phenyl)-3-hydrazonopropan-1-amine;
(Z)-3-hydrazono-3-(3-((E)-2-(2,6,6-trimethylcyclohex-1-enyl)vinyl)phenyl)propan-1-amine;
(E)-2-(3-(2,6-dimethylstyryl)phenyl)ethanamine;
(E)-2-(3-(2-(2,6,6-trimethylcyclohex-1-enyl)vinyl)phenyl)ethanamine;
(E)-2-amino-1-(3-(2,6-dimethylstyryl)phenyl)ethanol;
(E)-2-amino-1-(3-(2-(2,6,6-trimethylcyclohex-1-enyl)vinyl)phenyl)ethanol;
(E)-1-(3-(3-aminopropyl)phenyl)-3-methylhex-1-en-3-ol; and
(E)-1-(3-(3-aminopropyl)phenyl)-3-ethylhex-1-en-3-ol.

In an additional embodiment is a pharmaceutical composition comprising a pharmaceutically acceptable carrier and a compound disclosed herein, including a compound of any one of Formula (A)-(K).

In yet another embodiment is a compound that inhibits 11-cis-retinol production with an IC50 of about 1 uM or less when assayed in vitro, utilizing extract of cells that express RPE65 and LRAT, wherein the extract further comprises CRALBP, wherein the compound is stable in solution for at least about 1 week at room temperature. In a specific embodiment, the compound inhibits 11-cis-retinol production with an IC50 of about 100 nM or less when assayed in vitro, utilizing extract of cells that express RPE65 and LRAT, wherein the extract further comprises CRALBP, wherein the compound is stable in solution for at least about 1 week at room temperature. In a further embodiment, the compound inhibits 11-cis-retinol production with an IC50 of about 10 nM or less when assayed in vitro, utilizing extract of cells that express RPE65 and LRAT, wherein the extract further comprises CRALBP, wherein the compound is stable in solution for at least about 1 week at room temperature.

In an additional embodiment is a non-retinoid compound that inhibits an isomerase reaction resulting in production of 11-cis retinol, wherein said isomerase reaction occurs in RPE, and wherein said compound has an ED50 value of 1 mg/kg or less when administered to a subject. In a further embodiment is a non-retinoid compound of wherein the ED50 value is measured after administering a single dose of the compound to said subject for about 2 hours or longer. In an additional embodiment the compound is a styrenyl compound. In a further embodiment the compound is a non-retinoid compound.

In a further embodiment is a pharmaceutical composition comprising a pharmaceutically acceptable carrier and a compound that inhibits 11-cis-retinol production with an IC50 of about 1 uM or less when assayed in vitro, utilizing extract of cells that express RPE65 and LRAT, wherein the extract further comprises CRALBP, wherein the compound is stable in solution for at least about 1 week at room temperature. In an additional embodiment is a pharmaceutical composition comprising a pharmaceutically acceptable carrier and a non-retinoid compound that inhibits an isomerase reaction resulting in production of 11-cis retinol, wherein said isomerase reaction occurs in RPE, and wherein said compound has an ED50 value of 1 mg/kg or less when administered to a subject.

In a specific embodiment is a method of modulating chromophore flux in a retinoid cycle comprising introducing into a subject a compound disclosed herein, including a compound of any one of Formula (A)-(K). In a further embodiment the method results in a reduction of lipofuscin pigment accumulated in an eye of the subject. In yet another embodiment the lipofuscin pigment is N-retinylidene-N-retinyl-ethanolamine (A2E).

In yet another embodiment is a method for treating an ophthalmic disease or disorder in a subject, comprising administering to the subject the pharmaceutical composition described herein. In a further embodiment, the ophthalmic disease or disorder is age-related macular degeneration or Stargardt's macular dystrophy. In yet another embodiment the method results in a reduction of lipofuscin pigment accumulated in an eye of the subject. In yet another embodiment the lipofuscin pigment is N-retinylidene-N-retinyl-ethanolamine (A2E).

In additional embodiments, the ophthalmic disease or disorder is selected from retinal detachment, hemorrhagic retinopathy, retinitis pigmentosa, cone-rod dystrophy, Sorsby's fundus dystrophy, optic neuropathy, inflammatory retinal disease, diabetic retinopathy, diabetic maculopathy, retinal blood vessel occlusion, retinopathy of prematurity, or ischemia reperfusion related retinal injury, proliferative vitreoretinopathy, retinal dystrophy, hereditary optic neuropathy, Sorsby's fundus dystrophy, uveitis, a retinal injury, a retinal disorder associated with Alzheimer's disease, a retinal disorder associated with multiple sclerosis, a retinal disorder associated with Parkinson's disease, a retinal disorder associated with viral infection, a retinal disorder related to light overexposure, myopia, and a retinal disorder associated with AIDS.

In a further embodiment is a method of inhibiting dark adaptation of a rod photoreceptor cell of the retina comprising contacting the retina with a compound disclosed herein, including a compound of any one of Formula (A)-(K).

In an additional embodiment is a method of inhibiting regeneration of rhodopsin in a rod photoreceptor cell of the retina comprising contacting the retina with the compound of Formula (A), a compound that inhibits 11-cis-retinol production with an IC50 of about 1 uM or less when assayed in vitro, utilizing extract of cells that express RPE65 and LRAT, wherein the extract further comprises CRALBP, wherein the compound is stable in solution for at least about 1 week at room temperature, or a A non-retinoid compound that inhibits an isomerase reaction resulting in production of 11-cis retinol, wherein said isomerase reaction occurs in RPE, and wherein said compound has an ED50 value of 1 mg/kg or less when administered to a subject.

In a further embodiment is a method of reducing ischemia in an eye of a subject comprising administering to the subject the pharmaceutical composition of the compound of Formula (A), a compound that inhibits 11-cis-retinol production with an IC50 of about 1 uM or less when assayed in vitro, utilizing extract of cells that express RPE65 and LRAT, wherein the extract further comprises CRALBP, wherein the compound is stable in solution for at least about 1 week at room temperature, or a A non-retinoid compound that inhibits an isomerase reaction resulting in production of 11-cis retinol, wherein said isomerase reaction occurs in RPE, and wherein said compound has an ED50 value of 1 mg/kg or less when administered to a subject. In a further embodiment, the pharmaceutical composition is administered under conditions and at a time sufficient to inhibit dark adaptation of a rod photoreceptor cell, thereby reducing ischemia in the eye.

In a further embodiment is a method of inhibiting neovascularization in the retina of an eye of a subject comprising administering to the subject the pharmaceutical composition of a compound of Formula (A). In a specific embodiment, the pharmaceutical composition is administered under conditions and at a time sufficient to inhibit dark adaptation of a rod photoreceptor cell, thereby inhibiting neovascularization in the retina.

In a further embodiment is a method of inhibiting degeneration of a retinal cell in a retina comprising contacting the retina with the compound of the compound of Formula (A), a compound that inhibits 11-cis-retinol production with an IC50 of about 1 uM or less when assayed in vitro, utilizing extract of cells that express RPE65 and LRAT, wherein the extract further comprises CRALBP, wherein the compound is stable in solution for at least about 1 week at room temperature, or a a non-retinoid compound that inhibits an isomerase reaction resulting in production of 11-cis retinol, wherein said isomerase reaction occurs in RPE, and wherein said compound has an ED50 value of 1 mg/kg or less when administered to a subject. In a further embodiment, the pharmaceutical composition is administered under conditions and at a time sufficient to inhibit dark adaptation of a rod photoreceptor cell, thereby reducing ischemia in the eye. In a specific embodiment is the method wherein the retinal cell is a retinal neuronal cell. In a certain embodiment, the retinal neuronal cell is a photoreceptor cell.

Thus, the compounds can be represented by Formula (I):

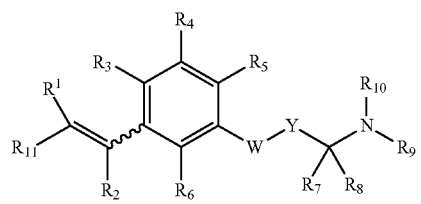

Formula (I)

as an isolated E or Z stereoisomer or a mixture of E and Z stereoisomers, as a tautomer or a mixture of tautomers, or as a pharmaceutically acceptable salt, hydrate, solvate, N-oxide or prodrug thereof, wherein:

$R_1$ and $R_2$ are each the same or different and independently hydrogen or alkyl;

$R_3$, $R_4$, $R_5$ and $R_6$ are each the same or different and independently hydrogen, halogen, —$OR_{12}$, alkyl or fluoroalkyl;

$R_7$ and $R_8$ are each the same or different and independently hydrogen or alkyl;

$R_9$ is hydrogen, alkyl, carbocyclyl or —C(=O)$R_{13}$;

$R_{10}$ is hydrogen or alkyl; or $R_9$ and $R_{10}$, together with the nitrogen atom to which they are attached, form an N-heterocyclyl;

$R_{11}$ is alkyl, alkenyl, aryl, carbocyclyl, heteroaryl or heterocyclyl;

$R_{12}$ is hydrogen or alkyl;

$R_{13}$ is alkyl, carbocyclyl or aryl;

W is —C($R_{14}$)($R_{15}$)—, —O—, —S—, —S(=O)—, —S(=O)$_2$— or —N($R_{12}$)—;

Y is —C($R_{16}$)($R_{17}$)—;

$R_{14}$ and $R_{15}$ are each the same or different and independently hydrogen, halogen, alkyl, fluoroalkyl, —$OR_{12}$, —$NR_{18}R_{19}$ or carbocyclyl; or $R_{14}$ and $R_{15}$ form an oxo;

$R_{16}$ and $R_{17}$ are each the same or different and independently hydrogen, halogen, alkyl, fluoroalkyl, —$NR_{18}R_{19}$ or carbocyclyl; or $R_{16}$ and $R_{17}$ form an oxo; or $R_{14}$ and $R_{16}$ together form a direct bond to provide a double bond connecting W and Y; or $R_{14}$ and $R_{16}$ together form a direct bond, and $R_{15}$ and $R_{17}$ together form a direct bond to provide a triple bond connecting W and Y;

$R_{18}$ and $R_{19}$ are each the same or different and independently hydrogen, alkyl, carbocyclyl, or —C(=O)$R_{13}$, provided that when $R_{11}$ is phenyl, the compound of Formula (I) is not:

2-amino-N-[2-methoxy-5-[(1Z)-2-(3,4,5-trimethoxyphenyl)ethenyl]phenyl]acetamide;

(2S,3R)-amino-3-hydroxy-N-[2-methoxy-5-[(1Z)-2-(3,4,5-trimethoxyphenyl)-ethenyl]phenyl]-butanamide;

L-glutamic acid, 1-[2-methoxy-5-[(1Z)-2-(3,4,5-trimethoxyphenyl)ethenyl]phenyl]ester;

glycine, 3-hydroxy-5-[(1E)-2-(4-hydroxyphenyl)ethenyl]phenyl ester;

(2S)-2-amino-N-[2-methoxy-5-[(1Z)-2-(3,4,5-trimethoxyphenyl)ethenyl]phenyl]propanamide;

(2S)-2-amino-3-hydroxy-N-[2-methoxy-5-[(1Z)-2-(3,4,5-trimethoxyphenyl)ethenyl]phenyl]propanamide;

(2S)-2-amino-N-[2-methoxy-5-[(1Z)-2-(3,4,5-trimethoxyphenyl)ethenyl]phenyl]-4-methyl-pentanamide;

(2S)-2-amino-N-[2-methoxy-5-[(1Z)-2-(3,4,5-trimethoxyphenyl)ethenyl]phenyl]-3-methyl-butanamide; or 2-amino-N-[2-methoxy-5-[(1Z)-2-(3,4,5-trimethoxyphenyl)ethenyl]phenylbutanamide.

In one embodiment, $R_1$ is hydrogen, and compound has a structure of Formula (Ia):

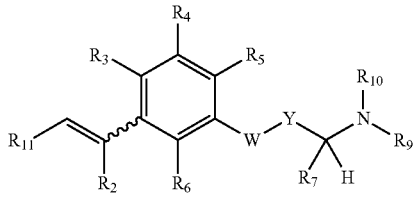

as an isolated E or Z stereoisomer or a mixture of E and Z stereoisomers, as a tautomer or a mixture of tautomers, or as a pharmaceutically acceptable salt, hydrate, solvate, N-oxide or prodrug thereof, wherein $R_2$ is H or $C_1$-$C_6$ alkyl;

each of $R_3$, $R_4$, $R_5$, and $R_6$ is the same or different and independently hydrogen, $C_1$-$C_6$ alkyl, or $C_1$-$C_6$ alkoxy;

$R_7$ is H or $C_1$-$C_6$ alkyl;

$R_9$ is hydrogen, $C_1$-$C_6$ alkyl, —(CH$_2$)$_n$OH wherein n is 1-6, or —C(=O)$R_{13}$;

$R_{10}$ is hydrogen or $C_1$-$C_6$ alkyl; or $R_9$ and $R_{10}$, together with the nitrogen atom to which they are attached, form an N-heterocyclyl;

W is —C($R_{14}$)($R_{15}$)—, —O—, —S—, —S(=O)—, —S(=O)$_2$— or —N(H)—;

Y is —C($R_{16}$)($R_{17}$)—;

$R_{12}$ is hydrogen or $C_1$-$C_6$ alkyl;

$R_{13}$ is $C_1$-$C_6$ alkyl;

$R_{14}$ and $R_{15}$ are each the same or different and independently hydrogen, halogen, $C_1$-$C_6$ alkyl, fluoroalkyl, —$OR_{12}$, —NH$_2$; or $R_{14}$ and $R_{15}$ form an oxo;

$R_{16}$ and $R_{17}$ are each the same or different and independently hydrogen, halogen, $C_1$-$C_6$ alkyl, —$OR_{12}$;

or $R_{16}$ and $R_{17}$ form an oxo;

$R_{14}$ and $R_{16}$ together form a direct bond to provide a double bond connecting W and Y; or $R_{14}$ and $R_{16}$ together form a direct bond, and $R_{15}$ and $R_{17}$ together form a direct bond to provide a triple bond connecting W and Y; and $R_{11}$ is alkyl; phenyl substituted with alkyl, —$OR_{12}$, —O(CH$_2$)$_n$OCH$_3$ wherein n is 1-6, alkenyl, alkynyl, halogen, fluoroalkyl, phenyl, —SCH$_3$, or aralkyl; naphthenyl naphthenyl optionally substituted with alkyl, halogen, or —$OR_{12}$; carbocyclyl; cyclohexenyl optionally substituted with alkyl, provided that $R_{11}$ is not 3,4,5-tri-methoxyphenyl.

In a specific embodiment, $R_2$ is hydrogen or n-butyl.

In certain specific embodiments, halogen is chloro or fluoro.

In other specific embodiments, each of $R_3$, $R_4$, $R_5$, and $R_6$ is the same or different and independently hydrogen, methyl or methoxy. In certain specific embodiments, at least two of $R_3$, $R_4$, $R_5$, and $R_6$ are hydrogen. In other certain specific embodiments, at least one of $R_3$, $R_4$, $R_5$, and $R_6$ is methyl or methoxy.

In a specific embodiment, $R_9$ is —(CH$_2$)$_n$OH wherein n is 2. In other specific embodiments, $R_9$ is —C(=O)$R_{13}$ wherein $R_{13}$ is methyl.

In another specific embodiment, each of $R_9$ and $R_{10}$ the same or different and independently hydrogen or methyl. In other specific embodiments, each of $R_9$ and $R_{10}$ is hydrogen.

In other specific embodiments, when W is —C($R_{14}$)($R_{15}$)—, $R_{14}$ and $R_{15}$ are each the same or different and independently hydrogen, fluoro, methyl, ethyl, trifluoromethyl, —OH, —OHCH$_3$, or —NH$_2$. In certain specific embodiments each of $R_{14}$ and $R_{15}$ is hydrogen.

In yet other specific embodiments Y is —CH$_2$—, —CH(CH$_3$)—, —CH(CH$_3$)$_2$—, —CHOH—, —CHF—, —CF$_2$—, or C(=O)—.

In other specific embodiments, $R_{11}$ is phenyl substituted with alkyl, —$OR_{12}$, —$O(CH_2)_nOCH_3$ wherein n is 1-6, alkenyl, alkynyl, halogen, fluoroalkyl, phenyl, or —$SCH_3$. In other certain specific embodiments, halogen is chloro. In yet other specific embodiments, n is 2.

In other embodiments, $R_{11}$ is naphthenyl substituted with —$OR_{12}$, wherein $R_{12}$ is hydrogen or $C_1$-$C_6$ alkyl. In yet another specific embodiment, $R_{11}$ is cyclohexenyl optionally substituted with $C_1$-$C_6$ alkyl; in another specific embodiment, $R_{11}$ is tri-methyl-cyclohexenyl. In other specific embodiments, $R_{11}$ is alkyl optionally substituted with —$OR_{12}$ wherein $R_{12}$ is hydrogen or $C_1$-$C_6$ alkyl.

One embodiment provides a compound having a structure of Formula (I) wherein $R_{11}$ is aryl or carbocyclyl, as defined herein.

A further embodiment provides a compound having a structure of Formula (I) wherein $R_{11}$ is aryl, which has a structure of Formula (II):

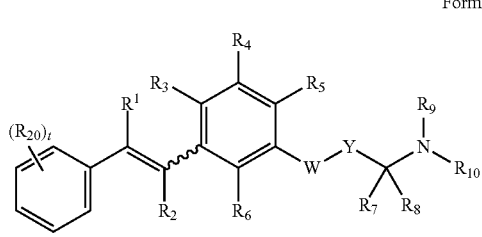

Formula (II)

as an isolated E or Z stereoisomer or a mixture of E and Z stereoisomers, as a tautomer or a mixture of tautomers, or as a pharmaceutically acceptable salt, hydrate, solvate, N-oxide or prodrug thereof, wherein:

$R_1$ and $R_2$ are each the same or different and independently hydrogen or alkyl;

$R_3$, $R_4$, $R_5$ and $R_6$ are each the same or different and independently hydrogen, halogen, —$OR_{12}$, alkyl or fluoroalkyl;

$R_7$ and $R_8$ are each the same or different and independently hydrogen or alkyl;

$R_9$ is hydrogen, alkyl, carbocyclyl or —C(=O)$R_{13}$;

$R_{10}$ is hydrogen or alkyl; or $R_9$ and $R_{10}$, together with the nitrogen atom to which they are attached, form an N-heterocyclyl;

$R_{12}$ is hydrogen or alkyl;

$R_{13}$ is alkyl, carbocyclyl or aryl;

W is —C($R_{14}$)($R_{15}$)—, —O—, —S—, —S(=O)—, —S(=O)$_2$— or —N($R_{12}$)—;

Y is —C($R_{16}$)($R_{17}$)—;

$R_{14}$ and $R_{15}$ are each the same or different and independently hydrogen, halogen, alkyl, fluoroalkyl, —$OR_{12}$, —$NR_{18}R_{19}$ or carbocyclyl; or $R_{14}$ and $R_{15}$ form an oxo;

$R_{16}$ and $R_{17}$ are each the same or different and independently hydrogen, halogen, alkyl, fluoroalkyl, —$OR_{12}$, —$NR_{18}R_{19}$ or carbocyclyl; or $R_{16}$ and $R_{17}$ form an oxo; or $R_{14}$ and $R_{16}$ together form a direct bond to provide a double bond connecting W and Y; or $R_{14}$ and $R_{16}$ together form a direct bond, and $R_{15}$ and $R_{17}$ together form a direct bond to provide a triple bond connecting W and Y;

$R_{18}$ and $R_{19}$ are each the same or different and independently hydrogen, alkyl, carbocyclyl, or —C(=O)$R_{13}$, t is 0, 1, 2, 3, 4 or 5; and each $R_{20}$ is the same or different and independently alkyl, —$OR_{12}$, —$SR_{12}$, alkenyl, alkynyl, halo, fluoroalkyl, aryl or aralkyl, or two adjacent $R_{20}$, together with the two carbon atoms to which they are attached, form a fused phenyl ring.

In one embodiment, each of $R_9$ and $R_{10}$ is hydrogen and the compound has a structure of Formula (IIa):

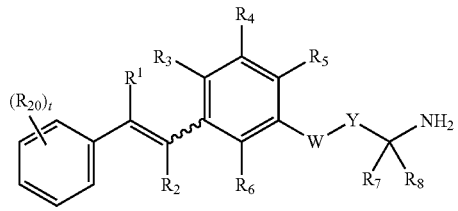

Formula (IIa)

In one embodiment, W is —C($R_{14}$)($R_{15}$)— and the linkage —W—Y—C($R_7$)($R_8$)— is an alkylene chain. Thus, the compound has a structure of Formula (IIb):

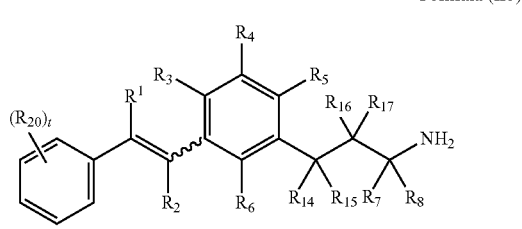

Formula (IIb)

as an isolated E or Z stereoisomer or a mixture of E and Z stereoisomers, as a tautomer or a mixture of tautomers, or as a pharmaceutically acceptable salt, hydrate, solvate, N-oxide or prodrug thereof, wherein:

$R_1$ and $R_2$ are each the same or different and independently hydrogen or alkyl;

$R_3$, $R_4$, $R_5$ and $R_6$ are each the same or different and independently hydrogen, halogen, —$OR_{12}$, alkyl or fluoroalkyl;

TABLE 1

| Compound No. | Compound Formula | Chemical Name |
| --- | --- | --- |
| 1 | ![structure] | (E)-3-(3-(2,6-dimethylstyryl)phenyl)propan-1-amine |

TABLE 1-continued

| Compound No. | Compound Formula | Chemical Name |
|---|---|---|
| 2 | 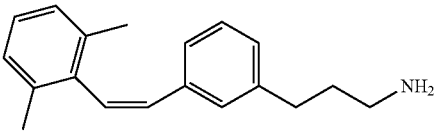 [SMILES: Cc1cccc(C)c1/C=C\c1cccc(CCCN)c1] | (Z)-3-(3-(2,6-dimethylstyryl)phenyl)propan-1-amine |
| 16 | 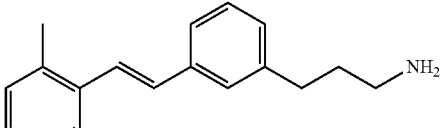 | (E)-3-(3-(2-methylstyryl)phenyl)propan-1-amine |
| 17 | 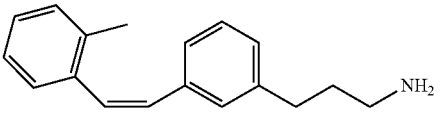 [SMILES: Cc1ccccc1/C=C\c1cccc(CCCN)c1] | (Z)-3-(3-(2-methylstyryl)phenyl)propan-1-amine |
| 28 | 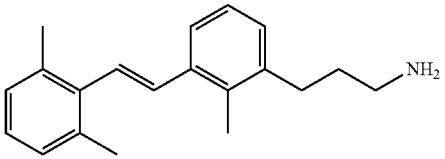 [SMILES: Cc1cccc(C)c1/C=C/c1cccc(CCCN)c1C] | (E)-3-(3-(2,6-dimethylstyryl)-2-methylphenyl)propan-1-amine |
| 29 | 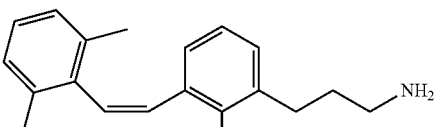 | (Z)-3-(3-(2,6-dimethylstyryl)-2-methylphenyl)propan-1-amine |
| 32 | 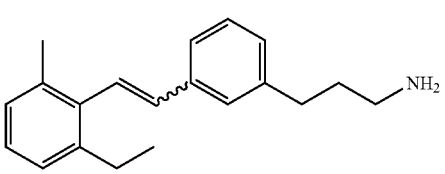 [SMILES: CCc1cccc(C)c1C=Cc1cccc(CCCN)c1] | (E/Z)-3-(3-(2-ethyl-6-methylstyryl)phenyl)propan-1-amine |
| 33 | 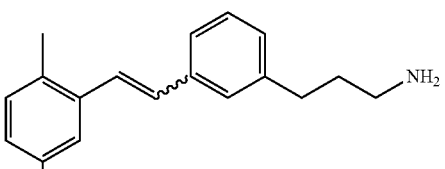 | (E/Z)-3-(3-(2,5-dimethylstyryl)phenyl)propan-1-amine |
| 34 | 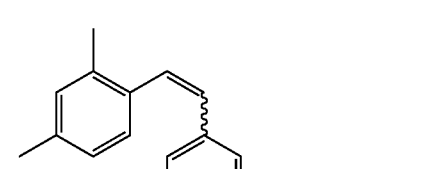 | (E/Z)-3-(3-(2,4-dimethylstyryl)phenyl)propan-1-amine |
| 35 | 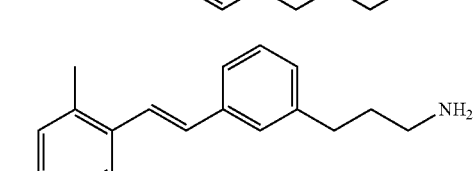 | (E)-3-(3-(2,4,6-trimethylstyryl)phenyl)propan-1-amine |

TABLE 1-continued

| Compound No. | Compound Formula | Chemical Name |
|---|---|---|
| 36 | | (E/Z)-3-(3-(2-ethylstyryl)phenyl)prpoan-1-amine |
| 37 | | (E/Z)-3-(3-(2-ethynylstyryl)phenyl)propan-1-amine |
| 38 | | (E/Z)-3-(3-(3,4-dimethylstyryl)phenyl)propan-1-amine |
| 39 | | (E/Z)-3-(3-(2-isopropylstyryl)phenyl)propan-1-amine |
| 40 | | (E/Z)-4-(3-(3,5-dimethylstyryl)phenyl)propan-1-amine |
| 41 | | (E/Z)-4-(3-(2-methoxystyryl)phenyl)propan-1-amine |
| 43 | | (E)-3-(3-(2,6-dichlorostyryl)phenyl)propan-1-amine |

TABLE 1-continued

| Compound No. | Compound Formula | Chemical Name |
|---|---|---|
| 44 | | (E/Z)-3-(3-(2,3-dimethylstyryl)phenyl)propan-1-amine |
| 46 | | (E)-3-(3-(2,6-dimethylstyryl)-4-fluorophenyl)propan-1-amine |
| 47 | | (E/Z)-3-(3-(2-(trifluoromethyl)styryl)phenyl)propan-1-amine |
| 48 | | (E)-3-(3-(2,6-dimethoxystyryl)phenyl)propan-1-amine |
| 49 | | (E)-3-(3-(2,6-bis(trifluoromethyl)styryl)-phenyl)propan-1-amine |
| 50 | | (E)-3-amino-1-(3-(2,6-dichlorostyryl)phenyl)propan-1-ol |
| 82 | | (E)-3-amino-1-(3-(2-chloro-6-methylstyryl)phenyl)propan-1-ol |
| 70 | | (E)-2-(3-(3-aminopropyl)styryl)phenol |

TABLE 1-continued

| Compound No. | Compound Formula | Chemical Name |
| --- | --- | --- |
| 71 | | (E)-3-(5-(2,6-dichlorostyryl)-2-methoxyphenyl)propan-1-amine |
| 74 | | (R,E)-1-amino-3-(3-(2,6-dichlorostyryl)phenyl)propan-2-ol |
| 75 | | (S,E)-1-amino-3-(3-(2,6-dichlorostyryl)phenyl)propan-2-ol |
| 76 | | (E/Z)-(3-(3-(2,6-diethoxystyryl)phenyl)propan-1-amine |
| 77 | | (E)-3-(3-(2-ethoxystyryl)phenyl)propan-1-amine |
| 78 | | (E/Z)-3-(3-(2-isopropoxystyryl)phenyl)propan-1-amine |
| 80 | | (E)-3-amino-1-(3-(2,6-dichlorostyryl)phenyl)propan-1-one |
| 81 | | (E)-1-amino-3-(3-(2,6-dichlorostyryl)phenyl)propan-2-one |

| Compound No. | Compound Formula | Chemical Name |
| --- | --- | --- |
| 86 | | (R,E)-3-amino-1-(3-(2,6-dichlorostyryl)phenyl)propan-1-ol |
| 87 | | (S,E)-3-amino-1-(3-(2,6-dichlorostyryl)phenyl)propan-1-ol |
| 88 | | (S,E)-3-(3-(2,6-dichlorostyryl)phenyl)-2-fluoropropan-1-amine |
| 89 | | (E)-3-(3-(2,6-dichlorostyryl)phenyl)-2,2-difluoropropan-1-amine |
| 90 | | (Z)-3-(3-(2-(2-methoxyethoxy)styryl)phenyl)-propan-1-amine |
| 91 | | (E)-3-(3-(3-methoxystyryl)phenyl)propan-1-amine |
| 93 | | (Z)-3-(3-(4-chlorostyryl)phenyl)propan-1-amine |
| 94 | | (E)-3-(3-(2-(biphenyl-2-yl)vinyl)phenyl)propan-1-amine |

TABLE 1-continued

| Compound No. | Compound Formula | Chemical Name |
|---|---|---|
| 97 | 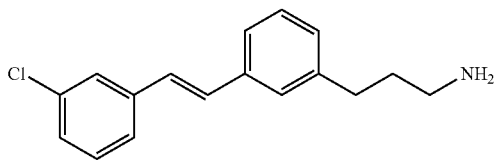 [SMILES: NCCCc1cccc(/C=C/c2cccc(Cl)c2)c1] | (E)-3-(3-(3-chlorostyryl)phenyl)propan-1-amine |
| 98 | 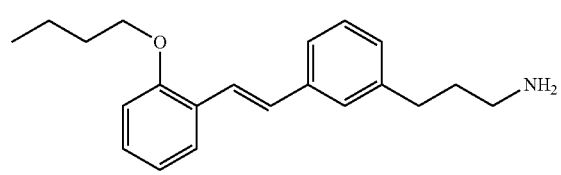 [SMILES: CCCCOc1ccccc1/C=C/c1cccc(CCCN)c1] | (E)-3-(3-(2-butoxystyryl)phenyl)propan-1-amine |
| 99 | 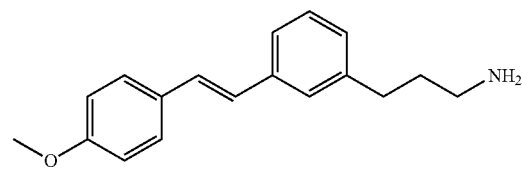 [SMILES: COc1ccc(/C=C/c2cccc(CCCN)c2)cc1] | (E)-3-(3-(4-methoxystyryl)phenyl)propan-1-amine |
| 109 | 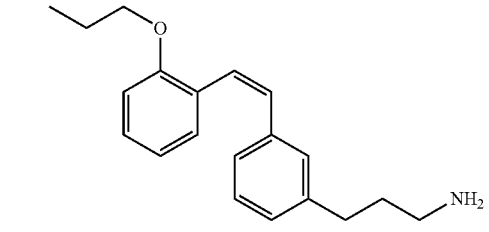 [SMILES: CCCOc1ccccc1/C=C\c1cccc(CCCN)c1] | (Z)-3-(3-(2-Propoxystyryl)phenyl)propan-1-amine |
| 107 | 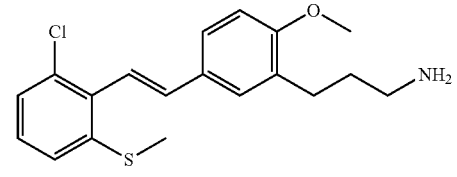 [SMILES: COc1ccc(/C=C/c2c(Cl)cccc2SC)cc1CCCN] | (E)-3-(5-(2-Chloro-6-(methylthio)styryl)-2-methoxyphenyl)propan-1-amine |
| 110 | 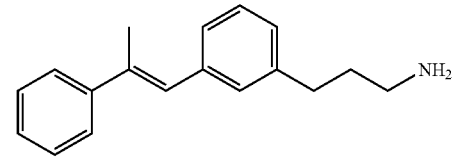 [SMILES: C/C(=C\c1cccc(CCCN)c1)c1ccccc1] | (E)-3-(3-(2-phenylprop-1-enyl)phenyl)propan-1-amine |

$R_7$ and $R_8$ are each the same or different and independently hydrogen or alkyl;

$R_{12}$ is hydrogen or alkyl;

$R_{13}$ is alkyl, carbocyclyl or aryl;

$R_{14}$ and $R_{15}$ are each the same or different and independently hydrogen, halogen, alkyl, fluoroalkyl, —$NR_{18}R_{19}$ or carbocyclyl; or $R_{14}$ and $R_{15}$ form an oxo;

$R_{16}$ and $R_{17}$ are each the same or different and independently hydrogen, halogen, alkyl, fluoroalkyl, —$OR_{12}$, —$NR_{18}R_{19}$ or carbocyclyl; or $R_{16}$ and $R_{17}$ form an oxo; or $R_{18}$ and $R_{19}$ are each the same or different and independently alkyl, carbocyclyl, or —C(=O)$R_{13}$, t is 0, 1, 2, 3, 4 or 5; and each $R_{20}$ is the same or different and independently alkyl, —$OR_{12}$, —$SR_{12}$, alkenyl, alkynyl, halo, fluoroalkyl, aryl or aralkyl, or two adjacent $R_{20}$, together with the two carbon atoms to which they are attached, form a fused phenyl ring.

In certain embodiments, t is 0, 1, 2 or 3, each $R_{20}$ is independently alkyl, —$OR_{12}$, alkynyl, phenyl, halo or fluoroalkyl, and $R_3$, $R_4$, $R_5$ and $R_6$ are each independently hydrogen, alkyl, —$OR_{12}$, halo or fluoroalkyl.

In certain embodiments, $R_7$, $R_8$, $R_{14}$, $R_{15}$, $R_{16}$ and $R_{17}$ are each independently hydrogen, halogen, alkyl or —$OR_{12}$, wherein $R_{12}$ is hydrogen or alkyl.

In certain specific embodiments, the compounds of Formula (I), (II), (IIa) or (IIb) have the structures shown in Table 1. Each of the compounds provided in Table 1 below and in the following Tables 2-11 as Compound Numbers may also be referred to herein as Example numbers. The Compound number corresponds to the Example number herein that describes the synthesis of the compound.

Table 1

In certain embodiments, a compound of formula (IIb) is provided wherein t is 2 or 3, two adjacent $R_{20}$, together with the two carbon atoms to which they are attached, form a fused phenyl ring; optionally, a third $R_{20}$ is alkyl or —$OR_{12}$; and $R_3$, $R_4$, $R_5$ and $R_6$ are each independently hydrogen, alkyl, halo or fluoroalkyl.

In other certain embodiments, $R_7$, $R_8$, $R_{14}$, $R_{15}$, $R_{16}$ and $R_{17}$ are each independently hydrogen, halogen, alkyl or —$OR_{12}$.

In certain specific embodiments, the compounds of Formula (I), (II), (IIa) or (IIb) have a structure shown in Table 2.

TABLE 2

| Compound No. | Compound Formula | Chemical Name |
|---|---|---|
| 92 | | (E)-3-(3-(2-(1-methoxynaphthalen-2-yl)vinyl)phenyl)propan-1-amine |
| 95 | | (Z)-3-(3-(2-(naphthalen-1-yl)vinyl)phenyl)propan-1-amine |
| 96 | | (Z)-3-(3-(2-(3-methoxynaphthalen-2-yl)vinyl)phenyl)propan-1-amine |
| 108 | | (E/Z)-3-(3-(2-(2-methoxynaphthalen-1-yl)vinyl)phenyl)propan-1-amine |

Another embodiment provides a compound having a structure of Formula (IIa) wherein W is —O—, —S—, —S(=O)—, —S(=O)$_2$— or —N($R_{12}$)—.

In certain embodiments, t is 0, 1, 2 or 3, each $R_{20}$ is independently alkyl, —$OR_{12}$ or halo, and $R_3$, $R_4$, $R_5$ and $R_6$ are each independently hydrogen, alkyl or halo. In certain specific embodiments, these compounds have a structure shown in Table 3.

TABLE 3

| Compound No. | Chemical Formula | Chemical Name |
|---|---|---|
| 15 | | (E)-2-amino-N-(3-(2,6-dimethylstyryl)phenyl)acetamide |

TABLE 3-continued

| Compound No. | Chemical Formula | Chemical Name |
| --- | --- | --- |
| 18 | | (E)-2-(3-(2,6-dimethylstyryl)phenylthio)ethanamine |
| 19 | | (E)-2-(3-(2,6-dimethylstyryl)phenyl-sulfinyl)ethanamine |
| 20 | | (E)-2-(3-(2,6-dimethylstyryl)phenyl-sulfonyl)ethanamine |
| 119 | | (S,E)-1-(3-(1-aminopropan-2-yloxy)styryl)cyclohexanol |
| 112 | | (E)-1-(3-(2-aminoethoxy)styryl)cyclohexanol |

Another embodiment provides a compound having a structure of Formula (IIa) wherein W and Y are connected by a double bond. One exemplary compound of this embodiment is shown in Table 3A:

TABLE 3A

| Compound No. | Chemical Formula | Chemical Name |
| --- | --- | --- |
| 45 | | (E/Z)-3-(3-(2,6-Dimethylstyryl)phenyl)prop-2-en-1-amine |

Another embodiment provides a compound having a structure of Formula (II), wherein $R_9$ and $R_{10}$ together with the nitrogen to which they are attached form a N-heterocyclyl. In certain embodiments, the N-heterocyclyl is morpholinyl, pyrrolidinyl, piperidinyl or piperazinyl.

In other certain embodiments, each of $R_1$ and $R_2$ is hydrogen, t is 0, 1, 2 or 3, each $R_{20}$ is independently alkyl or halo, and $R_3$, $R_4$, $R_5$ and $R_6$ are each independently hydrogen, alkyl or halo.

In certain embodiments, W is —C($R_{14}$)($R_{15}$)— and the linkage —W—Y—C($R_7$)($R_8$)— is an alkylene chain. In certain specific embodiments, exemplary compounds have a structure shown in Table 4.

TABLE 4

| Compound No. | Chemical Formula | Chemical Name |
| --- | --- | --- |
| 3 | | (E)-4-(3-(3-(2,6-dimethylstyryl)phenyl)propyl)morpholine |
| 4 | | (Z)-4-(3-(3-(2,6-dimethylstyryl)phenyl)propyl)morpholine |
| 5 | | (E)-1-(3-(3-(2,6-dimethylstyryl)phenyl)propyl)pyrrolidine |
| 6 | | (Z)-1-(3-(3-(2,6-dimethylstyryl)phenyl)propyl)pyrrolidine |
| 11 | | (E)-1-(3-(3-(2,6-dimethylstyryl)phenyl)propyl)piperidine |
| 12 | | (Z)-1-(3-(3-(2,6-dimethylstyryl)phenyl)propyl)piperidine |
| 13 | | (E)-1-(3-(3-(2,6-dimethylstyryl)phenyl)propyl)piperazine |
| 14 | | (Z)-1-(3-(3-(2,6-dimethylstyryl)phenyl)propyl)piperazine |

Another embodiment provides a compound having a structure of Formula (II), wherein $R_9$ is alkyl or —C(=O)$R_{13}$, wherein $R_{13}$ is alkyl, and $R_{10}$ is hydrogen or alkyl.

In certain embodiments, each of $R_1$ and $R_2$ is hydrogen, t is 0, 1, 2 or 3, each $R_{20}$ is independently alkyl or halo, and $R_3$, $R_4$, $R_5$ and $R_6$ are each independently hydrogen, alkyl or halo.

In yet other certain embodiments, W is —C($R_{14}$)($R_{15}$)— and the linkage —W—Y—C($R_7$)($R_8$)— is an alkylene chain. In specific embodiments, the compound has a structure shown in Table 5.

TABLE 5

| Compound No. | Chemical Formula | Chemical Name |
|---|---|---|
| 7 | 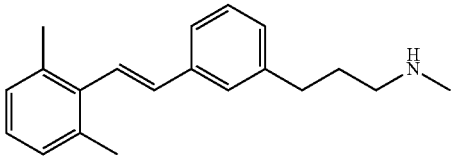 [SMILES: CNCCCc1cccc(/C=C/c2c(C)cccc2C)c1] | (E)-3-(3-(2,6-dimethylstyryl)phenyl)-N-methylpropan-1-amine |
| 8 | 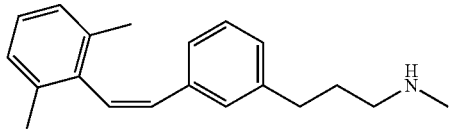 [SMILES: CNCCCc1cccc(/C=C\c2c(C)cccc2C)c1] | (Z)-3-(3-(2,6-dimethylstyryl)phenyl)-N-methylpropan-1-amine |
| 9 | 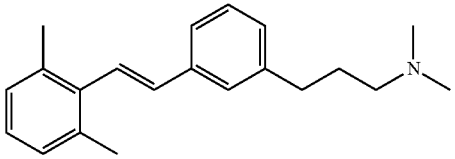 [SMILES: Cc1cccc(C)c1/C=C/c1cccc(CCCN(C)C)c1] | (E)-3-(3-(2,6-dimethylstyryl)phenyl)-N,N-dimethylpropan-1-amine |
| 10 | 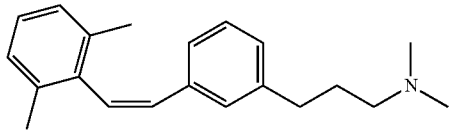 | (Z)-3-(3-(2,6-dimethylstyryl)phenyl)-N,N-dimethylpropan-1-amine |
| 51 | 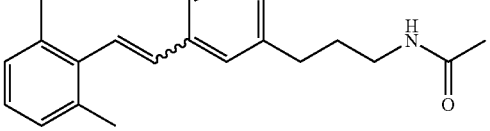 | (E/Z)-N-(3-(3-(2,6-dimethylstyryl)phenyl)propyl)acetamide |
| 52 | 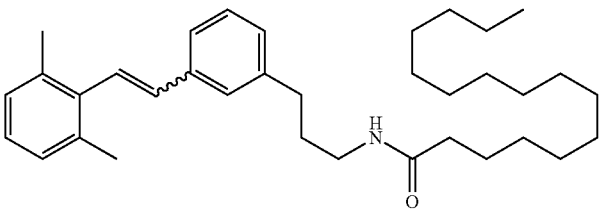 [SMILES: CCCCCCCCCCCCCCCC(=O)NCCCc1cccc(C=Cc2c(C)cccc2C)c1] | (E/Z)-N-(3-(3-(2,6-dimethylstyryl)phenyl)propyl)pentadecanamide |

A further embodiment provides a compound having a structure of Formula (I) wherein $R_{11}$ is carbocyclyl, as defined herein.

In certain embodiments, $R_{11}$ is 5-, 6-, or 7-member cycloalkyl ring.

In certain specific embodiments, $R_{11}$ is cyclohexyl. One exemplary compound of this embodiment is shown in Table 5A:

TABLE 5A

| Compound No. | Chemical Formula | Chemical Name |
|---|---|---|
| 22 | 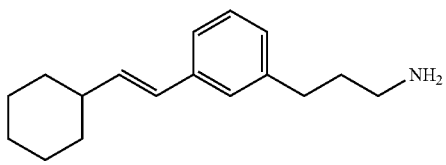 [SMILES: NCCCc1cccc(/C=C/C2CCCCC2)c1] | (E)-3-(3-(2-cyclohexylvinyl)phenyl)propan-1-amine |

In another embodiment, $R_{11}$ is a 5-, 6-, or 7-member cycloalkenyl.

In yet other embodiments, $R_{11}$ is cyclohexenyl and the compound has a structure of Formula (III):

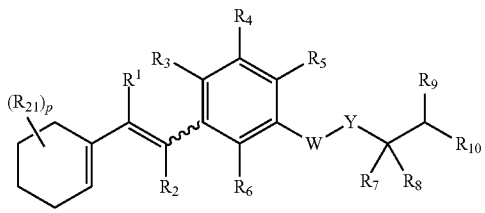

Formula (III)

as an isolated E or Z stereoisomer or a mixture of E and Z stereoisomers, as a tautomer or a mixture of tautomers, or as a pharmaceutically acceptable salt, hydrate, solvate, N-oxide or prodrug thereof, wherein:

$R_1$ and $R_2$ are each the same or different and independently hydrogen or alkyl;

$R_3$, $R_4$, $R_5$ and $R_6$ are each the same or different and independently hydrogen, halogen, —$OR_{12}$, alkyl or fluoroalkyl;

$R_7$ and $R_8$ are each the same or different and independently hydrogen or alkyl;

$R_9$ is hydrogen, alkyl, carbocyclyl or —C(=O)$R_{13}$;

$R_{10}$ is hydrogen or alkyl; or $R_9$ and $R_{10}$, together with the nitrogen atom to which they are attached, form an N-heterocyclyl;

$R_{12}$ is hydrogen or alkyl;

$R_{13}$ is alkyl, carbocyclyl or aryl;

W is —C($R_{14}$)($R_{15}$)—, —O—, —S—, —S(=O)—, —S(=O)$_2$— or —N($R_{12}$)—;

Y is —C($R_{16}$)($R_{17}$)—;

$R_{14}$ and $R_{15}$ are each the same or different and independently hydrogen, halogen, alkyl, fluoroalkyl, —$OR_{12}$, —$NR_{18}R_{19}$ or carbocyclyl; or $R_{14}$ and $R_{15}$ form an oxo;

$R_{16}$ and $R_{17}$ are each the same or different and independently hydrogen, halogen, alkyl, fluoroalkyl, —$OR_{12}$, —$NR_{18}R_{19}$ or carbocyclyl; or $R_{16}$ and $R_{17}$ form an oxo; or $R_{14}$ and $R_{16}$ together form a direct bond to provide a double bond connecting W and Y; or $R_{14}$ and $R_{16}$ together form a direct bond, and $R_{15}$ and $R_{17}$ together form a direct bond to provide a triple bond connecting W and Y;

$R_{18}$ and $R_{19}$ are each the same or different and independently hydrogen, alkyl, carbocyclyl, or —C(=O)$R_{13}$, p is 0, 1, 2, 3, 4, 5, 7, 8 or 9; and each $R_{21}$ is the same or different and independently alkyl, —$OR_{12}$, alkenyl, alkynyl, halo, fluoroalkyl or aralkyl.

In certain embodiments, W is —C($R_{14}$)($R_{15}$)— and the linkage —W—Y—C($R_7$)($R_8$)— is an alkylene chain. Thus, the compound has a structure of Formula (IIIa):

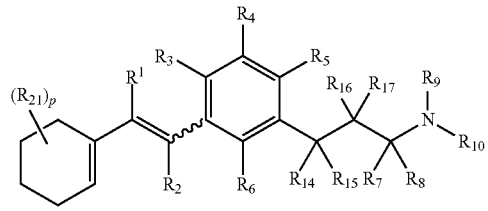

Formula (IIIa)

as an isolated E or Z stereoisomer or a mixture of E and Z stereoisomers, as a tautomer or a mixture of tautomers, or as a pharmaceutically acceptable salt, hydrate, solvate, N-oxide or prodrug thereof, wherein:

$R_1$ and $R_2$ are each the same or different and independently hydrogen or alkyl;

$R_3$, $R_4$, $R_5$ and $R_6$ are each the same or different and independently hydrogen, halogen, —$OR_{12}$, alkyl or fluoroalkyl;

$R_7$ and $R_8$ are each the same or different and independently hydrogen or alkyl;

$R_9$ is hydrogen, alkyl, carbocyclyl or —C(=O)$R_{13}$;

$R_{10}$ is hydrogen or alkyl; or $R_9$ and $R_{10}$, together with the nitrogen atom to which they are attached, form an N-heterocyclyl;

$R_{12}$ is hydrogen or alkyl;

$R_{13}$ is alkyl, carbocyclyl or aryl;

$R_{14}$ and $R_{15}$ are each the same or different and independently hydrogen, halogen, alkyl, fluoroalkyl, —$OR_{12}$, —$NR_{18}R_{19}$ or carbocyclyl; or $R_{14}$ and $R_{15}$ form an oxo;

$R_{16}$ and $R_{17}$ are each the same or different and independently hydrogen, halogen, alkyl, fluoroalkyl, —$OR_{12}$, —$NR_{18}R_{19}$ or carbocyclyl; or $R_{16}$ and $R_{17}$ form an oxo; or $R_{14}$ and $R_{16}$ together form a direct bond to provide a double bond connecting W and Y; or $R_{14}$ and $R_{16}$ together form a direct bond, and $R_{15}$ and $R_{17}$ together form a direct bond to provide a triple bond connecting W and Y;

$R_{18}$ and $R_{19}$ are each the same or different and independently hydrogen, alkyl, carbocyclyl, or —C(=O)$R_{13}$, p is 0, 1, 2, 3, 4, 5, 7, 8 or 9; and each $R_{21}$ is the same or different and independently alkyl, —$OR_{12}$, alkenyl, alkynyl, halo, fluoroalkyl or aralkyl.

One embodiment provides a compound having a structure of Formula (IIIa) wherein each of $R_9$ and $R_{10}$ is hydrogen.

In certain embodiments, each of $R_1$ and $R_2$ is hydrogen, p is 0, 1, 2 or 3, each $R_{21}$ is independently alkyl, halo or fluoroalkyl, and each of $R_3$, $R_4$, $R_5$ and $R_6$ is independently hydrogen, alkyl, halo, fluoroalkyl or —$OR_{12}$.

In other certain embodiments, $R_7$, $R_8$, $R_{14}$, $R_{15}$, $R_{16}$ and $R_{17}$ are each independently hydrogen, halogen, alkyl, fluoroalkyl, —$OR_{12}$ or —$NR_{18}R_{19}$, wherein $R_{12}$ is hydrogen or alkyl, and $R_{18}$ and $R_{19}$ are each independently hydrogen or alkyl. In certain specific embodiments, a compound of formula (I), (III) or (IIIa) has a structure as shown in Table 6.

TABLE 6

| Compound No. | Chemical Formula | Chemical Name |
|---|---|---|
| 21 | ![structure] | (E)-3-(3-(2-(2,6,6-trimethylcyclohexyl-1-enyl)vinyl)phenyl)propan-1-amine |

TABLE 6-continued

| Compound No. | Chemical Formula | Chemical Name |
|---|---|---|
| 25 | | (E)-3-amino-1-(3-(2-(2,6,6-trimethylcyclohex-1-enyl)vinyl)phenyl)propan-1-ol |
| 105 | | (S,E)-3-amino-1-(3-(2-(2,6,6-trimethylcyclohex-1-enyl)vinyl)phenyl)propan-1-ol |
| 106 | | (R,E)-3-Amino-1-(3-(2-(2,6,6-trimethylcyclohex-1-enyl)vinyl)phenyl)propan-1-ol |
| 26 | | (E)-2-methyl-3-(3-(2-(2,6,6-trimethylcyclohex-1-enyl)vinyl)phenyl)propan-1-amine |
| 27 | | (E)-3-(3-(2-(2,6,6-trimethylcyclohex-1-enyl)vinyl)phenyl)butan-1-amine |
| 53 | | (E)-3-(2-methyl-5-(2-(2,6,6-trimethylcyclohex-1-enyl)vinyl)phenyl)propan-1-amine |
| 54 | | (E/Z)-4-amino-2-(3-(2-(2,6,6-trimethylcyclohex-1-enyl)vinyl)phenyl)butan-2-ol |
| 55 | | (E)-3-fluoro-3-(3-(2-(2,6,6-trimethylcyclohex-1-enyl)vinyl)phenyl)propan-1-amine |
| 57 | | (E)-4-amino-1,1,1-trifluoro-2-(3-(2-(2,6,6-trimethylcyclohex-1-enyl)vinyl)phenyl)butan-2-ol |

TABLE 6-continued

| Compound No. | Chemical Formula | Chemical Name |
| --- | --- | --- |
| 58 | | (E)-3-amino-2,2-dimethyl-1-(3-(2-(2,6,6-trimethylcyclohex-1-enyl)vinyl)phenyl)propan-1-ol |
| 59 | | (E)-3-amino-2-methyl-1-(3-(2-(2,6,6-trimethylcyclohex-1-enyl)vinyl)phenyl)propan-1-ol |
| 61 | | (E)-1-(3-(2-(2,6,6-trimethylcyclohex-1-enyl)vinyl)phenyl)propane-1,3-diamine |
| 62 | | (E)-4,4,4-trifluoro-3-(3-(2-(2,6,6-trimethylcyclohex-1-enyl)vinyl)phenyl)butan-1-amine |
| 64 | | (E)-3-methoxy-3-(3-(2-(2,6,6-trimethylcyclohex-1-enyl)vinyl)phenyl)propan-1-amine |
| 65 | | (E)-4-(3-(2-(2,6,6-trimethylcyclohex-1-enyl)vinyl)phenyl)butan-2-amine |
| 66 | | (E)-1-amino-3-(3-(2-(2,6,6-trimethylcyclohex-1-enyl)vinyl)phenyl)propan-2-ol |
| 111 | | (E)-1-(3-(3-amino-1-hydroxypropyl)styryl)cyclohexanol |
| 113 | | (E)-1-(3-((1R,2R)-3-amino-1-hydroxy-2-methylpropyl)styryl)cyclohexanol |

TABLE 6-continued

| Compound No. | Chemical Formula | Chemical Name |
| --- | --- | --- |
| 114 | | (E)-1-(3-(3-amino-1-hydroxypropyl)-5-fluorostyryl)cyclohexanole |
| 115 | | (E)-1-(3-(3-amino-1-hydroxypropyl)-2-fluorostyryl)cyclohexanol |
| 116 | | (E)-4-(3-(3-amino-1-hydroxypropyl)styryl)heptan-4-ol |
| 117 | | (1S,2S)-3-amino-1-(3-((E)-2-(1-hydroxycyclohexyl)vinyl)phenyl)propane-1,2-diol |
| 118 | | (1R,2R)-3-amino-1-(3-((E)-2-(1-hydroxycyclohexyl)vinyl)phenyl)propane-1,2-diol |
| 120 | | (E)-1-(5-(3-amino-1-hydroxypropyl)-2-methoxystyryl)cyclohexanol |
| 121 | | (E)-1-(3-(3-amino-1-hydroxypropyl)-4-chlorostyryl)cyclohexanol |
| 122 | | (E)-1-(3-(3-amino-1-hydroxypropyl)-4-methylstyryl)cyclohexanol |
| 123 | | (E)-1-(3-(3-amino-1-hydroxypropyl)-5-methylstyryl)cyclohexanol |

TABLE 6-continued

| Compound No. | Chemical Formula | Chemical Name |
| --- | --- | --- |
| 124 | | (1S,2R)-3-amino-1-(3-((E)-2-(1-hydroxycyclohexyl)vinyl)phenyl)propane-1,2-diol |
| 125 | | (E)-2-(3-(3-amino-1-hydroxypropyl)styryl)cyclohexanol |
| 126 | | (E)-1-(5-(3-amino-1-hydroxypropyl)-2-fluorostyryl)cyclohexanol |
| 127 | | (E)-1-(3-(3-amino-1-hydroxypropyl)-5-methoxystyryl)cyclohexanol |
| 128 | | (E)-1-(3-(3-amino-1-hydroxypropyl)-4-fluorostyryl)cyclohexanol |
| 129 | | (1R,2S)-3-amino-1-(3-((E)-2-(1-hydroxycyclohexyl)vinyl)phenyl)propane-1,2-diol |
| 130 | | (E)-1-(3-(3-amino-1-hydroxypropyl)-5-chlorostyryl)cyclohexanol |
| 131 | | (E)-1-(3-(3-amino-1-hydroxypropyl)-2-methoxystyryl)cyclohexanol |

Another embodiment provides a compound having a structure of Formula (IIIa) wherein $R_9$ is alkyl and $R_{10}$ is hydrogen.

In certain embodiments, each of $R_1$ and $R_2$ is hydrogen, p is 0, 1, 2 or 3, each $R_{21}$ is independently alkyl, halo or fluoroalkyl, and each of $R_3$, $R_4$, $R_5$ and $R_6$ is independently hydrogen, alkyl, halo, fluoroalkyl or —$OR_{12}$.

In certain embodiments, $R_7$, $R_8$, $R_{14}$, $R_{15}$, $R_{16}$ and $R_{17}$ are each independently hydrogen, halogen, alkyl, fluoroalkyl or —$OR_{12}$, wherein $R_{12}$ is hydrogen or alkyl. In certain specific embodiments, the compound of formula (III) and (IIIa) has a structure shown in Table 7.

TABLE 7

| Compound No. | Chemical Formula | Chemical Name |
|---|---|---|
| 42 | 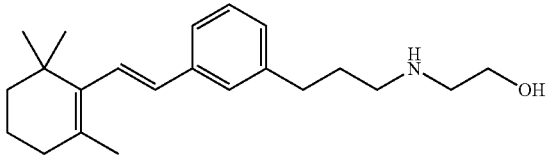 [SMILES: CC1=C(/C=C/c2cccc(CCCNCCO)c2)C(C)(C)CCC1] | (E)-2-(3-(3-(2-(2,6,6-trimethylcyclohex-1-enyl)vinyl)phenyl)propylamino)ethanol |
| 63 | 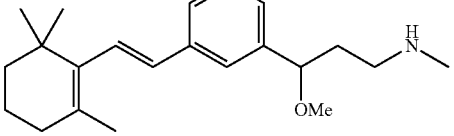 | (E)-3-methoxy-N-methyl-3-(3-(2-(2,6,6-trimethylcyclohex-1-enyl)vinyl)phenyl)propan-1-amine |

Another embodiment provides a compound of Formula (IIIa), wherein $R_7$, $R_8$, $R_{16}$ and $R_{17}$ are each independently hydrogen, halogen, alkyl, fluoroalkyl or —$OR_{12}$, wherein $R_{12}$ is hydrogen or alkyl, and $R_{14}$ and $R_{15}$ together form oxo. In certain specific embodiments, a compound of formula (III) and (IIIa) has a structure shown in Table 8.

TABLE 8

| Compound No. | Chemical Formula | Chemical Name |
|---|---|---|
| 56 | 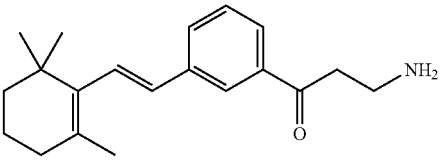 | (E)-3-amino-1-(3-(2-(2,6,6-trimethylcyclohex-1-enyl)vinyl)phenyl)propan-1-one |
| 60 | 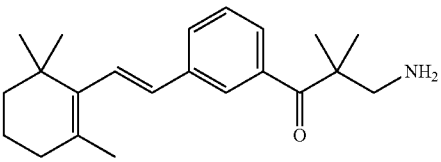 [SMILES: CC1=C(/C=C/c2cccc(C(=O)C(C)(C)CN)c2)C(C)(C)CCC1] | (E)-3-amino-2,2-dimethyl-1-(3-(2-(2,6,6-trimethylcyclohex-1-enyl)vinyl)phenyl)propan-1-one |
| 72 | 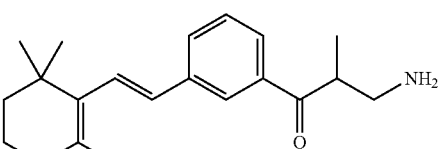 | (E)-3-amino-2-methyl-1-(3-(2-(2,6,6-trimethylcyclohex-1-enyl)vinyl)phenyl)propan-1-one |
| 73 | 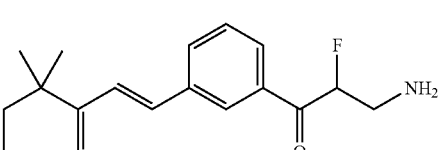 | (E)-3-amino-2-fluoro-1-(3-(2-(2,6,6-trimethylcyclohex-1-enyl)vinyl)phenyl)propan-1-one |

A further embodiment provides a compound having a structure of Formula (III) wherein W is —NH— or —O—.

In one embodiment, each of $R_1$, $R_2$, $R_9$ and $R_{10}$ is hydrogen.

In certain embodiments, p is 0, 1, 2 or 3, each $R_{21}$ is independently alkyl or halo, and $R_3$, $R_4$, $R_5$ and $R_6$ are each independently hydrogen, alkyl, halo or fluoroalkyl. In certain embodiments, the compounds of Formula (I) or (III) are those shown in Table 9.

TABLE 9

| Compound No. | Chemical Formula | Chemical Name |
|---|---|---|
| 31 |  | (E)-2-(3-(2-(2,6,6-trimethylcyclohex-1-enyl)vinyl)phenoxy)ethanamine |
| 30 |  | (E)-2-amino-N-(3-(2-(2,6,6-trimethylcyclohex-1-enyl)vinyl)phenyl)acetamide |

A further embodiment provides a compound having a structure of Formula (III) wherein W and Y are connected by a double or triple bond.

In one embodiment, each of $R_1$, $R_2$, $R_9$ and $R_{10}$ is hydrogen.

In certain embodiments, p is 0, 1, 2 or 3, each $R_{21}$ is independently alkyl or halo, $R_3$, $R_4$, $R_5$ and $R_6$ are each independently hydrogen, alkyl, halo or fluoroalkyl, and $R_{15}$ and $R_{17}$ are each independently hydrogen, alkyl or halogen. In certain specific embodiments, a compound of Formula (I) or (III) has a structure shown in Table 10.

TABLE 10

| Compound No. | Chemical Formula | Chemical Name |
|---|---|---|
| 68 |  | (E)-3-(3-(2-(2,6,6-trimethylcyclohex-1-enyl)vinyl)phenyl)prop-2-yn-1-amine |
| 67 |  | (E)-2-fluoro-3-(3-((E)-2-(2,6,6-trimethylcyclohex-1-enyl)vinyl)phenyl)prop-2-en-1-amine |

A further embodiment provides a compound having a structure of Formula (I) wherein $R_{11}$ is alkyl.

In one embodiment, each of $R_9$ and $R_{10}$, is hydrogen.

In certain embodiments, W is —C($R_{14}$)($R_{15}$)— and the linkage —W—Y—C($R_7$)($R_8$)— is an alkylene chain. In certain embodiments, $R_1$, $R_2$, $R_3$, $R_4$, $R_5$ and $R_6$ are each independently hydrogen or alkyl.

In certain specific embodiments, a compound of Formula (I) wherein $R_{11}$ is alkyl has a structure shown in Table 11.

TABLE 11

| Compound No. | Chemical Formula | Chemical Name |
|---|---|---|
| 23 | | (E)-3-(3-(pent-1-enyl)phenyl)propan-1-amine |
| 24 | | (E)-3-(3-(hept-1-enyl)phenyl)propan-1-amine |
| 69 | | (E)-3-(3-(non-4-en-5-yl)phenyl)propan-1-amine |
| 79 | | (E)-4-(3-(3-aminopropyl)phenyl)-2-methylbut-3-en-2-ol |
| 83 | | (E)-4-(3-(3-aminopropyl)styryl)heptan-4-ol |
| 84 | | (E)-1-(3-(3-aminopropyl)phenyl)hex-1-en-3-ol |
| 85 | | (E)-4-(3-(2-aminoethoxy)styryl)heptan-4-ol |
| 100 | | (E)-1-(3-(3-aminopropyl)phenyl)-3-ethylpent-1-en-3-ol |
| 101 | | (E)-3-(3-(3-aminopropyl)phenyl)prop-2-en-1-ol |
| 102 | | (E)-3-(3-(3-methoxyprop-1-enyl)phenyl)propan-1-amine |

TABLE 11-continued

| Compound No. | Chemical Formula | Chemical Name |
| --- | --- | --- |
| 103 | | (E)-1-(3-(3-aminopropyl)phenyl)-3-methylhex-1-en-3-ol |
| 104 | | (E)-1-(3-(3-aminopropyl)phenyl)-3-ethylhex-1-en-3-ol |

In certain specific embodiments, a compound of Formula (A) has a structure shown in Table 12.

TABLE 12

| | | |
| --- | --- | --- |
| 132 | | (E)-4-(3-(2,6-Dimethylstyryl)phenyl)butan-1-amine |
| 133 | | 1-(3-(2,6-Dimethylstyryl)phenyl)-N,N-dimethylmethanamine |
| 134 | | 4-(3-(2,6-Dimethylstyryl)benzyl)morpholine |
| 135 | | (E)-(3-(2-(2,6,6-trimethylcyclohex-1-enyl)vinyl)phenyl)methanamine |
| 136 | | (E)-(3-(2-(2,6,6-trimethylcyclohex-1-enyl)vinyl)phenyl)methanamine |
| 137 | | (E)-(3-(2-(2,6,6-trimethylcyclohex-1-enyl)vinyl)phenyl)methanamine |

DEFINITIONS

As used in the specification and appended claims, unless specified to the contrary, the following terms have the meaning indicated:

As used herein and in the appended claims, the singular forms "a," "and," and "the" include plural referents unless the context clearly dictates otherwise. Thus, for example, reference to "a compound" includes a plurality of such compounds, and reference to "the cell" includes reference to one or more cells (or to a plurality of cells) and equivalents thereof known to those skilled in the art, and so forth. When ranges are used herein for physical properties, such as molecular weight, or chemical properties, such as chemical formulae, all combinations and subcombinations of ranges and specific embodiments therein are intended to be included. The term "about" when referring to a number or a numerical range means that the number or numerical range referred to is an approximation within experimental variability (or within statistical experimental error), and thus the number or numerical range may vary between 1% and 15% of the stated number or numerical range. The term "comprising" (and related terms such as "comprise" or "comprises" or "having" or "including") is not intended to exclude that in other certain embodiments, for example, an embodiment of any composition of matter, composition, method, or process, or the like, described herein, may "consist of" or "consist essentially of" the described features.

"Amino" refers to the $NH_2$ radical.
"Cyano" refers to the —CN radical.
"Nitro" refers to the —$NO_2$ radical.
"Oxa" refers to the —O— radical.
"Oxo" refers to the =O radical.
"Oximo" refers to the =N—OH radical.
"Imino" refers to the =N—H radical.
"Hydrazino" refers to the =N—$NH_2$ radical.
"Thioxo" refers to the =S radical.

"Alkyl" refers to a straight or branched hydrocarbon chain radical consisting solely of carbon and hydrogen atoms, containing no unsaturation, having from one to fifteen carbon atoms. In certain embodiments, an alkyl comprises one to eight carbon atoms. In other embodiments, an alkyl comprises one to six carbon atoms. The alkyl is attached to the rest of the molecule by a single bond, for example, methyl (Me), ethyl (Et), n-propyl, 1-methylethyl (iso-propyl), n-butyl, n-pentyl, 1,1-dimethylethyl (t-butyl), 3-methylhexyl, 2-methylhexyl, and the like. Unless stated otherwise specifically in the specification, an alkyl group is optionally substituted by one or more of the following substituents: halo, cyano, nitro, oxo, thioxo, trimethylsilanyl, —$OR^a$, —$SR^a$, —OC(O)—$R^a$, —$N(R^a)_2$, —C(O)$R^a$, —C(O)O$R^a$, —C(O)N($R^a)_2$, —N($R^a$)C(O)O$R^a$, —N($R^a$)C(O)$R^a$, —N($R^a$)S(O)$_t R^a$ (where t is 1 or 2), —S(O)$_t OR^a$ (where t is 1 or 2) and —S(O)$_t$N($R^a)_2$ (where t is 1 or 2) where each $R^a$ is independently hydrogen, alkyl, fluoroalkyl, carbocyclyl carbocyclylalkyl, aryl, aralkyl, heterocyclyl, heterocyclylalkyl, heteroaryl or heteroarylalkyl.

"Alkenyl" refers to a straight or branched hydrocarbon chain radical group consisting solely of carbon and hydrogen atoms, containing at least one double bond, and having from two to twelve carbon atoms. In certain embodiments, an alkenyl comprises two to eight carbon atoms. In other embodiments, an alkenyl comprises two to four carbon atoms. The alkenyl is attached to the rest of the molecule by a single bond, for example, ethenyl (i.e., vinyl), prop-1-enyl (i.e., allyl), but-1-enyl, pent-1-enyl, penta-1,4-dienyl, and the like. Unless stated otherwise specifically in the specification, an alkenyl group is optionally substituted by one or more of the following substituents: halo, cyano, nitro, oxo, thioxo, trimethylsilanyl, —$OR^a$, —$SR^a$, —OC(O)—$R^a$, —$N(R^a)_2$, —C(O)$R^a$, —C(O)O$R^a$, —C(O)N($R^a)_2$, —N($R^a$)C(O)O$R^a$, —N($R^a$)C(O)$R^a$, —N($R^a$)S(O)$_t R^a$ (where t is 1 or 2), —S(O)$_t OR^a$ (where t is 1 or 2) and —S(O), N($R^a)_2$ (where t is 1 or 2) where each $R^a$ is independently hydrogen, alkyl, fluoroalkyl, carbocyclyl carbocyclylalkyl, aryl, aralkyl, heterocyclyl, heterocyclylalkyl, heteroaryl or heteroarylalkyl.

"Alkynyl" refers to a straight or branched hydrocarbon chain radical group consisting solely of carbon and hydrogen atoms, containing at least one triple bond, having from two to twelve carbon atoms. In certain embodiments, an alkynyl comprises two to eight carbon atoms. In other embodiments, an alkynyl has two to four carbon atoms. The alkynyl is attached to the rest of the molecule by a single bond, for example, ethynyl, propynyl, butynyl, pentynyl, hexynyl, and the like. Unless stated otherwise specifically in the specification, an alkynyl group is optionally substituted by one or more of the following substituents: halo, cyano, nitro, oxo, thioxo, trimethylsilanyl, —$OR^a$, —$SR^a$, —OC(O)—$R^a$, —$N(R^a)_2$, —C(O)$R^a$, —C(O)O$R^a$, —C(O)N($R^a)_2$, —N($R^a$)C(O)O$R^a$, —N($R^a$)C(O)$R^a$, —N($R^a$)S(O)$_t R^a$ (where t is 1 or 2), —S(O)$_t OR^a$ (where t is 1 or 2) and —S(O)$_t$N($R^a)_2$ (where t is 1 or 2) where each $R^a$ is independently hydrogen, alkyl, fluoroalkyl, carbocyclyl carbocyclylalkyl, aryl, aralkyl, heterocyclyl, heterocyclylalkyl, heteroaryl or heteroarylalkyl.

"Alkylene" or "alkylene chain" refers to a straight or branched divalent hydrocarbon chain linking the rest of the molecule to a radical group, consisting solely of carbon and hydrogen, containing no unsaturation and having from one to twelve carbon atoms, for example, methylene, ethylene, propylene, n-butylene, and the like. The alkylene chain is attached to the rest of the molecule through a single bond and to the radical group through a single bond. The points of attachment of the alkylene chain to the rest of the molecule and to the radical group can be through one carbon in the alkylene chain or through any two carbons within the chain. Unless stated otherwise specifically in the specification, an alkylene chain is optionally substituted by one or more of the following substituents: halo, cyano, nitro, aryl, cycloalkyl, heterocyclyl, heteroaryl, oxo, thioxo, trimethylsilanyl, —$OR^a$, —$SR^a$, —OC(O)—$R^a$, —$N(R^a)_2$, —C(O)$R^a$, —C(O)O$R^a$, —C(O)N($R^a)_2$, —N($R^a$)C(O)O$R^a$, —N($R^a$)C(O)$R^a$, —N($R^a$)S(O)$_t R^a$ (where t is 1 or 2), —S(O)$_t OR^a$ (where t is 1 or 2) and —S(O), N($R^a)_2$ (where t is 1 or 2) where each $R^a$ is independently hydrogen, alkyl, fluoroalkyl, carbocyclyl carbocyclylalkyl, aryl, aralkyl, heterocyclyl, heterocyclylalkyl, heteroaryl or heteroarylalkyl.

"Alkenylene" or "alkenylene chain" refers to a straight or branched divalent hydrocarbon chain linking the rest of the molecule to a radical group, consisting solely of carbon and hydrogen, containing at least one double bond and having from two to twelve carbon atoms, for example, ethenylene, propenylene, n-butenylene, and the like. The alkenylene chain is attached to the rest of the molecule through a double bond or a single bond and to the radical group through a double bond or a single bond. The points of attachment of the alkenylene chain to the rest of the molecule and to the radical group can be through one carbon or any two carbons within the chain. Unless stated otherwise specifically in the specification, an alkenylene chain is optionally substituted by one or more of the following substituents: halo, cyano, nitro, aryl, cycloalkyl, heterocyclyl, heteroaryl, oxo, thioxo, trimethylsilanyl, —$OR^a$, —$SR^a$, —OC(O)—$R^a$, —$N(R^a)_2$, —C(O)$R^a$, —C(O)O$R^a$, —C(O)N($R^a)_2$, —N($R^a$)C(O)O$R^a$, —N($R^a$)C(O)$R^a$, —N($R^a$)S(O)$_t R^a$ (where t is 1 or 2), —S(O)$_t OR^a$ (where t is 1 or 2) and —S(O)$_t$N($R^a)_2$ (where t is 1 or 2) where each $R^a$ is independently hydrogen, alkyl, fluoroalkyl, cycloalkyl, cycloalkylalkyl, aryl (optionally substituted with one or more halo groups), aralkyl, heterocyclyl, heterocyclylalkyl, heteroaryl or heteroarylalkyl, and where each of the above substituents is unsubstituted unless otherwise indicated.

"Aryl" refers to a radical derived from an aromatic monocyclic or multicyclic hydrocarbon ring system by removing a hydrogen atom from a ring carbon atom. The aromatic monocyclic or multicyclic hydrocarbon ring system contains only hydrogen and carbon from six to eighteen carbon atoms, where at least one of the rings in the ring system is fully unsaturated, i.e., it contains a cyclic, delocalized (4n+2) π-electron system in accordance with the Hückel theory. Aryl groups include, but are not limited to, groups such as phenyl, fluorenyl, and naphthyl. Unless stated otherwise specifically in the specification, the term "aryl" or the prefix "ar-" (such as in "aralkyl") includes aryl radicals optionally substituted by one or more substituents independently selected from alkyl, alkenyl, alkynyl, halo, fluoroalkyl, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —$R^b$—$OR^a$, —$R^b$—$OC(O)$—$R^a$, —$R^b$—$N(R^a)_2$, —$R^b$—$C(O)R^a$, —$R^b$—$C(O)OR^a$, —$R^b$—$C(O)N(R^a)_2$, —$R^b$—O—$R^c$—$C(O)N(R^a)_2$, —$R^b$—$N(R^a)C(O)OR^a$, —$R^b$—$N(R^a)C(O)R^a$, —$R^b$—$N(R^a)S(O)_tR^a$ (where t is 1 or 2), —$R^b$—$S(O)_tOR^a$ (where t is 1 or 2) and —$R^b$—$S(O)_tN(R^a)_2$ (where t is 1 or 2), where each $R^a$ is independently hydrogen, alkyl, fluoroalkyl, cycloalkyl, cycloalkylalkyl, aryl (optionally substituted with one or more halo groups), aralkyl, heterocyclyl, heterocyclylalkyl, heteroaryl or heteroarylalkyl, each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"Aralkyl" refers to a radical of the formula —$R^d$-aryl where $R^c$ is an alkylene chain as defined above, for example, benzyl, diphenylmethyl and the like. The alkylene chain part of the aralkyl radical is optionally substituted as described above for an alkylene chain. The aryl part of the aralkyl radical is optionally substituted as described above for an aryl group.

"Aralkenyl" refers to a radical of the formula —$R^d$-aryl where $R^d$ is an alkenylene chain as defined above. The aryl part of the aralkenyl radical is optionally substituted as described above for an aryl group. The alkenylene chain part of the aralkenyl radical is optionally substituted as defined above for an alkenylene group.

"Aralkynyl" refers to a radical of the formula —$R^e$-aryl, where $R^e$ is an alkynylene chain as defined above. The aryl part of the aralkynyl radical is optionally substituted as described above for an aryl group. The alkynylene chain part of the aralkynyl radical is optionally substituted as defined above for an alkynylene chain.

"Carbocyclyl" refers to a stable non-aromatic monocyclic or polycyclic hydrocarbon radical consisting solely of carbon and hydrogen atoms, which include fused or bridged ring systems, having from three to fifteen carbon atoms. In certain embodiments, a carbocyclyl comprises three to ten carbon atoms. In other embodiments, a carbocyclyl comprises five to seven carbon atoms. The carbocyclyl is attached to the rest of the molecule by a single bond. Carbocyclyl is saturated, (i.e., containing single C—C bonds only) or unsaturated (i.e., containing one or more double bonds or triple bonds.) A fully saturated carbocyclyl radical is also referred to as "cycloalkyl." Examples of monocyclic cycloalkyls include, e.g., cyclopropyl, cyclobutyl, cyclopentyl, cyclohexyl, cycloheptyl, and cyclooctyl. An unsaturated carbocyclyl is also referred to as "cycloalkenyl." Examples of monocyclic cycloalkenyls include, e.g., cyclopentenyl, cyclohexenyl, cycloheptenyl, and cyclooctenyl. Polycyclic carbocyclyl radicals include, for example, adamantyl, norbornyl (i.e., bicyclo[2.2.1]heptanyl), norbornenyl, decalinyl, 7,7-dimethyl-bicyclo[2.2.1]heptanyl, and the like. Unless otherwise stated specifically in the specification, the term "carbocyclyl" includes carbocyclyl radicals that are optionally substituted by one or more substituents independently selected from alkyl, alkenyl, alkynyl, halo, fluoroalkyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —$R^b$—$OR^a$, —$R^b$—$SR^a$, —$R^b$—$OC(O)$—$R^a$, —$R^b$—$N(R^a)_2 R^b$—$C(O)R^a$, —$R^b$—$C(O)OR^a$, —$R^b$—$C(O)N(R^a)_2$, —$R^b$—$N(R^a)C(O)OR^a$, —$R^b$—$N(R^a)C(O)R^a$, —$R^b$—$N(R^a)S(O)_tR^a$ (where t is 1 or 2), —$R^b$—$S(O)_tOR^a$ (where t is 1 or 2) and —$R^b$—$S(O)_tN(R^a)_2$ (where t is 1 or 2), where each $R^a$ is independently hydrogen, alkyl, fluoroalkyl, cycloalkyl, cycloalkylalkyl, aryl, aralkyl, heterocyclyl, heterocyclylalkyl, heteroaryl or heteroarylalkyl, each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"Carbocyclylalkyl" refers to a radical of the formula —$R^c$-carbocyclyl where $R^c$ is an alkylene chain as defined above. The alkylene chain and the carbocyclyl radical is optionally substituted as defined above.

"Halo" or "halogen" refers to bromo, chloro, fluoro or iodo.

"Fluoroalkyl" refers to an alkyl radical, as defined above, that is substituted by one or more fluoro radicals, as defined above, for example, trifluoromethyl, difluoromethyl, 2,2,2-trifluoroethyl, 1-fluoromethyl-2-fluoroethyl, and the like. The alkyl part of the fluoroalkyl radical is optionally substituted as defined above for an alkyl group.

"Heterocyclyl" refers to a stable 3- to 18-membered non-aromatic ring radical that comprises two to twelve carbon atoms and from one to six heteroatoms selected from nitrogen, oxygen and sulfur. Unless stated otherwise specifically in the specification, the heterocyclyl radical is a monocyclic, bicyclic, tricyclic or tetracyclic ring system, which includes fused or bridged ring systems. The heteroatoms in the heterocyclyl radical are optionally oxidized. One or more nitrogen atoms, if present, are optionally quaternized. The heterocyclyl radical is partially or fully saturated. The heterocyclyl is attached to the rest of the molecule through any atom of the ring(s). Examples of such heterocyclyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl. Unless stated otherwise specifically in the specification, the term "heterocyclyl" includes heterocyclyl radicals as defined above that are optionally substituted by one or more substituents selected from alkyl, alkenyl, alkynyl, halo, fluoroalkyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, $-R^b-OR^a$, $-R^b-SR^a$, $-R^b-OC(O)-R^a$, $-R^b-N(R^a)_2$, $-R^b-C(O)R^a$, $-R^b-C(O)OR^a$, $-R^b-C(O)N(R^a)_2$, $-R^b-O-R'-C(O)N(R^a)_2$, $-R^b-N(R^a)C(O)OR^a$, $-R^b-N(R^a)C(O)R^a$, $-R^b-N(R^a)S(O)_tR^a$ (where t is 1 or 2), $-R^b-S(O)_tOR^a$ (where t is 1 or 2) and $-R^b-S(O)_tN(R^a)_2$ (where t is 1 or 2), where each $R^a$ is independently hydrogen, alkyl, fluoroalkyl, cycloalkyl, cycloalkylalkyl, aryl, aralkyl, heterocyclyl, heterocyclylalkyl, heteroaryl or heteroarylalkyl, each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"N-heterocyclyl" refers to a heterocyclyl radical as defined above containing at least one nitrogen and where the point of attachment of the heterocyclyl radical to the rest of the molecule is through a nitrogen atom in the heterocyclyl radical. An N-heterocyclyl radical is optionally substituted as described above for heterocyclyl radicals. Examples of such N-heterocyclyl radicals include, but are not limited to, morpholinyl, piperidinyl, piperazinyl, pyrrolidinyl, pyrazolidinyl, imidazolinyl, and imidazolidinyl.

"Heterocyclylalkyl" refers to a radical of the formula $-R^c$-heterocyclyl where $R^c$ is an alkylene chain as defined above. If the heterocyclyl is a nitrogen-containing heterocyclyl, the heterocyclyl is attached to the alkyl radical at the nitrogen atom. The alkylene chain of the heterocyclylalkyl radical is optionally substituted as defined above for an alkylene chain. The heterocyclyl part of the heterocyclylalkyl radical is optionally substituted as defined above for a heterocyclyl group.

"Heteroaryl" refers to a radical derived from a 3- to 18-membered aromatic ring radical that comprises two to seventeen carbon atoms and from one to six heteroatoms selected from nitrogen, oxygen and sulfur. As used herein, the heteroaryl radical is a monocyclic, bicyclic, tricyclic or tetracyclic ring system, wherein at least one of the rings in the ring system is fully unsaturated, i.e., it contains a cyclic, delocalized (4n+2) π-electron system in accordance with the Hückel theory. Heteroaryl groups include fused or bridged ring systems. The heteroatoms in the heteroaryl radical are optionally oxidized. One or more nitrogen atoms, if present, are optionally quaternized. The heteroaryl is attached to the rest of the molecule through any atom of the ring(s). Examples of heteroaryls include, but are not limited to, azepinyl, acridinyl, benzimidazolyl, benzindolyl, 1,3-benzodioxolyl, benzofuranyl, benzooxazolyl, benzo[d]thiazolyl, benzothiadiazolyl, benzo[b][1,4]dioxepinyl, benzo[b][1,4]oxazinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzothieno[3,2-d]pyrimidinyl, benzotriazolyl, benzo[4,6]imidazo[1,2-a]pyridinyl, carbazolyl, cinnolinyl, cyclopenta[d]pyrimidinyl, 6,7-dihydro-5H-cyclopenta[4,5]thieno[2,3-d]pyrimidinyl, 5,6-dihydrobenzo[h]quinazolinyl, 5,6-dihydrobenzo[h]cinnolinyl, 6,7-dihydro-5H-benzo[6,7]cyclohepta[1,2-c]pyridazinyl, dibenzofuranyl, dibenzothiophenyl, furanyl, furanonyl, furo[3,2-c]pyridinyl, 5,6,7,8,9,10-hexahydrocycloocta[d]pyrimidinyl, 5,6,7,8,9,10-hexahydrocycloocta[d]pyridazinyl, 5,6,7,8,9,10-hexahydrocycloocta[d]pyridinyLisothiazolyl, imidazolyl, indazolyl, indolyl, indazolyl, isoindolyl, indolinyl, isoindolinyl, isoquinolyl, indolizinyl, isoxazolyl, 5,8-methano-5,6,7,8-tetrahydroquinazolinyl, naphthyridinyl, 1,6-naphthyridinonyl, oxadiazolyl, 2-oxoazepinyl, oxazolyl, oxiranyl, 5,6,6a,7,8,9,10,10a-octahydrobenzo[h]quinazolinyl, 1-phenyl-1H-pyrrolyl, phenazinyl, phenothiazinyl, phenoxazinyl, phthalazinyl, pteridinyl, purinyl, pyrrolyl, pyrazolyl, pyrazolo[3,4-d]pyrimidinyl, pyridinyl, pyrido[3,2-d]pyrimidinyl, pyrido[3,4-d]pyrimidinyl, pyrazinyl, pyrimidinyl, pyridazinyl, pyrrolyl, quinazolinyl, quinoxalinyl, quinolinyl, isoquinolinyl, tetrahydroquinolinyl, 5,6,7,8-tetrahydroquinazolinyl, 5,6,7,8-tetrahydrobenzo[4,5]thieno[2,3-d]pyrimidinyl, 6,7,8,9-tetrahydro-5H-cyclohepta[4,5]thieno[2,3-d]pyrimidinyl, 5,6,7,8-tetrahydropyrido[4,5-c]pyridazinyl, thiazolyl, thiadiazolyl, triazolyl, tetrazolyl, triazinyl, thieno[2,3-d]pyrimidinyl, thieno[3,2-d]pyrimidinyl, thieno[2,3-c]pridinyl, and thiophenyl (i.e. thienyl). Unless stated otherwise specifically in the specification, the term "heteroaryl" includes heteroaryl radicals as defined above which are optionally substituted by one or more substituents selected from alkyl, alkenyl, alkynyl, halo, fluoroalkyl, haloalkenyl, haloalkynyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, $-R^b-SR^a$, $-R^b-OC(O)-R^a$, $-R^b-N(R^a)_2$, $-R^b-C(O)R^a$, $-R^b-C(O)OR^a$, $-R^b-C(O)N(R^a)_2$, $-R^b-O-R^c-C(O)N(R^a)_2$, $-R^b-N(R^a)C(O)OR^a$, $-R^b-N(R^a)C(O)R^a$, $-R^b-N(R^a)S(O)_tR^a$ (where t is 1 or 2), $-R^b-S(O)_tOR^a$ (where t is 1 or 2) and $-R^b-S(O)_tN(R^a)_2$ (where t is 1 or 2), where each $R^a$ is independently hydrogen, alkyl, fluoroalkyl, cycloalkyl, cycloalkylalkyl, aryl, aralkyl, heterocyclyl, heterocyclylalkyl, heteroaryl or heteroarylalkyl, each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"N-heteroaryl" refers to a heteroaryl radical as defined above containing at least one nitrogen and where the point of attachment of the heteroaryl radical to the rest of the molecule is through a nitrogen atom in the heteroaryl radical. An N-heteroaryl radical is optionally substituted as described above for heteroaryl radicals.

"Heteroarylalkyl" refers to a radical of the formula $-R^c$-heteroaryl, where $R^c$ is an alkylene chain as defined above. If the heteroaryl is a nitrogen-containing heteroaryl, the heteroaryl is attached to the alkyl radical at the nitrogen atom. The alkylene chain of the heteroarylalkyl radical is optionally substituted as defined above for an alkylene chain. The heteroaryl part of the heteroarylalkyl radical is optionally substituted as defined above for a heteroaryl group.

The compounds, or their pharmaceutically acceptable salts may contain one or more asymmetric centers and may thus give rise to enantiomers, diastereomers, and other stereoisomeric forms that may be defined, in terms of absolute stereochemistry, as (R)- or (S')- or, as (D)- or (L)- for amino acids. When the compounds described herein contain olefinic double bonds or other centers of geometric asymmetry, and unless specified otherwise, it is intended that the compounds include both E and Z geometric isomers (e.g., cis or trans.)

Likewise, all possible isomers, as well as their racemic and optically pure forms, and all tautomeric forms are also intended to be included.

A "stereoisomer" refers to a compound made up of the same atoms bonded by the same bonds but having different three-dimensional structures, which are not interchangeable. It is therefore contemplated that various stereoisomers and mixtures thereof includes "enantiomers," which refers to two stereoisomers whose molecules are nonsuperimposeable mirror images of one another.

A "tautomer" refers to a proton shift from one atom of a molecule to another atom of the same molecule. The compounds presented herein may exist as tautomers. Tautomers are compounds that are interconvertible by migration of a hydrogen atom, accompanied by a switch of a single bond and adjacent double bond. In solutions where tautomerization is possible, a chemical equilibrium of the tautomers will exist. The exact ratio of the tautomers depends on several factors, including temperature, solvent, and pH. Some examples of tautomeric pairs include:

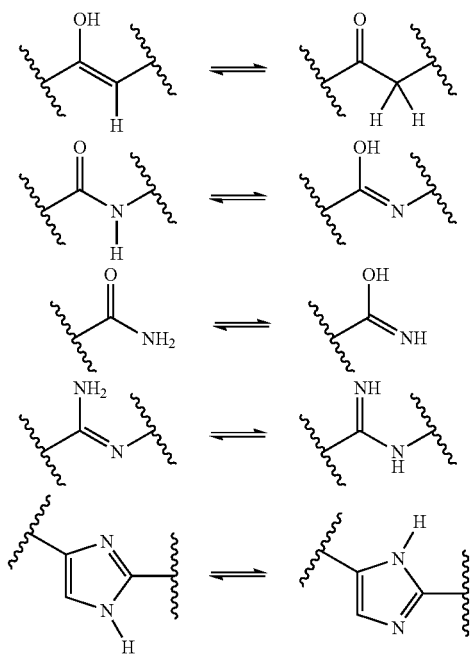

"Optional" or "optionally" means that a subsequently described event or circumstance may or may not occur and that the description includes instances when the event or circumstance occurs and instances in which it does not. For example, "optionally substituted aryl" means that the aryl radical may or may not be substituted and that the description includes both substituted aryl radicals and aryl radicals having no substitution.

"Pharmaceutically acceptable salt" includes both acid and base addition salts. A pharmaceutically acceptable salt of any one of the styrenyl derivative compounds described herein is intended to encompass any and all pharmaceutically suitable salt forms. Preferred pharmaceutically acceptable salts of the compounds described herein are pharmaceutically acceptable acid addition salts and pharmaceutically acceptable base addition salts.

"Pharmaceutically acceptable acid addition salt" refers to those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid, hydroiodic acid, hydrofluoric acid, phosphorous acid, and the like. Also included are salts that are formed with organic acids such as aliphatic mono- and dicarboxylic acids, phenyl-substituted alkanoic acids, hydroxy alkanoic acids, alkanedioic acids, aromatic acids, aliphatic and aromatic sulfonic acids, etc. and include, for example, acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Exemplary salts thus include sulfates, pyrosulfates, bisulfates, sulfites, bisulfites, nitrates, phosphates, monohydrogenphosphates, dihydrogenphosphates, metaphosphates, pyrophosphates, chlorides, bromides, iodides, acetates, trifluoroacetates, propionates, caprylates, isobutyrates, oxalates, malonates, succinate suberates, sebacates, fumarates, maleates, mandelates, benzoates, chlorobenzoates, methylbenzoates, dinitrobenzoates, phthalates, benzenesulfonates, toluenesulfonates, phenylacetates, citrates, lactates, malates, tartrates, methanesulfonates, and the like. Also contemplated are salts of amino acids, such as arginates, gluconates, and galacturonates (see, for example, Berge S. M. et al., "Pharmaceutical Salts," *Journal of Pharmaceutical Science,* 66:1-19 (1997), which is hereby incorporated by reference in its entirety). Acid addition salts of basic compounds may be prepared by contacting the free base forms with a sufficient amount of the desired acid to produce the salt according to methods and techniques with which a skilled artisan is familiar.

"Pharmaceutically acceptable base addition salt" refers to those salts that retain the biological effectiveness and properties of the free acids, which are not biologically or otherwise undesirable. These salts are prepared from addition of an inorganic base or an organic base to the free acid. Pharmaceutically acceptable base addition salts may be formed with metals or amines, such as alkali and alkaline earth metals or organic amines. Salts derived from inorganic bases include, but are not limited to, sodium, potassium, lithium, ammonium, calcium, magnesium, iron, zinc, copper, manganese, aluminum salts and the like. Salts derived from organic bases include, but are not limited to, salts of primary, secondary, and tertiary amines, substituted amines including naturally occurring substituted amines, cyclic amines and basic ion exchange resins, for example, isopropylamine, trimethylamine, diethylamine, triethylamine, tripropylamine, ethanolamine, diethanolamine, 2-dimethylaminoethanol, 2-diethylaminoethanol, dicyclohexylamine, lysine, arginine, histidine, caffeine, procaine, N,N-dibenzylethylenediamine, chloroprocaine, hydrabamine, choline, betaine, ethylenediamine, ethylenedianiline, N-methylglucamine, glucosamine, methylglucamine, theobromine, purines, piperazine, piperidine, N-ethylpiperidine, polyamine resins and the like. See Berge et al., supra.

"Non-retinoid compound" refers to any compound that is not a retinoid. A retinoid is a compound that has a diterpene skeleton possessing a trimethylcyclohexenyl ring and a polyene chain that terminates in a polar end group. Examples of retinoids include retinaldehyde and derived imine/hydrazide/oxime, retinol and any derived ester, retinyl amine and any derived amide, retinoic acid and any derived ester or amide. A non-retinoid compound can comprise though not require an internal cyclic group (e.g., aromatic group). A non-retinoid compound can contain though not require a styrenyl group.

"Prodrugs" is meant to indicate a compound that may be converted under physiological conditions or by solvolysis to a biologically active compound described herein. Thus, the term "prodrug" refers to a precursor of a biologically active compound that is pharmaceutically acceptable. A prodrug may be inactive when administered to a subject, but is converted in vivo to an active compound, for example, by hydrolysis. The prodrug compound often offers advantages of solubility, tissue compatibility or delayed release in a mammalian organism (see, e.g., Bundgard, H., Design of Prodrugs (1985), pp. 7-9, 21-24 (Elsevier, Amsterdam).

A discussion of prodrugs is provided in Higuchi, T., et al., "Pro-drugs as Novel Delivery Systems," A.C.S. Symposium Series, Vol. 14, and in Bioreversible Carriers in Drug Design, ed. Edward B. Roche, American Pharmaceutical Association and Pergamon Press, 1987, both of which are incorporated in full by reference herein.

As used herein, "treatment" or "treating," or "palliating" or "ameliorating" are used interchangeably herein. These terms refers to an approach for obtaining beneficial or desired results including but not limited to therapeutic benefit and/or a prophylactic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient may still be afflicted with the underlying disorder. For prophylactic benefit, the compositions may be administered to a patient at risk of developing a particular disease, or to a patient reporting one or more of the physiological symptoms of a disease, even though a diagnosis of this disease may not have been made.

The term "prodrug" is also meant to include any covalently bonded carriers, which release the active compound in vivo when such prodrug is administered to a mammalian subject. Prodrugs of an active compound, as described herein, may be prepared by modifying functional groups present in the active compound in such a way that the modifications are cleaved, either in routine manipulation or in vivo, to the parent active compound. Prodrugs include compounds wherein a hydroxy, amino or mercapto group is bonded to any group that, when the prodrug of the active compound is administered to a mammalian subject, cleaves to form a free hydroxy, free amino or free mercapto group, respectively. Examples of prodrugs include, but are not limited to, acetate, formate and benzoate derivatives of alcohol or amine functional groups in the active compounds and the like.

Preparation of the Styrenyl Derivative Compounds

In general, the compounds used in the reactions described herein are made according to organic synthesis techniques known to those skilled in this art, starting from commercially available chemicals and/or from compounds described in the chemical literature. "Commercially available chemicals" are obtained from standard commercial sources including Acros Organics (Pittsburgh Pa.), Aldrich Chemical (Milwaukee Wis., including Sigma Chemical and Fluka), Apin Chemicals Ltd. (Milton Park UK), Avocado Research (Lancashire U.K.), BDH Inc. (Toronto, Canada), Bionet (Cornwall, U.K.), Chemservice Inc. (West Chester Pa.), Crescent Chemical Co. (Hauppauge N.Y.), Eastman Organic Chemicals, Eastman Kodak Company (Rochester N.Y.), Fisher Scientific Co. (Pittsburgh Pa.), Fisons Chemicals (Leicestershire UK), Frontier Scientific (Logan Utah), ICN Biomedicals, Inc. (Costa Mesa Calif.), Key Organics (Cornwall U.K.), Lancaster Synthesis (Windham N.H.), Maybridge Chemical Co. Ltd. (Cornwall U.K.), Parish Chemical Co. (Orem Utah), Pfaltz & Bauer, Inc. (Waterbury Conn.), Polyorganix (Houston Tex.), Pierce Chemical Co. (Rockford Ill.), Riedel de Haen A G (Hanover, Germany), Spectrum Quality Product, Inc. (New Brunswick, N.J.), TCI America (Portland Oreg.), Trans World Chemicals, Inc. (Rockville Md.), and Wako Chemicals USA, Inc. (Richmond Va.).

Methods known to one of ordinary skill in the art are identified through various reference books and databases. Suitable reference books and treatise that detail the synthesis of reactants useful in the preparation of compounds described herein, or provide references to articles that describe the preparation, include for example, "Synthetic Organic Chemistry", John Wiley & Sons, Inc., New York; S. R. Sandler et al., "Organic Functional Group Preparations," 2nd Ed., Academic Press, New York, 1983; H. O. House, "Modern Synthetic Reactions", 2nd Ed., W. A. Benjamin, Inc. Menlo Park, Calif. 1972; T. L. Gilchrist, "Heterocyclic Chemistry", 2nd Ed., John Wiley & Sons, New York, 1992; J. March, "Advanced Organic Chemistry: Reactions, Mechanisms and Structure", 4th Ed., Wiley-Interscience, New York, 1992. Additional suitable reference books and treatise that detail the synthesis of reactants useful in the preparation of compounds described herein, or provide references to articles that describe the preparation, include for example, Fuhrhop, J. and Penzlin G. "Organic Synthesis: Concepts, Methods, Starting Materials", Second, Revised and Enlarged Edition (1994) John Wiley & Sons ISBN: 3-527-29074-5; Hoffman, R. V. "Organic Chemistry, An Intermediate Text" (1996) Oxford University Press, ISBN 0-19-509618-5; Larock, R. C. "Comprehensive Organic Transformations: A Guide to Functional Group Preparations" 2nd Edition (1999) Wiley-VCH, ISBN: 0-471-19031-4; March, J. "Advanced Organic Chemistry: Reactions, Mechanisms, and Structure" 4th Edition (1992) John Wiley & Sons, ISBN: 0-471-60180-2; Otera, J. (editor) "Modem Carbonyl Chemistry" (2000) Wiley-VCH, ISBN: 3-527-29871-1; Patai, S. "Patai's 1992 Guide to the Chemistry of Functional Groups" (1992) Interscience ISBN: 0-471-93022-9; Quin, L. D. et al. "A Guide to Organophosphorus Chemistry" (2000) Wiley-Interscience, ISBN: 0-471-31824-8; Solomons, T. W. G. "Organic Chemistry" 7th Edition (2000) John Wiley & Sons, ISBN: 0-471-19095-0; Stowell, J. C., "Intermediate Organic Chemistry" 2nd Edition (1993) Wiley-Interscience, ISBN: 0-471-57456-2; "Industrial Organic Chemicals: Starting Materials and Intermediates: An Ullmann's Encyclopedia" (1999) John Wiley & Sons, ISBN: 3-527-29645-X, in 8 volumes; "Organic Reactions" (1942-2000) John Wiley & Sons, in over 55 volumes; and "Chemistry of Functional Groups" John Wiley & Sons, in 73 volumes.

Specific and analogous reactants may also be identified through the indices of known chemicals prepared by the Chemical Abstract Service of the American Chemical Society, which are available in most public and university libraries, as well as through on-line databases (the American Chemical Society, Washington, D.C., may be contacted for more details). Chemicals that are known but not commercially available in catalogs may be prepared by custom chemical synthesis houses, where many of the standard chemical supply houses (e.g., those listed above) provide custom synthesis services. A reference for the preparation and selection of pharmaceutical salts of the styrenyl derivative compounds described herein is P. H. Stahl & C. G. Wermuth "Handbook of Pharmaceutical Salts", Verlag Helvetica Chimica Acta, Zurich, 2002.

Generally speaking, the compounds disclosed herein can be prepared in a stepwise manner involving an olefin formation and a side chain formation.

In certain embodiments, an olefin intermediate can be first constructed, which forms the precursor to the styrenyl core structure. A side chain moiety, which is a precursor to the linkage and the nitrogen-containing moiety of the compounds disclosed herein, can then be attached to the olefin intermediate.

In other embodiments, the compounds disclosed herein can be prepared by first preparing a phenyl intermediate having an appropriate side chain, followed by an olefin formation to provide the styrenyl core structure.

The following Methods illustrate various synthetic pathways for preparing olefin intermediates and the side chain moieties. One skilled in the art will recognize that a method for olefin formation can be combined with a method for side chain formation to provide the compounds disclosed herein. For example, Method A can be combined with any of Method K, Methods K and U, Methods K and L, Methods K and AB, Methods T and L, Method R, Method S, Method J, Method E, Methods R and U, and the like. Similarly, Method C can be combined with Method J.

Olefin Formation:

Methods A-I below describe various approaches to olefin formation.

More specifically, Method A illustrates constructing an olefin intermediate (A-3) in a Wittig reaction. Depending on the sequence of the reactions, Ar can be a phenyl derivative compound that is already attached to a side chain moiety, or Ar may comprise a reactive group (appropriately protected), which will be coupled to a side chain moiety after the olefin formation step.

According to Method A, a phosphonium ylide reagent (or "Wittig reagent") (A-1) can be coupled to a benzaldehyde or ketone derivative (A-2) to provide the olefin intermediate (A-3) in the presence of a base. The geometry of the resulting A-3 may depend on the reactivity of the ylide reagent. Triphenylphosphonium-based ylide reagent (R is phenyl) typically produces predominantly (E) or trans-styrenes; whereas trialkylphosphonium-based ylide reagent (R is alkyl) produces predominantly (Z) or cis-styrene. The E or Z stereoisomers can be separated by, for example, chromatography or other known methods in the art.

The ylide reagent (A-1) can be prepared according to known methods in the art. For example, $R_{11}$—$CH_2OH$ can be converted to the corresponding ylide reagent (A-1) in the presence of triphenylphosphine hydrobromide. The benzaldehyde or ketone derivative (A-2) may be commercially available or can be prepared by known methods in the art.

The olefin intermediate (A-3) may also be prepared by coupling a phosphonium ylide reagent derivatized from the Ar group (A-4) and an aldehyde or ketene derivative of $R_{11}$ (A-5). The ylide reagent (A-4) can be prepared from, for example, a benzyl alcohol, whereas (A-5) can be prepared by known methods in the art or can be obtained from commercial vendors.

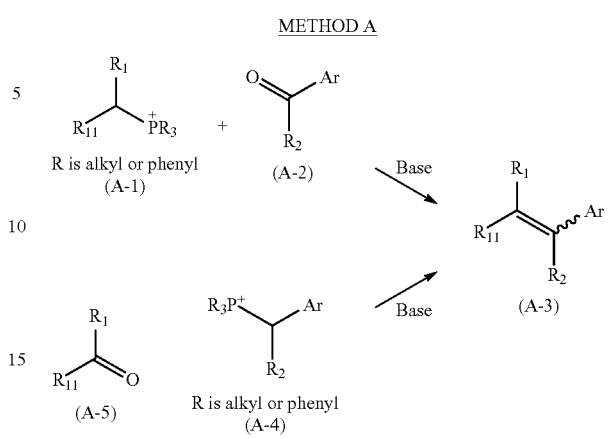

Method AE shows a coupling reaction similar to the Wittig reaction of Method A, except that a phosphorus ylide is used in place of the phosphonium ylide. The phosphorus ylide can be coupled to an aldehyde or ketone in the presence of a base (Wittig-Horner-Emmons reaction.)

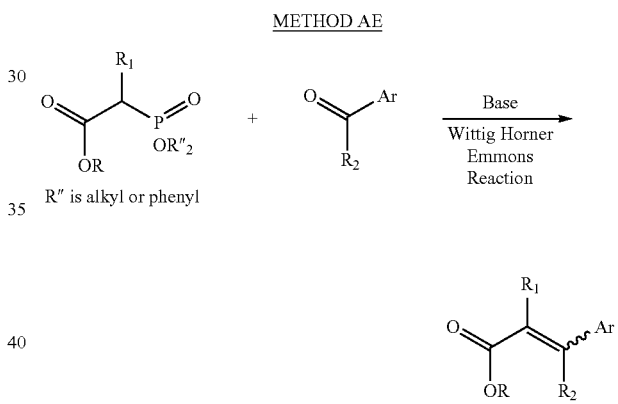

In addition, elimination reactions can be used to form olefin bonds. Methods B-D illustrate various approaches to forming alcohol precursors that can undergo alcohol dehydration in acidic conditions to produce olefin bonds. The Ar group is typically activated with a metal (e.g., Li) to facilitate the alcohol formation. Grignard reagent can also be used in place of the metal.

As discussed above in connection with Method A, the alcohol precursor in each of Methods B-D can also be prepared by using a metal activated $R_{11}$ group and an Ar group derivatized with a carbonyl group or a cyclopropyl group.

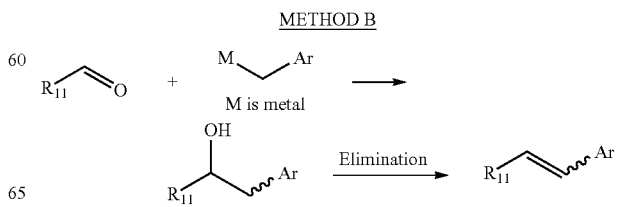

METHOD C

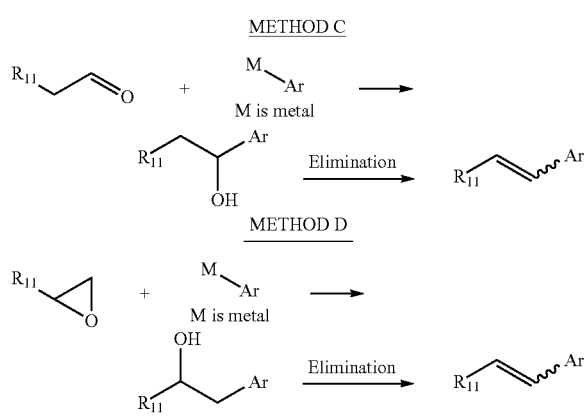

METHOD D

Methods E-G illustrate coupling an olefin or an activated olefin directly with an aryl halide in the presence of a palladium(0) catalyst. In certain embodiments, the olefin can be activated by a transition metal (e.g., Zn or Sn), or boronic acid (e.g., Suzuki reaction), as are known in the art. The halo substituent of the aryl group can be, for example, bromo or iodo.

Palladium catalysts suitable for coupling reactions are known to one skilled in the art. Exemplary palladium(0) catalysts include, for example, tetrakis(triphenylphosphine)palladium(0) [Pd(PPh$_3$)$_4$] and tetrakis(tri(o-tolylphosphine)palladium(0), tetrakis(dimethylphenylphosphine)palladium (0), tetrakis(tris-p-methoxyphenylphosphine)palladium(0) and the like. It is understood that a palladium (II) salt can also be used, which generates the palladium (O) catalyst in situ. Suitable palladium (II) salts include, for example, palladium diacetate [Pd(OAc)$_2$], bis(triphenylphosphine)-palladium diacetate and the like.

METHOD E

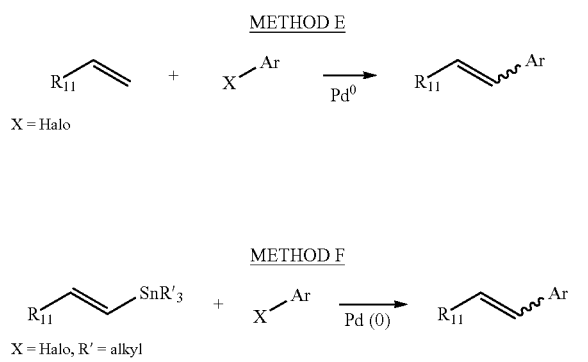

METHOD F

METHOD G

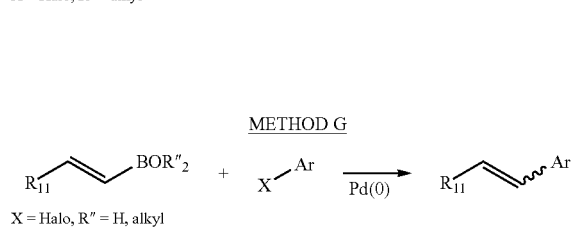

An olefin intermediate can also be constructed from an alkyne addition/hydrogenation reaction. Depending on the reaction conditions (syn or anti addition), cis or trans configuration can be formed.

Method H illustrates a syn-addition, i.e., both hydrogens are added from one side of the alkyne molecule, which results in a cis olefin configuration. Typically, hydrogen gas can be used in the presence of a catalyst (e.g., Pd on carbon or platinum) to effect a syn addition.

METHOD H

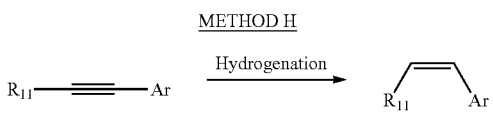

Method I illustrate an anti-addition, i.e., an adding agent is added to opposite sides of the alkyne molecule, resulting in a trans olefin configuration. The adding agent can be, for example, aluminum hydride reagents, lithium/NH$_3$ reagents and the like.

METHOD I

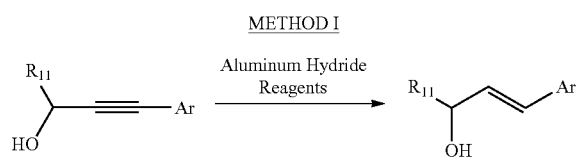

Side Chain Formation and Modification

Methods J-T and AA-AD below describe various approaches to side chain formation and modifications.

Generally speaking, a suitably substituted phenyl derivative can be coupled to a diverse range of side chains, which may be further modified to provide the final linkages and the nitrogen-containing moieties of the compounds disclosed herein.

Method J illustrates an aryl halide coupled with an allyl alcohol in the presence of a palladium(0) catalyst. The terminal alcohol group of allyl alcohol has been simultaneously oxidized to an aldehyde group, which can be further reduced to an amine (—NR$_9$R$_{10}$)

METHOD J

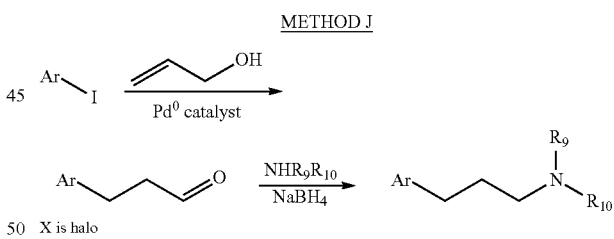

Method K illustrates an aldol condensation between an aryl aldehyde or aryl ketone with a nitrile reagent comprising at least one α-hydrogen. The resulting condensation intermediate can be further reduced to an amine (—NR9R$_{10}$)

METHOD K

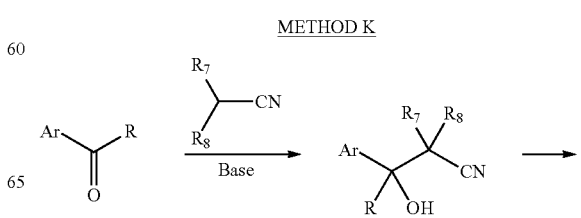

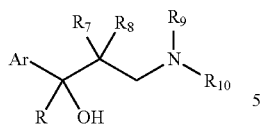

R = H, Me, CF$_3$

Method AA shows an acylation reaction to form a ketone-based linkage. One skilled in the art will recognize that the R' group may comprise functional groups that can be further modified.

METHOD AA

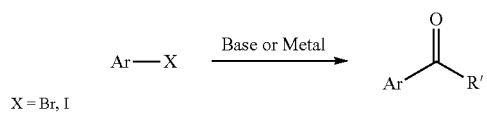

X = Br, I

Method R shows a ring-opening reaction of an epoxide reagent to form a 3-carbon side chain linkage.

METHOD R

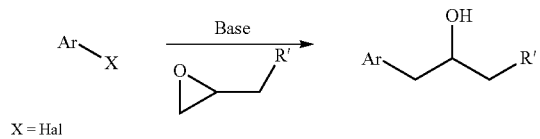

X = Hal

Method S shows the formation of a triple bond linkage based on a Sonogashira reaction. Typically, palladium(0) catalyst is used in combination with a base to couple an aryl halide with a acetylene derivative. R' can be further modified, as described herein.

METHOD S

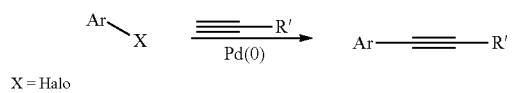

X = Halo

Method T shows the formation of a double bond linkage based on a Heck reaction. Typically, palladium(0) catalyst is used in combination with a base to couple an aryl halide with a vinyl derivative. R' can be further modified, as described herein.

METHOD T

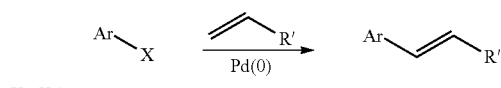

X = Halo

Methods M-P illustrate attachments of side chain moieties by heteroatoms. Method M shows a side chain precursor (R'OH) attached to an aryl derivative via an oxygen atom in a condensation reaction in which a molecule of H$_2$O is eliminated. R' may comprise functional groups that can be further modified to prepare linkages and nitrogen-containing moieties of the compounds disclosed herein.

METHOD M

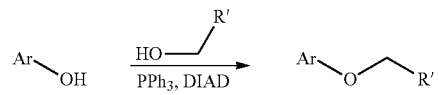

Method N shows a similar coupling reaction that provides a sulfur linking atom. Method O illustrates an oxidation step of the sulfur linking atom to provide S(O)— or —S(O)$_2$—, depending on the degree of oxidation.

METHOD N

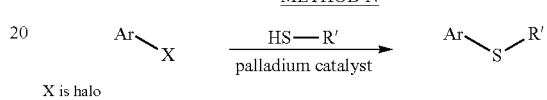

X is halo

METHOD O

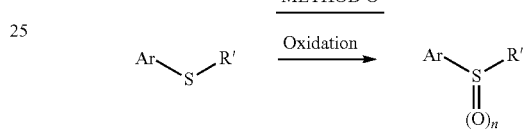

n = 1, 2

Method P shows the formation of an amide-containing linkage, in which a aniline derivative is coupled with a carboxylic acid derivative. The carboxylic acid derivative can be activated to facilitate the amide formation. Suitable activating reagents include, for example, 1,3-dicyclohexylcarbodiimide (DCC), 1,1'-carbonyldiimidazole (CDI), 1-ethyl-3-(3-dimethylaminopropyl)carbodiimide hydrochloride (EDCL), benzotriazol-1-yl-oxy-tris(dimethylamino)phosphonium hexafluorophosphate (BOP), and 1,3-diisopropylcarbodiimide (DICD).

METHOD P

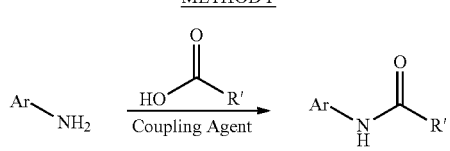

After attachment, the side chain moiety can be further modified to provide the final linkage and the terminal nitrogen-containing moiety for the compounds disclosed herein. The following methods illustrate a variety of synthetic pathways to manipulate or modify the side chain moiety by reduction, oxidation, nucleophilic or electrophilic substitution, fluorination, acylation and the like. As a result, a diverse group of linkages can be synthesized.

Method L illustrates an amination process in which carboxylic acid is converted to an amine. Typically, the carboxylic acid (or ester) can be first reduced to primary alcohol, which can then be converted to an amine via mesylate, halide, azide, phthalimide, or Mitsunobu reaction and the like. Suitable reducing agents include, for example, sodium borohydride (NaBH$_4$), sodium cyanoborohydride (NaBH$_3$CN), sodium triacetoxyborohydride (NaBH(OCOCH$_3$)$_3$), lithium aluminum hydride (LiAlH₄) and the like. As shown, the resulting amine can be further functionalized, by known methods in the art.

METHOD L

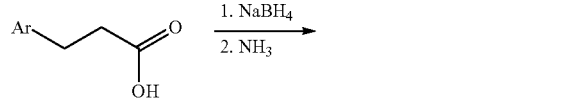

Additional or alternative modifications can be carried out according to the methods illustrated below.

METHOD Q

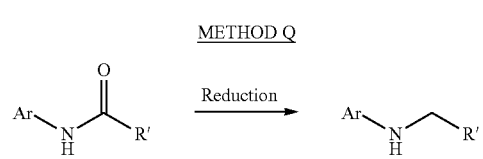

METHOD U

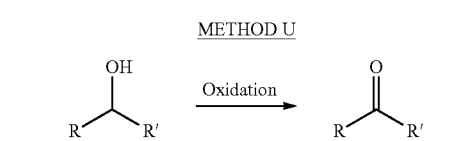

METHOD V

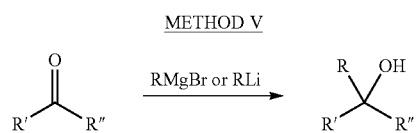

METHOD W

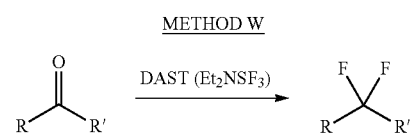

METHOD X

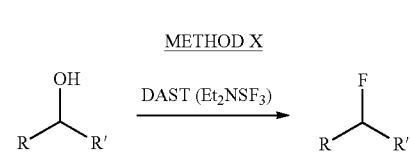

METHOD Y

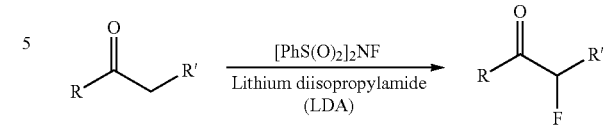

METHOD Z

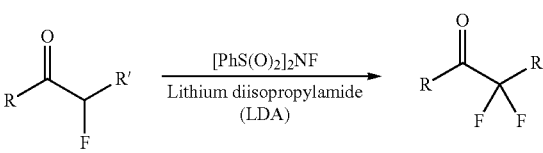

METHOD AB

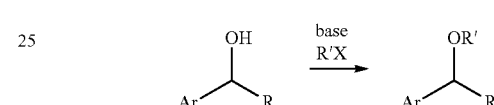

R' = alkyl
X = halo

METHOD AC

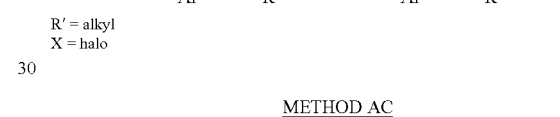

METHOD AD

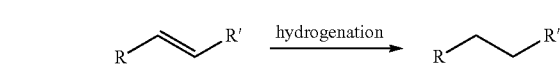

METHOD AE

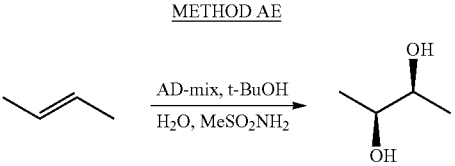

Scheme I illustrates a complete synthetic sequence for preparing one example of the compounds disclosed herein.

SCHEME I

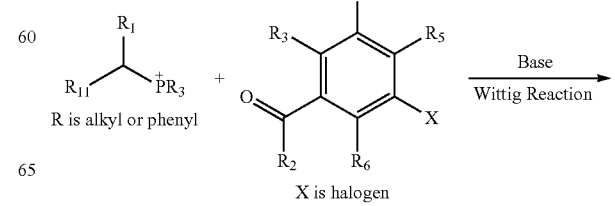

R is alkyl or phenyl

X is halogen

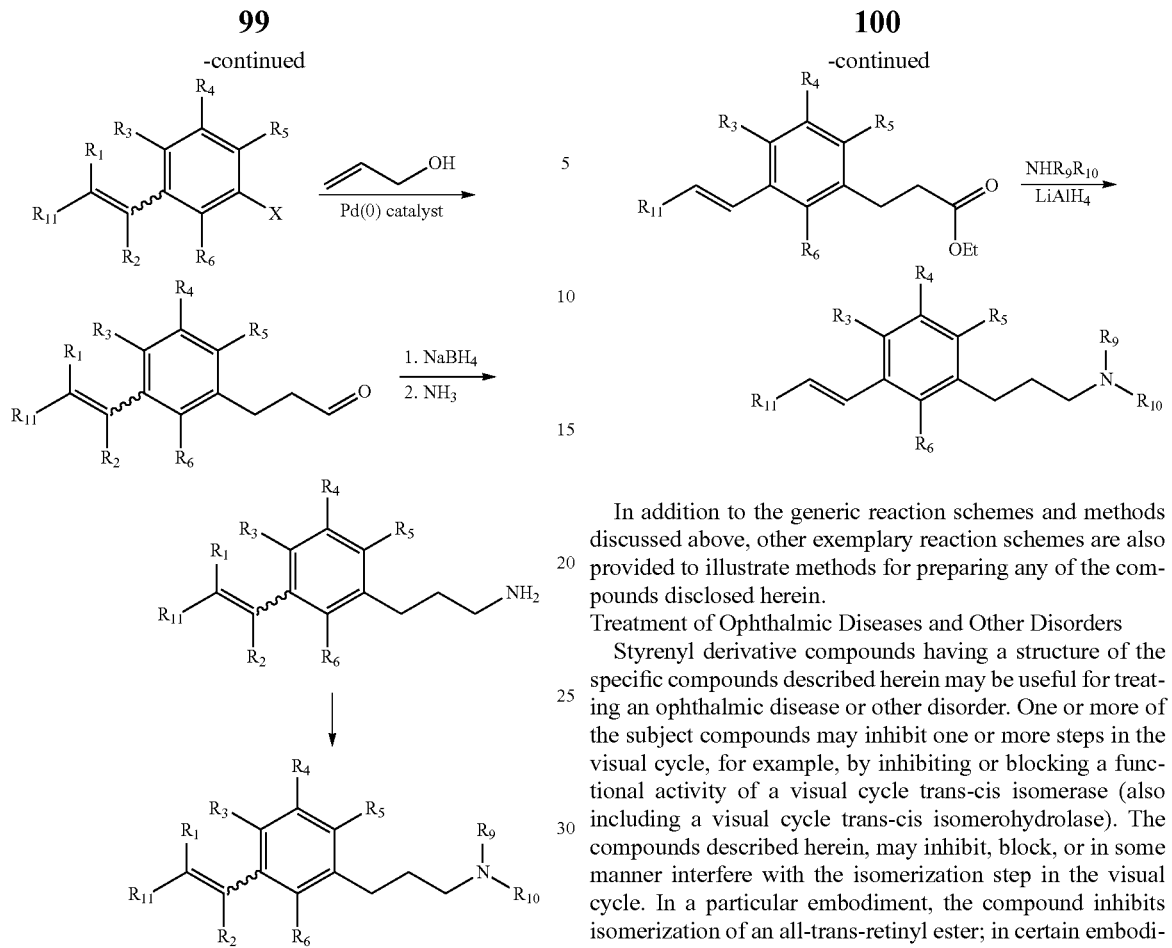

In Scheme I, an olefin intermediate is first constructed, followed by coupling to a side chain moiety. Further modification of the side chain moiety by reduction affords the compounds disclosed herein having a propylene linkage and a terminal amine. Other nitrogen-containing moieties can be further derived from the terminal amine, according to known methods in the art.

One skilled in the art should recognize, however, that the order of the reactions may vary. Thus, in other embodiments, as shown in Scheme II, a side chain attachment is initially performed, followed by olefin formation.

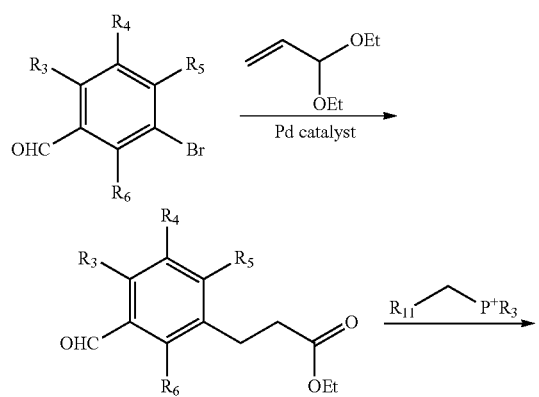

In addition to the generic reaction schemes and methods discussed above, other exemplary reaction schemes are also provided to illustrate methods for preparing any of the compounds disclosed herein.

Treatment of Ophthalmic Diseases and Other Disorders

Styrenyl derivative compounds having a structure of the specific compounds described herein may be useful for treating an ophthalmic disease or other disorder. One or more of the subject compounds may inhibit one or more steps in the visual cycle, for example, by inhibiting or blocking a functional activity of a visual cycle trans-cis isomerase (also including a visual cycle trans-cis isomerohydrolase). The compounds described herein, may inhibit, block, or in some manner interfere with the isomerization step in the visual cycle. In a particular embodiment, the compound inhibits isomerization of an all-trans-retinyl ester; in certain embodiments, the all-trans-retinyl ester is a fatty acid ester of all-trans-retinol, and the compound inhibits isomerization of all-trans-retinol to 11-cis-retinol. The compound may bind to, or in some manner interact with, and inhibit the isomerase activity of at least one visual cycle isomerasé, which may also be referred to herein and in the art as a retinal isomerase or an isomerohydrolase. The compound may block or inhibit binding of an all-trans-retinyl ester substrate to an isomerase. Alternatively, or in addition, the compound may bind to the catalytic site or region of the isomerase, thereby inhibiting the capability of the enzyme to catalyze isomerization of an all-trans-retinyl ester substrate. In general, at least one isomerase that catalyzes the isomerization of all-trans-retinyl esters is believed to be located in the cytoplasm of RPE cells.

A method for determining the effect of a compound on isomerization process may be performed in vitro as described herein and in the art (Stecher et al., *J Biol Chem* 274:8577-85 (1999); see also Golczak et al., *Proc. Natl. Acad. Sci. USA* 102:8162-67 (2005)). Retinal pigment epithelium (RPE) microsome membranes isolated from an animal (such as bovine, porcine, human, for example) may serve as the source of the isomerase. The capability of the styrenyl derivative compounds to inhibit isomerase may also be determined by an in vivo murine isomerase assay. Brief exposure of the eye to intense light ("photobleaching" of the visual pigment or simply "bleaching") is known to photo-isomerize almost all 11-cis-retinal in the retina. The recovery of 11-cis-retinal after bleaching can be used to estimate the activity of isomerase in vivo (see, e.g., Maeda et al., *J. Neurochem* 85:944-956 (2003); Van Hooser et al., *J Biol Chem* 277: 19173-82, 2002). Electroretinographic (ERG) recording may be performed as previously described (Haeseleer et al., *Nat. Neurosci.* 7:1079-87 (2004); Sugitomo et al., *J. Toxicol. Sci.*

22 Suppl 2:315-25 (1997); Keating et al., *Documenta Ophthalmologica* 100:77-92 (2000)). See also Deigner et al., *Science*, 244: 968-971 (1989); Gollapalli et al., *Biochim Biophys Acta*. 1651: 93-101 (2003); Parish, et al., *Proc. Natl. Acad. Sci. USA* 95:14609-13 (1998); Radu, et al., *Proc Natl Acad Sci USA* 101: 5928-33 (2004)). In certain embodiments, compounds that are useful for treating a subject who has or who is at risk of developing any one of the ophthalmic and retinal diseases or disorders described herein have $IC_{50}$ levels (compound concentration at which 50% of isomerase activity is inhibited) as measured in the isomerase assays described herein or known in the art that is less than about 1 µM; in other embodiments, the determined $IC_{50}$ level is less than about 10 nM; in other embodiments, the determined $IC_{50}$ level is less than about 50 nM; in certain other embodiments, the determined $IC_{50}$ level is less than about 100 nM; in other certain embodiments, the determined $IC_{50}$ level is less than about 10 uM; in other embodiments, the determined $IC_{50}$ level is less than about 50 µM; in other certain embodiments, the determined $IC_{50}$ level is less than about 100 µM or about 500 µM; in other embodiments, the determined $IC_{50}$ level is between about 1 µM and 10 µM; in other embodiments, the determined $IC_{50}$ level is between about 1 nM and 10 nM. When administered into a subject, one or more compounds of the present invention exhibits an ED50 value of about 5 mg/kg, 5 mg/kg or less as ascertained by inhibition of an isomerase reaction that results in production of 11-cis retinol. In some embodiments, the compounds of the present invention have ED50 values of about 1 mg/kg when administered into a subject. In other embodiments, the compounds of the present invention have ED50 values of about 0.1 mg/kg when administered into a subject. The ED50 values can be measured after about 2 hours, 4 hours, 6 hours, 8 hours or longer upon administering a subject compound or a pharmaceutical composition thereof. The compounds described herein may be useful for treating a subject who has an ophthalmic disease or disorder such as age-related macular degeneration or Stargardt's macular dystrophy. In one embodiment, the compounds described herein may inhibit (i.e., prevent, reduce, slow, abrogate, or minimize) accumulation of lipofuscin pigments and lipofuscin-related and/or associated molecules in the eye. In another embodiment, the compounds may inhibit (i.e., prevent, reduce, slow, abrogate, or minimize) N-retinylidene-N-retinylethanolamine (A2E) accumulation in the eye. The ophthalmic disease may result, at least in part, from lipofuscin pigments accumulation and/or from accumulation of A2E in the eye. Accordingly, in certain embodiments, methods are provided for inhibiting or preventing accumulation of lipofuscin pigments and/or A2E in the eye of a subject. These methods comprise administering to the subject a composition comprising a pharmaceutically acceptable or suitable excipient (i.e., pharmaceutically acceptable or suitable carrier) and a styrenyl derivative compound as described in detail herein.

Accumulation of lipofuscin pigments in retinal pigment epithelium (RPE) cells has been linked to progression of retinal diseases that result in blindness, including age-related macular degeneration (De Laey et al., *Retina* 15:399-406 (1995)). Lipofuscin granules are autofluorescent lysosomal residual bodies (also called age pigments). The major fluorescent species of lipofuscin is A2E (an orange-emitting fluorophore), which is a positively charged Schiff-base condensation-product formed by all-trans retinaldehyde with phosphatidylethanolamine (2:1 ratio) (see, e.g., Eldred et al., *Nature* 361:724-6 (1993); see also, Sparrow, *Proc. Natl. Acad. Sci. USA* 100:4353-54 (2003)). Much of the indigestible lipofuscin pigment is believed to originate in photoreceptor cells; deposition in the RPE occurs because the RPE internalize membranous debris that is discarded daily by the photoreceptor cells. Formation of this compound is not believed to occur by catalysis by any enzyme, but rather A2E forms by a spontaneous cyclization reaction. In addition, A2E has a pyridinium bisretinoid structure that once formed may not be enzymatically degraded. Lipofuscin, and thus A2E, accumulate with aging of the human eye and also accumulate in a juvenile form of macular degeneration called Stargardt's disease, and in several other congenital retinal dystrophies.

A2E may induce damage to the retina via several different mechanisms. At low concentrations, A2E inhibits normal proteolysis in lysosomes (Holz et al., *Invest. Ophthalmol. Vis. Sci.* 40:737-43 (1999)). At higher, sufficient concentrations, A2E may act as a positively charged lysosomotropic detergent, dissolving cellular membranes, and may alter lysosomal function, release proapoptotic proteins from mitochondria, and ultimately kill the RPE cell (see, e.g., Eldred et al., supra; Sparrow et al., *Invest. Ophthalmol. Vis. Sci.* 40:2988-95 (1999); Holz et al., supra; Finneman et al., *Proc. Natl. Acad. Sci. USA* 99:3842-347 (2002); Suter et al., *J. Biol. Chem.* 275:39625-30 (2000)). A2E is phototoxic and initiates blue light-induced apoptosis in RPE cells (see, e.g., Sparrow et al., *Invest. Ophthalmol. Vis. Sci.* 43:1222-27 (2002)). Upon exposure to blue light, photooxidative products of A2E are formed (e.g., epoxides) that damage cellular macromolecules, including DNA (Sparrow et al., *J. Biol. Chem.* 278(20):18207-13 (2003)). A2E self-generates singlet oxygen that reacts with A2E to generate epoxides at carbon-carbon double bonds (Sparrow et al., supra). Generation of oxygen reactive species upon photoexcitation of A2E causes oxidative damage to the cell, often resulting in cell death. An indirect method of blocking formation of A2E by inhibiting biosynthesis of the direct precursor of A2E, all-trans-retinal, has been described (see U.S. Patent Application Publication No. 2003/0032078). However, the usefulness of the method described therein is limited because generation of all-trans retinal is an important component of the visual cycle. Other therapies described include neutralizing damage caused by oxidative radical species by using superoxide-dismutase mimetics (see, e.g., U.S. Patent Application Publication No. 2004/0116403) and inhibiting A2E-induced cytochrome C oxidase in retinal cells with negatively charged phospholipids (see, e.g., U.S. Patent Application Publication No. 2003/0050283).

The styrenyl derivative compounds described herein may be useful for preventing, reducing, inhibiting, or decreasing accumulation (i.e., deposition) of A2E and A2E-related and/or derived molecules in the RPE. Without wishing to be bound by theory, because the RPE is critical for the maintenance of the integrity of photoreceptor cells, preventing, reducing, or inhibiting damage to the RPE may inhibit degeneration (enhance the survival or increase cell viability) of retinal neuronal cells, particularly, photoreceptor cells. Compounds that bind specifically to or interact with A2E A2E-related and/or derived molecules or that affect A2E formation or accumulation may also reduce, inhibit, prevent, or decrease one or more toxic effects of A2E or of A2E-related and/or derived molecules that result in retinal neuronal cell (including a photoreceptor cell) damage, loss, or neurodegeneration, or in some manner decrease retinal neuronal cell viability. Such toxic effects include induction of apoptosis, self-generation of singlet oxygen and generation of oxygen reactive species; self-generation of singlet oxygen to form A2E-epoxides that induce DNA lesions, thus damaging cellular DNA and inducing cellular damage; dissolving cellular membranes; altering lysosomal function; and effecting release of proapoptotic proteins from mitochondria.

In other embodiments, the compounds described herein may be used for treating other ophthalmic diseases or disorders, for example, glaucoma, retinal detachment, cone-rod dystrophy, hemorrhagic or hypertensive retinopathy, retinitis pigmentosa, optic neuropathy, inflammatory retinal disease, proliferative vitreoretinopathy, genetic retinal dystrophies, traumatic injury to the optic nerve (such as by physical injury, excessive light exposure, or laser light), hereditary optic neuropathy, neuropathy due to a toxic agent or caused by adverse drug reactions or vitamin deficiency, Sorsby's fundus dystrophy, uveitis, a retinal disorder associated with Alzheimer's disease, a retinal disorder associated with multiple sclerosis; a retinal disorder associated with viral infection (cytomegalovirus or herpes simplex virus), a retinal disorder associated with Parkinson's disease, a retinal disorder associated with AIDS, or other forms of progressive retinal atrophy or degeneration. In another specific embodiment, the disease or disorder results from mechanical injury, chemical or drug-induced injury, thermal injury, radiation injury, light injury, laser injury. The subject compounds are useful for treating both hereditary and non-hereditary retinal dystrophy. These methods are also useful for preventing ophthalmic injury from environmental factors such as light-induced oxidative retinal damage, laser-induced retinal damage, "flash bomb injury," or "light dazzle," refractive errors including but not limited to myopia (see, e.g., Quinn G E et al. Nature 1999; 399:113-114; Zadnik K et al. Nature 2000; 404:143-144; Gwiazda J et al. Nature 2000; 404: 144).

In other embodiments, methods are provided herein for inhibiting neovascularization (including but not limited to neovascular glucoma) in the retina using any one or more of the styrenyl derivative compounds described herein, substructures thereof, and the specific styrenyl compounds recited herein). In certain other embodiments, methods are provided for reducing hypoxia in the retina using the compounds described herein. These methods comprise administering to a subject, in need thereof, a composition comprising a pharmaceutically acceptable or suitable excipient (i.e., pharmaceutically acceptable or suitable carrier) and a styrenyl derivative compound as described in detail herein, including a compound having the structure as set forth herein, substructures thereof, and the specific styrenyl compounds recited herein.

Merely by way of explanation and without being bound by any theory, and as discussed in further detail herein, dark-adapted rod photoreceptors engender a very high metabolic demand (i.e., expenditure of energy (ATP consumption) and consumption of oxygen). The resultant hypoxia may cause and/or exacerbate retinal degeneration, which is likely exaggerated under conditions in which the retinal vasculature is already compromised, including, but not limited to, such conditions as diabetic retinopathy, macular edema, diabetic maculopathy, retinal blood vessel occlusion (which includes retinal venous occlusion and retinal arterial occlusion), retinopathy of prematurity, ischemia reperfusion related retinal injury, as well as in the wet form of age-related macular degeneration (AMD). Furthermore, retinal degeneration and hypoxia may lead to neovascularization, which in turn may worsen the extent of retinal degeneration. The styrenyl derivative compounds described herein that modulate the visual cycle can be administered to prevent, inhibit, and/or delay dark adaptation of rod photoreceptor cells, and may therefore reduce metabolic demand, thereby reducing hypoxia and inhibiting neovascularization.

By way of background, oxygen is a critical metabolite for preservation of retinal function in mammals, and retinal hypoxia may be a factor in many retinal diseases and disorders that have ischemia as a component. In most mammals (including humans) with dual vascular supply to the retina, oxygenation of the inner retina is achieved through the intraretinal microvasculature, which is sparse compared to the choriocapillaris that supplies oxygen to the RPE and photoreceptors. The different vascular supply networks create an uneven oxygen tension across the thickness of the retina (Cringle et al., *Invest. Ophthalmol. Vis. Sci.* 43:1922-27 (2002)). Oxygen fluctuation across the retinal layers is related to both the differing capillary densities and disparity in oxygen consumption by various retinal neurons and glia.

Local oxygen tension can significantly affect the retina and its microvasculature by regulation of an array of vasoactive agents, including, for example, vascular endothelial growth factor (VEGF). (See, e.g., Werdich et al., *Exp. Eye Res.* 79:623 (2004); Arden et al., Br. J. Ophthalmol. 89:764 (2005)). Rod photoreceptors are believed to have the highest metabolic rate of any cell in the body (see, e.g., Arden et al., supra). During dark adaptation, the rod photoreceptors recover their high cytoplasmic calcium levels via cGMP-gated calcium channels with concomitant extrusion of sodium ions and water. The efflux of sodium from the cell is an ATP-dependent process, such that the retinal neurons consume up to an estimated five times more oxygen under scotopic (i.e., dark adapted), compared with photopic (i.e., light adapted) conditions. Thus, during characteristic dark adaptation of photoreceptors, the high metabolic demand leads to significant local reduction of oxygen levels in the dark-adapted retina (Ahmed et al, *Invest. Ophthalmol. Vis. Sci.* 34:516 (1993)).

Without being bound by any one theory, retinal hypoxia may be further increased in the retina of subjects who have diseases or conditions such as, for example, central retinal vein occlusion in which the retinal vasculature is already compromised. Increasing hypoxia may increase susceptibility to sight-threatening, retinal neovascularization. Neovascularization is the formation of new, functional microvascular networks with red blood cell perfusion, and is a characteristic of retinal degenerative disorders, including, but not limited to, diabetic retinopathy, retinopathy of prematurity, wet AMD and central retinal vein occlusions. Preventing or inhibiting dark adaptation of rod photoreceptor cells, thereby decreasing expenditure of energy and consumption of oxygen (i.e., reducing metabolic demand), may inhibit or slow retinal degeneration, and/or may promote regeneration of retinal cells, including rod photoreceptor cells and retinal pigment epithelial (RPE) cells, and may reduce hypoxia and may inhibit neovascularization.

Methods are described herein for inhibiting (i.e., reducing, preventing, slowing or retarding, in a biologically or statistically significant manner) degeneration of retinal cells (including retinal neuronal cells as described herein and RPE cells) and/or for reducing (i.e., preventing or slowing, inhibiting, abrogating in a biologically or statistically significant manner) retinal ischemia. Methods are also provided for inhibiting (i.e., reducing, preventing, slowing or retarding, in a biologically or statistically significant manner) neovascularization in the eye, particularly in the retina. Such methods comprise contacting the retina, and thus, contacting retinal cells (including retinal neuronal cells such as rod photoreceptor cells, and RPE cells) with at least one of the styrenyl derivative compounds described herein that inhibits at least one visual cycle trans-cis isomerase (which may include inhibition of isomerization of an all-trans-retinyl ester), under conditions and at a time that may prevent, inhibit, or delay dark adaptation of a rod photoreceptor cell in the retina. As described in further detail herein, in particular embodiments, the compound that contacts the retina interacts with an isomerase enzyme or enzymatic complex in a RPE cell in the retina and inhibits, blocks, or in some manner interferes with the catalytic activity of the isomerase. Thus, isomerization of an all-trans-retinyl ester is inhibited or reduced. The at least one strenyl derivative compound (or composition comprising at least one compound) may be administered to a subject who has developed and manifested an ophthalmic disease or disorder or who is at risk of developing an ophthalmic disease or disorder, or to a subject who presents or who is at risk of presenting a condition such as retinal neovascularization or retinal ischemia.

By way of background, the visual cycle (also called retinoid cycle) refers to the series of enzyme and light-mediated conversions between the 11-cis and all-trans forms of retinol/retinal that occur in the photoreceptor and retinal pigment epithelial (RPE) cells of the eye. In vertebrate photoreceptor cells, a photon causes isomerization of the 11-cis-retinylidene chromophore to all-trans-retinylidene coupled to the visual opsin receptors. This photoisomerization triggers conformational changes of opsins, which, in turn, initiate the biochemical chain of reactions termed phototransduction (Filipek et al., *Annu. Rev. Physiol.* 65 851-79 (2003)). After absorption of light and photoisomerization of 11-cis-retinal to all-trans retinal, regeneration of the visual chromophore is a critical step in restoring photoreceptors to their dark-adapted state. Regeneration of the visual pigment requires that the chromophore be converted back to the 11-cis-configuration (reviewed in McBee et al., *Prog. Retin Eye Res.* 20:469-52 (2001)). The chromophore is released from the opsin and reduced in the photoreceptor by retinol dehydrogenases. The product, all-trans-retinol, is trapped in the adjacent retinal pigment epithelium (RPE) in the form of insoluble fatty acid esters in subcellular structures known as retinosomes (Imanishi et al., *J. Cell Biol.* 164:373-78 (2004)).

During the visual cycle in rod receptor cells, the 11-cis retinal chromophore within the visual pigment molecule, which is called rhodopsin, absorbs a photon of light and is isomerized to the all-trans configuration, thereby activating the phototransduction cascade. Rhodopsin is a G-protein coupled receptor (GPCR) that consists of seven membrane-spanning helices that are interconnected by extracellular and cytoplasmic loops. When the all-trans form of the retinoid is still covalently bound to the pigment molecule, the pigment is referred to as metarhodopsin, which exists in different forms (e.g., metarhodopsin I and metarhodopsin II). The all-trans retinoid is then hydrolyzed and the visual pigment is in the form of the apoprotein, opsin, which is also called apo-rhodopsin in the art and herein. This all-trans retinoid is transported or chaperoned out of the photoreceptor cell and across the extracellular space to the RPE cells, where the retinoid is converted to the 11-cis isomer. The movement of the retinoids between the RPE and photoreceptors cells is believed to be accomplished by different chaperone polypeptides in each of the cell types. See Lamb et al., *Progress in Retinal and Eye Research* 23:307-80 (2004).

Under light conditions, rhodopsin continually transitions through the three forms, rhodopsin, metarhodopsin, and apo-rhodopsin. When most of the visual pigment is in the rhodopsin form (i.e., bound with 11-cis retinal), the rod photoreceptor cell is in a "dark-adapted" state. When the visual pigment is predominantly in the metarhodopsin form bound with all-trans-retinal), the state of the photoreceptor cell is referred to as a "light-adapted," and when the visual pigment is apo-rhodopsin (or opsin) and no longer has bound chromophore, the state of the photoreceptor cell is referred to as "rhodopsin-depleted." Each of the three states of the photoreceptor cell has different energy requirements, and differing levels of ATP and oxygen are consumed. In the dark-adapted state, rhodopsin has no regulatory effect on cation channels, which are open, resulting in an influx of cations ($Na^+/K^+$ and $Ca^{2+}$). To maintain the proper level of these cations in the cell during the dark state, the photoreceptor cells actively transport the cations out of the cell via ATP-dependent pumps. Thus maintenance of this "dark current" requires a large amount of energy, resulting in high metabolic demand. In the light-adapted state, metarhodopsin triggers an enzymatic cascade process that results in hydrolysis of GMP, which in turn, closes cation-specific channels in the photoreceptor cell membrane. In the rhodopsin-depleted state, the chromophore is hydrolyzed from metarhodopsin to form the apoprotein, opsin (apo-rhodopsin), which partially regulates the cation channels such that the rod photoreceptor cells exhibit an attenuated current compared with the photoreceptor in the dark-adapted state, resulting in a moderate metabolic demand.

Under normal light conditions, the incidence of rod photoreceptors in the dark adapted state is small, in general, 2% or less, and the cells are primarily in the light-adapted or rhodopsin-depleted states, which overall results in a relatively low metabolic demand compared with cells in the dark-adapted state. At night, however, the relative incidence of the dark-adapted photoreceptor state increases profoundly, due to the absence of light adaptation and to the continued operation of the "dark" visual cycle in RPE cells, which replenishes the rod photoreceptor cells with 11-cis-retinal. This shift to dark adaptation of the rod photoreceptor causes an increase in metabolic demand (that is, increased ATP and oxygen consumption), leading ultimately to retinal hypoxia and subsequent initiation of angiogenesis. Most ischaemic insults to the retina therefore occur in the dark, for example, at night during sleep.

Without being bound by any theory, therapeutic intervention during the "dark" visual cycle may prevent retinal hypoxia and neovascularization that are caused by high metabolic activity in the dark-adapted rod photoreceptor cell. Merely by way of one example, altering the "dark" visual cycle by administering any one of the compounds described herein, which is an isomerase inhibitor, rhodopsin (i.e., 11-cis retinal bound) may be reduced or depleted, preventing or inhibiting dark adaptation of rod photoreceptors. This in turn may reduce retinal metabolic demand, attenuating the night-time risk of retinal ischemia and neovascularization, and thereby inhibiting or slowing retinal degeneration.

In one embodiment, at least one of the compounds described herein, substructures thereof, and the specific styrenyl compounds recited herein) that, for example, blocks, reduces, inhibits, or in some manner attenuates the catalytic activity of a visual cycle isomerase in a statistically or biologically significant manner, may prevent, inhibit, or delay dark adaptation of a rod photoreceptor cell, thereby inhibiting (i.e., reducing, abrogating, preventing, slowing the progression of, or decreasing in a statistically or biologically significant manner) degeneration of retinal cells (or enhancing survival of retinal cells) of the retina of an eye. In another embodiment, the styrenyl derivative compounds may prevent or inhibit dark adaptation of a rod photoreceptor cell, thereby reducing ischemia (i.e., decreasing, preventing, inhibiting, slowing the progression of ischemia in a statistically or biologically significant manner). In yet another embodiment, any one of the styrenyl compounds described herein may prevent dark adaptation of a rod photoreceptor cell, thereby inhibiting neovascularization in the retina of an eye. Accordingly, methods are provided herein for inhibiting retinal cell degeneration, for inhibiting neovascularization in the retina of an eye of a subject, and for reducing ischemia in an eye of a subject wherein the methods comprise administering at least one styrenyl compound described herein, under conditions and at a time sufficient to prevent, inhibit, or delay dark adaptation of a rod photoreceptor cell. These methods and compositions are therefore useful for treating an ophthalmic disease or disorder including, but not limited to, diabetic retinopathy, diabetic maculopathy, retinal blood vessel occlusion, retinopathy of prematurity, or ischemia reperfusion related retinal injury.

The styrenyl compounds described herein, substructures thereof, and the specific styrenyl compounds recited herein) may prevent (i.e., delay, slow, inhibit, or decrease) recovery of the visual pigment chromophore, which may prevent or inhibit or retard the formation of retinals and may increase the level of retinyl esters, which perturbs the visual cycle, inhibiting regeneration of rhodopsin, and which prevents, slows, delays or inhibits dark adaptation of a rod photoreceptor cell. In certain embodiments, when dark adaptation of rod photoreceptor cells is prevented in the presence of the compound, dark adaptation is substantially prevented, and the number or percent of rod photoreceptor cells that are rhodopsin-depleted or light adapted is increased compared with the number or percent of cells that are rhodopsin-depleted or light-adapted in the absence of the agent. Thus, in certain embodiments when dark adaptation of rod photoreceptor cells is prevented (i.e., substantially prevented), only at least 2% of rod photoreceptor cells are dark-adapted, similar to the percent or number of cells that are in a dark-adapted state during normal, light conditions. In other certain embodiments, at least 5-10%, 10-20%, 20-30%, 30-40%, 40-50%, 50-60%, or 60-70% of rod photoreceptor cells are dark-adapted after administration of an agent. In other embodiments, the compound acts to delay dark adaptation, and in the presence of the compound dark adaptation of rod photoreceptor cells may be delayed 30 minutes, one hour, two hours, three hours, or four hours compared to dark adaptation of rod photoreceptors in the absence of the compound. By contrast, when a styrenyl compound is administered such that the compound effectively inhibits isomerization of substrate during light-adapted conditions, the compound is administered in such a manner to minimize the percent of rod photoreceptor cells that are dark-adapted, for example, only 2%, 5%, 10%, 20%, or 25% of rod photoreceptors are dark-adapted (see e.g., U.S. Patent Application Publication No. 2006/0069078; Patent Application No. PCT/US2007/002330).

In the retina in the presence of at least one styrenyl compound, regeneration of rhodopsin in a rod photoreceptor cell may be inhibited or the rate of regeneration may be reduced (i.e., inhibited, reduced, or decreased in a statistically or biologically significant manner), at least in part, by preventing the formation of retinals, reducing the level of retinals, and/or increasing the level of retinyl esters. To determine the level of regeneration of rhodopsin in a rod photoreceptor cell, the level of regeneration of rhodopsin (which may be called a first level) may be determined prior to permitting contact between the compound and the retina (i.e., prior to administration of the agent). After a time sufficient for the compound and the retina and cells of the retina to interact, (i.e., after administration of the compound), the level of regeneration of rhodopsin (which may be called a second level) may be determined. A decrease in the second level compared with the first level indicates that the compound inhibits regeneration of rhodopsin. The level of rhodopsin generation may be determined after each dose, or after any number of doses, and ongoing throughout the therapeutic regimen to characterize the effect of the agent on regeneration of rhodopsin.

In certain embodiments, the subject in need of the treatments described herein, may have a disease or disorder that results in or causes impairment of the capability of rod photoreceptors to regenerate rhodopsin in the retina. By way of example, inhibition of rhodopsin regeneration (or reduction of the rate of rhodopsin regeneration) may be symptomatic in patients with diabetes. In addition to determining the level of regeneration of rhodopsin in the subject who has diabetes before and after administration of a styrenyl compound described herein, the effect of the compound may also be characterized by comparing inhibition of rhodopsin regeneration in a first subject (or a first group or plurality of subjects) to whom the compound is administered, to a second subject (or second group or plurality of subjects) who has diabetes but who does not receive the agent.

In another embodiment, a method is provided for preventing or inhibiting dark adaptation of a rod photoreceptor cell (or a plurality of rod photoreceptor cells) in a retina comprising contacting the retina and at least one of the styrenyl compounds described herein, substructures thereof, and the specific styrenyl compounds recited herein), under conditions and at a time sufficient to permit interaction between the agent and an isomerase present in a retinal cell (such as an RPE cell). A first level of 11-cis-retinal in a rod photoreceptor cell in the presence of the compound may be determined and compared to a second level of 11-cis-retinal in a rod photoreceptor cell in the absence of the compound. Prevention or inhibition of dark adaptation of the rod photoreceptor cell is indicated when the first level of 11-cis-retinal is less than the second level of 11-cis-retinal.

Inhibiting regeneration of rhodopsin may also include increasing the level of 11-cis-retinyl esters present in the RPE cell in the presence of the compound compared with the level of 11-cis-retinyl esters present in the RPE cell in the absence of the compound (i.e., prior to administration of the agent). A two-photon imaging technique may be used to view and analyze retinosome structures in the RPE, which structures are believed to store retinyl esters (see, e.g., Imanishi et al., *J. Cell Biol.* 164:373-83 (2004), Epub 2004 Jan. 26.). A first level of retinyl esters may be determined prior to administration of the compound, and a second level of retinyl esters may be determined after administration of a first dose or any subsequent dose, wherein an increase in the second level compared to the first level indicates that the compound inhibits its regeneration of rhodopsin.

Retinyl esters may be analyzed by gradient HPLC according to methods practiced in the art (see, for example, Mata et al., *Neuron* 36:69-80 (2002); Trevino et al. *J. Exp. Biol.* 208: 4151-57 (2005)). To measure 11-cis and all-trans retinals, retinoids may be extracted by a formaldehyde method (see, e.g., Suzuki et al., *Vis. Res.* 28:1061-70 (1988); Okajima and Pepperberg, *Exp. Eye Res.* 65:331-40 (1997)) or by a hydroxylamine method (see, e.g., Groenendijk et al., *Biochim. Biophys. Acta.* 617:430-38 (1980)) before being analyzed on isocratic HPLC (see, e.g., Trevino et al., supra). The retinoids may be monitored spectrophotometrically (see, e.g., Maeda et al., J. Neurochem. 85:944-956 (2003); Van Hooser et al., *J. Biol. Chem.* 277:19173-82 (2002)).

In another embodiment of the methods described herein for treating an ophthalmic disease or disorder, for inhibiting retinal cell degeneration (or enhancing retinal cell survival), for inhibiting neovascularization, and for reducing ischemia in the retina, preventing or inhibiting dark adaptation of a rod photoreceptor cell in the retina comprises increasing the level of apo-rhodopsin (also called opsin) in the photoreceptor cell. The total level of the visual pigment approximates the sum of rhodopsin and apo-rhodopsin and the total level remains constant. Therefore, preventing, delaying, or inhibiting dark adaptation of the rod photoreceptor cell may alter the ratio of apo-rhodopsin to rhodopsin. In particular embodiments, preventing, delaying, or inhibiting dark adaptation by administering a styrenyl compound described herein may increase the ratio of the level of apo-rhodopsin to the level of rhodopsin compared to the ratio in the absence of the agent (for example, prior to administration of the agent). An increase in the ratio (i.e., a statistically or biologically significant increase) of apo-rhodopsin to rhodopsin indicates that the percent or number of rod photoreceptor cells that are rhodopsin-depleted is increased and that the percent or number of rod photoreceptor cells that are dark-adapted is decreased. The ratio of apo-rhodopsin to rhodopsin may be determined throughout the course of therapy to monitor the effect of the agent.

Determining or characterizing the capability of compound to prevent, delay, or inhibit dark adaptation of a rod photoreceptor cell may be determined in animal model studies. The level of rhodopsin and the ratio of apo-rhodopsin to rhodopsin may be determined prior to administration (which may be called a first level or first ratio, respectively) of the agent and then after administration of a first or any subsequent dose of the agent (which may be called a second level or second ratio, respectively) to determine and to demonstrate that the level of apo-rhodopsin is greater than the level of apo-rhodopsin in the retina of animals that did not receive the agent. The level of rhodopsin in rod photoreceptor cells may be performed according to methods practiced in the art and provided herein (see, e.g., Example 114).

Also provided herein are methods for inhibiting (reducing, slowing, preventing) degeneration and enhancing retinal neuronal cell survival (or prolonging cell viability) comprising administering to a subject a composition comprising a pharmaceutically acceptable carrier and a styrenyl derivative compound described in detail herein, including a compound having any one of the structures set forth herein, substructures thereof, and specific styrenyl compounds recited herein. A retinal neuronal cell includes a photoreceptor cell, a bipolar cell, a horizontal cell, a ganglion cell, and an amacrine cell. In another embodiment, methods are provided for enhancing survival or inhibiting degeneration of a mature retinal cell such as a RPE cell or a Müller glial cell. In another embodiment, a method for preventing or inhibiting photoreceptor degeneration in an eye of a subject or a method for restoring photoreceptor function in an eye of a subject is provided that comprises administering to the subject a composition comprising a styrenyl derivative compound as described herein and a pharmaceutically or acceptable carrier (i.e., excipient or vehicle). Such methods comprise administering to a subject a pharmaceutically acceptable excipient and a styrenyl derivative compound described herein, including a compound having any one of the structures set forth herein or substructures thereof described herein. Without wishing to be bound by theory, the compounds described herein may inhibit an isomerization step of the retinoid cycle and/or may slow chromophore flux in a retinoid cycle in the eye.

The ophthalmic disease may result, at least in part, from lipofuscin pigment(s) accumulation and/or from accumulation of N-retinylidene-N-retinylethanolamine (A2E) in the eye. Accordingly, in certain embodiments, methods are provided for inhibiting or preventing accumulation of lipofuscin pigment(s) and/or A2E in the eye of a subject. These methods comprise administering to the subject a composition comprising a pharmaceutically acceptable carrier and a styrenyl compound as described in detail herein, including a compound having the structure as set forth herein or substructures thereof.

A styrenyl compound can be administered to a subject who has an excess of a retinoid in an eye (e.g., an excess of 11-cis-retinol or 11-cis-retinal), an excess of retinoid waste products or intermediates in the recycling of all-trans-retinal, or the like. Methods described herein and practiced in the art may be used to determine whether the level of one or more endogenous retinoids in a subject are altered (increased or decreased in a statistically significant or biologically significant manner) during or after administration of any one of the compounds described herein. As described in greater detail herein, rhodopsin, which is composed of the protein opsin and retinal (a vitamin A form), is located in the membrane of the photoreceptor cell in the retina of the eye and catalyzes the only light-sensitive step in vision. The 11-cis-retinal chromophore lies in a pocket of the protein and is isomerized to all-trans retinal when light is absorbed. The isomerization of retinal leads to a change of the shape of rhodopsin, which triggers a cascade of reactions that lead to a nerve impulse that is transmitted to the brain by the optic nerve.

Methods of determining endogenous retinoid levels in a vertebrate eye, and an excess or deficiency of such retinoids, are disclosed in, for example, U.S. Patent Application Publication No: 2005/0159662 (the disclosure of which is incorporated by reference herein in its entirety). Other methods of determining endogenous retinoid levels in a subject, which is useful for determining whether levels of such retinoids are above the normal range, and include for example, analysis by high pressure liquid chromatography (HPLC) of retinoids in a biological sample from a subject. For example, retinoid levels can be determined in a biological sample that is a blood sample (which includes serum or plasma) from a subject. A biological sample may also include vitreous fluid, aqueous humor, intraocular fluid, subretinal fluid, or tears.

For example, a blood sample can be obtained from a subject, and different retinoid compounds and levels of one or more of the retinoid compounds in the sample can be separated and analyzed by normal phase high pressure liquid chromatography (HPLC) (e.g., with a HP 1100 HPLC and a Beckman, Ultrasphere-Si, 4.6 mm×250 mm column using 10% ethyl acetate/90% hexane at a flow rate of 1.4 ml/minute). The retinoids can be detected by, for example, detection at 325 nm using a diode-array detector and HP Chemstation A.03.03 software. An excess in retinoids can be determined, for example, by comparison of the profile of retinoids (i.e., qualitative, e.g., identity of specific compounds, and quantitative, e.g., the level of each specific compound) in the sample with a sample from a normal subject. Persons skilled in the art who are familiar with such assays and techniques and will readily understand that appropriate controls are included.

As used herein, increased or excessive levels of endogenous retinoid, such as 11-cis-retinol or 11-cis-retinal, refer to levels of endogenous retinoid higher than those found in a healthy eye of a young vertebrate of the same species. Administration of a styrenyl derivative compound and reduce or eliminate the requirement for endogenous retinoid. In certain embodiments, the level of endogenous retinoid may be compared before and after any one or more doses of the agent is administered to a subject to determine the effect of the agent on the level of endogenous retinoids in the subject.

In another embodiment, the methods described herein for treating an ophthalmic disease or disorder, for inhibiting neovascularization, and for reducing ischemia in the retina comprise administering at least one of the compounds described herein, thereby effecting a decrease in metabolic demand, which includes effecting a reduction in ATP consumption and in oxygen consumption in rod photoreceptor cells. As described herein, consumption of ATP and oxygen in a dark-adapted rod photoreceptor cell is greater than in rod photoreceptor cells that are light-adapted or rhodopsin-depleted; thus, use of the agents in the methods described herein may reduce the consumption of ATP in the rod photoreceptor cells that are prevented, inhibited, or delayed from dark adaptation compared with rod photoreceptor cells that are dark-adapted (such as the cells prior to administration or contact with the agent or cells that are never exposed to the agent).

The methods described herein that may prevent or inhibit dark adaptation of a rod photoreceptor cell may therefore reduce hypoxia (i.e., reduce in a statistically or biologically significant manner) in the retina. For example, the level of hypoxia (a first level) may be determined prior to initiation of the treatment regimen, that is, prior to the first dosing of the compound (or a composition, as described herein, comprising the compound). The level of hypoxia (for example, a second level) may be determined after the first dosing, and/or after any second or subsequent dosing to monitor and characterize hypoxia throughout the treatment regimen. A decrease (reduction) in the second (or any subsequent) level of hypoxia compared to the level of hypoxia prior to initial administration indicates that the compound and the treatment regiment prevent dark adaptation of the rod photoreceptor cells and may be used for treating ophthalmic diseases and disorders. Consumption of oxygen, oxygenation of the retina, and/or hypoxia in the retina may be determined using methods practiced in the art. For example, oxygenation of the retina may be determined by measuring the fluorescence of flavoproteins in the retina (see, e.g., U.S. Pat. No. 4,569,354). Another exemplary method is retinal oximetry that measures blood oxygen saturation in the large vessels of the retina near the optic disc. Such methods may be used to identify and determine the extent of retinal hypoxia before changes in retinal vessel architecture can be detected.

A subject in need of any one or more of the methods of treatment described herein may be a human or may be a non-human primate or other animal (i.e., veterinary use) who has developed symptoms of an ophthalmic disease or disorder or who is at risk for developing an ophthalmic disease or disorder. Examples of non-human primates and other animals include but are not limited to farm animals, pets, and zoo animals (e.g., horses, cows, buffalo, llamas, goats, rabbits, cats, dogs, chimpanzees, orangutans, gorillas, monkeys, elephants, bears, large cats, etc.).

Retinal Cells

The retina of the eye is a thin, delicate layer of nervous tissue. The major landmarks of the retina are the area centralis in the posterior portion of the eye and the peripheral retina in the anterior portion of the eye. The retina is thickest near the posterior sections and becomes thinner near the periphery. The area centralis is located in the posterior retina and contains the fovea and foveola and, in primates, contains the macula. The foveola contains the area of maximal cone density and, thus, imparts the highest visual acuity in the retina. The foveola is contained within the fovea, which is contained within the macula.

The peripheral or anterior portion of the retina increases the field of vision. The peripheral retina extends anterior to the equator of the eye and is divided into four regions: the near periphery (most posterior), the mid-periphery, the far periphery, and the ora serrata (most anterior). The ora serrata denotes the termination of the retina.

The term neuron (or nerve cell) as understood in the art and used herein denotes a cell that arises from neuroepithelial cell precursors. Mature neurons (i.e., fully differentiated cells) display several specific antigenic markers. Neurons may be classified functionally into three groups: (1) afferent neurons (or sensory neurons) that transmit information into the brain for conscious perception and motor coordination; (2) motor neurons that transmit commands to muscles and glands; and (3) interneurons that are responsible for local circuitry; and (4) projection interneurons that relay information from one region of the brain to anther region and therefore have long axons. Interneurons process information within specific subregions of the brain and have relatively shorter axons. A neuron typically has four defined regions: the cell body (or soma); an axon; dendrites; and presynaptic terminals. The dendrites serve as the primary input of information from other neural cells. The axon carries the electrical signals that are initiated in the cell body to other neurons or to effector organs. At the presynaptic terminals, the neuron transmits information to another cell (the postsynaptic cell), which may be another neuron, a muscle cell, or a secretory cell.

The retina is composed of several types of neuronal cells. As described herein, the types of retinal neuronal cells that may be cultured in vitro by this method include photoreceptor cells, ganglion cells, and interneurons such as bipolar cells, horizontal cells, and amacrine cells. Photoreceptors are specialized light-reactive neural cells and comprise two major classes, rods and cones. Rods are involved in scotopic or dim light vision, whereas photopic or bright light vision originates in the cones by the presence of trichromatic pigments. Many neurodegenerative diseases that result in blindness, such as age-related macular degeneration, genetic macular dystrophies, retinitis pigmentosa, etc, affect photoreceptors.

Extending from their cell bodies, the photoreceptors have two morphologically distinct regions, the inner and outer segments. The outer segment lies furthermost from the photoreceptor cell body and contains disks that convert incoming light energy into electrical impulses (phototransduction). The outer segment is attached to the inner segment with a very small and fragile cilium. The size and shape of the outer segments vary between rods and cones and are dependent upon position within the retina. See Hogan, "Retina" in *Histology of the Human Eye: an Atlas and Text Book* (Hogan et al. (eds). W B Saunders; Philadelphia, Pa. (1971)); *Eye and Orbit*, $8^{th}$ Ed., Bron et al., (Chapman and Hall, 1997).

Ganglion cells are output neurons that convey information from the retinal interneurons (including horizontal cells, bipolar cells, amacrine cells) to the brain. Bipolar cells are named according to their morphology, and receive input from the photoreceptors, connect with amacrine cells, and send output radially to the ganglion cells. Amacrine cells have processes parallel to the plane of the retina and have typically inhibitory output to ganglion cells. Amacrine cells are often subclassified by neurotransmitter or neuromodulator or peptide (such as calretinin or calbindin) and interact with each other, with bipolar cells, and with photoreceptors. Bipolar cells are retinal interneurons that are named according to their morphology; bipolar cells receive input from the photoreceptors and sent the input to the ganglion cells. Horizontal cells modulate and transform visual information from large numbers of photoreceptors and have horizontal integration (whereas bipolar cells relay information radially through the retina).

Other retinal cells that may be present in the retinal cell cultures described herein include glial cells, such as Müller glial cells, and retinal pigment epithelial cells (RPE). Glial cells surround nerve cell bodies and axons. The glial cells do not carry electrical impulses but contribute to maintenance of normal brain function. Müller glia, the predominant type of glial cell within the retina, provide structural support of the retina and are involved in the metabolism of the retina (e.g., contribute to regulation of ionic concentrations, degradation of neurotransmitters, and remove certain metabolites (see, e.g., Kljavin et al., *J. Neurosci.* 11:2985 (1991))). Müller's fibers (also known as sustentacular fibers of retina) are sustentacular neuroglial cells of the retina that run through the thickness of the retina from the internal limiting membrane to the bases of the rods and cones where they form a row of junctional complexes.

Retinal pigment epithelial (RPE) cells form the outermost layer of the retina, separated from the blood vessel-enriched choroids by Bruch's membrane. RPE cells are a type of phagocytic epithelial cell, with some functions that are macrophage-like, which lies immediately below the retinal photoreceptors. The dorsal surface of the RPE cell is closely apposed to the ends of the rods, and as discs are shed from the rod outer segment they are internalized and digested by RPE cells. RPE cells also produce, store, and transport a variety of factors that contribute to the normal function and survival of photoreceptors. Another function of RPE cells is to recycle vitamin A as it moves between photoreceptors and the RPE during light and dark adaptation in the process known as the visual cycle.

Described herein is an exemplary long-term in vitro cell culture system permits and promotes the survival in culture of mature retinal cells, including retinal neurons, for at least 2-4 weeks, over 2 months, or for as long as 6 months. The cell culture system may be used for identifying and characterizing the styrenyl derivative compounds that are useful in the methods described herein for treating and/or preventing an ophthalmic disease or disorder or for preventing or inhibiting accumulation in the eye of lipofuscin(s) and/or A2E. Retinal cells are isolated from non-embryonic, non-tumorigenic tissue and have not been immortalized by any method such as, for example, transformation or infection with an oncogenic virus. The cell culture system may comprise all the major retinal neuronal cell types (photoreceptors, bipolar cells, horizontal cells, amacrine cells, and ganglion cells), and also may include other mature retinal cells such as retinal pigment epithelial cells and Müller glial cells.

For example, a blood sample can be obtained from a subject, and different retinoid compounds and levels of one or more of the retinoid compounds in the sample can be separated and analyzed by normal phase high pressure liquid chromatography (HPLC) (e.g., with a HP1100 HPLC and a Beckman, Ultrasphere-Si, 4.6 mm×250 mm column using 10% ethyl acetate/90% hexane at a flow rate of 1.4 nil/minute). The retinoids can be detected by, for example, detection at 325 nm using a diode-array detector and HP Chemstation A.03.03 software. An excess in retinoids can be determined, for example, by comparison of the profile of retinoids (i.e., qualitative, e.g., identity of specific compounds, and quantitative, e.g., the level of each specific compound) in the sample with a sample from a normal subject. Persons skilled in the art who are familiar with such assays and techniques and will readily understand that appropriate controls are included.

As used herein, increased or excessive levels of endogenous retinoid, such as 11-cis-retinol or 11-cis-retinal, refer to levels of endogenous retinoid higher than those found in a healthy eye of a young vertebrate of the same species. Administration of a styrenyl derivative compound and reduce or eliminate the requirement for endogenous retinoid.

In Vivo and In Vitro Methods for Determining Therapeutic Effectiveness of Compounds In one embodiment, methods are provided for using the compounds described herein for enhancing or prolonging retinal cell survival, including retinal neuronal cell survival and RPE cell survival. Also provided herein are methods for inhibiting or preventing degeneration of a retinal cell, including a retinal neuronal cell (e.g., a photoreceptor cell, an amacrine cell, a horizontal cell, a bipolar cell, and a ganglion cell) and other mature retinal cells such as retinal pigment epithelial cells and Müller glial cells using the compounds described herein. Such methods comprise, in certain embodiments, administration of a styrenyl derivative compound as described herein. Such a compound is useful for enhancing retinal cell survival, including photoreceptor cell survival and retinal pigment epithelia survival, inhibiting or slowing degeneration of a retinal cell, and thus increasing retinal cell viability, which can result in slowing or halting the progression of an ophthalmic disease or disorder or retinal injury, which are described herein.

The effect of a styrenyl derivative compound on retinal cell survival (and/or retinal cell degeneration) may be determined by using cell culture models, animal models, and other methods that are described herein and practiced by persons skilled in the art. By way of example, and not limitation, such methods and assays include those described in Oglivie et al., *Exp. Neurol.* 161:675-856 (2000); U.S. Pat. No. 6,406,840; WO 01/81551; WO 98/12303; U.S. Patent Application No. 2002/0009713; WO 00/40699; U.S. Pat. No. 6,117,675; U.S. Pat. No. 5,736,516; WO 99/29279; WO 01/83714; WO 01/42784; U.S. Pat. No. 6,183,735; U.S. Pat. No. 6,090,624; WO 01/09327; U.S. Pat. No. 5,641,750; U.S. Patent Application Publication No. 2004/0147019; and U.S. Patent Application Publication No. 2005/0059148.

Exemplary methods are described herein and practiced by persons skilled in the art for determining the level of enzymatic activity of a visual cycle isomerase in the presence of any one of the compounds described herein. A compound that decreases isomerase activity may be useful for treating an ophthalmic disease or disorder. Thus, methods are provided herein for detecting inhibition of isomerase activity comprising contacting (i.e., mixing, combining, or in some manner permitting the compound and isomerase to interact) a biological sample comprising the isomerase and a styrenyl derivative compound described herein and then determining the level of enzymatic activity of the isomerase. A person having skill in the art will appreciate that as a control, the level of activity of the isomerase in the absence of a compound or in the presence of a compound known not to alter the enzymatic activity of the isomerase can be determined and compared to the level of activity in the presence of the compound. A decrease in the level of isomerase activity in the presence of the compound compared to the level of isomerase activity in the absence of the compound indicates that the compound may be useful for treating an ophthalmic disease or disorder, such as age-related macular degeneration or Stargardt's disease. A decrease in the level of isomerase activity in the presence of the compound compared to the level of isomerase activity in the absence of the compound indicates that the compound may also be useful in the methods described herein for inhibiting or preventing dark adaptation, inhibiting neovascularization and reducing hypoxia and thus useful for treating an ophthalmic disease or disorder, for example, diabetic retinopathy, diabetic maculopathy, retinal blood vessel occlusion, retinopathy of prematurity, or ischemia reperfusion related retinal injury.

The capability of a styrenyl compound described herein to inhibit or to prevent dark adaptation of a rod photoreceptor cell by inhibiting regeneration of rhodopsin may be determined by in vitro assays and/or in vivo animal models. By way of example, inhibition of regeneration may be determined in a mouse model in which a diabetes-like condition is induced chemically or in a diabetic mouse model (see, e.g., Phipps et al., *Invest. Ophthalmol. Vis. Sci.* 47:3187-94 (2006); Ramsey et al., *Invest. Ophthalmol. Vis. Sci.* 47:5116-24 (2006)). The level of rhodopsin (a first level) may be determined (for example, spectrophotometrically) in the retina of animals prior to administration of the agent and compared with the level (a second level) of rhodopsin measured in the retina of animals after administration of the agent. A decrease in the second level of rhodopsin compared with the first level of rhodopsin indicates that the agent inhibits regeneration of rhodopsin. The appropriate controls and study design to determine whether regeneration of rhodopsin is inhibited in a statistically significant or biologically significant manner can be readily determined and implemented by persons skilled in the art.

Methods and techniques for determining or characterizing the effect of any one of the compounds described herein on dark adaptation and rhodopsin regeneration in rod photoreceptor cells in a mammal, including a human, may be performed according to procedures described herein and practiced in the art. For example, detection of a visual stimulus after exposure to light (i.e., photobleaching) versus time in darkness may be determined before administration of the first dose of the compound and at a time after the first dose and/or any subsequent dose. A second method for determining prevention or inhibition of dark adaptation by the rod photoreceptor cells includes measurement of the amplitude of at least one, at least two, at least three, or more electroretinogram components, which include, for example, the a-wave and the b-wave. See, for example, Lamb et al., supra; Asi et al., *Documenta Ophthalmologica* 79:125-39 (1992).

Inhibiting regeneration of rhodopsin by a styrenyl compound described herein may comprise reducing the level of the chromophore, 11-cis-retinal, that is produced and present in the RPE cell, and consequently reducing the level of 11-cis-retinal that is present in the photoreceptor cell. Thus, the compound, when permitted to contact the retina under suitable conditions and at a time sufficient to prevent dark adaptation of a rod photoreceptor cell and to inhibit regeneration of rhodopsin in the rod photoreceptor cell, effects a reduction in the level of 11-cis-retinal in a rod photoreceptor cell (i.e., a statistically significant or biologically significant reduction). That is, the level of 11-cis retinal in a rod photoreceptor cell is greater prior to administration of the compound when compared with the level of 11-cis-retinal in the photoreceptor cell after the first and/or any subsequent administration of the compound. A first level of 11-cis-retinal may be determined prior to administration of the compound, and a second level of 11-cis-retinal may be determined after administration of a first dose or any subsequent dose to monitor the effect of the compound. A decrease in the second level compared to the first level indicates that the compound inhibits regeneration of rhodopsin and thus inhibits or prevents dark adaptation of the rod photoreceptor cells.

An exemplary method for determining or characterizing the capability of a styrenyl compound to reduce retinal hypoxia includes measuring the level of retinal oxygenation, for example, by Magnetic Resonance Imaging (MRI) to measure changes in oxygen pressure (see, e.g., Luan et al., *Invest. Ophthalmol. Vis. Sci.* 47:320-28 (2006)).

Animal models may be used to characterize and identify compounds that may be used to treat retinal diseases and disorders. A recently developed animal model may be useful for evaluating treatments for macular degeneration has been described by Ambati et al. (Nat. Med. 9:1390-97 (2003); Epub 2003 Oct. 19). This animal model is one of only a very few exemplary animal models presently available for evaluating a compound or any molecule for use in treating (including preventing) progression or development of a a retinal disease or disorder. Animal models in which the ABCR gene, which encodes an ATP-binding cassette transporter located in the rims of photoreceptor outer segment discs, may be used to evaluate the effect of a compound. Mutations in the ABCR gene are associated with Stargardt's disease, and heterozygous mutations in ABCR have been associated with AMD. Accordingly, animals have been generated with partial or total loss of ABCR function and may used to characterize the styrenyl compounds described herein. (See, e.g, Mata et al., *Invest. Ophthalmol. Sci.* 42:1685-90 (2001); Weng et al., *Cell* 98:13-23 (1999); Mata et al., *Proc. Natl. Acad. Sci. USA* 97:7154-49 (2000); US 2003/0032078; U.S. Pat. No. 6,713,300).

The effect of any one of the compounds described herein may be determined in a diabetic retinopathy animal model, such as described in Luan et al. or may be determined in a normal animal model, in which the animals have been light or dark adapted in the presence and absence of any one of the compounds described herein. Another exemplary method for determining the capability of the agent to reduce retinal hypoxia measures retinal hypoxia by deposition of a hydroxyprobe (see, e.g., de Gooyer et al. (*Invest. Ophthalmol. Vis. Sci.* 47:5553-60 (2006)). Such a technique may be performed in an animal model using Rho$^-$/Rho$^-$ knockout mice (see de Gooyer et al., supra) in which at least one compound described herein is administered to group(s) of animals in the presence and absence of the at least one compound, or may be performed in normal, wildtype animals in which at least one compound described herein is administered to group(s) of animals in the presence and absence of the at least one compound. Other animal models include models for determining photoreceptor function, such as rat models that measure elctroretinographic (ERG) oscillatory potentials (see, e.g., Liu et al., *Invest. Ophthalmol. Vis. Sci.* 47:5447-52 (2006); Akula et al., *Invest. Ophthalmol. Vis. Sci.* 48:4351-59 (2007); Liu et al., *Invest. Ophthalmol. Vis. Sci.* 47:2639-47 (2006); Dembinska et al., *Invest. Ophthalmol. Vis. Sci.* 43:2481-90 (2002); Penn et al., *Invest. Ophthalmol. Vis. Sci.* 35:3429-35 (1994); Hancock et al., *Invest. Ophthalmol. Vis. Sci.* 45:1002-1008 (2004)).

Accordingly, cell culture methods, such as the method described herein, is particularly useful for determining the effect of a compound described herein on retinal neuronal cell survival. Exemplary cell culture models are described herein and described in detail in U.S. Patent Application Publication No. US 2005-0059148 and U.S. Patent Application Publication No. US2004-0147019 (which are incorporated by reference in their entirety), which are useful for determining the capability of a styrenyl derivative compound as described herein to enhance or prolong survival of neuronal cells, particularly retinal neuronal cells, and of retinal pigment epithelial cells, and inhibit, prevent, slow, or retard degeneration of an eye, or the retina or retinal cells thereof, or the RPE, and which compounds are useful for treating ophthalmic diseases and disorders.

The cell culture model comprises a long-term or extended culture of mature retinal cells, including retinal neuronal cells (e.g., photoreceptor cells, amacrine cells, ganglion cells, horizontal cells, and bipolar cells). The cell culture system and methods for producing the cell culture system provide extended culture of photoreceptor cells. The cell culture system may also comprise retinal pigment epithelial (RPE) cells and Müller glial cells.

The retinal cell culture system may also comprise a cell stressor. The application or the presence of the stressor affects the mature retinal cells, including the retinal neuronal cells, in vitro, in a manner that is useful for studying disease pathology that is observed in a retinal disease or disorder. The cell culture model provides an in vitro neuronal cell culture system that will be useful in the identification and biological testing of a styrenyl derivative compound that is suitable for treatment of neurological diseases or disorders in general, and for treatment of degenerative diseases of the eye and brain in particular. The ability to maintain primary, in vitro-cultured cells from mature retinal tissue, including retinal neurons over an extended period of time in the presence of a stressor enables examination of cell-to-cell interactions, selection and analysis of neuroactive compounds and materials, use of a controlled cell culture system for in vitro CNS and ophthalmic tests, and analysis of the effects on single cells from a consistent retinal cell population.

The cell culture system and the retinal cell stress model comprise cultured mature retinal cells, retinal neurons, and a retinal cell stressor, which may be used for screening and characterizing a styrenyl derivative compound that are capable of inducing or stimulating the regeneration of CNS tissue that has been damaged by disease. The cell culture system provides a mature retinal cell culture that is a mixture of mature retinal neuronal cells and non-neuronal retinal cells. The cell culture system may comprise all the major retinal neuronal cell types (photoreceptors, bipolar cells, horizontal cells, amacrine cells, and ganglion cells), and may also include other mature retinal cells such as RPE and Müller glial cells. By incorporating these different types of cells into the in vitro culture system, the system essentially resembles an "artificial organ" that is more akin to the natural in vivo state of the retina.

Viability of one or more of the mature retinal cell types that are isolated (harvested) from retinal tissue and plated for tissue culture may be maintained for an extended period of time, for example, from two weeks up to six months. Viability of the retinal cells may be determined according to methods described herein and known in the art. Retinal neuronal cells, similar to neuronal cells in general, are not actively dividing cells in vivo and thus cell division of retinal neuronal cells would not necessarily be indicative of viability. An advantage of the cell culture system is the ability to culture amacrine cells, photoreceptors, and associated ganglion projection neurons and other mature retinal cells for extended periods of time, thereby providing an opportunity to determine the effectiveness of a styrenyl derivative compound described herein for treatment of retinal disease.

The biological source of the retinal cells or retinal tissue may be mammalian (e.g., human, non-human primate, ungulate, rodent, canine, porcine, bovine, or other mammalian source), avian, or from other genera. Retinal cells including retinal neurons from post-natal non-human primates, post-natal pigs, or post-natal chickens may be used, but any adult or post-natal retinal tissue may be suitable for use in this retinal cell culture system.

In certain instances, the cell culture system may provide for robust long-term survival of retinal cells without inclusion of cells derived from or isolated or purified from non-retinal tissue. Such a cell culture system comprises cells isolated solely from the retina of the eye and thus is substantially free of types of cells from other parts or regions of the eye that are separate from the retina, such as the ciliary body, iris, choroid, and vitreous. Other cell culture methods include the addition of non-retinal cells, such as ciliary body cell and/or stem cells (which may or may not be retinal stem cells) and/or additional purified glial cells.

The in vitro retinal cell culture systems described herein may serve as physiological retinal models that can be used to characterize aspects of the physiology of the retina. This physiological retinal model may also be used as a broader general neurobiology model. A cell stressor may be included in the model cell culture system. A cell stressor, which as described herein is a retinal cell stressor, adversely affects the viability or reduces the viability of one or more of the different retinal cell types, including types of retinal neuronal cells, in the cell culture system. A person skilled in the art would readily appreciate and understand that as described herein a retinal cell that exhibits reduced viability means that the length of time that a retinal cell survives in the cell culture system is reduced or decreased (decreased lifespan) and/or that the retinal cell exhibits a decrease, inhibition, or adverse effect of a biological or biochemical function (e.g., decreased or abnormal metabolism; initiation of apoptosis; etc.) compared with a retinal cell cultured in an appropriate control cell system (e.g., the cell culture system described herein in the absence of the cell stressor). Reduced viability of a retinal cell may be indicated by cell death; an alteration or change in cell structure or morphology; induction and/or progression of apoptosis; initiation, enhancement, and/or acceleration of retinal neuronal cell neurodegeneration (or neuronal cell injury).

Methods and techniques for determining cell viability are described in detail herein and are those with which skilled artisans are familiar. These methods and techniques for determining cell viability may be used for monitoring the health and status of retinal cells in the cell culture system and for determining the capability of the styrenyl derivative compounds described herein to alter (preferably increase, prolong, enhance, improve) retinal cell or retinal pigment epithelial cell viability or retinal cell survival.

The addition of a cell stressor to the cell culture system is useful for determining the capability of a styrenyl derivative compound to abrogate, inhibit, eliminate, or lessen the effect of the stressor. The retinal cell culture system may include a cell stressor that is chemical (e.g., A2E, cigarette smoke concentrate); biological (for example, toxin exposure; beta-amyloid; lipopolysaccharides); or non-chemical, such as a physical stressor, environmental stressor, or a mechanical force (e.g., increased pressure or light exposure) (see, e.g., US 2005-0059148).

The retinal cell stressor model system may also include a cell stressor such as, but not limited to, a stressor that may be a risk factor in a disease or disorder or that may contribute to the development or progression of a disease or disorder, including but not limited to, light of varying wavelengths and intensities; A2E; cigarette smoke condensate exposure; oxidative stress (e.g., stress related to the presence of or exposure to hydrogen peroxide, nitroprusside, $Zn^{++}$, or $Fe^{++}$); increased pressure (e.g., atmospheric pressure or hydrostatic pressure), glutamate or glutamate agonist (e.g., N-methyl-D-aspartate (NMDA); alpha-amino-3-hydroxy-5-methylisoxazole-4-proprionate (AMPA); kainic acid; quisqualic acid; ibotenic acid; quinolinic acid; aspartate; trans-1-aminocyclopentyl-1,3-dicarboxylate (ACPD)); amino acids (e.g., aspartate, L-cysteine; beta-N-methylamine-L-alanine); heavy metals (such as lead); various toxins (for example, mitochondrial toxins (e.g., malonate, 3-nitroproprionic acid; rotenone, cyanide); MPTP (1-methyl-4-phenyl-1,2,3,6,-tetrahydropyridine), which metabolizes to its active, toxic metabolite MPP+(1-methyl-4-phenylpryidine)); 6-hydroxydopamine; alpha-synuclein; protein kinase C activators (e.g., phorbol myristate acetate); biogenic amino stimulants (for example, methamphetamine, MDMA (3-4 methylenedioxymethamphetamine)); or a combination of one or more stressors. Useful retinal cell stressors include those that mimic a neurodegenerative disease that affects any one or more of the mature retinal cells described herein. A chronic disease model is of particular importance because most neurodegenerative diseases are chronic. Through use of this in vitro cell culture system, the earliest events in long-term disease development processes may be identified because an extended period of time is available for cellular analysis.

A retinal cell stressor may alter (i.e., increase or decrease in a statistically significant manner) viability of retinal cells such as by altering survival of retinal cells, including retinal neuronal cells and RPE cells, or by altering neurodegeneration of retinal neuronal cells and/or RPE cells. Preferably, a retinal cell stressor adversely affects a retinal neuronal cell or RPE cell such that survival of a retinal neuronal cell or RPE cell is decreased or adversely affected (i.e., the length of time during which the cells are viable is decreased in the presence of the stressor) or neurodegeneration (or neuron cell injury) of the cell is increased or enhanced. The stressor may affect only a single retinal cell type in the retinal cell culture or the stressor may affect two, three, four, or more of the different cell types. For example, a stressor may alter viability and survival of photoreceptor cells but not affect all the other major cell types (e.g., ganglion cells, amacrine cells, horizontal cells, bipolar cells, RPE, and Müller glia). Stressors may shorten the survival time of a retinal cell (in vivo or in vitro), increase the rapidity or extent of neurodegeneration of a retinal cell, or in some other manner adversely affect the viability, morphology, maturity, or lifespan of the retinal cell.

The effect of a cell stressor (in the presence and absence of a styrenyl derivative compound) on the viability of retinal cells in the cell culture system may be determined for one or more of the different retinal cell types. Determination of cell viability may include evaluating structure and/or a function of a retinal cell continually at intervals over a length of time or at a particular time point after the retinal cell culture is prepared. Viability or long term survival of one or more different retinal cell types or one or more different retinal neuronal cell types may be examined according to one or more biochemical or biological parameters that are indicative of reduced viability, such as apoptosis or a decrease in a metabolic function, prior to observation of a morphological or structural alteration.

A chemical, biological, or physical cell stressor may reduce viability of one or more of the retinal cell types present in the cell culture system when the stressor is added to the cell culture under conditions described herein for maintaining the long-term cell culture. Alternatively, one or more culture conditions may be adjusted so that the effect of the stressor on the retinal cells can be more readily observed. For example, the concentration or percent of fetal bovine serum may be reduced or eliminated from the cell culture when cells are exposed to a particular cell stressor (see, e.g., US 2005-0059148). Alternatively, retinal cells cultured in media containing serum at a particular concentration for maintenance of the cells may be abruptly exposed to media that does not contain any level of serum.

The retinal cell culture may be exposed to a cell stressor for a period of time that is determined to reduce the viability of one or more retinal cell types in the retinal cell culture system. The cells may be exposed to a cell stressor immediately upon plating of the retinal cells after isolation from retinal tissue. Alternatively, the retinal cell culture may be exposed to a stressor after the culture is established, or any time thereafter. When two or more cell stressors are included in the retinal cell culture system, each stressor may be added to the cell culture system concurrently and for the same length of time or may be added separately at different time points for the same length of time or for differing lengths of time during the culturing of the retinal cell system. A styrenyl compound may be added before the retinal cell culture is exposed to a cell stressor, may be added concurrently with the cell stressor, or may be added after exposure of the retinal cell culture to the stressor.

Photoreceptors may be identified using antibodies that specifically bind to photoreceptor-specific proteins such as opsins, peripherins, and the like. Photoreceptors in cell culture may also be identified as a morphologic subset of immunocytochemically labeled cells by using a pan-neuronal marker or may be identified morphologically in enhanced contrast images of live cultures. Outer segments can be detected morphologically as attachments to photoreceptors.

Retinal cells including photoreceptors can also be detected by functional analysis. For example, electrophysiology methods and techniques may be used for measuring the response of photoreceptors to light. Photoreceptors exhibit specific kinetics in a graded response to light. Calcium-sensitive dyes may also be used to detect graded responses to light within cultures containing active photoreceptors. For analyzing stress-inducing compounds or potential neurotherapeutics, retinal cell cultures can be processed for immunocytochemistry, and photoreceptors and/or other retinal cells can be counted manually or by computer software using photomicroscopy and imaging techniques. Other immunoassays known in the art (e.g., ELISA, immunoblotting, flow cytometry) may also be useful for identifying and characterizing the retinal cells and retinal neuronal cells of the cell culture model system described herein.

The retinal cell culture stress models may also be useful for identification of both direct and indirect pharmacologic agent effects by the bioactive agent of interest, such as a styrenyl derivative compound as described herein. For example, a bioactive agent added to the cell culture system in the presence of one or more retinal cell stressors may stimulate one cell type in a manner that enhances or decreases the survival of other cell types. Cell/cell interactions and cell/extracellular component interactions may be important in understanding mechanisms of disease and drug function. For example, one neuronal cell type may secrete trophic factors that affect growth or survival of another neuronal cell type (see, e.g., WO 99/29279).

In another embodiment, a styrenyl derivative compound is incorporated into screening assays comprising the retinal cell culture stress model system described herein to determine whether and/or to what level or degree the compound increases viability (i.e., increases in a statistically significant or biologically significant manner) of a plurality of retinal cells. A person skilled in the art would readily appreciate and understand that as described herein a retinal cell that exhibits increased viability means that the length of time that a retinal cell survives in the cell culture system is increased (increased lifespan) and/or that the retinal cell maintains a biological or biochemical function (normal metabolism and organelle function; lack of apoptosis; etc.) compared with a retinal cell cultured in an appropriate control cell system (e.g., the cell culture system described herein in the absence of the compound). Increased viability of a retinal cell may be indicated by delayed cell death or a reduced number of dead or dying cells; maintenance of structure and/or morphology; lack of or delayed initiation of apoptosis; delay, inhibition, slowed progression, and/or abrogation of retinal neuronal cell neurodegeneration or delaying or abrogating or preventing the effects of neuronal cell injury. Methods and techniques for determining viability of a retinal cell and thus whether a retinal cell exhibits increased viability are described in greater detail herein and are known to persons skilled in the art.

In certain embodiments, a method is provided for determining whether a styrenyl derivative compound, enhances survival of photoreceptor cells. One method comprises contacting a retinal cell culture system as described herein with a styrenyl compound under conditions and for a time sufficient to permit interaction between the retinal neuronal cells and the compound. Enhanced survival (prolonged survival) may be measured according to methods described herein and known in the art, including detecting expression of rhodopsin.

The capability of a styrenyl derivative compound to increase retinal cell viability and/or to enhance, promote, or prolong cell survival (that is, to extend the time period in which retinal cells, including retinal neuronal cells, are viable), and/or impair, inhibit, or impede degeneration as a direct or indirect result of the herein described stress may be determined by any one of several methods known to those skilled in the art. For example, changes in cell morphology in the absence and presence of the compound may be determined by visual inspection such as by light microscopy, confocal microscopy, or other microscopy methods known in the art. Survival of cells can also be determined by counting viable and/or nonviable cells, for instance. Immunochemical or immunohistological techniques (such as fixed cell staining or flow cytometry) may be used to identify and evaluate cytoskeletal structure (e.g., by using antibodies specific for cytoskeletal proteins such as glial fibrillary acidic protein, fibronectin, actin, vimentin, tubulin, or the like) or to evaluate expression of cell markers as described herein. The effect of a styrenyl derivative compound on cell integrity, morphology, and/or survival may also be determined by measuring the phosphorylation state of neuronal cell polypeptides, for example, cytoskeletal polypeptides (see, e.g., Sharma et al., *J. Biol. Chem.* 274:9600-06 (1999); Li et al., *J. Neurosci.* 20:6055-62 (2000)). Cell survival or, alternatively cell death, may also be determined according to methods described herein and known in the art for measuring apoptosis (for example, annexin V binding, DNA fragmentation assays, caspase activation, marker analysis, e.g., poly(ADP-ribose) polymerase (PARP), etc.).

In the vertebrate eye, for example, a mammalian eye, the formation of A2E is a light-dependent process and its accumulation leads to a number of negative effects in the eye. These include destabilization of retinal pigment epithelium (RPE) membranes, sensitization of cells to blue-light damage, and impaired degradation of phospholipids. Products of the oxidation of A2E (and A2E related molecules) by molecular oxygen (oxiranes) were shown to induce DNA damage in cultured RPE cells. All these factors lead to a gradual decrease in visual acuity and eventually to vision loss. If reducing the formation of retinals during vision processes were possible, this reduction would lead to decreased amounts of A2E in the eye. Without wishing to be bound by theory, decreased accumulation of A2E may reduce or delay degenerative processes in the RPE and retina and thus may slow down or prevent vision loss in dry AMD and Stargardt's Disease.

In another embodiment, methods are provided for treating and/or preventing degenerative diseases and disorders, including neurodegenerative retinal diseases and ophthalmic diseases as described herein. A subject in need of such treatment may be a human or non-human primate or other animal who has developed symptoms of a degenerative retinal disease or who is at risk for developing a degenerative retinal disease. As described herein a method is provided for treating (which includes preventing or prophylaxis) an ophthalmic disease or disorder by administrating to a subject a composition comprising a pharmaceutically acceptable carrier and a styrenyl derivative compound. As described herein, a method is provided for enhancing survival of neuronal cells such as retinal neuronal cells, including photoreceptor cells, and/or inhibiting degeneration of retinal neuronal cells by administering the pharmaceutical compositions described herein comprising a styrenyl derivative compound.

Enhanced survival (or prolonged or extended survival) of one or more retinal cell types in the presence of a styrenyl derivative compound indicates that the compound may be an effective agent for treatment of a degenerative disease, particularly a retinal disease or disorder, and including a neurodegenerative retinal disease or disorder. Cell survival and enhanced cell survival may be determined according to methods described herein and known to a skilled artisan including viability assays and assays for detecting expression of retinal cell marker proteins. For determining enhanced survival of photoreceptor cells, opsins may be detected, for instance, including the protein rhodopsin that is expressed by rods.

In another embodiment, the subject is being treated for Stargardt's disease or Stargardt's macular degeneration. In Stargardt's disease, which is associated with mutations in the ABCA4 (also called ABCR) transporter, the accumulation of all-trans-retinal has been proposed to be responsible for the formation of a lipofuscin pigment, A2E, which is toxic towards retinal cells and causes retinal degeneration and consequently loss of vision.

In yet another embodiment, the subject is being treated for age-related macular degeneration (AMD). In various embodiments, AMD can be wet or dry form. In AMD, vision loss primarily occurs when complications late in the disease either cause new blood vessels to grow under the macula or the macula atrophies. Without intending to be bound by any particular theory, the accumulation of all-trans-retinal has been proposed to be responsible for the formation of a lipofuscin pigment, N-retinylidene-N-retinylethanolamine (A2E) and A2E related molecules, which are toxic towards RPE and retinal cells and cause retinal degeneration and consequently loss of vision.

A neurodegenerative retinal disease or disorder for which the compounds and methods described herein may be used for treating, curing, preventing, ameliorating the symptoms of, or slowing, inhibiting, or stopping the progression of, is a disease or disorder that leads to or is characterized by retinal neuronal cell loss, which is the cause of visual impairment. Such a disease or disorder includes but is not limited to age-related macular degeneration (including dry-form and wet-form of macular degeneration) and Stargardt's macular dystrophy.

Age-related macular degeneration as described herein is a disorder that affects the macula (central region of the retina) and results in the decline and loss of central vision. Age-related macular degeneration occurs typically in individuals over the age of 55 years. The etiology of age-related macular degeneration may include both environmental influences and genetic components (see, e.g., Lyengar et al., Am. J. Hum. Genet. 74:20-39 (2004) (Epub 2003 Dec. 19); Kenealy et al., *Mol. Vis.* 10:57-61 (2004); Gorin et al., *Mol. Vis.* 5:29 (1999)). More rarely, macular degeneration occurs in younger individuals, including children and infants, and generally, these disorders results from a genetic mutation. Types of juvenile macular degeneration include Stargardt's disease (see, e.g., Glazer et al., *Ophthalmol. Clin. North Am.* 15:93-100, viii (2002); Weng et al., *Cell* 98:13-23 (1999)); Doyne's honeycomb retinal dystrophy (see, e.g., Kermani et al., *Hum. Genet.* 104:77-82 (1999)); Sorsby's fundus dystrophy, Malattia Levintinese, fundus flavimaculatus, and autosomal dominant hemorrhagic macular dystrophy (see also Seddon et al., *Ophthalmology* 108:2060-67 (2001); Yates et al., *J. Med. Genet.* 37:83-7 (2000); Jaakson et al., *Hum. Mutat.* 22:395-403 (2003)).

Geographic atrophy of the RPE is an advanced form of non-neovascular dry-type age-related macular degeneration, and is associated with atrophy of the choriocapillaris, RPE, and retina.

Stargardt's macular degeneration, a recessive inherited disease, is an inherited blinding disease of children. The primary pathologic defect in Stargardt's disease is also an accumulation of toxic lipofuscin pigments such as A2E in cells of the retinal pigment epithelium (RPE). This accumulation appears to be responsible for the photoreceptor death and severe visual loss found in Stargardt's patients. The compounds described herein may slow the synthesis of 11-cis-retinaldehyde (11 cRAL or retinal) and regeneration of -rhodopsin by inhibiting isomerase in the visual cycle. Light activation of rhodopsin results in its release of all-trans-retinal, which constitutes the first reactant in A2E biosynthesis. Treatment with styrenyl derivative compounds may inhibit lipofuscin accumulation and thus delay the onset of visual loss in Stargardt's and AMD patients without toxic effects that would preclude treatment with a styrenyl derivative compound. The compounds described herein may be used for effective treatment of other forms of retinal or macular degeneration associated with lipofuscin accumulation.

Administration of a styrenyl derivative compound to a subject can prevent formation of the lipofuscin pigment, A2E (and A2E related molecules), that is toxic towards retinal cells and causes retinal degeneration. In certain embodiments, administration of a styrenyl derivative compound can lessen the production of waste products, e.g., lipofuscin pigment, A2E (and A2E related molecules), ameliorate the development of AMD (e.g., dry-form) and Stargardt's disease, and reduce or slow vision loss (e.g., choroidal neovascularization and/or chorioretinal atrophy). In previous studies, with 13-cis-retinoic acid (Accutane® or Isotretinoin), a drug commonly used for the treatment of acne and an inhibitor of 11-cis-retinol dehydrogenase, has been administered to patients to prevent A2E accumulation in the RPE. However, a major drawback in this proposed treatment is that 13-cis-retinoic acid can easily isomerize to all-trans-retinoic acid. All-trans-retinoic acid is a very potent teratogenic compound that adversely affects cell proliferation and development. Retinoic acid also accumulates in the liver and may be a contributing factor in liver diseases.

In yet other embodiments, a styrenyl derivative compound is administered to a subject such as a human with a mutation in the ABCA4 transporter in the eye. The styrenyl derivative compound can also be administered to an aging subject. As used herein, an aging human subject is typically at least 45, or at least 50, or at least 60, or at least 65 years old. In Stargardt's disease, which is associated with mutations in the ABCA4 transporter, the accumulation of all-trans-retinal has been proposed to be responsible for the formation of a lipofuscin pigment, A2E (and A2E related molecules), that is toxic towards retinal cells and causes retinal degeneration and consequently loss of vision. Without wishing to be bound by theory, a styrenyl derivative compound described herein may be a strong inhibitor of the isomerase protein involved in the visual cycle. Treating patients with a styrenyl derivative compound as described herein may prevent or slow the formation of A2E (and A2E related molecules) and can have protective properties for normal vision.

In other certain embodiments, one or more of the compounds described herein may be used for treating other ophthalmic diseases or disorders, for example, glaucoma, retinal detachment, hemorrhagic retinopathy, retinitis pigmentosa, an inflammatory retinal disease, proliferative vitreoretinopathy, retinal dystrophy, hereditary optic neuropathy, Sorsby's fundus dystrophy, uveitis, a retinal injury, optical neuropathy, and retinal disorders associated with other neurodegenerative diseases such as Alzheimer's disease, multiple sclerosis, Parkinson's disease or other neurodegenerative diseases that affect brain cells, a retinal disorder associated with viral infection, or other conditions such as AIDS. A retinal disorder also includes light damage to the retina that is related to increased light exposure (i.e., overexposure to light), for example, accidental strong or intense light exposure during surgery; strong, intense, or prolonged sunlight exposure, such as at a desert or snow covered terrain; during combat, for example, when observing a flare or explosion or from a laser device, and the like. Retinal diseases can be of degenerative or non-degenerative nature. Non-limiting examples of degenerative retinal diseases include age-related macular degeneration, and Stargardt's macular dystrophy. Examples of non-degenerative retinal diseases include but are not limited hemorrhagic retinopathy, retinitis pigmentosa, optic neuropathy, inflammatory retinal disease, diabetic retinopathy, diabetic maculopathy, retinal blood vessel occlusion, retinopathy of prematurity, or ischemia reperfusion related retinal injury, proliferative vitreoretinopathy, retinal dystrophy, hereditary optic neuropathy, Sorsby's fundus dystrophy, uveitis, a retinal injury, a retinal disorder associated with Alzheimer's disease, a retinal disorder associated with multiple sclerosis, a retinal disorder associated with Parkinson's disease, a retinal disorder associated with viral infection, a retinal disorder related to light overexposure, and a retinal disorder associated with AIDS.

In other certain embodiments, one or more of the compounds described herein may be used for treating, curing, preventing, ameliorating the symptoms of, or slowing, inhibiting, or stopping the progression of, certain ophthalmic diseases and disorders including but not limited to diabetic retinopathy, diabetic maculopathy, diabetic macular edema, retinal ischemia, ischemia-reperfusion related retinal injury, and retinal blood vessel occlusion (including venous occlusion and arterial occlusion).

Diabetic retinopathy is a leading cause of blindness in humans and is a complication of diabetes. Non-proliferative retinopathy may be mild, moderate, or severe, and if left untreated, the disease can progress to proliferative retinopathy, a more serious form of diabetic retinopathy. Proliferative retinopathy occurs when new blood vessels proliferate in and around the retina. Consequently, bleeding into the vitreous, swelling of the retina, and/or retinal detachment may occur, leading to blindness.

Other ophthalmic diseases and disorders that may be treated using the compounds, compositions, and methods described herein include diseases, disorders, and conditions that are associated with, exacerbated by, or caused by ischemia in the retina. Retinal ischemia includes ischemia of the inner retina and the outer retina. Retinal ischemia can occur from either choroidal or retinal vascular diseases, such as central or branch retinal vision occlusion, sickle cell retinopathy, collagen vascular diseases and thrombocytopenic purpura, Eales disease, and systemic lupus erythematosus.

Retinal ischemia may be associated with retinal blood vessel occlusion. In the United States, both branch and central retinal vein occlusions are the second most common retinal vascular diseases after diabetic retinopathy. About 7% to 10% of patients who have retinal venous occlusive disease in one eye eventually have bilateral disease. Visual field loss commonly occurs from macular edema, ischemia, or vitreous hemorrhage secondary to disc or retinal neovascularization induced by the release of vascular endothelial growth factor.

Arteriolosclerosis at sites of retinal arteriovenous crossings (areas in which arteries and veins share a common adventitial sheath) causes constriction of the wall of a retinal vein by a crossing artery. The constriction results in thrombus formation and subsequent occlusion of the vein. The blocked vein may lead to macular edema and hemorrhage secondary to breakdown in the blood-retina barrier in the area drained by the vein, disruption of circulation with turbulence in venous flow, endothelial damage, and ischemia. Clinically, areas of ischemic retina appear as feathery white patches called cotton-wool spots.

Branch retinal vein occlusions with abundant ischemia cause acute central and paracentral visual field loss corresponding to the location of the involved retinal quadrants. Retinal neovascularization due to ischemia may lead to vitreous hemorrhage and subacute or acute vision loss.

Two types of central retinal vein occlusion, ischemic and nonischemic, may occur depending on whether widespread retinal ischemia is present. Even in the nonischemic type, the macula may still be ischemic. Approximately 25% central retinal vein occlusion is ischemic. Diagnosis of central retinal vein occlusion can usually be made on the basis of characteristic ophthalmoscopic findings, including retinal hemorrhage in all quadrants, dilated and tortuous veins, and cotton-wool spots. Macular edema and foveal ischemia can lead to vision loss. Extracellular fluid increases interstitial pressure, which may result in areas of retinal capillary closure (i.e., patchy ischemic retinal whitening) or occlusion of a cilioretinal artery.

Patients with ischemic central retinal vein occlusion are more likely to present with a sudden onset of vision loss and have visual acuity of less than 20/200, a relative afferent pupillary defect, abundant intraretinal hemorrhages, and extensive nonperfusion on fluorescein angiography. The natural history of ischemic central retinal vein occlusion is associated with poor outcomes: eventually, approximately two-thirds of patients who have ischemic central retinal vein occlusion will have ocular neovascularization and one-third will have neovascular glaucoma. The latter condition is a severe type of glaucoma that may lead to rapid visual field and vision loss, epithelial edema of the cornea with secondary epithelial erosion and predisposition to bacterial keratitis, severe pain, nausea and vomiting, and, eventually, phthisis bulbi (atrophy of the globe with no light perception).

As used herein, a patient (or subject) may be any mammal, including a human, that may have or be afflicted with a neurodegenerative disease or condition, including an ophthalmic disease or disorder, or that may be free of detectable disease. Accordingly, the treatment may be administered to a subject who has an existing disease, or the treatment may be prophylactic, administered to a subject who is at risk for developing the disease or condition. Treating or treatment refers to any indicia of success in the treatment or amelioration of an injury, pathology or condition, including any objective or subjective parameter such as abatement; remission; diminishing of symptoms or making the injury, pathology, or condition more tolerable to the patient; slowing in the rate of degeneration or decline; making the final point of degeneration less debilitating; or improving a subject's physical or mental well-being.

The treatment or amelioration of symptoms can be based on objective or subjective parameters; including the results of a physical examination. The term "therapeutic effect" refers to the reduction, elimination, or prevention of the disease, symptoms of the disease, or sequelae of the disease in the subject. Treatment includes restoring or improving retinal neuronal cell functions (including photoreceptor function) in a vertebrate visual system, for example, such as visual acuity and visual field testing etc., as measured over time (e.g., as measured in weeks or months). Treatment also includes stabilizing disease progression (i.e., slowing, minimizing, or halting the progression of an ophthalmic disease and associated symptoms) and minimizing additional degeneration of a vertebrate visual system. Treatment also includes prophylaxis and refers to the administration of a styrenyl derivative compound to a subject to prevent degeneration or further degeneration or deterioration or further deterioration of the vertebrate visual system of the subject and to prevent or inhibit development of the disease and/or related symptoms and sequelae. The term treating also includes the administration of the compounds or agents described herein to treat pain, hyperalgesia, allodynia, or nociceptive events and to prevent or delay, to alleviate, or to arrest or inhibit development of the symptoms or conditions associated with pain, hyperalgesia, allodynia, nociceptive events, or other disorders.

Various methods and techniques practiced by a person skilled in the medical and opthalmological arts to determine and evaluate a disease state and/or to monitor and assess a therapeutic regimen include, for example, fluorescein angiogram, fundus photography, indocyanine green dye tracking of the choroidal circulatory system, opthalmoscopy, optical coherence tomography (OCT), electroretinography, and visual acuity testing.

A fluorescein angiogram involves injecting a fluorescein dye intravenously and then observing any leakage of the dye as it circulates through the eye. Intravenous injection of indocyanine green dye may also be used to determine if vessels in the eye are compromised, particularly in the choroidal circulatory system that is just behind the retina. Fundus photography may be used for examining the optic nerve, macula, blood vessels, retina, and the vitreous. Microaneurysms are visible lesions in diabetic retinopathy that may be detected in digital fundus images early in the disease (see, e.g., U.S. Patent Application Publication No. 2007/0002275). An ophthalmoscope may be used to examine the retina and vitreous. Opthalmoscopy is usually performed with dilated pupils, to allow the best view inside the eye. Two types of ophthalmoscopes may be used: direct and indirect. The direct ophthalmoscope is generally used to view the optic nerve and the central retina. The periphery, or entire retina, may be viewed by using an indirect ophthalmoscope. Optical coherence tomography (OCT) produces high resolution, high speed, non-invasive, cross-sectional images of body tissue. OCT is noninvasive and provides detection of microscopic early signs of disruption in tissues.

A subject or patient refers to any vertebrate or mammalian patient or subject to whom the compositions described herein can be administered. The term "vertebrate" or "mammal" includes humans and non-human primates, as well as experimental animals such as rabbits, rats, and mice, and other animals, such as domestic pets (such as cats, dogs, horses), farm animals, and zoo animals. Subjects in need of treatment using the methods described herein may be identified according to accepted screening methods in the medical art that are employed to determine risk factors or symptoms associated with an ophthalmic disease or condition described herein or to determine the status of an existing ophthalmic disease or condition in a subject. These and other routine methods allow the clinician to select patients in need of therapy using the methods and formulations described herein.

Pharmaceutical Compositions

In certain embodiments, a styrenyl derivative compound described herein may be administered as a pure chemical. In other embodiments, the styrenyl derivative compound can be combined with a pharmaceutically suitable or acceptable carrier (also referred to herein as a pharmaceutically suitable (or acceptable) excipient, physiologically suitable (or acceptable) excipient, or physiologically suitable (or acceptable) carrier) selected on the basis of a chosen route of administration and standard pharmaceutical practice as described, for example, in *Remington: The Science and Practice of Pharmacy* (Gennaro, 21$^{st}$ Ed. Mack Pub. Co., Easton, Pa. (2005)), the disclosure of which is hereby incorporated herein by reference, in its entirety.

Accordingly, provided herein is a pharmaceutical composition comprising one or more styrenyl derivative compounds, or a stereoisomer, prodrug, pharmaceutically acceptable salt, hydrate, solvate, acid salt hydrate, N-oxide or isomorphic crystalline form thereof, of a compound described herein, together with one or more pharmaceutically acceptable carriers therefore and, optionally, other therapeutic and/or prophylactic ingredients. The carrier(s) is acceptable or suitable if the carrier is compatible with the other ingredients of the composition and not deleterious to the recipient of the composition. A pharmaceutically acceptable or suitable composition includes an ophthalmologically suitable or acceptable composition.

Thus, another embodiment provides a pharmaceutical composition comprising a pharmaceutically acceptable excipient and a compound having a structure of Formula (I):

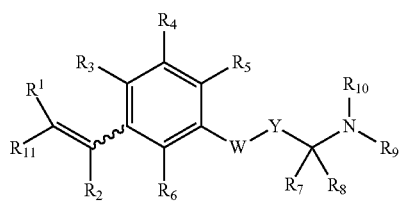

Formula (I)

as an isolated E or Z stereoisomer or a mixture of E and Z stereoisomers, as a tautomer or a mixture of tautomers, or as a pharmaceutically acceptable salt, hydrate, solvate, N-oxide or prodrug thereof, wherein:

prodrug thereof, wherein:

$R_1$ and $R_2$ are each the same or different and independently hydrogen or alkyl;

$R_3$, $R_4$, $R_5$ and $R_6$ are each the same or different and independently hydrogen, halogen, —$OR_{12}$, alkyl or fluoroalkyl;

$R_7$ and $R_8$ are each the same or different and independently hydrogen or alkyl;

$R_9$ is hydrogen, alkyl, carbocyclyl or —C(=O)$R_{13}$;

$R_{10}$ is hydrogen or alkyl; or $R_9$ and $R_{10}$, together with the nitrogen atom to which they are attached, form an N-heterocyclyl;

$R_{11}$ is alkyl, alkenyl, aryl, carbocyclyl, heteroaryl or heterocyclyl;

$R_{12}$ is hydrogen or alkyl;

$R_{13}$ is alkyl, carbocyclyl or aryl;

W is —C($R_{14}$)($R_{15}$)—, —O—, —S—, —S(=O)$_2$— or —N($R_{12}$)—;

Y is —C($R_{16}$)($R_{17}$)—;

$R_{14}$ and $R_{15}$ are each the same or different and independently hydrogen, halogen, alkyl, fluoroalkyl, —$OR_{12}$, —$NR_{18}R_{19}$ or carbocyclyl; or $R_{14}$ and $R_{15}$ form an oxo;

$R_{16}$ and $R_{17}$ are each the same or different and independently hydrogen, halogen, alkyl, fluoroalkyl, —$OR_{12}$, —$NR_{18}R_{19}$ or carbocyclyl; or $R_{16}$ and $R_{17}$ form an oxo; or $R_{14}$ and $R_{16}$ together form a direct bond to provide a double bond connecting W and Y; or $R_{14}$ and $R_{16}$ together form a direct bond, and $R_{15}$ and $R_{17}$ together form a direct bond to provide a triple bond connecting W and Y;

$R_{18}$ and $R_{19}$ are each the same or different and independently hydrogen, alkyl, carbocyclyl, or —C(=O)$R_{13}$, In certain embodiments, the pharmaceutical composition comprises a compound of Formula (I), as defined herein, provided that when $R_{11}$ is phenyl, the compound is not:

2-amino-N-[2-methoxy-5-[(1Z)-2-(3,4,5-trimethoxyphenyl)ethenyl]phenyl]acetamide;

(2S,3R)-amino-3-hydroxy-N-[2-methoxy-5-[(1Z)-2-(3,4,5-trimethoxyphenyl)-ethenyl]phenyl]-butanamide;

L-glutamic acid, 1-[2-methoxy-5-[(1Z)-2-(3,4,5-trimethoxyphenyl)ethenyl]phenyl]ester;

glycine, 3-hydroxy-5-[(1E)-2-(4-hydroxyphenyl)ethenyl]phenyl ester;

(2S)-2-amino-N-[2-methoxy-5-[(1Z)-2-(3,4,5-trimethoxyphenyl)ethenyl]phenyl]propanamide;

(2S)-2-amino-3-hydroxy-N-[2-methoxy-5-[(1Z)-2-(3,4,5-trimethoxyphenyl)ethenyl]phenyl]propanamide;

(2S)-2-amino-N-[2-methoxy-5-[(1Z)-2-(3,4,5-trimethoxyphenyl)ethenyl]phenyl]-4-methyl-pentanamide;

(2S)-2-amino-N-[2-methoxy-5-[(1Z)-2-(3,4,5-trimethoxyphenyl)ethenyl]phenyl]-3-methyl-butanamide; or 2-amino-N-[2-methoxy-5-[(1Z)-2-(3,4,5-trimethoxyphenyl)ethenyl]phenylbutanamide.

Various embodiments further provide pharmaceutical compositions comprising a pharmaceutically acceptable excipient and a compound of any one of Formulae (I), (II), (IIa), (IIb), (III) and (IIIa):

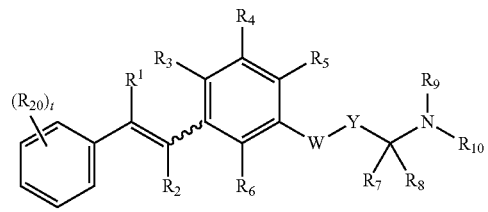

Formula (II)

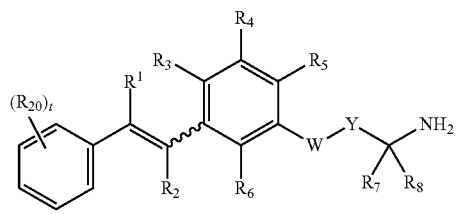

Formula (IIa)

-continued

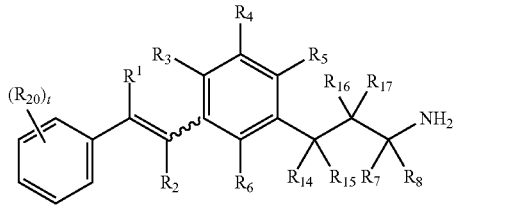

Formula (IIb)

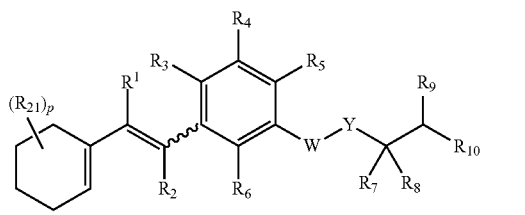

Formula (III)

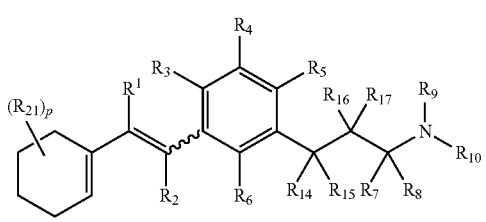

Formula (IIIa)

wherein, t, p, $R_1$, $R_2$, $R_3$, $R_4$, $R_5$, $R_6$, $R_7$, $R_8$, $R_9$, $R_{10}$, $R_{14}$, $R_{15}$, $R_{16}$, $R_{17}$, $R_{20}$, $R_{21}$, W and Y are as defined above and herein. Specific embodiments provided herein include pharmaceutical compositions comprising a pharmaceutically acceptable excipient and a compound described in any one of Tables 1-11 provided herein.

A pharmaceutical composition (e.g., for oral administration or delivery by injection, or combined devices, or for application as an eye drop) may be in the form of a liquid, semi-solid, or solid. A liquid pharmaceutical composition may include, for example, one or more of the following: sterile diluents such as water for injection, saline solution, preferably physiological saline, Ringer's solution, isotonic sodium chloride, fixed oils that may serve as the solvent or suspending medium, polyethylene glycols, glycerin, propylene glycol or other solvents; antibacterial agents; antioxidants; chelating agents; buffers and agents for the adjustment of tonicity such as sodium chloride or dextrose. A parenteral preparation can be enclosed in ampoules, disposable syringes or multiple dose vials made of glass or plastic. The use of physiological saline is preferred, and an injectable pharmaceutical composition or a composition that is delivered ocularly is preferably sterile.

A styrenyl derivative compound can be administered to human or other nonhuman vertebrates. In certain embodiments, the compound is substantially pure, in that it contains less than about 5% or less than about 1%, or less than about 0.1%, of other organic small molecules, such as contaminating intermediates or by-products that are created, for example, in one or more of the steps of a synthesis method. In other embodiments, a combination of one or more styrenyl derivative compounds can be administered.

A styrenyl derivative compound can be delivered to a subject by any suitable means, including, for example, orally, parenterally, intraocularly, intravenously, intraperitoneally, intranasally (or other delivery methods to the mucous membranes, for example, of the nose, throat, and bronchial tubes), or by local administration to the eye, or by an intraocular or periocular device. Modes of local administration can include, for example, eye drops, intraocular injection, or periocular injection. Periocular injection typically involves injection of the synthetic isomerization inhibitor, i.e., styrenyl derivative compound under the conjunctiva or into the Tennon's space (beneath the fibrous tissue overlying the eye). Intraocular injection typically involves injection of the styrenyl derivative compound into the vitreous (also called intravitreal injection). In certain embodiments, the administration is non-invasive, such as by eye drops or oral dosage form, or as a combined device.

A styrenyl derivative compound can be formulated for administration using pharmaceutically acceptable (suitable) carriers or vehicles as well as techniques routinely used in the art. A pharmaceutically acceptable or suitable carrier includes an ophthalmologically suitable or acceptable carrier. A carrier is selected according to the solubility of the styrenyl derivative compound. Suitable ophthalmological compositions include those that are administrable locally to the eye, such as by eye drops, injection or the like. In the case of eye drops, the formulation can also optionally include, for example, ophthalmologically compatible agents such as isotonizing agents such as sodium chloride, concentrated glycerin, and the like; buffering agents such as sodium phosphate, sodium acetate, and the like; surfactants such as polyoxyethylene sorbitan mono-oleate (also referred to as Polysorbate 80), polyoxyl stearate 40, polyoxyethylene hydrogenated castor oil, and the like; stabilization agents such as sodium citrate, sodium edentate, and the like; preservatives such as benzalkonium chloride, parabens, and the like; and other ingredients. Preservatives can be employed, for example, at a level of from about 0.001 to about 1.0% weight/volume. The pH of the formulation is usually within the range acceptable to ophthalmologic formulations, such as within the range of about pH 4 to 8.

For injection, the styrenyl derivative compound can be provided in an injection grade saline solution, in the form of an injectable liposome solution, slow-release polymer system, or the like. Intraocular and periocular injections are known to those skilled in the art and are described in numerous publications including, for example, Spaeth, Ed., Ophthalmic Surgery: Principles of Practice, W. B. Sanders Co., Philadelphia, Pa., 85-87, 1990.

For delivery of a composition comprising at least one of the compounds described herein via a mucosal route, which includes delivery to the nasal passages, throat, and airways, the composition may be delivered in the form of an aerosol. The compound may be in a liquid or powder form for intramucosal delivery. For example, the composition may delivered via a pressurized aerosol container with a suitable propellant, such as a hydrocarbon propellant (e.g., propane, butane, isobutene). The composition may be delivered via a non-pressurized delivery system such as a nebulizer or atomizer.

Suitable oral dosage forms include, for example, tablets, pills, sachets, or capsules of hard or soft gelatin, methylcellulose or of another suitable material easily dissolved in the digestive tract. Suitable nontoxic solid carriers can be used which include, for example, pharmaceutical grades of mannitol, lactose, starch, magnesium stearate, sodium saccharin, talcum, cellulose, glucose, sucrose, magnesium carbonate, and the like. (See, e.g., *Remington: The Science and Practice of Pharmacy* (Gennaro, 21$^{st}$ Ed. Mack Pub. Co., Easton, Pa. (2005)).

The styrenyl derivative compounds described herein may be formulated for sustained or slow-release. Such compositions may generally be prepared using well known technology and administered by, for example, oral, periocular, intraocular, rectal or subcutaneous implantation, or by implantation at the desired target site. Sustained-release formulations may contain an agent dispersed in a carrier matrix and/or contained within a reservoir surrounded by a rate controlling membrane. Excipients for use within such formulations are biocompatible, and may also be biodegradable; preferably the formulation provides a relatively constant level of active component release. The amount of active compound contained within a sustained-release formulation depends upon the site of implantation, the rate and expected duration of release, and the nature of the condition to be treated or prevented.

Systemic drug absorption of a drug or composition administered via an ocular route is known to those skilled in the art (see, e.g., Lee et al., *Int. J. Pharm.* 233:1-18 (2002)). In one embodiment, a styrenyl derivative compound is delivered by a topical ocular delivery method (see, e.g., *Curr. Drug Metab.* 4:213-22 (2003)). The composition may be in the form of an eye drop, salve, or ointment or the like, such as, aqueous eye drops, aqueous ophthalmic suspensions, non-aqueous eye drops, and non-aqueous ophthalmic suspensions, gels, ophthalmic ointments, etc. For preparing a gel, for example, carboxyvinyl polymer, methyl cellulose, sodium alginate, hydroxypropyl cellulose, ethylene maleic anhydride polymer and the like can be used.

The dose of the composition comprising at least one of the styrenyl derivative compounds described herein may differ, depending upon the patient's (e.g., human) condition, that is, stage of the disease, general health status, age, and other factors that a person skilled in the medical art will use to determine dose. When the composition is used as eye drops, for example, one to several drops per unit dose, preferably 1 or 2 drops (about 50 µl per 1 drop), may be applied about 1 to about 6 times daily.

Pharmaceutical compositions may be administered in a manner appropriate to the disease to be treated (or prevented) as determined by persons skilled in the medical arts. An appropriate dose and a suitable duration and frequency of administration will be determined by such factors as the condition of the patient, the type and severity of the patient's disease, the particular form of the active ingredient, and the method of administration. In general, an appropriate dose and treatment regimen provides the composition(s) in an amount sufficient to provide therapeutic and/or prophylactic benefit (e.g., an improved clinical outcome, such as more frequent complete or partial remissions, or longer disease-free and/or overall survival, or a lessening of symptom severity). For prophylactic use, a dose should be sufficient to prevent, delay the onset of, or diminish the severity of a disease associated with degeneration of a retinal cell including neurodegeneration of retinal neuronal cells, ischemia, and/or neovascularization of the retina. Optimal doses may generally be determined using experimental models and/or clinical trials. The optimal dose may depend upon the body mass, weight, or blood volume of the patient.

The doses of the styrenyl derivative compounds can be suitably selected depending on the clinical status, condition and age of the subject, dosage form and the like. In the case of eye drops, a styrenyl derivative compound can be administered, for example, from about 0.01 mg, about 0.1 mg, or about 1 mg, to about 25 mg, to about 50 mg, to about 90 mg per single dose. Eye drops can be administered one or more times per day, as needed. In the case of injections, suitable doses can be, for example, about 0.0001 mg, about 0.001 mg, about 0.01 mg, or about 0.1 mg to about 10 mg, to about 25 mg, to about 50 mg, or to about 90 mg of the styrenyl derivative compound, one to seven times per week. In other embodiments, about 1.0 to about 30 mg of the styrenyl derivative compound can be administered one to seven times per week.

Oral doses can typically range from 1.0 to 1000 mg, administered one to four times, or more, per day. An exemplary dosing range for oral administration is from 10 to 250 mg one to three times per day. If the composition is a liquid formulation, the composition may comprise at least 0.1% active compound at particular mass or weight (e.g., from 1.0 to 1000 mg) per unit volume of carrier, for example, from about 2% to about 60%.

In certain embodiments, at least one styrenyl compound described herein may be administered under conditions and at a time that inhibits or prevents dark adaptation of rod photoreceptor cells. In certain embodiments, the compound is administered to a subject at least 30 minutes (half hour), 60 minutes (one hour), 90 minutes (1.5 hour), or 120 minutes (2 hours) prior to sleeping. In certain embodiments, the compound may be administered at night before the subject sleeps. In other embodiments, a light stimulus may be blocked or removed during the day or under normal light conditions by placing the subject in an environment in which light is removed, such as placing the subject in a darkened room or by applying an eye mask over the eyes of the subject. When the light stimulus is removed in such a manner or by other means contemplated in the art, the agent may be administered prior to sleeping.

The doses of the compounds that may be administered to prevent or inhibit dark adaptation of a rod photoreceptor cell can be suitably selected depending on the clinical status, condition and age of the subject, dosage form and the like. In the case of eye drops, the compound (or the composition comprising the compound) can be administered, for example, from about 0.01 mg, about 0.1 mg, or about 1 mg, to about 25 mg, to about 50 mg, to about 90 mg per single dose. In the case of injections, suitable doses can be, for example, about 0.0001 mg, about 0.001 mg, about 0.01 mg, or about 0.1 mg to about 10 mg, to about 25 mg, to about 50 mg, or to about 90 mg of the compound, administered any number of days between one to seven days per week prior to sleeping or prior to removing the subject from all light sources. In certain other embodiments, for administration of the compound by eye drops or injection, the dose is between 1-10 mg (compound)/kg (body weight of subject) (i.e., for example, 80-800 mg total per dose for a subject weighing 80 kg). In other embodiments, about 1.0 to about 30 mg of compound can be administered one to seven times per week. Oral doses can typically range from about 1.0 to about 1000 mg, administered any number of days between one to seven days per week. An exemplary dosing range for oral administration is from about 10 to about 800 mg once per day prior to sleeping. In other embodiments, the composition may be delivered by intravitreal administration.

Also provided are methods of manufacturing the compounds and pharmaceutical compositions described herein. A composition comprising a pharmaceutically acceptable excipient or carrier and at least one of the styrenyl derivative compounds described herein may be prepared by synthesizing the compound according to any one of the methods described herein or practiced in the art and then formulating the compound with a pharmaceutically acceptable carrier. Formulation of the composition will be appropriate and dependent on several factors, including but not limited to, the delivery route, dose, and stability of the compound.

Other embodiments and uses will be apparent to one skilled in the art in light of the present disclosures. The following examples are provided merely as illustrative of various embodiments and shall not be construed to limit the invention in any way.

EXAMPLES

Unless otherwise noted, reagents and solvents were used as received from commercial suppliers. Anhydrous solvents and oven-dried glassware were used for synthetic transformations generally considered sensitive to moisture and/or oxygen. These transformations were conducted under nitrogen or argon atmosphere. Chromatography was performed on silica gel unless otherwise noted. Flash chromatography conducted with a gradient was performed on a Biotage chromatography system. Proton and carbon nuclear magnetic resonance spectra were obtained on a Bruker AMX 500 spectrometer at 500 or 300 MHz for proton and 125 or 75 MHz for carbon, as noted. Spectra are given in ppm (S) and coupling constants, J, are reported in Hertz. Tetramethylsilane was used as an internal standard for proton spectra and the solvent peak was used as the reference peak for carbon spectra. Mass spectra were obtained on a Finnigan LCQ Duo LCMS ion trap electrospray ionization (ESI) mass spectrometer or a PESCiex API 150EX mass spectrometer using atmospheric chemical ionization (APCI). HPLC analyses were obtained using a Symmetry C18 column (250×4.6 mm, Waters) with UV detection at 254 nm using a standard solvent gradient program (Methods 1, 2 and 4), a Pursuit C18 column (100×4.0 mm, Varian) with UV detection at 254 nm using a standard solvent gradient program (Method 3), a Hypersil BDS C18 column (250×4.6 mm, Phenomenex) with detection at 254 nm using a standard solvent gradient program (Methods 5 and 6), a Luna 5μ C18 (2) column (250×4.6 mm, Phenomenex) with detection at 254 nm using a standard solvent gradient program (Method 7), or a Gemini C18 column (150×4.6 mm, 5μ, Phenomenex) with detection at 220 nm using a standard solvent gradient program (Method 8).

Method 1

| Time (min) | Flow (mL/min) | % A | % B |
|---|---|---|---|
| 0.0 | 1.0 | 90.0 | 10.0 |
| 15.0 | 1.0 | 0.0 | 100.0 |
| 20.0 | 1.0 | 0.0 | 100.0 |

A = Water with 0.05% Trifluoroacetic Acid
B = Acetonitrile with 0.05% Trifluoroacetic Acid

Method 2

| Time (min) | Flow (mL/min) | % A | % B |
|---|---|---|---|
| 0.0 | 1.0 | 70.0 | 30.0 |
| 15.0 | 1.0 | 0.0 | 100.0 |
| 20.0 | 1.0 | 0.0 | 100.0 |

A = Water with 0.05% Trifluoroacetic Acid
B = Acetonitrile with 0.05% Trifluoroacetic Acid

Method 3

| Time (min) | Flow (mL/min) | % A | % B |
|---|---|---|---|
| 0.0 | 2.0 | 75.0 | 25.0 |
| 5.0 | 2.0 | 5.0 | 95.0 |
| 9.59 | 2.0 | 5.0 | 95.0 |
| 10.0 | 2.0 | 75.0 | 25.0 |

A = Water with 0.05% Trifluoroacetic Acid
B = Acetonitrile with 0.05% Trifluoroacetic Acid

Method 4

| Time (min) | Flow (mL/min) | % A | % B |
|---|---|---|---|
| 0.0 | 1.0 | 70.0 | 30.0 |
| 15.0 | 1.0 | 0.0 | 100.0 |
| 25.0 | 1.0 | 0.0 | 100.0 |

A = Water with 0.05% Trifluoroacetic Acid
B = Acetonitrile with 0.05% Trifluoroacetic Acid

Method 5

| Time (min) | Flow (mL/min) | % A | % B |
|---|---|---|---|
| 0.0 | 1.0 | 70.0 | 30.0 |
| 15.0 | 1.0 | 0.0 | 100.0 |
| 20.0 | 1.0 | 0.0 | 100.0 |

A = Water with 0.05% Trifluoroacetic Acid
B = Acetonitrile with 0.05% Trifluoroacetic Acid

Method 6

| Time (min) | Flow (mL/min) | % A | % B |
|---|---|---|---|
| 0.0 | 1.0 | 90.0 | 10.0 |
| 15.0 | 1.0 | 0.0 | 100.0 |
| 20.0 | 1.0 | 0.0 | 100.0 |

A = Water with 0.05% Trifluoroacetic Acid
B = Acetonitrile with 0.05% Trifluoroacetic Acid

Method 7

| Time (min) | Flow (mL/min) | % A | % B |
|---|---|---|---|
| 0.0 | 1.0 | 70.0 | 30.0 |
| 17.0 | 1.0 | 0.0 | 100.0 |
| 22.0 | 1.0 | 0.0 | 100.0 |
| 25.0 | 1.0 | 70.0 | 30.0 |

A = Water with 0.05% Trifluoroacetic Acid
B = Acetonitrile with 0.05% Trifluoroacetic Acid

Method 8

| Time (min) | Flow (mL/min) | % A | % B |
|---|---|---|---|
| 0.0 | 1.0 | 70.0 | 30.0 |
| 6.0 | 1.0 | 20.0 | 80.0 |
| 9.0 | 1.0 | 5.0 | 95.0 |

A = Water with 0.05% Trifluoroacetic Acid
B = Acetonitrile with 0.05% Trifluoroacetic Acid

Method 9

| Time (min) | Flow (mL/min) | % A | % B |
|---|---|---|---|
| 0.0 | 1.0 | 90.0 | 10.0 |
| 6.0 | 1.0 | 20.0 | 80.0 |
| 9.0 | 1.0 | 5.0 | 95.0 |

A = Water with 0.05% Trifluoroacetic Acid
B = Acetonitrile with 0.05% Trifluoroacetic Acid

Method 10

| Time (min) | Flow (mL/min) | % A | % B |
|---|---|---|---|
| 0.0 | 1.0 | 90.0 | 10.0 |
| 10.0 | 1.0 | 5.0 | 95.0 |

A = Water with 0.05% Trifluoroacetic Acid
B = Acetonitrile with 0.05% Trifluoroacetic Acid
Column = Gemini C18, 4.6 × 150 mm, 5μ

General Preparative HPLC Conditions:

Preparative HPLC (Method 1) was performed using a Luna 5μ C18 column (250×21.2 mm, Phenomenex) with UV detection at 254 nm and the solvent gradient program:

Preparative HPLC (Method 1)

| Time (min) | Flow (mL/min) | % A | % B |
|---|---|---|---|
| 0.0 | 15.0 | 80.0 | 20.0 |
| 30.0 | 15.0 | 0.0 | 100.0 |

A = Water with 0.05% Trifluoroacetic Acid
B = Acetonitrile with 0.05% Trifluoroacetic Acid Preparative HPLC (Method 2) was performed using a YMC ODA-A column (500 mm×30 mm×10μ) at ambient temperature with detection at 220 nm using an injection volume of 5 mL and a standard solvent gradient program.

Preparative HPLC (Method 2)

| Time (min) | Flow (mL/min) | % A | % B |
|---|---|---|---|
| 0.0 | 30 | 90 | 10 |
| 5.0 | 30 | 90 | 10 |
| 25 | 30 | 20 | 80 |
| 35 | 30 | 80 | 80 |

A = Water with 0.05% Trifluoroacetic Acid
B = Acetonitrile with 0.05% Trifluoroacetic Acid Chiral HPLC analyses were obtained using a Chiralpak IA column (4.6 mm×250 mm, 5μ) with diode array detection. The eluent was 95% heptane-EtOH containing 0.1% ethanesulfonic acid. The flow rate was 1 mL/min and the column temperature was 40° C.

Example 1

Preparation of (E)-3-(3-(2,6-dimethylstyryl)phenyl)propan-1-amine

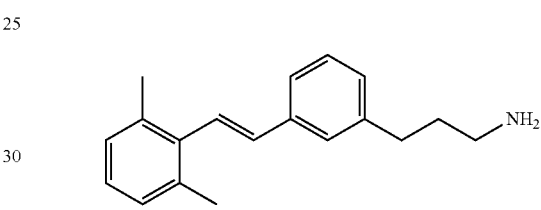

SCHEME 1

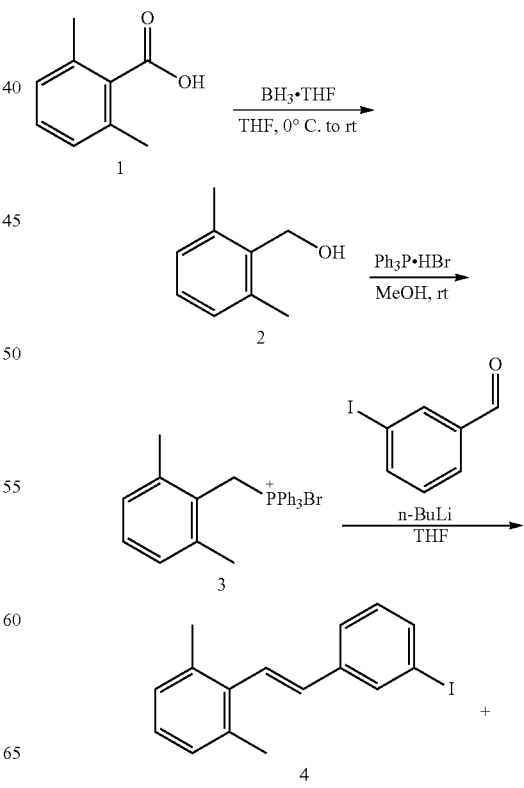

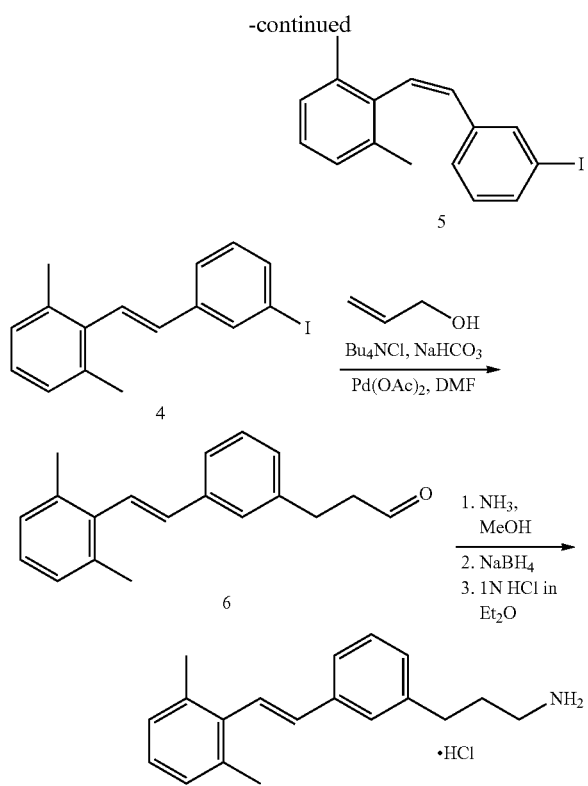

(E)-3-(3-(2,6-dimethylstyryl)phenyl)propan-1-amine was prepared following the method described in Scheme 1. (See, also, Methods A and J)

Step 1:
To a stirred solution of 2,6-dimethylbenzoic acid (1) (10.0 g, 66.6 mmol) in THF (100 mL) at 0° C. was added borane-THF complex (80 mL, 1M solution in THF, 80.0 mmol) dropwise over 20 min and then the reaction mixture was warmed to room temperature. After 64 h the reaction mixture was quenched by slow addition of methanol (70 mL) and the resulting solution concentrated. The residue was suspended in ethyl acetate (300 mL) and washed with water (4×50 mL) and brine (50 mL), and the organic layer was dried ($Na_2SO_4$), filtered and concentrated. The residue was dried in vacuo to give 2 (9.10 g, >99%) as a white solid: $^1H$ NMR (500 MHz, $CDCl_3$) δ 7.13-7.03 (m, 3H), 4.74 (d, J=5.1 Hz, 2H), 2.43 (s, 6H), 1.28 (t, J=5.2 Hz, 1H); ESI MS m/z 119 $[M+H-H_2O]^+$.

Step 2:
To a stirred solution of triphenylphosphine hydrobromide (22.0 g, 64.0 mmol) in MeOH (80 mL) was added a solution of 2 (8.72 g, 64.0 mmol) in methanol (70 mL) and the reaction mixture stirred at room temperature for 48 h. The reaction solution was concentrated under reduced pressure, the residue triturated with a mixture of acetone (20 mL) and diethyl ether (50 mL). The precipitate was collected by vacuum filtration, washed with diethyl ether (30 mL) and hexanes (30 mL), and dried in vacuo to provide 3 (23.0 g, 78%) as a white solid: mp 240-246° C.; $^1H$ NMR (300 MHz, DMSO-$d_6$) δ 7.95-7.51 (m, 15H), 7.15 (dt, J=7.7, 2.6 Hz, 1H), 6.96 (d, J=7.7 Hz, 2H), 4.94 (d, J=14.6 Hz, 2H), 1.76 (s, 6H); ESI MS m/z 381 $[M-Br]^+$; HPLC (Method 5) 97.0% (AUC), $t_R$=13.78 min.

Step 3:
To a stirred suspension of 3 (8.76 g, 19.0 mmol) in THF (60 mL) at 78° C. was added n-butyl lithium (7.8 mL, 2.5M solution in hexanes, 19.5 mmol) and the reaction mixture warmed to room temperature. After 30 min the reaction mixture was again cooled to −78° C., a solution of 3-iodobenzaldehyde (4.41 g, 19.0 mmol) in THF (15 mL) was added, and then the reaction mixture was warmed to room temperature. After 1 hr, the reaction was quenched with saturated aqueous ammonium chloride (50 mL) and extracted with ethyl acetate (2×100 mL). The combined organic layers were concentrated and the resulting residue was dissolved in methanol (70 mL). To this was then added hexanes (400 mL) and water (30 mL) and phases were mixed. The hexanes layer was separated, washed with 70% methanol/water (100 mL), dried ($Na_2SO_4$), filtered and concentrated. The residue was purified by flash column chromatography (silica gel, hexanes) to give 4 (2.12 g, 33%) as a white solid and 5 (1.15 g, 18%) as a colorless oil.

4: $^1H$ NMR (500 MHz, $CDCl_3$) δ 7.84 (s, 1H), 7.59 (d, J=7.7 Hz, 1H), 7.44 (d, J=7.7 Hz, 1H), 7.10-7.06 (m, 5H), 6.49 (d, J=16.6 Hz, 1H), 2.35 (s, 6H).

5: $^1H$ NMR (500 MHz, $CDCl_3$) δ 7.44 (d, J=7.8 Hz, 1H), 7.37 (s, 1H), 7.13 (t, J=7.5 Hz, 1H), 7.04 (d, J=7.6 Hz, 2H), 6.88 (d, J=7.9 Hz, 1H), 6.81 (t, J=7.8 Hz, 1H), 6.59 (d, J=12.2 Hz, 1H), 6.53 (d, J=12.2 Hz, 1H), 2.14 (s, 6H).

Step 4
To a stirred solution of 4 (1.86 g, 5.60 mmol) in DMF (5 mL) was added sodium bicarbonate (1.49 g, 17.7 mmol), tetrabutylammonium chloride (1.58 g, 5.70 mmol), and allyl alcohol (0.683 g, 11.8 mmol). The reaction flask was purged with nitrogen for 10 min and then palladium acetate (0.029 g, 0.130 mmol) was added. The color of the solution changed from yellow to orange. After purging with nitrogen for an additional 10 min the solution was stirred under nitrogen at room temperature. After 18 h the solution was diluted with ethyl acetate (50 mL), the resulting mixture washed with water (25 mL), 5% aqueous lithium chloride solution (25 mL), and brine (25 mL). The organics were dried ($MgSO_4$), filtered and concentrated to afford a dark oil. Purification by column chromatography (silica, 0-20% ethyl acetate/hexanes) provided 1.05 g (71%) of 6 as a colorless oil: $^1H$ NMR (500 MHz, $CDCl_3$) δ 9.85 (t, J=1.1 Hz, 1H), 7.39 (d, J=7.8 Hz, 1H), 7.32-7.29 (m, 2H), 7.12-7.07 (m, 5H), 6.57 (d, J=16.6 Hz, 1H), 2.99 (t, J=7.6 Hz, 2H), 2.84-2.38 (m, 2H), 2.37 (s, 6H).

Step 5:
To a stirred solution of 6 (0.848 g, 3.20 mmol) in methanol (50 mL) was added 7N ammonia in methanol (9.0 mL) and a small scoop of powered sieves. The flask was stoppered and stirred for 1.5 h, at which time sodium borohydride (0.184 g, 4.90 mmol) was added. The solution was stirred for an additional 3 h, filtered over diatomaceous earth, the filter cake rinsed with methanol (25 mL) and the filtrate concentrated. The resulting residue was dissolved in ethyl acetate (50 mL) and this solution was washed with water (25 mL). The aqueous phase was extracted with ethyl acetate (2×25 mL), the combined organics washed with brine (25 mL), dried ($MgSO_4$), filtered and concentrated. Purification by column chromatography (silica, 99:1 to 95:5 methylene chloride/7N ammonia in methanol) afforded 0.368 g (43%) of (E)-3-(3-(2,6-dimethylstyryl)phenyl)propan-1-amine.

The salt was formed as follows:
To a stirred solution of (E)-3-(3-(2,6-dimethylstyryl)phenyl)propan-1-amine (0.296 g, 1.10 mmol) in diethyl ether (15 mL) was added 1N HCl in diethyl ether (1.2 mL, 1.20 mmol), resulting in immediate precipitation of a white solid. The suspension was stirred for 1.5 h, filtered and dried under vacuum to afford 0.314 g (95%) of (E)-3-(3-(2,6-dimethylstyryl)phenyl)propan-1-amine hydrochloride as a light yellow solid: mp 135-136° C.; $^1H$ NMR (500 MHz, $CD_3OD$) δ 7.40 (d, J=11.0 Hz, 2H), 7.31 (t, J=7.6 Hz, 1H), 7.21 (s, 1H), 7.17-7.14 (m, 1H), 7.04 (s, 3H), 6.58 (d, J=16.6 Hz, 1H), 2.95 (t, J=7.7 Hz, 1H), 2.75 (t, J=7.6 Hz, 2H), 2.34 (s, 6H), 2.00 (quint, J=7.7 Hz, 2H), 1.90 (m, 2H); $^{13}C$ NMR (75 MHz, $CD_3OD$) δ 142.2, 139.4, 138.2, 137.1, 135.2, 130.0, 128.9, 128.7, 128.3, 127.9, 127.4, 125.4, 40.4, 33.5, 30.4, 21.2; ESI MS m/z 266 [M+H]+; HPLC (Method 2) >99% (AUC), $t_R$=16.4 min. Calcd for $C_{19}H_{23}N \cdot HCl$: C, 75.60; H, 8.01; N, 4.64. Found: C, 75.25; H, 7.99; N, 4.66.

Example 2

Preparation of (Z)-3-(3-(2,6-dimethylstyryl)phenyl)propan-1-amine

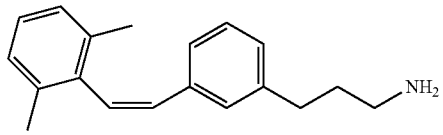 [SMILES: Cc1cccc(C)c1/C=C\c1cccc(CCCN)c1]

(Z)-3-(3-(2,6-dimethylstyryl)phenyl)propan-1-amine was prepared following the method used in Example 1.

Step 1:

(Z)-3-(3-(2,6-Dimethylstyryl)phenyl)propanal was prepared following the method described in Example 1. Purification by column chromatography (silica, 0-20% ethyl acetate/hexanes) gave (0.054 g, 26%) of a yellow oil: $R_f$ 0.56 (silica gel, 90:10 methylene chloride/7N ammonia in methanol); $^1$H NMR (500 MHz, $CD_3OD$) δ $^1$H NMR (500 MHz, $CDCl_3$) δ 9.67 (t, J=1.3 Hz, 1H), 7.10 (q, J=7.7 Hz, 2H), 7.06-7.03 (m, 2H), 6.95 (d, J=7.6 Hz, 1H), 6.85 (d, J=7.8 Hz, 1H), 6.76 (s, 1H), 6.62 (d, J=12.2 Hz, 1H), 6.54 (d, J=12.2 Hz, 1H), 2.75 (t, J=7.6 Hz, 2H), 2.53-2.50 (m, 2H), 2.14 (s, 6H); ESI MS m/z 247 [M+H–$H_2O$]+.

Step 2:

Reductive amination of (Z)-3-(3-(2,6-Dimethylstyryl)phenyl)propanal with ammonia following the method described in Example 1 followed by purification by column chromatography (silica, 99:1 to 95:5 methylene chloride/7N ammonia in methanol), followed by further purification by Preparative HPLC (Method 1) afforded Example 2 as a yellow oil. Yield (0.054 g, 26%): $R_f$ 0.56 (silica gel, 90:10 methylene chloride/7N ammonia in methanol); $^1$H NMR (500 MHz, $CD_3OD$) δ 7.10-7.07 (m, 1H), 7.04-7.0 (m, 3H), 6.95 (d, J=7.6 Hz, 1H), 6.81 (d, J=7.2 Hz, 1H), 6.78 (s, 1H), 6.66 (d, J=12.2 Hz, 1H), 6.53 (d, J=12.2 Hz, 1H), 2.48-2.40 (m, 4H), 2.12 (s, 6H); 1.55 (quint, J=7.3 Hz, 2H); $^{13}$C NMR (75 MHz, $CD_3OD$) δ 143.0, 138.9, 138.5, 136.6, 132.3, 129.7, 129.2, 129.0, 128.5, 128.4, 128.0, 126.9, 41.8, 35.2, 33.9, 20.4; ESI MS m/z 266 [M+H]+; HPLC (Method 2) >99% (AUC), $t_R$=8.19 min. HRMS calcd for $C_{19}H_{23}N$ [M+H]: 266.190. Found: 266.1909.

Example 3

Preparation of (E)-4-(3-(3-(2,6-dimethylstyryl)phenyl)propyl)morpholine

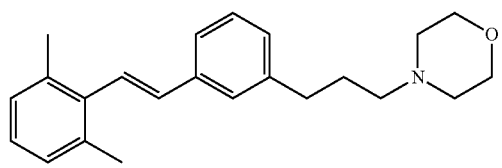 [SMILES: Cc1cccc(C)c1/C=C/c1cccc(CCCN2CCOCC2)c1]

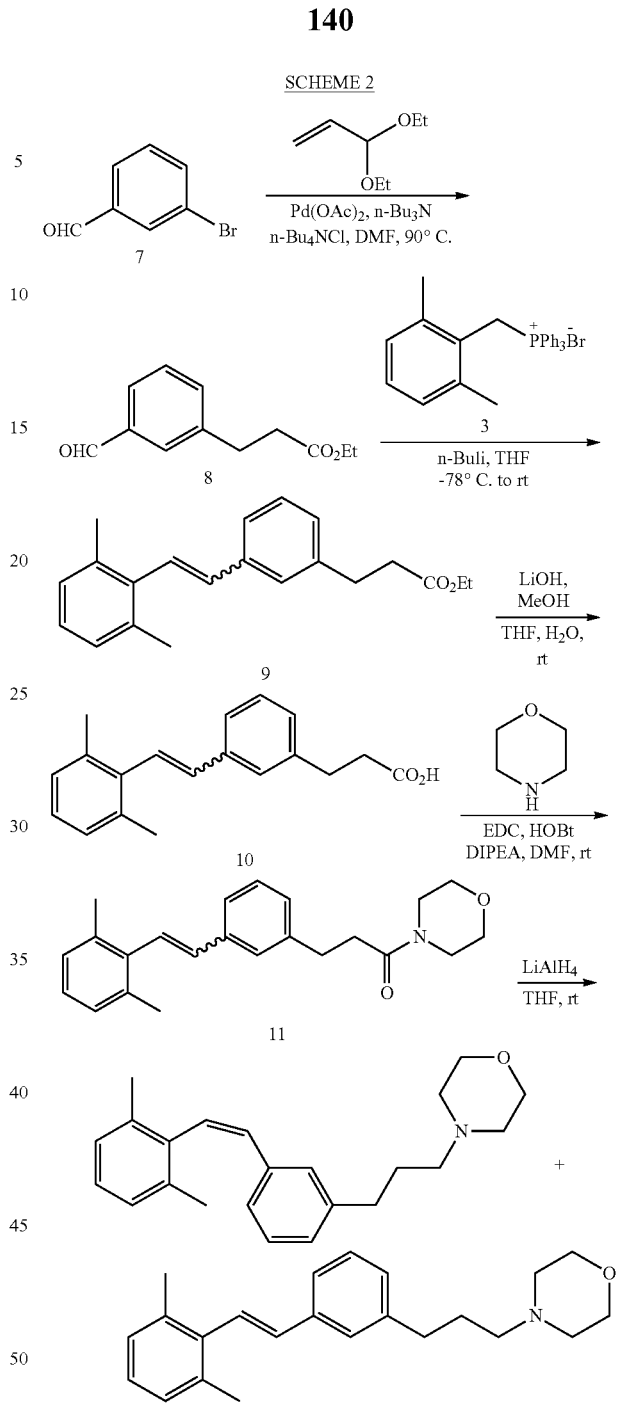

(E)-4-(3-(3-(2,6-Dimethylstyryl)phenyl)propyl)morpholine was prepared following the method described in Scheme 2.

Step 1:

To a stirred solution of 3-bromobenzaldehyde (7) (3.70 g, 20.0 mmol), acrolein diethyl acetal (7.81 g, 60.0 mmol) and tributylamine (7.41 g, 40.0 mmol) in DMF (40 mL) was added tetrabutylammonium chloride (5.56 g, 20.0 mmol) followed by palladium(II) acetate (0.135 g, 0.601 mmol) and the reaction mixture was heated at 90° C. After 27 h the reaction mixture was cooled to room temperature, diluted with 2N hydrochloric acid (20 mL), and extracted with a 1:1 mixture of diethyl ether and hexanes (3×150 mL), the combined extracts were washed with water (3×100 mL), dried (Na₂SO₄), filtered and concentrated. The resulting residue was purified by flash column chromatography (silica gel, 90:10 hexanes/ethyl acetate) to give 8 (2.97 g, 72%) as a light yellow oil: ¹H NMR (500 MHz, CDCl₃) δ 10.00 (s, 1H), 7.74-7.45 (m, 4H), 4.13 (q, J=7.1 Hz, 2H), 3.04 (t, J=7.6 Hz, 2H), 2.66 (t, J=7.6 Hz, 2H), 1.23 (t, J=7.1 Hz, 3H).

Step 2:

Compound 9 was prepared following the procedure described for the synthesis of Compound 4, as a colorless oil, and as a mixture of cis and trans isomers. The isomers were not separated at this time. Yield (4.10 g, 92%), trans-/cis-isomer ratio 2:1.

trans-isomer: ¹H NMR (500 MHz, CDCl₃) δ 7.36-6.80 (m, 8H), 6.59 (d, J=16.6 Hz, 1H), 4.14 (m, 2H), 2.98 (t, J=7.7 Hz, 2H), 2.66 (t, J=7.7 Hz, 2H), 2.37 (s, 6H), 1.23 (m, 3H);

cis-isomer: ¹H NMR (500 MHz, CDCl₃) δ 7.36-6.80 (m, 7H), 6.62 (d, J=12.2 Hz, 1H), 6.53 (d, J=12.2 Hz, 1H), 4.09 (m, 2H), 2.75 (t, J=7.7 Hz, 2H), 2.40 (t, J=7.7 Hz, 2H), 2.14 (s, 6H), 1.23 (m, 3H); ESI MS m/z 263 [M+H−EtOH]⁺.

Step 3:

To a stirred solution of 9 (4.10 g, 13.3 mmol) in methanol (20 mL), THF (20 mL) and water (10 mL) was added lithium hydroxide (0.956 g, 39.9 mmol) at room temperature. After 3 h the reaction mixture was concentrated, the residue was diluted with brine (20 mL) and the resulting mixture was acidified with 2N hydrochloric acid to pH 2. The aqueous mixture was extracted with methylene chloride (3×100 mL) and the combined extracts were dried (Na₂SO₄), filtered and concentrated. The resulting residue was dried in vacuo to give 10 as a colorless oil. Yield (3.73 g, quant.), trans-/cis-isomer ratio 2:1.

trans-isomer: ¹H NMR (500 MHz, CDCl₃) δ 7.39-6.80 (m, 8H), 6.58 (d, J=16.6 Hz, 1H), 3.00 (t, J=7.6 Hz, 2H), 2.72 (t, J=7.6 Hz, 2H), 2.37 (s, 6H);

cis-isomer: ¹H NMR (500 MHz, CDCl₃) δ 7.39-6.80 (m, 7H), 6.62 (d, J=12.2 Hz, 1H), 6.54 (d, J=12.2 Hz, 1H), 2.73 (t, J=7.7 Hz, 2H), 2.46 (t, J=7.7 Hz, 2H), 2.14 (s, 6H); ESI MS m/z 263 [M+H−H₂O].

Step 4:

To a stirred solution of 10 (0.300 g, 1.07 mmol) in DMF (10 mL) was added N,N-diisopropylethylamine (0.690 g, 5.34 mmol), 1-hydroxybenzotriazole (0.289 g, 2.14 mmol), 1-(3-dimethylaminopropyl)-3-ethylcarbodiimide hydrochloride (0.410 g, 2.14 mmol) and morpholine (0.189 g, 2.17 mmol) at room temperature. After 18 h the reaction mixture was diluted with ethyl acetate (100 mL) and washed sequentially with 10% aqueous potassium carbonate (2×20 mL), water (2×20 mL) and brine (20 mL). The organic layer was dried (Na₂SO₄), filtered and concentrated. The residue was purified by flash column chromatography (silica gel, 60:40 hexanes/ethyl acetate) to give 11 as a colorless oil. Yield (0.335 g, 90%.), trans-/cis-isomer ratio 2:1 trans:cis.

trans-isomer: ¹H NMR (500 MHz, CDCl₃) δ 7.38-6.79 (m, 8H), 6.58 (d, J=16.6 Hz, 1H), 3.63-3.28 (m, 8H), 3.02 (t, J=7.6 Hz, 2H), 2.65 (t, J=7.6 Hz, 2H), 2.37 (s, 6H); cis-isomer: ¹H NMR (500 MHz, CDCl₃) δ 7.38-6.79 (m, 7H), 6.63 (d, J=12.2 Hz, 1H), 6.53 (d, J=12.2 Hz, 1H), 3.63-3.28 (m, 8H), 2.77 (t, J=7.7 Hz, 2H), 2.35 (t, J=7.7 Hz, 2H), 2.15 (s, 6H); ESI MS m/z 350 [M+H]⁺.

Step 5:

To a stirred solution of 11 (0.332 g, 0.950 mmol) in THF (5 mL) was added lithium aluminum hydride (0.108 g, 2.85 mmol) at room temperature. After 18 h the reaction mixture was cooled to 0° C., quenched with 2N aqueous sodium hydroxide (0.23 mL), the resulting suspension was diluted with MTBE (50 mL), filtered and concentrated. The resulting residue was purified by Preparative HPLC (Method 1) to give (E)-4-(3-(3-(2,6-Dimethylstyryl)phenyl)propyl)morpholine as a colorless oil. Yield (0.114 g, 36%): R_f 0.81 (silica gel, 50:40:10 ethyl acetate/hexanes/7N ammonia in methanol); ¹H NMR (500 MHz, CD₃OD) δ 7.34 (m, 2H), 7.26 (t, J=7.5 Hz, 1H), 7.15 (d, J=16.7 Hz, 1H), 7.11 (d, J=7.5 Hz, 1H), 7.03 (s, 3H), 6.56 (d, J=16.7 Hz, 1H), 3.68 (t, J=4.6 Hz, 4H), 2.66 (t, J=7.5 Hz, 2H), 2.45 (br s, 4H), 2.39 (t, J=7.7 Hz, 2H), 2.33 (s, 6H), 1.86 (m, 2H); ¹³C NMR (125 MHz, CD₃OD) δ 143.8, 139.2, 138.4, 137.2, 135.5, 129.9, 129.0, 128.9, 128.0, 127.9, 127.6, 125.0, 67.8, 59.6, 54.9, 34.7, 29.2, 21.3; ESI MS m/z 336 [M+H]⁺; HPLC (Method 5) >99% (AUC), t_R=13.86 min. HRMS Calcd for C₂₃H₂₉NO [M+H]: 336.2327. Found: 336.2312.

Example 4

Preparation of (Z)-4-(3-(3-(2,6-dimethylstyryl)phenyl)propyl)morpholine

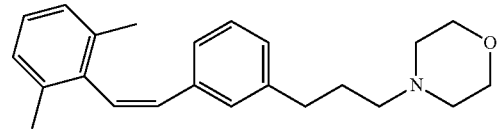 [SMILES: Cc1cccc(C)c1/C=C\c1cccc(CCCN2CCOCC2)c1]

(Z)-4-(3-(3-(2,6-Dimethylstyryl)phenyl)propyl)morpholine was isolated during the synthesis of Example 3 as a colorless oil. Yield (0.039 g, 12%): ¹H NMR (500 MHz, CD₃OD) δ 7.05 (m, 4H), 6.95 (d, J=7.6 Hz, 1H), 6.83 (d, J=7.7 Hz, 1H), 6.77 (s, 1H), 6.66 (d, J=12.2 Hz, 1H), 6.54 (d, J=12.2 Hz, 1H), 3.68 (t, J=4.6 Hz, 4H), 2.38 (m, 6H), 2.21 (t, J=7.5 Hz, 2H), 2.13 (s, 6H), 1.58 (m, 2H); ¹³C NMR (125 MHz, CD₃OD) δ 143.1, 139.1, 138.7, 136.7, 132.5, 129.8, 129.4, 129.0, 128.7, 128.6, 128.2, 127.3, 67.8, 59.5, 54.9, 34.5, 28.8, 20.6; ESI MS m/z 336 [M+H]⁺; HPLC (Method 5) >99% (AUC), t_R=14.40 min HRMS Calcd for C₂₃H₂₉NO [M+H]: 336.2327. Found: 336.2311.

Example 5

Preparation of (E)-1-(3-(3-(2,6-dimethylstyryl)phenyl)propyl)pyrrolidine

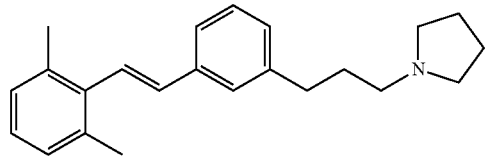 [SMILES: Cc1cccc(C)c1/C=C/c1cccc(CCCN2CCCC2)c1]

(E)-1-(3-(3-(2,6-Dimethylstyryl)phenyl)propyl)pyrrolidine was prepared following the method used in Example 3.

Step 1:

Coupling of acid 10 with pyrrolidine gave 3-(3-(2,6-dimethylstyryl)phenyl)-1-(pyrrolidin-1-yl)propan-1-one as a colorless oil. Yield (0.26 g, 90%), isomer ratio 2:1 trans:cis.

trans-isomer: ¹H NMR (500 MHz, CDCl₃) δ 7.36-6.82 (m, 8H), 6.58 (d, J=16.6 Hz, 1H), 3.48 (t, J=6.9 Hz, 2H), 3.31 (t, J=6.9 Hz, 2H), 3.02 (t, J=7.6 Hz, 2H), 2.60 (t, J=7.6 Hz, 2H), 2.37 (s, 6H), 1.92-1.79 (m, 4H);

cis-isomer: ¹H NMR (500 MHz, CDCl₃) δ 7.36-6.82 (m, 7H), 6.63 (d, J=12.2 Hz, 1H), 6.52 (d, J=12.2 Hz, 1H), 3.44 (t, J=6.9 Hz, 2H), 3.22 (t, J=6.9 Hz, 2H), 2.78 (t, J=7.7 Hz, 2H), 2.31 (t, J=7.7 Hz, 2H), 2.15 (s, 6H), 1.92-1.79 (m, 4H); ESI MS m/z 334 [M+H]$^+$.

Step 2:

Reduction of 3-(3-(2,6-dimethylstyryl)phenyl)-1-(pyrrolidin-1-yl)propan-1-one followed by purification by Preparative HPLC (Method 1) gave Example 5 (0.095 g, 39%) as a colorless oil: $R_f$ 0.75 (silica gel, 50:40:10 ethyl acetate/hexanes/7N ammonia in methanol); $^1$H NMR (500 MHz, CD$_3$OD) δ 7.34 (m, 2H), 7.27 (t, J=7.5 Hz, 1H), 7.16 (d, J=16.7 Hz, 1H), 7.11 (d, J=7.5 Hz, 1H), 7.03 (s, 3H), 6.57 (d, J=16.7 Hz, 1H), 2.67 (t, J=7.6 Hz, 2H), 2.53 (m, 6H), 2.34 (s, 6H), 1.88 (m, 2H), 1.80 (m, 4H); $^{13}$C NMR (125 MHz, CD$_3$OD) δ 143.8, 139.2, 138.4, 137.3, 135.5, 129.9, 129.0, 128.9, 128.0, 127.8, 127.6, 125.0, 57.2, 55.2, 34.9, 31.6, 24.3, 21.3; ESI MS m/z 320 [M+H]$^+$; HPLC (Method 5) >99% (AUC), $t_R$=15.21 min. HRMS Calcd for C$_{23}$H$_{29}$N [M+H]: 320.2378. Found: 320.2376.

Example 6

Preparation of (Z)-1-(3-(3-(2,6-dimethylstyryl)phenyl)propyl)pyrrolidine

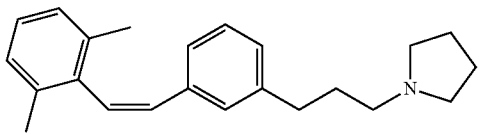 [SMILES: Cc1cccc(C)c1/C=C\c1cccc(CCCN2CCCC2)c1]

(Z)-1-(3-(3-(2,6-dimethylstyryl)phenyl)propyl)pyrrolidine was isolated during the synthesis of Example 5 as a colorless oil. Yield (0.035 g, 14%); $R_f$ 0.75 (silica gel, 50:40:10 ethyl acetate/hexanes/7N ammonia in methanol); $^1$H NMR (500 MHz, CD$_3$OD) δ 7.05 (m, 4H), 6.95 (d, J=7.6 Hz, 1H), 6.83 (d, J=7.7 Hz, 1H), 6.77 (s, 1H), 6.65 (d, J=12.2 Hz, 1H), 6.54 (d, J=12.2 Hz, 1H), 2.48 (m, 4H), 2.39 (t, J=7.6 Hz, 2H), 2.33 (m, 2H), 2.13 (s, 6H), 1.79 (m, 4H), 1.61 (m, 2H); $^{13}$C NMR (125 MHz, CD$_3$OD) δ 143.1, 139.1, 138.7, 136.7, 132.5, 129.8, 129.4, 129.0, 128.7, 128.6, 128.2, 127.3, 57.1, 55.2, 34.8, 31.3, 24.3, 20.6; ESI MS m/z 320 [M+H]$^+$; HPLC (Method 5) >99% (AUC), $t_R$=15.56 min. HRMS Calcd for C$_{23}$H$_{29}$N [M+H]: 320.237. Found: 320.2365.

Example 7

Preparation of (E)-3-(3-(2,6-dimethylstyryl)phenyl)-N-methylpropan-1-amine

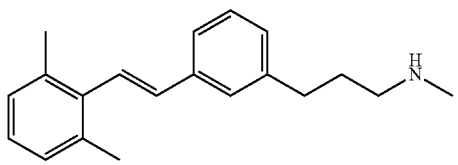

(E)-3-(3-(2,6-Dimethylstyryl)phenyl)-N-methylpropan-1-amine was prepared following the method used to prepare Example 3.

Step 1:

Coupling of acid 10 with methylamine gave 3-(3-(2,6-dimethylstyryl)phenyl)-N-methylpropanamide as a colorless oil. Yield (0.277 g, 88%), isomer ratio 2:1 trans:cis.

trans-isomer: $^1$H NMR (300 MHz, CDCl$_3$) δ 7.37-6.78 (m, 8H), 6.57 (d, J=16.6 Hz, 1H), 5.47 (br s, 1H), 3.00 (t, J=7.4 Hz, 2H), 2.78 (d, J=4.8 Hz, 3H), 2.49 (t, J=7.4 Hz, 2H), 2.36 (s, 6H);

cis-isomer: $^1$H NMR (500 MHz, CDCl$_3$) δ 7.37-6.78 (m, 7H), 6.63 (d, J=12.2 Hz, 1H), 6.53 (d, J=12.2 Hz, 1H), 5.18 (br s, 1H), 2.76 (t, J=7.4 Hz, 2H), 2.71 (d, J=4.8 Hz, 3H), 2.17 (t, J=7.4 Hz, 2H), 2.14 (s, 6H).

Step 2:

Reduction of 3-(3-(2,6-dimethylstyryl)phenyl)-N-methylpropanamide followed by purification by Preparative HPLC (Method 1) gave Example 7 (0.080 g, 30%) as a colorless oil: $R_f$ 0.65 (silica gel, 50:40:10 ethyl acetate/hexanes/7N ammonia in methanol); $^1$H NMR (500 MHz, CD$_3$OD) δ 7.35 (m, 2H), 7.27 (t, J=7.5 Hz, 1H), 7.16 (d, J=16.7 Hz, 1H), 7.11 (d, J=7.5 Hz, 1H), 7.03 (s, 3H), 6.57 (d, J=16.7 Hz, 1H), 2.67 (t, J=7.6 Hz, 2H), 2.58 (t, J=7.6 Hz, 2H), 2.36 (s, 3H), 2.34 (s, 6H), 1.85 (m, 2H); $^{13}$C NMR (75 MHz, CD$_3$OD) δ 143.8, 139.2, 138.4, 137.3, 135.5, 129.9, 129.0, 128.9, 128.0, 127.9, 127.5, 125.0, 52.3, 36.2, 34.6, 32.2, 21.3; ESI MS m/z 280 [M+H]$^+$; HPLC (Method 5) 90.4% (AUC), $t_R$=14.39 min. HRMS Calcd for C$_{20}$H$_{25}$N [M+H]: 280.206. Found: 280.2062.

Example 8

Preparation of (Z)-3-(3-(2,6-dimethylstyryl)phenyl)-N-methylpropan-1-amine

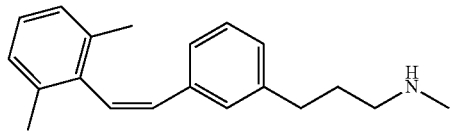 [SMILES: CNCCCc1cccc(/C=C\c2c(C)cccc2C)c1]

(Z)-3-(3-(2,6-Dimethylstyryl)phenyl)-N-methylpropan-1-amine was isolated during the synthesis of Example 7 as a colorless oil. Yield (0.025 g, 10%): $R_f$ 0.65 (silica gel, 50:40:10 ethyl acetate/hexanes/7N ammonia in methanol); $^1$H NMR (500 MHz, CD$_3$OD) δ 7.05 (m, 4H), 6.96 (d, J=7.6 Hz, 1H), 6.82 (d, J=7.7 Hz, 1H), 6.78 (s, 1H), 6.65 (d, J=12.2 Hz, 1H), 6.54 (d, J=12.2 Hz, 1H), 2.40 (m, 4H), 2.32 (s, 3H), 2.12 (s, 6H), 1.60 (m, 2H); $^{13}$C NMR (75 MHz, CD$_3$OD) δ 143.0, 139.1, 138.7, 136.7, 132.5, 129.9, 129.4, 129.1, 128.7, 128.6, 128.2, 127.1, 60.0, 36.0, 34.4, 31.6, 20.5; ESI MS m/z 280 [M+H]$^+$; HPLC (Method 5) 97.3% (AUC), $t_R$=14.64 min. HRMS Calcd for C$_{20}$H$_{25}$N [M+H]: 280.206. Found: 280.2063.

Example 9

Preparation of (E)-3-(3-(2,6-dimethylstyryl)phenyl)-N,N-dimethylpropan-1-amine

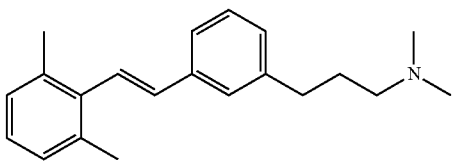 [SMILES: Cc1cccc(C)c1/C=C/c1cccc(CCCN(C)C)c1]

(E)-3-(3-(2,6-Dimethylstyryl)phenyl)-N,N-dimethylpropan-1-amine was prepared following the method used to prepare Example 3.

Step 1:

Coupling of acid 10 with dimethylamine gave (E)-3-(3-(2,6-dimethylstyryl)phenyl)-N,N-dimethylpropanamide as a colorless oil. Yield (0.273 g, 83%), isomer ratio 2:1 trans:cis.

trans-isomer: $^1$H NMR (300 MHz, CDCl$_3$) δ 7.38-6.81 (m, 8H), 6.58 (d, J=16.6 Hz, 1H), 3.03-2.87 (m, 8H), 2.65 (t, J=7.6 Hz, 2H), 2.37 (s, 6H);

cis-isomer: $^1$H NMR (500 MHz, CDCl$_3$) δ 7.38-6.81 (m, 7H), 6.63 (d, J=12.2 Hz, 1H), 6.53 (d, J=12.2 Hz, 1H), 3.03-2.87 (m, 6H), 2.76 (t, J=7.7 Hz, 2H), 2.36 (t, J=7.7 Hz, 2H), 2.15 (s, 6H).

Step 2:

Reduction of 3-(3-(2,6-dimethylstyryl)phenyl)-N,N-dimethylpropanamide followed by purification by Preparative HPLC (Method 1) gave Example 9 (0.101 g, 39%) as a colorless oil: R$_f$ 0.81 (silica gel, 50:40:10 ethyl acetate/hexanes/7N ammonia in methanol); NMR (500 MHz, CD$_3$OD) δ 7.35 (m, 2H), 7.27 (t, J=7.5 Hz, 1H), 7.16 (d, J=16.7 Hz, 1H), 7.11 (d, J=7.5 Hz, 1H), 7.03 (s, 3H), 6.57 (d, J=16.7 Hz, 1H), 2.65 (t, J=7.6 Hz, 2H), 2.37 (m, 2H), 2.34 (s, 6H), 2.24 (s, 6H), 1.84 (m, 2H); $^{13}$C NMR (125 MHz, CD$_3$OD) δ 143.7, 139.2, 138.4, 137.3, 135.5, 129.9, 129.0, 128.9, 128.0, 127.8, 127.6, 125.0, 60.3, 45.6, 34.7, 30.3, 21.3; ESI MS m/z 294 [M+H]$^+$; HPLC (Method 5) >99% (AUC), t$_R$=15.33 min. HRMS Calcd for C$_{21}$H$_{27}$N [M+H]: 294.222. Found: 294.2219.

Example 10

Preparation of (Z)-3-(3-(2,6-dimethylstyryl)phenyl)-N,N-dimethylpropan-1-amine

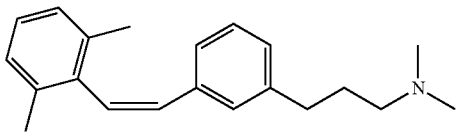 [SMILES: Cc1cccc(C)c1/C=C\c1cccc(CCCN(C)C)c1]

(Z)-3-(3-(2,6-Dimethylstyryl)phenyl)-N,N-dimethylpropan-1-amine was isolated during the synthesis of Example 9 as a colorless oil. Yield (0.038 g, 15%): R$_f$ 0.81 (silica gel, 50:40:10 ethyl acetate/hexanes/7N ammonia in methanol); NMR (500 MHz, CD$_3$OD) δ 7.05 (m, 4H), 6.95 (d, J=7.6 Hz, 1H), 6.83 (d, J=7.7 Hz, 1H), 6.77 (s, 1H), 6.65 (d, J=12.2 Hz, 1H), 6.54 (d, J=12.2 Hz, 1H), 2.38 (t, J=7.6 Hz, 2H), 2.18 (m, 8H), 2.12 (s, 6H), 1.55 (m, 2H); $^{13}$C NMR (125 MHz, CD$_3$OD) δ 143.0, 139.1, 138.7, 136.7, 132.4, 129.8, 129.4, 129.0, 128.7, 128.6, 128.2, 127.3, 60.2, 45.5, 34.6, 29.9, 20.6; ESI MS m/z 294 [M+H]$^+$; HPLC (Method 5) >99% (AUC), t$_R$=15.49 min. HRMS Calcd for C$_{21}$H$_{27}$N [M+H]: 294.222. Found: 294.2224.

Example 11

Preparation of (E)-1-(3-(3-(2,6-dimethylstyryl)phenyl)propyl)piperidine

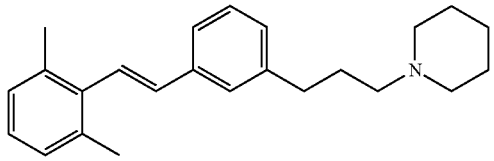 [SMILES: Cc1cccc(C)c1/C=C/c1cccc(CCCN2CCCCC2)c1]

(E)-1-(3-(3-(2,6-Dimethylstyryl)phenyl)propyl)piperidine was prepared following the method used to prepare Example 3.

Step 1:

Coupling of acid 10 with piperidine gave 3-(3-(2,6-dimethylstyryl)phenyl)-1-(piperidin-1-yl)propan-1-one as a colorless oil. Yield (0.330 g, 89%), isomer ratio 2:1 trans:cis.

trans-isomer: NMR (300 MHz, CDCl$_3$) δ 7.37-6.80 (m, 8H), 6.58 (d, J=16.6 Hz, 1H), 3.57 (t, J=5.7 Hz, 2H), 3.36 (t, J=5.5 Hz, 2H), 3.00 (t, J=7.5 Hz, 2H), 2.65 (t, J=7.5 Hz, 2H), 2.37 (s, 6H), 1.64-1.47 (m, 6H);

cis-isomer: $^1$H NMR (500 MHz, CDCl$_3$) δ 7.37-6.80 (m, 7H), 6.63 (d, J=12.2 Hz, 1H), 6.53 (d, J=12.2 Hz, 1H), 3.53 (t, J=5.7 Hz, 2H), 3.26 (t, J=5.5 Hz, 2H), 2.75 (t, J=7.5 Hz, 2H), 2.35 (t, J=7.5 Hz, 2H), 2.15 (s, 6H), 1.64-1.47 (m, 6H); ESI MS m/z 348 [M+H]$^+$.

Step 2:

Reduction of 3-(3-(2,6-dimethylstyryl)phenyl)-1-(piperidin-1-yl)propan-1-one followed by purification by Preparative HPLC (Method 1) gave Example 11 (0.106 g, 34%) as a colorless oil: R$_f$ 0.73 (silica gel, 50:40:10 ethyl acetate/hexanes/7N ammonia in methanol); $^1$H NMR (500 MHz, CD$_3$OD) δ 7.34 (m, 2H), 7.26 (t, J=7.5 Hz, 1H), 7.16 (d, J=16.7 Hz, 1H), 7.10 (d, J=7.5 Hz, 1H), 7.03 (s, 3H), 6.56 (d, J=16.7 Hz, 1H), 2.64 (t, J=7.6 Hz, 2H), 2.38 (m, 6H), 2.34 (s, 6H), 1.87 (m, 2H), 1.60 (m, 4H), 1.46 (m, 2H); $^{13}$C NMR (75 MHz, CD$_3$OD) δ 143.8, 139.2, 138.4, 137.3, 135.5, 129.9, 129.0, 128.9, 128.0, 127.9, 127.6, 125.0, 60.1, 55.7, 34.9, 29.4, 26.6, 25.4, 21.3; ESI MS m/z 334 [M+H]$^+$; HPLC (Method 5) >99% (AUC), t$_R$=13.14 min. HRMS Calcd for C$_{24}$H$_{31}$N [M+H]: 334.253. Found: 334.2520.

Example 12

Preparation of (Z)-1-(3-(3-(2,6-dimethylstyryl)phenyl)propyl)piperidine

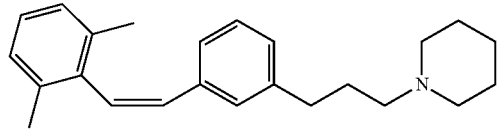 [SMILES: Cc1cccc(C)c1/C=C\c1cccc(CCCN2CCCCC2)c1]

(Z)-1-(3-(3-(2,6-Dimethylstyryl)phenyl)propyl)piperidine was isolated during the synthesis of Example 11 as a colorless oil. Yield (0.027 g, 9%): R$_f$ 0.73 (silica gel, 50:40:10 ethyl acetate/hexanes/7N ammonia in methanol); $^1$H NMR (500 MHz, CD$_3$OD) δ 7.05 (m, 4H), 6.95 (d, J=7.6 Hz, 1H), 6.83 (d, J=7.7 Hz, 1H), 6.76 (s, 1H), 6.65 (d, J=12.2 Hz, 1H), 6.54 (d, J=12.2 Hz, 1H), 2.36 (m, 6H), 2.19 (m, 2H), 2.12 (s, 6H), 1.58 (m, 6H), 1.46 (m, 2H); $^{13}$C NMR (75 MHz, CD$_3$OD) δ 143.1, 139.0, 138.7, 136.7, 132.5, 129.8, 129.4, 128.9, 128.7, 128.6, 128.1, 127.3, 59.9, 55.6, 34.8, 28.9, 26.6, 25.3, 20.6; ESI MS m/z 334 [M+H]$^+$; HPLC (Method 5)

98.7% (AUC), $t_R$=13.72 min. HRMS Calcd for $C_{24}H_{31}N$ [M+H]: 334.253. Found: 334.2527.

Example 13

Preparation of (E)-1-(3-(3-(2,6-dimethylstyryl)phenyl)propyl)piperazine

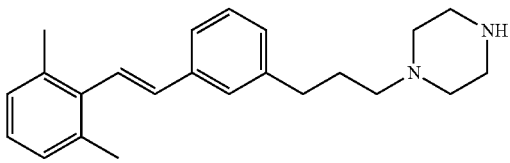 [SMILES: Cc1cccc(C)c1/C=C/c1cccc(CCCN2CCNCC2)c1]

SCHEME 3

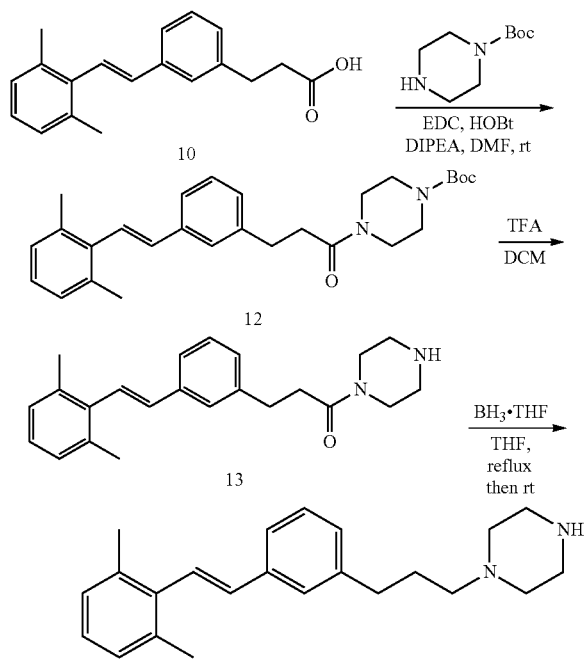

(E)-3-(3-(2,6-dimethylstyryl)phenyl)-1-(piperazin-1-yl)propan-1-one was prepared following the method shown in Scheme 3.

Step 1:

tert-Butyl 4-(3-(3-(2,6-Dimethylstyryl)phenyl)propanoyl)piperazine-1-carboxylate (12) was prepared from Compound 10 and N-Boc-piperazine following the method used to prepare Example 3. Yield (0.445 g, 95%) of a colorless oil as a mixture of trans-/cis-isomers. Isomer ratio 2:1 trans:cis.

trans-isomer: $^1$H NMR (300 MHz, CDCl$_3$) δ 7.38-6.79 (m, 8H), 6.57 (d, J=16.6 Hz, 1H), 3.62-3.26 (m, 8H), 3.02 (t, J=7.5 Hz, 2H), 2.67 (t, J=7.5 Hz, 2H), 2.36 (s, 6H), 1.46 (s, 9H);

cis-isomer: $^1$H NMR (500 MHz, CDCl$_3$) δ 7.38-6.79 (m, 7H), 6.63 (d, J=12.2 Hz, 1H), 6.53 (d, J=12.2 Hz, 1H), 3.62-3.26 (m, 8H), 2.76 (t, J=7.5 Hz, 2H), 2.35 (t, J=7.5 Hz, 2H), 2.15 (s, 6H), 1.48 (s, 9H); ESI MS m/z 449 [M+H]$^+$.

Step 2:

To a stirred solution of tert-Butyl 4-(3-(3-(2,6-Dimethylstyryl)phenyl)propanoyl)piperazine-1-carboxylate (12) (0.450 g, 1.00 mmol) in methylene chloride (6 mL) was added trifluoroacetic acid (3 mL) at room temperature. After 1 h, the reaction mixture was basified by slow addition of saturated aqueous sodium bicarbonate (30 mL) followed by 10% aqueous potassium carbonate to pH 10. The resulting mixture was extracted with hexanes (3×50 mL) and the combined extracts were dried (Na$_2$SO$_4$), filtered and concentrated. The resulting residue was purified by Preparative HPLC (Method 1) to give (E)-3-(3-(2,6-dimethylstyryl)phenyl)-1-(piperazin-1-yl)propan-1-one (13) (0.147 g, 42%) as a colorless oil. R$_f$ 0.58 (silica gel, 50:40:10 ethyl acetate/hexanes/7N ammonia in methanol); $^1$H NMR (500 MHz, CD$_3$OD) δ 7.41 (s, 1H), 7.37 (d, J=7.7 Hz, 1H), 7.28 (t, J=7.5 Hz, 1H), 7.18 (d, J=16.7 Hz, 1H), 7.15 (d, J=7.5 Hz, 1H), 7.03 (s, 3H), 6.57 (d, J=16.7 Hz, 1H), 3.53 (t, J=5.1 Hz, 2H), 3.41 (t, J=5.1 Hz, 2H), 2.95 (t, J=7.4 Hz, 2H), 2.71 (m, 4H), 2.59 (t, J=5.1 Hz, 2H), 2.34 (s, 6H); $^{13}$C NMR (75 MHz, CD$_3$OD) δ 173.5, 142.8, 139.3, 138.3, 137.3, 135.4, 130.1, 129.1, 129.0, 128.3, 127.9, 127.7, 125.5, 47.9, 46.7, 46.4, 43.6, 35.5, 32.9, 21.3; ESI MS m/z 349 [M+H]$^+$; HPLC (Method 5) >99% (AUC), $t_R$=10.63 min. HRMS Calcd for $C_{23}H_{28}N_2O$ [M+H]: 349228. Found: 349.2275.

Step 3:

To a stirred solution of (E)-3-(3-(2,6-dimethylstyryl)phenyl)-1-(piperazin-1-yl)propan-1-one (13) (0.138 g, 0.396 mmol) in THF (5 mL) was added borane-THF complex (0.79 mL, 1M solution in THF, 0.790 mmol) and the reaction mixture heated to reflux. After 1 h the reaction mixture was cooled to room temperature and another portion of borane-THF complex (0.40 mL, 1M solution in THF, 0.400 mmol) was added. After 18 h the reaction was quenched by slow addition of methanol (10 mL), concentrated, the resulting residue suspended in 6N hydrochloric acid (5 mL) and heated at 90° C. After 0.5 h the mixture was cooled to room temperature and basified to pH 12 with 2N aqueous sodium hydroxide. The resulting suspension was extracted with methylene chloride (3×50 mL) and the combined extracts dried (Na$_2$SO$_4$), filtered and concentrated. The resulting residue was purified by flash column chromatography (silica gel, 50:46:4 ethyl acetate/hexanes/7N ammonia in methanol) to give Example 13 as a colorless oil. Yield (0.062 g, 47%): R$_f$ 0.60 (silica gel, 50:40:10 ethyl acetate/hexanes/7N ammonia in methanol); $^1$H NMR (500 MHz, CD$_3$OD) δ 7.35 (m, 2H), 7.27 (t, J=7.5 Hz, 1H), 7.17 (d, J=16.7 Hz, 1H), 7.11 (d, J=7.5 Hz, 1H), 7.03 (s, 3H), 6.57 (d, J=16.7 Hz, 1H), 2.84 (t, J=5.0 Hz, 4H), 2.66 (t, J=7.6 Hz, 2H), 2.41 (m, 6H), 2.34 (s, 6H), 1.86 (m, 2H); $^{13}$C NMR (125 MHz, CD$_3$OD) δ 143.8, 139.2, 138.4, 137.2, 135.5, 129.9, 129.0, 128.9, 128.0, 127.9, 127.6, 125.0, 59.8, 54.9, 46.2, 34.7, 29.2, 21.3; ESI MS m/z 335 [M+H]$^+$; HPLC (Method 5) >99% (AUC), $t_R$=10.11 min. HRMS Calcd for $C_{23}H_{30}N_2$ [M+H]: 335.248. Found: 335.2491.

Example 14

Preparation of (Z)-1-(3-(3-(2,6-dimethylstyryl)phenyl)propyl)piperazine

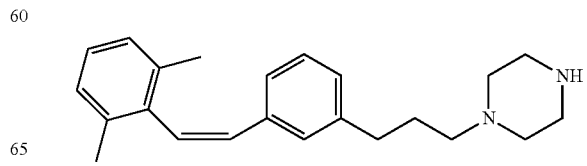

(Z)-1-(3-(3-(2,6-dimethylstyryl)phenyl)propyl)piperazine was prepared following the method used to prepare Example 3.

Step 1:

(Z)-3-(3-(2,6-dimethylstyryl)phenyl)-1-(piperazin-1-yl) propan-1-one was isolated during the synthesis of Example 13 as a colorless oil. Yield (0.073 g, 21%): $R_f$ 0.58 (silica gel, 50:40:10 ethyl acetate/hexanes/7N ammonia in methanol); $^1$H NMR (500 MHz, CD$_3$OD) δ 7.05 (m, 4H), 6.98 (d, J=7.6 Hz, 1H), 6.84 (d, J=7.7 Hz, 1H), 6.80 (s, 1H), 6.66 (d, J=12.2 Hz, 1H), 6.55 (d, J=12.2 Hz, 1H), 3.50 (t, J=5.0 Hz, 2H), 3.31 (m, 2H), 2.68 (m, 6H), 2.40 (t, J=8.2 Hz, 2H), 2.12 (s, 6H); $^{13}$C NMR (75 MHz, CD$_3$OD) δ 173.2, 142.1, 139.2, 138.7, 136.8, 132.3, 130.0, 129.6, 129.1, 128.7, 128.2, 127.4, 44.8, 46.8, 46.4, 43.6, 35.4, 32.6, 20.6; ESI MS m/z 349 [M+H]$^+$; HPLC (Method 5) >99% (AUC), $t_R$=11.12 min. HRMS Calcd for C$_{23}$H$_{28}$N$_2$O [M+H]: 349.228. Found: 349.2271.

Step 2:

(Z)-1-(3-(3-(2,6-dimethylstyryl)phenyl)propyl)piperazine was prepared following the method used in Example 13. Yield (0.046 g, 75%) of a colorless oil: $R_f$ 0.60 (silica gel, 50:40:10 ethyl acetate/hexanes/7N ammonia in methanol); $^1$H NMR (500 MHz, CD$_3$OD) δ 7.05 (m, 4H), 6.95 (d, J=7.6 Hz, 1H), 6.83 (d, J=7.7 Hz, 1H), 6.76 (s, 6.65 (d, J=12.2 Hz, 1H), 6.54 (d, J=12.2 Hz, 1H), 2.83 (t, J=5.0 Hz, 4H), 2.38 (m, 6H), 2.20 (m, 2H), 2.12 (s, 6H), 1.58 (m, 2H); $^{13}$C NMR (75 MHz, CD$_3$OD) δ 143.1, 139.1, 138.7, 136.7, 132.5, 129.8, 129.4, 129.0, 128.7, 128.6, 128.1, 127.3, 59.7, 54.9, 46.2, 34.6, 28.9, 20.6; ESI MS m/z 335 [M+H]$^+$; HPLC (Method 5) 97.0% (AUC), $t_R$=9.92 mm. HRMS Calcd for C$_{23}$H$_{30}$N$_2$ [M+H]: 335.248. Found: 335.2491.

Example 15

Preparation of (E)-2-amino-N-(3-(2,6-dimethylstyryl)phenyl)acetamide

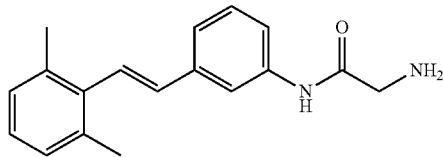 [SMILES: Cc1cccc(C)c1/C=C/c1cccc(NC(=O)CN)c1]

SCHEME 4

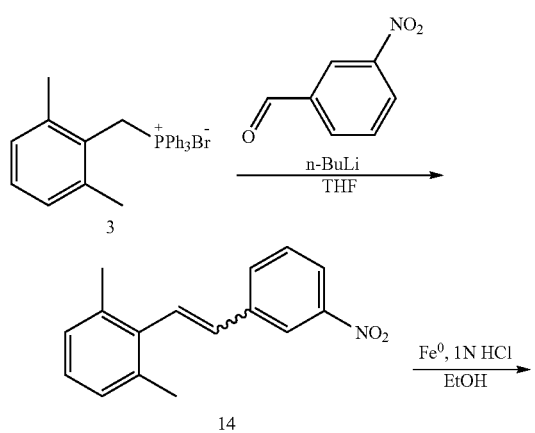

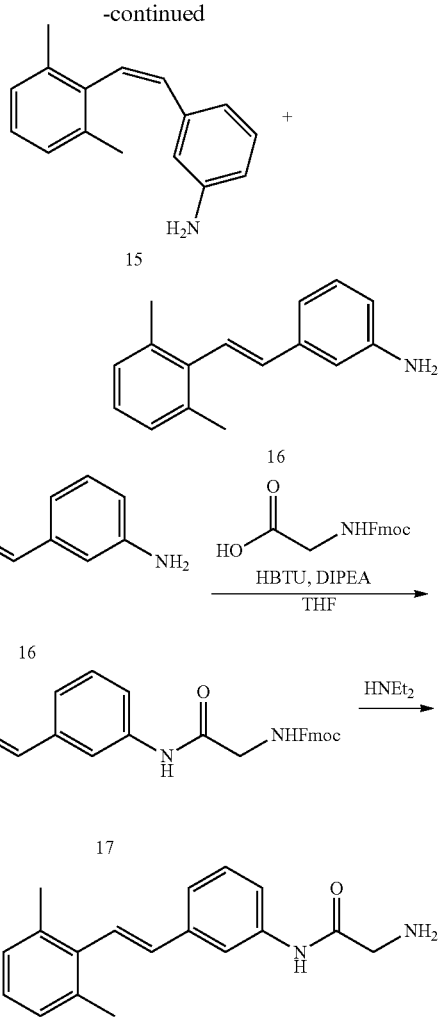

(E)-3-amino-N-(3-(2,6-dimethylstyryl)phenyl)acetamide was prepared following the method described in Scheme 4.

Step 1:

Coupling of Wittig reagent 3 with 3-nitrobenzaldehyde following the method used to prepare Example 4 gave olefin 14 as a yellow solid. Yield (0.486 g, 87%), isomer ratio 3:1 trans:cis.

cis-isomer: $^1$H NMR (500 MHz, CDCl$_3$) δ 7.96 (d, J=7.2 Hz, 1H), 7.87 (d, J=1.6 Hz, 1H), 7.25-7.23 (m, 1H), 7.16-7.06 (m, 4H), 6.74 (d, J=11.4 Hz, 1H), 6.69 (d, J=12.2 Hz, 1H), 2.14 (s, 6H);

trans-isomer: NMR (500 MHz, CDCl$_3$) δ 8.34 (d, J=1.9 Hz, 1H), 8.12-8.10 (m, 1H), 7.78 (d, J=7.8 Hz, 1H), 7.53 (t, J=8.0 Hz, 1H), 7.25-7.23 (m, 1H), 7.16-7.06 (m, 3H), 6.65 (d, J=16.6 Hz, 114), 2.38 (s, 6H).

Step 2:

To a stirred solution of 14 (0.486 g, 1.9 mmol) in ethanol (25 mL) was added iron (1.08 g, 10 mmol) and 1N HCl (2.0 mL, 2.0 mmol) and the resulting suspension was heated at 60° C. After 1.5 h the mixture was cooled to room temperature and filtered over diatomaceous earth. The filter cake was washed with ethanol (50 mL), the filtrate concentrated, the residue was dissolved in ethyl acetate (100 mL), and the resulting solution washed with saturated aqueous sodium bicarbonate (2×50 mL). The combined aqueous phases were extracted with ethyl acetate (75 mL) and the combined organics were dried (MgSO$_4$), filtered and concentrated. Purification by column chromatography (silica, 0-15% ethyl acetate/hexanes) provided (0.071 g, 17%) of 15 as a yellow solid and (0.348 g, 82%) of 16 as a yellow solid.

15: ¹H NMR (500 MHz, CDCl₃) δ 7.10 (t, J=7.7 Hz, 1H), 7.02 (d, J=7.5 Hz, 2H), 6.92 (t, J=7.8 Hz, 1H), 6.55 (d, J=12.3 Hz, 1H), 6.49 (d, J=12.5 Hz, 1H), 6.47-6.45 (m, 1H), 6.41 (d, J=7.6 Hz, 1H), 6.31-6.30 (m, 1H), 3.43 (br s, 2H), 2.16 (s, 6H).

16: ¹H NMR (500 MHz, CDCl₃) δ 7.16 (t, J=7.8 Hz, 1H), 7.08-7.04 (m, 4H), 6.91 (d, J=7.8 Hz, 1H), 6.84-6.83 (m, 1H), 7.62 (dd, J=7.9, 2.2 Hz, 1H), 5.52 (d, J=16.7 Hz, 1H), 3.69 (br s, 2H), 2.36 (s, 6H).

Step 3:

To a stirred solution of 16 (0.132 g, 0.590 mmol) and Fmoc-β-alanine (0.306 g, 0.980 mmol) in THF (5 mL) was added HBTU (0.490 g, 1.31 mmol), followed by N,N-diisopropylethylamine (0.245 g, 1.89 mmol). The reaction mixture was stirred overnight, then concentrated under reduced pressure. The residue was purified by flash chromatography (silica gel, 0-50% ethyl acetate/hexanes) followed by trituration with methylene chloride to provide 17 as a white solid. Yield (0.163 g, 53%): ¹H NMR (500 MHz, CDCl₃) δ 7.74 (d, J=7.4 Hz, 2H), 7.69 (s, 1H), 7.57 (d, J=7.3 Hz, 2H), 7.45-7.27 (m, 8H), 7.12 (d, J=16.5 Hz, 1H), 7.10-7.06 (m, 3H), 6.60 (d, J=16.7 Hz, 1H), 5.47 (br s, 1H), 4.39 (d, J=6.6 Hz, 2H), 4.21 (d, J=6.8 Hz, 1H), 3.59 (d, J=4.9 Hz, 2H), 2.65 (br s, 2H), 2.36 (s, 6H)); ESI MS m/z 517 [M+H]⁺.

Step 4:

To a stirred solution of 16 (0.135 g, 0.600 mmol) and Fmoc-glycine (0.294 g, 0.990 mmol) in THF (5 mL) was added HBTU (0.494 g, 1.31 mmol), followed by N,N-diisopropylethylamine (0.245 g, 1.89 mmol). The reaction mixture was stirred overnight, then concentrated under reduced pressure. The residue was purified by flash chromatography (silica gel, 0-50% ethyl acetate/hexanes) to provide 17 as a white solid. Yield (0.311 g, quant.): ¹H NMR (500 MHz, CDCl₃) δ 8.10 (br s, 1H), 7.34 (d, J=7.5 Hz, 2H), 7.65 (s, 1H), 7.57 (d, J=7.3 Hz, 2H), 7.39-7.36 (m, 3H), 7.31-7.27 (m, 4H), 7.12-7.05 (m, 4H), 6.54 (d, J=16.6 Hz, 1H), 5.64 (br s, 1H), 4.48 (d, J=6.8 Hz, 2H), 4.23 (t, J=6.8 Hz, 1H), 4.03 (br s, 2H), 2.35 (s, 6H); ESI MS m/z 503 [M+H]⁺.

Step 5:

A solution of 17 (0.311 g, 0.60 mmol) in diethylamine (5 mL) was stirred at room temperature. After 4 h the reaction mixture was concentrated to an oily residue which was purified by flash column chromatography (silica gel, 1-10% 7N ammonia in methanol/methylene chloride) to provide Example 15 as a yellow gum. Yield (0.119 g, 71%): $R_f$ 0.59 (silica gel, 95:5 methylene chloride/7N ammonia in methanol); ¹H NMR (500 MHz, CD₃OD) δ 7.81 (s, 1H), 7.47 (d, 0.1=7.8 Hz, 1H), 7.31 (t, J=7.8 Hz, 1H), 7.27 (d, J=7.7 Hz, 1H), 7.19 (d, J=16.7 Hz, 1H), 7.04 (s, 3H), 6.57 (d, J=16.6 Hz, 1H), 3.43 (s, 2H), 2.35 (s, 6H); ¹³C NMR (125 MHz, CD₃OD) δ 173.6, 140.0, 139.7, 138.0, 137.1, 134.9, 130.2, 128.9, 128.6, 127.8, 123.3, 120.2, 118.6, 45.7, 21.2; ESI MS m/z 281 [M+H]⁺; HPLC (Method 5) >99% (AUC), $t_R$=10.88 min. HRMS calcd for C₁₈H₂₀N₂O [M+H]: 281.165. Found: 281.1664.

Example 16

Preparation of (E)-3-(3-(2-methylstyryl)phenyl)propan-1-amine

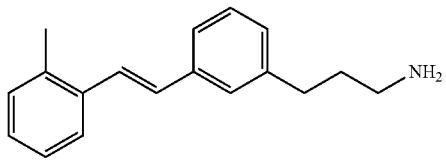 [SMILES: Cc1ccccc1/C=C/c1cccc(CCCN)c1]

(E)-3-(3-(2-methylstyryl)phenyl)propan-1-amine was prepared following the method used in Example 1.

Step 1:

Coupling of 3-iodobenzaldehyde with (2-methylbenzyl)triphenylphosphonium bromide followed by flash chromatography (silica gel, eluent: hexanes) gave (E)-1-(3-iodostyryl)-2-methylbenzene as a colorless oil. Yield (0.498 g, 36%): ¹H NMR (500 MHz, CDCl₃) δ 7.87-7.86 (m, 1H), 7.59-7.55 (m, 2H), 7.45 (d, J=7.8 Hz, 1H), 7.30 (d, J=16.2 Hz, 1H), 7.23-7.18 (m, 3H), 7.09 (t, J=7.9 Hz, 1H), 6.86 (d, J=16.2 Hz, 1H), 2.43 (s, 3H) and (Z)-1-(3-iodostyryl)-2-methylbenzene as a colorless oil. Yield (0.0.540 g, 39%): ¹H NMR (500 MHz, CDCl₃) δ 7.47-7.45 (m, 2H), 7.21-7.15 (m, 2H), 7.11-7.01 (m, 3H), 6.85 (t, J=7.8 Hz, 1H), 6.68 (d, J=12.2 Hz, 1H), 6.49 (d, J=12.1 Hz, 1H), 2.26 (s, 3H).

Step 2:

Coupling of (E)-1-(3-iodostyryl)-2-methylbenzene with allyl alcohol gave (E)-3-(3-(2-Methylstyryl)phenyl)propanal as a yellow oil. Yield (0.103 g, 52%): ¹H NMR (500 MHz, CDCl₃) δ 9.85 (t, J=1.2 Hz, 1H), 7.59 (d, J=7.2 Hz, 1H), 7.38 (d, J=7.8 Hz, 1H), 7.33-7.28 (m, 3H), 7.22-7.18 (m, 3H), 7.10 (d, J=7.5 Hz, 1H), 6.96 (d, J=16.1 Hz, 1H), 2.99 (t, J=7.6 Hz, 2H), 2.84-2.31 (m, 2H), 2.44 (s, 3H); ESI MS m/z 233 [M+H–H₂O]]⁺.

Step 3:

Reductive amination of (E)-3-(3-(2-Methylstyryl)phenyl)propanal with ammonia gave Example 16 as a yellow oil. Yield (0.017 g, 16%): $R_f$ 0.35 (silica gel, 95:5 methylene chloride/7N ammonia in methanol); ¹H NMR (500 MHz, CD₃OD) δ 7.58 (d, J=7.3 Hz, 1H), 7.40-7.37 (m, 3H), 7.27 (t, J=7.6 Hz, 1H), 7.17-7.10 (m, 4H), 7.00 (d, J=16.2 Hz, 1H), 2.73 (t, J=7.4 Hz, 2H), 2.69 (t, J=7.7 Hz, 2H), 2.41 (s, 3H), 1.86 (quint, J=7.5 Hz, 2H); ¹³C NMR (75 MHz, CD₃OD) δ 143.8, 139.2, 137.7, 136.9, 131.4, 131.2, 129.8, 128.8, 128.5, 127.7, 127.3, 126.3, 125.1, 42.1, 35.6, 34.2, 20.0; ESI MS m/z 252 [M+H]⁺; HPLC (Method 2) 98.6% (AUC), $t_R$=8.86 min. HRMS calcd for C₁₈H₂₁N [M+H]: 252.1752. Found: 252.1748.

Example 17

Preparation of (Z)-3-(3-(2-methylstyryl)phenyl)propan-1-amine

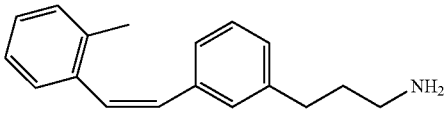 [SMILES: Cc1ccccc1/C=C\c1cccc(CCCN)c1]

(Z)-3-(3-(2-methylstyryl)phenyl)propan-1-amine was prepared following the method used in Example 1.

Step 1:

Coupling of (Z)-1-(3-iodostyryl)-2-methylbenzene with allyl alcohol gave (Z)-3-(3-(2-Methylstyryl)phenyl)propanal as a yellow oil. Yield (0.075 g, 37%): ¹H NMR (500 MHz, CDCl₃) δ 9.70 (s, 1H), 7.21-7.03 (m, 5H), 6.97-6.95 (m, 2H), 6.89 (s, 1H), 6.65 (d, J=12.1 Hz, 1H), 6.59 (d, J=12.1 Hz, 1H), 2.78 (t, J=7.5 Hz, 2H), 2.58-2.55 (m, 2H), 2.26 (s, 3H); ESI MS m/z 233 [M+H–H₂O]⁺.

Step 2:

Reductive amination of (Z)-3-(3-(2-Methylstyryl)phenyl)propanal with ammonia gave Example 22 as a yellow oil. Yield (0.016 g, 21%): $R_f$ 0.57 (silica gel, 95:5 methylene chloride/7N ammonia in methanol); ¹H NMR (500 MHz, CD₃OD) δ 7.18 (d, J=7.6 Hz, 1H), 7.15-7.12 (m, 1H), 7.06-7.01 (m, 3H), 6.96 (d, J=7.7 Hz, 1H), 6.89 (d, J=7.4 Hz, 2H), 6.65 (d, J=12.2 Hz, 1H), 6.61 (d, J=12.2 Hz, 1H), 4.50 (t, J=7.3 Hz, 2H), 2.44 (t, J=7.6 Hz, 2H), 2.22 (s, 3H), 1.59 (quint, J=7.4 Hz, 2H); $^{13}$C NMR (75 MHz, CD$_3$OD) δ142.9, 138.7, 138.5, 137.1, 131.9, 131.1, 130.5, 130.0, 129.9, 129.2, 128.3, 127.6, 126.8, 41.9, 35.3, 34.0, 20.0; ESI MS m/z 252 [M+H]$^+$; HPLC (Method 2) 92.9% (AUC), t$_R$=11.53 min. HRMS calcd for C$_{18}$H$_{21}$N [M+H]: 252.175. Found: 252.1761.

Example 18

Preparation of (E)-2-(3-(2,6-dimethylstyryl)phenylthio)ethanamine

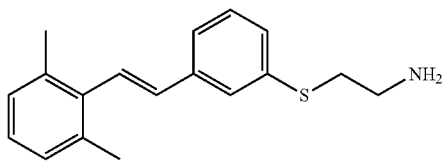 [SMILES: Cc1cccc(C)c1/C=C/c1cccc(SCCN)c1]

SCHEME 5

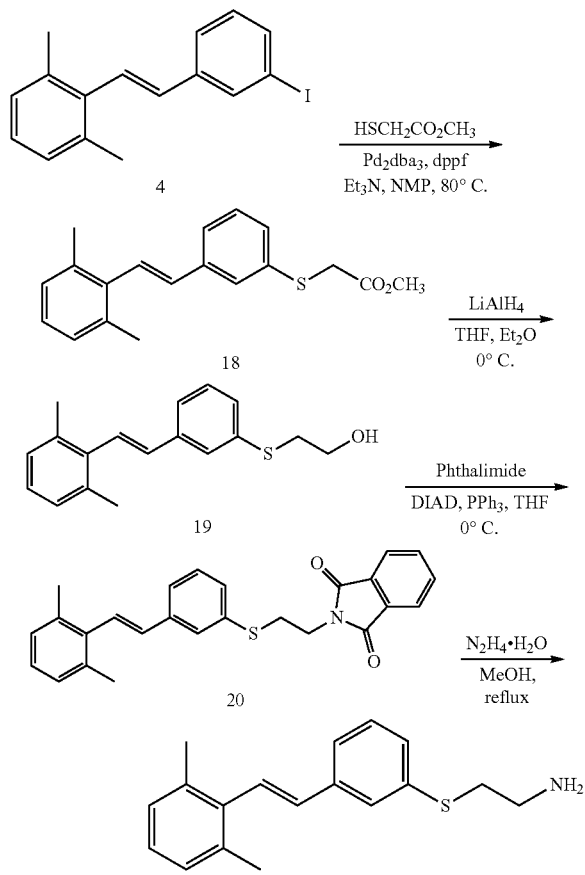

(E)-2-(3-(2,6-dimethylstyryl)phenylthio)ethanamine was prepared following the method shown in Scheme 5.

Step 1:

To a stirred solution of (E)-2-(3-iodostyryl)-1,3-dimethylbenzene (4) (0.551 g, 1.65 mmol) in NMP (10 mL) was added Et$_3$N (0.501 g, 4.95 mmol). The resulting solution was purged with nitrogen for 2 min and tris(dibenzylideneacetone)dipalladium(0) (0.076 g, 0.083 mmol) was added followed by 1,1'-bis(diphenylphosphino)ferrocene (0.183 g, 0.330 mmol). After 0.5 h methyl thioglycolate (0.531 g, 5.00 mmol) was added and the reaction mixture was heated at 80° C. After 26 h the reaction mixture was cooled to room temperature and diluted with water (50 mL). The resulting mixture was extracted with ethyl acetate (3×50 mL) and the combined organics were dried (Na$_2$SO$_4$), filtered and concentrated. The residue was purified by flash column chromatography (silica gel, 90:10 hexanes/ethyl acetate) to provide (E)-2-(3-(2,6-dimethylstyryl)phenylthio)ethylamine (18) (0.473 g, 92%) as a colorless oil: $^1$H NMR (500 MHz, CDCl$_3$) δ 7.54 (s, 1H), 7.34 (m, 3H), 7.12 (d, J=16.4 Hz, 1H), 7.08 (m, 3H), 6.55 (d, J=16.4 Hz, 1H), 3.73 (s, 3H), 3.69 (s, 2H), 2.36 (s, 6H).

Step 2:

To a stirred solution of 18 (0.259 g, 0.829 mmol) in THF (5 mL) at 0° C. was added lithium aluminum hydride (1.70 mL, 1M solution in diethyl ether, 1.70 mmol) at 0° C. After 10 min the reaction was quenched with saturated aqueous ammonium chloride (0.25 mL), diluted with MTBE (100 mL), the resulting suspension filtered and the filtrate concentrated. The resulting residue was purified by flash column chromatography (silica gel, 70:30 hexanes/ethyl acetate) to give 19 as a colorless oil. Yield (0.213 g, 90%): $^1$H NMR (300 MHz, CDCl$_3$) δ 7.50 (s, 1H), 7.36-7.26 (m, 3H), 7.11 (d, J=16.4 Hz, 1H), 7.07 (m, 3H), 6.54 (d, J=16.4 Hz, 1H), 3.76 (q, J=6.0 Hz, 2H), 3.14 (t, J=6.0 Hz, 2H), 2.36 (s, 6H), 2.27 (t, J=6.0 Hz, 1H).

Step 3:

To a stirred solution of 19 (0.208 g, 0.731 mmol) and phthalimide (0.215 g, 1.46 mmol) in THF (15 mL) at 0° C. was added diisopropyl azodicarboxylate (0.365 g, 1.81 mmol), followed by solution of triphenylphosphine (0.479 g, 1.83 mmol) in THF (2 mL). After 30 min the reaction mixture was diluted with brine (20 mL), extracted with hexanes (3×50 mL) and the combined extracts dried (Na$_2$SO$_4$), filtered and concentrated. The resulting residue was purified by flash column chromatography (silica gel, 90:10 hexanes/ethyl acetate) to give 20 as a colorless syrup. Yield (0.265 g, 88%): $^1$H NMR (500 MHz, CDCl$_3$) δ 7.78 (m, 2H), 7.67 (m, 2H), 7.55 (s, 1H), 7.32-7.19 (m, 3H), 7.17 (d, J=16.4 Hz, 1H), 7.08 (m, 3H), 6.52 (d, J=16.4 Hz, 1H), 3.97 (t, J=6.8 Hz, 2H), 3.27 (t, J=6.8 Hz, 2H), 2.39 (s, 6H).

Step 4:

A stirred solution of 20 (0.265 g, 0.641 mmol) and hydrazine monohydrate (0.096 g, 1.92 mmol) in methanol (10 mL) was heated at reflux for 2 h, cooled to room temperature and concentrated under reduced pressure. The residue was triturated with ethyl acetate (100 mL), the resulting suspension filtered. The filtrate was concentrated under reduced pressure and the residue purified by flash column chromatography (silica gel, hexanes/ethyl acetate/7M ammonia in methanol (50:46:4) to provide (E)-2-(3-(2,6-dimethylstyryl)phenylthio)ethanamine as a colorless oil. Yield (0.163 g, 90%): R$_f$ 0.58 (silica gel, 50:40:10 ethyl acetate/hexanes/7N ammonia in methanol); $^1$H NMR (500 MHz, CDCl$_3$) δ 7.52 (s, 1H), 7.38 (m, 1H), 7.29 (m, 2H), 7.19 (d, J=16.4 Hz, 1H), 7.03 (s, 3H), 6.56 (d, J=16.4 Hz, 1H), 3.05 (t, J=6.8 Hz, 2H), 2.82 (t, J=6.8 Hz, 2H), 2.33 (s, 6H); $^{13}$C NMR (75 MHz, CDCl$_3$) δ 140.0, 138.1, 137.7, 137.3, 134.7, 130.5, 129.9, 129.1, 129.0, 128.8, 128.0, 125.3, 41.7, 37.6, 21.3; ESI MS m/z 284

[M+H]⁺; HPLC (Method 2) 98.5% (AUC), t_R=7.91 min. HRMS calcd for C₁₈H₂₁NS [M+H–NH₃]: 267.120. Found: 267.1195.

Example 19

Preparation of (E)-2-(3-(2,6-dimethylstyryl)phenyl-sulfinyl)ethanamine

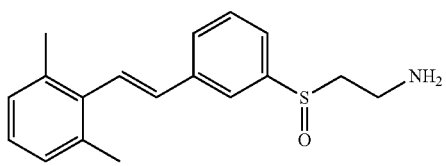 [SMILES: Cc1cccc(C)c1/C=C/c1cccc(S(=O)CCN)c1]

SCHEME 6

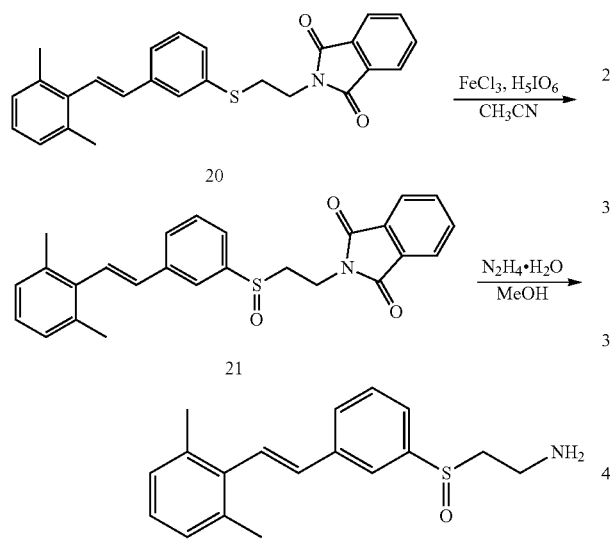

(E)-2-(3-(2,6-dimethylstyryl)phenylsulfinyl)ethanamine was prepared following method shown in scheme 6.

Step 1:

To a suspension of 20 (0.252 g, 0.610 mmol) in acetonitrile (1.5 mL) was added iron (III) chloride (0.003 g, 0.018 mmol). After 5 min periodic acid (0.168 g, 0.740 mmol) was added in one portion. The solution was then stirred for 10 min and 10% aqueous sodium thiosulfate (7 mL) was added. The resulting mixture was extracted with methylene chloride (3×20 mL), the combined organics dried (MgSO₄), filtered and concentrated to provide of 21 as a yellow oil. Yield (0.382 g, >99%): ¹H NMR (500 MHz, CDCl₃) δ 7.82-7.80 (m, 3H), 7.72-7.70 (m, 2H), 7.51-7.44 (m, 3H), 7.22 (d, J=16.6 Hz, 1H), 7.11-7.08 (m, 3H), 6.59 (d, J=16.5 Hz, 1H), 4.15-4.11 (m, 2H), 3.31-3.27 (m, 2H), 2.38 (s, 6H); ESI MS m/z 430 [M+H]⁺.

Step 2:

Deprotection of Compound 21 following the method described in Example 18 gave Example 19 as a yellow oil. Yield (0.115 g, 63%): R_f 0.56 (silica gel, 90:10 Methylene Chloride/7N Ammonia in Methanol); ¹H NMR (500 MHz, CD₃OD) δ 7.87 (s, 1H), 7.75-7.73 (m, 1H), 7.61-7.58 (m, 2H), 7.34 (d, J=16.7 Hz, 1H), 7.05 (s, 3H), 6.69 (d, J=16.7 Hz, 1H), 3.12-3.08 (m, 2H), 3.04-2.96 (m, 2H), 2.35 (s, 6H); ¹³C NMR (125 MHz, CD₃OD) δ 143.2, 139.2, 136.1, 135.7, 132.3, 129.5, 129.0, 128.8, 127.5, 126.6, 122.5, 121.0, 58.7, 35.1, 19.7; ESI MS m/z 300 [M+H]⁺; HPLC (Method 2) 97.4% (AUC), t_R=5.73 min. HRMS calcd for C₁₈H₂₁NOS [M+H]: 300.142. Found: 300.1409.

Example 20

Preparation of (E)-2-(3-(2,6-dimethylstyryl)phenyl-sulfonyl)ethanamine

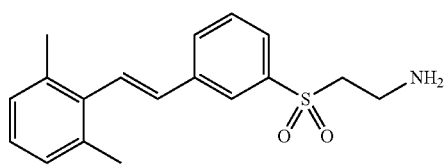 [SMILES: Cc1cccc(C)c1/C=C/c1cccc(S(=O)(=O)CCN)c1]

SCHEME 7

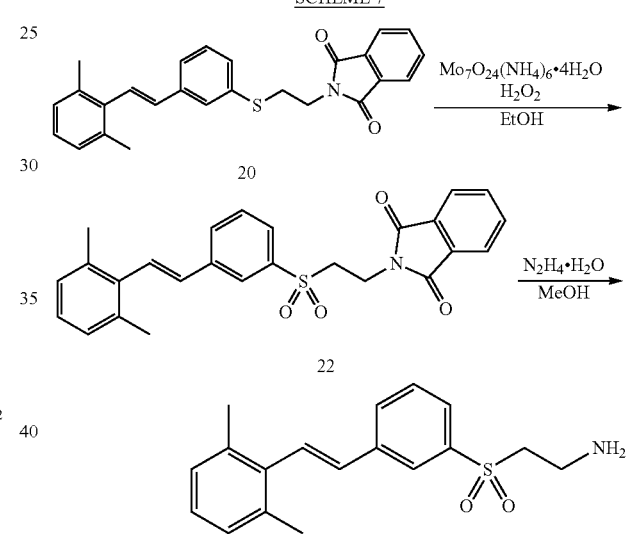

(E)-2-(3-(2,6-dimethylstyryl)phenylsulfonyl)ethanamine was prepared following method shown in scheme 7.

Step 1:

To a stirred solution of 20 (0.250 g, 0.60 mmol) at 0° C. was added ammonium molybdate tetrahydrate (0.226 g, 0.18 mmol) and hydrogen peroxide (0.50 mL, 35% solution, 5.70 mmol). After 30 min the solution was warmed to room temperature and stirred for an additional 16 h. After this time the solution was cooled to 0° C. and quenched by addition of 10% Na₂S₂O₃ (25 mL) and brine (25 mL). The resulting solution was extracted with ethyl acetate (3×50 mL) and the combined organics were dried (MgSO₄), filtered and concentrated. Purification by flash column chromatography (silica gel, 0-40% ethyl acetate/hexanes) provided 0.198 g (74%) of 22 as a white solid: ¹H NMR (500 MHz, CDCl₃) δ 8.04 (s, 1H), 7.81-7.78 (m, 3H), 7.70-7.68 (m, 2H), 7.59 (d, J=7.8 Hz, 1H), 7.48 (t, J=7.8 Hz, 1H), 7.26 (d, J=16.5 Hz, 1H), 7.12-7.09 (m, 3H), 6.60 (d, J=16.7 Hz, 1H), 4.11 (d, J=6.5 Hz, 2H), 3.65 (t, J=6.5 Hz, 2H), 2.40 (s, 6H); ESI MS m/z 446 [M+H]⁺.

Step 2:

Deprotection of Compound 22 following the method described in Example 18 gave Example 20 as a yellow semi-solid. Yield (0.113 g, 81%): R$_f$ 0.70 (silica gel, 90:10 Methylene Chloride/7N Ammonia in Methanol); $^1$H NMR (500 MHz, CD$_3$OD) δ 8.05 (s, 1H), 7.93 (d, J=7.8 Hz, 1H), 7.82 (d, J=7.9 Hz, 1H), 7.65 (t, J=7.8 Hz, 1H), 7.37 (d, J=16.7 Hz, 1H), 7.06 (s, 3H), 6.72 (d, J=16.7 Hz, 1H), 3.39 (t, J=6.7 Hz, 2H), 2.98 (t, J=6.7 Hz, 2H), 2.36 (s, 6H); $^{13}$C NMR (125 MHz, CD$_3$OD) δ 141.2, 140.7, 137.5, 137.2, 133.3, 132.4, 131.2, 131.0, 129.0, 128.2, 127.7, 126.5, 58.9, 36.8, 21.1; ESI MS m/z 316 [M+H]$^+$; HPLC (Method 2) 98.4% (AUC), t$_R$=6.76 min. HRMS calcd for C$_{18}$H$_{21}$NO$_2$S [M+H]: 316.137. Found: 316.1372.

Example 21

Preparation of (E)-3-(3-(2-(2,6,6-trimethylcyclohex-1-enyl)vinyl)phenyl)propan-1-amine

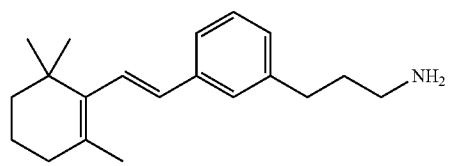 [SMILES: CC1=C(/C=C/c2cccc(CCCN)c2)C(C)(C)CCC1]

SCHEME 8

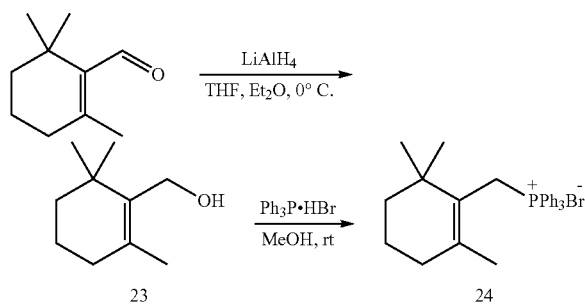

SCHEME 9

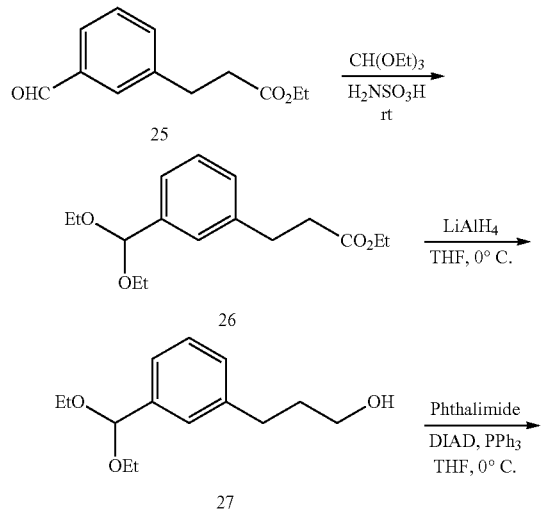

SCHEME 10

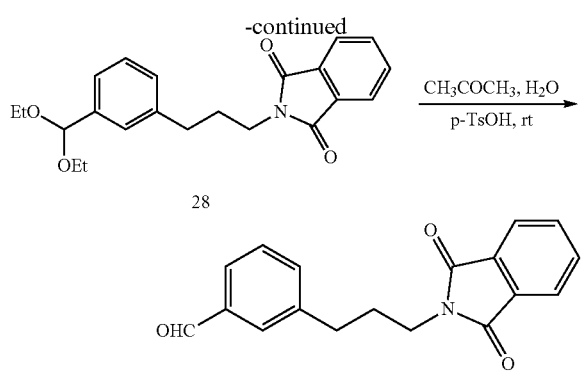

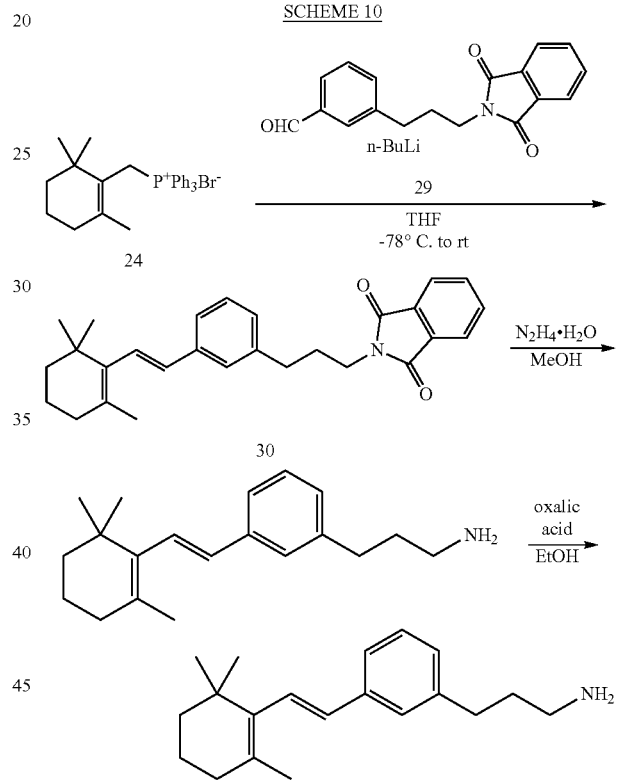

(E)-3-(3-(2-(2,6,6-Trimethylcyclohex-1-enyl)vinyl)phenyl)propan-1-amine was prepared by coupling triphenyl((2,6,6-trimethylcyclohex-1-enyl)methyl)phosphonium bromide (24) (Scheme 8) with 3-(3-(1,3-dioxoisoindolin-2-yl)propyl)benzaldehyde (29) (Scheme 9).

Step 1:

To a stirred solution of 2,6,6-trimethylcyclohex-1-enecarbaldehyde (10.0 g, 65.7 mmol) in anhydrous diethyl ether (100 mL) cooled to 0° C. was added lithium aluminum hydride (26.3 mL, 1M solution in THF, 26.3 mmol) dropwise over 10 min under nitrogen, the solution stirred at 0° C. for 10 min and quenched with 2N aqueous sodium hydroxide (2 mL). The resulting suspension diluted with MTBE (200 mL) and filtered. The filter cake was washed with MTBE (50 mL). The combined filtrate was concentrated under reduced pressure and the resulting residue dried in vacuo to provide 23 as a white solid. Yield (9.28 g, 92%): $^1$H NMR (500 MHz, CDCl$_3$) δ 4.14 (d, J=3.4 Hz, 2H), 1.75 (s, 3H), 1.60 (m, 2H), 1.60 (m, 2H), 1.44 (m, 2H), 1.04 (s, 6H), 0.97 (t, J=3.4 Hz, 1H); ESI MS m/z 137 [M+H–H$_2$O]$^+$.

Step 2:

To a stirred solution of triphenylphosphine hydrobromide (20.0 g, 58.3 mmol) in MeOH (50 mL) was added a solution of 23 (8.99 g, 58.4 mmol) in methanol (40 mL) and the reaction mixture stirred at room temperature for 18 h. The reaction solution was concentrated under reduced pressure, the residue triturated with a mixture of acetone (15 mL) and diethyl ether (200 mL) and the solvent decanted. The resulting residue was then triturated with a mixture of acetone (10 mL), ethyl acetate (50 mL) and diethyl ether (300 mL) and the solvent decanted again. The residue was dried in vacuo to provide coupling triphenyl((2,6,6-trimethylcyclohex-1-enyl) methyl)phosphonium bromide (26) as a white foam. Yield (21.9 g, 78%: NMR (500 MHz, DMSO-d$_6$) δ 7.90-7.70 (m, 15H), 4.30 (d, J=15.1 Hz, 2H), 2.02 (m, 2H), 1.61 (d, J=5.7 Hz, 3H), 1.54 (m, 2H), 1.37 (m, 2H), 0.72 (s, 6H); ESI MS m/z 399 [M−Br]$^+$.

Step 3:

To a stirred solution of ethyl 3-(3-formylphenyl)propanoate (25) 6.78 g, 32.9 mmol) in triethyl orthoformate (9.80 g, 66.1 mmol) was added sulfamic acid (0.319 g, 3.29 mmol) at room temperature. After 67 h the reaction mixture was diluted with a mixture of MTBE and hexanes (1:1, 100 mL), filtered and the filtrate concentrated. The residue was purified by flash column chromatography (silica gel, 85:15 hexanes/ethyl acetate) to give 26 as a colorless oil. Yield (7.31 g, 79%): NMR (500 MHz, CDCl$_3$) δ 7.29 (m, 3H), 7.15 (d, J=7.3 Hz, 1H), 5.47 (s, 1H), 4.12 (q, J=7.1 Hz, 2H), 3.63-3.50 (m, 4H), 2.96 (t, J=7.6 Hz, 2H), 2.62 (t, J=7.6 Hz, 2H), 1.23 (m, 9H).

Step 4:

Compound 26 was reduced following the procedure used in Example 18 to give 27 as a colorless oil. Yield (6.04 g, quant;): $^1$H NMR (500 MHz, CDCl$_3$) δ 7.31-7.13 (m, 4H), 5.47 (s, 1H), 3.65-3.52 (m, 6H), 2.71 (t, J=7.6 Hz, 2H), 1.88 (m, 3H), 1.23 (m, 6H); ESI MS m/z 221 [M+H–H$_2$O].

Step 5:

Compound 27 was converted to the phthalimide following the procedure used in Example 18 to give 28 as a colorless oil. Yield (8.55 g, 92%): $^1$H NMR (300 MHz, CDCl$_3$) 0.5-7.83 (m, 2H), 7.70 (m, 2H), 7.29-7.14 (m, 4H), 5.45 (s, 1H), 3.75 (t, J=7.2 Hz, 2H), 3.63-3.49 (m, 4H), 2.70 (t, J=7.6 Hz, 2H), 2.03 (m, 2H), 1.23 (m, 6H).

Step 6:

To a stirred solution of 28 (8.55 g, 23.3 mmol) in 5:1 acetone/water (60 mL) was added p-toluenesulfonic acid monohydrate (0.443 g, 2.33 mmol). After 4 h, the reaction mixture was concentrated under reduced pressure. The residue was dissolved in ethyl acetate (200 mL), the resulting solution washed with saturated aqueous sodium bicarbonate (2×50 mL) and brine (50 mL), dried (Na$_2$SO$_4$), filtered and concentrated under reduced pressure to provide 29 as an off-white solid (6.77 g, 99%): $^1$H NMR (500 MHz, CDCl$_3$) δ 9.97 (s, 1H), 7.82 (m, 2H), 7.71 (m, 3H), 7.66 (d, J=7.5 Hz, 1H), 7.48 (d, J=7.6 Hz, 1H), 7.42 (t, J=7.5 Hz, 1H), 3.77 (t, J=7.1 Hz, 2H), 2.78 (t, J=7.6 Hz, 2H), 2.08 (m, 2H); ESI MS m/z 294 [M+H]$^+$.

Step 7:

Triphenyl((2,6,6-trimethylcyclohex-1-enyl)methyl)phosphonium bromide (24) was coupled with 3-(3-(1,3-dioxoisoindolin-2-yl)propyl)benzaldehyde (29) following the method described in Example 1 to give Compound 30 as a yellow oil (Scheme 11). Yield (0.283 g, 68%): $^1$H NMR (500 MHz, CDCl$_3$) δ 7.82 (dd, J=5.4, 3.1 Hz, 2H), 7.69 (dd, J=5.5, 3.0 Hz, 2H), 7.21-7.17 (m, 3H), 7.05 (d, J=6.8 Hz, 1H), 6.65 (d, J=16.3 Hz, 1H), 6.28 (d, J=16.3 Hz, 1H), 3.77 (t, J=7.2 Hz, 2H), 2.69 (t, J=7.8 Hz, 2H), 2.08-2.02 (m, 4H), 1.75 (s, 3H), 1.65-1.61 (m, 2H), 1.50-1.48 (m, 2H), 1.06 (s, 6H); ESI MS m/z 414 [M+H]$^+$.

Step 8:

Deprotection following the method used in Example 18 gave Example 22 as a yellow oil. Yield (0.888 g, 87%): $^1$H NMR (500 MHz, CD$_3$OD) δ 7.23-7.19 (m, 3H), 7.06-7.04 (m, 1H), 6.67 (d, J=16.4 Hz, 1H), 6.29 (d, J=16.3 Hz, 1H), 2.67-2.62 (m, 4H), 2.05 (t, J=6.1 Hz, 2H), 1.79 (q, J=7.5 Hz, 2H), 1.74 (s, 3H), 1.69-1.64 (m, 2H), 1.52-1.50 (m, 2H), 1.06 (s, 6H); ESI MS m/z 284 [M+H]$^+$.

Example 22 was further purified by conversion to the oxalate salt using the following procedure: To a stirred solution of (E)-3-(3-(2-(2,6,6-Trimethylcyclohex-1-enyl)vinyl) phenyl)propan-1-amine (0.426 g, 1.50 mmol) in ethanol (3 mL) was added oxalic acid (2.0 mL, 20% solution in ethanol) at room temperature. After 30 min the suspension was filtered and the resulting solid dried to provide (E)-3-(3-(2-(2,6,6-Trimethylcyclohex-1-enyl)vinyl)phenyl)propan-1-amine oxalate salt as a white solid (0.433 g, 71%): $^1$H NMR (500 MHz, DMSO-d$_6$) δ 7.31 (d, J=7.6 Hz, 2H), 7.26 (t, J=7.6 Hz, 1H), 7.07 (d, J=7.5 Hz, 1H), 6.72 (d, J=16.3 Hz, 1H), 6.32 (d, J=16.4 Hz, 1H), 2.79 (t, J=7.6 Hz, 2H), 2.64 (t, J=7.7 Hz, 2H), 2.02 (t, J=6.1 Hz, 2H), 1.86 (quint, J=7.7 Hz, 2H), 1.73 (s, 3H), 1.65-1.58 (m, 2H), 1.48-1.45 (m, 2H), 1.05 (s, 6H); $^{13}$C NMR (75 MHz, CD$_3$OD) δ 164.2, 141.2, 137.6, 137.1, 132.4, 129.0, 128.7, 127.1, 126.9, 125.9, 123.7, 33.9, 32.4, 31.8, 28.8, 21.4, 18.7; ESI MS m/z 284 [M+H]$^+$; HPLC (Method 2) 98.3% (AUC), t$_R$=9.99 min. HRMS calcd for C$_{20}$H$_{29}$N [M+H]: 284.237. Found: 284.2364; Anal. Calcd for C$_{20}$H$_{29}$N.1.35C$_2$H$_4$O$_4$: C, 67.32; H, 7.89; N, 3.46. Found: C, 67.31; H, 8.12; N, 3.47.

Example 22

Preparation of (E)-3-(3-(2-cyclohexylvinyl)phenyl)propan-1-amine

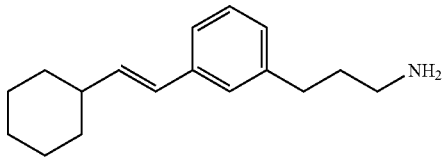 [SMILES: NCCCc1cccc(/C=C/C2CCCCC2)c1]

Step 1:

Coupling of aldehyde 29 with (cyclohexylmethy)ltriphenylphosphonium bromide following the method used in Example 1 gave 2-(3-(3-(2-Cyclohexylvinyl)phenyl)propyl) isoindoline-1,3-dione as a yellow oil. Yield (0.118 g, 56%) Isomer ratio trans:cis >9:1: $^1$H NMR (500 MHz, CDCl$_3$) δ 7.84-7.81 (m, 2H), 7.72-7.68 (m, 2H), 7.20 (t, J=7.5 Hz, 1H), 7.16-7.00 (m, 3H), 6.25 (d, J=11.8 Hz, 1H), 5.46 (t, J=10.8 Hz, 1H), 3.76 (t, J=7.2 Hz, 2H), 2.68 (t, J=7.9 Hz, 2H), 2.65-2.51 (m, 1H), 2.07-2.01 (m, 2H), 1.80-1.63 (m, 4H), 1.40-1.11 (m, 6H); ESI MS m/z 374 [M+H]$^+$.

Step 2:

Deprotection following the method used in Example 18 gave (E)-3-(3-(2-Cyclohexylvinyl)phenyl)propan-1-amine (0.066 g, 85%). Purification by Preparative HPLC (Method 1) provided Example 22 as a yellow oil (0.037 g, 48%): R$_f$ 0.39 (silica gel, 95:5 Methylene Chloride/7N Ammonia in Methanol); NMR (500 MHz, CD$_3$OD) δ 7.22 (t, J=7.7 Hz, 1H), 7.06 (d, J=8.8 Hz, 3H), 6.29 (d, J=11.7 Hz, 1H), 5.45 (d, J=11.6 Hz, 1H), 2.68-2.62 (m, 4H), 2.58-2.52 (m, 1H), 1.82-1.65 (m, 6H), 1.33-1.14 (m, 6H); $^{13}$C NMR (75 MHz, CD$_3$OD) δ 143.1, 139.6, 136.3, 129.7, 129.2, 128.3, 127.7, 127.1, 42.0, 38.4, 35.4, 34.4, 34.2, 27.1, 26.9; ESI MS m/z 244 [M+H]$^+$; HPLC (Method 2) 98.2% (AUC), $t_R$=9.78 min. HRMS calcd for C$_{17}$H$_{25}$N [M+H]: 244.206. Found: 244.2056.

Example 23

Preparation of (E)-3-(3-(pent-1-enyl)phenyl)propan-1-amine

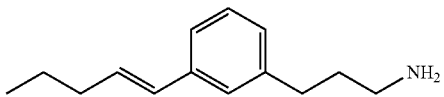

Step 1:
Coupling of aldehyde 29 with butyltriphenylphosphonium bromide following the method used in Example 1 gave 2-(3-(3-(pent-1-enyl)phenyl)propyl)isoindoline-1,3-dione as a yellow oil. Yield (0.198 g, 46%), isomer ratio 5:1: $^1$H NMR (500 MHz, CDCl$_3$) δ 7.84-7.81 (m, 2H), 7.72-7.68 (m, 2H), 7.22-7.01 (m, 4H), 6.37-6.16 (m, 1H), 5.66-5.61 (m, 1H), 3.76 (t, J=7.2 Hz, 2H), 2.69-2.65 (m, 2H), 2.31-2.15 (m, 2H), 2.04 (quint, J=7.5 Hz, 2H), 1.51-1.40 (m, 2H), 0.97-0.92 (m, 3H).

Step 2:
Deprotection following the methods used in Example 18 gave 3-(3-(pent-1-enyl)phenyl)propan-1-amine (0.106 g, 88%) as a 3:1 mixture of trans- and cis-isomers. A portion of the sample was purified using Preparative HPLC (Method 1) to provide Example 23 as a yellow oil: R$_f$ 0.75 (silica gel, 90:10 methylene chloride/7N ammonia in methanol); $^1$H NMR (500 MHz, CD$_3$OD) δ 7.22 (t, J=7.6 Hz, 1H), 7.09-7.04 (m, 3H), 6.39 (d, J=11.6 Hz, 1H), 5.64 (dt, J=11.7, 7.3 Hz, 1H), 2.67-2.62 (m, 4H), 2.31-2.26 (m, 2H), 1.78 (quint, J=7.4 Hz, 2H), 1.47, (hex, J=7.4 Hz, 2H), 0.93 (t, J=7.4 Hz, 3H); $^{13}$C NMR (125 MHz, CD$_3$OD) δ 143.1, 139.2, 133.5, 130.3, 130.0, 129.2, 127.7, 127.3, 42.1, 35.7, 34.3, 21.8, 24.2, 14.2; ESI MS m/z 204 [M+H]$^+$; HPLC (Method 2) >99% (AUC), $t_R$=6.41 min. HRMS calcd for C$_{14}$H$_{21}$N [M+H]: 204.175. Found: 204.1751.

Example 24

Preparation of (E)-3-(3-(hept-1-enyl)phenyl)propan-1-amine

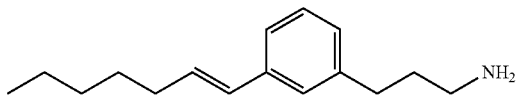 [SMILES: CCCCC/C=C/c1cccc(CCCN)c1]

Step 1:
Coupling of aldehyde 29 with hexyltriphenylphosphonium bromide following the method used in Example 1 gave 2-(3-(3-(hept-1-enyl)phenyl)propyl)isoindoline-1,3-dione as a yellow oil. Yield (0.297 g, 68%), isomer ratio 5:1: $^1$H NMR (500 MHz, CDCl$_3$) δ 7.84-7.80 (m, 2H), 7.72-7.68 (m, 2H), 7.22-7.11 (m, 2H), 7.09-7.01 (m, 2H), 6.35-6.18 (m, 1H), 5.67-5.61 (m, 1H), 3.75 (t, J=7.2 Hz, 2H), 2.67 (q, J=7.6 Hz, 2H), 2.32-2.16 (m, 2H), 2.04 (quint, J=7.4 Hz, 2H), 1.48-1.40 (m, 2H), 1.34-1.26 (m, 4H), 0.92-0.86 (m, 3H).

Step 2:
Deprotection following the methods used in Example 18 gave 3-(3-(hent-1-enyl)phenyl)propan-1-amine (0.141 g, 74%) as a mixture of trans- and cis-isomers. A portion of the sample was purified using Preparative HPLC (Method 1) to provide Example 24 as a yellow oil: R$_f$ 0.71 (silica gel, 90:10 Methylene Chloride/7N Ammonia in Methanol); $^1$H NMR (500 MHz, CD$_3$OD) δ 7.22 (t, J=7.6 Hz, 1H), 7.09-7.05 (m, 3H), 6.38 (d, J=11.7 Hz, 1H), 5.66-5.61 (m, 1H), 2.64 (q, J=8.1 Hz, 4H), 2.32-2.27 (m, 2H), 1.78 (quint, J=7.6 Hz, 2H), 1.45, (quint, J=7.4 Hz, 2H), 1.34-1.30 (m, 4H), 0.90-0.87 (m, 3H); $^{13}$C NMR (125 MHz, CD$_3$OD) δ143.1, 139.2, 133.7, 130.2, 129.9, 129.1, 127.6, 127.3, 42.1, 35.6, 34.2, 32.7, 30.7, 29.6, 23.6, 14.4; ESI MS m/z 232 [M+H]$^+$; HPLC (Method 2) >99% (AUC), $t_R$=8.79 min. HRMS calcd for C$_{16}$H$_{25}$N [M+H]: 232.206. Found: 232.2060.

Example 25

Preparation of (E)-3-amino-1-(3-(2-(2,6,6-trimethyl-cyclohex-1-enyl)vinyl)phenylpropan-1-ol

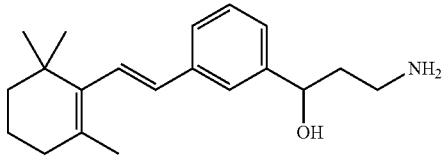 [SMILES: CC1=C(/C=C/c2cccc(C(O)CCN)c2)C(C)(C)CCC1]

SCHEME 11

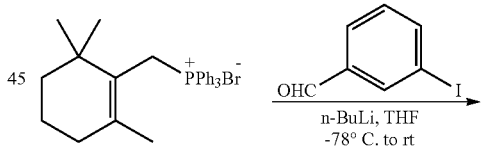

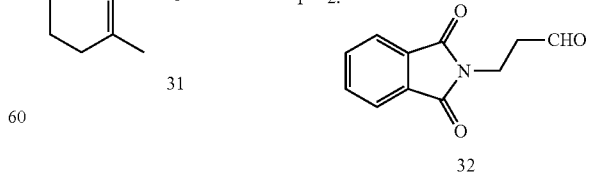

THF, -20° C. to rt

3. N$_2$H$_4$·H$_2$O, MeOH, reflux

-continued

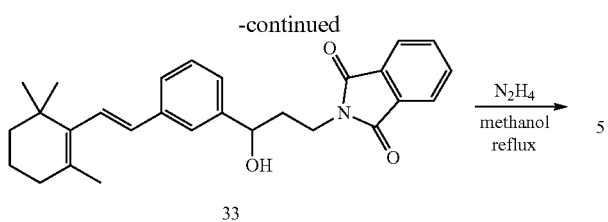

33

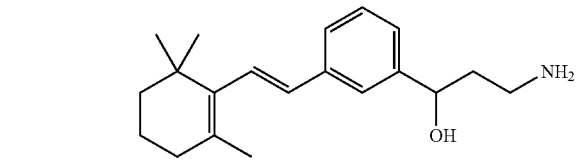

(E)-3-amino-1-(3-(2-(2,6,6-trimethylcyclohex-1-enyl)vinyl)phenyl)propan-1-ol was prepared following the method shown in Scheme 11.

Step 1:

Coupling of 3-iodobenzaldehyde with 24 following the method used in Example 1 gave 1-Iodo-3-(2-(2,6,6-trimethylcyclohex-1-enyl)vinyl)benzene (31) as a colorless oil. Yield (1.29 g, 85%): isomer ratio 9:1 trans-/cis-isomers.

trans-isomer: $^1$H NMR (500 MHz, CDCl$_3$) δ 7.74 (t, J=1.5 Hz, 1H), 7.53 (d, J=7.8 Hz, 1H), 7.34 (d, J=7.8 Hz, 1H), 7.04 (t, J=7.8 Hz, 1H), 6.66 (d, J=16.2 Hz, 1H), 6.23 (d, J=16.2 Hz, 1H), 2.03 (t, J=6.2 Hz, 2H), 1.74 (s, 3H), 1.63 (m, 2H), 1.48 (m, 2H), 1.05 (s, 6H);

cis-isomer: $^1$H NMR (500 MHz, CDCl$_3$) δ 7.88 (t, J=1.5 Hz, 1H), 7.47 (d, J=7.8 Hz, 1H), 7.34 (d, J=7.8 Hz, 1H), 6.98 (t, J=7.8 Hz, 1H), 6.28 (d, J=12.4 Hz, 1H), 6.13 (d, J=12.4 Hz, 1H), 1.96 (t, J=6.2 Hz, 2H), 1.66 (m, 2H), 1.54 (m, 2H), 1.52 (s, 3H), 1.05 (s, 6H).

Step 2:

To a stirred solution of 31 (0.300 g, 0.852 mmol) in THF (10 mL) was added isopropylmagnesium chloride (0.46 mL, 2M solution in THF, 0.920 mmol) at room temperature. After 1 h the reaction mixture was cooled to 20° C. and a solution of 3-(1,3-dioxoisoindolin-2-yl)propanal (32) (0.144 g, 0.709 mmol) in THF (3 mL) added. The resulting solution was warmed to room temperature, quenched with brine (20 mL) and extracted with ethyl acetate (3×50 mL). The combined organics were dried (Na$_2$SO$_4$), filtered and concentrated to give 33 which was used without purification in the next step Step 3:

Compound 33 was dissolved in methanol (15 mL) and hydrazine monohydrate (0.086 g, 1.71 mmol) added and the reaction mixture was heated at reflux. After 5 h the reaction mixture was cooled to room temperature, concentrated to an oil. The residue was purified by flash column chromatography (silica gel, 50:40:10 ethyl acetate/hexanes/7N ammonia in methanol) to provide Example 25 as a colorless oil. Yield (0.060 g, 24%): R$_f$0.17 (silica gel, 50:40:10 ethyl acetate/hexanes/7N ammonia in methanol); $^1$H NMR (500 MHz, CD$_3$OD) δ 7.42 (s, 1H), 7.31-7.20 (m, 3H), 6.72 (dd, J=16.2, 0.6 Hz, 1H), 6.32 (d, J=16.2 Hz, 1H), 4.73 (dd, J=8.1, 5.2 Hz, 1H), 2.76 (m, 2H), 2.05 (t, J=6.2 Hz, 2H), 1.90 (m, 2H), 1.75 (s, 3H), 1.66 (m, 2H), 1.52 (m, 2H), 1.07 (s, 6H); $^{13}$C NMR (125 MHz, CDCl$_3$) δ 146.9, 139.5, 139.1, 134.6, 130.5, 129.7, 128.8, 126.1, 125.9, 124.5, 73.7, 42.8, 40.9, 39.8, 35.4, 34.0, 29.5, 22.0, 20.5; ESI MS m/z 300 [M+H]$^+$; HPLC (Method 2) 93.5% (AUC), t$_R$=9.72 min. HRMS calcd for C$_{20}$H$_{29}$NO [M+H]: 300.232. Found: 300.2328.

Example 26

Preparation of (E)-2-methyl-3-(3-(2-(2,6,6-trimethylcyclohex-1-enyl)vinyl)phenyl)propan-1-amine

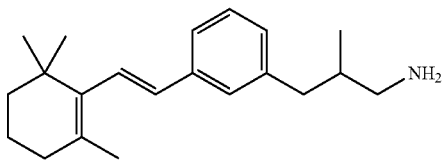 [SMILES: CC1=C(/C=C/c2cccc(CC(C)CN)c2)C(C)(C)CCC1]

SCHEME 12

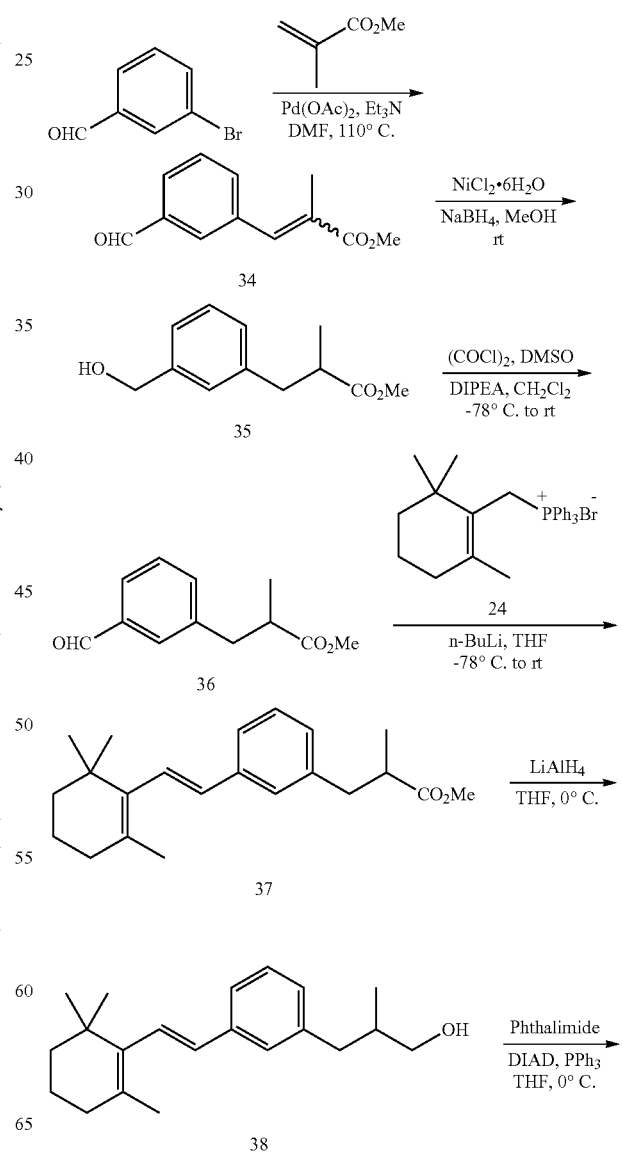

-continued

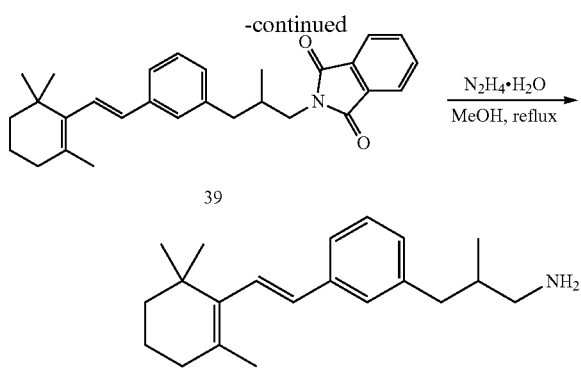

39

$\xrightarrow{\text{N}_2\text{H}_4\cdot\text{H}_2\text{O}}_{\text{MeOH, reflux}}$ (E)-2-methyl-3-(3-(2-(2,6,6-trimethylcyclohex-1-enyl)vinyl)phenyl)propan-1-amine was prepared following the method shown in Scheme 12.

Step 1:

To a stirred solution of 3-bromobenzaldehyde (2.00 g, 10.8 mmol), methyl methacrylate (1.35 g, 13.5 mmol), triethylamine (1.67 g, 16.5 mmol) and triphenylphosphine (0.567 g, 2.16 mmol) in DMF (15 mL) was added palladium acetate (0.121 g, 0.539 mmol) and the reaction mixture was heated at 110° C. After 17 h the reaction mixture was cooled to room temperature, diluted with ethyl acetate (150 mL), the resulting suspension washed with water (4×50 mL) and separated. The organic layer was dried ($Na_2SO_4$), filtered and concentrated. The residue was purified by flash column chromatography (silica gel, 90:10 hexanes/ethyl acetate) to provide 34 as a light yellow oil. Yield (0.790 g, 36%): $^1$H NMR (500 MHz, $CDCl_3$) δ 10.05 (s, 1H), 7.89-7.47 (m, 4H), 5.54 (m, 1H), 3.84 (s, 3H), 2.13 (s, 3H).

Step 2:

To a stirred solution of ester 34 (0.420 g, 2.06 mmol) and nickel(II) chloride hexahydrate (0.489 g, 2.06 mmol) in methanol (30 mL) was added sodium borohydride (0.234 g, 6.19 mmol) portionwise over 5 min at room temperature. After the addition was complete, the reaction mixture was stirred for 5 min and quenched with saturated aqueous ammonium chloride (10 mL). The resulting suspension was filtered through a short pad of diatomaceous earth and washed with methanol (50 mL). The combined filtrates were evaporated to dryness and the residue was partitioned between ethyl acetate (100 mL) and saturated aqueous ammonium chloride (50 mL). The organic layer was separated, dried ($Na_2SO_4$), filtered and concentrated. The residue was dried in vacuo to provide 35 (0.417 g, 97%) as a colorless oil: $^1$H NMR (300 MHz, $CDCl_3$) δ 7.30-7.08 (m, 4H), 4.67 (s, 2H), 3.64 (s, 3H), 3.04 (m, 1H), 2.81-2.63 (m, 2H), 1.15 (d, J=6.8 Hz, 3H).

Step 3:

To a stirred solution of oxalyl chloride (0.381 g, 3.00 mmol) in anhydrous methylene chloride (8 mL) cooled to 78° C. was added anhydrous DMSO (0.703 g, 9.00 mmol). After 30 mm a solution of 35 (0.417 g, 2.00 mmol) in anhydrous methylene chloride (10 mL) was added, the solution stirred for an additional 30 min, and N,N'-diisopropylethylamine (1.29 g, 10.0 mmol) was added. The resulting solution was warmed to room temperature, quenched with saturated aqueous ammonium chloride (20 mL), and extracted with methylene chloride (3×50 mL). The combined organic layers were dried ($Na_2SO_4$), filtered and concentrated under reduced pressure. The resulting residue was purified by flash column chromatography (silica gel, 90:10 hexanes/ethyl acetate) to provide 36 as a colorless oil. Yield (0.288 g, 70%): $^1$H NMR (500 MHz, $CDCl_3$) δ 10.00 (s, 1H), 7.73 (m, 1H), 7.69 (s, 1H), 7.45 (m, 2H), 3.64 (s, 3H), 3.09 (m, 1H), 2.77 (m, 2H), 1.18 (d, J=6.8 Hz, 3H).

Step 4:

Coupling of aldehyde 36 with Wittig reagent 24 following the method used in Example 1 gave (E)-ethyl 2-methyl-3-(3-(2-(2,6,6-trimethylcyclohex-1-enyl)vinyl)phenyl)propanoate (37) as a colorless oil. Yield (0.368 g, 81%): $^1$H NMR (500 MHz, $CDCl_3$) δ 7.26-7.16 (m, 3H), 7.01 (m, 1H), 6.65 (dd, J=16.3, 0.85 Hz, 1H), 6.30 (d, J=16.3 Hz, 1H), 3.65 (s, 3H), 3.03 (m, 1H), 2.76 (m, 1H), 2.65 (m, 1H), 2.03 (t, J=6.0 Hz, 2H), 1.75 (s, 3H), 1.64 (m, 2H), 1.49 (m, 2H), 1.17 (d, J=6.9 Hz, 3H), 1.06 (s, 6H).

Step 5:

Reduction of ester 37 following the method used in Example 18 gave alcohol 38 as a colorless oil. Yield (0.327 g, 97%): $^1$H NMR (500 MHz, $CDCl_3$) δ 7.24 (m, 2H), 7.19 (s, 1H), 7.03 (d, J=6.8 Hz, 1H), 6.67 (d, J=16.3 Hz, 1H), 6.32 (d, J=16.3 Hz, 1H), 3.58-3.48 (m, 2H), 2.75 (dd, J=13.5, 6.4 Hz, 1H), 2.42 (dd, J=13.5, 8.0 Hz, 1H), 2.04 (t, J=6.0 Hz, 2H), 1.98 (m, 1H), 1.76 (s, 3H), 1.64 (m, 2H), 1.49 (m, 2H), 1.28 (t, J=5.7 Hz, 1H), 1.06 (s, 6H), 0.94 (d, J=6.9 Hz, 3H).

Step 6:

Alcohol 38 was converted to phthalimide 39 following the method used in Example 18 to give 39 as a colorless oil. Yield (0.419 g, 89%): $^1$H NMR (500 MHz, $CDCl_3$) δ 7.78 (m, 2H), 7.67 (m, 2H), 7.15 (m, 3H), 7.00 (d, J=7.1 Hz, 1H), 6.63 (d, J=16.3 Hz, 1H), 6.26 (d, J=16.3 Hz, 1H), 3.67 (dd, J=13.7, 7.0 Hz, 1H), 3.58 (dd, J=13.6, 7.2 Hz, 1H), 2.69 (m, 1H), 2.47 (m, 2H), 2.04 (t, J=6.0 Hz, 2H), 1.76 (s, 3H), 1.64 (m, 2H), 1.49 (m, 2H), 1.07 (s, 6H), 0.92 (d, J=6.9 Hz, 3H).

Step 7:

Deprotection of phthalimide 39 following the method used in Example 18 gave (E)-3-(3-(2-(2,6,6-Trimethylcyclohex-1-enyl)vinyl)phenyl)butan-1-amine as a colorless oil. Yield (0.105 g, 36%): $R_f$ 0.58 (silica gel, 50:40:10 ethyl acetate/hexanes/7N ammonia in methanol); $^1$H NMR (500 MHz, $CD_3OD$) δ 7.21 (m, 3H), 7.03 (dt, J=6.8, 1.6 Hz, 1H), 6.68 (dd, J=16.4, 0.83 Hz, 1H), 6.30 (d, J=16.4 Hz, 1H), 2.70 (dd, 0.1=13.4, 6.3 Hz, 1H), 2.61 (dd, J=12.7, 5.7 Hz, 1H), 2.47 (dd, J=12.7, 7.1 Hz, 1H), 2.37 (dd, J=13.4, 8.2 Hz, 1H), 2.05 (t, J=6.1 Hz, 2H), 1.84 (m, 1H), 1.75 (s, 3H), 1.66 (m, 2H), 1.51 (m, 2H), 1.06 (s, 6H), 0.90 (d, J=6.7 Hz, 3H); $^{13}$C NMR (125 MHz, $CDCl_3$) δ 142.6, 139.4, 139.1, 134.7, 130.4, 129.6, 129.1, 128.5, 128.0, 124.7, 48.6, 42.1, 40.9, 39.2, 35.4, 34.0, 29.5, 22.0, 20.5, 17.9; ESI MS m/z 298 [M+H]$^+$; HPLC (Method 2) 98.4% (AUC), $t_R$=11.5 min. HRMS calcd for $C_{21}H_{31}N$ [M+H]: 298.253. Found: 298.2542.

Example 27

Preparation of (E)-3-(3-(2-(2,6,6-trimethylcyclohex-1-enyl)vinyl)phenyl)butan-1-amine

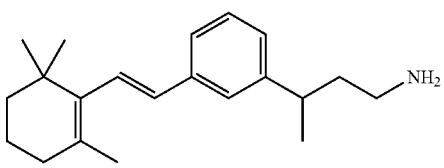 [SMILES: CC1=C(/C=C/c2cccc(C(C)CCN)c2)C(C)(C)CCC1]

(E)-3-(3-(2-(2,6,6-Trimethylcyclohex-1-enyl)vinyl)phenyl)butan-1-amine was prepared following the method used in Example 26.

Step 1:

Coupling of 3 bromobenzaldehyde with ethyl crotonate following the method used in Example 26 gave ethyl 3-(3-formylphenyl)but-2-enoate as a light yellow oil Yield (0.547, 23%): $^1$H NMR (300 MHz, CDCl$_3$) δ 10.05 (s, 1H), 7.99 (t, J=1.6 Hz, 1H), 7.87 (dt, J=7.6, 1.3 Hz, 1H), 7.74 (m, 1H), 7.56 (t, J=7.6 Hz, 1H), 6.19 (q, J=1.2 Hz, 1H), 4.23 (q, J=7.2 Hz, 2H), 2.61 (d, J=1.2 Hz, 3H), 1.33 (t, J=7.2 Hz, 3H).

Step 2:

Reduction of ethyl 3-(3-formylphenyl)but-2-enoate following the method used in Example 26 gave ethyl 3-(3-(hydroxymethyl)phenyl)butanoate as a colorless oil. Yield (0.427 g, 95%): $^1$H NMR (300 MHz, CDCl$_3$) δ 7.32-7.15 (m, 4H), 4.68 (s, 2H), 4.07 (q, J=7.2 Hz, 2H), 3.29 (m, 1H), 2.56 (m, 2H), 1.30 (d, J=7.0 Hz, 3H), 1.19 (t, J=7.2 Hz, 3H).

Step 3:

Oxidation of ethyl 3-(3-(hydroxymethyl)phenyl)butanoate following the method used in Example 26 gave ethyl 3-(3-formylphenyl)butanoate as a colorless oil. Yield (0.307 g, 68%): $^1$H NMR (300 MHz, CDCl$_3$) δ 10.01 (s, 1H), 7.73 (m, 2H), 7.50 (m, 2H), 4.06 (q, J=7.2 Hz, 2H), 3.37 (m, 1H), 2.64 (dd, J=15.2, 7.4 Hz, 1H), 2.58 (dd, J=15.2, 7.6 Hz, 1H), 1.34 (d, J=7.0 Hz, 3H), 1.17 (t, J=7.2 Hz, 3H).

Step 4:

Coupling of ethyl 3-(3-formylphenyl)butanoate with Wittig reagent 24 following the method used in Example 1 gave (E)-ethyl 3-(3-(2-(2,6,6-trimethylcyclohex-1-enyl)vinyl)phenyl)butanoate as a colorless oil. Yield (0.383 g, 81%): $^1$H NMR (500 MHz, CDCl$_3$) δ 7.25 (m, 3H), 7.07 (m, 1H), 6.66 (dd, J=16.3, 0.68 Hz, 1H), 6.31 (d, J=16.3 Hz, 1H), 4.09 (q, J=7.0 Hz, 2H), 3.28 (m, 1H), 2.65-2.52 (m, 2H), 2.04 (t, J=6.2 Hz, 2H), 1.76 (s, 3H), 1.64 (m, 2H), 1.49 (m, 2H), 1.30 (d, J=6.9 Hz, 3H), 1.20 (t, J=7.0 Hz, 3H), 1.06 (s, 6H).

Step 5:

Reduction of (E)-ethyl 3-(3-(2-(2,6,6-trimethylcyclohex-1-enyl)vinyl)phenyl)butanoate following the method used in Example 18 gave (E)-3-(3-(2-(2,6,6-trimethylcyclohex-1-enyl)vinyl)phenyl)butan-1-ol as a colorless oil. Yield (0.312 g, 93%): $^1$H NMR (500 MHz, CDCl$_3$) δ 7.27 (m, 2H), 7.20 (s, 1H), 7.03 (m, 1H), 6.67 (d, J=16.3 Hz, 1H), 6.32 (d, J=16.3 Hz, 1H), 3.60 (m, 2H), 2.89 (m, 1H), 2.04 (t, J=6.0 Hz, 2H), 1.88 (q, J=7.3 Hz, 2H), 1.76 (s, 3H), 1.64 (m, 2H), 1.49 (m, 2H), 1.29 (d, J=7.0 Hz, 3H), 1.14 (t, J=5.3 Hz, 3H), 1.07 (s, 6H).

Step 6:

Conversion of (E)-3-(3-(2-(2,6,6-trimethylcyclohex-1-enyl)vinyl)phenyl)butan-1-ol with phthalimide following the method used in Example 18 gave (E)-2-(3-(3-(2-(2,6,6-trimethylcyclohex-1-enyl)vinyl)phenyl)butyl)isoindoline-1,3-dione as a colorless oil. Yield (0.416 g, 93%): $^1$H NMR (500 MHz, CDCl$_3$) δ 7.75 (m, 2H), 7.64 (m, 2H), 7.18 (s, 1H), 7.16 (t, J=7.6 Hz, 1H), 7.10 (d, J=7.7 Hz, 1H), 7.05 (d, J=7.5 Hz, 1H), 6.64 (d, J=16.3 Hz, 1H), 6.27 (d, J=16.3 Hz, 1H), 3.67 (t, J=7.1 Hz, 2H), 2.78 (m, 1H), 2.12 (m, 1H), 2.04 (t, J=6.0 Hz, 2H), 1.93 (m, 1H), 1.77 (s, 3H), 1.64 (m, 2H), 1.49 (m, 2H), 1.30 (d, J=7.0 Hz, 3H), 1.08 (s, 6H).

Step 7:

Deprotection of (E)-2-(3-(3-(2-(2,6,6-trimethylcyclohex-1-enyl)vinyl)phenyl)butyl)isoindoline-1,3-dione following the method used in Example 18 gave (E)-3-(3-(2-(2,6,6-trimethylcyclohex-1-enyl)vinyl)phenyl)butan-1-amine as a colorless oil. Yield (0.196 g, 68%), R$_f$ 0.38 (silica gel, 50:40:10 ethyl acetate/hexanes/7N ammonia in methanol); $^1$H NMR (500 MHz, CDCl$_3$) δ 7.23 (m, 3H), 7.06 (m, 1H), 6.68 (dd, J=16.4, 0.83 Hz, 1H), 6.30 (d, J=16.4 Hz, 1H), 2.77 (m, 1H), 2.58-2.48 (m, 2H), 2.05 (t, J=6.1 Hz, 2H), 1.78 (m, 2H), 1.75 (s, 3H), 1.66 (m, 2H), 1.50 (m, 2H), 1.26 (d, J=7.0 Hz, 3H), 1.07 (s, 6H); $^{13}$C NMR (75 MHz, CDCl$_3$) δ 148.8, 139.6, 139.1, 134.8, 130.4, 129.9, 128.5, 126.8, 126.0, 124.8, 42.3, 41.1, 40.9, 39.2, 35.5, 34.0, 29.5, 23.1, 22.0, 20.5; ESI MS m/z 298 [M+H]$^+$; HPLC (Method 2) 97.5% (AUC), t$_R$=11.5 min. HRMS calcd for C$_{21}$H$_{31}$N [M+H]: 298.253. Found: 298.2527.

Example 28

Preparation of (E)-3-(3-(2,6-dimethylstyryl)-2-methylphenyl)propan-1-amine

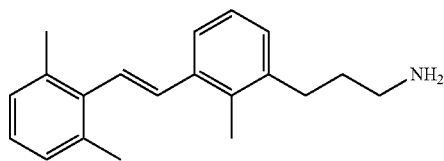 [SMILES: Cc1cccc(C)c1/C=C/c1cccc(CCCN)c1C]

SCHEME 13

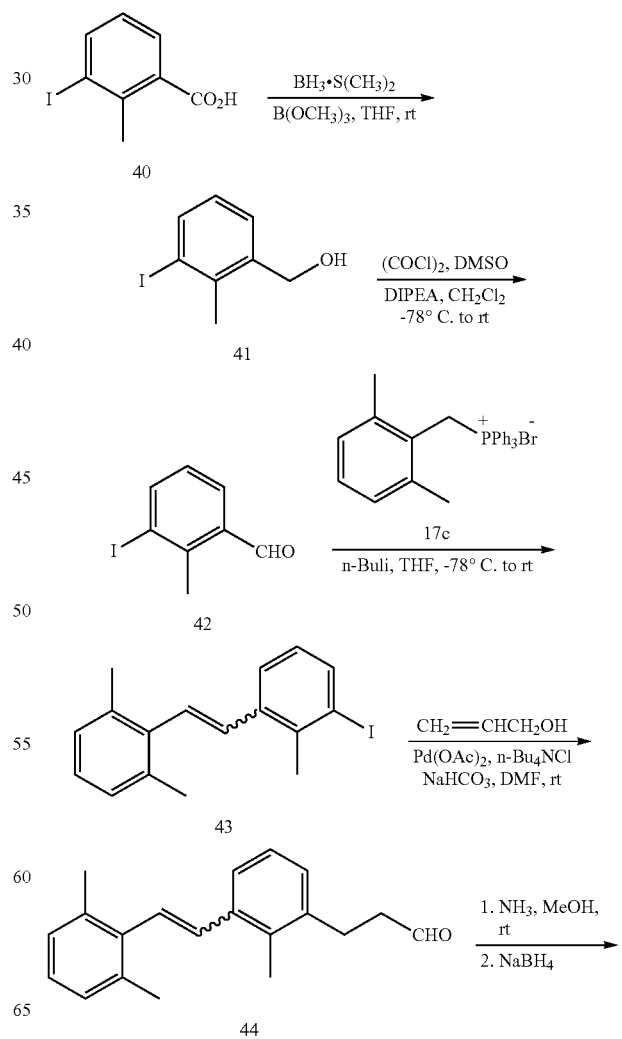

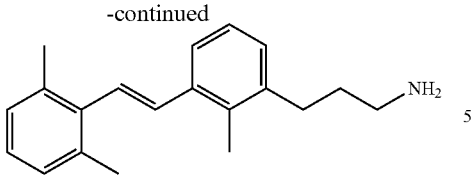

(E)-3-(3-(2,6-Dimethylstyryl)-2-methylphenyl)propan-1-amine was prepared following the method shown in Scheme 13.

Step 1:

To a stirred solution of 3-iodo-2-methylbenzoic acid (40) (5.00 g, 19.1 mmol) and trimethyl borate (7 mL) in THF (5 mL) was added borane-dimethyl sulfide complex (11.5 mL, 2M solution in THF, 23.0 mmol) dropwise at such rate that after gas evolution stopped it remained at a gentle reflux and after the addition was complete the reaction mixture was cooled to room temperature. After 1.5 h the reaction mixture was quenched by slow addition of methanol (10 mL), the resulting mixture was concentrated, and the residue was dissolved in methylene chloride (100 mL). The resulting solution was washed with 2M aqueous sodium hydroxide (80 mL) and water (100 mL), and the organic layer was dried ($Na_2SO_4$), filtered and concentrated. The residue was purified by flash column chromatography (silica gel, 60:36:4 methylene chloride/hexanes/MTBE) to give 41 as a white solid. Yield (4.36 g, 92%): $^1$H NMR (500 MHz, $CDCl_3$) δ 7.79 (d, J=7.9 Hz, 1H), 7.34 (d, J=7.9 Hz, 1H), 6.89 (t, J=7.9 Hz, 1H), 4.72 (d, J=5.8 Hz, 2H), 2.47 (s, 3H), 1.58 (t, J=5.8 Hz, 1H).

Step 2:

Alcohol 41 was oxidized following the method used in Example 26 to give aldehyde 42 as a light yellow solid. Yield (1.39 g, 93%): $^1$H NMR (300 MHz, $CDCl_3$) δ 10.19 (s, 1H), 8.07 (d, J=7.9 Hz, 1H), 7.79 (d, J=7.9 Hz, 1H), 7.09 (t, J=7.9 Hz, 1H), 2.79 (s, 3H).

Step 3:

Aldehyde 42 was coupled with Wittig reagent 3 following the method used in Example 1 to give olefin 43 as a white semi-solid. Yield (0.641 g, 65%), isomer ratio 4:1 trans:cis: $^1$H NMR (300 MHz, $CDCl_3$) δ 7.80-6.45 (m, 8H), 2.51-2.07 (m, 9H).

Step 4:

Coupling of olefin 43 with allyl alcohol following the method used in Example 1 gave aldehyde 44 as a light yellow oil. Yield (0.398 g, 86%), isomer ratio 4:1 trans:cis: $^1$H NMR (500 MHz, $CDCl_3$) δ 9.83 (m, 1H), 7.49-6.58 (m, 8H), 2.98 (m, 2H), 2.72 (m, 2H), 2.45-2.07 (n, 9H); ESI MS m/z 261 [M+H–$H_2O$]$^+$.

Step 5:

Reductive amination of aldehyde 44 with ammonia following the method used in Example 1 followed by purification by Preparative HPLC (Method 1) gave (E)-3-(3-(2,6-Dimethylstyryl)-2-methylphenyl)propan-1-amine as a light yellow oil. Yield (0.038 g, 10%): $R_f$ 0.55 (silica gel, 50:40:10 ethyl acetate/hexanes/7N ammonia in methanol); $^1$H NMR (500 MHz, $CD_3OD$) δ 7.43 (dd, J=7.5, 1.3 Hz, 1H), 7.10 (m, 2H), 7.03 (s, 3H), 6.91 (d, J=16.6 Hz, 1H), 6.87 (d, J=16.6 Hz, 1H), 2.70 (t, J=7.4 Hz, 4H), 2.37 (s, 6H), 2.32 (s, 3H), 1.74 (m, 2H); $^{13}$C NMR (125 MHz, $CD_3OD$) δ 141.9, 139.3, 138.7, 137.1, 134.7, 134.6, 130.0, 129.9, 129.0, 127.8, 127.0, 125.3, 42.5, 34.8, 32.5, 21.4, 15.5; ESI MS m/z 280 [M+H]$^+$; HPLC (Method 5) >99% (AUC), $t_R$=12.11 min. HRMS Calcd for $C_{20}H_{25}N$ [M+H]: 280.206. Found: 280.2052.

Example 29

Preparation of (Z)-3-(3-(2,6-dimethylstyryl)-2-methylphenyl)propan-1-amine

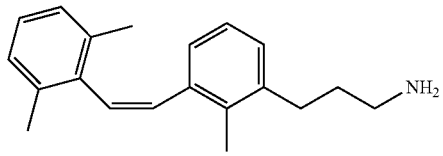 [SMILES: Cc1cccc(C)c1/C=C\c1cccc(CCCN)c1C]

(V)-3-(3-(2,6-Dimethylstyryl)-2-methylphenyl)propan-1-amine as was isolated during the synthesis of Example 28 as a light yellow oil. Yield (0.036 g, 9%): $R_f$ 0.55 (silica gel, 50:40:10 ethyl acetate/hexanes/7N ammonia in methanol); $^1$H NMR (500 MHz, $CD_3OD$) δ 6.98 (t, J=7.8 Hz, 1H), 6.93 (d, J=7.5 Hz, 1H), 6.90 (d, J=7.5 Hz, 2H), 6.87 (d, J=12.1 Hz, 1H), 6.68 (t, J=7.6 Hz, 1H), 6.61 (d, J=12.1 Hz, 1H), 6.49 (d, J=7.6 Hz, 1H), 2.67 (t, J=7.4 Hz, 2H), 2.66 (t, J=7.3 Hz, 2H), 2.30 (s, 3H), 2.05 (s, 6H), 1.70 (n, 2H); $^{13}$C NMR (125 MHz, $CD_3OD$) δ 141.6, 138.7, 137.9, 136.9, 134.6, 132.2, 129.9, 129.4, 128.5, 127.8, 127.5, 126.1, 42.5, 34.7, 32.4, 20.6, 15.6; ESI MS m/z 280 [M+H]$^+$; HPLC (Method 5) >99% (AUC), $t_R$=12.43 mm. HRMS Calcd for $C_{20}H_{25}N$ [M+H]: 280.206. Found: 280.2053.

Example 30

Preparation of (E)-2-amino-N-(3-(2-(2,6,6-trimethylcyclohex-1-enyl)vinyl)phenyl)acetamide

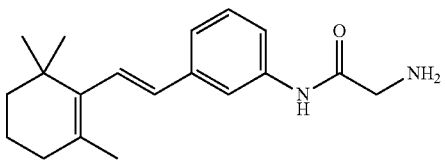 [SMILES: CC1=C(/C=C/c2cccc(NC(=O)CN)c2)C(C)(C)CCC1]

(E)-2-amino-N-(3-(2-(2,6,6-trimethylcyclohex-1-enyl)vinyl)phenyl)acetamide was prepared following the method used in Example 15.

Step 1:

Coupling of Wittig reagent 24 with 3-nitrobenzaldehyde gave 1-nitro-3-(2-(2,6,6-trimethylcyclohex-1-enyl)vinyl)benzene as a light yellow oil. Yield (0.639 g, 95%), isomer ratio 4:1 ratio trans:cis.

trans-isomer: $^1$H NMR (300 MHz, $CDCl_3$) δ 8.24 (t, J=1.9 Hz, 1H), 8.04 (m, 1H), 7.69 (d, J=7.7 Hz, 1H), 7.47 (t, J=8.0 Hz, 1H), 6.83 (dd, J=16.3, 0.85 Hz, 1H), 6.40 (d, J=16.3 Hz, 1H), 2.06 (t, J=6.2 Hz, 2H), 1.81 (s, 3H), 1.65 (m, 2H), 1.52 (m, 2H), 1.08 (s, 6H);

cis-isomer: $^1$H NMR (300 MHz, $CDCl_3$) δ 8.48 (t, J=1.9 Hz, 1H), 8.00 (m, 1H), 7.65 (d, J=7.7 Hz, 1H), 7.41 (t, J=8.0 Hz, 1H), 6.46 (d, J=12.4 Hz, 1H), 6.29 (d, J=12.4 Hz, 1H), 1.98 (m, 2H), 1.65 (m, 2H), 1.57 (m, 2H), 1.41 (s, 3H), 1.08 (s, 6H).

Step 2:

Reduction of 1-nitro-3-(2-(2,6,6-trimethylcyclohex-1-enyl)vinyl)benzene following the method described in Example 15 gave 3-(2-(2,6,6-trimethylcyclohex-1-enyl)vinyl)aniline as a light yellow oil. Yield (0.639 g, 95%), isomer ratio 4:1 trans:cis. trans-isomer: $^1$H NMR (300 MHz, CDCl$_3$) δ 7.11 (t, J=7.8 Hz, 1H), 6.82 (d, J=7.7 Hz, 1H), 6.75 (t, J=2.0 Hz, 1H), 6.63 (dd, J=16.3, 0.85 Hz, 1H), 6.56 (ddd, J=7.9, 2.3, 0.80 Hz, 1H), 6.25 (d, J=16.3 Hz, 1H), 3.65 (br s, 2H), 2.03 (t, J=6.2 Hz, 2H), 1.75 (s, 3H), 1.63 (m, 2H), 1.50 (m, 2H), 1.05 (s, 6H);

cis-isomer: $^1$H NMR (300 MHz, CDCl$_3$) δ 7.04 (t, J=7.8 Hz, 1H), 6.88 (d, J=7.7 Hz, 1H), 6.77 (t, J=2.0 Hz, 1H), 6.53 (m, 1H), 6.30 (d, J=12.4 Hz, 1H), 6.04 (d, J=12.4 Hz, 1H), 3.54 (br s, 2H), 1.96 (m, 2H), 1.63 (m, 2H), 1.53 (m, 2H), 1.44 (s, 3H), 1.07 (s, 6H).

Step 3:

Amidation of 3-(2-(2,6,6-trimethylcyclohex-1-enyl)vinyl)aniline following the method described in Example 15 gave (9H-Fluoren-9-yl)methyl 2-oxo-2-(3-(2-(2,6,6-trimethylcyclohex-1-enyl)vinyl)phenylamino)ethylcarbamate as a white foam. Yield (0.175 g, 74%), isomer ratio 10:1 trans:cis;

trans-isomer: $^1$H NMR (500 MHz, CDCl$_3$) δ 7.76 (m, 3H), 7.59 (m, 2H), 7.51 (s, 1H), 7.40 (m, 3H), 7.30 (m, 3H), 7.18 (m, 1H), 6.69 (d, J=16.3 Hz, 1H), 6.31 (d, J=16.3 Hz, 1H), 5.46 (br s, 1H), 4.50 (m, 2H), 4.24 (t, J=6.7 Hz, 1H), 4.00 (br s, 2H), 2.04 (t, J=6.2 Hz, 2H), 1.75 (s, 3H), 1.64 (m, 2H), 1.48 (m, 2H), 1.06 (s, 6H);

cis-isomer: $^1$H NMR (500 MHz, CDCl$_3$) δ 7.76 (m, 3H), 7.59 (m, 2H), 7.51 (s, 1H), 7.40 (m, 3H), 7.30 (m, 3H), 7.18 (m, 1H), 6.36 (d, J=12.4 Hz, 1H), 6.12 (d, J=12.4 Hz, 1H), 5.46 (br s, 1H), 4.50 (m, 2H), 4.24 (t, J=6.7 Hz, 1H), 4.00 (br s, 2H), 1.96 (m, 2H), 1.64 (m, 2H), 1.52 (m, 2H), 1.42 (s, 3H), 1.06 (s, 6H).

Step 4:

Deprotection of (9H-Fluoren-9-yl)methyl 2-oxo-2-(3-(2-(2,6,6-trimethylcyclohex-1-enyl)vinyl)phenylamino)ethylcarbamate following the method used in Example 15, followed by purification by Preparative HPLC (Method 1) gave (E)-2-amino-N-(3-(2-(2,6,6-trimethylcyclohex-1-enyl)vinyl)phenyl)acetamide as a colorless semi-solid. Yield (0.039 g, 39%): R$_f$ 0.53 (silica gel, 50:40:10 ethyl acetate/hexanes/7N ammonia in methanol); $^1$H NMR (500 MHz, CDCl$_3$) δ 7.68 (s, 1H), 7.41 (d, J=8.0 Hz, 1H), 7.26 (t, J=7.8 Hz, 1H), 7.14 (d, J=7.7 Hz, 1H), 6.71 (d, J=16.3 Hz, 1H), 6.30 (d, J=16.3 Hz, 1H), 3.42 (s, 2H), 2.06 (t, J=6.2 Hz, 2H), 1.75 (s, 3H), 1.67 (m, 2H), 1.51 (m, 2H), 1.07 (s, 6H); $^{13}$C NMR (125 MHz, CDCl$_3$) δ 173.9, 140.3, 140.0, 139.0, 134.2, 130.7, 130.2, 129.3, 123.2, 119.9, 118.4, 45.8, 40.9, 35.4, 34.0, 29.5, 22.0, 20.5; ESI MS m/z 299 [M+H]$^+$; HPLC (Method 2) 97.5% (AUC), t$_R$=9.99 min. HRMS calcd for C$_{19}$H$_{26}$N$_2$O [M+H]: 299.212. Found: 299.2125.

Example 31

Preparation of (E)-2-(3-(2-(2,6,6-trimethylcyclohex-1-enyl)vinyl)phenoxy)ethanamine

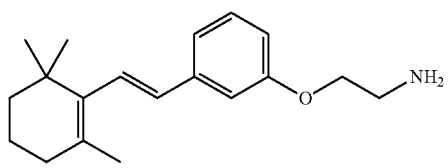 [SMILES: CC1=C(/C=C/c2cccc(OCCN)c2)C(C)(C)CCC1]

SCHEME 14

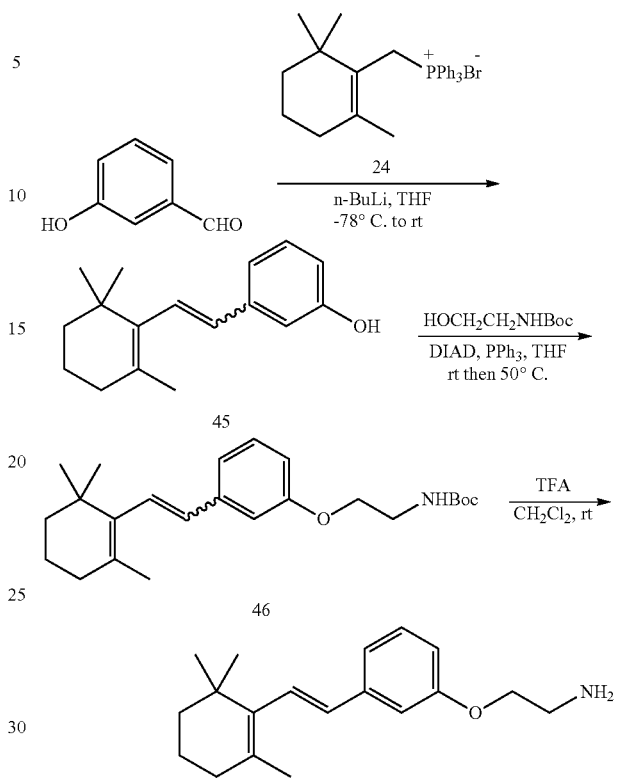

(E)-2-(3-(2-(2,6,6-trimethylcyclohex-1-enyl)vinyl)phenoxy)ethanamine was prepared following the method shown in Scheme 14.

Step 1:

Coupling of 3-hydroxybenzaldehyde with Wittig reagent 24 following the method used in Example 1 gave olefin 45 as a light yellow oil. Yield (0.543 g, 68%), isomer ratio 8:1 ratio trans:cis: $^1$H NMR (300 MHz, CDCl$_3$) δ 7.19 (t, J=7.8 Hz, 1H), 6.97 (d, J=7.7 Hz, 1H), 6.89 (t, J=2.3 Hz, 1H), 6.69 (m, 1H), 6.64 (dd, J=16.3, 0.87 Hz, 1H), 6.27 (d, J=16.3 Hz, 1H), 2.03 (t, J=6.2 Hz, 2H), 1.75 (s, 3H), 1.62 (m, 2H), 1.48 (m, 2H), 1.05 (s, 6H); The cis-isomer: $^1$H NMR (300 MHz, CDCl$_3$) δ 7.12 (t, J=7.8 Hz, 1H), 7.01 (d, J=7.7 Hz, 1H), 6.92 (t, J=2.3 Hz, 1H), 6.69 (m, 1H), 6.34 (d, J=12.4 Hz, 1H), 6.10 (d, J=16.3 Hz, 1H), 1.96 (m, 2H), 1.62 (m, 2H), 1.48 (m, 2H), 1.43 (s, 3H), 1.07 (s, 6H).

Step 2:

To a stirred solution of olefin 45 (0.507 g, 2.09 mmol) and tert-butyl 2-hydroxyethylcarbamate (1.35 g, 8.37 mmol) in THF (5 mL) was added triphenylphosphine (2.19 g, 8.35 mmol) followed by a solution of diisopropyl azodicarboxylate (1.69 g, 8.36 mmol) in THF (3 mL) dropwise over 10 min at room temperature. After 70 h the reaction mixture was heated at 50 C for an additional 18 h. After this time the reaction mixture was cooled to room temperature, partitioned between brine (50 mL) and ethyl acetate (100 mL). The organic layer was separated, dried (Na$_2$SO$_4$), filtered and concentrated. The resulting residue was purified by flash column chromatography (silica gel, 80:20 hexanes/ethyl acetate) to give 46 as a colorless syrup (0.731 g, 91%): ESI MS m/z 330 [M+H−C$_4$H$_8$]$^+$.

Step 3:

Deprotection of 46 following the method used in Example 13 gave (E)-2-(3-(2-(2,6,6-trimethylcyclohex-1-enyl)vinyl)

phenoxy)ethanamine as a colorless oil. Yield (0.060 g, 11%): $R_f$ 0.37 (silica gel, 50:40:10 ethyl acetate/hexanes/7N ammonia in methanol); $^1$H NMR (500 MHz, CDCl$_3$) δ 7.21 (t, J=7.9 Hz, 1H), 6.99 (m, 2H), 6.81 (dd, J=7.8, 2.0 Hz, 1H), 6.69 (dd, J=16.3, 0.79 Hz, 1H), 6.29 (d, J=16.3 Hz, 1H), 4.03 (t, 0.1=5.3 Hz, 2H), 3.01 (t, J=5.3 Hz, 2H), 2.05 (t, J=6.2 Hz, 2H), 1.75 (s, 3H), 1.66 (m, 2H), 1.51 (m, 2H), 1.06 (s, 6H); $^{13}$C NMR (125 MHz, CDCl$_3$) 160.8, 141.0, 139.0, 134.5, 130.7, 130.6, 129.0, 120.0, 114.5, 113.2, 70.4, 42.1, 40.9, 35.4, 34.0, 29.5, 22.0, 20.5; ESI MS m/z 286 [M+H]$^+$; HPLC (Method 2) 94.8% (AUC), $t_R$=10.2 min. HRMS calcd for C$_{19}$H$_{27}$1\TO [M+H]: 286.2171. Found: 286.2162.

Example 32

Preparation of (E/Z)-3-(3-(2-ethyl-6-methylstyryl)phenyl)propan-1-amine

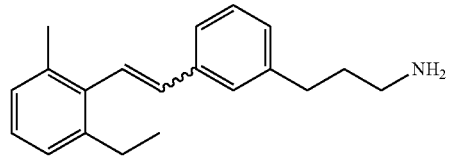 [SMILES: CCc1cccc(C)c1C=Cc1cccc(CCCN)c1]

(E/Z)-3-(3-(2-Ethyl-6-methylstyryl)phenyl)propan-1-amine was prepared following the method described in Example 21, except that phthalimide 29 was synthesized according to Scheme 15.

SCHEME 15

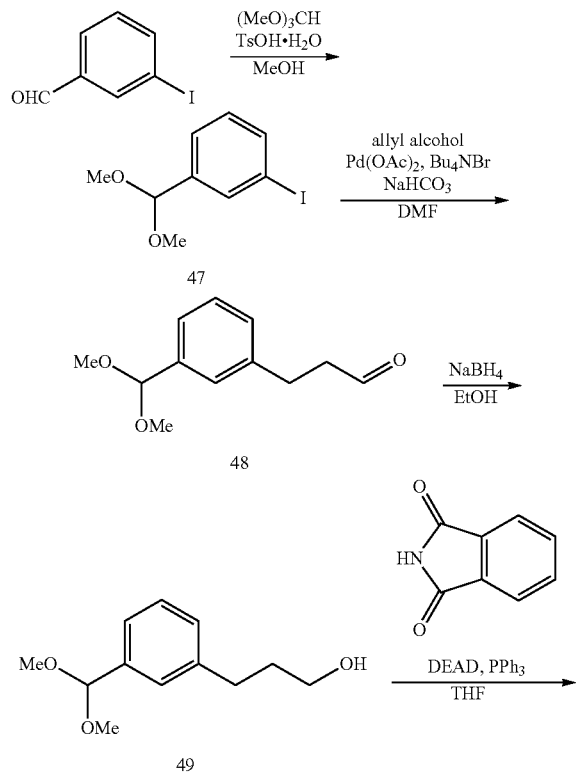

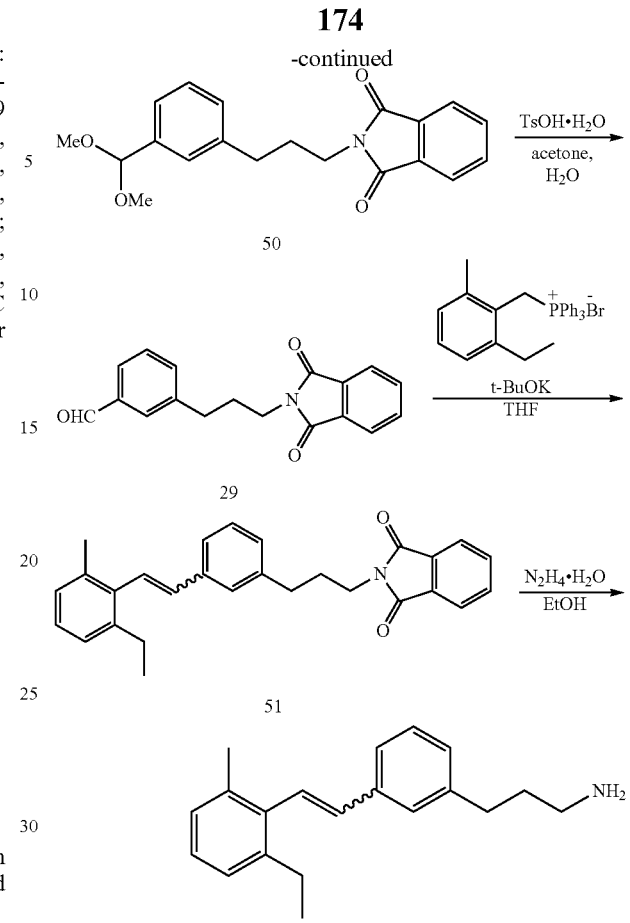

Step 1:

To a solution of 3-iodobenzaldehyde (8.92 g, 38.5 mmol) in anhydrous MeOH (40 mL) was added trimethyl orthoformate (7 mL, 64 mmol) and p-toluenesulfonic acid hydrate (0.36 g, 1.9 mmol). The mixture was stirred for 15 min, then partitioned between EtOAc and saturated aqueous NaHCO$_3$. The combined organics were washed with brine, dried over MgSO$_4$ and concentrated under reduced pressure to give iodide 47 as a white solid. Yield (10.7 g, 100%): $^1$H NMR (400 MHz, DMSO-d$_6$) δ 7.71-7.73 (m, 2H), 7.40 (d, J=8.0 Hz, 1H), 7.19-7.23 (m, 1H), 5.36 (s, 1H), 3.24 (s, 6H).

Step 2:

A mixture of NaHCO$_3$ (11.63 g, 138.4 mmol) and tetrabutylammonium bromide (13.1 g, 40.64 mmol) in degassed DMF (~95 mL, degassed by bubbling with argon for 20 min) was further degassed with argon for 5 min. Allyl alcohol (4.71 g, 81.1 mmol) and iodide 47 (10.29 g, 37.0 mmol) were added and the mixture purged twice (alternately put under vacuum and argon). Pd(OAc)$_2$ (0.5116 g, 2.28 mmol) was added and the mixture purged again. The reaction mixture was heated at 60° C. under argon for 5.5 h then cooled to room temperature. The mixture was concentrated under reduced pressure and the residue suspended in EtOAc and sonicated. The solids were removed by filtration and the filtrate partially concentrated under reduced pressure. The residue was washed with saturated aqueous NaHCO$_3$ and brine, treated with activated charcoal and MgSO$_4$ and concentrated under reduced pressure. Purification by flash chromatography (20% EtOAc-hexanes) gave aldehyde 48 as an oil. Yield (6.20 g, 80%): $^1$H NMR (400 MHz, DMSO-d$_6$) 3.9.71 (s, 1H), 7.29 (t, J=8.0 Hz, 1H), 7.19-7.24 (m, 3H), 5.34 (s, 1H), 3.23 (s, 6H), 2.88 (t, J=8.0 Hz, 2H), 2.75-2.79 (m, 2H).

Step 3:

To a solution of aldehyde 48 (6.20 g, 29.8 mmol) in EtOH (absolute, 50 mL) was added NaBH$_4$ (0.699 g, 18.5 mmol). The mixture was stirred for 15 min then partially concentrated under reduced pressure. The residue was partitioned between EtOAc and saturated aqueous NaHCO$_3$ and the combined organics were washed with water and brine. The solution was dried over MgSO$_4$ and concentrated under reduced pressure to give alcohol 49 as a colorless liquid. Yield (6.11 g, 98%).

Step 4:

To an ice cold solution of alcohol 49 (6.11 g, 29.06 mmol) in THF (100 mL) was added phthalimide (4.53 g, 30.8 mmol), and triphenylphosphine (9.606 g, 36.6 mmol). Diethyl azodicarboxylate (6.702 g, 38.5 mmol) was added and the mixture stirred for 10 min. After warming to room temperature, the reaction mixture was concentrated under reduced pressure. 10% EtOAc-hexanes was added and the mixture sonicated. The solids were removed by filtration, washed with 20% EtOAc-heptane, and the filtrate was concentrated under reduced pressure. Purification by flash chromatography (25-30% EtOAc-heptane) gave phthalimide 50 as a white waxy solid. Yield (9.77 g, 99%): $^1$H NMR (400 MHz, DMSO-d$_6$) δ 7.80-7.89 (m, 4H), 7.15-7.28 (m, 4H), 5.32 (s, 1H), 3.60 (t, J=8.0 Hz, 2H), 3.22 (s, 6H), 2.64 (t, J=8.0 Hz, 2H), 1.87-1.99 (m, 2H).

Step 5:

To a solution of phthalimide 50 (5.66 g, 16.67 mmol) in acetone-water (5:1, 50 mL) was added p-toluenesulfonic acid hydrate (0.2116 g, 1.11 mmol). The mixture was stirred for 3 h then concentrated under reduced pressure. The residue was partitioned between EtOAc and water and the combined organics were washed with brine, dried over MgSO$_4$ and concentrated under reduced pressure to give phthalimide 29 as a white solid. Yield (4.48 g, 92%). The NMR data was consistent with data reported above.

Step 6:

Preparation of 2-ethyl-6-methylbenzylphosphonium bromide: To a solution of 2-ethyl-6-methylbenzylbromide (0.432 g, 2.03 mmol) in toluene (10 mL) was added triphenylphosphine (0.6018 g, 2.29 mmol). The mixture was heated at 100° C. for 4 h. After cooling to room temperature, the precipitate was collected by filtration and washed with toluene to give 2-ethyl-6-methylbenzylphosphonium bromide as a solid. Yield (0.958 g, 99%). $^1$H NMR (400 MHz, DMSO-d$_6$) δ 7.90-7.92 (m, 3H), 7.69 (ddd, J=8.4, 8.4, 3.6 Hz, 6H), 7.49-7.55 (m, 6H), 7.20 (ddd, J=7.6, 7.6, 2.8 Hz, 1H), 7.02 (d, J=8.0 Hz, 1H), 6.94 (d, J=7.6 Hz, 1H), 4.91 (d, J=14.7 Hz, 2H), 2.05 (q, J=6.7 Hz, 2H), 1.75 (s, 3H), 0.78 (t, J=6.7 Hz, 3H).

To an ice cold solution of 2-ethyl-6-methylbenzylphosphonium bromide (0.9473 g, 1.99 mmol) and 18-crown-6 (0.0769 g, 0.29 mmol) in CH$_2$Cl$_2$ (10 mL) under argon was added potassium tert-butoxide (0.242 g, 2.16 mmol). The mixture was stirred at 0° C. for 2 h. An ice cold solution of phthalimide 29 (0.394 g, 0.34 mmol) in CH$_2$Cl$_2$ (10 mL) was added and the mixture was stirred at 0° C. for 45 min, then allowed to warm to room temperature and stirred for 1.5 h. The mixture was concentrated under reduced pressure then triturated with 10% EtOAc-heptane. Solids were removed by filtration and the filtrate concentrated under reduced pressure. Purification by flash chromatography (20 to 50% EtOAc-hexanes gradient) gave phthalimide 51 as an oil. Yield (0.505 g, 92%): $^1$H NMR (400 MHz, DMSO-d$_6$) δ 7.78-7.86 (m, 4H), 7.34 (s, 1H), 7.34 (d, J=7.6 Hz, 1H), 7.23 (t, J=8.0 Hz, 1H), 7.21 (d, J=16.8 Hz, 1H), 7.04-7.13 (m, 4H), 6.54 (d, J=16.8 Hz, 1H), 3.62 (t, J=6.8 Hz, 2H), 2.64 (t, J=7.4 Hz, 4H), 2.29 (s, 3H), 1.90-1.99 (m, 2H), 1.11 (t, J=6.8 Hz, 3H).

Step 7:

To a solution of phthalimide 51 (0.5049 g, 1.24 mmol) in EtOH (absolute, 10 mL) was added hydrazine hydrate (0.2 mL, 4.1 mmol). The mixture was stirred at room temperature for 1 h then heated to reflux for 2 h. After cooling to room temperature, the mixture was concentrated under reduced pressure. The residue was suspended in heptane and the solids removed by filtration. The filtrate was concentrated under reduced pressure to give Example 32 as a colorless oil. Yield (0.230 g, 66%), trans-/cis-isomer ratio 5:1. Trans-isomer: $^1$H NMR (400 MHz, DMSO-d$_6$) 67.38-7.39 (m, 2H), 7.26 (t, J=7.6 Hz, 1H), 7.21 (d, J=16.8 Hz, 1H), 7.03-7.12 (m, 4H), 6.56 (d, J=16.4 Hz, 1H), 2.60-2.68 (m, 4H), 2.54 (t, J=6.8 Hz, 2H), 2.29 (s, 3H), 1.60-1.68 (m, 2H), 1.11 (t, J=6.8 Hz, 3H).

Example 33

Preparation of (E/Z)-3-(3-(2,5-dimethylstyryl)phenyl)propan-1-amine

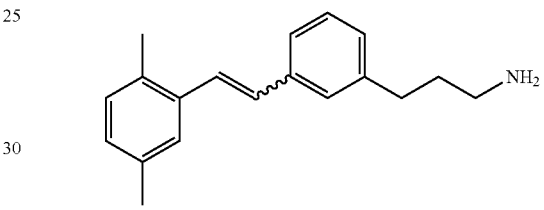

(E/Z)-3-(3-(2,5-Dimethylstyryl)phenyl)propan-1-amine was prepared following the method described in Example 32.

Step 1:

To a suspension of the crude 2,5-dimethylmethylbenzyltriphenylphosphonium bromide in THF (10 mL) and CH$_2$Cl$_2$ (5 mL) were added potassium tert-butoxide (0.163 g, 1.45 mmol) and 18-crown-6 (0.163 g, 1.45 mmol). The mixture was stirred at room temperature under argon for 30 min then sonicated for 1 min. A solution of phthalimide 29 (0.193 g, 0.658 mmol) in CH$_2$Cl$_2$ (2 mL) was added and the mixture stirred at room temperature for 2 h. The mixture was concentrated under reduced pressure and the residue partitioned between EtOAc and saturated aqueous NH$_4$Cl. The combined organics were washed with brine, dried over MgSO$_4$ and concentrated under reduced pressure. Purification by flash chromatography (20 to 50% EtOAc-hexanes) gave (E)-2-(3-(3-(2,5-dimethylstyryl)phenyl)propyl)isoindoline-1,3-dione as an oil. Yield (0.225 g, 86%), trans-/cis-isomer 1:1.5. Cis-isomer: $^1$H NMR (400 MHz, CDCl$_3$) δ 7.69-7.76 (m, 4H), 6.91-7.44 (m, 7H) 6.63 (d, J=12.0 Hz, 1H), 6.57 (d, J=12.0 Hz, 1H), 3.81 (t, J=7.2 Hz, 2H), 2.75 (t, J=7.6 Hz, 2H), 2.44 (s, 3H), 2.39 (s, 3H), 2.08-2.17 (m, 2H).

Step 2:

(E)-2-(3-(3-(2,5-dimethylstyryl)phenyl)propyl)isoindoline-1,3-dione was deprotected following the method used in Example 32 to afford Example 33 as an oil. Trans-/cis-isomer 2:1. Trans-isomer: $^1$H NMR (400 MHz, CD$_3$OD) δ 7.35-7.43

(m, 3H), 7.28 (t, J=8.0 Hz, 1H), 6.88-7.19 (m, 5H), 2.70 (t, J=8.0 Hz, 4H), 2.38 (s, 3H), 2.34 (s, 3H), 1.80-1.87 (m, 2H).

Example 34

Preparation of (E/Z)-3-(3-(2,4-dimethylstyryl)phenyl)propan-1-amine

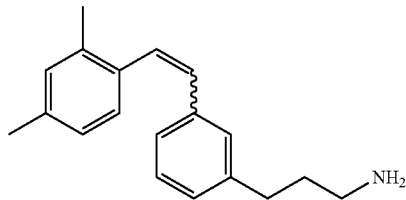 [SMILES: Cc1ccc(C=Cc2cccc(CCCN)c2)c(C)c1]

(E/Z)-3-(3-(2,4-Dimethylstyryl)phenyl)propan-1-amine was prepared following the method described in Example 32.
Step 1:
Phthalimide 29 was coupled with 2,4-dimethylmethylbenzyltriphenylphosphonium bromide and purified by flash chromatography (20 to 50% EtOAc-hexanes gradient) to give (E)-2-(3-(3-(2,4-dimethylstyryl)phenyl)propyl)isoindoline-1,3-dione as an oil. Yield (0.3974 g, 92%), trans-/cis-isomer ratio 1.2:1. Cis-isomer: $^1$H NMR (400 MHz, CDCl$_3$) δ 7.80-7.88 (m, 4H), 6.80-7.55 (m, 7H), 6.62 (d, J=12.0 Hz, 1H), 6.57 (d, J=12.0 Hz, 1H), 3.63 (t, J=7.2 Hz, 2H), 2.65 (t, J=7.2 Hz, 2H), 2.37 (s, 3H), 2.27 (s, 3H), 1.95 (quint, J=7.2 Hz, 2H).
Step 2:
(E)-2-(3-(3-(2,4-dimethylstyryl)phenyl)propyl)isoindoline-1,3-dione was deprotected following the method used in Example 32 to afford Example 34 as an oil. Yield (0.0422 g, 16%), trans-/cis-isomer ratio 1:2. cis-isomer: $^1$H NMR (400 MHz, DMSO-d$_6$) δ 6.93-7.11 (m, 5H), 6.88 (t, J=6.4, 21H), 6.63 (d, J=12.0 Hz, 1H), 6.59 (d, J=12.0 Hz, 1H), 2.43 (t, J=6.8 Hz, 4H), 2.25 (s, 3H), 2.17 (s, 3H), 1.47 (quint, J=6.8 Hz, 2H), 1.31 (br s, 2H).

Example 35

Preparation of (E)-3-(3-(2,4,6-trimethylstyryl)phenyl)propan-1-amine

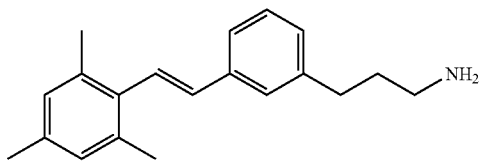 [SMILES: Cc1cc(C)c(/C=C/c2cccc(CCCN)c2)c(C)c1]

(E)-3-(3-(2,4,6-Trimethylstyryl)phenyl)propan-1-amine was prepared according to the method used in Example 32.
Step 1:
Phthalimide 29 was coupled with 2,4,6-trimethylbenzyltriphenylphosphonium bromide to give (E)-2-(3-(3-(2,4,6-trimethylstyryl)phenyl)propyl)isoindoline-1,3-dione. Yield (0.2485 g, 46%), trans-/cis-isomer ratio 4:1. Trans-isomer: $^1$H NMR (400 MHz, CDCl$_3$) δ 7.84-7.87 (m, 2H), 7.72-7.74 (m, 2H), 7.26-7.36 (m, 3H), 7.16 (s, 1H), 7.12 (d, J=16.4 Hz, 1H), 6.94 (s, 2H), 6.57 (d, J=16.8 Hz, 1H), 3.82 (t, J=7.2 Hz, 2H), 2.76 (t, J=7.2 Hz, 2H), 2.39 (s, 6H), 2.33 (s, 3H), 2.10-2.17 (m, 2H).

Step 2:
(E)-2-(3-(3-(2,4,6-Trimethylstyryl)phenyl)propyl)isoindoline-1,3-dione was deprotected to afford Example 35 as an oil. Yield (60%): $^1$H NMR (400 MHz, CD$_3$OD) δ 7.33-7.35 (m, 2H), 7.27 (t, J=7.2 Hz, 1H), 7.14 (d, J=16.4 Hz, 1H), 7.12 (d, J=7.2 Hz, 1H), 6.87 (s, 2H), 6.55 (d, J=16.8 Hz, 1H), 2.66-2.70 (m, 4H), 2.32 (s, 6H), 2.26 (s, 3H), 1.82 (quint, J=7.6 Hz, 21-1).

Example 36

Preparation of (E/Z)-3-(3-(2-ethylstyryl)phenyl)propan-1-amine

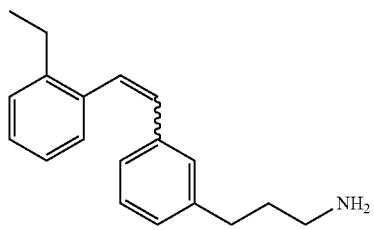

(E)-3-(3-(2-Ethylstyryl)phenyl)propan-1-amine was prepared according to the method used in Example 32.
Step 1:
Phthalimide 29 was coupled with 2-ethylbenzyltriphenylphosphonium bromide according to the method used in Example 32, except that the reaction was stirred at room temperature for 3.5 h. Purification by flash chromatography (20 to 50% EtOAc-hexanes gradient) gave (E/Z)-2-(3-(3-(2-ethylstyryl)phenyl)propyl)isoindoline-1,3-dione as an oil. Yield (0.4158 g, 83%), trans-/cis-isomer ratio 1:1. Cis-isomer: $^1$H NMR (400 MHz, DMSO-d$_6$) δ 7.80-7.91 (m, 4H), 6.83-7.47 (m, 8H), 6.73 (d, J=12.0 Hz, 1H), 6.60 (d, J=12.0 Hz, 1H), 3.49 (t, J=7.2 Hz, 2H), 2.79 (q, J=7.6 Hz, 2H), 2.43 (t, J=7.2 Hz, 2H), 1.71 (quint, J=7.2 Hz, 2H), 1.10 (t, J=7.6 Hz, 3H).
Step 2:
(E/Z)-2-(3-(3-(2-Ethylstyryl)phenyl)propyl)isoindoline-1,3-dione was deprotected to afford Example 36 as an oil. Yield (0.1263 g, 45%), trans-/cis-isomer ratio 1:3. Cis-isomer: $^1$H NMR (400 MHz, DMSO-d$_6$) δ 6.86-7.31 (m, 8H), 6.74 (d, J=12.0 Hz, 1H), 6.63 (d, J=12.4 Hz, 1H), 2.63 (t, J=7.2 Hz, 2H), 2.57-2.59 (m, 2H), 2.41 (t, J=7.2 Hz, 2H), 1.45 (quint, J=7.2 Hz, 2H), 1.12 (t, J=7.6 Hz, 3H).

Example 37

Preparation of (E/Z)-3-(3-(2-ethynylstyryl)phenyl)propan-1-amine

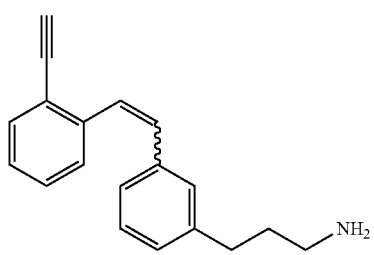 [SMILES: C#Cc1ccccc1C=Cc1cccc(CCCN)c1]

(E/Z)-3-(3-(2-Ethynylstyryl)phenyl)propan-1-amine was prepared according to the method used in Example 32.

Step 1:

2-Ethynylbenzyltriphenylphosphonium bromide was prepared from 2-ethynylbenzyl bromide to give a white solid. Yield (0.599 g, 60%): $^1$H NMR (400 MHz, DMSO-$d_6$) δ 7.71-7.98 (m, 19H), 5.18 (d, J=12.0 Hz, 2H), 4.20 (s, 1H).

Step 2:

Phthalimide 29 was coupled with 2-ethynyllbenzyltriphenylphosphonium bromide and purified by flash chromatography (10 to 50% EtOAc-hexanes gradient) to give (E)-2-(3-(3-(2-ethynylstyryl)phenyl)propyl)isoindoline-1,3-dione. Yield (0.3055 g, 78%), trans-/cis-isomer ratio 1.3:1. Cis-isomer: $^1$H NMR (400 MHz, DMSO-$d_6$) δ 7.80-7.87 (m, 4H), 7.40-7.54 (m, 1H), 7.35 (t, J=7.6 Hz, 1H), 7.29 (dt, J=7.6, 2.4 Hz, 2H), 6.99-7.21 (m, 3H), 6.92 (d, J=7.6 Hz, 1H), 6.75 (d, J=12.0 Hz, 1H), 6.69 (d, J=12.0 Hz, 1H), 4.41 (s, 1H), 3.52 (t, J=7.2 Hz, 2H), 2.47-2.51 (m, 21-1), 1.76 (quint, J=7.6 Hz, 2H).

Step 3:

(E)-2-(3-(3-(2-ethynylstyryl)phenyl)propyl)isoindoline-1,3-dione was deprotected to afford Example 37 as an oil. Yield (0.0417 g, 20%), trans-/cis-isomer ratio 1:2. Cis-isomer: $^1$H NMR (400 MHz, MeOD) δ 7.02-7.53 (m, 8H), 6.84 (d, J=12.0 Hz, 1H), 6.71 (d, J=12.0 Hz, 1H), 3.76 (s, 1H), 2.86 (t, J=8.0 Hz, 2H), 2.59 (t, J=8.0 Hz, 2H), 1.87 (quint, J=8.0, 2H).

Example 38

Preparation of (E/Z)-3-(3-(3,4-dimethylstyryl)phenyl)propan-1-amine

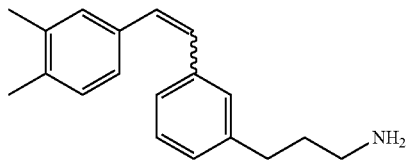 [SMILES: Cc1ccc(C=Cc2cccc(CCCN)c2)cc1C]

(E/Z)-3-(3-(3,4-Dimethylstyryl)phenyl)propan-1-amine was prepared according to the method used in Example 32.

Step 1:

3,4-Dimethylbenzyltriphenylphosphonium bromide was coupled with phthalimide 29 to give (E/Z)-2-(3-(3-(3,4-dimethylstyryl)phenyl)propyl)isoindoline-1,3-dione as an oil. Yield (0.2311 g, 42%), trans-/cis-isomer ratio=1:1. Cis-isomer: $^1$H NMR (400 MHz, CDCl$_3$) δ 7.69-7.76 (m, 4H), 6.96-7.35 (m, 7H), 6.54 (d, J=12.8 Hz, 1H), 6.50 (d, J=12.4 Hz, 1H), 3.80 (t, J=7.6 Hz, 2H), 2.74 (t, J=7.6 Hz, 2H), 2.32 (s, 3H), 2.30 (s, 3H), 2.11 (quint, J=7.6 Hz, 2H).

Step 2:

(E/Z)-2-(3-(3-(3,4-Dimethylstyryl)phenyl)propyl)isoindoline-1,3-dione was deprotected to give Example 38 as an oil. Trans-/cis-isomer ratio 1:1.7. Cis-isomer: $^1$H NMR (400 MHz, DMSO-$d_6$) δ 7.32-7.39 (m, 3H), 7.26 (t, J=8.0 Hz, 1H), 6.85-7.22 (m, 5H), 2.78-2.86 (m, 2H), 2.69 (t, J=7.6 Hz, 2H), 2.30 (s, 3H), 2.27 (s, 3H), 1.85 (quint, J=7.6 Hz, 2H).

Example 39

Preparation of (E/Z)-3-(3-(2-isopropylstyryl)phenyl)propan-1-amine

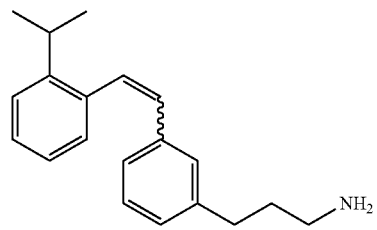

(E/Z)-3-(3-(2-Isopropylstyryl)phenyl)propan-1-amine was prepared according to the method used in Example 32.

Step 1:

2-Isopropyllbenzyltriphenylphosphonium bromide was prepared from 2-isopropylbenzyl bromide according to the method used in Example 32, except that the reaction was heated for 2 h. The product was isolated as a white solid. Yield (1.05 g, 82%): $^1$H NMR (400 MHz, DMSO-$d_6$) δ 7.71-7.72 (m, 3H), 7.60-7.62 (m, 6H), 7.57-7.60 (m, 6H), 7.24-7.29 (m, 2H), 6.99 (t, J=7.0 Hz, 1H), 6.87 (dq, J=7.6, 1.2 Hz, 1H), 5.01 (d, J=5.1 Hz, 2H), 2.55-2.62 (m, 1H), 0.73 (d, J=6.8 Hz, 6H).

Step 2:

Phthalimide 29 was coupled with 2-isopropyllbenzyltriphenylphosphonium bromide according to the method used in Example 32, except that the reaction was not warmed to room temperature. Purification by flash chromatography (10 to 50% EtOAc-hexanes gradient) gave (E)-2-(3-(3-(2-isopropylstyryl)phenyl)propyl)isoindoline-1,3-dione as an oil. Yield (0.4283 g, 73%), trans-/cis-isomer ratio ~1:1. Trans-isomer: $^1$H NMR (400 MHz, DMSO-$d_6$) δ 7.78-7.84 (m, 4H), 7.56 (d, J=8.0 Hz, 1H), 7.51 (d, J=16.0 Hz, 1H), 7.46 (s, 1H), 6.80-7.30 (m, 7H), 3.47 (t, J=6.8 Hz, 2H), 3.08-3.14 (m, 1H), 2.39 (t, J=6.8 Hz, 2H), 1.61-1.68 (m, 2H), 1.09 (d, J=6.8 Hz, 6H).

Step 3:

(E)-2-(3-(3-(2-Isopropylstyryl)phenyl)propyl)isoindoline-1,3-dione was deprotected according to the method used in Example 32 except that the reaction was heated to reflux for 1.3 h. Example 39 was isolated as an oil. Yield (0.1838 g, 63%), trans-/cis-isomer ratio 1:3. Cis-isomer: $^1$H NMR (400 MHz, DMSO-$d_6$) δ 7.18-7.34 (m, 2H), 7.01-7.10 (m, 2H), 6.92-6.98 (m, 2H), 6.81-6.84 (m, 2H), 6.77 (d, J=12.0 Hz, 1H), 6.61 (d, J=12.0 Hz, 1H), 3.08-3.15 (m, 1H), 2.32-2.48 (m, 4H), 1.36-1.42 (m, 2H), 1.24 (br s, 2H), 1.12 (d, J=6.8 Hz, 6H).

Example 40

Preparation of (E/Z)-4-(3-(3,5-dimethylstyryl)phenyl)propan-1-amine

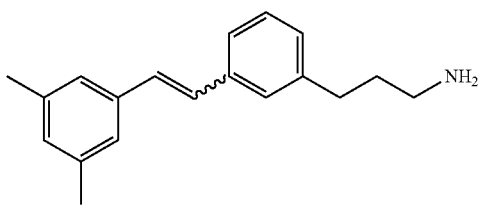 [SMILES: Cc1cc(C)cc(C=Cc2cccc(CCCN)c2)c1]

(E/Z)-4-(3-(3,5-Dimethylstyryl)phenyl)propan-1-amine was prepared according to the method used in Example 32.

Step 1:

3,5-Dimethylbenzyltriphenylphosphonium bromide was coupled with phthalimide 29. Purification by flash chromatography (10 to 50% EtOAc-hexanes gradient) gave (E)-2-(3-(3-(3,5-dimethylstyryl)phenyl)propyl)isoindoline-1,3-dione as a white solid. Yield (0.3263 g, 55%): $^1$H NMR (400 MHz, DMSO-$d_6$) δ 7.81-7.88 (m, 4H), 7.00-7.44 (m, 6H), 6.71-6.90 (m, 2H), 6.53 (s, 1H), 3.64 (t, J=7.2 Hz, 2H), 2.65 (t, J=7.2 Hz, 2H), 1.70-1.77 (m, 2H), 2.29 (s, 6H).

Step 2:

(E)-2-(3-(3-(3,5-Dimethylstyryl)phenyl)propyl)isoindoline-1,3-dione was deprotected to give Example 40 as an oil. Yield (0.1632 g, 82%), trans-/cis-isomer ratio 1:1.3. Cis-isomer: $^1$H NMR (400 MHz, DMSO-$d_6$) δ 7.02-7.40 (m, 5H), 6.82-6.89 (m, 2H), 6.54 (d, J=12.4 Hz, 1H), 6.50 (d, J=12.4 Hz, 1H), 2.54 (t, J=6.8 Hz, 2H), 2.43-2.46 (m, 2H), 2.14 (s, 6H), 1.46-1.54 (m, 2H), 1.30 (br s, 2H).

Example 41

Preparation of (E/Z)-4-(3-(2-methyloxystyryl)phenyl)propan-1-amine

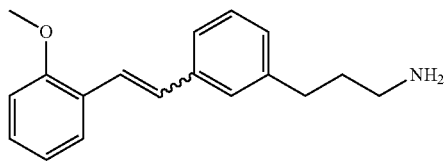 [SMILES: COc1ccccc1C=Cc1cccc(CCCN)c1]

(E/Z)-4-(3-(2-Methoxystyryl)phenyl)propan-1-amine was prepared according to the method used in Example 32.

Step 1:

2-Methoxybenzyltriphenylphosphonium bromide was coupled with phthalimide 29 to give (E)-2-(3-(3-(2-methoxystyryl)phenyl)propyl)isoindoline-1,3-dione as a white solid. Yield (0.5590 g, quant.), trans-/cis-isomer ratio 1:1. Trans-isomer: $^1$H NMR (400 MHz, DMSO-$d_6$) δ 7.81-7.88 (m, 4H), 7.52-7.65 (m, 5H), 6.69-7.41 (m, 4H), 6.57 (d, J=16.8 Hz, 1H), 3.76 (s, 3H), 3.52 (t, J=6.8 Hz, 2H), 2.48 (t, J=8.0 Hz, 2H), 1.91-1.99 (m, 2H).

Step 2:

(E)-2-(3-(3-(2-methoxystyryl)phenyl)propyl)isoindoline-1,3-dione was deprotected to give Example 41 as an oil. Yield (0.260 g, 73%), trans-/cis-isomer ratio 1:1. Trans-isomer: $^1$H NMR (400 MHz, DMSO-$d_6$) δ 6.90-7.65 (m, 9H), 6.57 (d, J=16.8 Hz, 1H), 3.78 (s, 3H), 2.52 (t, J=6.8 Hz, 2H), 2.41-2.46 (m, 2H), 1.22-1.26 (m, 2H), 1.14 (br s, 2H).

Example 42

Preparation of (E)-2-(3-(3-(2-(2,6,6-trimethylcyclohex-1-enyl)vinyl)phenyl)propylamino)ethanol

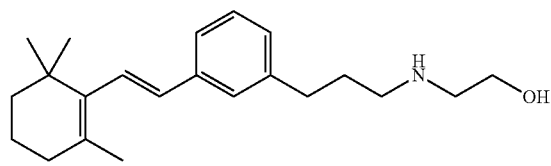 [SMILES: CC1=C(/C=C/c2cccc(CCCNCCO)c2)C(C)(C)CCC1]

(E)-2-(3-(3-(2-(2,6,6-Trimethylcyclohex-1-enyl)vinyl)phenyl)propylamino)ethanol was prepared according to Scheme 16.

SCHEME 16

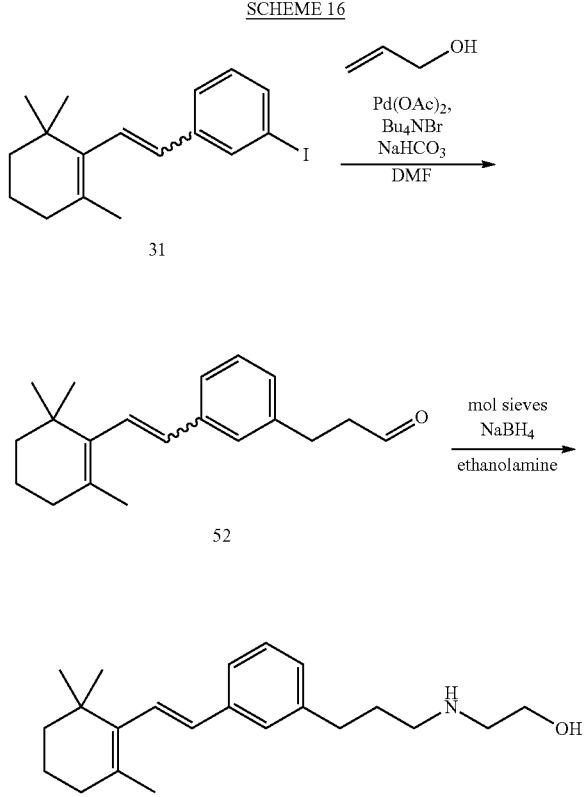

Step 1:

Iodide 31 was reacted with allyl alcohol following the method used in Example 32. Following the reaction, the mixture was partitioned between EtOAc and water. The combined organics were washed with water and brine, dried over $Na_2SO_4$ and concentrated under reduced pressure. Purification by flash chromatography (0 to 20% EtOAc-hexanes gradient) gave aldehyde 52 as a yellow oil. Yield (0.375 g, 63%).

Step 2:

To a solution of aldehyde 52 (0.325 g, 1.15 mmol) in MeOH (2 mL) was added ethanolamine (0.08 g, 1.4 mmol) and 4 Å molecular sieves. The mixture was stirred for 2 h, then $NaBH_4$ (0.068 g, 1.8 mmol) was added and the reaction was stirred overnight. Solids were removed by filtration and the filtrate was concentrated under reduced pressure. The residue was partitioned between EtOAc and water then the combined organics were washed with brine, dried over $Na_2SO_4$ and concentrated under reduced pressure. Purification was conducted by flash chromatography (0-10% 7 M $NH_3$-MeOH in EtOAc) three times. HPLC purification (30 to 90% MeCN—$H_2O$ gradient) gave Example 42 as an oil. Yield (0.033 g, 9%), trans-/cis-isomer ratio 9:1. Trans-isomer: $^1$H NMR (400 MHz, CDCl$_3$) δ 7.21-7.26 (m, 3H), 7.03-7.05 (m, 1H), 6.66 (d, J=16.4 Hz, 1H), 6.31 (d, J=16.4 Hz, 1H), 3.56 (t, J=5.1 Hz, 2H), 2.69 (t, J=5.2 Hz, 2H), 2.57-2.62 (m, 4H), 2.55 (br s, 2H), 1.96 (t, J=6.1 Hz, 2H), 1.72-1.80 (m, 2H), 1.76 (s, 3H), 1.54-1.60 (m, 2H), 1.40-1.47 (m, 2H), 1.06 (s, 6H).

Example 43

Preparation of (E)-3-(3-(2,6-dichlorostyryl)phenyl)propan-1-amine

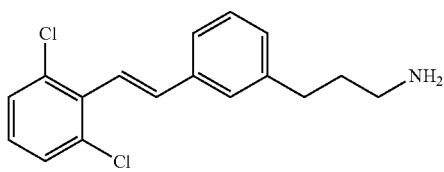 [SMILES: NCCCc1cccc(/C=C/c2c(Cl)cccc2Cl)c1]

(E)-3-(3-(2,6-Dichlorostyryl)phenyl)propan-1-amine was prepared according to the method used in Example 32.

Step 1:

2,6-Dichlorobenzyltriphenylphosphonium bromide was coupled with phthalimide 29. Purification by flash chromatography (10 to 50% EtOAc-hexanes gradient) gave (E)-2-(3-(3-(2,6-dichlorostyryl)phenyl)propyl)isoindoline-1,3-dione as a white solid. Yield (0.7041 g, 96%): $^1$H NMR (400 MHz, DMSO-d$_6$) δ 7.78-7.86 (m, 4H), 7.51 (d, J=8.4 Hz, 2H), 7.44 (s, 1H), 7.37 (d, J=7.6 Hz, 1H), 7.31 (d, J=8.4 Hz, 1H), 7.27 (t, J=7.2 Hz, 1H), 7.18 (d, J=7.6 Hz, 1H), 7.11 (d, J=16.4 Hz, 1H), 7.01 (d, J=16.8 Hz, 1H), 3.62 (t, J=6.8 Hz, 2H), 2.65 (t, J=7.4 Hz, 2H), 1.88-1.98 (m, 2H).

Step 2:

(E)-2-(3-(3-(2,6-dichlorostyryl)phenyl)propyl)isoindoline-1,3-dione was deprotected and purified by flash chromatography (1:5:5 7 M NH$_3$-MeOH:EtOAc:heptane) to give Example 43 as an oil. Yield (0.1123 g, 23%): $^1$H NMR (400 MHz, DMSO-d$_6$) δ 7.51 (d, J=8.2 Hz, 2H), 7.40-7.42 (m, 2H), 7.27-7.33 (m, 2H), 7.16 (d, J=7.2 Hz, 1H), 7.12 (d, J=16.8 Hz, 1H), 7.03 (d, J=16.6 Hz, 1H), 2.61 (t, J=7.8 Hz, 2H), 2.53 (t, J=7.9 Hz, 2H), 1.61-1.72 (m, 2H), 1.40 (br s, 2H).

Example 44

Preparation of (E/Z)-3-(3-(2,3-dimethylstyryl)phenyl)propan-1-amine

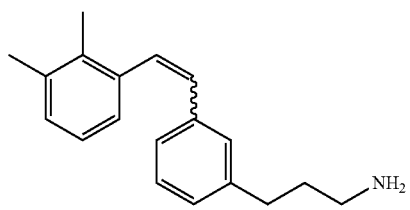 [SMILES: Cc1cccc(C=Cc2cccc(CCCN)c2)c1C]

(E/Z)-3-(3-(2,3-Dimethylstyryl)phenyl)propan-1-amine was prepared according to the method used in Example 32.

Step 1:

To an ice cold solution of 2,3-dimethylbenzyltriphenylphosphonium bromide (1.1197 g, 2.43 mmol) in CH$_2$Cl$_2$ (10 mL) was added a solution of potassium tert-butoxide (2.5 mL of a 1 M solution in THF, 2.5 mmol). The mixture was stirred for 5 min, then a solution of phthalimide 29 (0.3380 g, 1.15 mmol) in CH$_2$Cl$_2$ (10 mL) was added. The mixture was warmed to room temperature, stirred for 20 min then concentrated under reduced pressure. 10% EtOAc-heptane was added and the solids were removed by filtration. The filtrate was concentrated under reduced pressure. Purification by repeated flash chromatography (6 to 40% EtOAc-hexanes gradient then 10% EtOAc-hexanes) gave (Z)-2-(3-(3-(2,3-dimethylstyryl)phenyl)propyl)isoindoline-1,3-dione as an oil. Yield (0.1871 g, 41%), trans-/cis-isomer ratio 1:11.7. Cis-isomer: $^1$H NMR (400 MHz, CDCl$_3$) δ 7.85 (dd, J=5.6, 2.8 Hz, 2H), 7.72 (dd, J=5.2, 3.2 Hz, 2H), 7.04 (t, J=7.6 Hz, 1H), 6.88-6.98 (m, 6H), 6.68 (d, J=12.0 Hz, 1H), 6.56 (d, J=12.0 Hz, 1H), 3.64 (t, J=7.2 Hz, 2H), 2.52 (t, J=7.6 Hz, 2H), 2.52 (s, 3H), 2.17 (s, 3H), 1.80-1.88 (m, 2H).

Step 2:

(Z)-2-(3-(3-(2,3-Dimethylstyryl)phenyl)propyl)isoindoline-1,3-dione was deprotected and purified according to the method used in Example 32 to give Example 43 as an oil. Yield (0.0662 g, 54%), trans-/cis-isomer ratio 1:4. Cis-isomer: $^1$H NMR (400 MHz, DMSO-d$_6$) δ 6.82-7.07 (m, 7H), 6.68 (d, J=12.0 Hz, 1H), 6.59 (d, J=12.0 Hz, 1H), 2.41 (t, J=7.6 Hz, 4H), 2.25 (s, 3H), 2.14 (s, 3H), 1.40-1.46 (m, 2H), 1.32 (br s, 2H).

Example 45

Preparation of (E/Z)-3-(3-(2,6-dimethylstyryl)phenyl)prop-2-en-1-amine

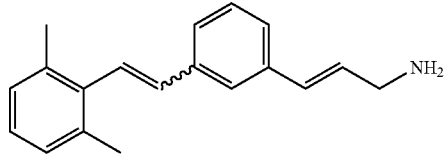 [SMILES: Cc1cccc(C)c1C=Cc1cccc(/C=C/CN)c1]

(E/Z)-3-(3-(2,6-Dimethylstyryl)phenyl)prop-2-en-1-amine (isomer ratio 80:20 trans:cis) was prepared according to Scheme 17.

SCHEME 17

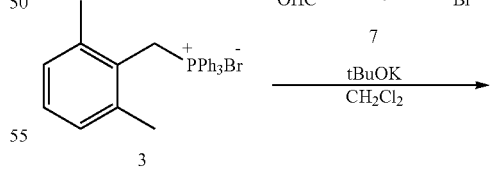

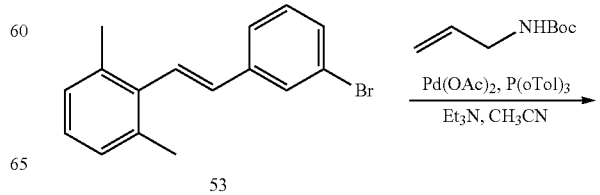

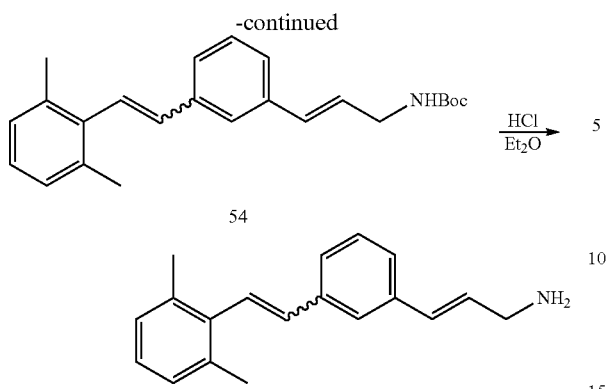

Step 1:

To a solution of 2,6-dimethylbenzylphosphonium bromide (3.46 g, 7.5 mmol) in CH$_2$Cl$_2$ (20 mL) was added a solution of potassium tert-butoxide (7.5 mL of a 1 M solution in THF, 7.5 mmol). The mixture was stirred at room temperature for 10 min, then 3-bromobenzaldehyde (0.925 g, 5 mmol) was added and the mixture stirred for 4 h. The reaction mixture was concentrated under reduced pressure and partitioned between EtOAc and water then solids were removed by filtration. The combined organics were washed with brine, dried over MgSO$_4$ and concentrated under reduced pressure. Purification by flash chromatography (7 to 60% EtOAc-hexanes gradient) gave aryl bromide 53 as a colorless oil. Yield (0.930 g, 65%), trans-/cis-isomer ratio 10:1.

trans-isomer: NMR (400 MHz, DMSO-d$_6$) δ 7.81 (t, J=1.6 Hz, 1H), 7.59-7.61 (m, 1H), 7.44-7.46 (m, 1H), 7.27-7.34 (m, 2H), 7.04-7.14 (m, 3H), 6.64 (d, J=16.8 Hz, 1H), 2.30 (s, 6H).

Step 2:

To a solution of aryl bromide 53 (0.343 g, 1.2 mmol) and tert-butyl allylcarbamate (0.189 g, 1.2 mmol) in triethylamine (0.33 mL, 2.4 mmol) and acetonitrile (5 mL) was added Pd(OAc)$_2$ (0.014 g, 0.06 mmol) and tri-o-tolylphosphine (0.018 g, 0.06 mmol). The mixture was bubbled with argon then heated to 70° C. for 6 h. After cooling to room temperature, the mixture was concentrated under reduced pressure and partitioned between EtOAc and water. The combined organics were washed with brine, treated with activated charcoal and dried over a mixture of MgSO$_4$ and Na$_2$SO$_4$. After concentration under reduced pressure, purification by flash chromatography (2 to 20% EtOAc-hexanes gradient) gave impure allyl amine 54 as an oil. Yield (0.059 g, contaminated with 50% tert-butyl allylcarbamate; 10% yield): $^1$H NMR (400 MHz, DMSO-d$_6$) δ 7.45 (d, J=6.4 Hz, 1H), 7.28-7.34 (m, 2H), 7.24 (d, J=6.4 Hz, 1H), 7.03-7.10 (m, 5H), 6.64 (d, J=16.8 Hz, 1H), 6.46 (d, J=16.0 Hz, 1H), 6.27 (dt, J=15.6, 5.6 Hz, 1H), 3.72 (t, J=5.6 Hz, 2H), 2.31 (s, 6H), 1.36 (s, 9H).

Step 3:

To a solution of allyl amine 54 (0.059 g, impure; 0.11 mmol) in diethyl ether (2 mL) was added a solution of HCl-diethyl ether (3 mL of 10 M solution, 30 mmol). The mixture was stirred at room temperature for 1 h then concentrated under reduced pressure. To the residue was added 7 M NH$_3$-MeOH (5 mL) and the solution was concentrated under reduced pressure. Purification by flash chromatography (15% 7 M NH$_3$ in MeOH-EtOAc) gave Example 45 (80% all-trans) as a colorless oil. Yield (0.0202 g, 70%). Trans-isomer: $^1$H NMR (400 MHz, DMSO-d$_6$) δ 7.59 (br s, 1H), 7.41-7.45 (m, 1H), 7.29-7.31 (m, 2H), 7.23 (d, J=16.9 Hz, 1H), 7.01-7.15 (m, 3H), 6.64 (d, J=16.8 Hz, 1H), 6.49-6.53 (m, 1H), 6.43 (t, J=4.8 Hz, 1H), 3.32 (dd, J=5.2, 1.2 Hz, 2H), 2.31 (s, 6H).

Example 46

Preparation of (E)-3-(3-(2,6-dimethylstyryl)-4-fluorophenyl)propan-1-amine

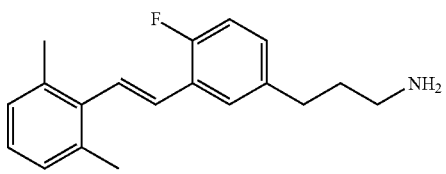 [SMILES: Cc1cccc(C)c1/C=C/c1cc(CCCN)ccc1F]

(E)-3-(3-(2,6-Dimethylstyryl)-4-fluorophenyl)propan-1-amine was prepared according to the method used in Example 1 with modifications by replacing 3-iodobenzaldehyde with 6-fluoro-3-iodobenzaldehyde in Step 3.

Step 1:

To a solution of 2,6-dimethylbenzyltriphenylphosphonium bromide (2.21 g, 4.8 mmol) in CH$_2$Cl$_2$ (30 mL) was added a solution of potassium tert-butoxide (5 mL of a 1 M solution in THF, 5 mmol) and the mixture was stirred at 0° C. for 15 min. The mixture was cooled to −78° C. and 6-fluoro-3-iodobenzaldehyde (1.0 g, 4.0 mmol) was added. The reaction mixture was allowed to warm to room temperature and stirred overnight. The mixture was partitioned between EtOAc and water and the combined organics were washed with 1 M HCl and brine, dried over Na$_2$SO$_4$ and concentrated under reduced pressure. Purification by flash chromatography (100% hexanes) gave (E)-2-(2-fluoro-5-iodostyryl)-1,3-dimethylbenzene (0.280 g) and (Z)-2-(2-fluoro-5-iodostyryl)-1,3-dimethylbenzene (0.472 g) with additional product collected as an E/Z mixture (0.450 g). Total yield (1.20 g, 85%). Trans-isomer: $^1$H NMR (400 MHz, DMSO-d$_6$) δ 8.12 (dd, J=7.2, 2.4 Hz, 1H), 7.63 (dq, J=8.8, 2.4 Hz, 1H), 7.34 (d, J=16.8 Hz, 1H), 7.04-7.09 (m, 4H), 6.61 (d, J=16.8 Hz, 1H), 2.30 (s, 6H).

Step 2:

(E)-2-(2-Fluoro-5-iodostyryl)-1,3-dimethylbenzene was coupled with allyl alcohol according to the method in Example 42. Purification by flash chromatography (40% CH$_2$Cl$_2$-hexanes) gave (E)-3-(3-(2,6-dimethylstyryl)-4-fluorophenyl)propanal as an oil. Yield (0.115 g, 52%): $^1$H NMR (400 MHz, DMSO-d$_6$) δ 9.72 (t, J=1.2 Hz, 1H), 7.64 (dd, J=7.2, 2.4 Hz, 1H), 7.27 (d, J=16.8 Hz, 1H), 7.09-7.19 (m, 2H), 7.06 (s, 3H), 6.67 (d, J=16.8 Hz, 1H), 2.78-2.89 (m, 4H), 2.31 (s, 6H).

Step 3:

To a solution of (E)-3-(3-(2,6-dimethylstyryl)-4-fluorophenyl)propanal (0.110 g, 0.39 mmol) in anhydrous MeOH (5 mL) was added a solution of NH$_3$-MeOH (10 mL of a 7 M solution). The reaction mixture was stored at −5° C. overnight, then warmed to room temperature. NaBH$_4$ (0.148 g, 3.9 mmol) was added and the mixture was stirred at room temperature for 2 h. After concentration under reduced pressure, the residue was partitioned between saturated aqueous NaHCO$_3$ and EtOAc. The combined organics were dried over Na$_2$SO$_4$ and concentrated under reduced pressure. Purification by flash chromatography (5 to 10% 7 M NH$_3$-MeOH in CH$_2$Cl$_2$) gave Example 46 as an oil. (Yield 0.022 g, 20%): $^1$H NMR (400 MHz, CDCl$_3$) δ 7.40 (dd, J=7.2, 2.4 Hz, 1H), 7.17 (d, J=16.8 Hz, 1H), 7.04-7.10 (m, 4H), 6.99 (dd, J=10.4, 8.4

Hz, 1H), 6.74 (d, J=16.8 Hz, 1H), 2.78 (t, J=7.2 Hz, 2H), 2.68 (t, J=8.0 Hz, 2H), 2.39 (s, 6H), 1.77-1.85 (m, 2H).

Example 47

Preparation of (E/Z)-3-(3-(2-(trifluoromethyl)styryl)phenyl)propan-1-amine

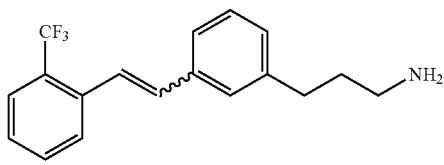 [SMILES: NCCCc1cccc(C=Cc2ccccc2C(F)(F)F)c1]

(E/Z)-3-(3-(2-(Trifluoromethyl)styryl)phenyl)propan-1-amine was prepared according to the method used in Example 32.
Step 1:
2-Trifluoromethylbenzyltriphenylphosphonium bromide was coupled with phthalimide 29 following the method used in Example 44 except that the reaction was conducted at −78° C. instead of 0° C. before warming to room temperature. Purification by flash chromatography (10 to 40% EtOAc-hexanes gradient) gave (E)-2-(3-(3-(2-trifluoromethylstyryl)phenyl)propyl)isoindoline-1,3-dione (0.0797 g, trans-/cis-isomer ratio 15.6:1) as an oil and (Z)-2-(3-(3-(2-trifluoromethylstyryl)phenyl)propyl)isoindoline-1,3-dione (0.1139 g, trans-/cis-isomer ratio 8.1:1) as an oil. Yield (0.1936 g total, 83%): Trans-isomer: $^1$H NMR (400 MHz, CDCl$_3$) δ 7.69-7.73 (m, 2H), 7.68 (d, J=7.6 Hz, 1H), 7.56-7.63 (m, 3H), 7.45 (t, J=7.6 Hz, 1H), 7.34 (dq, J=16.0, 2.0 Hz, 1H), 7.21-7.28 (m, 3H), 7.14-7.19 (m, 1H), 7.05 (d, J=7.6 Hz, 1H), 6.93 (d, J=16.4 Hz, 1H), 3.69 (t, J=7.2 Hz, 2H), 2.64 (t, J=7.2 Hz, 2H), 1.95-2.04 (m, 2H).
Step 2:
(E)-2-(3-(3-(2-Trifluorostyryl)phenyl)propyl)isoindoline-1,3-dione was deprotected according to the method used in Example 32, except that the reaction was heated at 60° C. overnight. Purification by flash chromatography (10% 7 M NH$_3$ in MeOH-EtOAc) gave Example 47 as an oil. Yield (0.0180 g, 32%), trans-/cis-isomer ratio 5.2:1. Trans-isomer: $^1$H NMR (400 MHz, CDCl$_3$) δ 7.77 (d, J=8.0 Hz, 1H), 7.65 (t, J=8.0 Hz, 1H), 7.54 (t, J=7.6 Hz, 1H), 7.46 (dq, J=16.4, 1.2 Hz, 1H), 7.26-7.38 (m, 4H), 7.14 (d, J=7.2 Hz, 1H), 7.06 (d, J=16.4 Hz, 1H), 2.68-2.78 (m, 4H), 1.72-1.84 (m, 2H), 1.20 (br s, 2H).

Example 48

Preparation of (E)-3-(3-(2,6-dimethyloxystyryl)phenyl)propan-1-amine

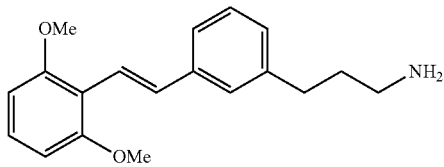 [SMILES: COc1cccc(OC)c1/C=C/c1cccc(CCCN)c1]

(E)-3-(3-(2,6-dimethoxystyryl)phenyl)propan-1-amine was prepared according to the method used in Example 32.
Step 1:
2,6-Dimethoxybenzyltriphenylphosphonium bromide was coupled with phthalimide 29 following the method used in Example 44, except that the reaction was stirred overnight after warming up to room temperature. After concentration under reduced pressure, the residue was partitioned between EtOAc and water. The combined organics were washed with brine, dried over MgSO$_4$ and concentrated under reduced pressure. Purification by flash chromatography (7 to 60% EtOAc-hexanes gradient) gave (E)-2-(3-(3-(2,6-dimethoxystyryl)phenyl)propyl)isoindoline-1,3-dione as a light yellow oil. Yield (0.317 g, 82%): NMR (400 MHz, DMSO-d$_6$) δ 7.79-7.84 (m, 4H), 7.42 (d, J=17.2 Hz, 1H), 7.17-7.32 (m, 5H), 7.06-7.09 (m, 1H), 6.58 (d, J=8.4 Hz, 2H), 3.83 (s, 6H), 3.61 (t, J=7.2 Hz, 2H), 2.63 (t, J=8.0 Hz, 2H), 1.88-1.96 (m, 2H).
Step 2:
(E)-2-(3-(3-(2,6-dimethoxystyryl)phenyl)propyl)isoindoline-1,3-dione was deprotected according to the method used in Example 32 except that the reaction was conducted overnight at room temperature in MeOH. After concentration under reduced pressure, the residue was suspended in EtOAc and sonicated then solids were removed by filtration. The filtrate was concentrated under reduced pressure. Purification by flash chromatography (0.3% concentrated aqueous NH$_4$OH/10% 7 M NH$_3$-MeOH/90% EtOAc) gave Example 48 as a colorless oil. Yield (0.179 g, 83%): $^1$H NMR (400 MHz, DMSO-d$_6$) δ 7.44 (d, J=16.8 Hz, 1H), 7.31 (d, J=16.8 Hz, 1H), 7.27 (s, 2H), 7.25 (d, J=7.6 Hz, 1H), 7.19 (t, J=8.4 Hz, 1H), 7.05 (d, J=7.2 Hz, 1H), 6.68 (d, J=8.4 Hz, 2H), 3.83 (s, 6H), 2.59 (t, J=7.2 Hz, 2H), 2.53 (t, J=8.0 Hz, 2H), 1.60-1.67 (m, 2H), 1.35 (br s, 2H).

Example 49

Preparation of (E)-3-(3-(2,6-bis(trifluoromethyl)styryl)phenyl)propan-1-amine

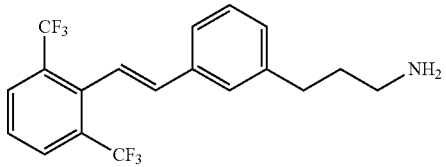 [SMILES: NCCCc1cccc(/C=C/c2c(C(F)(F)F)cccc2C(F)(F)F)c1]

(E)-3-(3-(2,6-Bis(trifluoromethyl)styryl)phenyl)propan-1-amine was prepared according to the method used in Example 32.
Step 1:
To a solution of 2,6-bis(trifluoromethyl)benzyl bromide (0.400 g, 1.30 mmol) in toluene (5 mL) was added triphenylphosphine (0.375 g, 1.43 mmol). The mixture was heated to reflux for 24 h. After cooling to room temperature, hexanes (10 mL) was added and the mixture was stirred for 1 h. The solid was collected by filtration and rinsed with hexanes to give 2,6-bis(trifluoromethyl)benzyltriphenylphosphonium bromide as a white solid. Yield (0.446 g, 60%): $^1$H NMR (400 MHz, DMSO-d$_6$) δ 8.02 (d, J=8.0 Hz, 2H), 7.57-7.87 (m, 16H), 5.17 (d, J=15.2 Hz, 2H).
Step 2:
2,6-Bis(trifluoromethyl)benzyltriphenylphosphonium bromide was coupled with phthalimide 29 following the method used in Example 46. Purification by flash chromatography (30% diethyl ether-hexanes) gave (E)-2-(3-(3-(2,6-bis (trifluoromethyl)styryl)phenyl)propyl)isoindoline-1,3-dione as an oil. Yield (0.227 g, 62%): $^1$H NMR (400 MHz, DMSO-$d_6$) δ 8.09 (d, J=8.0 Hz, 2H), 7.78-7.84 (m, 4H), 7.75 (t, J=7.6 Hz, 1H), 7.28-7.38 (m, 3H), 7.27 (t, J=7.6 Hz, 1H), 7.19 (d, J=7.2 Hz, 1H), 6.57 (d, J=16.8 Hz, 1H), 3.62 (t, J=6.8 Hz, 2H), 2.64 (t, J=8.0 Hz, 2H), 1.88-1.96 (m, 2H).

Step 3:

(E)-2-(3-(3-(2,6-Bis(trifluoromethyl)styryl)phenyl)propyl)isoindoline-1,3-dione was deprotected according to the method used in Example 48. After concentration under reduced pressure, the residue was suspended in diethyl ether and sonicated. Solids were removed by filtration and the filtrate was concentrated under reduced pressure. Purification by flash chromatography (10% 7 M $NH_3$ in MeOH/$CH_2Cl_2$) gave Example 49 as an oil. Yield (0.102 g, 63%): $^1$H NMR (400 MHz, DMSO-$d_6$) δ 8.09 (d, J=8.0 Hz, 2H), 7.75 (t, J=8.4 Hz, 1H), 7.27-7.38 (m, 4H), 7.16 (d, J=7.6 Hz, 1H), 6.59 (d, J=16.8 Hz, 1H), 2.61 (t, J=6.8 Hz, 2H), 2.55 (t, J=8.0 Hz, 2H), 1.88 (br s, 2H), 1.61-1.68 (m, 2H).

Example 50

Preparation of (E)-3-amino-1-(3-(2,6-dichlorostyryl)phenyl)propan-1-ol

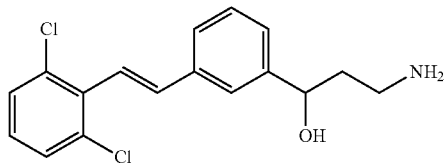 [SMILES: NCCC(O)c1cccc(/C=C/c2c(Cl)cccc2Cl)c1]

(E)-3-Amino-1-(3-(2,6-dichlorostyryl)phenyl)propan-1-ol was prepared according to Scheme 18.

SCHEME 18

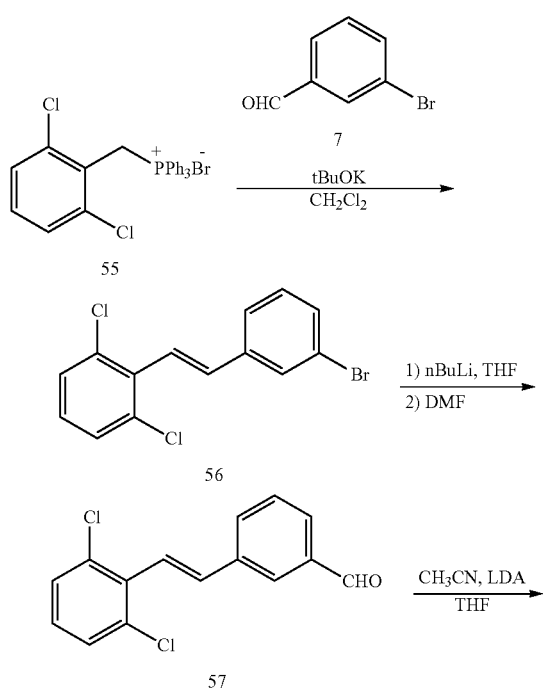

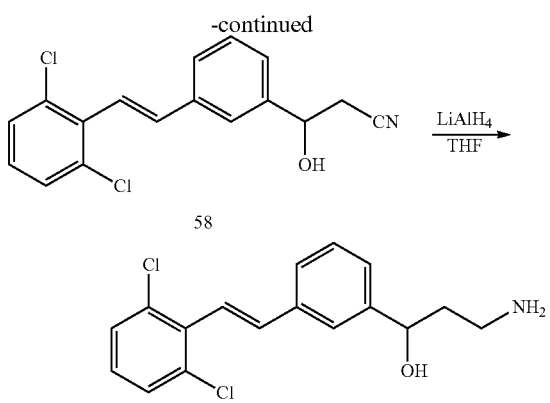

Step 1:

2,6-Dichlorobenzyltriphenylphosphonium bromide (55) was coupled with 3-bromobenzaldehyde (7) according to the method in Example 46 except that the reaction was warmed to room temperature briefly after the addition of potassium tert-butoxide. It was cooled to −78° C. again before the addition of 3-bromobenzaldehyde. After warming to room temperature and stirring overnight, the reaction mixture was concentrated under reduced pressure. The residue was triturated with ~5% EtOAc-hexanes and solids were removed by filtration. The filtrate was concentrated under reduced pressure and the residue was recrystallized from ~2-5% EtOAc-hexanes to give bromide 56 as a white crystalline solid. Yield (1.666 g, 78%): $^1$H NMR (400 MHz, DMSO-$d_6$) δ 7.84 (t, J=1.8 Hz, 1H), 7.59-7.65 (m, 2H), 7.50-7.59 (m, 2H), 7.31-7.37 (m, 2H), 7.21 (d, J=16.8 Hz, 1H), 7.08 (d, J=16.8 Hz, 1H).

Step 2:

To a −78° C. solution of bromide 56 (0.7008 g, 2.14 mmol) in THF (10 mL) was added n-butyl lithium (1.1 mL of a 2.5 M solution in THF, 2.75 mmol) and the mixture was stirred for 9 min. DMF (0.3 mL, 3.9 mmol) was added then the reaction mixture was stirred for 10 min. After allowing to warm to room temperature, additional DMF (0.3 mL, 3.9 mmol) was added and the reaction was stirred for 22 min. The mixture was partitioned between brine and EtOAc. The combined organics were washed with brine, dried over $MgSO_4$ and concentrated under reduced pressure. Purification by flash chromatography (10 to 40% EtOAc-hexanes gradient) gave aldehyde 57 as a white solid. Yield (0.359 g, 61%): $^1$H NMR (400 MHz, $CDCl_3$) δ 10.07 (s, 1H), 8.04 (t, J=1.6 Hz, 1H), 7.79-7.83 (m, 2H), 7.56 (t, J=7.6 Hz, 1H), 7.37 (d, J=7.6 Hz, 2H), 7.23 (d, J=8.0 Hz, 2H), 7.14 (t, J=8.4 Hz, 1H).

Step 3:

The glassware used in this synthetic transformation was dried with a heat gun under vacuum. To a −78° C. solution of lithium diisopropylamide (1.0 mL of a 2 M solution in THF, 2.0 mmol) in THF (3 mL) was added a solution of acetonitrile (0.1 mL, 1.88 mmol) in THF (5 mL) slowly via an addition funnel. The reaction mixture was stirred at −78° C. for 12 min, then a solution of aldehyde 57 (0.353 g, 1.27 mmol) in THF (6 mL) was added dropwise over 12 min.

Additional THF (3 mL) was added and the mixture was stirred for 25 min. After warming to room temperature, the reaction was quenched with brine and extracted with EtOAc. The combined organics were washed with brine, dried over $MgSO_4$ and concentrated under reduced pressure. Purification by flash chromatography (10 to 70% EtOAc-hexanes gradient) gave nitrile 58 as a white solid. Yield (0.357 g, 88%): $^1$H NMR (400 MHz, $CDCl_3$) δ 7.55 (d, J=1.2 Hz, 1H), 7.53 (t, J=1.2 Hz, 1H), 7.40-7.44 (m, 1H), 7.34-7.37 (m, 3H), 7.10-7.15 (m, 3H), 5.07-5.12 (m, 1H), 2.81 (dd, J=6.8, 2.0 Hz, 2H), 2.44 (d, J=3.6 Hz, 1H).

Step 4:

To an ice cold solution of nitrile 58 (0.357 g, 1.12 mmol) in THF (7 mL) was added a solution of LiAlH$_4$ (1 mL of a 2 M solution in THF, 2.0 mmol). The reaction mixture was stirred for 30 min at 0° C. then quenched with saturated aqueous Na$_2$SO$_4$. The solution was dried over MgSO$_4$ and concentrated under reduced pressure. Purification by flash chromatography (9:9:2 EtOAc:heptane:7 M NH$_3$-MeOH) gave Example 50 as an oil. Yield (0.0785 g, 22%): NMR (400 MHz, DMSO-d$_6$) δ 7.51-7.54 (s, 1H), 7.52 (d, J=8.0 Hz, 2H), 7.45 (d, J=7.6 Hz, 1H), 7.27-7.35 (m, 3H), 7.12 (d, J=16.8 Hz, 1H), 7.06 (d, J=16.8 Hz, 1H), 4.69 (t, J=7.2 Hz, 1H), 2.60-2.70 (m, 2H), 1.63-1.68 (m, 2H).

Example 51

Preparation of (E/Z)—N-(3-(3-(2,6-dimethylstyryl)phenyl)propyl)acetamide

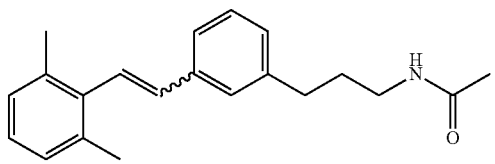 [SMILES: CC(=O)NCCCc1cccc(C=Cc2c(C)cccc2C)c1]

(E/Z)—N-(3-(3-(2,6-Dimethylstyryl)phenyl)propyl)acetamide (isomer ratio 80:20 trans:cis) was prepared according to Scheme 19.

SCHEME 19

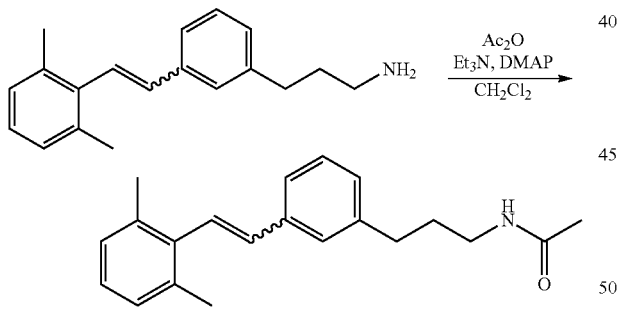

Step 1:

To a solution of (E/Z)-3-(3-(2,6-dimethylstyryl)phenyl)propan-1-amine (isomer ratio 80:20 trans:cis, Example 1) (0.049 g, 0.185 mmol) in CH$_2$Cl$_2$ (2 mL) was added triethylamine (0.065 mL, 0.47 mmol), acetic anhydride (0.020 mL, 0.21 mmol) and N,N-dimethylaminopyridine (~5 mg). The reaction mixture was stirred at room temperature for 1.25 h. The mixture was concentrated under reduced pressure and the residue was partitioned between EtOAc and water. The combined organics were washed with saturated aqueous NaHCO$_3$ and brine, dried over Na$_2$SO$_4$ and concentrated under reduced pressure. Purification by flash chromatography (50 to 100% EtOAc-hexanes gradient) gave Example 51 as a colorless oil. Yield (0.037 g, 65%), trans-/cis-isomer 5:1. Trans isomer: $^1$H NMR (400 MHz, CDCl$_3$) δ 7.29-7.35 (m, 3H), 7.08-7.11 (m, 5H), 6.57 (d, J=16.6 Hz, 1H), 5.43 (br s, 1H), 3.32 (dt, J=7.0, 6.1 Hz, 2H), 2.70 (t, J=8.0 Hz, 2H), 2.36 (s, 6H), 1.96 (s, 3H), 1.86-1.96 (m, 2H).

Example 52

Preparation of (E/Z)—N-(3-(3-(2,6-dimethylstyryl)phenyl)propyl)pentadecanamide

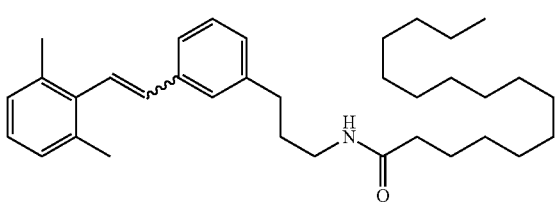 [SMILES: CCCCCCCCCCCCCCCC(=O)NCCCc1cccc(C=Cc2c(C)cccc2C)c1]

(E/Z)—N-(3-(3-(2,6-dimethylstyryl)phenyl)propyl)pentadecanamide was prepared according to the method used in Example 51.

Step 1:

To a solution of (E/Z)-3-(3-(2,6-dimethylstyryl)phenyl)propan-1-amine (isomer ratio 80:20 trans:cis, Example 1) (0.035 g, 0.132 mmol) in CH$_2$Cl$_2$ (2 mL) was added triethylamine (0.045 mL, 0.32 mmol), palmitoyl chloride (0.045 mL, 0.15 mmol) and N,N-dimethylaminopyridine (~2 mg). The reaction mixture was stirred at room temperature for 2 h. Additional triethylamine (0.045 mL, 0.32 mmol) and palmitoyl chloride (0.045 mL, 0.15 mmol) were added and the mixture was stirred for 1 h. The mixture was concentrated under reduced pressure and the residue was partitioned between EtOAc and water. The combined organics were washed with 5% aqueous NaHCO$_3$ and brine, dried over Na$_2$SO$_4$ and concentrated under reduced pressure. Purification by flash chromatography (0 to 75% EtOAc-hexanes gradient) gave Example 52 as a white semi-solid. Yield (0.060 g, 91%), trans-/cis-isomer ratio 5:1. Trans-isomer: $^1$H NMR (400 MHz, CDCl$_3$) δ 7.36 (d, J=7.6 Hz, 1H), 7.27-7.31 (m, 2H), 7.03-7.13 (m, 3H), 6.58 (d, J=16.4 Hz, 1H), 3.33 (dt, J=7.0, 6.1 Hz, 2H), 2.69 (t, J=7.6 Hz, 2H), 2.36 (s, 6H), 2.12-2.16 (m, 2H), 1.86-1.90 (m, 2H), 1.58-1.65 (m, 2H), 1.26 (m, 27H), 0.89 (t, J=6.8 Hz, 3H).

Example 53

Preparation of (E)-3-(2-methyl-5-(2-(2,6,6-trimethylcyclohex-1-enyl)vinyl)phenyl)propan-1-amine

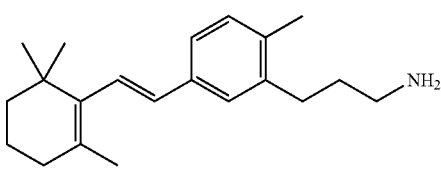 [SMILES: CC1=C(/C=C/c2ccc(C)c(CCCN)c2)C(C)(C)CCC1]

(E)-3-(2-methyl-5-(2-(2,6,6-trimethylcyclohex-1-enyl)vinyl)phenyl)propan-1-amine (80:20 trans:cis) was prepared according to the method used in Example 1.

Step 1:

To a −78° C. solution of triphenyl((2,6,6-trimethylcyclohex-1-enyl)methyl)phosphonium bromide (24) (0.3787 g, 0.79 mmol) and 18-crown-6 (0.0246 g, 0.093 mmol) in CH$_2$Cl$_2$ (7 mL) was added potassium tert-butoxide (0.0991 g, 0.88 mmol). The mixture was sonicated at room temperature under argon for 2 min, resulting in a deep red solution. The mixture was cooled to −78° C. then a solution of 3-iodo-4-methylbenzaldehyde (0.1742 g, 0.71 mmol) in CH$_2$Cl$_2$ (3 mL+2 mL) was added and stirred for 5 min. The reaction mixture was allowed to warm to room temperature. Additional phosphonium salt 24 (0.3725 g, 1.6 mmol), 3-iodo-4-methylbenzaldehyde (0.2538 g, 1.7 mmol) and potassium tert-butoxide (0.1548 g, 1.38 mmol) were then added and the reaction was stirred at room temperature for 4.3 h. The reaction was partitioned between EtOAc and water then the combined organics were washed with brine, dried over MgSO$_4$ and concentrated under reduced pressure. Purification by flash chromatography (6 to 50% EtOAc-hexanes gradient) gave (E)-2-iodo-1-methyl-4-(2-(2,6,6-trimethylcyclohex-1-enyl)vinyl)benzene as a white solid. Yield (0.26 g, 45%): NMR (400 MHz, DMSO-d$_6$) δ 7.91 (d, J=1.6 Hz, 1H), 7.44 (dd, J=7.6, 1.2 Hz, 1H), 7.29 (d, J=7.2 Hz, 1H), 6.71 (d, J=16.4 Hz, 1H), 6.28 (6, J=16.8 Hz, 1H), 2.35 (s, 3H), 2.01 (t, J=6.4 Hz, 2H), 1.72 (s, 3H), 1.57-1.64 (m, 2H), 1.43-1.47 (m, 2H), 1.04 (s, 6H).

Step 2:

(E)-2-iodo-1-methyl-4-(2-(2,6,6-trimethylcyclohex-1-enyl)vinyl)benzene was coupled with allyl alcohol following the method used in Example 32 except that the reaction was stirred at room temperature overnight after heating for 3 h at 60° C. Purification twice by flash chromatography (6 to 25% EtOAc-hexanes gradient) gave (E/Z)-3-(2-methyl-5-(2-(2,6,6-trimethylcyclohex-1-enyl)vinyl)phenyl)propanal as an oil. Yield (0.15 g, 71%); trans-/cis-isomer ratio 3:1. Trans-isomer: $^1$H NMR (400 MHz, DMSO-d$_6$) δ 9.75 (t, J=1.2 Hz, 1H), 7.19-7.27 (m, 2H), 7.09 (d, J=7.6 Hz, 1H), 6.64 (6, J=16.4 Hz, 1H), 6.27 (d, J=16.8 Hz, 1H), 2.83 (t, J=5.4 Hz, 2H), 2.75 (t, J=5.4 Hz, 2H), 2.25 (s, 3H), 2.01 (t, J=5.4 Hz, 2H), 1.74 (s, 3H), 1.58-1.63 (m, 2H), 1.39-1.47 (m, 2H), 1.06 (s, 6H).

Step 3:

Reductive amination of (E/Z)-3-(2-methyl-5-(2-(2,6,6-trimethylcyclohex-1-enyl)vinyl)phenyl)propanal was conducted according to the method used in Example 46 except that isopropanol-MeOH (1:2) was used as the solvent and the reaction was stirred briefly at 0° C. after the addition of NaBH$_4$. Purification by flash chromatography (1:1 EtOAc/hexanes then 1:5:5 7 M NH$_3$ in MeOH/EtOAc/hexanes) gave Example 53 as an oil. Yield (0.1450 g, 96%): $^1$H NMR (400 MHz, DMSO-d$_6$) δ 7.86 (br s, 3H), 7.21-7.23 (m, 2H), 7.11 (d, J=8.0 Hz, 1H), 6.64 (6, J=16.4 Hz, 1H), 6.27 (d, J=16.0 Hz, 1H), 2.83-2.88 (m, 2H), 2.62 (t, J=8.0 Hz, 2H), 2.25 (s, 3H), 1.99-2.09 (m, 2H), 1.76-1.84 (m, 2H), 1.72 (s, 3H), 1.57-1.61 (m, 2H), 1.45-1.47 (m, 2H), 1.04 (s, 6H).

Example 54

Preparation of (E/Z)-4-amino-2-O-(2-(2,6,6-trimethylcyclohex-1-enyl)vinyl)phenyl)butan-2-ol

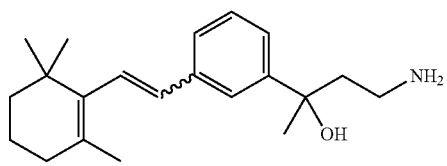 [SMILES: CC1=C(C=Cc2cccc(C(C)(O)CCN)c2)C(C)(C)CCC1]

(E/Z)-4-Amino-2-(3-(2-(2,6,6-trimethylcyclohex-1-enyl)vinyl)phenyl)butan-2-ol was prepared according to Scheme 20.

SCHEME 20

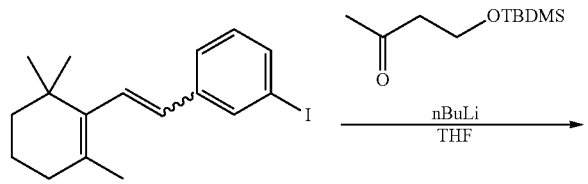

31

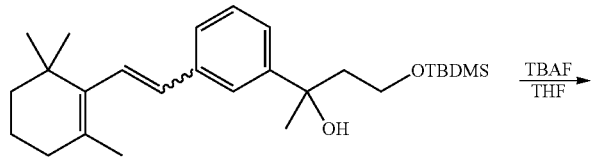

59

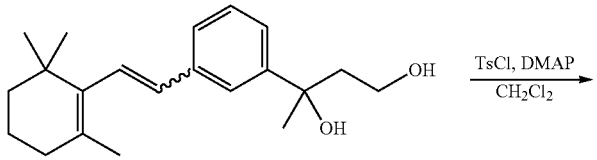

60

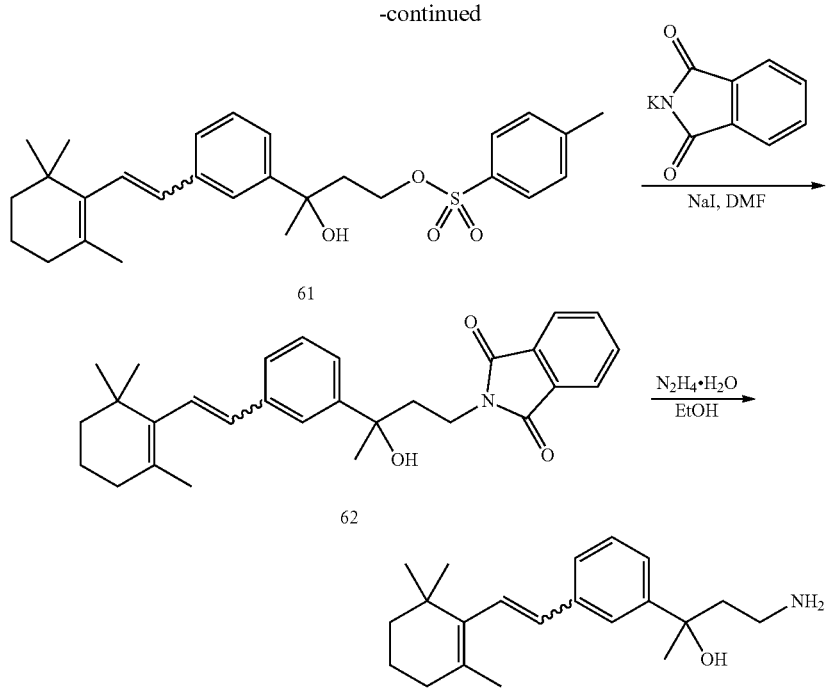

Step 1:

To a −78° C. solution of n-butyl lithium (2 mL of a 1.6 M solution in hexanes, 3.2 mmol) in THF (2 mL) was added a solution of iodide 31 (0.4394 g, 1.35 mmol) in THF (5 mL+1 mL) and the reaction mixture was stirred for 40 min. A solution of 4-(tert-butyldimethylsilyloxy)butan-2-one (0.5040 g, 2.49 mmol) in THF (5 mL) was added slowly and the mixture was stirred for 35 min. Additional 4-(tert-butyldimethylsilyloxy)butan-2-one (0.1458 g, 0.72 mmol) in THF (2 mL) was added. The mixture was stirred at −78° C. for 25 min then warmed to room temperature. The reaction was quenched with the addition of brine and extracted with EtOAc. The combined organics were washed with brine, dried over $MgSO_4$ and concentrated under reduced pressure. Purification by flash chromatography (2 to 20% EtOAc-hexanes gradient) provided alcohol 59 as an oil. Yield (0.1870 g, 32%): $^1$H NMR (400 MHz, DMSO-$d_6$) δ 7.56 (s, 1H), 7.29-7.38 (m, 3H), 6.76 (dd, J=16.4, 0.8 Hz, 1H), 6.41 (d, J=16.4 Hz, 1H), 5.00 (s, 1H), 3.66-3.72 (m, 1H), 3.44-3.50 (m, 1H), 2.09 (t, J=6.0 Hz, 2H), 2.03 (t, J=6.0 Hz, 2H), 1.80 (s, 3H), 1.65-1.67 (m, 2H), 1.52-1.55 (m, 2H), 1.50 (s, 3H), 1.19 (s, 6H), 0.87 (s, 9H), 0.00 (s, 6H).

Step 2:

To a solution of alcohol 59 (0.1870 g, 0.44 mmol) in THF (10 mL) was added a solution of tetrabutylammonium fluoride (1 mL of a 1 M solution in THF, 1 mmol). The reaction mixture was stirred for 30 min then concentrated under reduced pressure. The residue was partitioned between EtOAc and water and the combined organics were washed with water and brine. The solution was dried over $MgSO_4$ and concentrated under reduced pressure to give diol 60 as an oil. This material was taken on to the next step without further purification. $^1$H NMR (400 MHz, DMSO-$d_6$) 7.53 (s, 1H), 7.26-7.37 (m, 3H), 6.75 (dd, J=16.4, 0.8 Hz, 1H), 6.39 (d, J=16.4 Hz, 1H), 5.05 (s, 1H), 4.37 (t, J=5.0 Hz, 1H), 3.42-3.51 (m, 1H), 3.26-3.37 (m, 1H), 2.05 (t, J=7.2 Hz, 2H), 1.87-1.97 (m, 2H), 1.78 (s, 3H), 1.63-1.66 (m, 2H), 1.49-1.52 (m, 2H), 1.46 (s, 3H), 1.20 (s, 6H).

Step 3:

To a solution of diol 60 (0.436 mmol) in $CH_2Cl_2$ (5 mL) was added N,N-dimethylaminopyridine (0.1362 g, 1.11 mmol) and a solution of p-toluenesulfonyl chloride (0.0863 g, 0.75 mmol) in $CH_2Cl_2$ (3 mL). The reaction mixture was stirred at room temperature for 25 min then additional p-toluenesulfonyl chloride (0.0288 g, 0.15 mmol) in THF (1 mL) was added. The reaction was stirred for 1 h, 45 min and the mixture was partitioned between EtOAc and saturated aqueous $NaHCO_3$. The combined organics were washed with more saturated aqueous $NaHCO_3$ and brine, dried over $MgSO_4$ and concentrated under reduced pressure to give tosylate 61 as an oil. This material was taken on to the next synthetic step without further purification. Yield (0.2141 g crude, quant. for two steps): $^1$H NMR (400 MHz, DMSO-$d_6$) δ 7.70-7.73 (m, 2H), 7.46-7.48 (m, 3H), 7.36 (d, J=7.2 Hz, 1H), 7.22-7.29 (m, 2H), 6.74 (d, J=16.4 Hz, 1H), 6.37 (d, J=16.4 Hz, 1H), 5.23 (s, 1H), 4.05-4.12 (m, 1H), 3.78-3.86 (m, 1H), 2.45 (s, 3H), 2.11-2.32 (m, 4H), 1.78 (s, 3H), 1.62-1.68 (m, 2H), 1.48-1.56 (m, 2H), 1.43 (s, 3H), 1.09 (s, 6H).

Step 4:

To a solution of tosylate 61 (0.4362 mmol) in DMF (5 mL) was added potassium phthalimide (0.1570 g, 0.85 mmol). The reaction mixture was stirred at room temperature for 40 min then heated at 60° C. for 1 h. NaI (0.0831 g, 0.55 mmol) was added and heating was continued overnight. After cooling to room temperature, the mixture was concentrated under reduced pressure and partitioned between EtOAc and water. The combined organics were washed with water and brine, dried over $MgSO_4$ and concentrated under reduced pressure. Purification by flash chromatography (20 to 50% EtOAc-hexanes gradient) gave phthalimide 62 as an oil. Yield (0.1179 g, 61% from alcohol 59): $^1$H NMR (400 MHz, DMSO-$d_6$) δ 7.73-7.77 (m, 4H), 7.48 (s, 1H), 7.14-7.25 (m, 3H), 6.58 (d, J=16.0 Hz, 1H), 6.29 (d, 0.1=16.0 Hz, 1H), 5.12 (s, 1H), 3.56-3.61 (m, 1H), 3.39-3.47 (m, 1H), 2.12-2.18 (m, 1H), 1.94-2.03 (m, 3H), 1.73 (s, 3H), 1.56-1.62 (m, 2H), 1.42-1.56 (m, 5H), 1.05 (s, 6H).

Step 5:

Phthalimide 62 was deprotected according to the method used in Example 32 to give Example 54 as an oil. Yield (0.0628 g, 81%): $^1$H NMR (400 MHz, DMSO-$d_6$) δ 7.47 (s, 1H), 7.21-7.31 (m, 3H), 6.68 (dd, J=16.4, 0.8 Hz, 1H), 6.34 (d, J=16.4 Hz, 1H), 2.40-2.60 (m, 4H), 2.00 (t, J=6.0 Hz, 2H), 1.75-1.82 (m, 3H), 1.72 (s, 3H), 1.55-1.62 (m, 2H), 1.42-1.48 (m, 214), 1.37 (s, 3H), 1.03 (s, 6H).

Example 55

Preparation of (E)-3-fluoro-3-(3-(2-(2,6,6-trimethyl-cyclohex-1-enyl)vinyl)phenyl)propan-1-amine

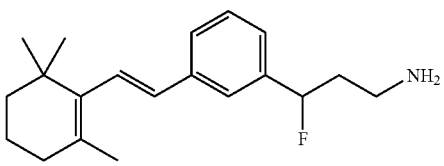 [SMILES: CC1=C(/C=C/c2cccc(C(F)CCN)c2)C(C)(C)CCC1]

(E)-3-Fluoro-3-(3-(2-(2,6,6-trimethylcyclohex-1-enyl)vinyl)phenyl)propan-1-amine was prepared according to Scheme 21.

SCHEME 21

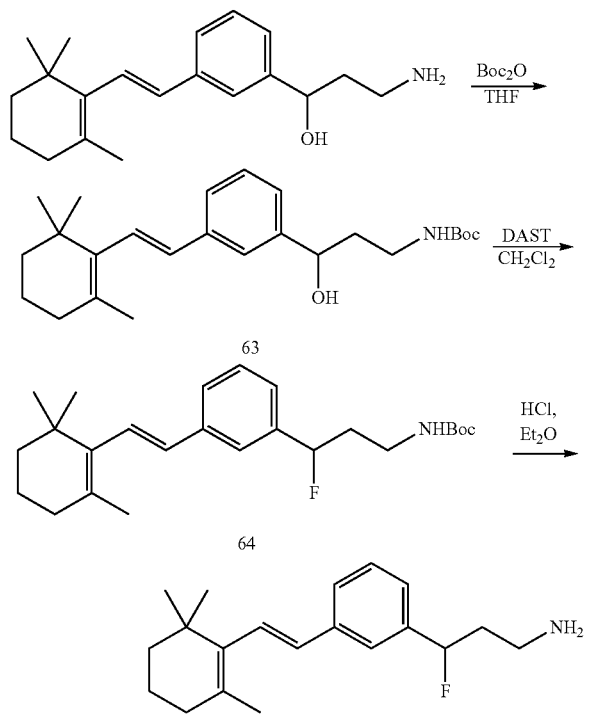

Step 1:

To a solution of (E)-3-amino-1-(3-(2,6-dimethylstyryl) phenyl)propan-1-ol (~0.68 mmol) in THF (3 mL) was added a solution of di-tert-butyl dicarbonate (0.1982 g, 0.91 mmol) in THF (3 mL). The reaction mixture was stirred at room temperature for 10 min then the mixture was concentrated under reduced pressure to give crude alcohol 63. This material was used in the next synthetic step without further purification. Yield (0.3137 g, quant.): $^1$H NMR (400 MHz, CDCl$_3$) δ 7.39 (s, 1H), 7.29-7.31 (m, 2H), 7.20 (dt, J=6.4, 2.0 Hz, 1H), 6.68 (dd, J=16.4, 0.8 Hz, 1H), 6.33 (d, J=16.4 Hz, 1H), 4.89 (s, 1H), 4.72-4.78 (m, 1H), 3.43-3.58 (m, 1H), 3.12-3.22 (m, 2H), 2.02-2.05 (m, 2H), 1.85-1.92 (m, 2H), 1.75 (s, 3H), 1.61-1.68 (m, 2H), 1.44-1.54 (m, 11H), 1.06 (s, 6H).

Step 2:

To a −78° C. solution of crude alcohol 63 (~0.6841 mmol) in CH$_2$Cl$_2$ (5 mL) was added (diethylamino)sulfur trifluoride (0.15 mL, 1.14 mmol). The reaction was stirred at −78° C. for 10 min then poured into a mixture of EtOAc and saturated aqueous NaHCO$_3$. The layers were separated and the aqueous layer was extracted with EtOAc. The combined organics were washed with brine, dried over MgSO$_4$ and concentrated under reduced pressure. Purification by flash chromatography (10 to 40% EtOAc-hexanes gradient) gave fluoride 64 as an oil. Yield (0.0946 g, 34%): $^1$H NMR (400 MHz, CDCl$_3$) δ 7.30-7.38 (m, 3H), 7.16 (d, J=7.6 Hz, 1H), 6.70 (d, J=16.0 Hz, 1H), 6.34 (d, J=16.0 Hz, 1H), 5.53 (ddd, J=48.4, 8.8, 4.0 Hz, 1H), 4.73 (br s, 1H), 3.24-3.40 (m, 2H), 2.08-2.20 (m, 2H), 2.04 (t, J=6.0 Hz, 2H), 1.76 (s, 3H), 1.60-1.68 (m, 2H), 1.42-1.54 (m, 11H), 1.06 (s, 6H).

Step 5:

Fluoride 64 was deprotected according to the method used in Example 45 except that the reaction was stirred at room temperature overnight. Purification by flash chromatography (5:5:1 EtOAc:hexanes: 7 M NH$_3$ in MeOH) gave Example 55 as an oil. Yield (0.0360 g, 51%): $^1$H NMR (400 MHz, CD$_3$OD) δ 7.20-7.37 (m, 4H), 6.72 (d, J=16.0 Hz, 1H), 6.33 (d, J=16.0 Hz, 1H), 5.56 (ddd, J=48.4, 8.8, 4.0 Hz, 1H), 2.76-2.82 (m, 2H), 1.91-2.20 (m, 4H), 1.75 (s, 3H), 1.63-1.69 (m, 2H), 1.49-1.52 (m, 2H), 1.06 (s, 6H).

Example 56

Preparation of (E)-3-amino-1-(3-(2-(2,6,6-trimethyl-cyclohex-1-enyl)vinyl)phenyl)propan-1-one

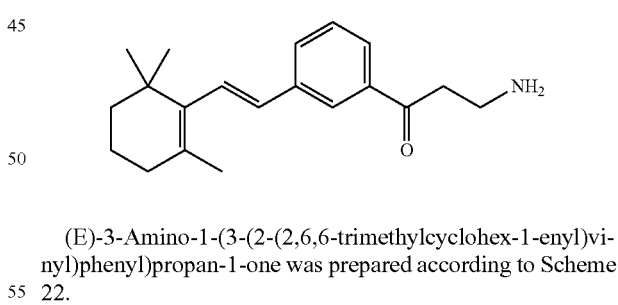

(E)-3-Amino-1-(3-(2-(2,6,6-trimethylcyclohex-1-enyl)vinyl)phenyl)propan-1-one was prepared according to Scheme 22.

SCHEME 22

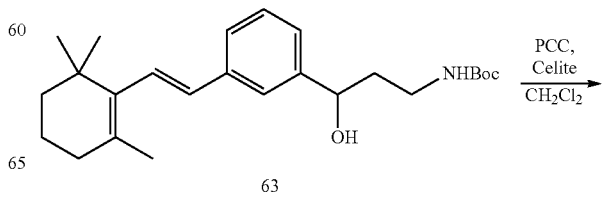

63

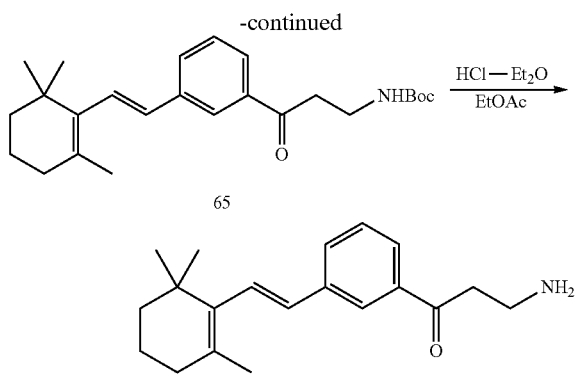

Step 1:
To a solution of alcohol 63 (0.3753 g, 0.94 mmol) in CH$_2$Cl$_2$ (15 mL) was added pyridinium chlorochromate (0.2662 g, 1.2 mmol) and Celite (0.45 g). The reaction mixture was stirred for 1 h then the solids were removed by filtration through Celite. The filtrate was concentrated under reduced pressure. Purification by flash chromatography (10 to 30% EtOAc-hexanes gradient) provided ketone 65 as an oil. Yield (0.1038 g, 28%): $^1$H NMR (400 MHz, CDCl$_3$) δ 7.95 (s, 1H), 7.77 (d, J=7.6 Hz, 1H), 7.60 (d, J=7.6 Hz, 1H), 7.40 (t, J=7.6 Hz, 1H), 6.75 (dd, J=16.4, 0.8 Hz, 1H), 6.37 (dd, J=16.4, 0.8 Hz, 1H), 5.16 (br s, 1H), 3.55 (q, J=6.0 Hz, 2H), 3.21 (t, J=5.6 Hz, 2H), 2.04 (t, J=6.2 Hz, 2H), 1.75 (d, J=0.4 Hz, 3H), 1.61-1.67 (m, 2H), 1.48-1.51 (m, 2H), 1.42 (s, 9H), 1.06 (s, 6H).

Step 2:
To a solution of ketone 65 (0.1038 g, 0.26 mmol) in EtOAc (5 mL) was added a solution of HCl (5 mL of a 10 M solution in diethyl ether, 50 mmol) and the mixture was stirred for 5 min. Additional HCl (10 mL of a 10 M solution in diethyl ether, 100 mmol) was added and stirring continued for 5 min. The mixture was concentrated under reduced pressure then co-evaporated under reduced pressure with EtOAc, EtOH, EtOAc, toluene, EtOAc-hexanes and EtOAc successively. Example 56 hydrochloride was isolated as an oil. Yield (0.0974 g, quant.): $^1$H NMR (400 MHz, CDCl$_3$) δ 8.35 (br s, 3H), 7.83 (s, 1H), 7.67 (d, J=7.2 Hz, 1H), 7.49 (d, J=7.6 Hz, 1H), 7.24 (t, J=7.2 Hz, 1H), 6.64 (d, J=16.0 Hz, 1H), 6.26 (d, J=16.4 Hz, 1H), 3.52 (s, 2H), 3.45 (s, 2H), 1.95 (t, J=6.0 Hz, 2H), 1.65 (s, 3H), 1.52-1.58 (m, 2H), 1.39-1.41 (m, 2H), 0.96 (s, 6H).

Example 57

Preparation of (E)-4-amino-1,1,1-trifluoro-2-(3-(2-(2,6,6-trimethylcyclohex-1-enyl)vinyl)phenyl)butan-2-ol (E)-4-Amino-1,1,1-trifluoro-2-(3-(2-(2,6,6-trimethylcyclohex-1-enyl)vinyl)phenyl)butan-2-ol was prepared according to Scheme 23.

SCHEME 23

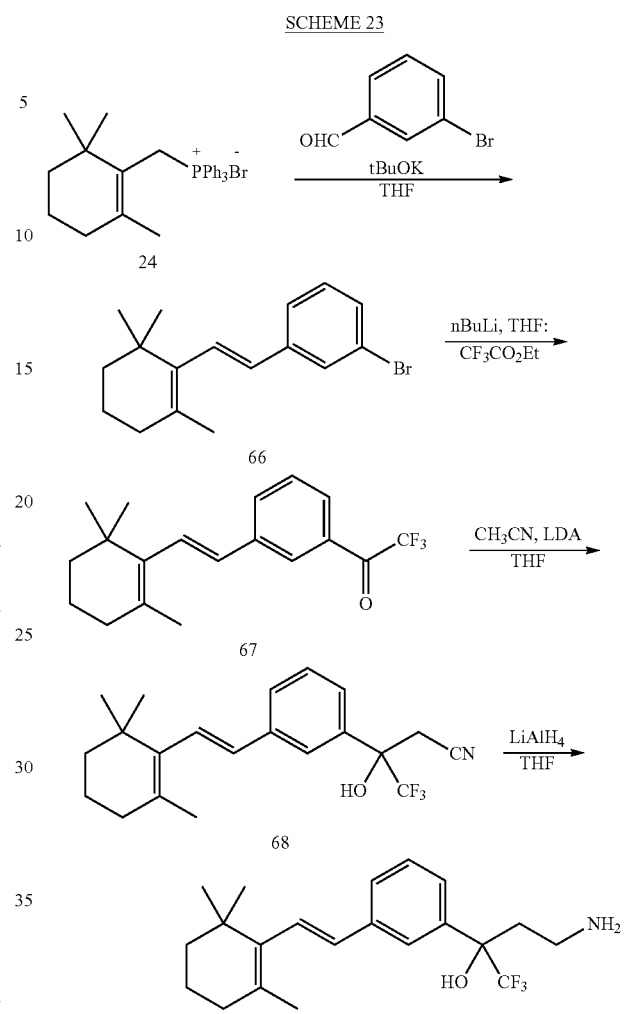

Step 1:
Phosphonium bromide 24 was coupled with 3-bromobenzaldehyde following the method used in Example 46. After stirring overnight, the reaction mixture was concentrated under reduced pressure. The residue was triturated with 5% EtOAc-hexanes and the solids were removed by filtration. The filtrate was concentrated under reduced pressure. Purification by flash chromatography (5% EtOAc-heptane) gave aryl bromide 66 as an oil. Yield (3.52 g, 87%): $^1$H NMR (400 MHz, CDCl$_3$) δ 7.47 (t, J=2.0 Hz, 1H), 7.22-7.27 (m, 2H), 7.10 (t, J=7.6 Hz, 1H), 6.60 (dd, J=16.0, 0.8 Hz, 1H), 6.19 (d, J=16.0 Hz, 1H), 1.97 (t, J=6.0 Hz, 2H), 1.67 (s, 3H), 1.54-1.60 (m, 2H), 1.41-1.44 (m, 2H), 0.99 (s, 6H).

Step 2:
To a −78° C. solution of aryl bromide 66 in THF (7 mL) under argon was added a solution of n-butyl lithium (0.75 mL of a 1.6 M solution in hexane, 1.2 mmol) and the mixture was stirred for 20 min. Ethyl trifluoroacetate (0.215 mL, 1.8 mmol) was added and the reaction mixture was allowed to warm to room temperature. The reaction was quenched with water. The mixture was partitioned between EtOAc and water and the combined organics were washed with brine, dried over MgSO$_4$ then concentrated under reduced pressure. Purification by flash chromatography (6 to 70% EtOAc-hexanes gradient) to give ketone 67 as a light yellow oil. Yield (0.200 g, 66%): $^1$H NMR (400 MHz, DMSO-d$_6$) δ 8.01-8.03 (m, 2H), 7.87 (dd, J=8.0, 1.2 Hz, 1H), 7.62 (t, J=8.0 Hz, 1H), 6.86 (dd, J=16.4, 0.8 Hz, 1H), 6.51 (d, J=16.4 Hz, 1H), 2.02 (t, J=6.0, 2H), 1.73 (s, 3H), 1.56-1.62 (m, 2H), 1.44-1.47 (m, 2H), 1.04 (s, 6H).

Step 3:

Reaction of ketone 67 with acetonitrile was conducted following the method used in Example 50 except that lithium diisopropylamide was added to the acetonitrile. Purification by flash chromatography (7 to 60% EtOAc-hexanes gradient) gave nitrile 68 as a colorless oil which solidified on standing. Yield (0.192 g, 80%): $^1$H NMR (400 MHz, DMSO-$d_6$) δ 7.69 (s, 1H), 7.55 (d, J=8.0 Hz, 1H), 7.47-7.50 (m, 2H), 7.39 (t, J=7.6 Hz, 1H), 6.78 (d, J=15.6 Hz, 1H), 6.38 (d, J=16.4 Hz, 1H), 3.75 (d, J=16.8 Hz, 1H), 3.37 (d, J=17.2 Hz, 1H), 2.02 (t, J=6.0 Hz, 1H), 1.73 (s, 3H), 1.56-1.62 (m, 2H), 1.44-1.47 (m, 2H), 1.04 (s, 6H).

Step 4:

Nitrile 68 was reduced with LiAlH$_4$ following the method used in Example 50 except that the reaction was stirred at 0° C. for 50 min. After the reaction was quenched, dried and concentrated under reduced pressure, the residue was suspended in hexanes and sonicated. The resulting solution was stored at −20° C. for 3 h and sonicated once during this time. The white crystals were collected by filtration and washed with hexanes to give Example 57 as a white solid (0.0495 g, 31% yield). Additional product was obtained by concentrating the mother liquor under reduced pressure to give a yellow oil (0.0604 g, 38% yield): $^1$H NMR (400 MHz, CDCl$_3$) δ 7.61 (s, 1H), 7.49 (d, J=7.6 Hz, 1H), 7.40 (d, J=7.6 Hz, 1H), 7.34 (t, J=7.6 Hz, 1H), 6.72 (d, J=16.4 Hz, 1H), 6.37 (d, J=16.8 Hz, 1H), 2.71-2.76 (m, 1H), 2.06-2.20 (m, 2H), 1.99-2.02 (m, 2H), 1.97 (s, 3H), 1.61-1.67 (m, 2H), 1.48-1.52 (m, 2H), 1.07 (s, 6H). One aliphatic proton is obscured by the peak for residual protonated DMSO.

Example 58

Preparation of (E)-3-amino-2,2-dimethyl-1-(3-(2-(2,6,6-trimethylcyclohex-1-enyl)vinyl)phenyl)propan-1-ol

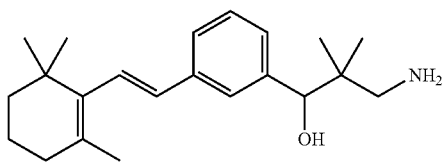 [SMILES: CC1=C(/C=C/c2cccc(C(O)C(C)(C)CN)c2)C(C)(C)CCC1]

(E)-3-Amino-2,2-dimethyl-1-(3-(2-(2,6,6-trimethylcyclohex-1-enyl)vinyl)phenyl)propan-1-ol was prepared according to Scheme 24.

SCHEME 24

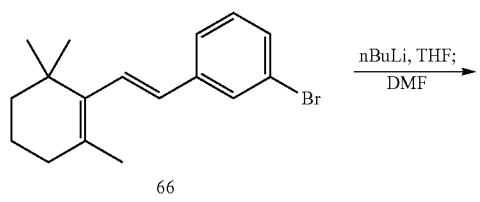

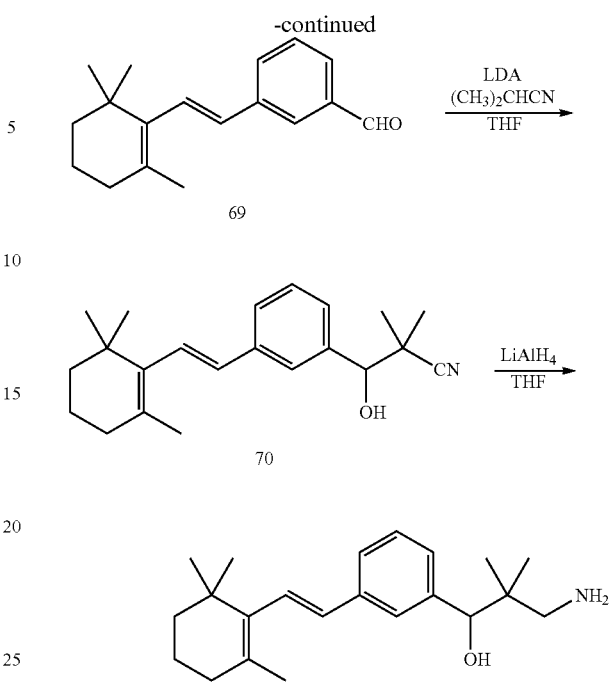

Step 1:

To a −78° C. solution of n-butyl lithium (2.5 mL of a 1.6 M solution in hexanes, 4.0 mmol) in THF (8 mL) was added a solution of aryl bromide 66 (0.9152 g, 3.0 mmol) in THF (12 mL). The reaction was stirred at −78° C. for 10 min then DMF (0.6 mL, 7.7 mmol) was added and the reaction was stirred for 5 min then allowed to warm to 60° C. The reaction was stirred for 5 min then quenched with saturated aqueous NH$_4$Cl. After warming to room temperature, the layers were separated and the aqueous layer was extracted with EtOAc. The combined organics were washed with brine, dried over MgSO$_4$ and concentrated under reduced pressure. Purification by flash chromatography (5 to 20% EtOAc-hexanes gradient) gave aldehyde 69 as an oil. Yield (0.6467 g, 85%): $^1$H NMR (400 MHz, CDCl$_3$) δ 10.0 (s, 1H), 7.90 (t, J=1.6 Hz, 1H), 7.72 (dt, J=7.6, 1.2 Hz, 1H), 7.65 (d, J=7.8 Hz, 1H), 7.48 (t, J=7.6 Hz, 1H), 6.79 (dd, J=16.2, 1.0 Hz, 1H), 6.40 (d, J=16.4 Hz, 1H), 2.04-2.07 (m, 2H), 1.77 (s, 3H), 1.62-1.68 (m, 2H), 1.49-1.52 (m, 2H), 1.07 (s, 6H).

Step 2:

Aldehyde 69 was reacted with isobutyronitrile according to the method used in Example 50. Purification by flash chromatography (10 to 70% EtOAc-hexanes gradient) gave nitrile 70 as an oil. (Yield (0.2235 g, 69%): $^1$H NMR (400 MHz, CDCl$_3$) δ 7.26-7.43 (m, 4H), 6.72 (dd, J=16.0, 0.8 Hz, 1H), 6.35 (d, J=16.0 Hz, 1H), 4.55 (d, J=3.2 Hz, 1H), 2.05-2.08 (m, 2H), 1.76 (s, 3H), 1.61-1.67 (m, 2H), 1.48-1.51 (m, 2H), 1.45 (s, 3H), 1.25 (s, 3H), 1.07 (s, 6H).

Step 3:

Nitrile 70 was reduced with LiAlH$_4$ according to the method used in Example 50 except that the reaction was stirred at 0° C. for 1.25 h. Purification by flash chromatography (2:9:9 (7 M NH$_3$ in MeOH)/EtOAc/hexanes) gave Example 58 as an oil. Yield (0.1750 g, 77%): $^1$H NMR (400 MHz, CD$_3$OD) δ 7.23-7.36 (m, 3H), 7.17 (dd, J=7.6, 1.2 Hz, 1H), 6.70 (dd, J=16.0, 0.8 Hz, 1H), 6.33 (d, J=16.0 Hz, 1H), 4.55 (s, 1H), 2.73 (d, J=13.2 Hz, 1H), 2.55 (d, J=13.2 Hz, 1H), 2.05 (t, J=6.4 Hz, 2H), 1.75 (s, 3H), 1.60-1.71 (m, 2H), 1.50-1.53 (m, 2H), 1.06 (s, 6H), 0.84 (s, 6H).

Example 59

Preparation of (E)-(SYN/ANTI)-3-amino-2-methyl-1-(3-(2-(2,6,6-trimethylcyclohex-1-enyl)vinyl)phenyl)propan-1-ol

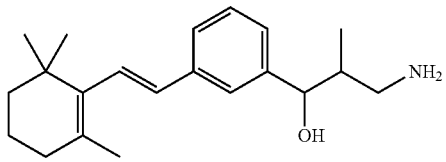 [SMILES: CC1=C(/C=C/c2cccc(C(O)C(C)CN)c2)C(C)(C)CCC1]

(E)-3-Amino-2-methyl-1-(3-(2-(2,6,6-trimethylcyclohex-1-enyl)vinyl)phenyl)propan-1-ol was prepared according to the method used in Example 58.

Step 1:

Aldehyde 69 was reacted with propionitrile according to the method used in Example 58. Purification twice by flash chromatography (10 to 70% EtOAc-hexanes gradient; then 10 to 30% EtOAc-hexanes gradient) gave both diastereomers of (E)-3-hydroxy-2-methyl-3-(3-(2-(2,6,6-trimethylcyclohex-1-enyl)vinyl)phenyl)propanenitrile. The first eluting diastereomer was isolated as an oil (0.0233 g). The second eluting diastereomer was isolated as an oil (0.1214 g). Total yield (0.1447 g, 47%):

Diastereomer 2: $^1$H NMR (400 MHz, CDCl$_3$) δ 7.32-7.41 (m, 3H), 7.20-7.26 (m, 1H), 6.72 (d, J=16.4 Hz, 1H), 6.35 (dd, J=16.4, 1.2 Hz, 1H), 4.81 (dd, J=6.0, 3.2 Hz, 1H), 3.01 (quint, J=7.2 Hz, 1H), 2.59 (d, J=3.2 Hz, 1H), 2.04 (t, J=6.4 Hz, 2H), 1.76 (s, 3H), 1.65 (quint, J=6.4 Hz, 2H), 1.50 (t, J=6.0 Hz, 2H), 1.28 (d, J=7.2 Hz, 3H), 1.07 (s, 6H).

Step 2:

Diastereomer 2 of (E)-3-hydroxy-2-methyl-3-(3-(2-(2,6,6-trimethylcyclohex-1-enyl)vinyl)phenyl)propanenitrile was reduced with LiAlH$_4$ according to the method used in Example 58. Purification by flash chromatography (7 M NH$_3$ in MeOH/EtOAc/hexanes 2:9:9) gave both diastereomers of Example 59 as an oil (2.8:1 diastereomeric mixture). Yield (0.0893 g, 73%). Major diastereomer: $^1$H NMR (400 MHz, CDCl$_3$) δ 7.26-7.38 (m, 3H), 7.18 (dt, J=6.8, 1.6 Hz, 1H), 6.68 (dd, J=16.0, 0.8 Hz, 1H), 6.35 (d, J=16.0 Hz, 1H), 4.98 (d, J=3.2 Hz, 1H), 2.94-2.96 (m, 2H), 2.03 (t, J=6.4 Hz, 2H), 1.98-2.01 (m, 1H), 1.76 (s, 3H), 1.64 (quint, J=6.4 Hz, 2H), 1.49 (t, J=6.0 Hz, 2H), 1.06 (s, 6H), 0.84 (d, J=7.2 Hz, 3H).

Example 60

Preparation of (E)-3-amino-2,2-dimethyl-1-(3-(2-(2,6,6-trimethylcyclohex-1-enyl)vinyl)phenyl)propan-1-one

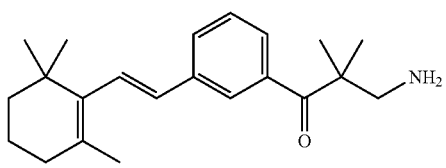 [SMILES: CC1=C(/C=C/c2cccc(C(=O)C(C)(C)CN)c2)C(C)(C)CCC1]

(E)-3-Amino-2,2-dimethyl-1-(3-(2-(2,6,6-trimethylcyclohex-1-enyl)vinyl)phenyl)propan-1-one was prepared according to the methods used in Examples 55 and 56.

Step 1:

(E)-3-Amino-2,2-dimethyl-1-(3-(2-(2,6,6-trimethylcyclohex-1-enyl)vinyl)phenyl)propan-1-ol (Example 58) was protected with di-tert-butyl dicarbonate according to the method used in Example 55 to give (E)-tert-butyl 3-hydroxy-2,2-dimethyl-3-(3-(2-(2,6,6-trimethylcyclohex-1-enyl)vinyl)phenyl)propylcarbamate as an oil. This compound was used in the next synthetic step without purification. Yield (0.1495 g, quant.).

Step 2:

(E)-Tert-butyl 3-hydroxy-2,2-dimethyl-3-(3-(2-(2,6,6-trimethylcyclohex-1-enyl)vinyl)phenyl)propylcarbamate (0.0809 g, 0.19 mmol) was reacted with pyridinium chlorochromate according to the method used in Example 56 except that the reaction time was 2 h, 15 min. Purification by flash chromatography (10 to 40% EtOAc-hexanes gradient) gave (E)-tert-butyl 2,2-dimethyl-3-oxo-3-(3-(2-(2,6,6-trimethylcyclohex-1-enyl)vinyl)phenyl)propylcarbamate as an oil. $^1$H NMR (400 MHz, CD$_3$OD) δ 7.72 (s, 1H), 7.58 (d, J=7.6 Hz, 1H), 7.52 (d, J=8.0 Hz, 1H), 7.35 (t, J=7.6 Hz, 1H), 6.72 (dd, J=16.0, 0.8 Hz, 1H), 6.33 (d, J=16.0 Hz, 1H), 5.05 (t, J=6.0 Hz, 1H), 3.38 (d, J=6.8 Hz, 2H), 2.04 (t, J=6.4 Hz, 2H), 1.76 (s, 3H), 1.61-1.67 (m, 2H), 1.48-1.50 (m, 2H), 1.36-1.42 (m, 15H), 1.06 (s, 6H).

Step 3:

To a solution of (E)-tert-butyl 2,2-dimethyl-3-oxo-3-(3-(2-(2,6,6-trimethylcyclohex-1-enyl)vinyl)phenyl)propylcarbamate (0.19 mmol) in EtOAc (2 mL) was added a solution of HCl (10 mL of a 10 M solution in diethyl ether, 100 mmol) and the mixture was stirred for 10 min. Additional HCl (5 mL of a 10 M solution in diethyl ether, 50 mmol) was added and the reaction was stirred for 10 min. The mixture was concentrated under reduced pressure to give Example 60 hydrochloride as an oil. Yield (0.0500 g, 73% for two steps): $^1$H NMR (400 MHz, CD$_3$OD) 0.5-9.52 (br s, 3H), 7.72 (s, 1H), 7.58 (d, J=7.6 Hz, 1H), 7.52 (d, J=8.0 Hz, 1H), 7.31 (t, J=7.6 Hz, 1H), 6.71 (d, J=16.0 Hz, 1H), 6.32 (d, J=16.0 Hz, 1H), 3.28 (br s, 2H), 2.02 (t, J=6.4 Hz, 2H), 1.73 (s, 3H), 146-1.66 (m, 10H), 1.04 (s, 6H).

Example 61

Preparation of (E)-1-(3-(2-(2,6,6-trimethylcyclohex-1-enyl)vinyl)phenyl)propane-1,3-diamine

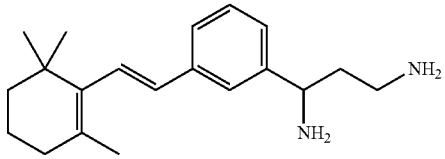 [SMILES: CC1=C(/C=C/c2cccc(C(N)CCN)c2)C(C)(C)CCC1]

(E)-1-(3-(2-(2,6,6-Trimethylcyclohex-1-enyl)vinyl)phenyl)propane-1,3-diamine was prepared according to Scheme 25.

SCHEME 25

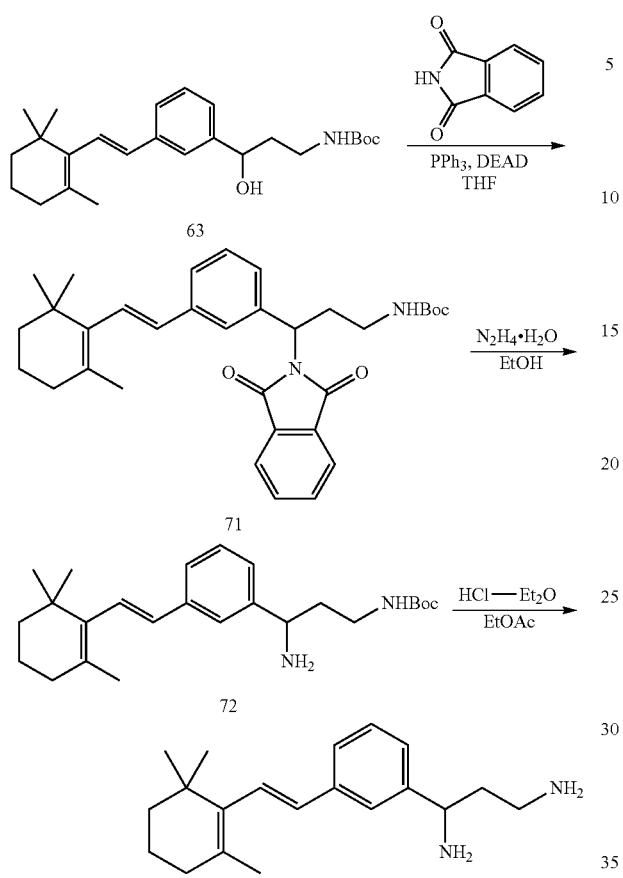

Step 1:

To a solution of alcohol 63 (0.2473 g, 0.62 mmol) in THF (7 mL) was added triphenylphosphine (0.3540 g, 135 mmol), phthalimide (0.2080 g, 1.41 mmol) and a solution of diethyl azodicarboxylate (0.2905 g, 1.67 mmol) in THF (3 mL). The reaction was stirred at room temperature for 5 min, then at 60° C. for 1 h. Additional triphenylphosphine (0.1369 g, 0.52 mmol), phthalimide (0.0974 g, 0.66 mmol) and diethyl azodicarboxylate (100 µL, 0.64 mmol) were added and the mixture was stirred at 50° C. overnight. The mixture was concentrated under reduced pressure. Purification by flash chromatography (10 to 70% EtOAc-hexanes gradient) provided phthalimide 71 as an oil. Yield 0.1659 g, 50%): $^1$H NMR (400 MHz, CDCl$_3$) δ 7.64-7.84 (m, 411), 7.48 (s, 1H), 7.41 (d, J=7.6 Hz, 1H), 7.34 (d, J=8.0 Hz, 1H), 7.24-7.29 (m, 1H), 6.67 (dd, J=16.0, 0.8 Hz, 1H), 6.30 (d, J=16.0 Hz, 1H), 5.41 (dd, J=10.0, 5.6 Hz, 1H), 4.72 (br s, 1H), 3.22-3.32 (m, 1H), 3.08-3.17 (m, 1H), 2.76-2.88 (m, 1H), 2.40-2.48 (m, 1H), 2.01 (t, J=6.0 Hz, 2H), 1.73 (s, 3H), 1.59-1.65 (m, 2H), 1.46-1.48 (m, 2H), 1.39 (s, 9H), 1.03 (s, 6H).

Step 2:

Phthalimide 71 was deprotected with hydrazine according to the method used in Example 32 except that the reaction was heated to reflux for 2.5 h. Purification by flash chromatography (7 M NH$_3$ in MeOH/EtOAc/hexanes 2:9:9) provided amine 72 as an oil. Yield 0.1719 g, 68%): NMR (400 MHz, CDCl$_3$) δ 7.26-7.31 (m, 3H), 7.13-7.17 (m, 1H), 6.68 (dd, J=16.0, 0.8 Hz, 1H), 6.32 (d, J=16.0 Hz, 1H), 4.99 (br s, 1H), 3.96 (dt J=6.0, 1.6 Hz, 1H), 3.15-3.27 (m, 211), 2.04 (t, J=6.4 Hz, 2H), 1.78-1.89 (m, 2H), 1.75 (s, 3H), 1.60-1.67 (m, 2H), 1.55 (br s, 2H), 1.41-1.51 (m, 11H), 1.06 (s, 6H).

Step 3:

To a solution of amine 72 in EtOAc (2 mL) was added a solution of HCl (20 mL of a 10 M solution in diethyl ether, 200 mmol). The reaction mixture was stirred at room temperature for 30 min then the solid was collected by filtration and washed with diethyl ether. The product was dried under vacuum to give Example 61 dihydrochloride as a white crystalline solid. Yield (0.0574 g, 62%): $^1$H NMR (400 MHz, DMSO-d$_6$) δ 8.72 (br s, 3H), 8.03 (br s, 3H), 7.76 (s, 1H), 7.37-7.47 (m, 3H), 6.83 (d, J=16.4 Hz, 1H), 6.35 (d, J=16.4 Hz, 1H), 4.39 (br s, 1H), 2.74-2.84 (m, 1H), 2.26-2.37 (m, 2H), 2.12-2.24 (m, 1H), 2.02 (t, J=6.4 Hz, 2H), 1.73 (s, 3H), 1.57-1.61 (m, 2H), 1.44-1.48 (m, 2H), 1.04 (s, 6H).

Example 62

Preparation of (E)-4,4,4-trifluoro-3-(3-(2-(2,6,6-trimethylcyclohex-1-enyl)vinyl)phenyl)butan-1-amine

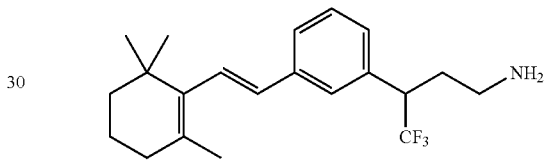

(E)-4,4,4-Trifluoro-3-(3-(2-(2,6,6-trimethylcyclohex-1-enyl)vinyl)phenyl)butan-1-amine was prepared according to Scheme 26.

SCHEME 26

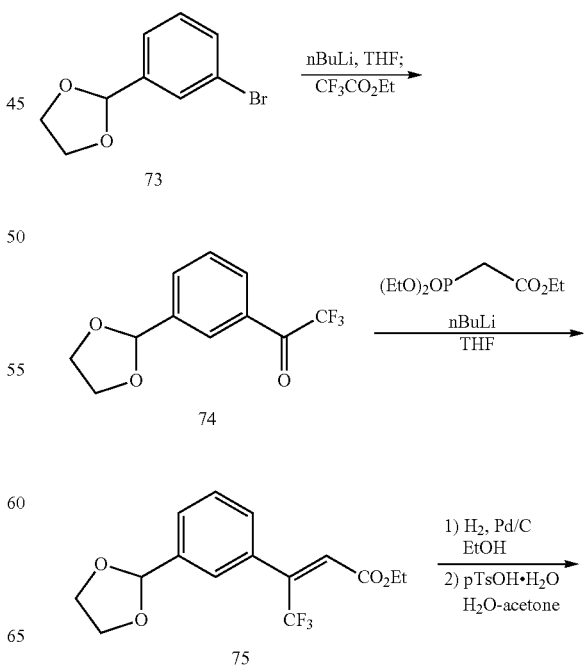

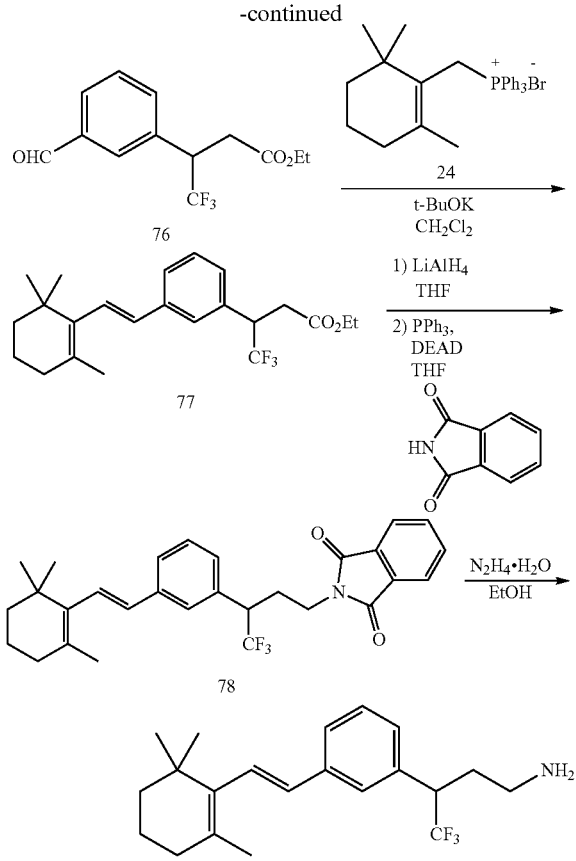

Step 1:

To a −78° C. solution of 2-(3-bromophenyl)-1,3-dioxolane (73) (2.29 g, 10.0 mmol) in THF (20 mL) under argon was added n-butyl lithium (7.5 mL of a 1.6 M solution in hexane, 12 mmol). The reaction mixture was stirred at −78° C. for 20 min then ethyl trifluoroacetate (2.2 mL, 18.0 mmol) was added rapidly. The reaction was allowed to warm to room temperature over 45 min then quenched with water. The mixture was partitioned between EtOAc and water and the combined organics were washed with brine, dried over $Na_2SO_4$ and concentrated under reduced pressure. Purification by flash chromatography (3 to 30% EtOAc-hexanes gradient) gave ketone 74 (contaminated with ~10% 73) as an oil. (1.83 g, 80%): $^1$H NMR (400 MHz, DMSO-$d_6$) δ 8.04-8.06 (m, 2H), 7.89 (dt, J=7.6, 1.2 Hz, 1H), 7.70 (dd, J=8.4, 7.6 Hz, 1H), 5.87 (s, 1H), 4.04-4.08 (m, 2H), 3.96-4.02 (m, 2H).

Step 2:

To an ice cold solution of triethyl phosphonoacetate (1.74 mL, 8.7 mmol) in THF under argon was added n-butyl lithium (6 mL of a 1.6 M solution in hexane, 9.6 mmol) over a ~5 min period. The reaction was allowed to warm to room temperature and stirred for 30 min. A solution of ketone 74 (1.80 g, 7.9 mmol) in THF (3 mL) was added dropwise and the reaction mixture was stirred for 5 h. The mixture was partitioned between EtOAc and water and the combined organics were dried over $Na_2SO_4$ and concentrated under reduced pressure. Purification by flash chromatography (7 to 60% EtOAc-hexanes gradient) gave alkene 75 (~9:1 isomer ratio) as a colorless oil. (Yield 1.62 g, 65%); trans-isomer: $^1$H NMR (400 MHz, DMSO-$d_6$) δ 7.52 (dt, J=6.4, 1.2 Hz, 1H), 7.44-7.48 (m, 1H), 7.29-7.31 (m, 2H), 6.89 (d, J=1.2 Hz, 1H), 5.74 (s, 1H), 4.02-4.05 (m, 2H), 3.92-4.00 (m, 4H), 0.93 (t, J=7.2 Hz, 3H).

Step 3:

To a degassed solution of alkene 75 in EtOH (abs, 20 mL) under argon was added 10% Pd/C (~20 mg). The reaction was placed under $H_2$ atmosphere and stirred for 5 h. The mixture was degassed, filtered through Celite, and the filtrate was concentrated under reduced pressure. Ethyl 3-(3-(1,3-dioxolan-2-yl)phenyl)-4,4,4-trifluorobutanoate was isolated as a colorless oil and used in the next synthetic step without purification. Yield (0.92 g, 97%): $^1$H NMR (400 MHz, DMSO-$d_6$) δ 7.39-7.46 (m, 4H), 5.71 (s, 1H), 3.94-4.04 (m, 7H), 2.95-3.09 (m, 2H), 1.03 (t, J=6.8 Hz, 3H).

Step 4:

To a solution of ethyl 3-(3-(1,3-dioxolan-2-yl)phenyl)-4,4,4-trifluorobutanoate (0.92 g, 2.89 mmol) in acetone (7 mL) and water (3 mL) was added p-toluenesulfonic acid (0.050 g, 0.26 mmol). The mixture was stirred at room temperature for 2.5 h then the volatiles were removed by concentration under reduced pressure. The residue was partitioned between EtOAc and water and the combined organics were washed with saturated aqueous $NaHCO_3$, water and brine. The solution was dried over a mixture of $MgSO_4$ and $Na_2SO_4$ and concentrated under reduced pressure. Purification by flash chromatography (7 to 60% EtOAc-hexanes gradient) gave aldehyde 76 as a colorless oil. Yield (0.589 g, 74%): $^1$H NMR (400 MHz, DMSO-$d_6$) δ 10.00 (s, 1H), 7.97 (s, 1H), 7.89 (dt, J=7.6, 1.2 Hz, 1H), 7.79 (d, J=8.0 Hz, 1H), 7.62 (t, J=7.6 Hz, 1H), 4.20-4.31 (m, 1H), 3.90-4.02 (m, 2H), 3.09-3.11 (m, 2H), 1.03 (t, J=6.8 Hz, 3H).

Step 5:

Aldehyde 76 was coupled with phosphonium salt 24 according to the method used in Example 46 except that the initial addition of potassium tert-butoxide was conducted at −78° C. instead of 0° C. After stirring overnight, the reaction mixture was concentrated under reduced pressure and the residue was partitioned between EtOAc and water. The combined organics were washed with brine, dried over $MgSO_4$ and concentrated under reduced pressure. Purification by flash chromatography (7 to 60% EtOAc-hexanes gradient) gave alkene 77 as a colorless oil. Yield (0.833 g, 98%): $^1$H NMR (400 MHz, DMSO-$d_6$) δ 7.51 (s, 1H), 7.45 (d, J=7.6 Hz, 1H), 7.31 (t, J=7.6 Hz, 1H), 7.25 (d, J=7.6 Hz, 1H), 6.76 (d, J=16.8 Hz, 1H), 6.34 (d, J=16.4 Hz, 1H), 3.93-4.09 (m, 3H), 2.98-3.10 (m, 2H), 2.01 (t, J=6.4 Hz, 2H), 1.72 (s, 3H), 1.55-1.61 (m, 214), 1.43-1.46 (m, 2H), 1.03-1.07 (m, 911).

Step 6:

To an ice-cold solution of alkene 77 (0.522 g, 1.32 mmol) in THF (10 mL) under argon was added a solution of $LiAlH_4$ (0.75 mL of a 2.0 M solution in THF, 1.5 mmol). The reaction was stirred at 0° C. for 30 min then diluted with diethyl ether and quenched with saturated aqueous $Na_2SO_4$. The solution was dried over $Na_2SO_4$ and $MgSO_4$ and filtered through Celite. The filtrate was concentrated under reduced pressure to give (E)-4,4,4-trifluoro-3-(3-(2-(2,6,6-trimethylcyclohex-1-enyl)vinyl)phenyl)butan-1-01 as a colorless oil. This compound was used in the next synthetic step without purification. Yield (0.470 g, quant.): $^1$H NMR (400 MHz, DMSO-$d_6$) δ 7.48 (d, J=7.6 Hz, 1H), 7.41 (s, 1H), 7.34 (t, J=7.6 Hz, 1H), 7.21 (d, J=7.6 Hz, 1H), 6.75 (d, J=16.4 Hz, 1H), 6.35 (d, J=16.4 Hz, 1H), 4.61 (dt, J=5.2, 0.4 Hz, 1H), 3.71 (ddd, J=9.6, 9.6, 4.4 Hz, 1H), 3.33-3.40 (m, 1H), 3.10-3.18 (m, 1H), 2.00-2.07 (m, 4H), 1.73 (s, 3H), 1.56- 1.62 (m, 2H), 1.44-1.47 (m, 2H), 1.04 (s, 6H).

Step 7:

To an ice-cold solution of (E)-4,4,4-trifluoro-3-(3-(2-(2,6,6-trimethylcyclohex-1-enyl)vinyl)phenyl)butan-1-ol (0.470 g, 1.32 mmol) in THF (10 mL) was added phthalimide (0.200 g, 1.35 mmol), triphenylphosphine (0.354 g, 1.35 mmol) and diethyl azodicarboxylate (0.213 mL, 1.35 mmol). The mixture was allowed to warm to room temperature and stirred for 48 h. The mixture was concentrated under reduced pressure and the residue was purified by flash chromatography (7 to 60% EtOAc-hexanes gradient) to give phthalimide 78 as a colorless oil. Yield (0.479 g, 75%): $^1$H NMR (400 MHz, DMSO-$d_6$) δ 7.72-7.78 (m, 4H), 7.39 (s, 1H), 7.29 (d, J=7.6 Hz, 1H), 7.24 (t, J=7.6 Hz, 1H), 7.17 (d, J=7.6 Hz, 1H), 6.71 (d, J=16.4 Hz, 1H), 6.28 (d, J=16.4 Hz, 1H), 3.72-3.81 (m, 1H), 3.46-3.59 (m, 2H), 2.26-2.33 (m, 2H), 2.02 (t, J=6.0 Hz, 2H), 1.74 (s, 3H), 1.56-1.62 (m, 2H), 1.44-1.47 (m, 2H), 1.06 (s, 6H).

Step 8:

To a solution of phthalimide 78 (0.475 g, 1.0 mmol) in EtOH (abs., 10 mL) was added hydrazine hydrate (0.145 mL, 3.0 mmol). The reaction was stirred at 70° C. overnight under argon. After cooling to room temperature, the reaction mixture was concentrated under reduced pressure. The residue was suspended in EtOAc, dried over MgSO$_4$, sonicated, and the solids were removed by filtration. The filtrate was concentrated under reduced pressure. A mixture of EtOAc-hexanes (50%) was added to the residue and the solids were removed by filtration. The filtrate was concentrated under reduced pressure to give Example 62 as a colorless oil. (Yield 0.322 g, 92%): $^1$H NMR (400 MHz, DMSO-d$_6$) δ 7.46 (d, J=7.6 Hz, 1H), 7.42 (s, 1H), 7.32 (t, J=7.6 Hz, 1H), 7.20 (d, J=7.6 Hz, 1H), 6.74 (d, f=16.4 Hz, 1H), 6.34 (d, J=16.4 Hz, 1H), 3.71-3.77 (m, 1H), 2.42-2.45 (m, 1H), 2.24-2.31 (m, 1H), 2.01 (t, J=6.0 Hz, 2H), 1.90-1.96 (m, 2H), 1.72 (s, 3H), 1.55-1.61 (m, 4H), 1.43-1.46 (m, 2H), 1.04 (s, 6H).

Example 63

Preparation of (E)-3-methoxy-N-methyl-3-(3-(2-(2,6,6-trimethylcyclohex-1-enyl)vinyl)phenyl)propan-1-amine

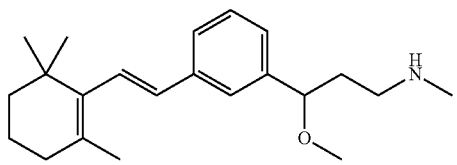 [SMILES: CNCCC(OC)c1cccc(/C=C/C2=C(C)CCCC2(C)C)c1]

(E)-3-Methoxy-N-methyl-3-(3-(2-(2,6,6-trimethylcyclohex-1-enyl)vinyl)phenyl)propan-1-amine was prepared according to Scheme 27.

Step 1:

To a solution of alcohol 63 (0.2586 g, 0.65 mmol) in DMSO (3 mL) was added iodomethane (0.07 mL, 1.12 mmol) and powdered KOH (0.0989 g, 1.76 mmol). The reaction was stirred at room temperature for 35 min then partitioned between EtOAc and water. The combined organics were washed with brine, dried over MgSO$_4$ and concentrated under reduced pressure. Purification by flash chromatography (10 to 30% EtOAc-hexanes gradient) afforded methyl amine 79 (0.0511 g, 18% yield) and ether 80 (0.1074 g, 40% yield) as oils.

Compound 79: $^1$H NMR (400 MHz, CDCl$_3$) δ 7.28-7.34 (m, 3H), 7.13 (d, J=7.2 Hz, 1H), 6.69 (d, J=16.4 Hz, 1H), 6.34 (d, J=16.4 Hz, 1H), 4.10 (dd, J=8.4, 4.8 Hz, 1H), 3.35 (br s, 2H), 3.23 (s, 3H), 2.85 (br s, 3H), 2.04 (t, J=6.0 Hz, 2H), 1.85-1.98 (m, 2H), 1.76 (s, 3H), 1.61-1.67 (m, 2H), 1.48-1.51 (m, 2H), 1.43 (s, 9H), 1.07 (s, 6H).

Compound 80: $^1$H NMR (400 MHz, CDCl$_3$) δ 7.28-7.34 (m, 3H), 7.13 (dt, J=7.2, 1.6 Hz, 1H), 6.69 (dd, J=16.4, 0.8 Hz, 1H), 6.33 (d, J=16.4 Hz, 1H), 4.19 (dd, J=8.4, 4.8 Hz, 1H), 3.18-3.22 (m, 5H), 2.04 (t, J=6.0 Hz, 2H), 1.83-1.96 (m, 2H), 1.76 (s, 3H), 1.60-1.67 (m, 2H), 1.48-1.51 (m, 2H), 1.44 (s, 9H), 1.07 (s, 6H).

Step 2:

Methyl amine 79 was deprotected according to the method used in Example 45. Purification by flash chromatography (2:9:9 (7 M NH$_3$ in MeOH)/EtOAc/hexanes) afforded Example 63 as an oil in 80% purity. Yield (0.0349 g, 83%): $^1$H NMR (400 MHz, CDCl$_3$) δ 7.26-7.34 (m, 3H), 7.14 (dt, J=7.2, 1.6 Hz, 1H), 6.70 (dd, J=16.4, 0.8 Hz, 1H), 6.33 (d, J=16.4 Hz, 1H), 4.23 (dd, J=8.0, 5.2 Hz, 1H), 3.23 (s, 3H), 2.68 (t, J=6.8 Hz, 1H), 2.43 (s, 3H), 1.96- 2.05 (m, 4H), 1.79-1.89 (m, 1H), 1.76 (s, 3H), 1.61-1.67 (m, 21-1), 1.41-1.50 (m, 2H), 1.06 (s, 6H).

SCHEME 27

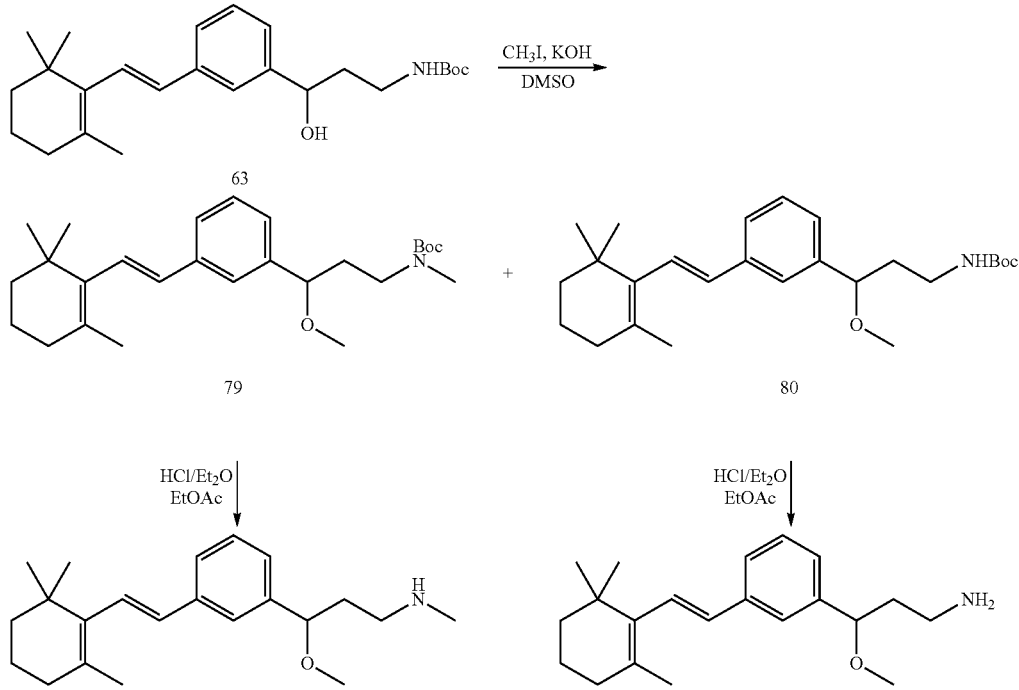

Example 64

Preparation of (E)-3-methoxy-3-(3-(2-(2,6,6-trimethylcyclohex-1-enyl)vinyl)phenyl)propan-1-amine

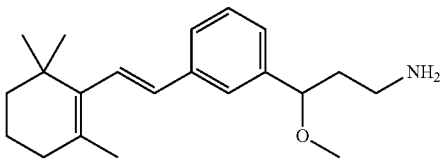 [SMILES: COC(CCN)c1cccc(/C=C/C2=C(C)CCCC2(C)C)c1]

(E)-3-Methoxy-3-(3-(2-(2,6,6-trimethylcyclohex-1-enyl)vinyl)phenyl)propan-1-amine was prepared according to Scheme 27. Step 1: Methyl amine 80 was deprotected according to the method used in Example 45. Purification by flash chromatography (7 M NH$_3$ in MeOH)/EtOAc/hexane 2:9:9) afforded Example 64 as an oil in 80% purity. Yield (0.0708 g, quant.): $^1$H NMR (400 MHz, CDCl$_3$) δ 7.25-7.34 (3H), 7.13-7.18 (m, 1H), 6.69 (dd, J=16.4, 0.8 Hz, 1H), 6.33 (d, J=16.4 Hz, 1H), 4.24 (dd, J=8.4, 5.2 Hz, 1H), 3.23 (s, 3H), 2.82 (t, J=6.8 Hz, 2H), 2.04 (t, J=8.4 Hz, 2H), 1.94-2.00 (m, 1H), 1.85 (s, 3H), 1.77-1.83 (m, 1H), 1.61-1.67 (m, 2H), 1.47-1.50 (m, 2H), 1.06 (s, 6H).

Example 65

Preparation of (E)-4-(3-(2-(2,6,6-trimethylcyclohex-1-enyl)vinyl)phenyl)butan-2-amine

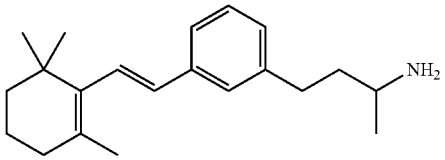 [SMILES: CC1=C(/C=C/c2cccc(CCC(C)N)c2)C(C)(C)CCC1]

(E)-4-(3-(2-(2,6,6-Trimethylcyclohex-1-enyl)vinyl)phenyl)butan-2-amine was prepared according to Scheme 28.

SCHEME 28

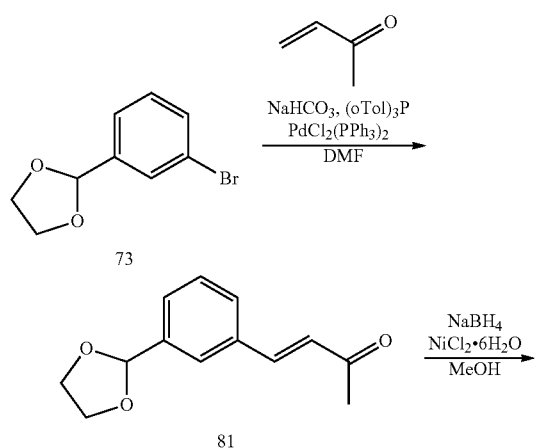

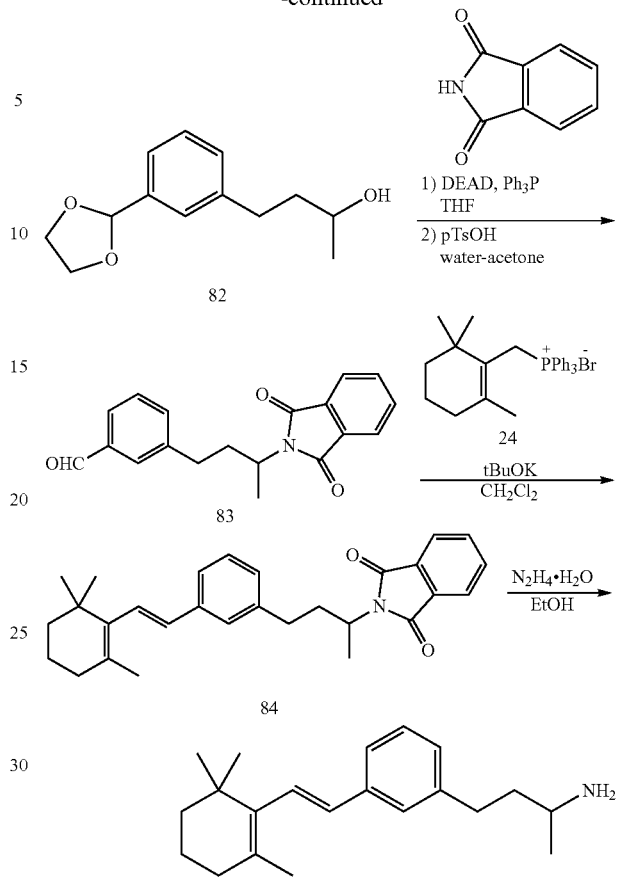

Step 1:

A solution of aryl bromide 73 (2.0 g, 8.8 mmol), 3-buten-2-one (0.926 g, 13.2 mmol), NaHCO$_3$ (1.4 g, 13.2 mmol), PdCl$_2$(PPh$_3$)$_2$ (0.309 g, 0.44 mmol) and tri(o-tolyl)phosphine (0.134 g, 0.44 mmol) in DMF (10 mL) was heated to reflux under argon for 2 h. After cooling to room temperature, solids were removed by filtration. The filtrate was diluted with CH$_2$Cl$_2$ and water. The combined organics were washed with water and brine, dried over MgSO$_4$ and concentrated under reduced pressure. Purification by flash chromatography (20 to 50% EtOAc-hexanes gradient) afforded alkene 81 as a yellow oil. Yield (1.5 g, 79%): $^1$H NMR (400 MHz, CDCl$_3$) δ 7.67-7.69 (m, 1H), 7.50-7.55 (m, 3H), 7.43 (t, J=7.6 Hz, 1H), 6.74 (t, J=16.2 Hz, 1H), 5.82 (s, 1H), 4.01-4.16 (m, 4H), 2.38 (s, 3H).

Step 2:

To a solution of alkene 81 (1.5 g, 6.9 mmol) in MeOH (90 mL) was added NiCl$_2$.H$_2$O (0.894 g, 6.9 mmol) then NaBH$_4$ (0.778 g, 20.6 mmol) portionwise. The mixture was stirred at room temperature for 15 min then the solids were removed by filtration. The filtrate was concentrated under reduced pressure and the residue was partitioned between CH$_2$Cl$_2$ and saturated aqueous NH$_4$Cl. The combined organics were dried over MgSO$_4$ and concentrated under reduced pressure. Purification by flash chromatography (20 to 50% EtOAc-hexanes gradient) provided alcohol 82 as a colorless oil. Yield (0.911 g, 60%).

Step 3:

Alcohol 82 was coupled with phthalimide according to the general method used in Example 32 to give 2-(4-(3-(1,3-dioxolan-2-yl)phenyl)butan-2-yl)isoindoline-1,3-dione as a white oily solid containing 10% phthalimide. Yield (0.686 g, 67%): $^1$H NMR (400 MHz, CDCl$_3$) δ 7.79 (dd, J=6.6, 2.8 Hz, 2H), 7.69 (dd, J=6.6, 2.8 Hz, 2H), 7.20-7.26 (m, 3H), 7.16-7.30 (m, 1H), 5.74 (s, 1H), 4.38-4.45 (m, 1H), 4.01-4.11 (m, 4H), 2.43-2.68 (m, 3H), 2.00-2.06 (m, 1H), 1.48 (d, J=6.8 Hz, 3H).

Step 4:

2-(4-(3-(1,3-Dioxolan-2-yl)phenyl)butan-2-yl)isoindoline-1,3-dione was deprotected according to the method used in Example 62 to give aldehyde 83 as a colorless oil. This compound was used in the next synthetic step without purification. Yield (0.544 g, quant.): $^1$H NMR (400 MHz, DMSO-d$_6$) δ 9.88 (s, 1H), 7.76-7.81 (m, 4H), 7.64 (s, 1H), 7.58 (dt, J=7.2, 1.2 Hz, 1H), 7.47 (dt, J=7.6, 1.2 Hz, 1H), 7.40 (t, J=7.6 Hz, 1H). 4.22-4.27 (m, 1H), 2.57-2.70 (m, 2H), 2.31-2.41 (m, 1H), 1.99-2.06 (m, 1H), 1.39 (d, J=7.2 Hz, 3H).

Step 5:

Aldehyde 83 was coupled with phosphonium salt 24 following the procedure in Example 44 except that the reaction mixture was stirred at room temperature for 3 h. Solids were removed by filtration through a pad of silica gel. The filtrate was concentrated under reduced pressure and the residue was purified by flash chromatography (0 to 20% EtOAc-hexanes gradient) to give alkene 84 as an oil. Yield (0.568 g, 75%): $^1$H NMR (400 MHz, DMSO-d$_6$) δ 7.74-7.81 (m, 4H), 7.18 (br s, 1H), 7.10-7.11 (m, 2H), 6.95-6.97 (m, 1H), 6.62 (dd, J=16.0, 0.8 Hz, 1H), 6.22 (d, J=16.0 Hz, 1H), 4.21-4.27 (m, 1H), 2.49-2.59 (m, 1H), 2.33-2.48 (m, 2H), 1.94-2.01 (m, 3H), 1.70 (s, 3H), 1.54-1.60 (m, 2H), 1.42-1.45 (m, 211), 1.40 (d, J=5.6 Hz, 3H), 1.00 (s, 6H).

Step 6:

To a solution of alkene 84 (0.500 g, 1.2 mmol) in EtOH (5 mL) was added hydrazine hydrate (0.30 g, 6.0 mmol). The reaction mixture was heated at 50-60° C. for 2 h. After cooling to room temperature, the mixture was concentrated under reduced pressure. The residue was partitioned between CH$_2$Cl$_2$ and water and the combined organics were dried over MgSO$_4$ and concentrated under reduced pressure. The crude material was purified by filtration through a pad of silica gel (0-5% MeOH—CH$_2$Cl$_2$ then 5% 7 M NH$_3$ in MeOH—CH$_2$Cl$_2$) to give Example 65 as a yellow oil. Yield (0.1970 g, 56%), trans-/cis-isomer ratio 15.6:1. Trans-isomer: $^1$H NMR (400 MHz, DMSO-d$_6$) δ 7.24-7.27 (m, 2H), 7.20 (t, J=8.0 Hz, 1H), 7.03 (d, J=7.2 Hz, 1H), 6.68 (d, J=16.4 Hz, 1H), 6.29 (d, J=16.0 Hz, 11-1), 2.76-2.77 (m, 1H), 2.56-2.59 (m, 2H), 2.0 (t, J=6.1 Hz, 2H), 1.70 (s, 3H), 1.40-1.64 (m, 6H), 0.99-1.02 (m, 9H).

Example 66

Preparation of (E)-1-amino-3-(3-(2-(2,6,6-trimethylcyclohex-1-enyl)vinyl)phenyl)propan-2-ol

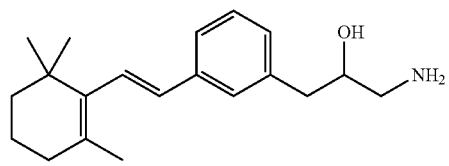 [SMILES: CC1=C(/C=C/c2cccc(CC(O)CN)c2)C(C)(C)CCC1]

(E)-1-Amino-3-(3-(2-(2,6,6-trixnethylcyclohex-1-enyl)vinyl)phenyl)propan-2-ol was prepared according to Scheme 29.

SCHEME 29

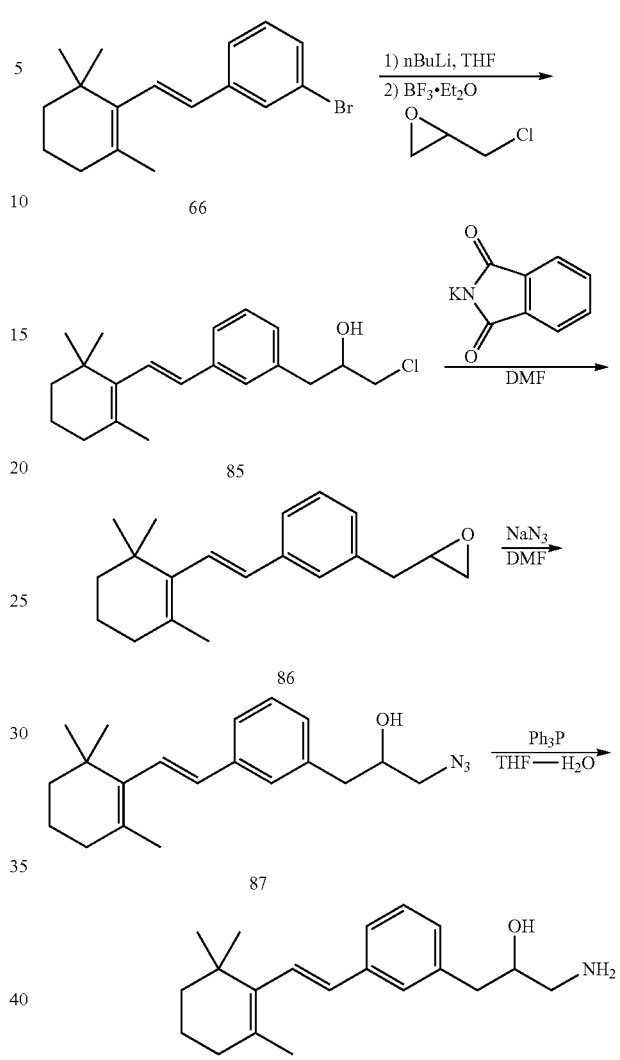

Step 1:

To a −78° C. solution of aryl bromide 66 (0.50 g, 1.64 mmol) in THF (4 mL) was added n-butyl lithium (1.1 mL of a 1.6 M solution in hexanes, 1.76 mmol) dropwise. The mixture was stirred for 10 min then BF$_3$-diethyl etherate (0.23 mL, 1.8 mmol) was added dropwise. After stirring for 3 min, a solution of epichlorohydrin (0.11 mL, 1.4 mmol) in THF (1 mL) was added dropwise over 3 min. The reaction mixture was stirred for 45 min at −78° C. then quenched with the dropwise addition of water. After warming to room temperature, the mixture was partitioned between MTBE and water. The combined organics were washed with water and brine, dried over Na$_2$SO$_4$ and concentrated under reduced pressure. Purification by flash chromatography (1:8 EtOAc:heptane) gave chlorohydrin 85. Yield (0.24 g, 57%): $^1$H NMR (400 MHz, CDCl$_3$) δ 7.28-7.31 (m, 2H), 7.22 (t, J=8.0 Hz, 1H), 7.07 (d, J=8.0 Hz, 1H), 6.69 (dd, J=16.4, 0.8 Hz, 1H), 6.30 (d, J=16.4 Hz, 1H), 5.16 (d, J=5.2 Hz, 1H), 3.86-3.89 (m, 1H), 3.56 (dd, J=10.8, 4.8 Hz, 1H), 3.47 (dd, J=10.8, 5.6 Hz, 1H), 2.79 (dd, J=13.6, 5.2 Hz, 1H), 2.65 (dd, J=13.6, 5.2 Hz, 1H), 2.00 (t, J=6.0 Hz, 2H), 1.71 (s, 3H), 1.55-1.62 (m, 2H), 1.43-1.46 (m, 2H), 1.03 (s, 6H).

Step 2:

To a solution of chlorohydrin 85 (0.22 g, 0.69 mmol) in DMF (5 mL) was added potassium phthalimide (0.128 g, 0.69 mmol) and the mixture was heated at 60° C. for 18 h. After cooling to room temperature, the mixture was partitioned between MTBE and water. The combined organics were washed with water, 5% aqueous LiCl and brine, dried over $Na_2SO_4$ and concentrated under reduced pressure. Purification by flash chromatography (0-5% then 30% EtOAc-heptane) provided epoxide 86 as a colorless oil. Yield (0.07 g, 36%): $^1$H NMR (400 MHz, CDCl$_3$) δ 7.26-7.33 (m, 3H), 7.12 (d, J=6.9 Hz, 1H), 6.69 (dd, J=16.2, 0.8 Hz, 1H), 6.34 (d, J=16.4 Hz, 1H), 3.16-3.20 (m, 1H), 2.93 (dd, J=14.4, 5.6 Hz, 1H), 2.80-2.84 (m, 2H), 2.59 (dd, J=4.8, 2.8 Hz, 1H), 2.05 (t, J=6.0 Hz, 2H), 1.78 (s, 3H), 1.62-1.70 (m, 2H), 1.49-1.52 (m, 2H), 1.08 (s, 6H).

Step 3:

To a solution of epoxide 86 (0.07 g, 0.25 mmol) in DMF (5 mL) was added NaN$_3$ (0.032 g, 0.49 mmol) and the mixture was heated at 65° C. for 15 h. Additional NaN$_3$ (0.032 g, 0.49 mmol) was added and the mixture was heated at 85° C. for 2 h. After cooling to room temperature, the mixture was partitioned between EtOAc and water. The combined organics were washed with water, 5% aqueous LiCl and brine, dried over Na$_2$SO$_4$ and concentrated under reduced pressure to give azide 87. This material was taken on to the next synthetic step without further purification. Yield (0.07 g, 87%).

Step 4:

To a solution of azide 87 in THF (3 mL) was added triphenylphosphine (0.059 g, 0.22 mmol) and water (1 mL). The reaction mixture was stirred at room temperature for 2 h then heated to reflux for 2 h. After cooling to room temperature, the mixture was partitioned between EtOAc and water. The combined organics were washed with water and brine, dried over Na$_2$SO$_4$ and concentrated under reduced pressure. Purification by flash chromatography (20% EtOAc-hexanes then 2:28:70 concentrated aqueous NH$_4$OH:EtOH:CH$_2$Cl$_2$) gave Example 66 as a colorless oil. Yield (0.0235 g, 31% for two steps): $^1$H NMR (400 MHz, DMSO-d$_6$) δ 7.19-7.28 (m, 3H), 7.06 (d, J=7.6 Hz, 1H), 6.68 (d, J=16.4 Hz, 1H), 6.29 (d, J=16.4 Hz, 1H), 4.75 (br s, 1H), 4.48 (br s, 2H), 3.62-3.70 (m, 1H), 2.58-2.71 (m, 4H), 2.00 (t, J=6.0 Hz, 2H), 1.71 (s, 3H), 1.57-1.60 (m, 2H), 1.43-1.46 (m, 2H), 1.03 (s, 6H).

Example 67

Preparation of (E)-2-fluoro-3-(3-((E/Z)-2-(2,6,6-trimethylcyclohex-1-enyl)vinyl)phenyl)prop-2-en-1-amine

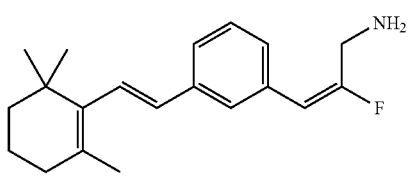 [SMILES: CC1=C(/C=C/c2cccc(/C=C(/F)CN)c2)C(C)(C)CCC1]

(E)-2-Fluoro-3-(3-((E/Z)-2-(2,6,6-trimethylcyclohex-1-enyl)vinyl)phenyl)prop-2-en-1-amine was prepared according to Scheme 30.

SCHEME 30

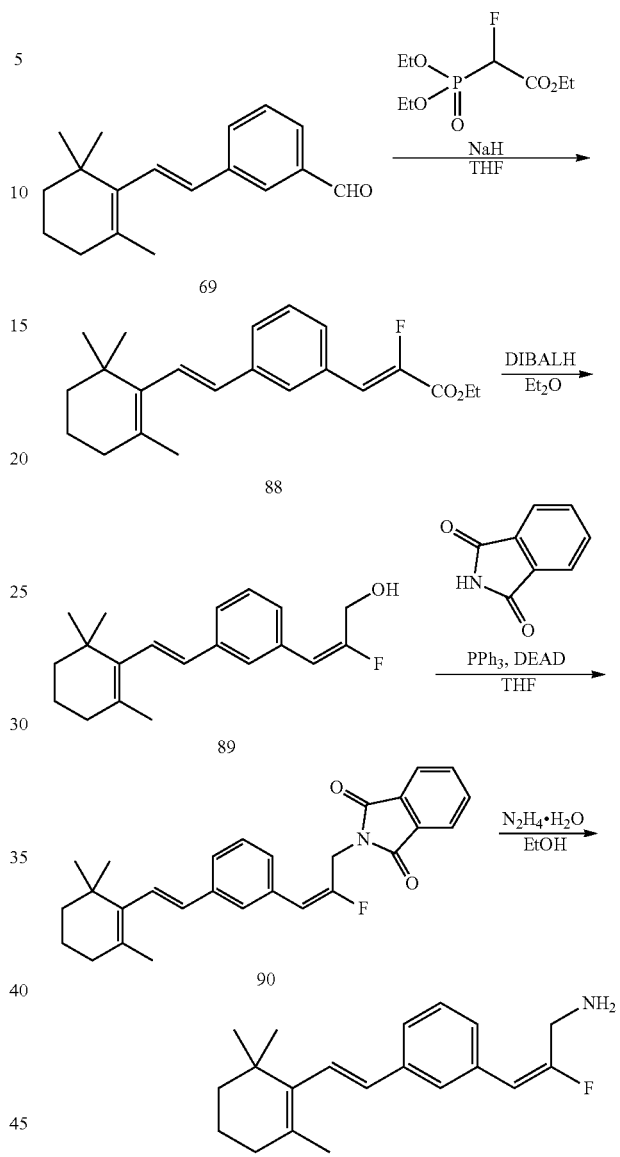

Step 1:

A solution of ethyl 2-(diethoxyphosphoryl)-2-fluoroacetate (0.5675 g, 2.34 mmol) in THF (5 mL) was added to a mixture of NaH (0.0652 g, 2.72 mmol) in THF (3 mL). The reaction mixture was stirred at room temperature for 10 min then cooled to −78° C. A solution of aldehyde 69 (0.3373 g, 1.33 mmol) in THF (7 mL) was added and the mixture was stirred for 1 h, 45 min. The mixture was allowed to warm to room temperature then heated at 60° C. overnight. A solution of ethyl 2-(diethoxyphosphoryl)-2-fluoroacetate (0.5 mL, 2.47 mmol) and NaH (0.0425 g, 1.77 mmol) in THF (5 mL) was added to the reaction mixture; the temperature was then increased to 70° C. and stirred overnight. After cooling to room temperature, the mixture was concentrated under reduced pressure and partitioned between hexanes and water. The combined organics were washed with brine, dried over MgSO$_4$ and concentrated under reduced pressure to give ester 88 as an oil. This material was used in the next synthetic step without purification. $^1$H NMR (400 MHz, CDCl$_3$) δ 7.46 (s, 1H), 7.30-7.38 (m, 3H), 6.92 (d, J=22.0 Hz, 1H), 6.69 (dd, J=16.4, 0.8 Hz, 1H), 6.33 (d, J=16.4 Hz, 1H), 4.25 (q, J=7.2 Hz, 2H), 2.05 (t, J=6.4 Hz, 2H), 1.76-1.77 (m, 3H), 1.62-1.68 (m, 2H), 1.49-1.52 (m, 2H), 1.23 (t, J=7.2 Hz, 3H), 1.07 (s, 6H).

Step 2:

To an ice-cold solution of ester 88 (~1.33 mmol) in diethyl ether (20 mL) was added a solution of diisobutyl aluminum hydride (DIBAL-H, 4 mL of a 1.0 M solution in THF, 4.0 mmol). The reaction was stirred at 0° C. overnight. After warming to room temperature, the mixture was partitioned between EtOAc and water. The combined organics were washed with saturated aqueous NH$_4$Cl and brine, dried over Na$_2$SO$_4$ and concentrated under reduced pressure. Purification by flash chromatography (10 to 50% EtOAc-hexanes gradient) gave alcohol 89 as an oil. Yield (0.1069 g, 27%): $^1$H NMR (400 MHz, CDCl$_3$) δ 7.26-7.35 (m, 3H), 7.10 (d, J=6.8 Hz, 1H), 6.70 (dd, J=16.4, 1.2 Hz, 1H), 6.41 (d, J=20.0 Hz, 1H), 6.33 (d, J=16.4 Hz, 1H), 4.39 (dd, J=21.6, 6.0 Hz, 2H), 2.05 (t, J=6.0 Hz, 2H), 1.89 (t, J=6.4 Hz, 1H), 1.76 (s, 3H), 1.62-1.68 (m, 2H), 1.48-1.51 (m, 2H), 1.07 (s, 6H).

Step 3:

To a solution of alcohol 89 (0.0969 g, 0.323 mmol), triphenylphosphine (0.1266 g, 0.48 mmol) and phthalimide (0.0580 g, 0.39 mmol) in THF (5 mL) was added a solution of diethyl azodicarboxylate (0.0880 g, 0.51 mmol) in THF 2 mL). The reaction was stirred at room temperature for 25 min then concentrated under reduced pressure. Purification by flash chromatography (6 to 50% EtOAc-hexanes gradient) gave phthalimide 90 as an oil. Yield (0.0847 g, 61%): $^1$H NMR (400 MHz, CDCl$_3$) δ 7.81-7.85 (m, 2H), 7.70-7.73 (m, 2H), 7.51 (s, 1H), 7.26-7.31 (m, 3H), 6.77 (dd, J=16.4, 0.8 Hz, 1H), 6.45 (d, J=22.0 Hz, 1H), 6.36 (d, J=16.4 Hz, 1H), 4.68 (d, J=15.6 Hz, 2H), 2.05 (t, J=6.4 Hz, 2H), 1.78 (s, 3H), 1.61-1.68 (m, 2H), 1.49-1.52 (m, 2H), 1.09 (s, 6H).

Step 4:

Phthalimide 90 was deprotected according to the method used in Example 32 except that the reaction was conducted at room temperature overnight. Example 67 was isolated as an oil. Yield (0.0544 g, 93%): $^1$H NMR (400 MHz, CDCl$_3$) δ 7.29-7.33 (m, 2H), 7.20 (s, 1H), 7.04 (dt, J=6.4, 1.6 Hz, 1H), 6.68 (dd, J=16.4, 0.8 Hz, 1H), 6.32 (d, J=16.4 Hz, 1H), 6.25 (d, J=22.0 Hz, 1H), 3.60 (d, J=21.6 Hz, 2H), 2.04 (t, J=6.4 Hz, 2H), 1.76 (s, 3H), 1.61-1.67 (m, 2H), 1.42-1.51 (m, 2H), 1.35 (br s, 2H), 1.09 (s, 6H).

Example 68

Preparation of (E)-3-(3-(2-(2,6,6-trimethylcyclohex-1-enyl)vinyl)phenyl)prop-2-yn-1-amine

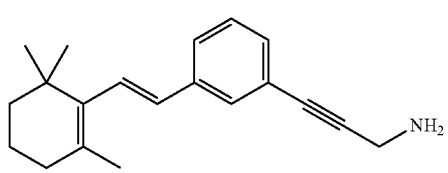 [SMILES: CC1=C(/C=C/c2cccc(C#CCN)c2)C(C)(C)CCC1]

(E)-3-(3-(2-(2,6,6-Trimethylcyclohex-1-enyl)vinyl)phenyl)prop-2-yn-1-amine was prepared according to Scheme 31.

SCHEME 31

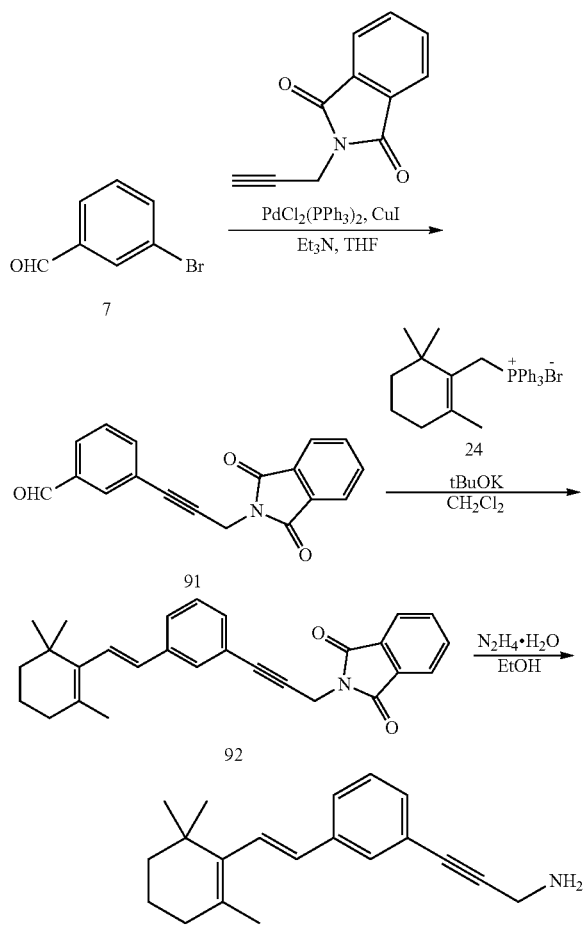

Step 1:

A solution of 2-(prop-2-ynyl)isoindoline-1,3-dione (1.85 g, 10.0 mmol) and 3-bromobenzaldehyde (1.16 mL, 10.0 mmol) in triethylamine (25 mL) and THF (25 mL) were degassed by bubbling with argon. PdCl$_2$(PPh$_3$)$_2$ (0.350 g, 0.05 mmol), and CuI (0.095 g, 0.5 mmol) were added and the mixture was degassed again then heated at 70° C. overnight. After cooling to room temperature, the mixture was diluted with EtOAc and the solids were removed by filtration. The filtrate was concentrated under reduced pressure and the residue was purified by flash chromatography (7 to 60% EtOAc-hexanes gradient) to give a light orange solid. This material was triturated with hexanes and the solids were removed by filtration. The filtrate was concentrated under reduced pressure to afford alkyne 91 as a light-yellow solid. (Yield 0.533 g, 18%): $^1$H NMR (400 MHz, DMSO-d$_6$) δ 9.98 (s, 1H), 7.88-7.96 (m, 6H), 7.76 (dt, J=7.6, 1.2 Hz, 1H), 7.60 (t, J=7.6 Hz, 1H), 4.68 (s, 2H).

Step 2:

Alkyne 91 was coupled with phosphonium salt 24 according to the method used in Example 44 except that the aldehyde was added neat and the reaction was stirred at room temperature for 30 min. The reaction mixture was partitioned between EtOAc and water and the combined organics were washed with water, dried over Na$_2$SO$_4$ and concentrated under reduced pressure. Purification by flash chromatography (7 to 60% EtOAc-hexanes gradient) gave alkene 92 as a light yellow foam. Yield (0.342 g, 83%): $^1$H NMR (400 MHz, DMSO-d$_6$) δ 7.84-7.92 (m, 4H), 7.53 (s, 1H), 7.51 (d, J=7.6 Hz, 1H), 7.23-7.31 (m, 2H), 6.77 (d, J=16.4 Hz, 1H), 6.33 (d, J=16.8 Hz, 1H), 4.62 (s, 2H), 1.99 (t, J=5.6 Hz, 2H), 1.68 (s, 3H), 1.52-1.59 (m, 2H), 1.41-1.44 (m, 2H), 1.00 (s, 6H).

Step 3:

Alkene 92 was deprotected according to the method used in Example 32 except that the reaction was heated at reflux for 3.5 h. After cooling to room temperature, the solids were removed from the mixture by filtration. The filtrate was concentrated under reduced pressure. The residue was suspended in hexanes and sonicated then solids were removed by filtration through Celite. The filtrate was concentrated under reduced pressure and the sonication/filtration procedure was repeated. Example 68 was isolated as an oil. Yield (0.196 g, 83%): NMR (400 MHz, DMSO-d$_6$) 7.43-7.47 (m, 2H), 7.29 (t, J=7.6 Hz, 1H), 7.20-7.23 (m, 1H), 6.74 (dd, J=16.4, 0.8 Hz, 1H), 6.32 (d, J=16.4 Hz, 1H), 3.48 (s, 2H), 2.00 (t, J=6.4 Hz, 1H), 1.79 (br s, 2H), 1.70 (s, 3H), 1.54-1.62 (m, 2H), 1.43-1.46 (m, 2H), 1.03 (s, 6H).

Example 69

Preparation of (E)-3-(3-(NON-4-en-5-yl)phenyl)propan-1-amine

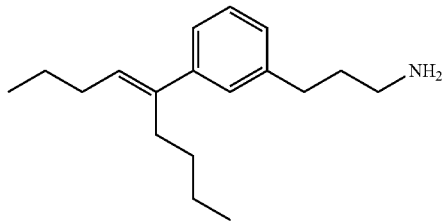 [SMILES: CCC/C=C(\CCCC)c1cccc(CCCN)c1]

(E)-3-(3-(Non-4-en-5-yl)phenyl)propan-1-amine was prepared according to Scheme 32.

SCHEME 32

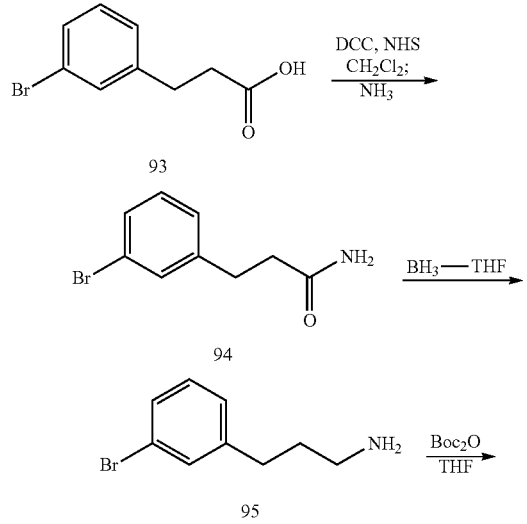

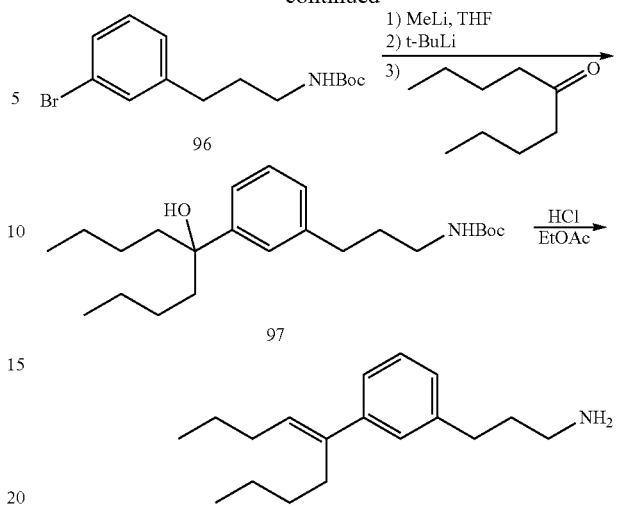

Step 1:

To a solution of 3-(3-bromophenyl)propionic acid (93) (5.0 g, 21.8 mmol) and N-hydroxysuccinimide (2.51 gr., 21.8 mmole) in CH$_2$Cl$_2$ (100 ml) was added dicyclohexylcarbodiimide (4.50 g, 21.8 mmol) and the mixture was stirred at room temperature for 45 min. The precipitate was removed by filtration and the filtrate was cooled in an ice bath. Ammonia gas was bubbled into the solution for 2 min then allowed to warm to room temperature overnight. The reaction mixture was concentrated under reduced pressure and the residue was dissolved in EtOAc. This solution was washed with saturated aqueous NaHCO$_3$ and brine, dried over Na$_2$SO$_4$ and concentrated under reduced pressure to an oil which was triturated with hexanes. The product was collected by filtration to give 3-(3-bromophenyl)propionamide (94) as a white solid. This material was taken on to the next synthetic step without further purification. Yield (4.62 g, 93%): NMR (400 MHz, DMSO-d$_6$) δ 7.40 (s, 1H), 7.35 (dt, J=6.4, 2.4 Hz, 1H), 7.26 (br s, 1H), 7.18-7.24 (m, 2H), 6.75 (br s, 1H), 2.78 (t, J=7.6 Hz, 2H), 2.34 (t, J=7.6 Hz, 2H).

Step 2:

To a solution of 3-(3-bromophenyl)propionamide (94) (4.5 g, 19.7 mmol) in THF (50 ml) under argon was added BH$_3$-THF complex (39.4 mL of a 1.0 M solution in THF, 39.4 mmol) and the mixture was stirred at room temperature for 18 h. The reaction was quenched with the cautious addition of 6 M HCl to pH 1. After stirring 4 h the solution was adjusted to pH>10 with the addition of 50% aqueous NaOH. This aqueous solution was extracted with EtOAc. The combined organics were washed with brine, dried over Na$_2$SO$_4$ and concentrated under reduced pressure to give 3-(3-bromophenyl)propan-1-amine (95) as an oil. This material was used in the next synthetic step without purification. $^1$H NMR (400 MHz, DMSO-d$_6$) δ 7.40 (s, 1H), 7.35 (dt, J=6.4, 2.4 Hz, 1H), 7.26 (br s, 1H), 7.18-7.24 (m, 2H), 6.75 (br s, 1H), 2.78 (t, J=7.6 Hz, 2H), 2.34 (t, J=7.6 Hz, 2H).

Step 3:

To a solution of amine 95 (~19.7 mmol) in THF (50 mL) was added di-tert-butyl dicarbonate (4.74 g, 21.7 mmol) and the mixture was stirred at room temperature for 3 h. The mixture was then concentrated under reduced pressure and purified by flash chromatography (30% diethyl ether-hexanes) to give aryl bromide 96 as an oil. (Yield 3.62 g, 58% for two steps): $^1$H NMR (400 MHz, DMSO-d$_6$) δ 7.33 (s, 1H), 7.26-7.34 (m, 1H), 7.08-7.20 (m, 2H), 4.55 (br s, 1H), 3.15 (q, J=6 Hz, 2H), 2.61 (t, J=8.0 Hz, 2H), 1.79 (quint, J=7.6 Hz, 2H), 1.44 (s, 9H).

Step 4:

To a −78° C. solution of aryl bromide 96 (0.650 g, 2.07 mmol, crude) in anhydrous THF (20 mL) was added MeLi (1.36 mL of a 1.6 M solution in diethyl ether, 2.17 mmol) and the mixture was stirred for 10 min. tert-Butyl lithium (2.5 mL of a 1.7 M solution in pentane, 4.24 mmol) was added and the reaction mixture was stirred at −78° C. for 45 min followed by the addition of 5-nonanone (0.324 g, 2.28 mmol). After allowing the mixture to warm to room temperature, the reaction was quenched with the addition of saturated aqueous NH$_4$Cl (15 mL) and the pH was adjusted to 5 with 1M HCl. The mixture was extracted with EtOAc and the combined organics were dried over Na$_2$SO$_4$ and concentrated under reduced pressure to give alcohol 97 as an oil. Yield (0.090 g, 12%): $^1$H NMR (400 MHz, DMSO-d$_6$) δ 7.14-7.19 (m, 3H), 6.97 (d, J=8.0 Hz, 1H), 6.87 (t, J=4.0 Hz, 1H), 4.48 (s, 1H), 2.92 (q, J=8.0 Hz, 2H), 2.53 (t, J=8.0 Hz, 2H), 1.59-1.74 (m, 6H), 1.37 (s, 9H), 1.15-1.23 (m, 6H), 0.84-0.91 (m, 2H), 0.77 (t, J=8.0 Hz. 6H).

Step 5:

A solution of alcohol 97 (0.081 g, 0.215 mmol) in HCl (2 mL of a 4.2 M solution in EtOAc, 8.4 mmol) was stirred at room temperature overnight then concentrated under reduced pressure. Example 69 hydrochloride was obtained as an oil. (Yield 0.066 g, quant.): $^1$H NMR (400 MHz, DMSO-d$_6$) δ 7.94 (br s, 3H), 7.11-7.37 (m, 3H), 7.07 (d, J=8.0 Hz, 1H), 5.63 (t, J=8.0 Hz, 1H), 2.77-2.80 (m, 2H), 2.64 (t, J=8.0 Hz, 2H), 2.47 (t, J=8.0 Hz, 2H), 2.15 (q, J=8.0 Hz, 2H), 1.81-1.91 (m, 2H), 1.44 (q, J=8.0 Hz, 2H), 1.17-1.27 (m, 4H), 0.93 (t, J=8.0 Hz, 3H), 0.83 (t, J=8.0 Hz, 3H).

Example 70

Preparation of (E)-2-(3-(3-aminopropyl)styryl)phenol

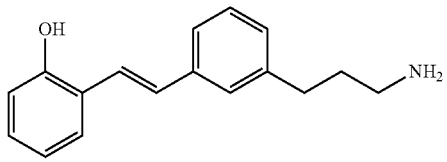 [SMILES: NCCCc1cccc(/C=C/c2ccccc2O)c1]

(E)-2-(3-(3-Aminopropyl)styryl)phenol was prepared according to Scheme 15 with modifications.

Step 1:

2-Hydroxybenzyltriphenylphosphonium bromide was coupled with phthalimide 29 according to the method used in Example 45 except that the reaction was stirred at room temperature overnight. The reaction mixture was then concentrated under reduced pressure and partitioned between EtOAc and water. The combined organics were washed with saturated aqueous NH$_4$Cl and water, dried over Na$_2$SO$_4$ and concentrated under reduced pressure. Purification by flash chromatography (5 to 60% EtOAc-hexanes gradient) gave (E)-2-(3-(2-hydroxystyryl)phenyl)propyl)isoindoline-1,3-dione as a light yellow foam. Yield (0.165 g, 43%): $^1$H NMR (400 MHz, DMSO-d$_6$) δ 9.69 (s, 1H), 7.78-7.84 (m, 4H), 7.53 (dd, J=8.0, 1.6 Hz, 1H), 7.28-7.38 (m, 3H), 7.22 (t, J=8.4 Hz, 1H), 7.05-7.14 (m, 3H), 6.76-6.86 (m, 2H), 3.61 (t, J=6.8 Hz, 2H), 2.63 (t, J=7.2 Hz, 2H), 1.89-1.97 (m, 2H).

Step 2:

(E)-2-(3-(3-(2-Hydroxystyryl)phenyl)propyl)isoindoline-1,3-dione was deprotected with hydrazine according to the method used in Example 68. After stirring overnight, the reaction mixture was concentrated under reduced pressure and the residue was suspended in 20% EtOAc-hexanes and sonicated. Solids were removed by filtration and the filtrate was concentrated under reduced pressure. Purification by flash chromatography (15% 7 M NH$_3$ in MeOH-EtOAc) gave Example 70 as a yellow foam. Yield (0.736 g, 69%): $^1$H NMR (400 MHz, DMSO-d$_6$) δ 7.54 (dd, J=8.0, 1.6 Hz, 1H), 7.31-7.39 (m, 3H), 7.24 (t, J=8.4 Hz, 1H), 7.15 (d, J=16.4 Hz, 1H), 7.05-7.09 (m, 2H), 6.85 (dd, J=8.0, 1.6 Hz, 1H), 6.79 (ddd, J=7.6, 0.8 Hz, 1H), 2.60 (t, J=6.8 Hz, 2H), 2.54 (t, J=7.2 Hz, 2H), 1.60-1.67 (m, 2H).

Example 71

Preparation of (E)-3-(5-(2,6-dichlorostyryl)-2-methoxyphenyl)propan-1-amine

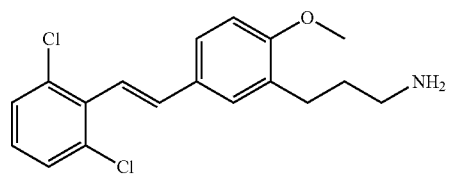 [SMILES: COc1ccc(/C=C/c2c(Cl)cccc2Cl)cc1CCCN]

(E)-3-(5-(2,6-Dichlorostyryl)-2-methoxyphenyl)propan-1-amine was prepared according to Scheme 33.

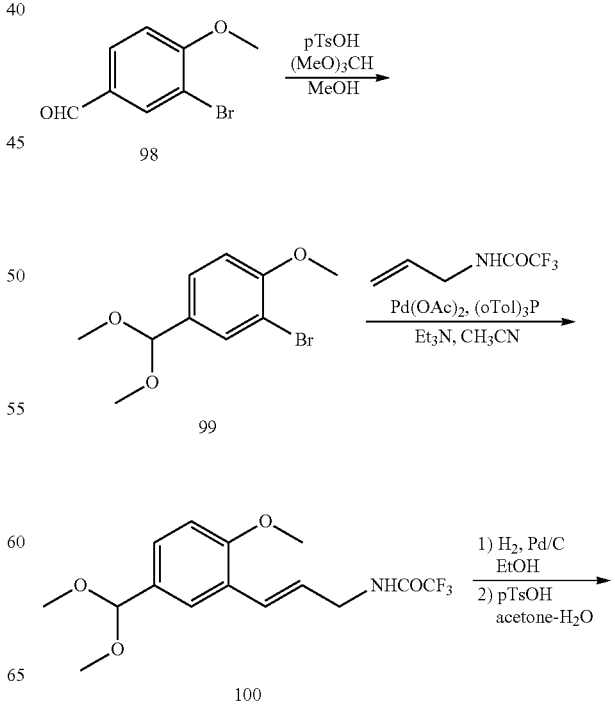

-continued

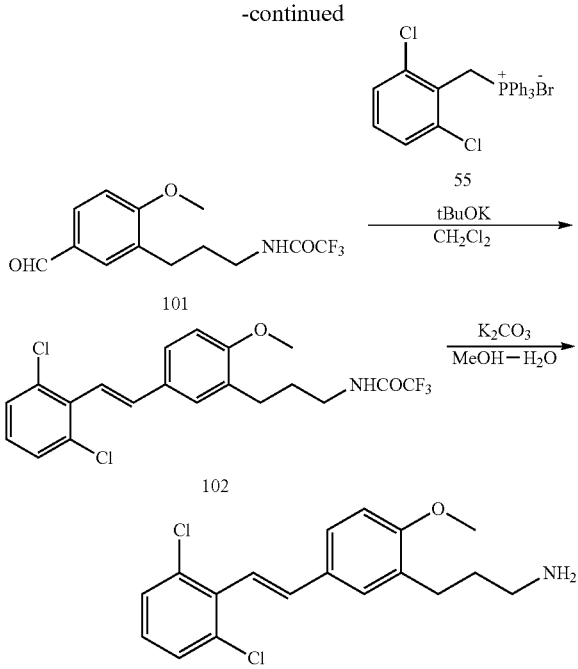

Step 1:
Aryl aldehyde 98 was protected according the method used in Example 32 except that the reaction mixture was stirred at room temperature for 1.5 h. Dimethyl acetal 99 was isolated as an oil. Yield (6.89 g, quant.): NMR (400 MHz, CDCl$_3$) δ 7.64 (d, J=2.0 Hz, 1H), 7.34 (dd, J=8.4, 2.0 Hz, 1H), 6.88 (d, J=8.4 Hz, 1H), 5.33 (s, 1H), 3.90 (s, 3H), 3.30 (s, 6H).

Step 2:
Dimethyl acetal 99 was coupled with N-allyl-2,2,2-trifluoroacetamide according to the method used in Example 45 except that the reaction was heated at 70° C. overnight. After cooling to room temperature, the mixture was concentrated under reduced pressure. The residue was suspended in EtOAc and the solids were removed by filtration. The filtrate was concentrated under reduced pressure and purified by flash chromatography (10 to 50% EtOAc-hexanes gradient) to give alkene 100 as a yellow oil which solidified upon standing under vacuum. (Yield (1.82 g, 56%): $^1$H NMR (400 MHz, CDCl$_3$) δ 7.48 (d, J=2.0 Hz, 1H), 7.32 (dd, J=8.4, 2.0 Hz, 1H), 6.91 (d, J=16.0 Hz, 1H), 6.87 (d, J=8.8 Hz, 1H), 6.40 (br s, 1H), 6.25 (dt, J=16.0, 6.8 Hz, 1H), 5.34 (s, 1H), 4.14 (t, J=6.8 Hz, 2H), 3.86 (s, 3H), 3.31 (s, 6H).

Step 3:
To a degassed solution of alkene 100 (0.8469 g, 2.54 mmol) in EtOH (abs., 15 mL) was added 10% Pd/C (0.0419 g). The mixture was placed under a H$_2$ atmosphere and stirred at room temperature for 3.5 h. Solids were removed by filtration and the filtrate was concentrated under reduced pressure to give crude N-(3-(5-(dimethoxymethyl)-2-methoxyphenyl)propyl)-2,2,2-trifluoroacetamide. This material was used in the next synthetic step without purification.

Step 4:
N-(3-(5-(dimethoxymethyl)-2-methoxyphenyl)propyl)-2,2,2-trifluoroacetamide was deprotected according to the method used in Example 32 except that the reaction was stirred for 1.5 h. Trifluoroacetamide 101 was isolated as white crystals. This material was used in the next synthetic step without purification. Yield (0.7118 g, 97% for two steps): $^1$H NMR (400 MHz, DMSO-d$_6$) δ 9.83 (s, 1H), 9.42 (br s, 1H), 7.78 (dd, J=8.4, 2.0 Hz, 1H), 7.69 (d, J=8.4 Hz, 1H), 7.15 (d, J=8.4 Hz, 1H), 3.87 (s, 3H), 3.18 (q, J=6.8 Hz, 2H), 2.60 (t, J=7.6 Hz, 2H), 1.71-1.79 (m, 2H).

Step 5:
Trifluoroacetamide 101 was coupled to phosphonium salt 55 according to the method used in Example 46 except that it was stirred at −78° C. overnight. After warming to room temperature, the reaction was heated to reflux for 2 h. The reaction mixture was cooled to room temperature then concentrated under reduced pressure. The residue was suspended in 5% EtOAc-heptane and sonicated. The solids were removed by filtration and the filtrate was concentrated under reduced pressure. Purification by flash chromatography (10 to 40% EtOAc-hexanes gradient) afforded alkene 102 as an oil. Yield (0.4765 g, 75%): NMR (400 MHz, CDCl$_3$) δ 7.39 (dd, J=8.4, 2.0 Hz, 114), 7.33-7.35 (m, 3H), 7.07-7.11 (m, 2H), 6.98 (d, J=16.4 Hz, 1H), 6.89 (d, J=8.8 Hz, 1H), 6.73 (br s, 1H), 3.88 (s, 3H), 3.33 (q, J=6.8 Hz, 2H), 2.74 (t, J=7.6 Hz, 2H), 1.87-1.94 (m, 211).

Step 6:
To a solution of alkene 102 (0.0488 g, 0.113 mmol) in MeOH—H$_2$O (5:1, 2 mL) was added K$_2$CO$_3$ (0.0352, 0.26 mmol). The mixture was stirred at room temperature for 20 min then EtOH (2 mL) was added and the mixture was stirred overnight. The reaction mixture was concentrated under reduced pressure and purified by flash chromatography (1:5:5 7 M NH$_3$ in MeOH:EtOAc:hexanes) to give Example 71 as an oil. Yield (0.0291 g, 77%): $^1$H NMR (400 MHz, CDCl$_3$) δ 7.32-7.37 (m, 4H), 7.05-7.12 (m, 2H), 6.98 (d, J=16.4 Hz, 1H), 6.85 (d, J=8.8 Hz, 1H), 3.85 (s, 3H), 2.74 (t, J=7.6 Hz, 2H), 2.68 (t, J=7.6 Hz, 2H), 1.73-1.80 (m, 2H), 1.27 (br s, 211).

Example 72

Preparation of (E)-3-amino-2-methyl-1-(3-(2-(2,6,6-trimethylcyclohex-1-enyl)vinyl)phenyl)propan-1-one

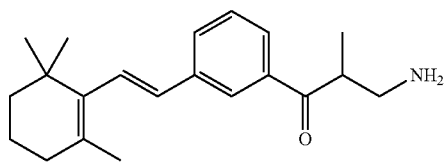 [SMILES: CC1=C(/C=C/c2cccc(C(=O)C(C)CN)c2)C(C)(C)CCC1]

(E)-3-Amino-2-methyl-1-(3-(2-(2,6,6-trimethylcyclohex-1-enyl)vinyl)phenyl)propan-1-one was prepared according to Scheme 22 with modifications.

Step 1:
(E)-3-Amino-2-methyl-1-(3-(2-(2,6,6-trimethylcyclohex-1-enyl)vinyl)phenyl)propan-1-ol (Example 59) was reacted with di-tert-butyl dicarbonate according the method used in Example 55 to give (E)-tert-butyl 3-hydroxy-2-methyl-3-(3-(2-(2,6,6-trimethylcyclohex-1-enyl)vinyl)phenyl)propylcarbamate as an oil. Yield (0.2728 g, 39%).

Step 2:
To a solution of (E)-tert-butyl 3-hydroxy-2-methyl-3-(3-(2-(2,6,6-trimethylcyclohex-1-enyl)vinyl)phenyl)propylcarbamate (0.2728 g, 0.64 mmol) in CH$_2$Cl$_2$ (10 mL) under argon was added MnO$_2$ (2.4751 g, 28.5 mmol). The mixture was stirred at room temperature overnight. The solids were removed by filtration and the filtrate was concentrated under reduced pressure. Purification by flash chromatography (10 to 50% EtOAc-hexanes gradient) gave (E)-tert-butyl 2-methyl-3-oxo-3-(3-(2-(2,6,6-trimethylcyclohex-1-enyl)vinyl)phenyl)propylcarbamate as an oil. (Yield 0.1333 g, 49%): $^1$H NMR (400 MHz, CDCl$_3$) δ 7.96 (s, 1H), 7.79 (d, J=7.6 Hz, 1H), 7.61 (d, J=7.6 Hz, 1H), 7.41 (t, J=8.0 Hz, 1H), 6.75 (dd, J=16.4, 0.8 Hz, 1H), 6.38 (d, J=16.4 Hz, 1H), 4.96 (br s, 1H), 3.76-3.81 (m, 1H), 3.40 (t, J=6.0 Hz, 2H), 2.04 (t, J=6.0 Hz, 2H), 1.76 (s, 3H), 1.61-1.72 (m, 2H), 1.46-1.51 (m, 2H), 1.40 (s, 9H), 1.19 (d, J=7.2 Hz, 3H), 1.06 (s, 6H).

Step 3:

(E)-tert-Butyl 2-methyl-3-oxo-3-(3-(2-(2,6,6-trimethylcyclohex-1-enyl)vinyl)phenyl)propylcarbamate was deprotected according to the method used in Example 61 except that the reaction was stirred for 1 h. After concentration, the residue was dissolved in EtOAc and concentrated under reduced pressure. This procedure was repeated with MeOH to give Example 72 hydrochloride as an oil. Yield (0.0533 g, quant.): $^1$H NMR (400 MHz, DMSO-d$_6$) δ 7.99 (s, 1H), 7.95 (br s, 3H), 7.82 (dd, J=8.0, 1.2 Hz, 2H), 7.51 (t, J=8.0 Hz, 1H), 6.83 (d, J=16.4 Hz, 1H), 6.46 (d, J=16.4 Hz, 1H), 3.92-3.98 (m, 1H), 3.18 (dd, J=12.8, 7.6 Hz, 1H), 2.89 (dd, J=12.8, 7.6 Hz, 1H), 2.02 (t, J=6.0 Hz, 2H), 1.73 (s, 3H), 1.56-1.62 (m, 2H), 1.44-1.47 (m, 2H), 1.16 (d, J=7.2 Hz, 3H), 1.04 (s, 6H).

Example 73

Preparation of (E)-3-amino-2-fluoro-1-(3-(2-(2,6,6-trimethylcyclohex-1-enyl)vinyl)phenyl)propan-1-one

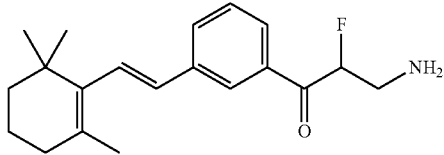 [SMILES: CC1=C(/C=C/c2cccc(C(=O)C(F)CN)c2)C(C)(C)CCC1]

(E)-3-Amino-2-fluoro-1-(3-(2-(2,6,6-trimethylcyclohex-1-enyl)vinyl)phenyl)propan-1-one was prepared according to Scheme 34.

SCHEME 34

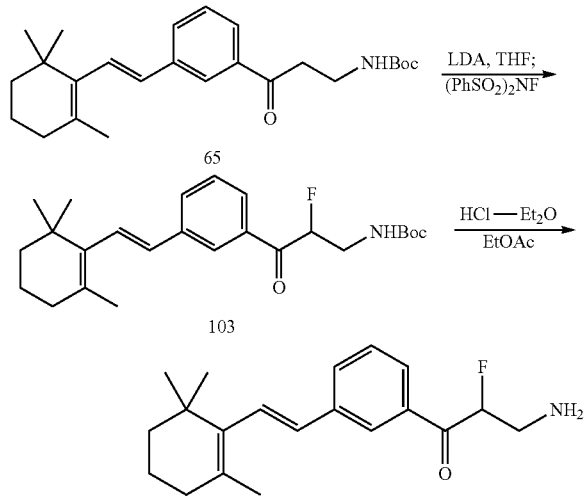

Step 1:

To a −78° C. solution of lithium diisopropylamide (1 mL of a 2 M solution in THF:heptane:ethyl benzene, 2.0 mmol) in THF (1 mL) was added a solution of ketone 65 (0.2855 g, 0.72 mmol) in THF (6 mL) slowly. The reaction mixture was stirred at −78° C. for 7 min, removed from the cooling bath for 6 min then cooled to −78° C. again. A solution of N-fluorobenzenesulfonimide (0.2750 g, 0.87 mmol) in THF (5 mL) was added dropwise slowly and the mixture was stirred at −78° C. for 25 min. The cooling bath was removed and the reaction was quenched with the addition of saturated aqueous NH$_4$Cl. The mixture was extracted with EtOAc and the combined organics were washed with brine, dried over MgSO$_4$ and concentrated under reduced pressure. Purification by flash chromatography (10 to 40% EtOAc-hexanes gradient) gave fluoride 103 as a gummy yellow solid. Yield (0.1634 g, 55%): $^1$H NMR (400 MHz, CDCl$_3$) δ 8.05 (s, 1H), 7.85 (d, J=7.6 Hz, 1H), 7.63 (d, J=7.6 Hz, 1H), 7.44 (t, J=8.0 Hz, 1H), 6.79 (d, J=16.4 Hz, 1H), 6.38 (d, J=16.4 Hz, 1H), 5.73-5.86 (m, 1H), 5.04 (br s, 1H), 3.80-3.95 (m, 1H), 3.40-3.52 (m, 1H), 2.04 (t, J=6.0 Hz, 2H), 1.75 (s, 3H), 1.55-1.67 (m, 2H), 1.47-1.52 (m, 2H), 1.43 (s, 9H), 1.06 (s, 6H).

Step 2:

Fluoride 103 was deprotected according to the method used in Example 72 to give Example 73 hydrochloride as an oil. Yield (0.0481 g, quant.): $^1$H NMR (400 MHz, DMSO-d$_6$) δ 8.32 (br s, 3H), 8.00 (s, 1H), 7.87 (d, J=8.0 Hz, 1H), 7.81 (d, J=8.0 Hz, 1H), 7.54 (t, J=8.0 Hz, 1H), 6.85 (d, J=16.4 Hz, 1H), 6.46 (d, J=16.4 Hz, 1H), 6.32 (ddd, J=47.6, 8.4, 2.8 Hz, 1H), 3.24-3.50 (m, 2H), 2.02 (t, J=6.0 Hz, 2H), 1.73 (s, 3H), 1.56-1.62 (m, 2H), 1.45-1.47 (m, 2H), 1.05 (s, 6H).

Example 74

Preparation of (R,E)-1-amino-3-(3-(2,6-dichlorostyryl)phenyl)propan-2-ol

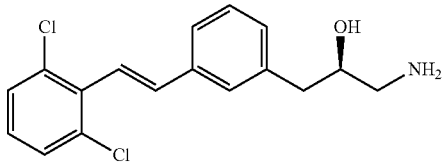 [SMILES: NC[C@H](O)Cc1cccc(/C=C/c2c(Cl)cccc2Cl)c1]

(R,E)-1-Amino-3-(3-(2,6-dichlorostyryl)phenyl)propan-2-ol was prepared from aryl bromide 56 according to Scheme 29 with modifications.

Step 1:

To a −78° C. solution of aryl bromide 56 (2.01 g, 6.13 mmol) in THF (16 mL) was added n-butyl lithium (3.8 mL of a 1.6 M solution in hexanes, 6.1 mmol) dropwise over 11 min. The mixture was stirred for 7 min then BF$_3$-diethyl etherate (0.7 mL, 5.5 mmol) was added dropwise. After stirring for 3 min, a solution of (R)-epichlorohydrin (0.38 mL, 4.8 mmol) in THF (4 mL) was added dropwise over 12 min. The reaction mixture was stirred for 1 h, 15 min at −78° C. then a second aliquot of BF$_3$-diethyl etherate (0.23 mL, 1.84 mmol) and (R)-epichlorohydrin (0.096 mL, 1.23 mmol) were added. The mixture was stirred for 15 min at −78° C. then additional BF$_3$-diethyl etherate (0.23 mL, 1.84 mmol) and (R)-epichlorohydrin (0.096 mL, 1.23 mmol) were added. The mixture was stirred for 30 min at −78° C. then quenched with water. After warming to room temperature, the mixture was partitioned between MTBE and water. The combined organics were washed with water and brine, dried over Na$_2$SO$_4$ and concentrated under reduced pressure. Purification by flash chromatography (1:6 EtOAc:heptane) gave (R,E)-1-chloro-3-(3-(2,6-dichlorostyryl)phenyl)propan-2-ol. Yield (0.67 g, 32%): $^1$H NMR (400 MHz, DMSO-d$_6$) δ 7.51 (d, J=8.0 Hz, 2H), 7.45 (d, J=7.6 Hz, 2H), 7.29-7.33 (m, 2H), 7.20 (d, J=7.6

Hz, 1H), 7.13 (d, J=16.6 Hz, 1H), 7.05 (d, J=16.6 Hz, 1H), 5.19 (d, J=5.6 Hz, 1H), 3.85-3.95 (m, 1H), 3.57 (dd, J=11.2, 4.8 Hz, 1H), 3.49 (dd, J=11.2, 5.6 Hz, 1H), 2.84 (dd, J=13.2, 4.8 Hz, 1H), 2.69 (dd, J=13.6, 8.0 Hz, 1H).

Step 2:

To a solution of (R,E)-1-chloro-3-(3-(2,6-dichlorostyryl)phenyl)propan-2-ol (0.67 g, 1.96 mmol) in DMF (20 mL) was added NaI (~25 mg, 0.16 mmol) and $NaN_3$ (0.64 g, 9.8 mmol) and the reaction mixture was heated at 75° C. overnight. After cooling to room temperature, the mixture was partitioned between EtOAc and water. The combined organics were washed with water, 5% aqueous LiCl and brine, filtered through $Na_2SO_4$ and concentrated under reduced pressure to give (R,E)-1-azido-3-(3-(2,6-dichlorostyryl)phenyl)propan-2-ol. This material was used in the next synthetic step without purification.

Step 3:

(R,E)-1-Azido-3-(3-(2,6-dichlorostyryl)phenyl)propan-2-ol was reduced according to the method used in Example 66 except that it was heated at 50° C. overnight. After cooling to room temperature, the mixture was partitioned between $CH_2Cl_2$ and saturated aqueous $NaHCO_3$. The combined organics were washed with brine, filtered through $Na_2SO_4$ and concentrated under reduced pressure. Purification by flash chromatography ($CH_2Cl_2$ then 1:14:85 conc. aq. $NH_4OH$:EtOH:$CH_2Cl_2$) gave Example 74 as a colorless oil. Yield (0.51 g, 81% for two steps): $^1H$ NMR (400 MHz, $CDCl_3$) δ 7.42 (d, J=7.6 Hz, 1H), 7.38 (s, 1H), 7.34 (d, J=8.0 Hz, 2H), 7.31 (t, J=7.4 Hz, 1H), 7.17 (d, J=7.2 Hz, 1H), 7.08-7.12 (m, 3H), 3.80-3.86 (m, 1H), 2.90 (dd, J=12.8, 3.6 Hz, 1H), 2.77-2.79 (m, 2H), 2.64 (dd, J=12.8, 8.4 Hz, 1H), 2.28 (br s, 3H). Chiral HPLC: 99.0% major enantiomer (AUC), $t_R$=16.354 min (minor enantiomer: 1.0%, $t_R$=15.024 min).

Example 75

Preparation of (S,E)-1-amino-3-(3-(2,6-dichlorostyryl)phenyl)propan-2-ol

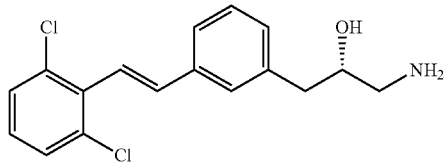 [SMILES: NC[C@@H](O)Cc1cccc(/C=C/c2c(Cl)cccc2Cl)c1]

(S,E)-1-Amino-3-(3-(2,6-dichlorostyryl)phenyl)propan-2-ol was prepared according to the method used in Example 74.

Step 1:

Aryl bromide 56 was coupled with (S)-epichlorohydrin according to the method used in Example 74 except that after the addition of a single aliquot of (S)-epichlorohydrin the reaction was warmed to 0° C. and stirred for 12 min. After quench (at −78° C.) and extractive workup, purification by flash chromatography (1:20 EtOAc:heptane to 1:6 EtOAc:heptane) gave (S,E)-1-chloro-3-(3-(2,6-dichlorostyryl)phenyl)propan-2-ol. Yield (2.04 g, 22%): the $^1H$ NMR data was consistent with data reported above.

Step 2:

(S,E)-1-Chloro-3-(3-(2,6-dichlorostyryl)phenyl)propan-2-ol was reacted with $NaN_3$ following the method used in Example 74 to give (S,E)-1-azido-3-(3-(2,6-dichlorostyryl)phenyl)propan-2-ol. This material was used in the next synthetic step without purification.

Step 3:

(S,E)-1-Azido-3-(3-(2,6-dichlorostyryl)phenyl)propan-2-ol was reduced and purified according to the method used in Example 74 to give Example 75 as a colorless oil. Yield (1.25 g, 67% for two steps): $^1H$ NMR (400 MHz, DMSO-$d_6$) δ 7.52 (d, J=8.4 Hz, 2H), 7.42-7.44 (m, 2H), 7.27-7.32 (m, 2H), 7.18 (d, J=7.4 Hz, 1H), 7.11 (d, J=16.6 Hz, 1H), 7.04 (d, J=16.6 Hz, 1H), 3.54-3.60 (m, 1H), 2.72 (dd, J=13.2, 4.8 Hz, 1H), 2.58 (dd, J=13.6, 8.0 Hz, 1H), 2.52 (dd, J=12.8, 4.4 Hz, 1H), 2.42 (dd, J=12.4, 6.4 Hz, 1H). Chiral HPLC: 98.5% major enantiomer (AUC), $t_R$=15.024 min (minor enantiomer: 1.5%, $t_R$=16.354 min).

Example 76

Preparation of (E/Z)-(3-(3-(2,6-diethoxystyryl)phenyl)propan-1-amine

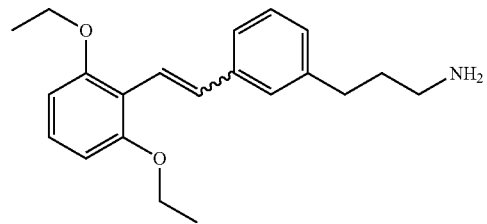 [SMILES: CCOc1cccc(OCC)c1C=Cc1cccc(CCCN)c1]

(E/Z)-(3-(3-(2,6-Diethoxystyryl)phenyl)propan-1-amine (isomer ratio 69:31 trans:cis) was prepared according to the method used in Example 32.

Step 1:

To an ice cold solution of 2,6-diethoxybenzyl alcohol (1.0 g, 5.2 mmol) in THF (10 mL) was added phosphorous tribromide (0.48 mL, 5.1 mmol) dropwise. The reaction was allowed to warm to room temperature and stirred for 1 h. After quenching the reaction with water, the mixture was extracted with EtOAc. The combined organics were washed with brine and dried over $Na_2SO_4$. The solution was concentrated under reduced pressure to give 2,6-diethoxybenzyl bromide as a brown oil. Yield (1.3 g, 98%).

Step 2:

To a solution of triphenylphosphine (1.31 g, 5.01 mmol) in toluene (6.5 mL) was added 2,6-diethoxybenzyl bromide (1.3 g, 5.01 mmol) and the mixture stirred at room temperature overnight. Diethyl ether was added and the solid was collected by filtration to give (2,6-diethoxybenzyl)triphenylphosphonium bromide as an off-white solid. Yield (1.58 g, 60%): $^1H$ NMR (400 MHz, DMSO-$d_6$) δ 7.83-7.87 (m, 3H), 7.68 (ddd, J=7.6, 7.6, 3.2 Hz, 6H), 7.55 (d, J=7.6 Hz, 3H), 7.52 (d, J=7.2 Hz, 3H), 7.18 (ddd, 0.1=8.4, 8.4, 2.4 Hz, 1H), 6.45 (d, J=8.4 Hz, 2H), 4.66 (d, J=14.0 Hz, 2H), 3.65 (q, J=6.8 Hz, 4H), 1.01 (t, J=6.8 Hz, 6H).

Step 2:

To an ice-cold mixture of phthalimide 29 (0.440 g, 1.5 mmol) in THF (25 mL) was added (2,6-diethoxybenzyl)triphenylphosphonium bromide (0.860 g, 1.65 mmol) and potassium tert-butoxide (0.336 g, 3.0 mmol) portionwise. The reaction was allowed to warm to room temperature and stirred for 2 h. The mixture was then quenched with water and extracted with EtOAc. The combined organics were washed with brine, dried over $Na_2SO_4$ and concentrated under reduced pressure. Purification by flash chromatography (7%

EtOAc-hexanes) gave (E)-2-(3-(3-(2,6-diethoxystyryl)phenyl)propyl)isoindoline-1,3-dione as a brown oil. Yield (0.055 g, 8%): ¹H NMR (400 MHz, CDCl₃) δ 7.80-7.83 (m, 2H), 7.67-7.70 (m, 2H), 7.62 (d, J=16.8 Hz, 1H), 7.45 (d, J=16.8 Hz, 1H), 7.29-7.31 (m, 1H), 7.22 (t, J=7.6 Hz, 1H), 7.17 (d, J=6.4 Hz, 1H), 7.11 (t, J=8.4 Hz, 1H), 7.06 (d, J=7.2 Hz, 1H), 6.60 (d, J=8.4 Hz, 2H), 4.11 (dt, J=7.2, 6.8 Hz, 4H), 3.78 (t, J=7.2 Hz, 2H), 2.71 (t, J=7.6 Hz, 2H), 2.03-2.11 (m, 2H), 1.50 (t, J=7.2 Hz, 6H).

Step 3:

To a solution of (E)-2-(3-(3-(2,6-diethoxystyryl)phenyl)propyl)isoindoline-1,3-dione (0.375 g, 0.824 mmol) in EtOH (5 mL) was added hydrazine hydrate (0.15 mL, 2.5 mmol). The mixture was heated to reflux for 1 h. After cooling to room temperature, diethyl ether was added and the white precipitate was removed by filtration. The filtrate was concentrated under reduced pressure to give Example 76 as a yellow oil. Yield (0.220 g, 82%): Trans-/cis-isomer ratio 2.2:1. Trans-isomer: ¹H NMR (400 MHz, CDCl₃) δ 7.66 (d, J=16.8 Hz, 1H), 7.47 (d, J=16.8 Hz, 1H), 7.04-7.37 (m, 5H), 6.56 (d, J=8.4 Hz, 2H), 4.10 (q, J=7.2 Hz, 4H), 2.65-2.78 (m, 4H), 1.75-1.84 (m, 2H), 1.49 (t, J=6.8 Hz, 6H).

Example 77

Preparation of (E)-3-(3-(2-ethoxystyryl)phenyl)propan-1-amine

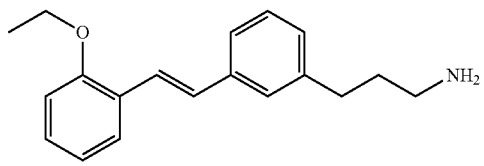 [SMILES: CCOc1ccccc1/C=C/c1cccc(CCCN)c1]

(E)-3-(3-(2-Ethoxystyryl)phenyl)propan-1-amine was prepared according to the method used in Example 32.

Step 1:

Phthalimide 29 was coupled with 2-ethoxybenzyltriphenylphosphonium bromide according to the method used in Example 76 except that the reaction was stirred at room temperature for 1 h. Purification by flash chromatography (10% EtOAc-hexanes) gave (E/Z)-2-(3-(3-(2-ethoxystyryl)phenyl)propyl)isoindoline-1,3-dione a yellow solid. Yield (0.258 g, 61%).

Step 2:

(E/Z)-2-(3-(3-(2-ethoxystyryl)phenyl)propyl)isoindoline-1,3-dione was deprotected following the method used in Example 76. Purification by Preparative HPLC (Method 2) gave Example 77 trifluoroacetate. Yield (0.0.035 g, 20%): 93% trans-isomer. Trans-isomer: ¹H NMR (400 MHz, CDCl₃) δ 7.91 (br s, 3H), 7.55 (dd, J=7.6, 1.2 Hz, 1H), 7.45 (d, J=16.4 Hz, 1H), 7.38 (d, J=8.0 Hz, 1H), 7.13-7.22 (3H), 7.09 (d, J=16.4 Hz, 1H), 7.00 (d, J=7.6 Hz, 1H), 6.92-6.95 (m, 1H), 6.87 (d, J=8.4 Hz, 1H), 4.08 (dt, J=7.2, 6.8 Hz, 2H), 2.82-2.87 (m, 2H), 2.65 (t, J=7.6 Hz, 2H), 1.93-2.02 (m, 2H), 1.45 (t, J=7.2 Hz, 3H).

Example 78

Preparation of (E/Z)-3-(3-(2-isopropoxystyryl)phenyl)propan-1-amine

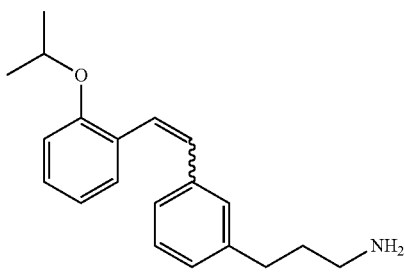 [SMILES: CC(C)Oc1ccccc1C=Cc1cccc(CCCN)c1]

(E/Z)-3-(3-(2-Isopropoxystyryl)phenyl)propan-1-amine was prepared according to the method used in Example 76.

Step 1:

2-Isopropoxybenzyltriphenylphosphonium bromide was prepared from 2-isopropoxylbenzyl bromide according to the method used in Example 76, except that 1.3 equivalents of triphenylphosphine was used. 2-Isopropoxybenzyltriphenylphosphonium bromide was isolated as a white solid. Yield (11.2 g, 99%): ¹H NMR (400 MHz, DMSO-d₆) δ 7.86-7.89 (m, 3H), 7.70 (dt, J=8.0, 3.2 Hz, 6H), 7.54-7.59 (m, 6H), 7.23-7.28 (m, 1H), 6.91 (dt, J=7.6, 2.0 Hz, 1H), 6.88 (d, J=8.4 Hz, 1H), 6.74 (t, J=7.6 Hz, 1H), 4.87 (d, J=14.4 Hz, 2H), 4.29 (quint, J=6.0 Hz, 1H), 0.91 (d, J=6.0 Hz, 6H).

Step 2:

Phthalimide 29 was coupled with 2-isopropoxybenzyltriphenylphosphonium bromide according to the method used in Example 76. Purification by flash chromatography (7% EtOAc-hexanes) gave (E/Z)-2-(3-(3-(2-isopropoxystyryl)phenyl)propyl)isoindoline-1,3-dione a yellow oil. Yield (0.375 g, 51%). Trans-isomer: ¹H NMR (400 MHz, CDCl₃) δ 780-7.85 (m, 2H), 7.67-7.72 (m, 2H), 7.58 (dd, J=7.6, 1.2 Hz, 1H), 7.43 (d, J=16.4 Hz, 1H), 7.31 (s, 1H), 7.03-7.24 (m, 5H), 6.97-6.99 (m, 1H), 6.93 (t, J=8.0 Hz, 1H), 6.87 (d, J=8.4 Hz, 1H), 4.55-4.61 (m, 1H), 3.78 (t, J=7.2 Hz, 2H), 2.71 (t, J=7.6 Hz, 2H), 2.04-2.12 (m, 2H), 1.40 (d, J=6.0 Hz, 6H).

Step 3:

(E/Z)-2-(3-(3-(2-isopropoxystyryl)phenyl)propyl)isoindoline-1,3-dione was deprotected following the method used in Example 76 except that the reaction was heated at reflux for 2 h. Example 78 was isolated as a yellow oil. Yield (0.150 g, 31%): Cis-/trans-isomer ratio 4:1. Cis-isomer: ¹H NMR (400 MHz, CDCl₃) δ 7.82 (br s, 3H), 6.87-7.14 (m, 8H), 6.70 (d, J=12.4 Hz, 1H), 6.55 (d, J=12.4 Hz, 1H), 4.49-4.57 (m, 1H), 2.77-2.84 (m, 2H), 2.54 (t, J=7.6 Hz, 2H), 1.72-1.89 (m, 2H), 1.29 (d, J=6.0 Hz, 6H)

Example 79

Preparation of (E)-4-(3-(3-aminopropyl)phenyl)-2-methylbut-3-en-2-ol

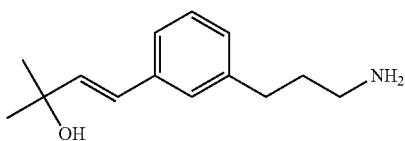 [SMILES: CC(C)(O)/C=C/c1cccc(CCCN)c1]

(E)-4-(3-(3-Aminopropyl)phenyl)-2-methylbut-3-en-2-ol was prepared according to Scheme 35.

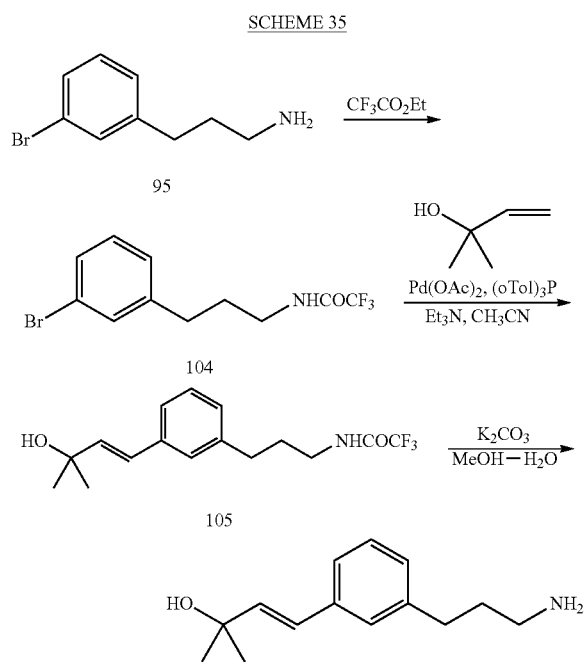

Step 1:
Crude 3-(3-bromophenyl)propan-1-amine (95) (404.6 mmol) was stirred with ethyl trifluoroacetate (30 ml) overnight. The mixture was concentrated under reduced pressure. Purification by flash chromatography (20% EtOAc-hexanes) gave trifluoroacetamide 104. Yield (21.1 g, 62%): $^1$H NMR (400 MHz, DMSO-$d_6$) δ 9.40 (br s, 1H), 7.43 (s, 1H), 7.36 (dt, J=7.2, 2.0 Hz, 1H), 7.19-7.25 (m, 2H), 3.16 (q, J=6.8 Hz, 2H), 2.57 (t, J=7.6 Hz, 2H), 1.77 (quint, J=7.2 Hz, 2H).

Step 2:
Aryl bromide 104 was coupled to 2-methyl-3-buten-2-ol according to the method used in Example 45 except that the reaction was heated at 100° C. overnight. The reaction mixture was partitioned between EtOAc and aqueous NH$_4$OAc. The combined extracts were washed with saturated aqueous NH$_4$OAc, saturated aqueous NaHCO$_3$, water and brine, dried over Na$_2$SO$_4$ and concentrated under reduced pressure. Purification by flash chromatography (30 to 90% EtOAc-hexanes gradient) gave alkene 105 as a light yellow semi-solid. Yield (0.3881 g, 73%): NMR (400 MHz, DMSO-$d_6$) δ 9.41 (br s, 1H), 7.18-7.23 (m, 3H), 7.02-7.04 (m, 1H), 6.45 (d, J=16.4 Hz, 1H), 6.36 (d, J=. 16.0 Hz, 1H), 3.17 (dt, J=7.0, 6.4 Hz, 2H), 2.56 (t, J=7.2 Hz, 2H), 1.77 (app dt, J=7.6 Hz, 2H), 1.24 (s, 6H).

Step 3:
To a solution of alkene 105 (0.3608 g, 1.14 mmol) in MeOH—H$_2$O (8:1, 22.5 mL) was added K$_2$CO$_3$ (0.37 g, 2.7 mmol) and the mixture was stirred at room temperature for 23 h. The mixture was concentrated under reduced pressure then dissolved in 2% MeOH-EtOAc and solids were removed by filtration. The filtrate was concentrated under reduced pressure and the residue was purified by flash chromatography (90 to 100% EtOAc-hexanes gradient then 10% 7 M NH$_3$ in MeOH-EtOAc) to give Example 79 as a colorless oil. Yield (0.198 g, 80%): $^1$H NMR (400 MHz, DMSO-$d_6$) δ 7.19-7.23 (m, 3H), 7.04-7.06 (m, 1H), 6.54 (d, J=16.0 Hz, 1H), 6.35 (d, J=16.0 Hz, 1H), 4.65 (s, 1H), 2.61-2.66 (m, 4H), 1.74-1.81 (m, 2H), 1.59 (br s, 1H), 1.37 (s, 6H).

Example 80

Preparation of (E)-3-amino-1-(3-(2,6-dichlorostyryl)phenyl)propan-1-one

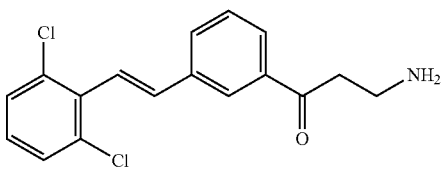 [SMILES: NCCC(=O)c1cccc(/C=C/c2c(Cl)cccc2Cl)c1]

(E)-3-Amino-1-(3-(2,6-dichlorostyryl)phenyl)propan-1-one was prepared according to Scheme 22 with modifications.

Step 1:
To a solution of (E)-3-amino-1-(3-(2,6-dichlorostyryl)phenyl)propan-1-ol (Example 50) (0.240 g, 0.745 mmol) in CH$_2$Cl$_2$ (10 mL) was added di-tert-butyl dicarbonate (0.2503 g, 1.15 mmol) and the mixture was stirred at room temperature for 30 min. MnO$_2$ (2.1897 g, 25.2 mmol) was then added and the reaction stirred at room temperature overnight. Solids were removed by filtration through a pad of silica gel and the filtrate was concentrated under reduced pressure. Purification by flash chromatography (10 to 50% EtOAc-hexanes gradient) afforded (E)-tert-butyl 3-(3-(2,6-dichlorostyryl)phenyl)-3-oxopropylcarbamate as an oil. Yield (0.0478 g, 31%): $^1$H NMR (400 MHz, CDCl$_3$) δ 8.05 (s, 1H), 7.88 (dt, J=8.0, 1.6 Hz, 1H), 7.75 (dt, J=8.0, 1.2 Hz, 1H), 7.49 (t, J=8.0 Hz, 1H), 7.35 (d, J=8.0 Hz, 2H), 7.19 (s, 2H), 7.13 (t, J=8.0 Hz, 1H), 5.15 br s, 1H), 3.56 (q, J=6.0 Hz, 2H), 3.24 (q, J=6.0 Hz, 2H), 1.43 (s, 9H).

Step 2:
(E)-tert-Butyl 3-(3-(2,6-dichlorostyryl)phenyl)-3-oxopropylcarbamate was deprotected according to the method used in Example 45 except that the reaction was stirred for 1.5 h. The precipitate was collected by filtration and dried under vacuum to give Example 80 hydrochloride as a white solid. Yield (0.0201 g, 50%): $^1$H NMR (400 MHz, DMSO-$d_6$) δ 8.15 (s, 1H), 7.96 (d, J=8.0 Hz, 1H), 7.92 (d, J=8.0 Hz, 1H), 7.77 (br s, 3H), 7.60 (t, J=8.0 Hz, 1H), 7.55 (d, J=8.0 Hz, 2H), 7.34 (t, J=8.0 Hz, 1H), 7.27 (d, J=16.8 Hz, 1H), 7.19 (d, J=16.8 Hz, 1H), 3.43 (t, J=6.4 Hz, 2H), 3.12-3.20 (m, 2H).

Example 81

Preparation of (E)-1-amino-3-(3-(2,6-dichlorostyryl)phenyl)propan-2-one

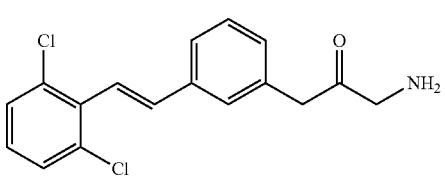 [SMILES: NCC(=O)Cc1cccc(/C=C/c2c(Cl)cccc2Cl)c1]

(E)-1-Amino-3-(3-(2,6-dichlorostyryl)phenyl)propan-2-one was prepared according to the methods used in Examples 55 and 56 with modifications.

Step 1:

To a solution of (S,E)-1-amino-3-(3-(2,6-dichlorostyryl)phenyl)propan-2-ol (Example 74) (1.19 g, 3.69 mmol) in THF (25 mL) was added N,N-diisopropylethylamine (0.675 mL, 3.88 mmol) and di-tert-butyl dicarbonate (0.85 g, 3.9 mmol). Additional THF (5 mL) was added and the reaction was stirred at room temperature for 3 h. The mixture was partitioned between EtOAc and 5% aqueous $NaHSO_4$ and the combined organics were washed with 5% aqueous $NaHSO_4$, water, saturated aqueous $NaHCO_3$, water and brine then dried over $Na_2SO_4$. The solution was concentrated under reduced pressure to give (E)-tert-butyl 3-(3-(2,6-dichlorostyryl)phenyl)-2-hydroxypropylcarbamate as a colorless oil. This material was used in the next synthetic step without purification. Yield (1.51 g, 97%): $^1$H NMR (400 MHz, DMSO-$d_6$) δ 7.52 (d, J=8.4 Hz, 2H), 7.42 (d, J=7.6 Hz, 2H), 7.27-7.32 (m, 2H), 7.17 (d, J=7.6 Hz, 1H), 7.11 (d, J=16.6 Hz, 1H), 7.04 (d, J=16.8 Hz, 1H), 6.69 (t, J=5.9 Hz, 1H), 4.72 (d, J=5.6 Hz, 1H), 3.66-3.74 (m, 1H), 2.86-3.05 (m, 2H), 2.72 (dd, J=14.0, 4.8 Hz, 1H), 2.54 (dd, J=13.6, 8.0 Hz, 1H), 1.36 (s, 9H).

Step 2:

To a solution of (E)-tert-butyl 3-(3-(2,6-dichlorostyryl)phenyl)-2-hydroxypropylcarbamate (1.08 g, 2.56 mmol) in $CH_2Cl_2$ (20 mL) was added Celite (0.8 g) and pyridinium chlorochromate (0.661 g, 3.06 mmol). The reaction mixture was stirred at room temperature for 1.5 h then additional Celite (0.70 g) and pyridinium chlorochromate (0.552 g, 2.56 mmol) were added. The mixture was stirred for 1 h then the solids were removed by filtration through Celite. The filtrate was concentrated under reduced pressure then purified by flash chromatography (10 to 70% EtOAc-hexanes gradient) to give (E)-tert-butyl 3-(3-(2,6-dichlorostyryl)phenyl)-2-oxopropylcarbamate. Yield (0.49 g, 45%): $^1$H NMR (400 MHz, DMSO-$d_6$) δ 7.52 (d, J=8.4 Hz, 2H), 7.48 (d, J=7.8 Hz, 1H), 7.42 (s, 1H), 7.29-7.36 (m, 2H), 7.15 (d, J=7.4 Hz, 1H), 7.12 (d, J=16.6 Hz, 1H), 7.04 (d, J=16.6 Hz, 1H), 7.05-7.06 (m, 1H), 3.88 (d, J=6.0 Hz, 2H), 3.78 (s, 2H), 1.36 (s, 9H).

Step 3:

To a solution of (E)-tert-butyl 3-(3-(2,6-dichlorostyryl)phenyl)-2-oxopropylcarbamate 0.133 g, 0.32 mmol) in EtOAc (1.5 mL) was added HCl-EtOAc (0.75 mL of a 4.2 M solution, 3.2 mmol) and the mixture was stirred at room temperature for 2 h. The white precipitate was collected by filtration and dried in a vacuum oven at 45° C. to give Example 81 as a white solid. Yield (0.0695 g, 62%): $^1$H NMR (400 MHz, DMSO-$d_6$) δ 8.11 (br s, 3H), 7.51-7.54 (m, 3H), 7.47 (s, 1H), 7.38 (t, J=7.6 Hz, 1H), 7.32 (t, J=8.0 Hz, 1H), 7.20 (d, J=7.6 Hz, 1H), 7.13 (d, J=16.6 Hz, 1H), 7.06 (d, J=16.6 Hz, 1H), 4.03 (br s, 2H), 3.92 (s, 2H).

Example 82

Preparation of (E)-3-amino-1-(3-(2-chloro-6-methylstyryl)phenyl)propan-1-ol

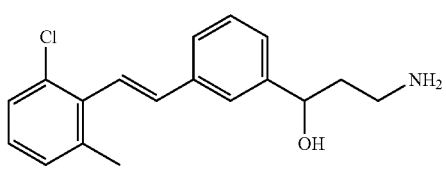 [SMILES: Cc1cccc(Cl)c1/C=C/c1cccc(C(O)CCN)c1]

(E)-3-Amino-1-(3-(2-chloro-6-methylstyryl)phenyl)propan-1-ol was prepared according to the method used in Example 50.

Step 1:

2-Chloro-6-methylbenzaldehyde was coupled to 3-bromobenzyltriphenylphosphonium bromide according to the method used in Example 46 except that the addition of potassium tert-butoxide was done at −78° C. and the reaction mixture was briefly removed from the cooling bath. Purification by flash chromatography (0 to 50% EtOAc-hexanes gradient) gave (E/Z)-2-(3-bromostyryl)-1-chloro-3-methylbenzene as an oil. Yield (0.43 g, 69%), trans-/cis-isomer ratio 1:1. Trans-isomer: $^1$H NMR (400 MHz, CDCl$_3$) δ 7.67 (t, J=2.0 Hz, 1H), 7.40-7.44 (m, 1H), 7.22-7.28 (m, 2H), 7.07-7.17 (m, 3H), 6.99 (t, J=8.0 Hz, 1H), 6.73 (d, J=16.8 Hz, 1H), 2.42 (s, 3H).

Step 2:

(E/Z)-2-(3-bromostyryl)-1-chloro-3-methylbenzene was carbonylated according to the method used in Example 50 except that additional DMF was not added at the end of the reaction. Purification by flash chromatography (10 to 50% EtOAc-hexanes gradient) was conducted twice to partially separate the geometric isomers. (E)-3-(2-chloro-6-methylstyryl)benzaldehyde was isolated as an oil. Yield 0.0792 g, 22%), trans-/cis-isomer ratio 11.5:1. Trans-isomer: $^1$H NMR (400 MHz, CDCl$_3$) δ 10.07 (s, 1H), 8.02 (t, J=2.0 Hz, 1H), 7.77-7.82 (m, 2H), 7.55 (t, J=8.0 Hz, 1H), 7.28 (dd, J=9.2, 1.6 Hz, 1H), 7.24 (d, J=16.0 Hz, 1H), 7.15 (d, J=6.4 Hz, 1H), 7.11 (t, J=7.6 Hz, 1H), 6.86 (d, J=16.4 Hz, 1H), 2.44 (s, 3H).

Step 3:

(E)-3-(2-Chloro-6-methylstyryl)benzaldehyde was reacted with acetonitrile according to the procedure used in Example 50. Purification by flash chromatography (10 to 70% EtOAc-hexanes gradient) gave (E)-3-(3-(2-chloro-6-methylstyryl)phenyl)-3-hydroxypropanenitrile as an oil. Yield 0.0708 g, 77%): NMR (400 MHz, CDCl$_3$) δ 7.51-7.53 (m, 2H), 7.41 (t, J=8.0 Hz, 1H), 7.25-7.33 (m, 2H), 7.07-7.20 (m, 3H), 6.80 (d, J=16.8 Hz, 1H), 5.08 (t, J=6.4 Hz, 1H), 2.80 (dd, J=6.4, 0.8 Hz, 2H), 2.43 (s, 3H).

Step 4:

(E)-3-(3-(2-Chloro-6-methylstyryl)phenyl)-3-hydroxypropanenitrile was reduced according to the method used in Example 50 except that 3.3 equivalents of LiAlH$_4$ were used in the reaction. Purification by flash chromatography (1:4:5 7 M NH$_3$ in MeOH: hexanes: EtOAc) was conducted twice to give Example 82 as an oil. Yield (0.0230 g, 32%): NMR (400 MHz, CDCl$_3$) δ 7.55 (s, 1H), 7.43 (d, J=7.6 Hz, 1H), 7.35 (t, J=7.6 Hz, 1H), 7.25-7.29 (m, 2H), 7.07-7.20 (m, 3H), 6.80 (d, J=16.8 Hz, 1H), 5.00 (dd, J=8.8, 3.2 Hz, 1H), 3.14 (ddd, J=12.4, 5.6, 4.0 Hz, 1H), 2.99 (ddd, J=13.2, 9.6, 4.0 Hz, 1H), 2.89 (br s, 2H), 2.43 (s, 3H), 1.88-1.94 (m, 1H), 1.75-1.84 (m, 1H).

Example 83

Preparation of (E)-4-(3-(3-aminopropyl)styryl)heptan-4-ol

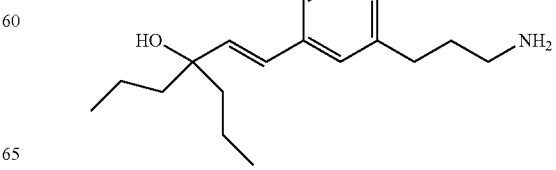

(E)-4-(3-(3-Aminopropyl)styryl)heptan-4-ol was prepared according to the method used in Example 79.

Step 1:

4-Vinylheptan-4-ol was coupled to aryl bromide 104 and purified by flash chromatography (20 to 80% EtOAc-hexanes gradient) to afford (E)-2,2,2-trifluoro-N-(3-(3-(3-hydroxy-3-propylhex-1-enyl)phenyl)propyl)acetamide as an oil. Yield (0.4966 g, 81%): NMR (400 MHz, DMSO-d$_3$) δ 9.40 (br s, 1H), 7.19-7.21 (m, 3H), 7.02 (dt, J=6.0, 1.2 Hz, 1H), 6.44 (d, J=16.0 Hz, 1H), 6.21 (d, J=16.0 Hz, 1H), 4.30 (s, 1H), 3.18 (q, J=6.4 Hz, 2H), 2.56 (t, J=7.2 Hz, 2H), 1.78 (quint, J=7.4 Hz, 2H), 1.41-1.47 (m, 4H), 1.18-1.36 (m, 4H), 0.83 (t, J=7.4 Hz, 6H).

Step 2:

(E)-2,2,2-Trifluoro-N-(3-(3-(3-hydroxy-3-propylhex-1-enyl)phenyl)propyl)acetamide was deprotected according to the method used in Example 79 except that 3 equivalents of K$_2$CO$_3$ were used. Following the reaction, solids were removed by filtration and the filtrate was concentrated under reduced pressure. The residue was dissolved in MeOH, dried over MgSO$_4$ and filtered through Celite. After concentration under reduced pressure, purification by flash chromatography (7:3 EtOAc:hexanes to 7:2:1 EtOAc:hexanes: 7 M NH$_3$ in MeOH gradient) gave Example 83 as a single trans isomer. Yield (0.348 g, quant.): $^1$H NMR (400 MHz, DMSO-d$_3$) δ 7.18-7.22 (m, 3H), 7.03-7.06 (m, 1H), 6.51 (d, J=16.0 Hz, 1H), 6.20 (d, J=16.4 Hz, 1H), 4.30 (br s, 1H), 2.66 (t, J=7.4 Hz, 2H), 2.64 (t, J=7.8 Hz, 2H), 1.75-1.82 (m, 2H), 1.53-1.59 (m, 4H), 1.33-1.44 (m, 4H), 0.92 (t, J=7.4 Hz, 6H).

Example 84

Preparation of (E)-1-(3-(3-aminopropyl)phenyl)hex-1-en-3-ol

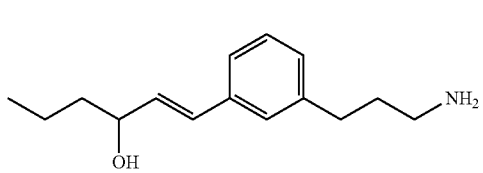 [SMILES: CCCC(O)/C=C/c1cccc(CCCN)c1]

(E)-1-(3-(3-Aminopropyl)phenyl)hex-1-en-3-ol was prepared according to the method used in Example 79 with modifications.

Step 1:

Hex-1-en-3-ol was coupled to aryl bromide 104 according to the method used in Example 79 except that 0.1 equivalents of tri(o-tolyl)phosphine were used. Purification by flash chromatography (10 to 50% EtOAc-hexanes gradient) afforded (E)-2,2,2-trifluoro-N-(3-(3-(3-hydroxyhex-1-enyl)phenyl)propyl)acetamide as a yellow oil. Yield (0.258 g, 39%): $^1$H NMR (400 MHz, CD$_3$OD) δ 7.21-7.24 (m, 3H), 7.01-7.08 (m, 1H), 6.63 (dd, J=16.0, 0.8 Hz, 1H), 6.21 (dd, J=16.0, 6.8 Hz, 1H), 4.19 (q, J=7.2 Hz, 1H), 2.63 (t, J=7.2 Hz, 2H), 1.85-1.91 (m, 2H), 1.42-1.66 (m, 6H), 0.95 (t, J=7.6 Hz, 3H).

Step 2:

To a solution of (E)-2,2,2-trifluoro-N-(3-(3-(3-hydroxyhex-1-enyl)phenyl)propyl)acetamide (0.258 g, 0.78 mmol) in MeOH (10 mL) was added concentrated aqueous NH$_4$OH (10 mL). The reaction mixture was capped and stirred at room temperature overnight. The mixture was partitioned between diethyl ether and water and the combined organics were washed with brine, dried over Na$_2$SO$_4$ and concentrated under reduced pressure. Purification by flash chromatography (10 to 20% 7 M NH$_3$ in MeOH-EtOAc gradient) afforded Example 84 as a single trans isomer. Yield (0.110 g, 60%): $^1$H NMR (400 MHz, DMSO-d$_6$) δ 7.18-7.21 (m, 3H), 7.01-7.04 (m, 1H), 6.44 (dd, J=16.0, 1.2 Hz, 1H), 6.21 (dd, J=16.0, 6.4 Hz, 1H), 4.07 (q, J=5.6 Hz, 1H), 2.51-2.57 (m, 4H), 1.57-1.64 (m, 2H), 1.26-1.49 (m, 6H), 0.87 (t, J=7.2 Hz, 3H).

Example 85

Preparation of (E)-4-(3-(2-aminoethoxy)styryl)heptan-4-ol

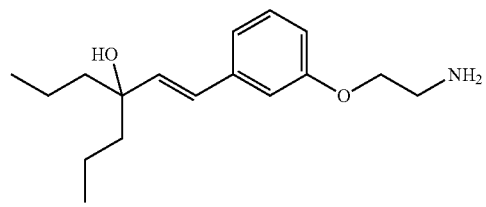 [SMILES: CCCC(O)(/C=C/c1cccc(OCCN)c1)CCC]

(E)-4-(3-(2-Aminoethoxy)styryl)heptan-4-ol was prepared according to Scheme 36.

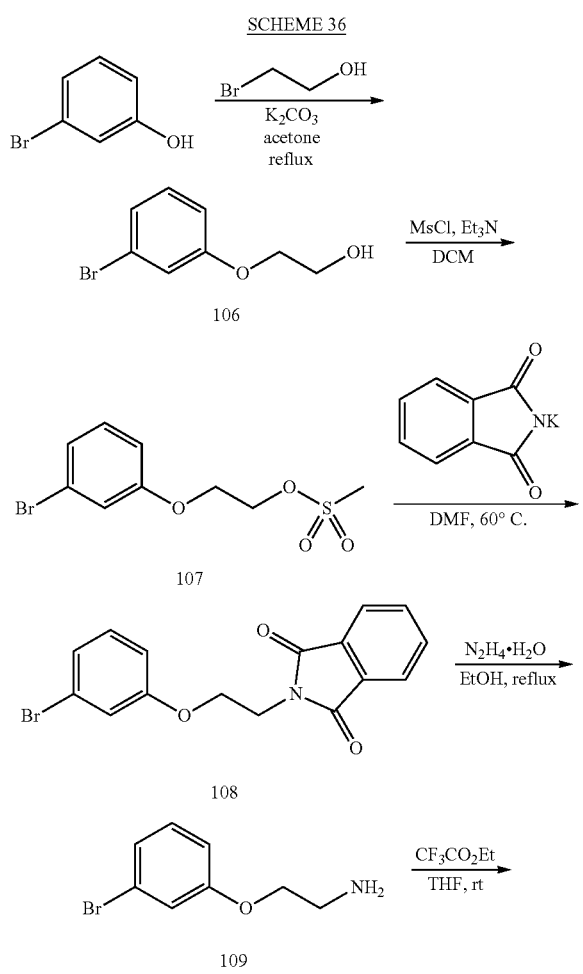

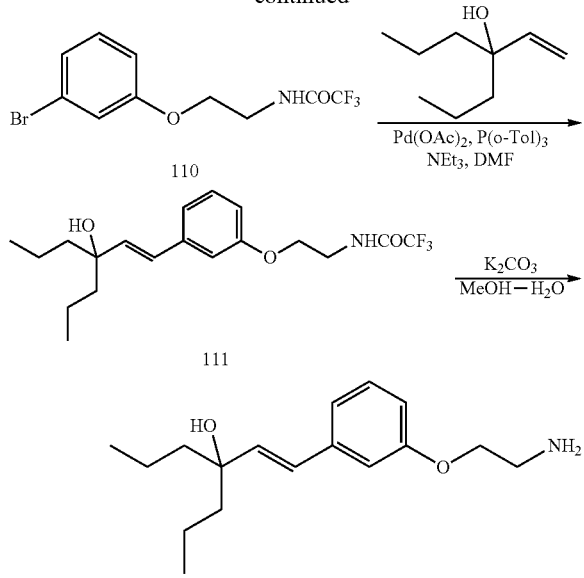

Step 1:

To a solution of 3-bromophenol (36.38 g, 210.3 mmol) in acetone (175 ml) was added K₂CO₃ (0.033 g, 237 mmol) and 2-bromoethanol (20 ml, 283.3 mmol). The reaction mixture was heated at reflux under argon for 4 days. After cooling to room temperature, the mixture was filtered and the filtrate was concentrated under reduced pressure. The residue was dissolved in diethyl ether (150 ml) and the solution was washed successively with water, 10% aqueous NaOH, 5% aqueous NaOH, water, and brine. The solution was dried over MgSO₄ and concentrated under reduced pressure to give 2-(3-bromophenoxyl)ethanol (106) as a light brown oil. Yield (21.07 g, 46%): ¹H NMR (400 MHz, CDCl₃) δ 7.14 (t, J=7.8 Hz, 1H), 7.07-7.12 (m, 2H), 6.85 (ddd, J=7.8, 2.4, 1.3 Hz, 1H), 4.05-4.07 (m, 2H), 3.93-3.97 (m, 2H), 2.11 (t, J=12.3 Hz. 1H).

Step 2:

To an ice cold mixture of 2-(3-bromophenoxyl)ethanol (106) (16.06 g, 74.0 mmol) and triethylamine (9.12 g, 90.13 ml) in anhydrous CH₂Cl₂ (120 ml) under argon was slowly added methanesulfonyl chloride (6 ml, 77.2 mmol). The reaction mixture was stirred at 0° C. for 15 min. The mixture was concentrated under reduced pressure and the residue was partitioned between EtOAc and water. The combined organics were washed with water and brine, dried over MgSO₄, and concentrated under reduced pressure to give 2-(3-bromophenoxyl)ethyl methanesulfonate (107) as a light brown oil. This product was used in the next synthetic step without further purification. Yield (21.32 g, 98%): ¹H NMR (400 MHz, CDCl₃) δ 7.16 (t, J=7.8 Hz, 1H), 7.11-7.14 (m, 1H), 7.06-7.07 (m, 1H), 6.39 (ddd, J=7.6, 2.5, 1.8 Hz, 1H), 4.54-4.57 (m, 2H), 4.21-4.24 (m, 2H), 3.08 (s, 3H).

Step 3:

To a solution of mesylate 107 (24.05 g, 81.5 mmol) in anhydrous DMF (160 ml) was added potassium phthalimide (15.53 g, 83.8 mmol) and the reaction mixture was stirred at 60° C. for 14 h. The mixture was concentrated under reduced pressure and the residue was partitioned between hexanes-EtOAc (7:1) and water. A precipitate formed which was collected by filtration, washed excessively with water and hexanes, then dried under vacuum to give N-(2-(3-bromophenoxyl)ethyl)phthalimide (108) as white fluffy crystals (22.05 g). The second batch was collected by concentrating the organic layer of the filtrate under reduced pressure and suspending the residue 10% EtOAc-hexanes. The mixture was washed with water and the precipitate collected by filtration, washed excessively with water, then hexanes and dried under vacuum to give phthalimide 108 (5.65 g). Combined yield (21.18 g, 98%). ¹H NMR (400 MHz, CDCl₃) δ 7.87 (dd, J=5.2, 2.8 Hz, 2H), 7.73 (dd, J=5.6, 3.2 Hz, 2H), 7.03-7.12 (m, 3H), 6.80 (ddd, J=8.0, 2.5, 1.4 Hz, 1H), 4.21 (t, J=6.9 Hz, 2H), 4.10 (t, J=6.0 Hz, 2H).

Step 4:

To a suspension of phthalimide 108 (22.82 g, 65.9 mmol) in absolute EtOH (200 ml) was added hydrazine hydrate (6 ml, 123.7 mmol) and the reaction mixture was heated at reflux under argon for 1.5 h. After cooling to room temperature, the mixture was filtered and the filtrate was concentrated under reduced pressure. The residue was resuspended in hexanes (100 ml) and the solids removed by filtration. The filtrate was concentrated under reduced pressure then the residue was taken up in EtOH and concentrated under reduced pressure. This procedure was repeated with toluene to give amine 109 as a thick yellow oil. Yield (10.63 g, 75%): ¹H NMR (400 MHz, CDCl₃) δ 7.11-7.15 (m, 1H), 7.06-7.09 (m, 2H), 6.84 (ddd, J=8.0, 2.5, 1.2 Hz, 1H), 3.96 (t, J=5.3 Hz, 2H), 3.07 (t, J=5.09 Hz, 2H), 1.43 (br s, 2H).

Step 5:

To a solution of amine 109 (10.63 g, 49.2 mmol) in anhydrous THF (80 ml) was added ethyl trifluoroacetate (12 ml, 100.6 mmol) and the reaction mixture was stirred at room temperature overnight. The resulting solution was concentrated under reduced pressure and the residue was dissolved in 50% EtOAc-hexanes. Purification by filtration through a layer of a silica gel, eluting with 50% EtOAc-hexanes gave bromide 110 as a pale yellow oil which crystallized upon standing to a pale yellow solid. Yield (13.69 g, 89%): ¹H NMR (400 MHz, CDCl₃) δ 7.16 (t, J=8.0 Hz, 1H), 7.12-7.14 (m, 1H), 7.05-7.07 (m, 1H), 6.83 (ddd, J=7.6, 2.5, 1.8 Hz, 1H), 6.75 (br s, 1H), 4.09 (t, J=4.9 Hz, 2H), 3.78 (q, J=5.5 Hz, 2H).

Step 6:

4-Vinylheptan-4-ol was coupled to aryl bromide 110 according to the method used in Example 84. Purification by flash chromatography (10 to 40% EtOAc-hexanes gradient) gave trifluoroacetamide 111 as a light amber oil. Yield (0.417 g, 77%): ¹H NMR (400 MHz, CD₃OD) δ 7.19 (t, J=8.0 Hz, 1H), 6.94-6.98 (m, 2H), 6.78 (ddd, J=8.4, 2.8, 0.8 Hz, 1H), 6.50 (d, J=16.4 Hz, 1H), 6.22 (d, J=16.0 Hz, 1H), 4.06-4.12 (m, 3H), 3.66 (t, J=5.6 Hz, 2H), 1.53-1.60 (m, 4H), 1.30-1.47 (m, 4H), 0.91 (t, J=7.2 Hz, 6H)

Step 7:

Trifluoroacetamide 111 was deprotected according to the method used in Example 79 except that 5 equivalents of K₂CO₃ were used. The mixture was concentrated under reduced pressure and the residue was partitioned between EtOAc and water. The combined organics were washed with brine, dried over Na₂SO₄ and concentrated under reduced pressure to give Example 85 as a single trans isomer. Yield (0.1134 g, 36%): ¹H NMR (400 MHz, CD₃OD) 7.17-7.21 (m, 1H), 6.95-6.97 (m, 2H), 6.78-6.81 (m, 1H), 6.50 (d, J=16.4 Hz, 1H), 6.22 (d, J=16.0 Hz, 1H), 4.00 (t, J=5.2 Hz, 2H), 2.99 (t, J=5.2 Hz, 2H), 1.53-1.60 (m, 4H), 1.28-1.48 (m, 4H), 0.92 (t, J=7.2 Hz, 6H).

Example 86

Preparation of (R,E)-3-amino-1-(3-(2,6-dichlorostyryl)phenyl)propan-1-ol

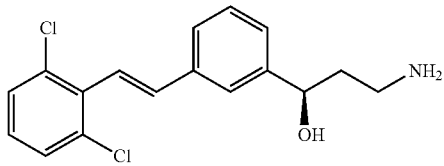 [SMILES: NCC[C@@H](O)c1cccc(/C=C/c2c(Cl)cccc2Cl)c1]

(R,E)-3-Amino-1-(3-(2,6-dichlorostyryl)phenyl)propan-1-ol is prepared according to Methods A, K and U and chiral reduction, as described herein.

Example 87

Preparation of (S,E)-3-amino-1-(3-(2,6-dichlorostyryl)phenyl)propan-1-ol

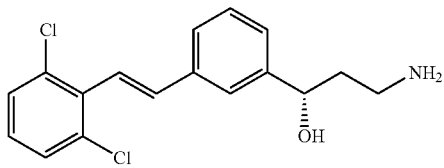 [SMILES: NCC[C@H](O)c1cccc(/C=C/c2c(Cl)cccc2Cl)c1]

(S,E)-3-Amino-1-(3-(2,6-dichlorostyryl)phenyl)propan-1-ol is prepared according to Methods A, K and U and chiral reduction, as described herein.

Example 88

Preparation of (S,E)-3-(3-(2,6-dichlorostyryl)phenyl)-2-fluoropropan-1-amine

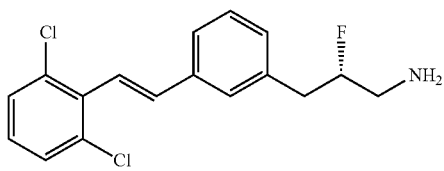 [SMILES: NC[C@@H](F)Cc1cccc(/C=C/c2c(Cl)cccc2Cl)c1]

(S,E)-3-(3-(2,6-dichlorostyryl)phenyl)-2-fluoropropan-1-amine is prepared according to Methods A, R and X, as described herein.

Example 89

Preparation of (E)-3-(3-(2,6-dichlorostyryl)phenyl)-2,2-difluoropropan-1-amine

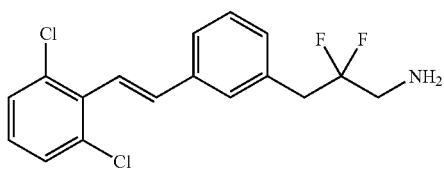 [SMILES: NCC(F)(F)Cc1cccc(/C=C/c2c(Cl)cccc2Cl)c1]

(E)-3-(3-(2,6-Dichlorostyryl)phenyl)-2,2-difluoropropan-1-amine was prepared according to Scheme 37.

SCHEME 37

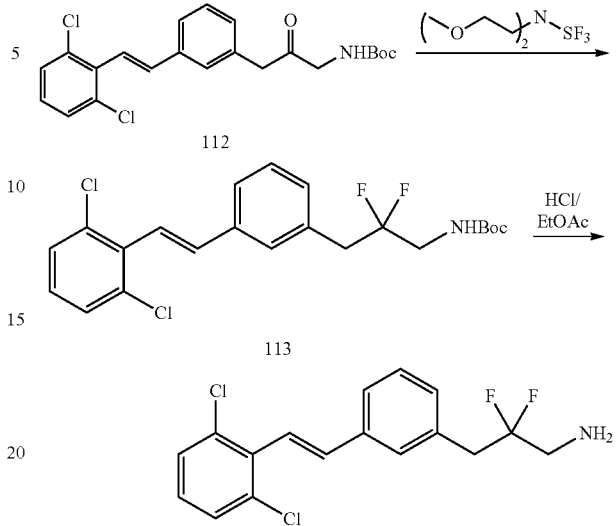

Step 1:

(E)-tert-butyl 3-(3-(2,6-dichlorostyryl)phenyl)-2-oxopropylcarbamate (112) (0.1633 g, 0.39 mmol) was stirred with bis(2-methoxyethyl)aminosulfur trifluoride (0.2 mL, 1.08 mmol) at room temperature for 1 h, 20 Additional bis(2-methoxyethyl)aminosulfur trifluoride (0.2 mL, 1.08 mmol) was added and the mixture was stirred at room temperature overnight. The mixture was purified by flash chromatography (10 to 40% EtOAc-hexanes gradient) to give difluoride 113 as an oil. Yield (0.0694 g, 41%): $^1$H NMR (400 MHz, CDCl$_3$) δ 7.49 (d, J=8.0 Hz, 1H), 7.43 (br s, 1H), 7.35 (t, J=7.6 Hz, 1H), 7.347 (d, J=8.0 Hz, 2H), 7.23 (d, J=7.2 Hz, 1H), 7.09-7.14 (m, 3H), 4.82 (br s, 1H), 3.54 (ddd, J=14.0, 14.0, 6.4 Hz, 2H), 3.21 (t, J=16.8 Hz, 2H), 1.46 (s, 9H).

Step 2:

To a solution of difluoride 113 (0.0694 g, 0.16 mmol) in EtOAc (0.5 mL) was added a solution of HCl (3 mL of a 4.6 M solution in EtOAc, 13.8 mmol) and the mixture was stirred for 3 h. The solid was collected by filtration and dried under vacuum to give Example 89 hydrochloride as a white solid. Yield (0.037 g, 62%): $^1$H NMR (400 MHz, DMSO-d$_6$) δ 8.39 (br s, 3H), 7.59 (d, J=7.6 Hz, 1H), 7.52-7.54 (m, 3H), 7.41 (t, J=7.6 Hz, 1H), 7.33 (t, J=8.0 Hz, 1H), 7.27 (d, J=7.6 Hz, 1H), 7.15 (d, J=16.4 Hz, 1H), 7.08 (d, 0.1=16.4 Hz, 1H), 3.36-3.45 (m, 4H).

Example 90

Preparation of (Z)-3-(3-(2-(2-methoxyethoxy)styryl)phenyl)-propan-1-amine

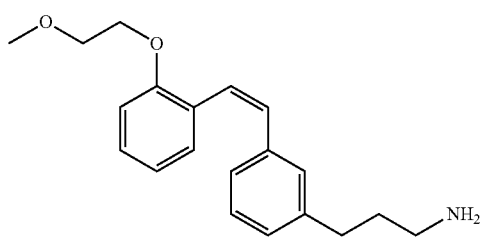 [SMILES: COCCOc1ccccc1/C=C\c1cccc(CCCN)c1]

(Z)-3-(3-(2-(2-Methoxyethoxy)styryl)phenyl)-propan-1-amine was prepared according to the method used in Example 77.

Step 1:

Phthalimide 29 was coupled with 2-(2-methoxyethoxyl)benzylphosphonium bromide according to the method used in Example 76 except that 2 equivalents of phosphonium salt were used and the reaction was stirred for 1 h at room temperature. Purification by flash chromatography (15% EtOAc-hexanes) gave (E/Z)-2-(3-(3-(2-(2-methoxyethoxy)styryl)phenyl)propyl)isoindoline-1,3-dione as a brown oil. Yield (0.700 g, 58%).

Step 2:

(E/Z)-2-(3-(3-(2-(2-Methoxyethoxy)styryl)phenyl)propyl)isoindoline-1,3-dione was deprotected following the method used in Example 76 except that the reaction was conducted at room temperature for 3 h. The mixture was concentrated under reduced pressure. The white solid was washed with diethyl ether and the decanted solution was concentrated under reduced pressure. The residue was purified by Preparative HPLC (Method 2) to give Example 90 trifluoroacetate. Yield (0.030 g, 9%): $^1$H NMR (DMSO-$d_6$) δ 7.66 (br s, 3H), 7.22 (t, J=8.0 Hz, 1H), 7.17 (t, J=8.0 Hz, 1H), 7.03-7.12 (m, 5H), 6.76 (t, J=7.2 Hz, 1H), 6.64 (d, J=12.4 Hz, 1H), 6.59 (d, J=12.0 Hz, 1H), 4.10 (t, J=4.4 Hz, 2H), 3.60 (t, J=4.8 Hz, 2H), 3.31 (s, 3H), 2.73 (t, J=7.2 Hz, 2H), 1.72-1.77 (m, 2H), 1.17-1.90 (m, 2H).

Example 91

Preparation of (E)-3-(3-(3-methyloxystyryl)phenyl)propan-1-amine

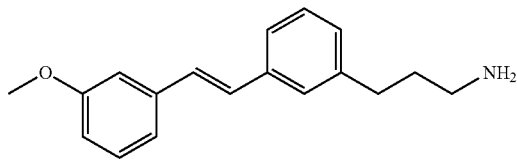 [SMILES: COc1cccc(/C=C/c2cccc(CCCN)c2)c1]

(E)-3-(3-(3-Methoxystyryl)phenyl)propan-1-amine was prepared according to the method used in Example 76.

Step 1:

Phthalimide 29 was coupled with (2-methoxybenzyl)triphenylphosphonium bromide according to the method used in Example 76. Purification by flash chromatography (8% EtOAc-hexanes) gave (E)-2-(3-(3-(3-methoxystyryl)phenyl)propyl)isoindoline-1,3-dione a brown semi-solid. Yield (0.090 g, 29%): $^1$H NMR (400 MHz, CDCl$_3$) δ 7.81-7.83 (m, 2H), 7.68-7.70 (m, 2H), 7.34 (s, 1H), 7.21-7.30 (m, 3H), 7.09-7.12 (m, 2H), 7.05 (s, 3H), 6.82 (dd, J=8.0, 2.0 Hz, 1H), 3.86 (s, 3H), 3.78 (t, J=7.2 Hz, 2H), 2.72 (t, J=7.6 Hz, 2H), 2.05-2.12 (m, 2H).

Step 2:

(E)-2-(3-(3-(3-Methoxystyryl)phenyl)propyl)isoindoline-1,3-dione was deprotected following the method used in Example 90 except that the reaction mixture was stirred overnight in methanol. Purification by preparative thin layer chromatography on silica gel gave Example 97. Yield (0.010 g, 16%): $^1$H NMR (400 MHz, DMSO-$d_6$) δ 7.42 (s, 1H), 7.39 (d, J=7.6 Hz, 1H), 7.25-7.29 (m, 2H), 7.21 (d, J=4.0 Hz, 2H), 7.15-7.16 (m, 2H), 7.09 (d, J=7.2 Hz, 1H), 6.82-6.83 (m, 1H), 3.77 (s, 3H), 2.53-2.63 (m, 4H), 1.65-1.72 (m, 2H).

Example 92

Preparation of (E)-3-(3-(2-(1-methoxynaphthalen-2-yl)vinyl)phenyl)propan-1-amine

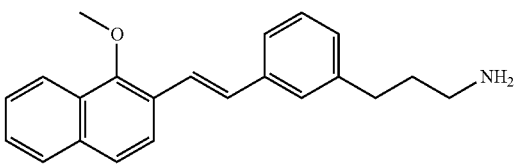 [SMILES: COc1c(/C=C/c2cccc(CCCN)c2)ccc2ccccc12]

(E)-3-(3-(2-(1-Methoxynaphthalen-2-yl)vinyl)phenyl)propan-1-amine was prepared according to the method used in Example 76.

Step 1:

(1-Methoxynaphthalen-2-ylmethyl)triphenylphosphonium bromide was prepared according to the method used in Example 76, except that 1.1 equivalents of triphenylphosphine were used in the reaction. Yield (1.25 g, 70%): $^1$H NMR (400 MHz, DMSO-$d_6$) δ 7.84-7.88 (m, 5H), 7.67-7.70 (m, 12H), 7.53-7.55 (m, 2H), 7.49 (d, J=8.4 Hz, 1H), 6.89 (d, J=8.4 Hz, 1H), 5.15 (dd, J=15.6, 2.8 Hz, 2H), 3.74 (s, 3H).

Step 2:

Phthalimide 29 was coupled with (1-methoxynaphthalen-2-ylmethyl)triphenylphosphonium bromide according to the method used in Example 76 except that 2 equivalents of the phosphonium salt were used. Purification by flash chromatography (10% EtOAc-hexanes) gave (E/Z)-2-(3-(3-(2-(1-methoxynaphthalen-2-yl)vinyl)phenyl)propyl)isoindoline-1,3-dione a yellow oil. The mixture was further purified by Preparative HPLC to give the cis-isomer (0.034 g, 4% yield) as a colorless oil and the trans-isomer (0.050 g, 7% yield) as a white solid. $^1$H NMR (400 MHz, CDCl$_3$) δ 8.15 (d, J=8.4 Hz, 1H), 7.81-7.83 (m, 3H), 7.77 (d, J=8.8 Hz, 1H), 7.68-7.71 (m, 2H), 7.63 (d, J=2.8 Hz, 1H), 7.59 (d, J=10.4 Hz, 1H), 7.44-7.54 (m, 2H), 7.42 (s, 1H), 7.37 (d, J=12.0 Hz, 1H), 7.26 (t, J=7.6 Hz, 1H), 7.17 (d, J=16.4 Hz, 1H), 7.12 (d, J=7.6 Hz, 1H), 3.99 (s, 3H), 3.79 (t, J=7.2 Hz, 2H), 2.74 (t, J=7.6 Hz, 2H), 2.06-2.14 (m, 2H).

Step 3:

(E)-2-(3-(3-(2-(1-methoxynaphthalen-2-yl)vinyl)phenyl)propyl)isoindoline-1,3-dione was deprotected following the method used in Example 76 except that the reaction was conducted in MeOH at room temperature for 2 h. The reaction was concentrated under reduced pressure. The white solid was washed with diethyl ether and the decanted solution was concentrated under reduced pressure. The residue was purified by preparative thin layer chromatography on silica gel (1:10:89 NH$_4$OH:MeOH:CH$_2$Cl$_2$) to give Example 92. Yield (0.020 g, 57%): $^1$H NMR (400 MHz, DMSO-$d_6$) δ 8.07 (d, J=8.4 Hz, 1H), 7.91 (d, J=8.8 Hz, 2H), 7.71 (d, J=8.8 Hz, 1H), 7.46-7.57 (m, 5H), 7.38 (d, J=16.4 Hz, 1H), 7.31 (t, J=7.6 Hz, 1H), 7.13 (d, J=7.6 Hz, 1H), 3.91 (s, 3H), 2.62-2.66 (m, 2H), 2.57 (t, J=6.8 Hz, 2H), 1.64-1.72 (m, 2H).

Example 93

Preparation of (Z)-3-(3-(4-chlorostyryl)phenyl)propan-1-amine

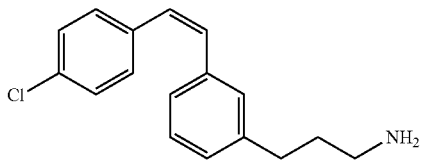 [SMILES: NCCCc1cccc(/C=C\c2ccc(Cl)cc2)c1]

(Z)-3-(3-(4-Chlorostyryl)phenyl)propan-1-amine was prepared according to the method used in Example 76.

Step 1:

Phthalimide 29 was coupled with (4-chlorobenzyl)triphenylphosphonium bromide according to the method used in Example 76. Purification by flash chromatography (7% EtOAc-hexanes) gave (E)-2-(3-(3-(4-chlorostyryl)phenyl)propyl)isoindoline-1,3-dione (0.120 g, 10%) and (Z)-2-(3-(3-(4-chlorostyryl)phenyl)propyl)isoindoline-1,3-dione (0.150 g, 13%) as yellow solids. Cis-isomer: $^1$H NMR (400 MHz, CDCl$_3$) δ 7.79-7.86 (m, 2H), 7.68-7.73 (m, 3H), 7.12-7.17 (m, 5H), 7.00-7.05 (m, 3H), 6.58 (d, J=12.0 Hz, 1H), 6.50 (d, J=12.0 Hz, 1H), 3.68 (t, J=7.2 Hz, 2H), 2.60 (t, J=7.6 Hz, 2H), 1.90-1.97 (m, 2H).

Step 2:

From another preparation, a mixture of (E/Z)-2-(3-(3-(4-chlorostyryl)phenyl)propyl)isoindoline-1,3-dione was deprotected following the method used in Example 76. The crude product was purified by Preparative HPLC (Method 2) to give Example 93 trifluoroacetate. Yield (0.020 g, 16%): $^1$H NMR (400 MHz, DMSO-d$_6$) δ 7.72 (br s, 3H), 7.31-7.34 (m, 2H), 7.21-7.25 (m, 3H), 7.09-7.10 (m, 2H), 7.05 (d, J=7.6 Hz, 1H), 6.67 (d, J=12.4 Hz, 1H), 6.60 (d, J=12.0 Hz, 1H), 2.75 (t, J=7.2 Hz, 2H), 2.56 (t, J=7.6 Hz, 2H), 1.73-1.81 (m, 2H).

Example 94

Preparation of (E)-3-(3-(2-(biphenyl-2-yl)vinyl)phenyl)propan-1-amine

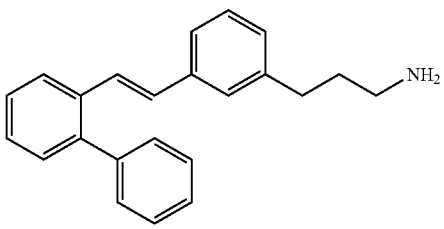 [SMILES: NCCCc1cccc(/C=C/c2ccccc2-c2ccccc2)c1]

(E)-3-(3-(2-(Biphenyl-2-yl)vinyl)phenyl)propan-1-amine was prepared according to the method used in Example 76.

Step 1:

Phthalimide 29 was coupled with biphenyl-2-ylmethyl triphenylphosphonium bromide. Purification by flash chromatography (5% EtOAc-hexanes) gave (E)-2-(3-(3-(2-(biphenyl-2-yl)vinyl)phenyl)propyl)isoindoline-1,3-dione (0.100 g, 13%) and (E/Z)-2-(3-(3-(2-(biphenyl-2-yl)vinyl)phenyl)propyl)isoindoline-1,3-dione (0.230 g, 30%) as colorless oils. Trans-isomer: $^1$H NMR (400 MHz, CDCl$_3$) δ 781-7.83 (m, 2H), 7.72-7.74 (m, 1H), 7.68-7.70 (m, 2H), 7.63-7.65 (m, 2H), 7.42-7.52 (m, 6H), 7.35-7.40 (m, 2H), 7.22-7.24 (m, 1H), 7.09-7.14 (m, 3H), 3.79 (t, J=7.2 Hz, 2H), 2.73 (t, J=7.6 Hz, 2H), 2.05-2.13 (m, 2H).

Step 2:

(E)-2-(3-(3-(2-(biphenyl-2-yl)vinyl)phenyl)propyl)isoindoline-1,3-dione was deprotected following the method used in Example 76 except that the reaction was conducted at room temperature for 36 h. Purification by preparative thin layer chromatography on silica gel gave Example 94. Yield (0.051 g, 71%): $^1$H NMR (400 MHz, DMSO-d$_6$) δ 7.84 (d, J=7.2 Hz, 1H), 7.71 (br s, 3H), 7.49 (t, J=7.2 Hz, 1H), 7.33-7.44 (m, 7H), 7.16-7.30 (m, 4H), 7.10 (d, J=7.2 Hz, 1H), 7.03 (d, J=16.4 Hz, 1H), 2.78 (t, J=7.6 Hz, 2H), 2.62 (t, J=7.6 Hz, 2H), 1.78-1.85 (m, 2H).

Example 95

Preparation of (Z)-3-(3-(2-(naphthalen-1-yl)vinyl)phenyl)propan-1-amine

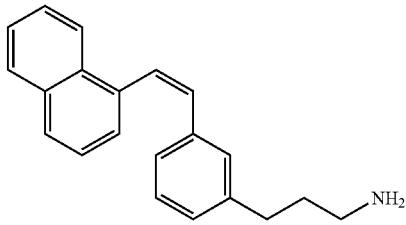 [SMILES: NCCCc1cccc(/C=C\c2cccc3ccccc23)c1]

(Z)-3-(3-(2-(Naphthalen-1-yl)vinyl)phenyl)propan-1-amine was prepared according to the method used in Example 76.

Step 1:

Phthalimide 29 was coupled with (naphthalen-1-ylmethyl)triphenylphosphonium bromide according to the method used in Example 76. Purification by flash chromatography (10% EtOAc-hexanes) gave (E/Z)-2-(3-(3-(2-(naphthalen-1-yl)vinyl)phenyl)propyl)isoindoline-1,3-dione a brown oil. Yield (0.090 g, 46%).

Step 2:

(E/Z)-2-(3-(3-(2-(naphthalen-1-yl)vinyl)phenyl)propyl)isoindoline-1,3-dione was deprotected following the method used in Example 76. The reaction was concentrated under reduced pressure. The white solid was washed with diethyl ether and the decanted solution was concentrated under reduced pressure. The residue was purified by Preparative HPLC (Method 2) to give Example 92 trifluoroacetate. Yield (0.020 g, 14%): $^1$H NMR (400 MHz, DMSO-d$_6$) δ 7.96-8.02 (m, 2H), 7.88 (d, J=8.0 Hz, 1H), 7.51-7.57 (m, 5H), 7.42 (t, J=7.6 Hz, 1H), 7.32 (d, J=6.8 Hz, 1H), 7.12 (d, J=12.4 Hz, 1H), 7.03 (t, J=7.2 Hz, 1H), 6.94-6.97 (m, 2H), 6.87 (d, J=12.4 Hz, 1H), 6.83 (d, J=7.6 Hz, 1H), 2.64 (t, J=7.6 Hz, 2H), 2.43 (t, J=7.6 Hz, 2H), 1.60-1.68 (m, 2H).

Example 96

Preparation of (Z)-3-(3-(2-(3-methoxynaphthalen-2-yl)vinyl)phenylpropan-1-amine

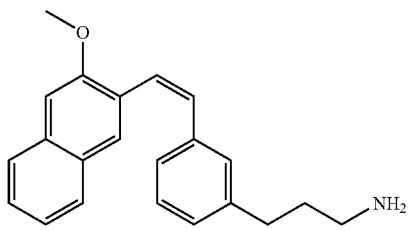 [SMILES: COc1cc2ccccc2cc1/C=C\c1cccc(CCCN)c1]

(Z)-3-(3-(2-(3-Methoxynaphthalen-2-yl)vinyl)phenyl)propan-1-amine was prepared according to the method used in Example 77.

Step 1:
Phthalimide 29 was coupled with (3-methoxynaphthalen-2-yl methyl)triphenylphosphonium bromide according to the method used in Example 76. Purification by flash chromatography (17% EtOAc-hexanes) gave (E/Z)-2-(3-(3-(2-(3-methoxynaphthalen-2-yl)vinyl)phenyl)propyl)isoindoline-1,3-dione a yellow oil. Yield (0.500 g, 40%).

Step 2:
(E/Z)-2-(3-(3-(2-(3-methoxynaphthalen-2-yl)vinyl)phenyl)propyl)isoindoline-1,3-dione was deprotected following the method used in Example 76. The crude product was purified by Preparative HPLC (Method 2) to give Example 96 trifluoroacetate. Yield (0.030 g, 10%): $^1$H NMR (400 MHz, DMSO-$d_6$) δ 7.81 (d, J=8.0 Hz, 1H), 7.69 (br s, 3H), 7.60 (s, 1H), 7.55 (d, J=8.0 Hz, 1H), 7.42 (ddd, J=9.2, 6.8, 1.2 Hz, 1H), 7.38 (s, 1H), 7.27 (ddd, J=8.4, 7.2, 1.2 Hz, 1H), 7.08-7.12 (m, 2H), 7.00-7.03 (m, 2H), 6.74 (d, J=12.4 Hz, 1H), 6.70 (d, J=12.4 Hz, 1H), 3.88 (s, 3H), 2.65-2.73 (m, 2H), 2.48-2.50 (m, 2H), 1.67-1.75 (m, 2H).

Example 97

Preparation of (E)-3-(3-(3-chlorostyryl)phenyl)propan-1-amine

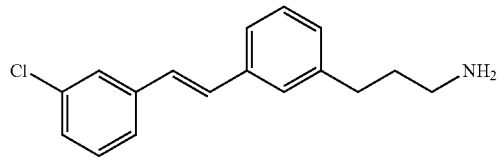 [SMILES: NCCCc1cccc(/C=C/c2cccc(Cl)c2)c1]

(E)-3-(3-(3-Chlorostyryl)phenyl)propan-1-amine was prepared according to the method used in Example 76.

Step 1:
Phthalimide 29 was coupled with 3-chlorobenzyltriphenylphosphonium bromide. Purification by flash chromatography (5% EtOAc-hexanes) gave (E)-2-(3-(3-(3-chlorostyryl)phenyl)propyl)isoindoline-1,3-dione (0.100 g, 30%) and (Z)-2-(3-(3-(3-chlorostyryl)phenyl)propyl)isoindoline-1,3-dione (0.180 g, 30%) as colorless oils. Trans-isomer: $^1$H NMR (400 MHz, CDCl$_3$) δ 7.80-7.84 (m, 2H), 7.68-7.72 (m, 2H), 7.50 (t, J=1.6 Hz, 1H), 7.37 (dt, J=7.6, 1.2 Hz, 1H), 7.35 (s, 1H), 7.29 (d, J=7.6 Hz, 1H), 7.21-7.26 (m, 3H), 7.12 (dt, J=6.4, 2.0 Hz, 1H), 7.03 (d, J=4.4 Hz, 2H), 3.78 (t, J=7.2 Hz, 2H), 2.72 (t, J=7.6 Hz, 2H), 2.05-2.12 (m, 2H).

Step 2:
From another preparation, a mixture of (E/Z)-2-(3-(3-(3-chlorostyryl)phenyl)propyl)isoindoline-1,3-dione was deprotected. The crude product was purified by Preparative HPLC (Method 2) to give Example 97 trifluoroacetate as a white solid. Yield (0.040 g, 67%): $^1$H NMR (400 MHz, DMSO-$d_6$) δ 7.73 (br s, 3H), 7.70 (s, 1H), 7.55 (d, J=7.6 Hz, 1H), 7.44-7.48 (m, 2H), 7.41 (t, J=8.0 Hz, 1H), 7.36 (d, J=4.0 Hz, 1H), 7.32-7.35 (m, 2H), 7.24 (t, J=16.4 Hz, 1H), 7.15 (d, J=7.6 Hz, 1H), 2.81 (t, J=7.2 Hz, 2H), 2.67 (t, J=7.6 Hz, 2H), 1.83-1.91 (m, 2H).

Example 98

Preparation of (E)-3-(3-(2-butoxystyryl)phenyl)propan-1-amine

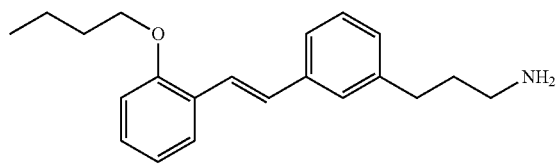 [SMILES: CCCCOc1ccccc1/C=C/c1cccc(CCCN)c1]

(E)-3-(3-(2-butoxystyryl)phenyl)propan-1-amine is prepared according to the method used in Example 32.

Example 99

Preparation of (E)-3-(3-(4-methyloxystyryl)phenyl)propan-1-amine

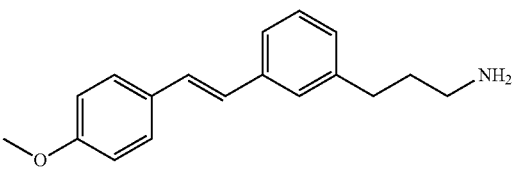 [SMILES: COc1ccc(/C=C/c2cccc(CCCN)c2)cc1]

(E)-3-(3-(4-Methoxystyryl)phenyl)propan-1-amin is prepared according to the method used in Example 32.

Example 100

Preparation of (E)-1-(3-(3-aminopropyl)phenyl)-3-ethylpent-1-en-3-ol

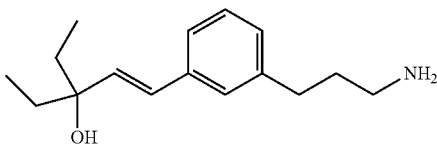 [SMILES: CCC(O)(/C=C/c1cccc(CCCN)c1)CC]

(E)-1-(3-(3-aminopropyl)phenyl)-3-ethylpent-1-en-3-ol was prepared according to the method used in Example 79.

Step 1:

3-Ethylpent-1-en-3-ol was coupled to aryl bromide 104. Purification by flash chromatography (20 to 65% EtOAc-hexanes gradient) gave (E)-N-(3-(3-(3-ethyl-3-hydroxypent-1-enyl)phenyl)propyl)-2,2,2-trifluoroacetamide as a light yellow syrup. Yield (0.401 g, 90%): $^1$H NMR (400 MHz, DMSO-d$_3$) δ 9.41 (br s, 1H), 7.19-7.22 (m, 3H), 7.01-7.04 (m, 1H), 6.46 (d, J=16.4 Hz, 1H), 6.18 (d, J=16.4 Hz, 1H), 4.27 (s, 1H), 3.18 (q, J=6.8 Hz, 2H), 2.55 (t, J=7.6 Hz, 2H), 1.76-1.79 (m, 2H), 1.49 (q, J=7.6 Hz, 4H), 0.79 (t, J=7.6 Hz, 6H).

Step 2:

(E)-N-(3-(3-(3-Ethyl-3-hydroxypent-1-enyl)phenyl)propyl)-2,2,2-trifluoroacetamide was deprotected then purified by flash chromatography (80 to 100% EtOAc-hexanes then 8-10% 7 M NH$_3$ in MeOH-EtOAc gradient) to give Example 100 as a colorless oil. Yield (0.2374 g, 85%): $^1$H NMR (400 MHz, DMSO-d$_6$) 7.17-7.20 (m, 3H), 7.00-7.02 (m, 1H), 6.45 (d, J=16.0 Hz, 1H), 6.17 (d, J=16.0 Hz, 1H), 4.27 (s, 1H), 2.50-2.57 (m, 4H), 1.57-1.64 (m, 2H), 1.49 (q, J=7.6 Hz, 4H), 1.36 (br s, 2H), 0.79 (t, J=7.6 Hz, 6H).

Example 101

Preparation of (E)-3-(3-(3-aminopropyl)phenyl)prop-2-en-1-ol

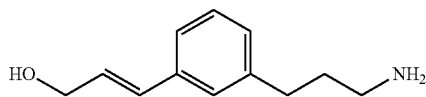 [SMILES: NCCCc1cccc(/C=C/CO)c1]

(E)-3-(3-(3-Aminopropyl)phenyl)prop-2-en-1-ol is prepared according to the method used in Example 79.

Example 102

Preparation of (E)-3-(3-(3-methoxyprop-1-enyl)phenyl)propan-1-amine-ol

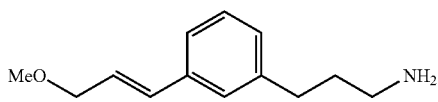 [SMILES: COC/C=C/c1cccc(CCCN)c1]

(E)-3-(3-(3-Methoxyprop-1-enyl)phenyl)propan-1-amine-ol was prepared according to the method used in Example 79.

Step 1:

Allyl methyl ether was coupled to aryl bromide 104 according to the method used in Example 84. Purification by flash chromatography twice (20 to 40% EtOAc-hexanes gradient) gave (E)-2,2,2-trifluoro-N-(3-(3-(3-methoxyprop-1-enyl)phenyl)propyl)acetamide as a yellow oil. Yield (0.060 g, 6%): $^1$H NMR (400 MHz, CDCl$_3$) δ 7.20-7.30 (m, 3H), 7.05-7.12 (m, 1H), 6.59 (d, J=16.0 Hz, 1H), 6.22-6.32 (m, 2H), 3.36-3.40 (m, 5H), 2.64-2.72 (m, 2H), 1.88-2.0 (m, 4H).

Step 2:

(E)-2,2,2-Trifluoro-N-(3-(3-(3-methoxyprop-1-enyl)phenyl)propyl)acetamide was deprotected according to the method used in Example 84. Purification by flash chromatography (0 to 10% 7 M NH$_3$ in MeOH-EtOAc) gave Example 102 as a colorless oil. Yield (0.023 g, 56%): $^1$H NMR (400 MHz, CDCl$_3$) δ 7.21-7.22 (m, 3H), 7.05-7.10 (m, 1H), 6.58 (dt, J=16.0, 1.2 Hz, 1H), 6.26 (dt, J=16.0, 6.0 Hz, 1H), 4.08 (dd, J=6.0, 1.6 Hz, 2H), 3.36 (s, 3H), 2.72 (t, J=6.8 Hz, 2H), 2.61 (t, J=8.0 Hz, 2H), 1.71-1.80 (m, 2H), 1.18-1.28 (m, 2H).

Example 103

Preparation of (E)-1-(3-(3-aminopropyl)phenyl)-3-methylhex-1-en-3-ol

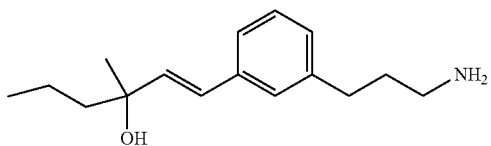 [SMILES: CCCC(C)(O)/C=C/c1cccc(CCCN)c1]

(E)-1-(3-(3-Aminopropyl)phenyl)-3-methylhex-1-en-3-ol is prepared according to the method used in Example 79.

Example 104

Preparation of (E)-1-(3-(3-aminopropyl)phenyl)-3-ethylhex-1-en-3-ol

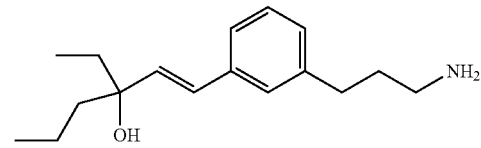 [SMILES: CCCC(O)(/C=C/c1cccc(CCCN)c1)CC]

(E)-1-(3-(3-Aminopropyl)phenyl)-3-ethylhex-1-en-3-ol is prepared according to the method used in Example 79.

Example 105

Preparation of (R,E)-3-amino-1-(3-(2-(2,6,6-trimethylcyclohex-1-enyl)vinyl)phenyl)propan-1-ol

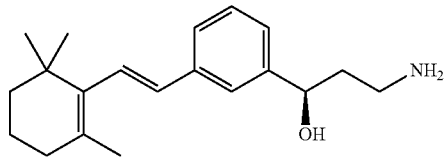 [SMILES: CC1=C(/C=C/c2cccc([C@H](O)CCN)c2)C(C)(C)CCC1]

(R,E)-3-Amino-1-(3-(2-(2,6,6-trimethylcyclohex-1-enyl)vinyl)phenyl)propan-1-ol (R/S stereochemistry is assumed not assigned) was prepared according to Scheme 38.

SCHEME 38

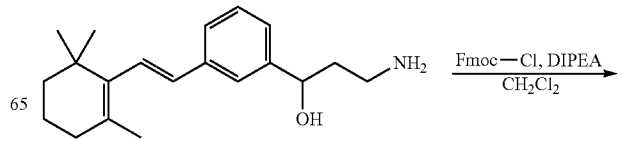

249

-continued

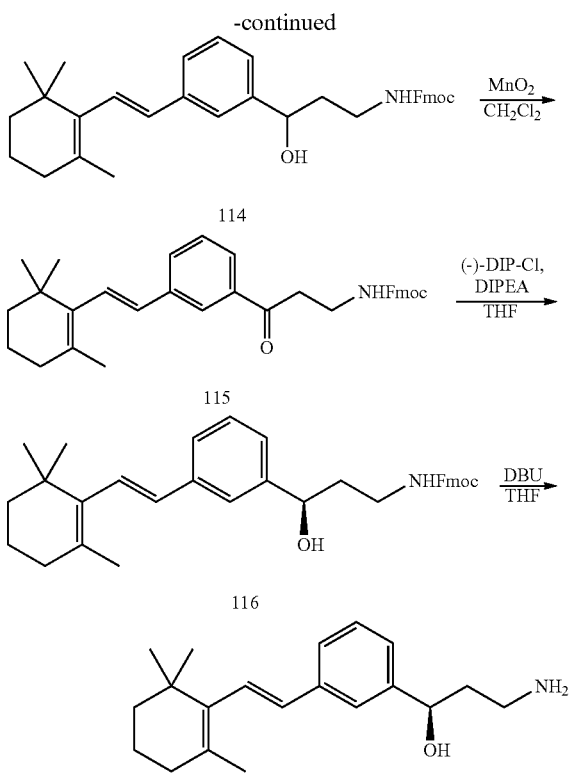

Step 1:
To a solution of (E)-3-amino-1-(3-(2-(2,6,6-trimethylcyclohex-1-enyl)vinyl)phenyl)propan-1-ol (Example 25) (0.5137 g, 1.57 mmol) in CH$_2$Cl$_2$ (8 mL) was added diisopropyl ethylamine (0.33 mL, 1.90 mmol) and a solution of 9-fluorenylmethoxycarbonyl chloride (0.4875 g, 1.88 mmol) in CH$_2$Cl$_2$ (2 mL). The reaction mixture was stirred for 35 min then concentrated under reduced pressure. Purification by flash chromatography (10 to 70% EtOAc-hexanes gradient) gave alcohol 114 as an oil. Yield (0.5564 g, 68%).

Step 2:
To a solution of alcohol 114 (0.5564, 1.07 mmol) in CH$_2$Cl$_2$ (20 mL) was added MnO$_2$ (3.10 g, 35.7 mmol) and the mixture was stirred at room temperature overnight. Solids were removed from the mixture by filtration through a pad of silica gel and the filtrate was concentrated under reduced pressure. Purification by flash chromatography (10 to 70% EtOAc-hexanes gradient) gave ketone 115 as an oil. Yield (0.4391 g, 79%): $^1$H NMR (400 MHz, CDCl$_3$) δ 7.98 (br s, 1H), 7.79 (d, J=8.0 Hz, 1H), 7.73 (d, J=7.6 Hz, 2H), 7.62 (d, J=7.6 Hz, 1H), 7.57 (d, J=7.6 Hz, 2H), 7.42 (t, J=7.6 Hz, 1H), 7.39 (t, J=7.6 Hz, 2H), 7.28 (t, J=7.6 Hz, 1H), 6.77 (dd, J=16.0, 0.8 Hz, 1H), 6.39 (dd, J=16.0, 0.8 Hz, 1H), 5.43 (t, J=6.0 Hz, 1H), 4.38 (d, J=6.8 Hz, 2H), 4.19 (t, J=6.8 Hz, 1H), 3.65 (q, J=5.6 Hz, 2H), 3.25 (t, J=5.2 Hz, 2H), 2.06 (t, J=6.0 Hz, 2H), 1.77 (s, 3H), 1.63-1.69 (m, 2H), 1.49-1.52 (m, 2H), 1.08 (s, 6H).

Step 3:
Preparation of (−)-B-chlorodiisopinocampheylborane solution ((−)-DIP-Cl): To an ice-cold solution of (−)-α-pinene (1.0042 g, 7.4 mmol) in hexanes (6 mL) under argon was added chloroborane-methyl sulfide complex (0.4 mL, 3.84 mmol) slowly. Additional (−)-α-pinene (0.17 mL, 1.09 mmol) was added and the mixture was stirred for 5 min then allowed to warm to room temperature over 3 min. The resulting solution was approximately 0.5 M.

250

To a −25° C. solution of ketone 115 (0.2117 g, 0.41 mmol) and diisopropyl ethylamine (0.020 mL, 0.115 mmol) in THF (2.5 mL) was added a solution of ((−)-DIP-Cl (1.6 mL of the 0.5 M solution, 0.80 mmol) over 5 min. The reaction mixture was cooled to −78° C. for 5 min then allowed to warm to room temperature. After stirring 30 min, additional (−)-DIP-Cl (1.6 mL of 0.5 M solution, 0.80 mmol) was added and the mixture was stirred for 2 h. Acetone (5 mL) was added then the mixture was concentrated under reduced pressure. The residue was partitioned between EtOAc and brine and the combined organics were dried over MgSO$_4$ and concentrated under reduced pressure. Purification by flash chromatography (10 to 50% EtOAc-hexanes gradient) gave alcohol 116 as an oil. Yield (0.1155 g, 54%): $^1$H NMR (400 MHz, CDCl$_3$) δ 7.76 (d, J=7.6 Hz, 2H), 7.60 (d, J=7.2 Hz, 2H), 7.27-7.42 (m, 7H), 7.19 (d, J=6.4 Hz, 1H), 6.70 (dd, J=16.0, 0.8 Hz, 1H), 6.34 (d, J=16.4 Hz, 1H), 5.14 (br s, 1H), 4.72 (t, J=7.2 Hz, 1H), 4.40-4.50 (m, 2H), 4.22 (t, J=6.8 Hz, 1H), 3.70 (t, J=6.4 Hz, 0.5H), 3.59 (t, J=6.8 Hz, 0.5H), 3.53-3.59 (m, 1H), 3.26-3.31 (m, 1H), 2.02-2.05 (m, 2H), 1.85-1.93 (m, 2H), 1.75 (s, 3H), 1.61-1.67 (m, 2H), 1.48-1.51 (m, 1H), 1.06 (s, 6H).

Step 4:
To a solution of alcohol 116 (0.0.0608 g, 0.117 mmol) in THF (2 mL) was added 1,8-diazabicyclo[5.4.0]undec-7-ene (0.034 g, 0.22 mmol). The mixture was stirred at room temperature for 20 min then concentrated under reduced pressure. The residue was partitioned between EtOAc and brine and the combined organics were dried over Na$_2$SO$_4$ and concentrated under reduced pressure. Purification by flash chromatography (5:9:1 to 5:5:1 EtOAc/hexanes/7 M NH$_3$ in MeOH gradient) gave Example 105 as an oil. Yield (0.011 g, 32%): The $^1$H NMR data was consistent with that of Example 25. Chiral HPLC: 92.9% major enantiomer (AUC), $t_R$=18.042 min (minor enantiomer: 7.1%, $t_R$=20.413 min).

Example 106

Preparation of (S,E)-3-amino-1-(3-(2-(2,6,6-trimethylcyclohex-1-enyl)vinyl)phenyl)propan-1-ol

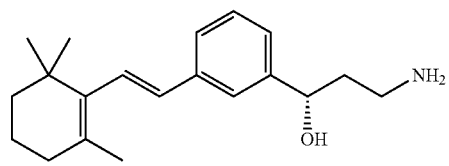

(S,E)-3-Amino-1-(3-(2-(2,6,6-trimethylcyclohex-1-enyl)vinyl)phenyl)propan-1-ol (R/S stereochemistry is assumed, not assigned) was prepared according to the method used in Example 105 with modifications.

Step 1:
Ketone 115 was reduced with a freshly prepared solution of (+)-B-chlorodiisopinocampheylborane solution ((+)-DIP-Cl) according to the method used in Example 105 to give (S,E)-(9H-fluoren-9-yl)methyl 3-hydroxy-3-(3-(2-(2,6,6-trimethylcyclohex-1-enyl)vinyl)phenyl)propylcarbamate as an oil. Yield (0.1096 g, 51%).

Step 2:
(S,E)-(9H-fluoren-9-yl)methyl 3-hydroxy-3-(3-(2-(2,6,6-trimethylcyclohex-1-enyl)vinyl)phenyl)propylcarbamate was deprotected and purified as described in Example 105 to give Example 106 as an oil. Yield (0.0140 g, 39%). The $^1$H NMR data was consistent with that of Example 25. Chiral HPLC; 96.0% major enantiomer (AUC), $t_R$=20.282 min (minor enantiomer: 3.9%, $t_R$=20.282 min)

Example 107

Preparation of (E)-3-(5-(2-chloro-6-(methylthio)styryl)-2-methoxyphenyl)propan-1-amine

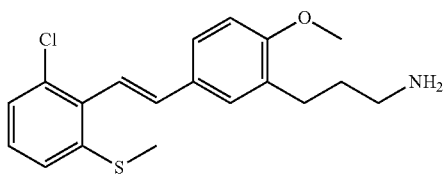 [SMILES: COc1ccc(/C=C/c2c(Cl)cccc2SC)cc1CCCN]

(E)-3-(5-(2-Chloro-6-(methylthio)styryl)-2-methoxyphenyl)propan-1-amine was prepared according to Scheme 39.

SCHEME 39

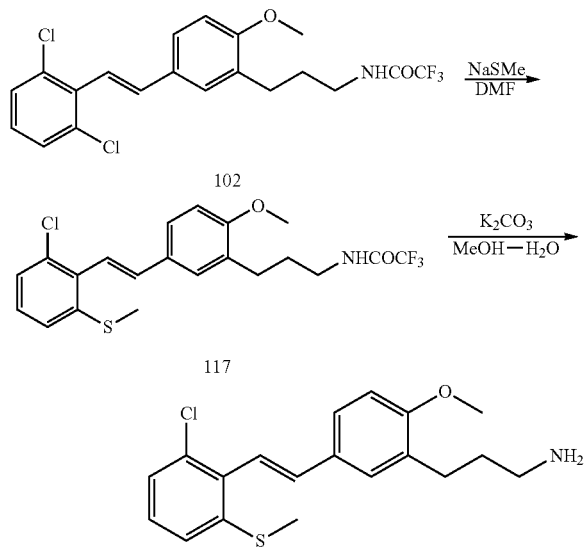

Step 1:
To a solution of dichloroarene 102 (0.3772 g, 0.87 mmol) in DMF (9 mL) was added sodium thiomethoxide (0.1176, 1.68 mmol). The mixture was heated at 100° C. for 2 h then cooled to room temperature and concentrated under reduced pressure. The residue was partitioned between EtOAc and water and the combined organics were washed with brine, dried over MgSO$_4$ and concentrated under reduced pressure. The reaction and extractive workup were repeated and the combined products were purified by flash chromatography (10 to 100% EtOAc-hexanes gradient) to give sulphide 126 as a white solid. Yield (0.3005 g, 82%): $^1$H NMR (400 MHz, CDCl$_3$) δ 7.39 (dd, J=8.4, 2.4 Hz, 1H), 7.33 (d, J=2.4 Hz, 1H), 7.21 (dd, J=8.4, 2.4 Hz, 1H), 7.15 (t, J=8.0 Hz, 1H), 7.11 (dd, J=7.6, 1.6 Hz, 1H), 6.94 (d, J=8.4 Hz, 2H), 6.89 (d, J=8.4 Hz, 1H), 6.77 (br s, 1H), 3.87 (s, 3H), 3.23 (q, J=6.4 Hz, 2H), 2.73 (t, J=7.6 Hz, 2H), 2.45 (s, 3H), 1.87-1.94 (m, 2H).

Step 2:
To a solution of sulphide 126 (0.1127 g, 0.25 mmol) in 7 M NH$_3$ in MeOH (8 mL) was added 25% aqueous NH$_4$OH (2 mL). The mixture was stirred at room temperature overnight then concentrated under reduced pressure. Purification by flash chromatography (5:5:1 EtOAc:hexanes: 7 M NH$_3$ in MeOH) gave Example 107 as an oil. Yield (0.0680 g, 77%): $^1$H NMR (400 MHz, CDCl$_3$) δ 7.34-7.36 (m, 2H), 7.20 (dd, J=8.4, 2.4 Hz, 1H), 7.13 (t, J=7.6 Hz, 1H), 7.10 (dd, J=8.0, 1.6 Hz, 1H), 6.97 (d, J=16.4 Hz, 1H), 6.92 (d, J=16.8 Hz, 1H), 6.83 (dd, J=7.2, 0.8 Hz, 1H), 3.84 (s, 3H), 2.73 (t, J=6.8 Hz, 2H), 2.68 (t, J=8.0 Hz, 2H), 2.41 (s, 3H), 1.74-1.78 (m, 2H), 1.18 (br s, 2H).

Example 108

Preparation of (E/Z)-3-(3-(2-(2-methoxynaphthalen-1-yl)vinyl)phenyl)propan-1-amine

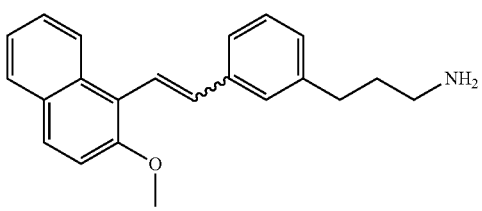 [SMILES: COc1ccc2ccccc2c1C=Cc1cccc(CCCN)c1]

(E/Z)-3-(3-(2-(2-Methoxynaphthalen-1-yl)vinyl)phenyl)propan-1-amine was prepared according to the method used in Example 76.

Step 1:
Phthalimide 29 was coupled with (2-methoxynapthalen-1-ylmethyl)triphenylphosphonium bromide according to the method used in Example 76 except that 2 equivalents of the phosphonium bromide were used. Purified by flash chromatography (10% EtOAc-hexanes) gave (E/Z)-2-(3-(3-(2-(2-methoxynaphthalen-1-yl)vinyl)phenyl)propyl)isoindoline-1,3-dione as an oil. Yield (0.160 g, 35%). Trans-isomer: $^1$H NMR (400 MHz, DMSO-d$_6$) δ 8.24 (d, J=8.8 Hz, 1H), 7.88-7.92 (m, 2H), 7.81-7.86 (m, 4H), 7.58 (d, J=16.4 Hz, 1H), 7.49-7.53 (m, 3H), 7.37-7.43 (m, 2H), 7.28 (t, J=7.6 Hz, 1H), 7.14-7.16 (m, 1H), 7.13 (d, J=16.8 Hz 1H), 3.97 (s, 3H), 3.65 (t, J=7.2 Hz, 2H), 2.69 (t, J=6.8 Hz, 2H), 1.94-2.00 (m, 2H).

Step 2:
(E/Z)-2-(3-(3-(2-(2-methoxynaphthalen-1-yl)vinyl)phenyl)propyl)isoindoline-1,3-dione was deprotected following the method used in Example 92. The residue was purified by Preparative HPLC (Method 2) to give Example 108 trifluoroacetate. Yield (0.080 g, 51%): trans-/cis-isomer ratio 2:1. Trans-isomer: $^1$H NMR (400 MHz, DMSO-d$_6$) δ 8.21 (d, J=8.4 Hz, 1H), 7.91 (t, J=8.8 Hz, 2H), 7.73 (br s, 3H), 7.59 (d, J=16.4 Hz, 1H), 7.50-7.52 (m, 4H), 7.33-7.45 (m, 2H), 7.12-7.45 (m, 2H), 3.98 (s, 3H), 2.75-2.86 (m, 2H), 2.70 (t, J=7.6 Hz, 2H), 1.86-1.94 (m, 2H).

Example 109

Preparation of (Z)-3-(3-(2-propoxystyryl)phenyl)propan-1-amine

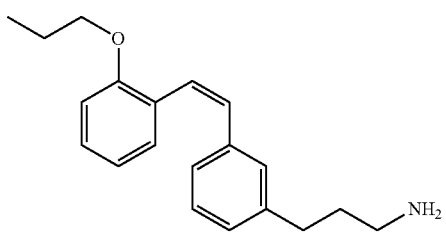 [SMILES: CCCOc1ccccc1/C=C\c1cccc(CCCN)c1]

(Z)-3-(3-(2-Propoxystyryl)phenyl)propan-1-amine was prepared according to the method used in Example 76.

Step 1:

2-Propoxybenzyltriphenylphosphonium bromide was prepared from 2-propoxylbenzyl bromide to give a white solid. Yield (2.4 g, 37%): $^1$H NMR (400 MHz, DMSO-$d_6$) δ 7.87-7.92 (m, 3H), 7.72 (dt, J=8.0, 3.2 Hz, 6H), 7.57-7.63 (m, 6H), 7.22-7.32 (m, 1H), 7.00-7.03 (m, 1H), 6.85 (d, J=8.4 Hz, 1H), 6.81 (t, J=7.2 Hz, 1H), 4.93 (d, J=14.4 Hz, 2H), 3.39 (t, J=6.8 Hz, 2H), 1.26-1.35 (m, 2H), 0.77 (t, J=7.2 Hz, 3H).

Step 2:

Phthalimide 29 was coupled with 2-propoxybenzyltriphenylphosphonium bromide according to the method used in Example 76 except that the reaction was stirred for 1 h at room temperature after the addition of potassium tert-butoxide. Purification by flash chromatography (15% EtOAc-hexanes) gave (E/Z)-2-(3-(3-(2-propoxystyryl)phenyl)propyl)isoindoline-1,3-dione a yellow oil. Yield (0.080 g, 31%); trans-1 cis-isomer ratio 1.3:1. Trans-isomer: $^1$H NMR (400 MHz, CDCl$_3$) δ 7.80-7.85 (m, 2H), 7.67-7.72 (m, 2H), 7.56-7.58 (m, 1H), 7.44 (d, J=16.4 Hz, 1H), 7.31 (s, 1H), 6.93-7.24 (m, 6H), 6.89 (d, J=8.4 Hz, 1H), 4.00 (t, J=6.4 Hz, 2H), 3.78 (t, J=7.2 Hz, 2H), 2.71 (t, J=7.6 Hz, 2H), 1.93-2.11 (m, 2H), 1.86-1.94 (m, 2H), 1.10 (t, J=7.2 Hz, 3H).

Step 3:

(E/Z)-2-(3-(3-(2-propoxystyryl)phenyl)propyl)isoindoline-1,3-dione was deprotected following the method used in Example 76 except that the reaction was heated at 70° C. for 1.5 h. After cooling to room temperature, the mixture was concentrated under reduced pressure. The white solid was washed with diethyl ether and the decanted solution was concentrated under reduced pressure. The residue was purified by Preparative HPLC (Method 2) to give Example 109 trifluoroacetate. Yield (0.120 g, 38%): $^1$H NMR (400 MHz, CDCl$_3$) δ 7.84 (br s, 3H), 7.09-7.18 (m, 4H), 6.99 (s, 1H), 6.92-6.94 (m, 1H), 6.86 (d, J=8.4 Hz, 1H), 6.68-6.72 (m, 2H), 6.55 (d, J=12.4 Hz, 1H), 3.92 (t, J=6.4 Hz, 2H), 2.80 (t, J=7.6 Hz, 2H), 2.53 (t, J=7.2 hz, 2H), 1.60-1.89 (m, 7H), 1.01 (t, J=7.2 Hz, 3H).

Example 110

Preparation of (E)-3-(3-(2-phenylprop-1-enyl)phenyl)propan-1-amine

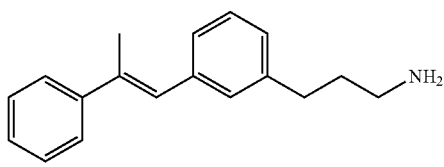 [SMILES: C/C(=C\c1cccc(CCCN)c1)c1ccccc1]

(E)-3-(3-(2-Phenylprop-1-enyl)phenyl)propan-1-amine was prepared according to the method shown in Scheme 40.

SCHEME 40

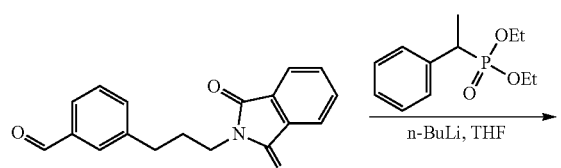

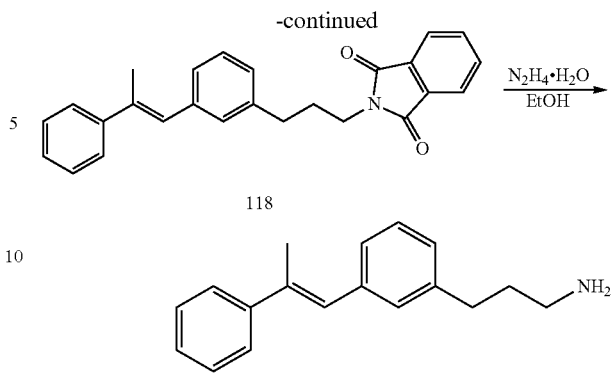

Step 1:

To a cooled solution (−78° C.) of diethyl 1-phenylethylphosphonate (1.016 g, 4.20 mmol) in anhydrous THF (10 mL) was added a solution of n-BuLi (2.5M in hexanes, 1.5 mL, 3.75 mmol) and the mixture was stirred at −78° C. for 10 min under argon. A solution of aldehyde 29 (0.485 g, 1.65 mmol) in anhydrous THF (10 mL) was added to the reaction mixture and the mixture was stirred at −78° C. for 10 min, then allowed to warm to room temperature over 1 h. Saturated aqueous NH$_4$Cl was added to the mixture followed by EtOAc. The layers were separated and the aqueous layer was extracted with EtOAc. The combined organic layers were washed with brine, dried with anhydrous MgSO$_4$, filtered and concentrated under reduced pressure. Purification by flash chromatography (10 to 30% EtOAc/hexane gradient) gave 118 as colorless oil. Yield (0.092 g, 15%): $^1$H NMR (400 MHz, DMSO-$d_6$) δ 7.78-7.84 (m, 4H), 7.51-7.55 (m, 2H), 7.33-7.38 (m, 2H), 7.20-7.29 (m, 3H), 7.06-7.16 (m, 2H), 6.80 (s, 1H), 3.60 (t, J=7.0 Hz, 2H), 2.63 (t, J=7.2 Hz, 2H), 2.19 (d, J=1.4 Hz, 3H), 1.88-1.96 (m, 211).

Step 2:

Deprotection of (E)-2-(3-(3-(2-phenylprop-1-enyl)phenyl)propyl)isoindoline-1,3-dione (118) with hydrazine following the method described in Example 18 except that EtOH was used as the solvent and the reaction mixture was stirred at room temperature for 16 hrs. Purification by flash chromatography (20 to 100% 20% 7N NH$_3$/MeOH in EtOAc/hexanes gave Example 110 as a colorless oil. Yield (0.018 g, 30%). $^1$H NMR (400 MHz, CD$_3$OD) δ 7.48-7.52 (m, 2H), 7.30-7.35 (m, 2H), 7.20-7.28 (m, 2H), 7.14-7.19 (m, 2H), 7.05-7.09 (m, 1H), 6.80 (s, 1H), 2.62-2.68 (m, 4H), 2.23 (d, J=1.4 Hz, 31-1), 1.74-1.82 (m, 2H). $^{13}$C NMR (100 MHz, CD$_3$OD) δ 144.1, 142.1, 138.6, 137.3, 129.1, 128.2, 128.0, 127.6, 127.0, 126.52, 126.49, 125.8, 40.9, 33.1, 16.6. ESI MS m/z 252.3 [M+H]$^+$; HPLC (Method 8) >95% (AUC), $t_R$=6.06 min.

Example 111

Preparation of (E)-1-(3-(3-amino-1-hydroxypropyl)styryl)cyclohexanol

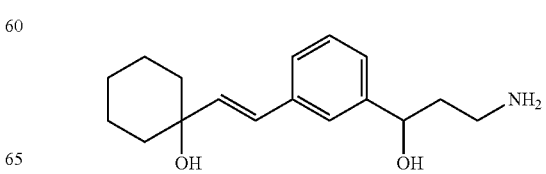

(E)-1-(3-(3-Amino-1-hydroxypropyl)styryl)cyclohexanol was prepared according to Scheme 41.

SCHEME 41

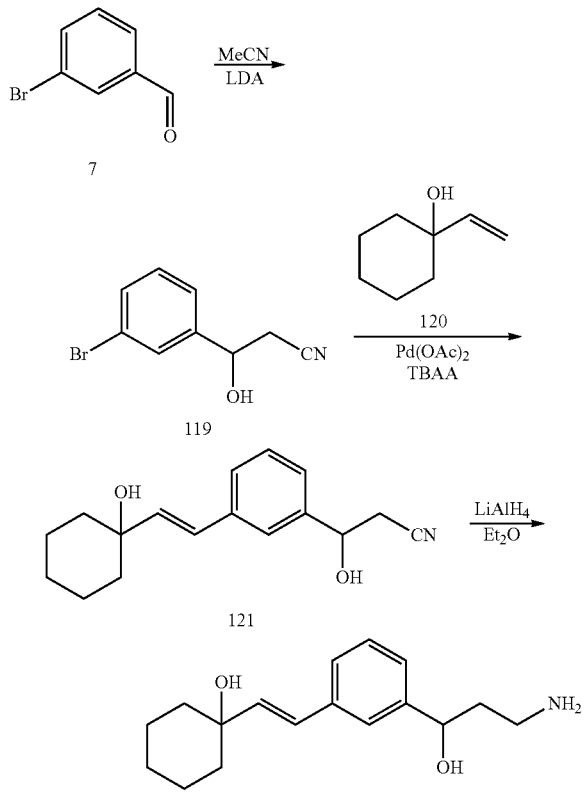

Step 1:

To a −78° C. solution of acetonitrile (1.05 mL, 20 mmol) in anhydrous THF (25 mL) under argon, was added lithium diisopropylamide (11 mL of a 2 M solution in THF, 22 mmol) dropwise. The resulting mixture was stirred at −78° C. for 15 min. A solution of 3-bromobenzaldehyde (7) (2.78 g, 15 mmol) in anhydrous THF (10 mL) was added dropwise. The reaction mixture was allowed to warm to room temperature, then concentrated under reduced pressure and diluted with EtOAc (75 mL). The solution was washed with water (50 mL) and brine (50 mL), dried over $Na_2SO_4$ and concentrated under reduced pressure. Purification by flash chromatography (20 to 100% EtOAc-hexanes gradient) gave 3-(3-bromophenyl)-3-hydroxypropanenitrile (120) as a light yellow oil. Yield (2.75 g, 81%): $^1$H NMR (400 MHz, DMSO-$d_6$) δ 7.60 (t, J=1.6 Hz, 1H), 7.46 (ddd, J=7.6, 2.0, 1.2 Hz, 1H), 7.40 (dd, J=7.6, 2.0 Hz, 1H), 7.31 (t, J=7.6 Hz, 1H), 6.05 (d, J=4.8 Hz, 1H), 2.94-2.80 (m, 2H).

Step 2:

A mixture of 1-vinylcyclohexanol (120) (0.25 g, 2 mmol), Palladium acetate (30 mg), 3-(3-bromophenyl)-3-hydroxypropanenitrile (119) (0.45 g, 2 mmol) and tetrabutylamonium acetae (1.0 g) was stirred at 90° C. under argon for 18 hours. The reaction mixture was cooled to room temperature and partitioned between water and ethyl acetate. The organic layer was dried over $Na_2SO_4$ and concentrated under reduced pressure. Purification by flash chromatography (10 to 50% EtOAc-hexanes gradient) gave olefin 121 as a white solid. Yield (0.50 g, 95%): $^1$H NMR (400 MHz, DMSO-$d_6$) δ 7.41 (s, 1H), 7.21-7.30 (m, 3H), 6.20 (d, J=16 Hz, 1H), 6.38 (d, J=16 Hz, 1H), 5.90 (d, J=1.6 Hz, 1H), 4.85 (q, J=4.8 Hz, 1H), 4.42 (s, 1H), 2.77-2.91 (m, 2H), 1.54-1.68 (m, 2H), 1.38-1.54 (m, 7H), 1.19-1.28 (m, 1H).

Step 3:

To a −10° C. solution of olefin 121 (0.35 g, 1.3 mmol) in ether (15 ml) was added LiAlH$_4$ (X mL of a 2 M in THF, 4.2 mmol). The reaction mixture was stirred at the temperature for 1.5 hours and the reaction was quenched by the addition of ice, followed br sat. aqueous $Na_2SO_4$. Ammonia (3 ml of a 7N solution in MeOH) was added. The mixture was then diluted with DCM (30 ml). The organic layer was dried over $Na_2SO_4$ and concentrated under reduced pressure. Purification by flash chromatography (10 to 15 to 25% 7N $NH_3$ in MeOH-DCM gradient) gave Example 111 as colorless oil, Yield (0.20 g, 56%): $^1$H NMR (400 MHz, DMSO-$d_6$) δ 7.33 (s, 1H), 7.20-7.22 (m, 2H), 7.11-7.14 (m, 1H), 6.50 (d, J=16 Hz, 1H), 6.36 (d, J=16 Hz, 1H), 4.63 (t, J=5.4 Hz, 1H), 4.39 (s, 1H), 2.54-2.64 (m, 2H), 1.56-1.78 (m, 411), 1.38-1.56 (m, 7H), 1.19-1.28 (m, 1H).

Example 112

((E)-1-(3-(2-aminoethoxy)styryl)cyclohexanol

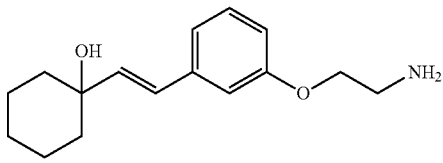 [SMILES: NCCOc1cccc(/C=C/C2(O)CCCCC2)c1]

(E)-1-(3-(2-Aminoethoxy)styryl)cyclohexanol was prepared according to the methods used in Examples 31, 11 and 18.

Step 1:

Alkylation of 3-iodophenol with 2-(2-hydroxyethyl)isoindoline-1,3-dione dione following method used in Example 31 gave 2-(2-(3-iodophenoxyl)ethyl)isoindoline-1,3-dione. Yield (2.8 g, 71%): $^1$H NMR (400 MHz, CDCl$_3$) δ 7.85-7.87 (m, 2H), 7.71-7.73 (m, 2H), 7.22-7.26 (m, 3H), 6.94 (t, J=8.4 Hz, 1H), 6.81:6.84 (m, 1H), 4.19 (t, J=5.6 Hz, 2H), 4.09 (t, J=5.2 Hz, 2H).

Step 2:

Coupling of 2-(2-(3-iodophenoxyl)ethyl)isoindoline-1,3-dione with olefin 120 following the method used in Example 111 gave (E)-2-(2-(3-(2-(1-hydroxycyclohexyl)vinyl)phenoxy)ethyl)isoindoline-1,3-dione. Yield (0.50 g, 95%): $^1$H NMR (400 MHz, DMSO-$d_6$) δ 7.81-7.88 (m, 4H), 7.15 (t, J=8.0 Hz, 1H), 6.90-6.92 (m, 2H), 6.69-6.71 (m, 111), 6.64 (d, J=16 Hz, 1H), 6.34 (d, J=16 Hz, 1H), 4.38 (s, 1H), 4.19 (t, J=6.0 Hz, 2H), 2.93 (t, J=6.0 Hz, 2H), 1.38-1.66 (m, 9H), 1.19-1.26 (m, 1H).

Step 3:

Deprotection of (E)-2-(2-(3-(2-(1-hydroxycyclohexyl)vinyl)phenoxy)ethyl)isoindoline-1,3-dione following the method used in Example 18 gave Example 112 as a colorless oil. Yield (0.20 g, 56%): $^1$H NMR (400 MHz, MeOD) δ 7.19 (t, J=8.0 Hz, 1H), 6.96-6.98 (m, 2H), 6.78-6.80 (m, 1H), 6.55 (d, J=16.4 Hz, 1H), 6.33 (d, J=16 Hz, 1H), 4.10 (t, J=5.2 Hz, 2H), 2.99 (t, J=5.2 Hz, 2H), 1.20-1.78 (m, 12H).

Example 113

(E)-1-(3-((1R,2R)-3-amino-1-hydroxy-2-methylpropyl)styryl)cyclohexanol

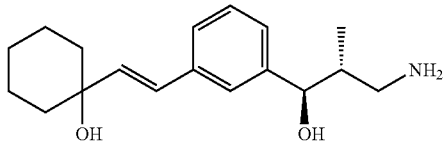 [SMILES: C[C@H](CN)[C@@H](O)c1cccc(/C=C/C2(O)CCCCC2)c1]

(E)-1-(3-((1R,2R)-3-Amino-1-hydroxy-2-methylpropyl)styryl)cyclohexanol was prepared according to Scheme 42.

SCHEME 42

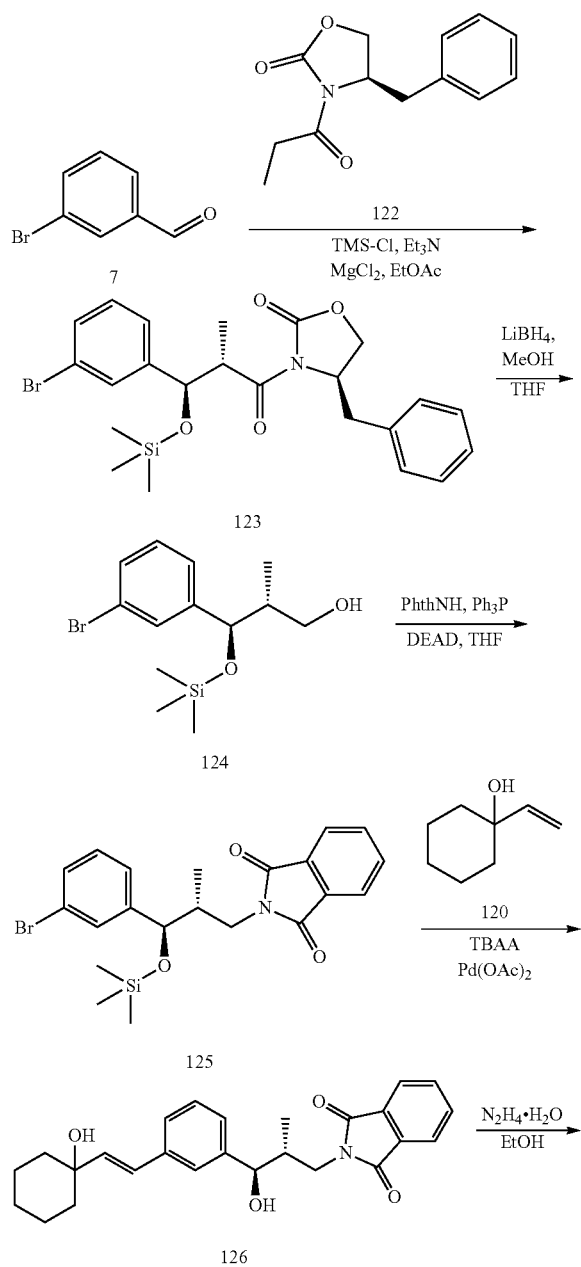

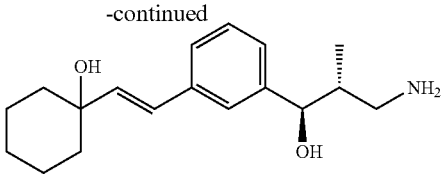

Step 1.

To a mixture of 3-bromobenzaldehyde (7) (4.16 g, 22.5 mmol), (R)-4-benzyl-3-propionyloxazolidin-2-one (122) (5.111 g, 21.9 mmol) and anhydrous $MgCl_2$ (0.21 g, 2.23 mmol) in ethyl acetate (40 mL) was added $Et_3N$ (6.3 mL, 45.2 mmol) and chlorotrimethylsilane (4.3 mL, 34.0 mmol) under argon. The reaction mixture was stirred for 22 hrs at room temperature, then filtered through a layer of a silica gel, washing with EtOAc. The filtrate was concentrated under reduced pressure and the residue was purified by flash chromatography (2 to 25% EtOAc/hexane gradient) to give oxazolidinone 123 as a colorless oil. Yield (9.79 g, 91%); $^1$H NMR (400 MHz, DMSO-$d_6$) δ 7.56 (t, J=1.8 Hz, 1H), 7.49 (ddd, J=1.2, 2.0, 7.8 Hz, 1H), 7.40 (dt, J=1.2, 7.6 Hz, 1H), 7.23-7.35 (m, 5H), 4.94 (d, J=9.4 Hz, 1H), 4.67-4.75 (m, 1H), 4.30 (t, J=8.6 Hz, 1H), 4.12 (dd, J=2.9, 8.8 Hz, 1H), 4.00-4.08 (m, 1H), 3.02 (dd, J=3.1, 13.5 Hz, 1H), 2.91 (dd, J=7.4, 13.5 Hz, 1H), 0.78 (d, J=7.0 Hz, 3H), -0.09 (s, 9H).

Step 2.

To an ice-cold solution of $LiBH_4$ (2M in THF, 65 mL, 130 mmol) was added MeOH (2.6 mL, 64.2 mmol) and the mixture was stirred at 0° C. for 5 mins. A solution of oxazolidinone 123 (9.59 g, 19.6 mmol) in anhydrous THF (170 mL) was added and reaction mixture was stirred at 0° C. for 1.5 hrs and then at room temperature for 1.5 hrs. An aqueous solution of $NH_4Cl$ (25%, 75 mL) was added slowly to reaction mixture for over 1 hr followed by addition of EtOAc and stirring was continued at room temperature until the mixture became clear. The layers were separated and the aqueous layer was extracted with EtOAc. The combined organic layers were washed with saturated brine, dried with anhydrous $MgSO_4$, filtered and concentrated under reduced pressure. The residue was purified by flash chromatography (5 to 30% EtOAc/hexane gradient) to give alcohol 124 as colorless oil. Yield (2.97 g, 48%); $^1$H NMR (400 MHz, DMSO-$d_6$) δ 7.38-7.43 (m, 2H), 7.24-7.27 (m. 2H), 4.58 (d, J=6.85 Hz, 1H), 4.38 (t, J=5.3 Hz, 1H), 3.32-3.38 (m, 1H), 3.22-3.29 (m, 1H), 1.73-1.80 (m, 1H), 0.61 (d, J=6.85 Hz, 3H), -0.05 (s, 9H).

Step 3.

DEAD (1.9 mL, 11.4 mmol) was added to a solution of alcohol 124 (2.97 g, 9.36 mmol), phthalimide (1.52 g, 10.3 mmol) and $Ph_3P$ (3.02 g, 11.5 mmol) in anhydrous THF (40 mL) and the mixture was stirred at room temperature for 1 hr. The solvent was concentrated under reduced pressure to give an orange residue which was vigorously stirred with 10% EtOAc in hexanes. The triphenylphosphine oxide precipitated and was removed by filtration, washing with 5% EtOAc in hexanes. The filtrate was concentrated under reduced pressure and the residue was purified by flash chromatography (5 to 30% EtOAc/hexane gradient) to give bromide 125 as colorless oil. Yield (3.97 g, 95%): $^1$H NMR (400 MHz, DMSO-$d_6$) δ 7.76-7.80 (m, 4H), 7.47 (t, J=1.8 Hz, 1H), 7.27-7.35 (m, 2H), 7.22 (t, J=7.8 Hz, 1H), 4.66 (d, J=5.7 Hz, 1H), 3.63 (dd, J=5.7, 13.7 Hz, 1H), 3.38 (dd, J=8.8, 13.5 Hz, 1H), 2.24-2.32 (m, 1H), 0.68 (d, J=6.8 Hz, 3H), -0.03 (s, 9H).

Step 4:

Bromide 125 was coupled with alkene 120 following the method used in Example 111. Purification by flash column chromatography (silica gel, 30% to 70% EtOAc/hexanes gradient) afforded phthalimide 126 as a colorless oil. Yield (0.281 g, 65%): $^1$H NMR (400 MHz, DMSO-d$_6$) δ 7.75-7.81 (m, 4H), 7.33-7.36 (m, 1H), 7.10-7.22 (m, 2H), 6.49 (d, J=16.0 Hz, 1H), 6.34 (d, J=16.0 Hz, 1H), 5.33 (d, J=4.3 Hz, 1H), 4.42 (dd, J=4.3, 5.9 Hz, 1H), 4.40 (s, 1H), 3.72 (dd, J=5.5, 13.7 Hz, 1H), 3.42 (dd, J=9.4, 13.7 Hz, 1H), 2.20-2.30 (m, 1H), 1.55-1.66 (m, 2H), 1.38-1.55 (m, 7H), 1.16-1.26 (m, 1H), 0.65 (d, J=6.9 Hz, 3H).

Step 5:
Deprotection of phthalimide 126 was performed following the method used in Example 32 except the reaction was heated at 50° C. overnight. Purification by flash column chromatography (silica gel, 50% to 100% of 20% 7N NH$_3$/MeOH in EtOAc/hexanes gradient) gave Example 113 as a white waxy solid. Yield (0.154 g, 94%): $^1$H NMR (400 MHz, MeOH-d$_4$) δ 7.35-7.38 (m, 1H), 7.23-7.30 (m, 2H), 7.16 (dt, J=1.4, 7.0 Hz, 1H), 6.60 (d, J=16.2 Hz, 1H), 6.35 (d, J=16.2 Hz, 1H), 4.40 (d, J=8.0 Hz, 1H), 2.83 (dd, J=5.5, 12.7 Hz, 1H), 2.67 (dd, J=5.9, 12.5 Hz, 1H), 1.79-1.89 (m, 1H), 1.47-1.76 (m, 9H), 1.26-1.40 (m, 1H), 0.72 (d, J=6.9 Hz, 3H). $^{13}$C NMR (100 MHz, MeOH-d$_4$) δ 144.5, 137.8, 137.6, 128.2, 126.8, 125.7, 125.2, 124.6, 78.6, 71.2, 45.3, 42.2, 37.5, 25.5, 21.9, 20.9, 13.9. ESI MS m/z 290.3 [M+H]$^+$; HPLC (Method 8) 93% (AUC), t$_R$=3.09 min.

Example 114

(E)-1-(3-(3-amino-1-hydroxypropyl)-5-fluorostyryl)cyclohexanol

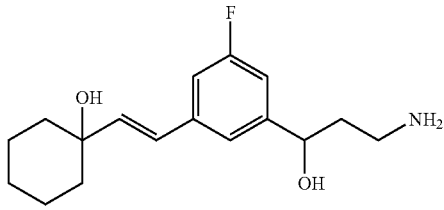

(E)-1-(3-(3-Amino-1-hydroxypropyl)-5-fluorostyryl)cyclohexanol was prepared according to the Methods used in Examples 50, 79 and 111.

Step 1:
Alkylation of 3-bromo-5-fluorobenzaldehyde with acetonitrile following the method used in Example 50 except KOBu-t was used instead of LDA gave 3-(3-bromo-5-fluorophenyl)-3-hydroxypropanenitrile as a light color oil. Yield (2.5 g, 86%): NMR (400 MHz, CDCl$_3$) δ 7.34 (bs, 1H), 7.21-7.24 (m, 1H), 7.08-7.11 (m, 1H), 5.02 (t, J=6.4 Hz, 1H), 2.75 (d, J=6.4 Hz, 2H).

Step 2:
To a solution of 3-(3-bromo-5-fluorophenyl)-3-hydroxypropanenitrile (2.50 g, 8.65 mmol) in THF (16.0 mL) was added borane methyl sulfide (1.20 g, 15.7 mmol). The mixture was heated to reflux for 2 h. After cooling to room temperature, saturated aqueous NaHCO$_3$ (10 mL) was added and the mixture was stirred for 1 h. The THF was removed under reduced pressure and the remaining aqueous portion was extracted with ethyl acetate (2×60 ml). The extract was dried (Na$_2$SO$_4$) and concentrated to give 3-amino-1-(3-bromo-5-fluorophenyl)propan-1-ol that was used in following reaction without further purification.

Step 3:
Protection of amine following the method used in Example 79 gave N-(3-(3-bromo-5-fluorophenyl)-3-hydroxypropyl)-2,2,2-trifluoroacetamide as a light yellow oil. Yield (1.0 g, 30% in 2 steps): $^1$H NMR (400 MHz, DMSO-d$_6$) δ 9.30 (m, 1H), 7.34-7.38 (m, 2H), 7.15-7.18 (m, 1H), 5.57 (d, J=4.4 Hz, 1H), 4.58-4.61 (m, 1H), 3.16- 3.30 (m, 2H), 1.70-1.88 (m, 2H).

Step 4:
Coupling of olefin 120 with N-(3-(3-bromo-5-fluorophenyl)-3-hydroxypropyl)-2,2,2-trifluoroacetamide following the method used in Example 111 except the reaction was done in 1 hour at 90° C., gave (E)-2,2,2-trifluoro-N-(3-(5-fluoro-3-(2-(1-hydroxycyclohexyl)vinyl)phenyl)-3-hydroxypropyl)acetamide as a light yellow oil. Yield (0.25 g, 54%): $^1$H NMR (400 MHz, DMSO-d$_6$) δ 9.32 (m, 1H), 6.94-7.18 (m, 3H), 6.51 (d, J=16 Hz, 1H), 6.43 (d, J=16 Hz, 1H), 5.42 (d, J=4.4 Hz, 1H), 4.54-4.59 (m, 1H), 3.18-3.28 (m, 2H), 1.73-1.83 (m, 2H), 1.18-1.68 (m, 10H).

Step 4:
Deprotection of (E)-2,2,2-trifluoro-N-(3-(5-fluoro-3-(2-(1-hydroxycyclohexyl)vinyl)phenyl)-3-hydroxypropyl)acetamide following the method used in Example 111 gave Example 115 as a light yellow oil. Yield (0.065 g, 43%): NMR (400 MHz, MeOD) δ 7.19 (s 1H), 6.99-7.02 (m, 1H), 6.93-6.96 (m, 1H), 6.58 (d, J=16 Hz, 1H), 6.40 (d, J=16 Hz, 1H), 4.72 (t, J=6.0 Hz, 1H), 2.75 (m, 2H), 1.28-1.86 (m, 12H).

Example 115

(E)-1-(3-(3-amino-1-hydroxypropyl)-2-fluorostyryl)cyclohexanol

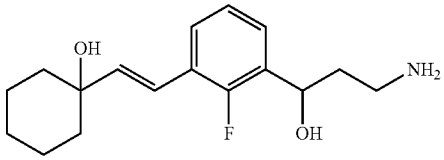 [SMILES: NCCC(O)c1cccc(/C=C/C2(O)CCCCC2)c1F]

(E)-1-(3-(3-Amino-1-hydroxypropyl)-2-fluorostyryl)cyclohexanol was prepared according to the methods used in Examples 50, 79 and 111.

Step 1:
Alkylation of 3-bromo-2-fluorobenzaldehyde following the method used in Example 50 gave 3-(3-bromo-2-fluorophenyl)-3-hydroxypropanenitrile as a light colored oil. Yield (1.1 g, 45%): $^1$H NMR (400 MHz, CDCl$_3$) δ 7.54 (t, J=7.2 Hz, 2H), 7.11 (td, J=7.6, 0.4 Hz, 1H), 5.37 (dd, J=6.8, 4.4 Hz, 1H), 2.73-2.91 (m, 2H).

Step 2;
Reduction of 3-(3-bromo-2-fluorophenyl)-3-hydroxypropanenitrile followed by protection of the amine following the method used in Example 79 gave N-(3-(3-bromo-2-fluorophenyl)-3-hydroxypropyl)-2,2,2-trifluoroacetamide as a light colored oil' Yield (0.30 g, 45%): NMR (400 MHz, DMSO-d$_6$) δ 7.54-7.58 (m, 1H), 7.45-7.49 (m, 1H), 7.12-7.17 (m, 1H), 4.86 (dd, J=6.8, 4.4 Hz, 1H), 3.27 (t, J=7.2 Hz, 2H), 1.73-1.86 (m, 2H).

Step 3:
Coupling of N-(3-(3-bromo-2-fluorophenyl)-3-hydroxypropyl)-2,2,2-trifluoroacetamide with olefin 120 following the method used in Example 111 gave (E)-2,2,2-trifluoro-N-(3-(2-fluoro-3-(2-(1-hydroxycyclohexyl)vinyl)phenyl)-3-hydroxypropyl)acetamide as a light yellow oil. Yield (0.13 g, 55%): $^1$H NMR (400 MHz, MeOD) δ 7.42 (td, J=7.6, 1.2 Hz, 1H), 7.36 (td, J=7.2, 1.2 Hz, 1H), 7.11 (t, J=8.0 Hz, 1H), 6.76

(d, J=16 Hz, 1H), 6.42 (d, J=16 Hz, 1H), 5.02 (dd, J=6.8, 4.4 Hz, 1H), 3.41 (t, J=7.2 Hz, 2H), 1.73-2.00 (m, 2H), 1.50-1.78 (m, 9H), 1.30-1.40 (m, 1H).

Step 4:

Deprotection of (E)-2,2,2-trifluoro-N-(3-(2-fluoro-3-(2-(1-hydroxycyclohexyl)vinyl)phenyl)-3-hydroxypropyl)acetamide following the method used in Example 111 gave Example 114 as a colorless oil. Yield (0.05 g, 56%): $^1$H NMR (400 MHz, DMSO-d$_6$) δ 7.39 (t, J=6.8 Hz, 1H), 7.29 (t, J=6.4 Hz, 1H), 7.09 (t, J=7.6 Hz, 1H), 6.62 (d, J=16 Hz, 1H), 6.42 (d, J=16 Hz, 1H), 4.88 (t, J=6.0 Hz, 1H), 2.57 (t, J=7.2 Hz, 2H), 1.10-1.68 (m, 12H).

Example 116

(E)-4-(3-(3-amino-1-hydroxypropyl)styryl)heptan-4-ol

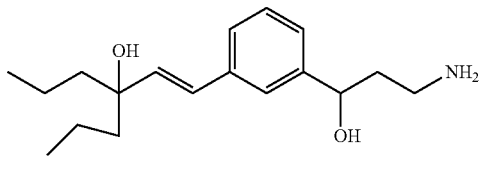 [SMILES: CCCC(O)(/C=C/c1cccc(C(O)CCN)c1)CCC]

(E)-4-(3-(3-Amino-1-hydroxypropyl)styryl)heptan-4-ol was prepared according to the Methods used in Example 50, 85 and 111.

Step 1:

Alkylation of 3-bromobenzaldehyde with acetonitrile following the method described in Example 50 gave 3-(3-bromophenyl)-3-hydroxypropanenitrile as a light yellow oil. Yield (2.75 g, 81%): NMR (400 MHz, DMSO-d$_6$) δ 7.60 (t, J=1.6 Hz, 1H), 7.46 (ddd, J=7.6, 2.0, 1.2 Hz, 1H), 7.40 (dd, J=7.6, 2.0 Hz, 1H), 7.31 (t, J=7.6 Hz, 1H), 6.05 (d, J=4.8 Hz, 1H), 2.94-2.80 (m, 2H).

Step 2:

Reduction of 3-(3-bromophenyl)-3-hydroxypropanenitrile following the method used in Example 50 gave 3-amino-1-(3-bromophenyl)propan-1-ol as a light green oil. Yield (2.30 g, 84%.) This material was used in the next step without further purification. $^1$H NMR (400 MHz, DMSO-d$_6$) δ 7.49 (m, 1H), 7.37 (dt, J=7.2, 1.6 Hz, 1H), 7.23-7.31 (m, 2H), 4.66 (t, J=6.8 Hz, 1H), 2.61 (m, 2H), 1.61 (q, J=6.8 Hz, 2H).

Step 3:

Protection of 3-amino-1-(3-bromophenyl)propan-1-ol following the method used in Example 85 except that the reaction mixture was stirred for 3 hours, gave N-(3-(3-bromophenyl)-3-hydroxypropyl)-2,2,2-trifluoroacetamide as an oil containing 15% of 2,2,2-trifluoro-N-(3-hydroxy-3-phenylpropyl)acetamide. Yield (1.96 g, 60%): NMR (400 MHz, DMSO-d$_6$) δ 9.33 (s, 1H), 7.51 (t, J=2.0 Hz, 1H), 7.41 (dt, J=7.6, 2.0 Hz, 1H), 7.25-7.32 (m, 2H), 5.46 (d, J=6.4 Hz, 1H), 4.55-4.60 (m, 1H), 3.20-3.23 (m, 2H), 1.75-1.82 (m, 2H).

Step 4:

Coupling of 4-vinylheptan-4-ol with N-(3-(3-bromophenyl)-3-hydroxypropyl)-2,2,2-trifluoroacetamide following the method in Example 111 except the reaction was done in 1 hour at 90° C. gave (E)-2,2,2-trifluoro-N-(3-hydroxy-3-(3-(3-hydroxy-3-propylhex-1-enyl)phenyl)propyl)acetamide as a light color oil. Yield (42 g, 45%): NMR (400 MHz, MeOD) δ 7.39 (s, 1H), 7.26-7.27 (m, 2H), 7.18-7.20 (m, 1H), 6.54 (d, J=16 Hz, 1H), 6.23 (d, J=16 Hz, 1H), 4.67 (t, J=6.4 Hz, 1H), 3.37 (t, J=7.2 Hz, 2H), 1.92-1.97 (m, 2H), 1.55-1.59 (m, 4H), 1.30-1.46 (m, 4H), 0.91 (t, J=7.6 Hz, 6H).

Step 5:

Deprotection of (E)-2,2,2-trifluoro-N-(3-hydroxy-3-(3-(3-hydroxy-3-propylhex-1-enyl)phenyl)propyl)acetamide following the method used in Example 111 gave Example 116 as a colorless oil. Yield (0.2 g, 63%): $^1$H NMR (400 MHz, MeOD) δ 7.39 (s, 1H), 7.24-7.26 (m, 2H), 7.18-7.20 (m, 1H), 6.53 (d, J=16 Hz, 1H), 6.23 (d, J=16 Hz, 1H), 4.71 (dd, J=8.0, 5.6 Hz, 1H), 2.68-2.79 (m, 2H), 1.78-1.94 (m, 2H), 1.54-1.59 (m, 4H), 1.30-1.46 (m, 4H), 0.91 (t, J=7.6 Hz, 6H).

Example 117

Preparation of (1S,2S)-3-amino-1-(3-((E)-2-(1-hydroxycyclohexyl)vinylphenyl)propane-1,2-diol

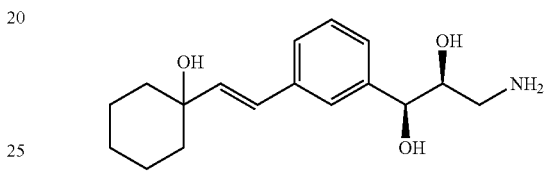

(1S,2S)-3-amino-1-(3-((E)-2-(1-hydroxycyclohexyl)vinyl)phenyl)propane-1,2-diol was prepared following the method described in Scheme 43.

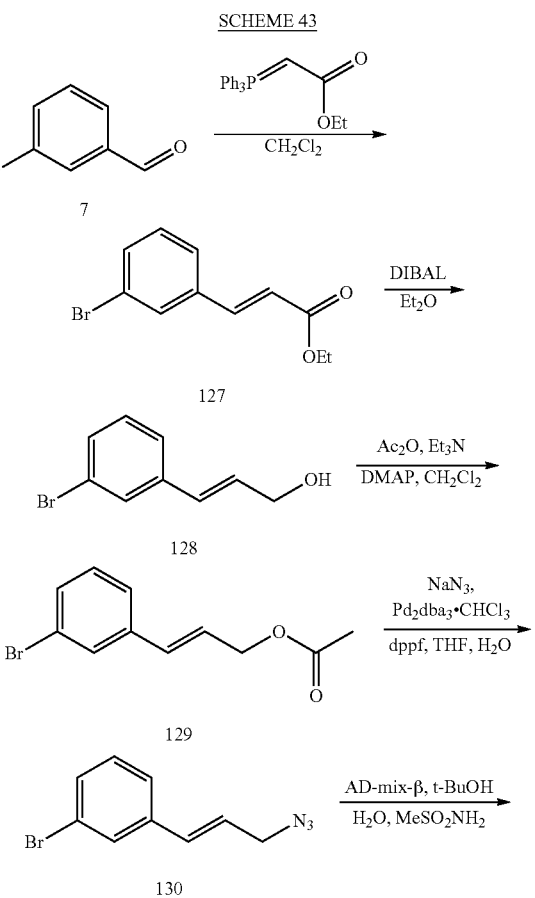

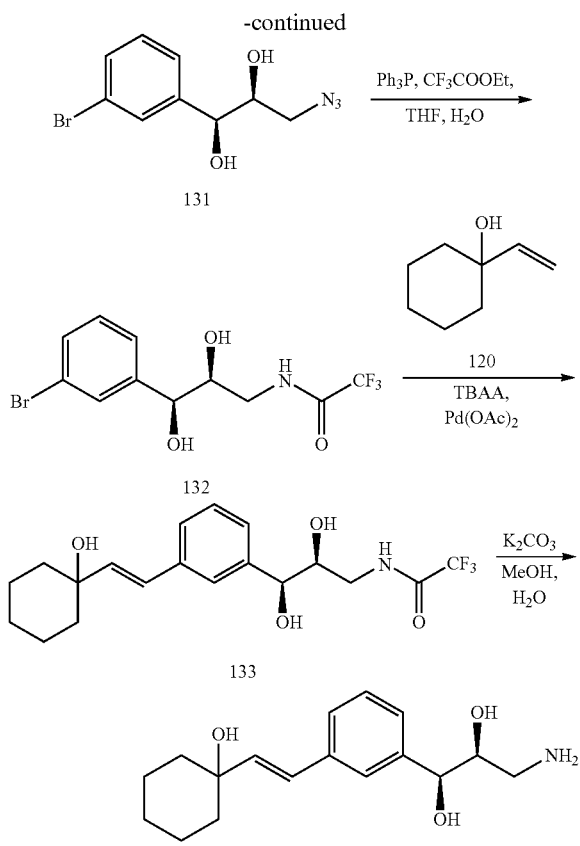

Step 1:

To an ice-cold solution of 3-bromobenzaldehyde (7) (3.9 mL, 33.30 mmol) in anhydrous dichloromethane (100 mL) was added (carbethoxymethylene)triphenylphosphorane (11.65 g, 33.44 mmol) and the reaction mixture was stirred at 0° C. for 5 min, then allowed to warm to room temperature over 30 min. Then the reaction mixture was concentrated under reduced pressure. White sticky solid was resuspended in 5% EtOAc/hexanes, stirred for 10 min at room temperature and then filtered. Filter cake was washed with hexanes, and the filtrate was concentrated under reduced pressure. The residue was purified by flash column chromatography (silica gel, hexanes to 10% EtOAc/hexanes gradient) to give allyl ester 127 as white solid. Yield (7.63 g, 90%). $^1$H NMR (400 MHz, DMSO-$d_6$) δ 7.95 (t, J=1.8 Hz, 1H), 7.70-7.72 (m, 1H), 7.59 (d, J=16.4 Hz, 1H), 7.58 (ddd, J=1.0, 2.0, 8.0 Hz, 1H), 7.35 (t, J=7.8 Hz, 1H), 6.69 (d, J=16.0 Hz, 1H), 4.17 (q, J=7.2 Hz, 2H), 1.23 (t, J=7.0 Hz, 3H).

Step 2.

To an ice-cold solution of ester 127 (7.63 g, 29.9 mmol) in diethyl ether (100 mL) was added a solution of diisobutyl aluminum hydride (DIBAL-H, 60 mL of a 1.0 M solution in $CH_2Cl_2$, 60.0 mmol). The reaction was stirred at 0° C. for 30 min after which aqueous solution of $NaHSO_4$ (2M, 42 mL) was added and the mixture was stirred for 1.5 hrs while warming to room temperature. Anhydrous $MgSO_4$ was added to the stirred reaction mixture, and after 30 min mixture was filtered, filtrate cake washed excessively with EtOAc, and filtrate was concentrated under reduced pressure to afford alcohol 128 as a colorless oil. Yield (6.42 g, quant.). $^1$H NMR (400 MHz, DMSO-$d_6$) δ 7.60 (t, J=1.8 Hz, 1H), 7.40 (dt, J=1.2, 7.6 Hz, 1H), 7.38 (ddd, J=1.0, 2.0, 8.0 Hz, 1H), 7.25 (t, J=7.6 Hz, 1H), 6.48-6.54 (m, 1H), 6.43 (dt, J=4.3, 16.0 Hz, 1H), 4.88 (t, J=5.5 Hz, 1H), 4.08-4.12 (m, 2H).

Step 3.

Acetylation of alcohol 128 following the method used in Example 51 after flash column chromatography (silica gel, 5% to 10% EtOAc/hexanes gradient) gave acetate 129 as a colorless oil. Yield (2.71 g, 89%). $^1$H NMR (400 MHz, DMSO-$d_6$) δ 7.66 (t, J=1.8 Hz, 1H), 7.40-7.46 (m, 2H), 7.27 (t, J=7.8 Hz, 1H), 6.58-6.65 (m, 1H), 6.42 (dt, J=5.9, 16.0 Hz, 1H), 4.66 (dd, J=1.4, 5.9 Hz, 1H), 2.04 (s, 3H).

Step 4.

A mixture of allyl acetate 129 (2.71 g, 10.6 mmol), sodium azide (0.787 g, 12.1 mmol), water (20 mL) and THF (50 mL) was degassed by bubbling argon for 3 min and tris-dibenzylideneacetonyl-bis-palladium-chloroform adduct (0.158 g, 0.17 mmol), diphenylphosphinoferrocene (0.1773 g, 0.32 mmol) were added to the reaction mixture. Air was evacuated by applying vacuum/argon 3× and then the reaction mixture was heated at 60° C. under argon for 4 hrs. The reaction mixture was concentrated under reduced pressure, water added to the residue and the product was extracted twice with hexanes, hexane layers were washed with saturated brine, dried with anhydrous $MgSO_4$, filtered and the filtrate was concentrated under reduced pressure. The residue was purified by flash column chromatography (silica gel, 5% to 30% EtOAc/hexanes gradient) to give allyl azide 130 as a colorless oil. Yield (1.90 g, 75%). $^1$H NMR (400 MHz, DMSO-$d_6$) δ 7.69 (t, J=1.8 Hz, 1H), 7.42-7.48 (m, 2H), 7.28 (t, J=7.8 Hz, 1H), 6.62-6.68 (m, 1H), 6.45 (dt, J=6.3, 15.8 Hz, 1H), 4.02 (dd, J=1.2, 6.3 Hz, 1H).

Step 5.

To a 100-ml round bottomed flask was placed $H_2O$ (19 mL) and tert-BuOH (19 mL) followed by AD-mix-β (5.61 g). The mixture was stirred at room temperature for 10 min after which $MeSO_2NH_2$ (0.36 g, 3.79 mmol) was added. The reaction mixture was cooled to 0° C., allyl azide 130 (0.90 g, 3.78 mmol) was added and stirred at 0° C. for 24 hrs. $Na_2SO_3$ (6.30 g) was added and the mixture was stirred for another hour after which EtOAc (50 mL) was added followed by sat. NaCl (50 mL). Layers were separated and aqueous layer extracted with EtOAc (3×25 mL). Combined organic layers were washed with brine (50 mL), dried with anhydrous $MgSO_4$ and filtered. Filtrate was concentrated under reduced pressure and the residue was purified by flash column chromatography (silica gel, 10% to 90% EtOAc/hexanes gradient) to give azido diol 131 as a thick colorless oil. Yield (1.02 g, 99%). $^1$H NMR (400 MHz, DMSO-$d_6$) δ 7.50 (t, J=1.6 Hz, 1H), 7.40 (ddd, J=1.2, 2.0, 7.6 Hz, 1H), 7.29-7.33 (m, 1H), 7.25 (t, J=7.6 Hz, 1H), 5.52 (d, J=5.1 Hz, 1H), 5.26 (d, J=5.9 Hz, 1H), 4.51 (t, J=4.7 Hz, 1H), 3.15 (dd, J=-3.3, 12.5 Hz, 1H), 3.02 (dd, J=8.0, 12.7 Hz, 1H).

Step 6.

A mixture of azido diol 131 (0.826 g, 3.037 mmol), triphenylphosphine (0.84 g, 3.20 mmol), THF (10 mL), water (0.2 mL) and ethyl trifluoroacetate (1 mL) was heated at 50° C. for 5 hrs, then concentrated under reduced pressure. The residue was purified by flash column chromatography (silica gel, 20% to 90% EtOAc/hexanes gradient) to give trifluoroacetamide 132 as white solid. Yield 0.73 g, 70%). $^1$H NMR (400 MHz, DMSO-$d_6$) δ 9.21 (t, J=5.3 Hz, 1H), 7.52 (t, J=1.6 Hz, 1H), 7.40 (ddd, J=1.2, 2.0, 7.8 Hz, 1H), 7.30-7.33 (m, 1H), 7.25 (t, J=7.6 Hz, 1H), 5.48 (d, J=5.1 Hz, 1H), 5.00 (d, J=5.9 Hz, 1H), 4.51 (t, J=4.7 Hz, 1H), 3.70-3.76 (m, 1H), 3.24 (dt, J=4.9, 13.3 Hz, 1H), 2.98 (ddd, J=5.7, 8.8, 13.3 Hz, 1H).

Step 7.

Coupling of bromide 132 with olefin 120 was performed following the method used in Example 111 except that reaction was heated at 90° C. for 5 hrs. Purification by flash column chromatography (silica gel, 20% to 70% EtOAc/ hexanes gradient) afforded alkene 133 as white foam. Yield (0.2128 g, 78%). $^1$H NMR (400 MHz, DMSO-$d_6$) δ 9.19 (t, J=5.3 Hz, 1H), 7.35-7.37 (m, 1H), 7.20-7.26 (m, 2H), 7.13-7.18 (m, 1H), 6.51 (d, J=16.2 Hz, 1H), 6.33 (d, J=16.0 Hz, 1H), 5.33 (d, J=4.9 Hz, 1H), 4.94 (d, J=5.7 Hz, 1H), 4.46 (t, J=4.8 Hz, 1H), 4.41 (s, 1H), 3.70-3.76 (m, 1H), 3.18 (dt, J=4.5, 13.3 Hz, 1H), 2.99 (ddd, J=6.1, 8.8, 14.3 Hz, 1H), 1.54-1.66 (m, 2H), 1.36-1.54 (m, 7H), 1.18-1.26 (m, 1H).

Step 8.

N-((2S,3S)-2,3-dihydroxy-3-(3-((E)-2-(1-hydroxycyclohexyl)vinyl)phenyl)propyl)-2,2,2-trifluoroacetamide (133) was deprotected according to the method used in Example 79 except that three equivalents of $K_2CO_3$ were used in a MeOH:$H_2O$ (2:1) mixture and the reaction mixture was heated at 50° C. for 5 hrs. Following the reaction, reaction mixture was concentrated under reduced pressure, resuspended in EtOAc/EtOH and purified by flash chromatography using a gradient of 50% 7N $NH_3$/MeOH in EtOAc/hexanes to give Example 117 as a colorless oil. Yield (0.118 g, 74%). $^1$H NMR (400 MHz, MeOH-$d_4$) δ 7.42-7.44 (m, 1H), 7.30 (dt, J=1.6, 7.6 Hz, 1H), 7.27 (t, J=7.4 Hz, 1H), 7.21 (dt, J=1.6, 7.2 Hz, 1H), 6.60 (d, J=16.0 Hz, 1H), 6.36 (d, J=16.0 Hz, 1H), 4.50 (d, J=5.9 Hz, 1H), 3.62-2.70 (m, 1H), 2.51-2.58 (m, 2H), 1.66-1.77 (m, 2H), 1.48-1.66 (m, 7H), 1.28-1.40 (m, 1H). $^{13}$C NMR (100 MHz, MeOH-$d_4$) δ 142.3, 137.9, 137.7, 128.3, 126.7, 125.7, 125.6, 124.6, 76.0, 75.8, 71.2, 43.6, 37.5, 25.5, 21.9, 20.9. ESI MS m/z 292.3 $[M+H]^+$; HPLC (Method 9) 97% (AUC), $t_R$=4.73 min.

Example 118

Preparation of (1R,2R)-3-amino-1-(3-((E)-2-(1-hydroxycyclohexyl)vinyl)phenyl)propane-1,2-diol

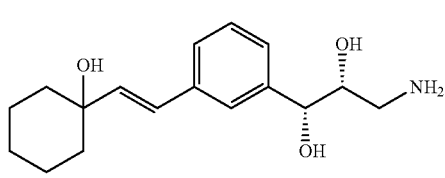 [SMILES: NC[C@@H](O)[C@H](O)c1cccc(/C=C/C2(O)CCCCC2)c1]

N-((2S,3S)-2,3-dihydroxy-3-(3-((E)-2-(1-hydroxycyclohexyl)vinyl)phenyl)propyl)-2,2,2-trifluoroacetamide was prepared according to the method used in Example 117.

Step 5.

Dihydroxylation of ally azide 130 was conducted using AD-mix-α to give (1R,2R)-3-azido-1-(3-bromophenyl)propane-1,2-diol. Yield (0.966 g, 96%). $^1$H NMR (400 MHz, DMSO-$d_6$) δ 7.50 (t, J=1.6 Hz, 1H), 7.40 (ddd, J=1.2, 2.0, 7.6 Hz, 1H), 7.29-7.33 (m, 1H), 7.25 (t, J=7.6 Hz, 1H), 5.52 (d, J=5.1 Hz, 1H), 5.26 (d, J=5.9 Hz, 1H), 4.51 (t, J=4.7 Hz, 1H), 3.15 (dd, J=3.3, 12.5 Hz, 1H), 3.02 (dd, J=8.0, 12.7 Hz, 1H).

Step 6.

Reduction and protection of (1R,2R)-3-azido-1-(3-bromophenyl)propane-1,2-diol gave N-((2R,3R)-3-(3-bromophenyl)-2,3-dihydroxypropyl)-2,2,2-trifluoroacetamide as a white solid. Yield 0.66 g, 69%). $^1$H NMR (400 MHz, DMSO-$d_6$) δ 9.21 (t, J=5.3 Hz, 1H), 7.52 (t, J=1.6 Hz, 1H), 7.40 (ddd, J=1.2, 2.0, 7.8 Hz, 1H), 7.30-7.33 (m, 1H), 7.25 (t, J=7.6 Hz, 1H), 5.48 (d, J=5.1 Hz, 1H), 5.00 (d, J=5.9 Hz, 1H), 4.51 (t, J=4.7 Hz, 1H), 3.70-3.76 (m, 1H), 3.24 (dt, J=4.9, 13.3 Hz, 1H), 2.98 (ddd, J=5.7, 8.8, 13.3 Hz, 1H).

Step 7.

Coupling of N-((2R,3R)-3-(3-bromophenyl)-2,3-dihydroxypropyl)-2,2,2-trifluoroacetamide with olefin 120 gave N-((2R,3R)-2,3-dihydroxy-3-(3-((E)-2-(1-hydroxycyclohexyl)vinyl)phenyl)propyl)-2,2,2-trifluoroacetamide as a brownish foam. Yield (0.1958 g, 82%). $^1$H NMR (400 MHz, DMSO-$d_6$) δ 9.19 (t, J=5.3 Hz, 1H), 7.35-7.37 (m, 1H), 7.20-7.26 (m, 2H), 7.13-7.18 (m, 1H), 6.51 (d, J=16.2 Hz, 1H), 6.33 (d, J=16.0 Hz, 1H), 5.33 (d, J=4.9 Hz, 1H), 4.94 (d, J=5.7 Hz, 1H), 4.46 (t, J=4.8 Hz, 1H), 4.41 (s, 1H), 3.70-3.76 (m, 1H), 3.18 (dt, J=4.5, 13.3 Hz, 1H), 2.99 (ddd, J=6.1, 8.8, 14.3 Hz, 1H), 1.54-1.66 (m, 2H), 1.36-1.54 (m, 7H), 1.18-1.26 (m, 1H).

Step 8.

Deprotection of N-((2S,3S)-2,3-dihydroxy-3-(3-((E)-2-(1-hydroxycyclohexyl)vinyl)phenyl)propyl)-2,2,2-trifluoroacetamide gave Example 118 as a colorless oil. Yield (0.16 g, quant.). $^1$H NMR (400 MHz, MeOH-$d_4$) δ 7.42-7.44 (m, 1H), 7.30 (dt, J=1.6, 7.6 Hz, 1H), 7.27 (t, J=7.4 Hz, 1H), 7.21 (dt, J=1.6, 7.2 Hz, 1H), 6.60 (d, J=16.0 Hz, 1H), 6.36 (d, J=16.0 Hz, 1H), 4.50 (d, J=5.9 Hz, 1H), 3.62-2.70 (m, 1H), 2.51-2.58 (m, 2H), 1.66-1.77 (m, 2H), 1.48-1.66 (m, 7H), 1.28-1.40 (m, 1H). $^{13}$C NMR (100 MHz, MeOH-$d_4$) δ 142.3, 137.9, 137.7, 128.3, 126.7, 125.7, 125.6, 124.6, 76.0, 75.8, 71.2, 43.6, 37.5, 25.5, 21.9, 20.9. ESI MS m/z 292.3 $[M+H]^+$; HPLC (Method 9) 96% (AUC), $t_R$=4.73 min.

Example 119

Preparation of (S,E)-1-(3-(1-aminopropan-2-yloxy)styryl)cyclohexanol

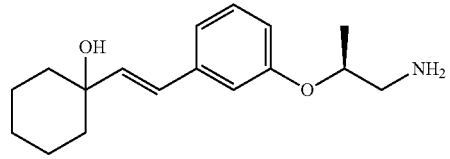 [SMILES: C[C@@H](CN)Oc1cccc(/C=C/C2(O)CCCCC2)c1]

(S,E)-1-(3-(1-aminopropan-2-yloxy)styryl)cyclohexanol was prepared following the method shown in scheme 44:

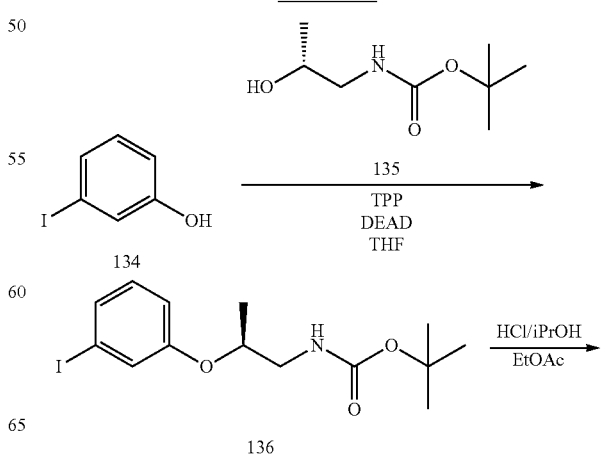

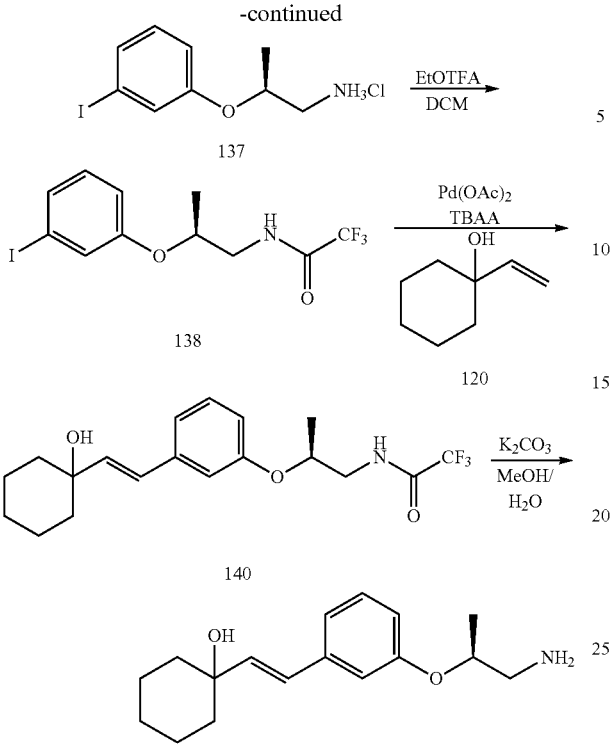

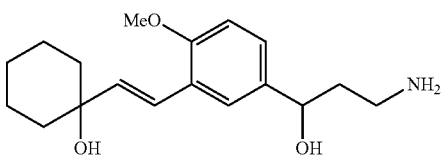 [SMILES: COc1ccc(C(O)CCN)cc1/C=C/C1(O)CCCCC1]

Step 1:

Diethylazodicarboxylate (17.4 g, 100 mmol) was added slowly to a solution of phenol 134 (18.5 g, 84 mmol), alcohol 135 (14.73 g, 84 mmol), and triphenyl phosphine (26.2 g, 100 mmol) in THF (200 mL) at 0° C. under argon. The reaction was allowed to warm to room temperature and stirred for 2 hours, then heated to 80° C. for 6 hours. The reaction was concentrated under reduced pressure, then triturated with diethyl ether and the resulting white solids removed by filtration. The filtrate was concentrated under reduce pressure and the residue was partitioned between ethyl acetate and 1N NaOH. The organic layers were combined, washed with brine, and concentrated under reduced pressure. Purification by flash chromatography (silica gel, eluent 5-15% ethylacetate/hexanes gradient) gave carbamate 136 as an impure yellow oil, which was carried on to the next step without further purification. Yield (17.3 g, 54%).

Step 2:

HCl (12 mL of a 4.8 M solution in iPrOH, 56 mmol) was added to a solution of carbamate 136 (10 g, 28 mmol) in ethyl acetate (25 mL). After stirring for 1 h, the product was collected by filtration and dried under reduced pressure, to give 137 hydrochloride as a white solid which was used in the next step without purification. Yield (2.9 g, 30%): $^1$H NMR (400 MHz, DMSO-$d_6$) δ 8.27 (brs, 3H), 7.24-7.28 (m, 2H), 6.98-7.12 (m, 2H), 4.68 (m, 1H), 2.90-3.10 (m, 2H), 1.22 (d, 3H).

Step 3:

Protection of 137 hydrochloride with ethyltrifluoroacetate following the method used in Example 79 gave trifluoroamide 138 as a yellow oil. Yield (3.4 g, quantitative): $^1$H NMR (400 MHz, CDCl$_3$) δ 7.29-7.33 (m, 1H), 7.24-7.26 (m, 1H), 6.99 (t, J=8.0 Hz, 1H), 6.83-6.87 (m, 1H), 6.75 (brs, 1H), 4.45-4.55 (m, 1H), 3.52-3.53 (m, 1H), 3.40-3.50 (m, 1H), 1.29 (d J=6.4 Hz, 3H).

Step 4:

Heck coupling of trifluoroamide 138 with 1-vinylcyclohexanol (120) following the method used in Example 111, gave alkene 139 as a yellow glassy oil. Yield (0.286 g, 80%): $^1$H NMR (400 MHz, CDCl$_3$) 7.22 (t, J=8.0 Hz, 1H), 6.98-7.04 (m, 1H), 6.90-6.93 (m, 1H), 6.73-6.78 (m, 2H), 6.57 (d, J=16 Hz, 1H), 6.32 (d, J=16 Hz, 1H), 4.50-4.59 (m, 1H), 3.72-3.80 (m, 1H), 3.40-3.49 (m, 1H), 1.50-1.74 (m, 10H), 1.32-1.38 (m, 1H), 1.30 (d, J=6.4 Hz, 3H).

Step 5:

Deprotection of styrene 139 following the method used in Example 85 gave Example 119 as a colorless oil. Yield (0.154 g, 72%): $^1$H NMR (400 MHz, CDCl$_3$) δ 7.20 (t, J=8.0 Hz, 1H), 6.93-6.98 (m, 2H), 6.76-6.80 (m, 1H), 6.57 (d, J=16 Hz, 1H), 6.31 (d, J=16 Hz, 1H), 4.32-4.42 (m, 1H), 2.88 (d, J=5.6 Hz, 2H), 1.50-1.74 (m, 12H), 1.28-1.37 (m, 1H), 1.26 (d, J=6.0 Hz, 3H); ESI MS m/z 276.3 [M+H].

Example 120

Preparation of (E)-1-(5-(3-amino-1-hydroxypropyl)-2-methyloxystyryl)cyclohexanol (E)-1-(5-(3-Amino-1-hydroxypropyl)-2-methoxystyryl)cyclohexanol was prepared following the methods used in Example 114:

Step 1:

Alkylation of 3-bromo-4-methoxybenzaldehyde with acetonitrile following the method used in Example 115 gave 3-(3-bromo-4-methoxyphenyl)-3-hydroxypropanenitrile as a pale orange oil. Yield (10.32 g, 96%): $^1$H NMR (400 MHz, DMSO-$d_6$) δ 7.58 (d, J=2.0 Hz, 1H), 7.35 (dd, J=8.8, 2.0 Hz, 1H), 7.07 (d, J=8.8 Hz, 1H), 5.93 (d, J=4.4 Hz, 1H), 4.85-4.81 (m, 1H). 3.81 (s, 3H), 2.86 (ABd, J=16.4, 4.8 Hz, 1H), 2.79 (ABd, J=16.8, 6.8 Hz, 1H).

Step 2:

Reduction of 3-(3-bromo-4-methoxyphenyl)-3-hydroxypropanenitrile with BH$_3$—S(CH$_3$)$_2$ followed by protection of the amine following the method in Example 114 gave N-(3-(3-bromo-4-methoxyphenyl)-3-hydroxypropyl)-2,2,2-trifluoroacetamide as an orange oil. Yield (5.76 g, 40%): $^1$H NMR (400 MHz, DMSO-$d_6$) δ 9.31 (bs, 1H), 7.49 (d, J=2.0 Hz, 1H), 7.26 (dd, J=8.8, 2.0 Hz, 1H), 5.32 (d, J=4.8 Hz, 1H), 4.53-4.49 (m, 1H), 3.80 (s, 3H), 3.24-3.15 (m, 2H), 1.79-1.72 (m, 2H).

Step 3:

Coupling of olefin 120 with N-(3-(3-bromo-4-methoxyphenyl)-3-hydroxypropyl)-2,2,2-trifluoroacetamide following the method used in Example 114 gave (E)-2,2,2-trifluoro-N-(3-hydroxy-3-(3-(2-(1-hydroxycyclohexyl)vinyl)-4-methoxyphenyl)propyl)acetamide as a light yellow oil. Yield (0.24 g, 28%): $^1$H NMR (400 MHz, DMSO-$d_6$) δ 9.32 (t, J=5.2 Hz, 1H), 7.38 (d, J=2.0 Hz, 1H), 7.12 (dd, J=8.4, 2.0 Hz, 1H), 6.89 (d, J=8.4 Hz, 1H), 6.80 (d, J=16.4 Hz, 1H), 6.28 (d, J=16.4 Hz, 1H), 5.19 (d, J=4.8 Hz, 1H), 4.52-4.48 (m, 2H), 4.38 (s, 1H), 3.75 (s, 3H), 3.24-3.19 (m, 2H), 1.80-1.75 (m, 2H), 1.65-1.39 (m, 9H), 1.25-1.19 (m, 1H).

Step 4:

Deprotection of (E)-2,2,2-trifluoro-N-(3-hydroxy-3-(3-(2-(1-hydroxycyclohexyl)vinyl)-4-methoxyphenyl)propyl) acetamide following the method used in Example 114 gave Example 120 as an off white solid. Yield (0.121 g, 68%): $^1$H NMR (400 MHz, DMSO-d$_6$) δ 7.36 (d, J=4.0 Hz, 1H), 7.10 (dd, J=8.4, 4.0 Hz, 1H), 6.87 (d, J=8.4 Hz, 1H), 6.79 (d, J=16.4 Hz, 1H), 6.27 (d, J=16.4 Hz, 1H), 4.59-4.56 (m, 1H), 4.37 (bs, 1H), 3.74 (s, 3H), 2.65-2.53 (m, 2H), 1.67-1.38 (m, 11H), 1.25-1.17 (m, 1H).

Example 121

Preparation of (E)-1-(3-(3-amino-1-hydroxypropyl)-4-chlorostyryl)cyclohexanol

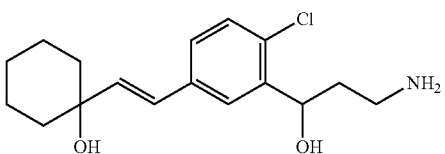 [SMILES: NCCC(O)c1cc(/C=C/C2(O)CCCCC2)ccc1Cl]

(E)-1-(3-(3-amino-1-hydroxypropyl)-4-chlorostyryl)cyclohexanol was prepared following the methods used in Example 114.

Step 1:

Alkylation of 5-bromo-2-chlorobenzaldehyde with acetonitrile following the method used in Example 114 gave 3-(5-bromo-2-chlorophenyl)-3-hydroxypropanenitrile as a pale yellow liquid. Yield (4.42 g, 75%): $^1$H NMR (400 MHz, DMSO-d$_6$) δ 7.74 (d, J=2.8 Hz, 1H), 7.53 (dd, J=8.8, 2.8 Hz, 1H), 7.39 (d, J=8.8 Hz, 1H), 6.30 (d, J=4.8 Hz, 1H), 5.13-5.09 (m, 1H), 2.96 (ABd, J=16.8, 4.8 Hz, 1H), 2.83 (ABd, J=17.0, 6.0 Hz, 1H).

Step 2:

Reduction of 3-(5-bromo-2-chlorophenyl)-3-hydroxypropanenitrile with BH$_3$-THF followed by protection of the amine following the method in Example 114 gave N-(3-(5-bromo-2-chlorophenyl)-3-hydroxypropyl)-2,2,2-trifluoroacetamide as an orange oil. Yield (2.6 g, 43%): $^1$H NMR (400 MHz, DMSO-d$_6$) δ 9.42 (bs, 1H), 7.67 (d, J=2.4 Hz, 1H), 7.45 (dd, J=8.8, 2.4 Hz, 1H), 7.33 (d, J=8.8 Hz, 1H), 5.64 (d, J=4.4 Hz, 1H), 3.33-3.29 (m, 2H), 1.96-1.80 (m, 1H), 1.68-1.59 (m, 1H).

Step 3:

Coupling of olefin 120 with N-(3-(5-bromo-2-chlorophenyl)-3-hydroxypropyl)-2,2,2-trifluoroacetamide following the method used in Example 114 except the reaction was done for 16 hr at 90° C., gave (E)-N-(3-(2-chloro-5-(2-(1-hydroxycyclohexyl)vinyl)phenyl)-3-hydroxypropyl)-2,2,2-trifluoroacetamide as a light yellow oil. Yield (0.30 g, 70%): $^1$H NMR (400 MHz, DMSO-d$_6$) δ 9.41 (t, J=5.6 Hz, 1H), 7.28-7.26 (m, 2H), 6.51 (d, J=16.0 Hz, 1H), 6.37 (d, J=16.0 Hz, 1H), 5.49 (d, J=4.4 Hz, 1H), 4.88-4.86 (m, 1H), 4.34 (bs, 1H), 3.34-3.29 (m, 2H), 1.87-1.80 (m, 1H), 1.70-1.39 (m, 10H), 1.25-1.19 (m, 1H).

Step 4:

Deprotection of (E)-N-(3-(2-chloro-5-(2-(1-hydroxycyclohexyl)vinyl)phenyl)-3-hydroxypropyl)-2,2,2-trifluoroacetamide following the method used in Example 114 gave Example 121 as an off white solid. Yield (0.145 g, 64%): $^1$H NMR (400 MHz, DMSO-d$_6$) δ 7.58 (s, 1H), 7.27-7.23 (m, 2H), 6.50 (d, J=16.4 Hz, 1H), 6.35 (d, J=16.4 Hz, 1H), 4.96-4.93 (m, 1H), 4.44 (bs, 1H), 2.70-2.63 (m, 2H), 2.47-1.38 (m, 11H), 1.25-1.16 (m, 1H).

Example 122

Preparation of (E)-1-(3-(3-amino-1-hydroxypropyl)-4-methylstyryl)cyclohexanol

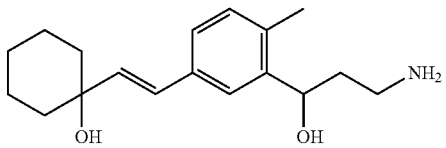 [SMILES: Cc1ccc(/C=C/C2(O)CCCCC2)cc1C(O)CCN]

(E)-1-(3-(3-Amino-1-hydroxypropyl)-4-methylstyryl)cyclohexanol was prepared according to the Methods used in Example 115.

Step 1:

Alkylation of 5-bromo-2-methylbenzaldehyde with acetonitrile following the method used in Example 114 gave 3-(5-bromo-2-methylphenyl)-3-hydroxypropanenitrile as a pale yellow oil. Yield (3.33 g, 86%): $^1$H NMR (400 MHz, DMSO-d$_6$) δ 7.61 (d, J=2.0 Hz, 1H), 7.35 (dd, J=8.0, 2.0 Hz, 1H), 7.09 (d, J=8.0 Hz, 1H), 5.96 (d, =4.4 Hz, 1H), 5.04-5.00 (m, 1H), 2.88 (ABd, J=16.8, 4.4 Hz, 1H), 2.77 (ABd, J=16.8, 6.4 Hz, 1H), 2.23 (s, 3H).

Step 2:

Reduction of 3-(3-bromo-2-methylphenyl)-3-hydroxypropanenitrile with BH$_3$—S(CH$_3$)$_2$ followed by protection of the amine following the method in Example 115 gave N-(3-(3-bromo-2-methylphenyl)-3-hydroxypropyl)-2,2,2-trifluoroacetamide as a pale yellow oil. Yield (3.25 g, 69%): $^1$H NMR (400 MHz, DMSO-d$_6$) δ 9.38 (bs, 1H), 7.53 (d, J=2.4 Hz, 1H), 7.28 (dd, J=8.0, 2.4 Hz, 1H), 7.05 (d, J=8.0 Hz, 1H), 4.73-4.70 (m, 1H), 3.36-3.26 (m, 2H), 2.17 (s, 3H), 1.79-1.71 (m, 1H), 1.68-1.59 (m, 1H).

Step 3:

Coupling of olefin 120 with N-(3-(3-bromo-2-methylphenyl)-3-hydroxypropyl)-2,2,2-trifluoroacetamide following the method used in Example 115 except the reaction was done for 16 hr at 90° C., gave (E)-2,2,2-trifluoro-N-(3-hydroxy-3-(5-(2-(1-hydroxycyclohexyl)vinyl)-2-methylphenyl)propyl) acetamide as a clear oil. Yield (0.372 g, 47%): $^1$H NMR (400 MHz, DMSO-d$_6$) δ 9.38 (t, J=5.2 Hz, 1H), 7.44 (d, J=2.0 Hz, 1H), 7.12 (dd, J=8.0, 2.0 Hz, 1H), 7.02 (d, J=8.0 Hz, 1H), 6.46 (d, J=16.4 Hz, 1H), 6.27 (d, J=16.4 Hz, 1H), 5.19 (d, J=3.6 Hz, 1H), 4.74-4.72 (m, 1H), 4.37 (bs, 1H), 3.33-3.28 (m, 2H), 2.19 (s, 3H), 1.80-1.38 (m, 11H), 1.25-1.16 (m, 1H).

Step 4:

Deprotection of (E)-2,2,2-trifluoro-N-(3-hydroxy-3-(5-(2-(1-hydroxycyclohexyl)vinyl)-2-methylphenyl)propyl)acetamide following the method used in Example 115 gave Example 122 as a pale yellow solid. Yield (0.145 g, 53%): $^1$H NMR (400 MHz, DMSO-d$_6$) δ 7.44 (d, J=1.6 Hz, 1H), 7.09 (dd, J=8.0, 1.6 Hz, 1H), 6.99 (d, J=8.0 Hz, 1H), 6.46 (d, J=16.0 Hz, 1H), 6.25 (d, J=16.0 Hz, 1H), 4.84-4.81 (m, 1H), 4.47 (bs, 1H), 2.73-2.61 (m, 2H), 2.21 (s, 3H), 1.73-1.38 (m, 11H), 1.25-1.16 (m, 1H).

Example 123

Preparation of (E)-1-(3-(3-amino-1-hydroxypropyl)-5-methylstyryl)cyclohexanol

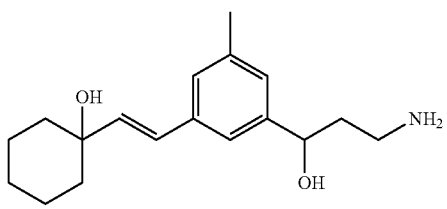 [SMILES: Cc1cc(/C=C/C2(O)CCCCC2)cc(C(O)CCN)c1]

(E)-1-(3-(3-Amino-1-hydroxypropyl)-5-methylstyrypcyclohexanol was prepared according to the Methods used in Examples 50, 79 and 111.

Step 1:

Alkylation of 3-bromo-5-methylbenzaldehyde following the method used in Example 50 gave 3-(3-bromo-5-methylphenyl)-3-hydroxypropanenitrile, which was used directly in the next step.

Step 2:

Reduction of 3-(3-bromo-5-methylphenyl)-3-hydroxypropanenitrile using borane methyl sulfide following the method used in Example 79 gave 3-amino-1-(3-bromo-5-methylphenyl)propan-1-ol which was used directly in the next step.

Step 3:

Treatment of 3-amino-1-(3-bromo-5-methylphenyl)propan-1-ol with ethyl trifluoroacetate following the method used in Example 79 gave N-(3-(3-bromo-5-methylphenyl)-3-hydroxypropyl)-2,2,2-trifluoroacetamide as a light colored oil. Yield (0.38 g, 22%, 3 steps): $^1$H NMR (400 MHz, CDCl$_3$) δ 7.29 (s, 1H), 7.26 (s, 1H), 7.05-7.07 (m, 1H), 4.80 (dd, J=8.8, 4.0 Hz, 1H), 3.62-3.75 (m, 1H), 3.36-3.44 (m, 1H), 2.33 (s, 3H), 1.90-2.0 (m, 2H).

Step 4:

Coupling of N-(3-(3-bromo-5-methylphenyl)-3-hydroxypropyl)-2,2,2-trifluoroacetamide with olefin 120 following the method used in Example 111 gave (E)-2,2,2-trifluoro-N-(3-hydroxy-3-(3-(2-(1-hydroxycyclohexyl)vinyl)-5-methylphenyl)propyl)acetamide as a light yellow oil. Yield (0.28 g, 65%): $^1$H NMR (400 MHz, DMSO-d$_6$) δ 9.34 (t, J=4.8 Hz, 1H), 7.12 (s, 1H), 7.05 (s, 1H), 7.96 (s, 1H), 6.46 (d, J=16 Hz, 1H), 6.32 (d, J=16 Hz, 1H), 5.24 (d, J=4.8 Hz, 1H), 4.50 (q, J=4.8 Hz, 1H), 4.38 (s, 1H), 3.22 (q, J=7.6 Hz, 2H), 2.25 (s, 3H), 1.65-1.70 (m, 2H), 1.54-1.68 (m, 2H), 1.37-1.53 (m, 7H), 1.18-1.26 (m, 1H).

Step 5:

Deprotection of (E)-2,2,2-trifluoro-N-(3-hydroxy-3-(3-(2-(1-hydroxycyclohexyl)vinyl)-5-methylphenyl) (E)-1-(3-(3-Amino-1-hydroxypropyl)-5-methylstyrypcyclohexanol. The free base was dissolved in ethyl acetate (10 ml) and HCl.EtOH (6.95 M, 2 ml) added. The mixture was concentrated under reduced pressure. To the residue was added 30% ethyl acetate/hexane (10 ml) and mixture was sonicated. Collection of the solid by filtration followed by drying gave Example 128 hydrochloride as a light color. Yield (0.07 g, 29%): $^1$H NMR (400 MHz, DMSO-d$_6$) δ 7.70 (bs, 3H), 7.18 (s, 1H), 7.14 (s, 1H), 6.96 (s, 1H), 6.79 (d, J=16.4 Hz, 1H), 6.38 (d, J=16.4 Hz, 1H), 5.91 (bs, 1H), 5.48 (d, J=2.8 Hz, 1H), 4.58-4.64 (m, 1H), 2.76-2.85 (m, 2H), 2.27 (s, 3H), 2.08-2.21 (m, 5H), 1.75-1.88 (m, 2H), 1.51-1.68 (m, 5H).

Example 124

Preparation of (1S,2R)-3-amino-1-((E)-2-(1-hydroxycyclohexyl)vinyl)phenylpropane-1,2-diol

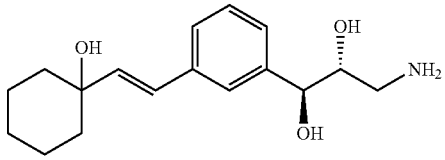 [SMILES: NC[C@@H](O)[C@@H](O)c1cccc(/C=C/C2(O)CCCCC2)c1]

(1S,2R)-3-amino-1-(3-((E)-2-(1-hydroxycyclohexyl)vinyl)phenyl)propane-1,2-diol was prepared following the method described in Scheme 45.

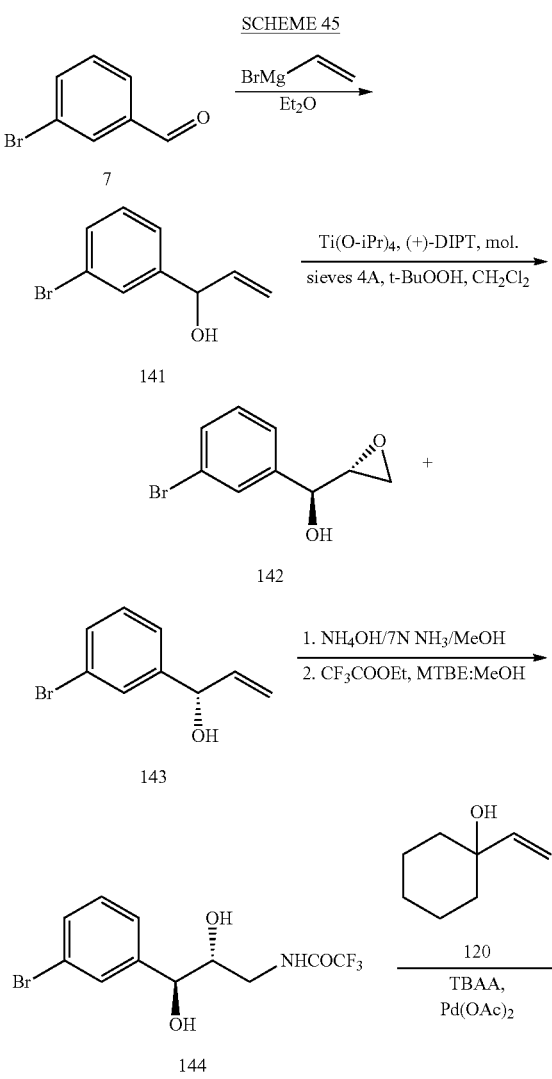

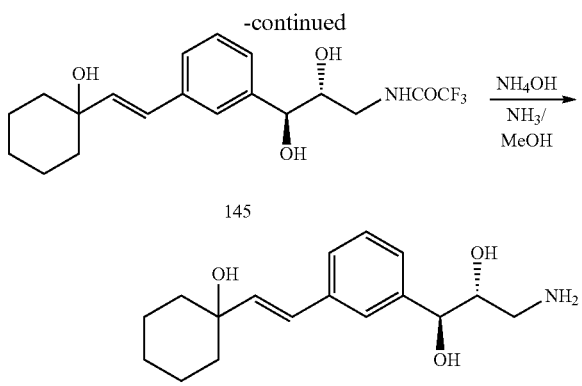

Step 1:

To an ice-cold solution of 3-bromobenzaldehyde (7) (3.2 mL, 27.3 mmol) in anhydrous diethyl ether (50 mL) was slowly added a fresh solution of vinyl magnesium bromide (30.0 mL of a 1.0 M solution in THF, 30 mmol). The reaction mixture was stirred at 0° C. for 20 min, after which aqueous solution of NH₄Cl (25%, 50 mL) was added. The mixture was allowed to warm to room temperature, layers were separated and aqueous layer was extracted with hexane. Combined organic layers were washed with brine, concentrated under reduced pressure and purified by flash column chromatography (silica gel, 5% to 300% EtOAc/hexanes gradient) to give allyl alcohol 141 as a colorless oil. Yield (4.22 g, 73%). $^1$H NMR (400 MHz, DMSO-d$_6$) δ 7.47-7.49 (m, 1H), 7.40 (dt, J=1.8, 7.4 Hz, 1H), 7.24-7.32 (m, 2H), 5.85-5.94 (m, 1H), 5.61 (d, J=4.5 Hz, 1H), 5.24 (dt, J=1.8, 17.0 Hz, 1H), 5.00-5.07 (m, 2H).

Step 2.

To a cold (−23° C.) mixture of powdered 4 Å molecular sieves (6.4 g) and titanium tetraisopropoxide (5.5 mL, 18.8 mmol) in anhydrous CH₂Cl₂ (110 mL) was added L-(+)-diisopropyl tartrate (DIPT, 4.7 mL, 22.49 mmol) under inert atmosphere. The reaction mixture was stirred at −20° C. and a solution of allyl alcohol 141 (4.0 g, 18.8 mmol) in anhydrous CH₂Cl₂ (80 mL) was added over 5 mins. After the reaction mixture was stirred at −20° C. for 30 min, tert-butyl hydroperoxide solution (5.0-6.0 M in nonane, 2 mL, ca 10.0 mmol) was added. The reaction mixture was stirred at −20° C. for 7.5 nrs, kept at −20° C. overnight, stirred at −20° C. for another 7 hrs and left at −20° C. and then kept at −20° C. for 43 Ins. An aqueous solution of L-tartaric acid (10%, 110 mL) was added to the reaction mixture, the mixture was stirred for 10 min at room temperature, then saturated aqueous solution of Na₂SO₄ (20 mL) was added. The mixture was stirred vigorously for 1 h at room temperature, layers were separated. Aqueous layer was extracted with diethyl ether, then with EtOAc. Combined organic layers were washed with brine, dried over anhydrous NaSO₄, filtered and the filtrate concentrated under reduced pressure. The residue was purified by flash column chromatography (silica gel, 30% to 70% EtOAc/hexanes gradient) to give a mixture of epoxide 142 and DIPT (1:1 molar ratio) as a colorless oil and unreacted (S)-1-(3-bromophenyl)prop-2-en-1-ol 143 (2.16 g) as a colorless oil. Crude epoxide 142 was re-purified by flash column chromatography (silica gel, 5% to 10% EtOAc/CH₂Cl₂ gradient) to give a mixture of epoxide 142 and DIPT (1:0.85 molar ratio) as a colorless oil, which was used in the next step without additional purification. Yield (3.44 g, 85.6%); $^1$H NMR (400 MHz, DMSO-d$_6$) δ 7.54 (t, J=1.6 Hz, 1H), 7.45 (ddd, J=1.2, 2.0, 7.8 Hz, 1H), 7.34-7.38 (m, 1H), 7.29 (t, J=7.6 Hz, 1H), 5.68 (d, J=4.5 Hz, 1H), 4.41 (t, J=4.7 Hz, 1H), 2.99-3.03 (m, 1H), 2.69 (ABd, J=5.5, 3.9 Hz, 1H), 2.63 (ABd, J=5.3, 2.7 Hz, 1H).

Step 3.

A solution of epoxide:DIPT 142 (0.47 g, 0.803 mmol), ammonium hydroxide (25%, 5 mL) and NH₃/MeOH (7N, 5 mL) was stirred in a pressure bottle at room temperature for 20 hrs, and then concentrated under reduced pressure. The residue was dissolved in MTBE:MeOH (1:1, 10 mL) and ethyl trifluoroacetate (3.0 mL) was added. The mixture was stirred at room temperature for 1 h, concentrated under reduced pressure and the residue was purified by flash column chromatography (silica gel, 30% to 60% EtOAc/hexanes gradient) to give trifluoroacetamide 144 as a colorless oil. Yield (0.248 g, 66%); $^1$H NMR (400 MHz, DMSO-d$_6$) δ 9.17 (br. t, 1H), 7.51 (t, J=1.8 Hz, 1H), 7.40 (ddd, J=1.2, 2.0, 7.9 Hz, 1H), 7.30-7.33 (m, 1H), 7.25 (t, J=7.8 Hz, 1H), 5.57 (d, J=4.7 Hz, 1H), 4.96 (d, J=6.06 Hz, 1H), 4.39 (t, J=5.5 Hz, 1H), 3.62-3.69 (m, 1H), 3.38 (dt, J=4.1, 13.7 Hz, 1H), 3.05-3.13 (m, 1H).

Step 4.

Coupling of bromide 144 with olefin 120 following the method used in Example 111 except that: anhydrous degassed DMF (1 mL) was used as the reaction solvent, the reaction was heated at 90° C. for 3 hrs then at 60° C. overnight. After addition of water, the product was extracted with EtOAc (3×). To give olefin 145, yield (0.194 g, 70%); $^1$H NMR (400 MHz, DMSO-d$_6$) δ 9.14 (t, J=5.7 Hz, 1H), 7.35-7.39 (m, 1H), 7.19-7.25 (m, 2H), 7.13-7.18 (m, 1H), 6.51 (d, J=16.0 Hz, 1H), 6.34 (d, J=16.0 Hz, 1H), 5.41 (d, J=4.5 Hz, 1H), 4.86 (d, J=6.3 Hz, 1H), 4.39-4.43 (m, 2H), 3.66-3.73 (m, 1H), 3.37 (ddd, J=3.3, 4.7, 13.3 Hz, 1H), 3.08-3.16 (m, 1H), 1.55-1.67 (m, 2H), 1.37-1.54 (m, 7H), 1.18-1.25 (m, 1H).

Step 5.

A mixture of trifluoroacetamide 145 (0.189 g, 0.488 mmol), NH₃/MeOH (7N, 3.0 mL) and ammonium hydroxide (10.0 mL) was stirred at room temperature for 68 hrs and concentrated under reduced pressure. The residue was purified by flash chromatography using a gradient of 50% to 100% 7N NH₃/MeOH in EtOAc/hexanes to give crude amine as a colorless oil. The amine was re-purified by flash chromatography using 20% 7N NH₃/MeOH in CH₂Cl₂ to give Example 124 as a colorless oil. Yield (0.065 g, 46%); NMR (400 MHz, MeOH-d$_4$) δ 7.42-7.45 (m, 1H), 7.22-7.32 (m, 3H), 6.61 (d, J=16.2 Hz, 1H), 6.36 (d, J=16.0 Hz, 1H), 4.58 (d, J=6.1 Hz, 1H), 3.71-3.76 (m, 1H), 2.92 (dd, J=3.5, 13.1 Hz, 1H), 2.77 (dd, J=8.0, 13.1 Hz, 1H), 1.47-1.76 (m, 9H), 1.25-1.40 (m, 1H); $^{13}$C NMR (100 MHz, MeOH-d$_4$) δ 142.7, 137.8, 137.5, 128.1, 126.9, 125.8, 125.4, 124.8, 76.1, 75.7, 71.2, 43.3, 37.5, 25.5, 21.9; ESI MS m/z 292.5 [M+H]⁺; HPLC (Method 10) 97% (AUC), t$_R$=5.44 min.

Example 125

Preparation of (E)-2-(3-(3-amino-1-hydroxypropyl)styryl)cyclohexanol

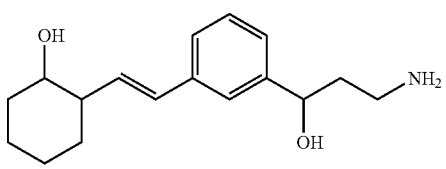 [SMILES: NCCC(O)c1cccc(/C=C/C2CCCCC2O)c1]

(E)-2-(3-(3-amino-1-hydroxypropyl)styryl)cyclohexanol was prepared following the method described in Scheme 46.

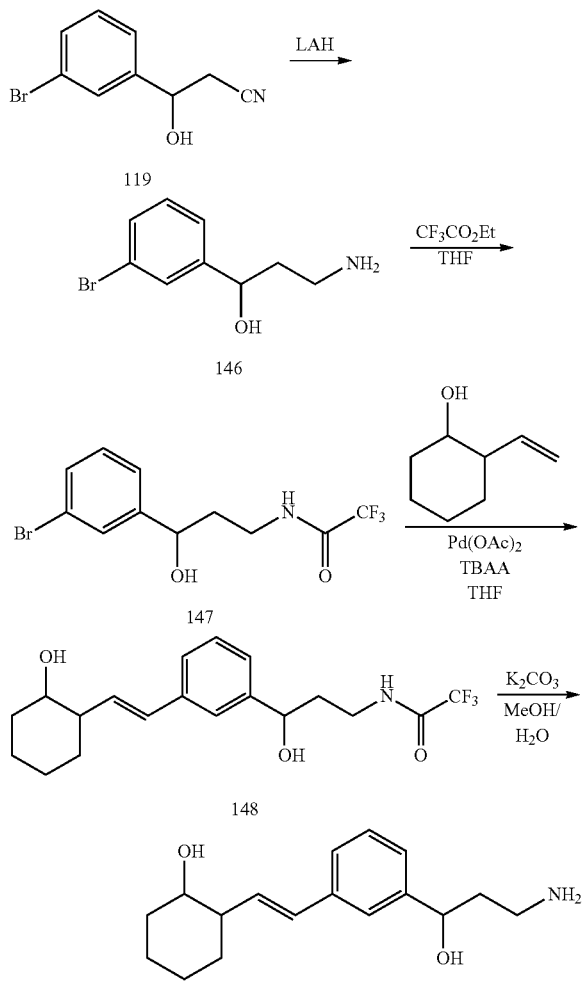

Step 1:
To an ice cold solution of 3-(3-bromophenyl)-3-hydroxypropanenitrile (119) (2.70 g, 11.9 mmol) in anhydrous THF (20 mL) under argon was added a solution of LiAlH$_4$ in THF (11.9 mL of a 2 M solution in THF, 23.8 mmol). The mixture was stirred at 0° C. for 45 min, diluted with ether (50 mL), and quenched with the dropwise addition of saturated aqueous Na$_2$SO$_4$ (approximately 2 mL). After drying over MgSO$_4$, the solution was filtered and concentrated under reduced pressure to give amine 146 as a light green oil. Yield (2.30 g, 84%.) This material was used in the next step without further purification. $^1$H NMR (400 MHz, DMSO-d$_6$) δ 7.49 (m, 1H), 7.37 (dt, J=7.2, 1.6 Hz, 1H), 7.23-7.31 (m, 2H), 4.66 (t, J=6.8 Hz, 1H), 2.61 (m, 2H), 1.61 (q, J=6.8 Hz, 2H).

Step 2:
To a solution of 3-amino-1-(3-bromophenyl)propan-1-ol (146) (2.30 g, 10 mmol) in anhydrous THF (20 mL) was added ethyl trifluoroacetate (4.0 mL, 33.5 mmol). The reaction mixture was stirred at room temperature for 3 h, then concentrated under reduced pressure. Purification by column chromatography (10 to 70% EtOAc-hexanes gradient) gave N-(3-(3-bromophenyl)-3-hydroxypropyl)-2,2,2-trifluoroacetamide (147) as an oil containing 15% of 2,2,2-trifluoro-N-(3-hydroxy-3-phenylpropyl)acetamide. Yield (1.96 g, 60%): $^1$H NMR (400 MHz, DMSO-d$_6$) δ 9.33 (s, 1H), 7.51 (t, J=2.0 Hz, 1H), 7.41 (dt, J=7.6, 2.0 Hz, 1H), 7.25-7.32 (m, 2H), 5.46 (d, J=6.4 Hz, 1H), 4.55-4.60 (m, 1H), 3.20-3.23 (m, 2H), 1.75-1.82 (m, 2H).

Step 3:
Heck coupling of 2-vinylcyclohexanol with bromide 147 following the method used in Example 111 gave trifluoroamide 148 as an orange oil. Yield (0.36 mg, 66%). $^1$H NMR (400 MHz, CDCl$_3$) δ 7.47 (brs, 1H), 7.24-7.34 (m, 3H), 7.14-7.20 (m, 1H), 6.48 (d, J=16 Hz, 1H), 6.09 (q, J=8.8 Hz, 1H), 4.83 (q, J=4.4 Hz, 1H), 3.60-3.70 (m, 1H), 3.28-3.44 (m, 2H), 2.38 (brs, 2H), 2.00-2.10 (m, 2H), 1.93-1.99 (m, 2H), 1.78-1.84 (m, 2H), 1.64-1.73 (m, 1H), 1.22-1.40 (m, 4H).

Step 4:
Deprotection of trifluoroacetamide 148 following the method used in Example 71 gave Example 125 as a white foamy solid. Yield (0.11 g, 41%). $^1$H NMR (400 MHz, CDCl$_3$) δ 7.43 (brs, 1H), 7.18-7.31 (m, 4H), 6.52 (d, J=16 Hz, 1H), 6.06-6.13 (m, 1H), 4.91-4.97 (brs, 1H), 3.29-3.35 (m, 1H), 3.04-3.16 (m, 1H), 2.90-3.00 (m, 1H), 2.65 (brs, 3H), 2.00-2.50 (2H), 1.64-1.90 (m, 5H), 1.18-1.40 (m, 4H). ESI MS m/z 276.3 [m+H]$^+$, 258.3 [m+H–H$_2$O]$^+$ Example 126

Preparation of (E)-1-(5-(3-amino-1-hydroxypropyl)-2-fluorostyryl)cyclohexanol

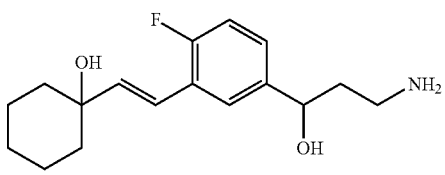 [SMILES: NCCC(O)c1ccc(F)c(/C=C/C2(O)CCCCC2)c1]

(E)-1-(5-(3-Amino-1-hydroxypropyl)-2-fluorostyryl)cyclohexanol was prepared according to the Methods used in Examples 115.

Step 1:
Alkylation of 3-bromo-4-fluorobenzaldehyde with acetonitrile following the method used in Example 115 gave 3-(3-bromo-4-fluorophenyl)-3-hydroxypropanenitrile as a pale yellow oil. Yield (4.2 g, 70%): $^1$H NMR (400 MHz, DMSO-d$_6$) δ 7.71 (dd, J=6.8, 2.0 Hz, 1H), 7.44 (ddd, J=8.4, 5.2, 2.4 Hz, 1H), 7.35 (t, J=8.8 Hz, 1H), 6.08 (bs, 1H), 4.90 (s, 1H), 2.90 (ABd, J=16.8, 5.2 Hz, 1H), 2.83 (ABd, J=16.8, 6.4 Hz, 1H).

Step 2:
Reduction of 3-(3-bromo-4-fluorophenyl)-3-hydroxypropanenitrile with BH$_3$-THF followed by protection of the amine following the method in Example 115 gave N-(3-(3-bromo-4-fluorophenyl)-3-hydroxypropyl)-2,2,2-trifluoroacetamide as a clear oil. Yield (4.3 g, 73%): $^1$H NMR (400 MHz, DMSO-d$_6$) δ 9.31 (bs, 1H), 7.62 (dd, J=6.8, 2.0 Hz, 1H), 7.37-7.33 (m, 1H), 7.30 (t, J=8.8 Hz, 1H), 5.48 (d, J=4.4 Hz, 1H), 4.60-4.56 (m, 1H), 3.28-3.15 (m, 2H), 1.84-1.71 (m, 2H).

Step 3:
Coupling of olefin 120 with N-(3-(5-bromo-4-fluorophenyl)-3-hydroxypropyl)-2,2,2-trifluoroacetamide following the method used in Example 115 except the reaction was done for 16 hr at 90° C., gave (E)-2,2,2-trifluoro-N-(3-(4-fluoro-3-(2-(1-hydroxycyclohexyl)vinyl)phenyl)-3-hydroxypropyl)acetamide as a light yellow oil. Yield (0.44 g, 51%): $^1$H NMR (400 MHz, DMSO-d$_6$) δ 9.33 (bs, 1H), 7.50 (dd, J=7.6, 2.2 Hz, 1H), 7.18 (ddd, J=8.0, 5.2, 2.0 Hz, 1H), 7.08 (dd, J=10.8, 8.4 Hz, 1H), 6.65 (d, J=16.4 Hz, 1H), 6.45 (d, J=16.4 Hz, 1H), 5.35 (bs, 1H), 4.56 (t, J=6.4 Hz, 1H), 4.49 (bs, 1H), 3.22 (bs, 2H), 1.81-1.76 (m, 2H), 1.63-1.39 (m, 9H), 1.26-1.17 (m, 1H).

Step 4:

Deprotection of (E)-2,2,2-trifluoro-N-(3-(4-fluoro-3-(2-(1-hydroxycyclohexyl)vinyl)phenyl)-3-hydroxypropyl)acetamide following the method used in Example 115 gave Example 126 as an off white solid. Yield (0.153 g, 47%): $^1$H NMR (400 MHz, DMSO-d$_6$) δ 7.48 (dd, J=7.6, 2.2 Hz, 1H), 7.15 (ddd, J=7.8, 5.1, 2.2 Hz, 1H), 7.06 (dd, J=10.8, 8.4 Hz, 1H), 6.65 (d, J=16.4 Hz, 1H), 6.43 (d, J=16.4 Hz, 1H), 4.64 (m, 1H), 4.49 (bs, 1H), 2.66-2.54 (m, 2H), 1.65-1.56 (m, 4H), 1.53-1.40 (m, 7H), 1.27-1.17 (m, 1H).

Example 127

Preparation of (E)-1-(3-(3-amino-1-hydroxypropyl)-5-methyloxystyryl)cyclohexanol

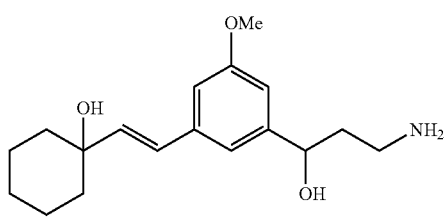 [SMILES: COc1cc(/C=C/C2(O)CCCCC2)cc(C(O)CCN)c1]

(E)-1-(3-(3-Amino-1-hydroxypropyl)-5-methoxystyryl)cyclohexanol was prepared according to the Methods used in Examples 115

Step 1:

Alkylation of 3-bromo-5-methoxybenzaldehyde with acetonitrile following the method used in Example 115 gave 3-(3-bromo-5-methoxyphenyl)-3-hydroxypropanenitrile as a pale yellow oil. Yield (4.1 g, 70%): $^1$H NMR (400 MHz, DMSO-d$_6$) δ 7.16-7.15 (m, 1H), 7.04-7.03 (m, 1H), 6.97-6.96 (m, 1H), 6.04 (d, J=4.8 Hz, 1H), 4.87-4.83 (m, 1H), 3.74 (s, 3H), 2.89 (ABd, J=16.4, 5.2 Hz, 1H), 2.81 (ABd, J=16.8, 6.8 Hz, 1H).

Step 2:

Reduction of 3-(3-bromo-5-methoxyphenyl)-3-hydroxypropanenitrile with BH$_3$-THF followed by protection of the amine following the method in Example 115 gave N-(3-(3-bromo-5-methoxyphenyl)-3-hydroxypropyl)-2,2,2-trifluoroacetamide as a clear oil. Yield (3.9 g, 68%): $^1$H NMR (400 MHz, DMSO-d$_6$) δ 9.30 (bs, 1H), 7.07 (t, J=1.2 Hz, 1H), 6.98-6.97 (m, 1H), 6.88-6.87 (m, 1H), 5.44 (d, J=4.8 Hz, 1H), 4.56-4.51 (m, 1H), 3.74 (m, 3H), 3.27-3.15 (m, 2H), 1.96-1.70 (m, 2H).

Step 3:

Coupling of olefin 120 with N-(3-(5-bromo-5-methoxyphenyl)-3-hydroxypropyl)-2,2,2-trifluoroacetamide following the method used in Example 115 except the reaction was done for 16 hr at 90° C., gave (E)-2,2,2-trifluoro-N-(3-hydroxy-3-(3-(2-(1-hydroxycyclohexyl)vinyl)-5-methoxyphenyl)propyl)acetamide as a light yellow oil. Yield (0.393 g, 48%): $^1$H NMR (400 MHz, DMSO-d$_6$) δ 9.32 (t, J=5.2, 1H), 6.93 (s, 1H), 6.79-6.78 (m, 1H), 6.73 (s, 1H), 6.47 (d, J=16.0 Hz, 1H), 6.34 (d, J=16.0 Hz, 1H), 5.29 (bs, 1H), 4.52 (t, =6.0 Hz, 1H), 4.39 (bs, 1H), 3.73 (s, 3H), 3.25-3.20 (m, 2H), 1.81-1.71 (m, 2H), 1.62-1.40 (m, 9H), 1.25-1.17 (m, 1H).

Step 4:

Deprotection of (E)-2,2,2-trifluoro-N-(3-hydroxy-3-(3-(2-(1-hydroxycyclohexyl)vinyl)-5-methoxyphenyl)propyl)acetamide following the method used in Example 115 gave Example 127 as a clear oil. Yield (0.162 g, 55%): $^1$H NMR (400 MHz, DMSO-d$_6$) δ 6.91 (s, 1H), 6.76-6.75 (m, 1H), 6.71 (s, 1H), 6.46 (d, J=16.0 Hz, 1H), 6.33 (d, J=16.0 Hz, 1H), 4.59 (t, J=6.4 Hz, 1H), 4.39 (bs, 1H), 3.72 (s, 3H), 2.66-2.55 (m, 2H), 1.63-1.57 (m, 411), 1.48-1.39 (m, 7H), 1.25-1.15 (m, 1H).

Example 128

Preparation of (E)-1-(3-(3-amino-1-hydroxypropyl)-4-fluorostyryl)cyclohexanol

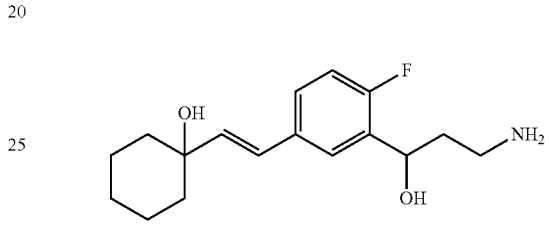

(E)-1-(3-(3-amino-1-hydroxypropyl)-4-fluorostyryl)cyclohexanol was prepared according to the Methods used in Examples 123.

Step 1:

Alkylation of 5-bromo-2-fluorobenzaldehyde gave 3-(5-bromo-2-fluorophenyl)-3-hydroxypropanenitrile, which was used directly in the next step.

Step 2:

Reduction of 3-(5-bromo-2-fluorophenyl)-3-hydroxypropanenitrile using borane methyl sulfide 3-amino-1-(5-bromo-2-fluorophenyl)propan-1-ol which was used directly in the next step.

Step 3:

Treatment of 3-amino-1-(5-bromo-2-fluorophenyl)propan-1-ol with ethyl trifluoroacetate gave N-(3-(5-bromo-2-fluorophenyl)-3-hydroxypropyl)-2,2,2-trifluoroacetamide as a light colored oil. Yield (0.95 g, 28% in 3 steps): $^1$H NMR (400 MHz, DMSO-d$_6$) δ 9.37 (t, J=4.8 Hz, 1H), 7.59 (dd, J=6.4, 2.8 Hz, 1H), 7.44-7.47 (m, 1H), 7.12 (dd, J=10.4, 8.8 Hz, 1H), 5.57 (d, J=4.8, Hz, 1H), 4.78-4.84 (m, 1H), 3.26 (q, J=6.8, Hz, 2H), 1.71-1.84 (m, 2H).

Step 4:

Coupling of N-(3-(5-bromo-2-fluorophenyl)-3-hydroxypropyl)-2,2,2-trifluoroacetamide with olefin 120 gave (E)-2,2,2-trifluoro-N-(3-(2-fluoro-5-(2-(1-hydroxycyclohexyl)vinyl)phenyl)-3-hydroxypropyl)acetamide as a light yellow oil. Yield (0.19 g, 42%): $^1$H NMR (400 MHz, MeOD) δ 7.54 (dd, J=7.2, 2.4 Hz, 1H), 7.27-7.31 (m, 1H), 6.97 (dd, J=10.4, 8.8 Hz, 1H), 6.58 (d, J=16.4 Hz, 1H), 6.30 (d, J=16 Hz, 1H), 4.99 (dd, J=8.0, 4.2 Hz, 1H), 4.41 (t, J=7.2 Hz, 2H), 1.91-2.02 (m, 2H), 1.50-1.78 (m, 9H), 1.28-1.39 (m, 1H).

Step 5:

Deprotection of (E)-2,2,2-trifluoro-N-(3-(2-fluoro-5-(2-(1-hydroxycyclohexyl)vinyl)phenyl)-3-hydroxypropyl)acetamide followed by HCL salt formation following the methods used in Example 123 gave. Example 128 hydrochloride as a light color solid. Yield (0.08 g, 49%): $^1$H NMR (400 MHz, MeOD) δ 7.59 (dd, J=6.4, 2.4 Hz, 1H), 7.32-7.36 (m, 1H), 6.99 (dd, J=10.4, 8.8 Hz, 1H), 6.74 (d, J=16.0 Hz, 1H), 6.43 (d, J=16.4 Hz, 1H), 5.89 (t, J=2.4 Hz, 1H), 5.11 (dd, J=8.4, 4.4 Hz, 1H), 3.02-3.16 (m, 2H), 2.14-2.38 (m, 4H), 1.95-2.08 (m, 3H), 1.54-1.78 (m, 5H).

Example 129

Preparation of (1R,2S)-3-amino-1-(3-((E)-2-(1-hydroxycyclohexyl)vinyl)phenyl)propane-1,2-diol

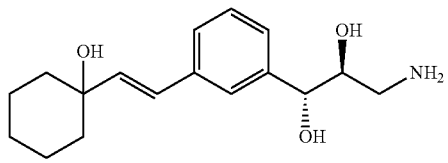 [SMILES: NC[C@H](O)[C@H](O)c1cccc(/C=C/C2(O)CCCCC2)c1]

(1R,2S)-3-amino-1-(3-((E)-2-(1-hydroxycyclohexyl)vinyl)phenyl)propane-1,2-diol is prepared according to the Methods used in Examples 124.

Step 1.

Epoxidation of (5)-1-(3-bromophenyl)prop-2-en-1-ol (141) following the method used in Example 124 except that one equivalent of t-BuOOH and D-(−)-diisopropyl tartrate were used gave (R)-(3-bromophenyl)((S)-oxiran-2-yl)methanol as a mixture with DIPT (1:1.5 molar ratio) as a colorless oil which was used in the next step without further purification. Yield (4.12 g). $^1$H NMR (400 MHz, DMSO-$d_6$) δ 7.50 (t, J=1.6 Hz, 1H), 7.40 (ddd, J=1.2, 2.0, 7.6 Hz, 1H), 7.29-7.33 (m, 1H), 7.25 (t, J=7.6 Hz, 1H), 5.52 (d, J=5.1 Hz, 1H), 5.26 (d, J=5.9 Hz, 1H), 4.51 (t, J=4.7 Hz, 1H), 3.15 (dd, J=3.3, 12.5 Hz, 1H), 3.02 (dd, J=8.0, 12.7 Hz, 1H).

Step 2.

Epoxide ring opening and trifluoroacetamide protection following the method used in Example 124 afforded N-((2S,3R)-3-(3-bromophenyl)-2,3-dihydroxypropyl)-2,2,2-trifluoroacetamide as a colorless oil. Yield (0.322 g, 42%). $^1$H NMR (400 MHz, DMSO-$d_6$) δ 9.17 (br. t, 1H), 7.51 (t, J=1.8 Hz, 1H), 7.40 (ddd, J=1.2, 2.0, 7.9 Hz, 1H), 7.30-7.33 (m, 1H), 7.25 (t, J=7.8 Hz, 1H), 5.57 (d, J=4.7 Hz, 1H), 4.96 (d, J=6.06 Hz, 1H), 4.39 (t, J=5.5 Hz, 1H), 3.62-3.69 (m, 1H), 3.38 (dt, J=4.1, 13.7 Hz, 1H), 3.05-3.13 (m, 1H).

Step 3.

Coupling of N-((2S,3R)-3-(3-bromophenyl)-2,3-dihydroxypropyl)-2,2,2-trifluoroacetamide with alkene 119 was performed following the method used in Example 124 to give N-((2S,3R)-2,3-dihydroxy-3-(3-((E)-2-(1-hydroxycyclohexyl)vinyl)phenyl)propyl)-2,2,2-trifluoroacetamide as a brownish foam. Yield (0.xxx g, xx %). $^1$H NMR (400 MHz, DMSO-$d_6$) 9.14 (t, J=5.7 Hz, 1H), 7.35-7.39 (m, 1H), 7.19-7.25 (m, 2H), 7.13-7.18 (m, 1H), 6.51 (d, J=16.0 Hz, 1H), 6.34 (d, J=16.0 Hz, 1H), 5.41 (d, J=4.5 Hz, 1H), 4.86 (d, J=6.3 Hz, 1H), 4.39-4.43 (m, 2H), 3.66-3.73 (m, 1H), 3.37 (ddd, J=3.3, 4.7, 13.3 Hz, 1H), 3.08-3.16 (m, 1H), 1.55-1.67 (m, 2H), 1.37-1.54 (m, 7H), 1.18-1.25 (m, 1H).

Step 4.

N-((2S,3R)-2,3-dihydroxy-3-(3-((E)-2-(1-hydroxycyclohexyl)vinyl)phenyl)propyl)-2,2,2-trifluoroacetamide was deprotected following the method used in Example 124 to give Example 129 as a colorless oil. Yield (0.xx g, xx %). $^1$H NMR (400 MHz, MeOH-$d_4$) δ 7.42-7.45 (m, 1H), 7.22-7.32 (m, 3H), 6.61 (d, J=16.2 Hz, 1H), 6.36 (d, J=16.0 Hz, 1H), 4.58 (d, J=6.1 Hz, 1H), 3.71-3.76 (m, 1H), 2.92 (dd, J=3.5, 13.1 Hz, 1H), 2.77 (dd, J=8.0, 13.1 Hz, 1H), 1.47-1.76 (m, 9H), 1.25-1.40 (m, 1H). $^{13}$C NMR (100 MHz, MeOH-$d_4$) δ 142.7, 137.8, 137.5, 128.1, 126.9, 125.8, 125.4, 124.8, 76.1, 75.7, 71.2, 43.3, 37.5, 25.5, 21.9; ESI MS m/z 292.3 [M+H]$^+$; HPLC (Method 9) 99% (AUC), $t_R$=5.31 min.

Example 130

Preparation of (E)-1-(3-(3-amino-1-hydroxypropyl)-5-chlorostyryl)cyclohexanol

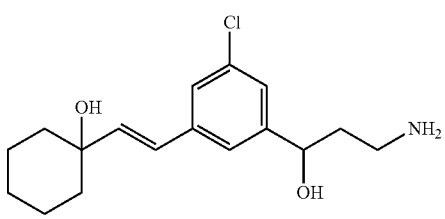 [SMILES: NCCC(O)c1cc(Cl)cc(/C=C/C2(O)CCCCC2)c1]

(E)-1-(3-(3-amino-1-hydroxypropyl)-5-chlorostyrypcyclohexanol is prepared according to the Methods used in Examples 115.

Step 1:

Alkylation of 5-bromo-3-chlorobenzaldehyde with acetonitrile following the method used in Example 115 gave 3-(5-bromo-3-chlorophenyl)-3-hydroxypropanenitrile as a clear oil. Yield (3.21 g, 54%): $^1$H NMR (400 MHz, DMSO-$d_6$) δ 7.62 (t, J=2.0 Hz, 1H), 7.58-7.57 (m, 1H), 7.49-4.48 (m, 1H), 6.18 (d, J=4.8 Hz, 1H), 4.93-4.90 (m, 1H), 2.93 (ABd, J=16.8, 5.2 Hz, 1H), 2.86 (ABd, J=17.2, 6.8 Hz, 1H).

Step 2:

Reduction of 3-(5-bromo-3-chlorophenyl)-3-hydroxypropanenitrile with BH$_3$-THF followed by protection of the amine following the method in Example 115 gave N-(3-(5-bromo-3-chlorophenyl)-3-hydroxypropyl)-2,2,2-trifluoroacetamide as a clear oil. Yield (3.15 g, 71%): $^1$H NMR (400 MHz, DMSO-$d_6$) δ 9.30 (bs, 1H), 7.55 (t, J=2.0 Hz, 1H), 7.49-7.48 (m, 1H), 7.394-7.387 (m, 1H), 5.57 (d, J=4.8 Hz, 1H), 3.30-3.15 (m, 2H), 1.86-1.70 (m, 2H).

Step 3:

Coupling of olefin 119 with N-(3-(5-bromo-3-chlorophenyl)-3-hydroxypropyl)-2,2,2-trifluoroacetamide following the method used in Example 115 except the reaction was done for 16 hr at 90° C., gave (E)-N-(3-(3-chloro-5-(2-(1-hydroxycyclohexyl)vinyl)phenyl)-3-hydroxypropyl)-2,2,2-trifluoroacetamide as a clear oil. Yield (0.521 g, 58%): $^1$H NMR (400 MHz, DMSO-$d_6$) δ 9.32 (t, J=5.0 Hz, 1H), 7.319-7.310 (m, 1H), 7.30 (s, 1H), 7.194-7.187 (m, 1H), 6.50 (d, J=16.0 Hz, 1H), 6.44 (d, J=16.0 Hz, 1H), 5.43 (d, J=4.8 Hz, 1H), 4.59-4.54 (m, 1H), 4.44 (s, 1H), 3.26-3.16 (m, 2H), 1.86-1.72 (m, 2H), 1.62-1.56 (m, 2H), 1.51-1.39 (m, 7H), 1.25-1.17 (m, 1H).

Step 4:

Deprotection of (E)-N-(3-(3-chloro-5-(2-(1-hydroxycyclohexyl)vinyl)phenyl)-3-hydroxypropyl)-2,2,2-trifluoroacetamide following the method used in Example 115 gave Example 130 as clear oil. Yield (0.3 g, 76%): $^1$H NMR (400 MHz, DMSO-$d_6$) δ 7.283-7.275 (m, 2H), 7.169-7.162 (m, 1H), 6.49 (d, J=16.0 Hz, 1H), 6.43 (d, J=16.0 Hz, 1H), 4.64 (t, J=5.8 Hz, 1H), 4.44 (bs, 1H), 2.66-2.54 (m, 2H), 1.63-1.56 (m, 4H), 1.51-1.39 (m, 7H), 1.25-1.63 (m, 1H).

Example 131

Preparation of (E)-4-(3-(2,6-dimethylstyryl)phenyl)butan-1-amine

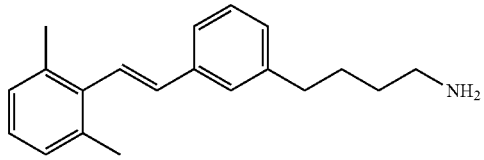 [SMILES: Cc1cccc(C)c1/C=C/c1cccc(CCCCN)c1]

(E)-4-(3-(2,6-Dimethylstyryl)phenyl)butan-1-amine was prepared following the method described in Scheme 47.

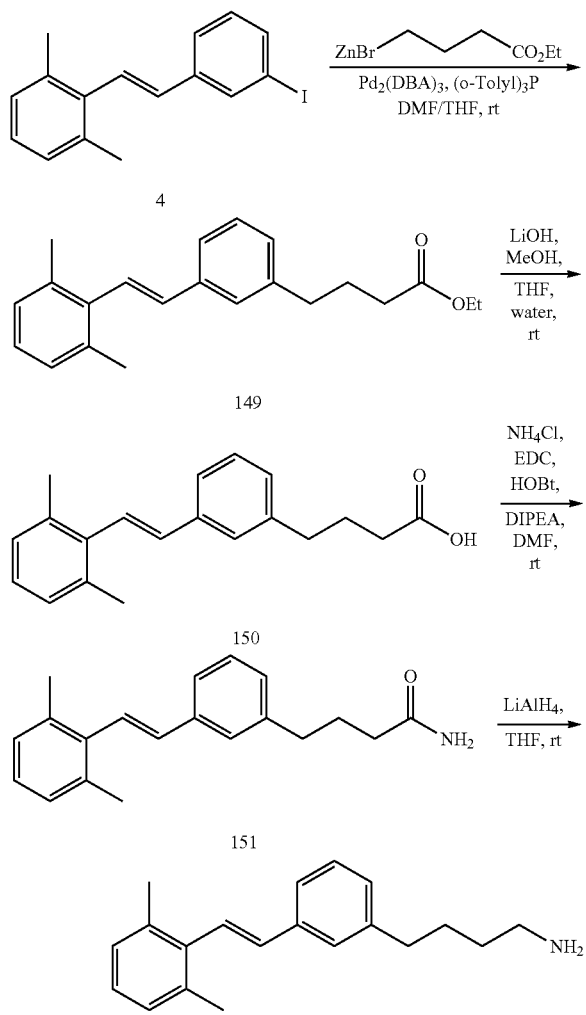

Step 1:

To a stirred solution of (E)-2-(3-iodostyryl)-1,3-dimethylbenzene (4) (0.143 g, 0.428 mmol), tris(dibenzylideneacetone)dipalladium(0) (0.020 g, 0.022 mmol) and tri(o-tolyl)phosphine (0.026 g, 0.085 mmol) in DMF (2 mL) was added 4-ethoxy-4-oxobutylzinc bromide (0.86 mL, 0.5M solution in THF, 0.430 mmol) at room temperature. After 22 h water (20 mL) was added, the mixture was extracted with ethyl acetate (3×50 mL), the combined extracts were washed with water (3×20 mL) and brine (20 mL), dried ($Na_2SO_4$), filtered and concentrated. The resulting residue was purified by flash column chromatography (silica gel, 96:4 hexanes/ethyl acetate) to give 149 as a colorless oil. Yield (0.119 g, 86%): ESI MS m/z 277 $[M+H-EtOH]^+$.

Step 2:

To a stirred solution of 149 (0.119 g, 0.369 mmol) in methanol (5 mL), THF (5 mL) and water (3 mL) was added lithium hydroxide (0.088 g, 3.67 mmol) at room temperature. After 3 h the reaction mixture was concentrated, the residue was diluted with brine (10 mL) and the resulting mixture was acidified with 4N hydrochloric acid to pH 2. The resulting mixture was extracted with ethyl acetate (3×50 mL) and the combined extracts were dried ($Na_2SO_4$), filtered and concentrated. The resulting residue was purified by flash column chromatography (silica gel, 90:10 methylene chloride/methanol) to give 150 as a colorless syrup. Yield (0.105 g, 96%): $^1$H NMR (300 MHz, $CDCl_3$) δ 7.43-7.07 (m, 8H), 6.57 (d, J=16.6 Hz, 1H), 2.70 (t, J=7.3 Hz, 2H), 2.41 (t, J=7.3 Hz, 2H), 2.37 (s, 6H), 2.00 (m, 2H); ESI MS m/z 277 $[M+H-H_2O]^+$.

Step 3:

To a stirred solution of 150 (0.105 g, 0.357 mmol) in DMF (5 mL) was added N,N-diisopropylethylamine (0.230 g, 1.78 mmol), 1-hydroxybenzotriazole (0.097 g, 0.717 mmol), 1-(3-dimethylaminopropyl)-3-ethylcarbodiimide hydrochloride (0.137 g, 0.715 mmol) and ammonium chloride (0.038 g, 0.710 mmol) at room temperature. After 16 h the reaction mixture was diluted with ethyl acetate (100 mL) and washed sequentially with 10% aqueous potassium carbonate (20 mL), water (2×20 mL) and brine (20 mL). The organic layer was dried ($Na_2SO_4$), filtered and concentrated. The residue was purified by flash column chromatography (silica gel, 60:40 methylene chloride/ethyl acetate) to give 151 as a colorless oil. Yield (0.040 g, 38%): $^1$H NMR (500 MHz, $CDCl_3$) δ 7.32 (m, 3H), 7.08 (m, 5H), 6.57 (d, J=16.6 Hz, 1H), 5.60 (br s, 1H), 5.48 (br s, 1H), 2.70 (t, J=7.3 Hz, 2H), 2.26 (t, J=7.3 Hz, 2H), 2.04 (s, 6H), 2.01 (m, 2H); ESI MS m/z 294 $[M+H]^+$.

Step 4:

To a stirred solution of 151 (0.040 g, 0.136 mmol) in THF (5 mL) was added lithium aluminum hydride (0.052 g, 1.37 mmol) at room temperature. After 66 h the reaction mixture was cooled to 0° C., quenched with 2N aqueous sodium hydroxide (0.1 mL), the resulting suspension was diluted with MTBE (50 mL), filtered and concentrated. The resulting residue was purified by flash column chromatography (silica gel, 50:46:4 ethyl acetate/hexanes/7N ammonia in methanol) followed by preparative HPLC to give Example 132 as a colorless oil. Yield (0.017 g, 45%): $R_f$ 0.65 (silica gel, 50:40:10 ethyl acetate/hexanes/7N ammonia in methanol); $^1$H NMR (500 MHz, $CD_3OD$) δ 7.35 (m, 2H), 7.26 (t, J=7.7 Hz, 1H), 7.16 (d, J=16.4 Hz, 1H), 7.11 (d, J=7.5 Hz, 1H), 7.03 (s, 3H), 6.57 (d, J=16.4 Hz, 1H), 2.68 (t, J=6.9 Hz, 2H), 2.66 (t, J=6.9 Hz, 2H), 2.34 (s, 6H), 1.68 (m, 2H), 1.54 (m, 211); $^{13}$C NMR (125 MHz, $CD_3OD$) δ 144.2, 139.1, 138.4, 137.3, 135.6, 129.8, 128.99, 128.98, 127.9, 127.8, 127.7, 124.9, 42.5, 36.8, 33.2, 30.1, 21.3; ESI MS m/z 280 $[M+H]^+$; HPLC

Example 132

Preparation of 1-(3-(2,6-dimethylstyryl)phenyl)-N,N-dimethylmethanamine

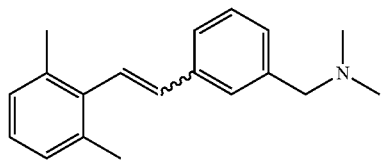 [SMILES: Cc1cccc(C)c1C=Cc1cccc(CN(C)C)c1]

1-(3-(2,6-Dimethylstyryl)phenyl)-N,N-dimethylmethanamine was prepared following the method used in Example 4.

Step 1:
Coupling of (2,6-dimethylbenzyl)triphenylphosphonium bromide with methyl 3-formylbenzoate following the method described in Example 1 gave methyl 3-(2,6-dimethylstyryl) benzoate as a white solid 2.20 g (71%), isomer ratio 2:1 trans:cis.

cis-isomer: $^1$H NMR (500 MHz, CDCl$_3$) δ 7.81-7.78 (m, 1H), 7.71-7.67 (m, 1H), 7.22-7.03 (m, 5H), 6.72-6.62 (m, 2H), 2.37 (s, 6H), 2.15 (s, 3H);

trans-isomer: $^1$H NMR (500 MHz, CDCl$_3$) δ 8.15 (d, J=1.6 Hz, 1H), 7.96-7.93 (m, 1H), 7.71-7.67 (m, 1H), 7.45 (t, J=7.8 Hz, 1H), 7.22-7.03 (m, 4H), 6.72-6.62 (m, 1H), 2.37 (s, 6H), 2.15 (s, 3H); ESI MS m/z 267 [M+H]$^+$.

Step 2:
Hydrolysis of methyl 3-(2,6-dimethylstyryl)benzoate gave 3-(2,6-dimethylstyryl)benzoic acid as a white solid. Yield (2.16 g, quant.), isomer ratio 2:1 trans:cis: $^1$H NMR (500 MHz, CDCl$_3$) δ 7.87 (d, J=7.5 Hz, 1H), 7.82 (s, 1H), 7.23-7.05 (m, 5H), 6.73-6.64 (m, 2H), 2.15 (s, 6H); The trans-isomer: $^1$H NMR (500 MHz, CDCl$_3$) δ 8.24 (s, 1H), 8.02 (d, J=7.7 Hz, 1H), 7.74 (d, J=7.6 Hz, 1H), 7.49 (t, J=7.7 Hz, 1H), 7.22-7.03 (m, 4H), 6.73-6.64 (m, 1H), 2.38 (s, 6H).

Step 3:
Coupling of 3-(2,6-dimethylstyryl)benzoic acid with dimethylamine gave 3-(2,6-Dimethylstyryl)-N,N-dimethylbenzamide as a yellow oil. Yield (0.223 g, 81%): cis-isomer: $^1$H NMR (500 MHz, CDCl$_3$) δ 7.23-7.17 (m, 2H), 7.11-6.98 (m, 5H), 6.67 (d, J=12.2 Hz, 1H), 6.58 (d, J=12.2 Hz, 1H), 3.00 (s, 3H), 2.66 (s, 3H), 2.15 (s, 6H); trans-isomer: $^1$H NMR (500 MHz, CDCl$_3$) δ 7.56 (s, 1H), 7.52 (d, J=7.9 Hz, 1H), 7.39 (t, J=7.6 Hz, 1H), 7.29 (d, J=7.5 Hz, 1H), 7.14 (d, J=16.6 Hz, 1H), 7.11-6.98 (m, 3H), 6.59 (d, J=16.6 Hz, 1H), 3.14 (s, 3H), 3.02 (s, 3H), 2.36 (s, 6H); ESI MS m/z 280 [M+H]$^+$.

Step 4:
Reduction of 3-(2,6-Dimethylstyryl)-N,N-dimethylbenzamide gave Example 133 as a yellow oil. Yield (0.062 g, 29%), isomer ratio 3.3:1 trans:cis: R$_f$0.95 (silica gel, 95:5 methylene chloride/7N ammonia in methanol); $^1$H NMR (500 MHz, CD$_3$OD) δ The cis-isomer: $^1$H NMR (500 MHz, CDCl$_3$) δ 7.10-6.99 (m, 6H), 6.93-6.92 (m, 1H), 6.86 (s, 1H), 6.69 (d, J=12.1 Hz, 1H), 3.23 (s, 213), 2.12 (s, 6H), 2.06 (s, 6H); The trans-isomer: $^1$H NMR (500 MHz, CDCl$_3$) δ 7.51 (s, 1H), 7.45 (d, J=7.7 Hz, 1H), 7.33 (t, J=7.7 Hz, 1H), 7.22-7.19 (m, 2H), 7.10-6.99 (m, 3H), 6.59 (d, J=16.6 Hz, 1H), 3.50 (s, 2H), 2.34 (s, 6H), 2.26 (s, 6H); $^{13}$C NMR (75 MHz, CD$_3$OD) δ 139.2, 139.1, 138.9, 138.3, 137.1, 136.5, 135.1, 132.1, 130.7, 130.2, 129.9, 129.7, 129.3, 128.9, 128.6, 128.5, 128.4, 128.3, 128.0, 127.8, 126.6, 64.9, 64.7, 45.3, 44.9, 21.2, 20.4; ESI MS m/z 266 [M+H]$^+$; HPLC (Method E) 98.9% (AUC), t$_R$=12.55 min. HRMS calcd for C$_{19}$H$_{23}$N [M+H]: 266.1908. Found: 266.1903.

Example 133

Preparation of 4-(3-(2,6-dimethylstyryl)benzyl)morpholine

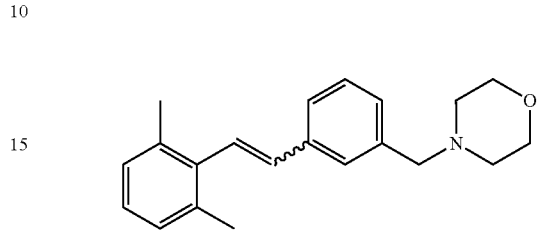

4-(3-(2,6-Dimethylstyryl)benzyl)morpholine was prepared following the method used in Example 4.

Step 1:
Coupling of 3-(2,6-dimethylstyryl)benzoic acid with N-methyl morpholine gave (3-(2,6-Dimethylstyryl)phenyl) (morpholino)methanone as a colorless oil. Yield (0.344 g, quant.) isomer ratio 2:1 trans:cis: cis-isomer: $^1$H NMR (500 MHz, CDCl$_3$) δ 7.28-7.22 (m, 2H), 7.19-7.06 (m, 4H), 6.93 (s, 1H), 6.68 (d, J=12.3 Hz, 1H), 6.60 (d, J=12.2 Hz, 1H), 3.79-3.50 (m, 8H), 2.14 (s, 6H); trans-isomer: $^1$H NMR (500 MHz, CDCl$_3$) δ 7.54 (d, J=8.7 Hz, 2H), 7.40 (d, J=7.6 Hz, 1H), 7.28-7.22 (m, 1H), 7.15 (d, J=16.7 Hz, 1H), 7.19-7.06 (m, 2H), 7.03 (d, J=7.6 Hz, 1H), 6.61 (d, J=16.7 Hz, 1H), 3.79-3.50 (m, 8H), 2.36 (s, 6H); ESI MS m/z 322 [M+H]$^+$.

Step 2:
Reduction of (3-(2,6-Dimethylstyryl)phenyl)(morpholino)methanone gave Example 134 as a yellow oil. Yield (0.030 g, 10%), isomer ration 3:1 trans:cis: R$_f$ 0.66 (silica gel, ethyl acetate); cis-isomer: $^1$H NMR (500 MHz, CDCl$_3$) δ 7.26-7.24 (m, 1H), 7.10-7.08 (m, 4H), 6.91-6.89 (m, 2H), 6.65 (d, J=12.3 Hz, 1H), 6.53 (d, J=12.3 Hz, 1H), 3.64 (t, J=4.7 Hz, 4H), 3.30 (s, 2H), 2.26 (t, J=4.3 Hz, 411), 2.14 (s, 6H); trans-isomer: $^1$H NMR (500 MHz, CDCl$_3$) δ 7.43 (d, J=6.4 Hz, 2H), 7.33 (d, J=7.8 Hz, 1H), 7.26-7.24 (m, 1H), 7.11 (d, J=16.7 Hz, 1H), 7.10-7.08 (m, 2H), 7.02 (d, J=7.5 Hz, 1H), 6.59 (d, J=16.7 Hz, 1H), 3.73 (t, J=4.7 Hz, 4H), 3.53 (s, 2H), 2.49 (d, J=3.8 Hz, 4H), 2.37 (s, 6H); $^{13}$C NMR (75 MHz, CDCl$_3$) δ 167.2, 138.0, 137.4, 137.0, 136.6, 136.2, 135.7, 135.3, 134.5, 133.3, 130.8, 130.3, 129.9, 128.9, 128.8, 128.6, 128.1, 127.9, 127.6, 127.1, 126.9, 125.9, 125.6, 125.1, 53.4, 41.0, 40.4, 39.7, 38.8, 32.0, 31.4, 21.1, 20.2; ESI MS m/z 308 [M+H]$^+$; HPLC (Method E) 97.2% (AUC), t$_R$=14.7 min. HRMS calcd for C$_{21}$H$_{25}$NO [M+H]: 308.2014. Found: 308.2003.

Example 134

Preparation of (E)-(3-(2-(2,6,6-trimethylcyclohex-1-enyl)vinyl)phenyl)methanamine

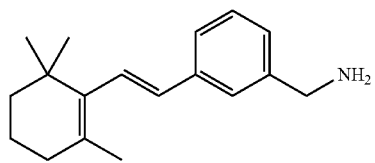 [SMILES: CC1=C(/C=C/c2cccc(CN)c2)C(C)(C)CCC1]

(E)-(3-(2-(2,6,6-trimethylcyclohex-1-enyl)vinyl)phenyl)methanamine was prepared following the method used in Example 3 and 32.

Step 1:

Coupling of Wittig salt 3 with methyl 3-formyl benzoate following the method used in Example 32 gave methyl 3-(2-(2,6,6-trimethylcyclohex-1-enyl)vinyl)benzoate (0.698 g, 88%) as a white foam: $^1$H NMR (500 MHz, CDCl$_3$) δ 8.14 (s, 1H), 7.96 (d, J=7.7 Hz, 1H), 7.64 (d, J=7.7 Hz, 1H), 7.42 (m, 1H), 6.77 (d, J=16.3 Hz, 1H), 6.39 (d, J=16.3 Hz, 1H), 2.05 (t, J=6.1 Hz, 2H), 1.77 (s, 3H), 1.65 (m, 2H), 1.50 (m, 2H), 1.08 (s, 6H); ESI MS m/z 271 [M+H]$^+$.

Step 2:

Hydrolysis of methyl 3-(2-(2,6,6-trimethylcyclohex-1-enyl)vinyl)benzoate following the procedure used in Example 3 gave 3-(2-(2,6,6-trimethylcyclohex-1-enyl)vinyl)benzoic acid as a white foam. Yield (0.698 g, 88%): $^1$H NMR (500 MHz, CDCl$_3$) δ 8.14 (s, 1H), 7.96 (d, J=7.7 Hz, 1H), 7.64 (d, J=7.7 Hz, 1H), 7.42 (m, 1H), 6.77 (d, J=16.3 Hz, 1H), 6.39 (d, J=16.3 Hz, 1H), 2.05 (t, J=6.1 Hz, 2H), 1.77 (s, 3H), 1.65 (m, 2H), 1.50 (m, 2H), 1.08 (s, 6H); ESI MS m/z 271 [M+H]$^+$ Step 3:

Amidation of 3-(2-(2,6,6-trimethylcyclohex-1-enyl)vinyl)benzoic acid following the procedure used in Example 3 gave 3-(2-(2,6,6-trimethylcyclohex-1-enyl)vinyl)benzamide as a white foam. Yield (0.279 g, 40%): $^1$H NMR (500 MHz, CDCl$_3$) δ 7.86 (t, J=1.5 Hz, 1H), 7.61 (d, J=7.7 Hz, 1H), 7.56 (d, J=7.7 Hz, 1H), 7.39 (t, J=7.7 Hz, 1H), 6.75 (d, J=16.3 Hz, 1H), 6.37 (d, J=16.3 Hz, 1H), 6.09 (br s, 1H), 5.71 (br s, 1H), 2.04 (t, J=6.1 Hz, 2H), 1.76 (s, 3H), 1.65 (m, 2H), 1.48 (m, 2H), 1.06 (s, 6H); ESI MS m/z 270 [M+H]$^+$.

Step 4:

Reduction of 3-(2-(2,6,6-trimethylcyclohex-1-enyl)vinyl)benzamide following the procedure used in Example 3 gave Example 135 as a light yellow oil. Yield (0.135 g, 51: R$_f$ 0.45 (silica gel, 50:35:15 hexanes/ethyl acetate/7N ammonia in methanol); $^1$H NMR (500 MHz, CD$_3$OD) δ 7.40 (s, 1H), 7.27 (m, 2H), 7.17 (m, 1H), 6.73 (d, J=16.3 Hz, 1H), 6.33 (d, J=16.3 Hz, 1H), 3.78 (s, 2H), 2.05 (t, J=6.0 Hz, 2H), 1.75 (s, 3H), 1.67 (m, 2H), 1.51 (m, 2H), 1.06 (s, 6H); $^{13}$C NMR (125 MHz, CD$_3$OD) δ 143.8, 139.6, 139.0, 134.4, 130.4, 129.8, 128.7, 127.3, 126.1, 125.7, 46.7, 40.8, 35.3, 33.9, 29.4, 21.9, 20.4; ESI MS m/z 256 [M+H]$^+$; HPLC (Method E) 98.2% (AUC), t$_R$=11.54 min. HRMS Calcd for C$_{18}$H$_{25}$N [M+H–NH$_3$]: 239.180. Found: 239.1793.

Example 135

Preparation of (E)-(3-(2-(2,6,6-trimethylcyclohex-1-enyl)vinyl)phenyl)methanamine

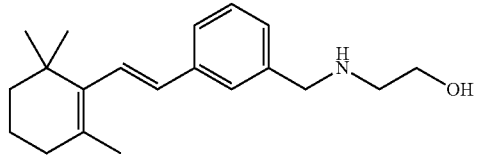 [SMILES: CC1=C(/C=C/c2cccc(CNCCO)c2)C(C)(C)CCC1]

(E)-(3-(2-(2,6,6-trimethylcyclohex-1-enyl)vinyl)phenyl)methanamine was prepared following the method used in Example 1.

Step 1:

Amidation of aldehyde 69 with ethanolamine following the method used in Example 1 gave Example 136 as a mixture of trans- and cis-isomers. Further purification by preparative HPLC provided Example 136 as a colorless oil. Yield (0.063 g, 37%): R$_f$ 0.27 (silica gel, 90:10 Methylene Chloride/7N Ammonia in Methanol); $^1$H NMR (500 MHz, CD$_3$OD) δ 7.55 (s, 1H), 7.44 (d, J=7.5 Hz, 1H), 7.33 (d, J=7.6 Hz, 1H), 7.25 (d, J=7.5 Hz, 1H), 7.21 (d, J=16.6 Hz, 1H), 7.03 (s, 3H), 6.60 (d, J=16.7 Hz, 1H), 3.82 (s, 2H), 3.69 (t, J=5.6 Hz, 2H), 2.76 (t, J=5.6 Hz, 2H), 2.34 (s, 6H); ESI MS m/z 282 [M+H]$^+$; HPLC (Method B) 91.0% (AUC), t$_R$=7.66 min. HRMS calcd for C$_{19}$H$_{23}$NO [M+H]: 282.1858. Found: 282.1846.

Example 136

(E)-2-(3-(2,6-dimethylstyryl)phenyl)ethanamine

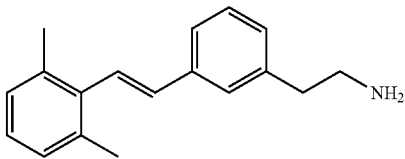 [SMILES: Cc1cccc(C)c1/C=C/c1cccc(CCN)c1]

(E)-2-(3-(2,6-dimethylstyryl)phenyl)ethanamine was prepared according to the methods used in Examples 1, 45, 50 and 55.

Step 1:

Protection of 2-(3-bromophenyl)ethanamine following the method used in Example 55 gave tert-butyl 3-bromophenethylcarbamate as a colorless oil. Yield (6.75 g, 100%): $^1$H NMR (400 MHz, DMSO-d$_6$) δ 7.35-7.38 (m, 2H), 7.17-7.25 (m, 2H), 6.84 (t, J=5.2 Hz, 1H), 3.08-3.16 (m, 2H), 2.67 (t, J=7.2 Hz, 2H), 1.33 (s, 9H).

Step 2:

Conversion of tert-butyl 3-bromophenethylcarbamate into tert-butyl 3-formylphenethylcarbamate following the method used in Example 50 gave the product as colorless oil. Yield (0.48, 38%). $^1$H NMR (400 MHz, DMSO-d$_6$) δ 9.97 (s, 1H), 7.71-7.74 (m, 2H), 7.49-7.54 (m, 2H), 6.88 (t, J=5.2 Hz, 1H), 3.14-3.19 (m, 2H), 2.77 (t, J=7.2 Hz, 2H), 1.33 (s, 9H).

Step 3:

Coupling of tert-butyl 3-formylphenethylcarbamate with Wittig salt 3 following the method used in Example 45 gave (E)-tert-butyl 3-(2,6-dimethylstyryl)phenethylcarbamate as a light yellow oil. Yield (0.43 g, 72%): $^1$H NMR (400 MHz, DMSO-d$_6$) δ 7.38-7.43 (m, 2H), 7.28 (t, J=8.0 Hz, 1H), 7.18 (d, J=16.8 Hz, 1H), 7.08-7.11 (m, 1H), 6.84-7.05 (m, 3H), 6.62 (d, J=16.8 Hz, 1H), 3.13-3.19 (m, 2H), 2.70 (t, J=7.2 Hz, 2H), 2.31 (s, 6H), 1.34 (s, 9H).

Step 4:

Deprotection of (E)-tert-butyl 3-(2,6-dimethylstyryl)phenethylcarbamate following the method used in Example 45 gave (E)-2-(3-(2,6-dimethylstyryl)phenyl)ethanamine in the form of HCl salt as white solid. Yield (0.27 g, 69%): $^1$H NMR (400 MHz, DMSO-d$_6$) δ 7.94 (bs, 3H), 7.46-7.49 (m, 2H), 7.33 (t, J=7.8 Hz, 1H), 7.22 (d, J=16.8 Hz, 1H), 7.17 (d, J=7.6 Hz, 1H), 7.07 (m, 3H), 6.63 (d, J=16.8 Hz, 1H), 3.01-3.12 (m, 2H), 2.87-2.91 (m, 2H), 2.31 (s, 6H).

Example 137

In Vitro Isomerase Inhibition

The capability of styrenyl derivative compounds to inhibit the activity of a visual cycle isomerase was determined.

Isomerase inhibition reactions was performed essentially as described (Stecher et al., *J Biol Chem* 274:8577-85 (1999);

see also Golczak et al., supra). Bovine Retinal Pigment Epithelium (RPE) microsome membranes were the source of a visual cycle isomerase.

RPE Microsome Membrane Preparation

RPE microsome membrane extracts may be purchased or prepared according to methods practiced in the art and stored at −80° C. Crude RPE microsome extracts were thawed in a 37° C. water bath, and then immediately placed on ice. 50 ml crude RPE microsomes were placed into a 50 ml Teflon-glass homogenizer (Fisher Scientific, catalog no. 0841416M) on ice, powered by a hand-held DeWalt drill, and homogenized ten times up and down on ice under maximum speed. This process was repeated until the crude RPE microsome solution was homogenized. The homogenate was then subjected to centrifugation (50.2 Ti rotor (Beckman, Fullerton, Calif.), 13,000 RPM; 15360 Rcf) for 15 minutes at 4° C. The supernatant was collected and subjected to centrifugation a5 42,000 RPM (160,000 Rcf; 50.2 Ti rotor) for 1 hour at 4° C. The supernatant was removed, and the pellets were suspended in 12 ml (final volume) cold 10 mM MOPS buffer, pH 7.0. The resuspended RPE membranes in 5 ml aliquots were homogenized in a glass-to-glass homogenizer (Fisher Scientific, catalog no. K885500-0021) to high homogeneity. Protein concentration was quantified using the BCA protein assay according to the manufacturer's protocol (Pierce, Rockford, Ill.; catalog no. 23227). The homogenized RPE preparations were stored at −80° C.

Isolation of Human Apo Cellular Retinaldehyde-Binding Protein (CRALBP)

Recombinant human apo cellular retinaldehyde-binding protein (CRALBP) was cloned and expressed according to standard methods in the molecular biology art (see Crabb et al., *Protein Science* 7:746-57 (1998); Crabb et al., *J. Biol. Chem.* 263:18688-92 (1988)). Briefly, total RNA was prepared from confluent ARPE19 cells (American Type Culture Collection, Manassas, Va.), cDNA was synthesized using an oligo(dT)$_{12-18}$ primer, and then DNA encoding CRALBP was amplified by two sequential polymerase chain reactions (see Crabb et al., *J. Biol. Chem.* 263:18688-92 (1988); Intres, et al., *J. Biol. Chem.* 269:25411-18 (1994); GenBank Accession No. L34219.1). The PCR product was sub-cloned into pTrcHis2-TOPO TA vector according to the manufacturer's protocol (Invitrogen Inc., Carlsbad, Calif.; catalog no. K4400-01), and then the sequence was confirmed according to standard nucleotide sequencing techniques. Recombinant 6×His-tagged human CRALBP was expressed in One Shot TOP 10 chemically competent *E. coli* cells (Invitrogen), and the recombinant polypeptide was isolated from *E. coli* cell lysates by nickel affinity chromatography using Ni Sepharose XK16-20 columns for HPLC (Amersham Bioscience, Pittsburgh, Pa.; catalog no. 17-5268-02). The purified 6×His-tagged human CRALBP was dialyzed against 10 mM bis-tris-Propane (BTP) and analyzed by SDS-PAGE. The molecular weight of the recombinant human CRALBP was approximately 39 kDal.

Isomerase Assay

Each styrenyl derivative compound and control compounds were reconstituted in ethanol to 0.1 M. Ten-fold serial dilutions ($10^{-2}$, $10^{-3}$, $10^{-4}$, $10^{-5}$, $10^{-6}$ M) in ethanol of each compound were prepared for analysis in the isomerase assay.

The isomerase assay was performed in 10 mM bis-tris-propane (BTP) buffer, pH 7.5, 0.5% BSA (diluted in BTP buffer), 1 mM sodium pyrophosphate, 20 µM all-trans retinol (in ethanol), and 6 µM apo-CRALBP. The test compounds (2 µl) (final 1/15 dilution of serial dilution stocks) were added to the above reaction mixture to which RPE microsomes were added. The same volume of ethanol was added to the control reaction (absence of test compound). Bovine RPE microsomes (9 µl) (see above) were then added, and the mixtures transferred to 37° C. to initiate the reaction (total volume=150 µl). The reactions were stopped after 30 minutes by adding methanol (300 µl). Heptane was added (300 µl) and mixed into the reaction mixture by pipetting. Retinoid was extracted by agitating the reaction mixtures, followed by centrifugation in a microcentrifuge. The upper organic phase was transferred to HPLC vials and then analyzed by HPLC using an Agilent 1100 HPLC system with normal phase column: SILICA (Agilent Technologies, dp 5µ, 4.6 mmX, 25 CM; running method had flow rate of 1.5 ml/min; injection volume 1000). The solvent components were 20% of 2% isopropanol in ethyl acetate and 80% of 100% hexane. The area under the $A_{318}$ nm curve represented the 11-cis retinol peak, which was calculated by Agilent Chemstation software and recorded manually. The $IC_{50}$ values (concentration of compound that gives 50% inhibition of 11-cis retinol formation in vitro) were calculated using GraphPad Prism® 4 Software (Irvine, Calif.). Each experiment was performed three times in duplicate. Inhibition of isomerase activity ($IC_{50}$) was determined for each compound.

The concentration dependent effect of the compounds disclosed herein on the retinol isomerization reaction can also be evaluated with a recombinant human enzyme system. In particular, the in vitro isomerase assay was performed essentially as in Golczak et al. 2005, PNAS 102: 8162-8167, ref. 3). A homogenate of HEK293 cell clone expressing recombinant human RPE65 and LRAT were the source of the visual enzymes, and exogenous all-trans-retinol (about 20 µM) was used as the substrate. Recombinant human CRALBP (about 80 ug/mL) was added to enhance the formation of 11cis-retinal. The 200 µL Bis-Tris Phosphate buffer (10 mM, pH 7.2) based reaction mixture also contains 0.5% BSA, and 1 mM NaPPi. In this assay, the reaction was carried out at 37° C. in duplicates for one hour and was terminated by addition of 300 µL methanol. The amount of reaction product, 11-cis-retinol, was measured by HPLC analysis following Heptane extraction of the reaction mixture. The Peak Area Units (PAUs) corresponding to 11cis-retinol in the HPLC chromatograms were recorded and concentration dependent curves analyzed by GraphPad Prism for $IC_{50}$ values. The ability of the numerous compounds disclosed herein to inhibit isomerization reaction is quantified and the respective IC50 value is determined. The table below summarises the 1050 values of various compounds of the present invention determined by either of the above two methods.

TABLE 13

| $IC_{50}$ | Compound/Example Number |
|---|---|
| ≤0.01 µM | 111, 113, 116 |
| ≤0.1 µM | 114, 115, 117, 120 |
| ≤1 µM | 1, 21, 22, 23, 24, 25, 26, 27, 31, 32, 41, 43, 45, 48, 49, 50, 54, 55, 56, 59, 61, 66, 68, 72, 73, 74, 75, 79, 80, 82, 83, 84, 85, 100, 105, 106 |
| ≤10 µM | 7, 16, 18, 19, 20, 28, 30, 33, 34, 35, 36, 37, 39, 44, 46, 47, 51, 63, 64, 65, 67, 69, 70, 77, 78, 81, 89, 93, 95, 96, 102 |
| ≤50 µM | 2, 3, 6, 8, 9, 11, 12, 15, 17, 29, 38, 40, 53, 58, 60, 62, 76, 107, 108, 109 |
| ≤100 µM | 5, 10, 42, 71 |
| ≤500 µM | 4, 13, 14, 57 |

Example 138

In Vivo Murine Isomerase Assay

The capability of styrenyl derivatives to inhibit isomerase is determined by an in vivo murine isomerase assay. Brief exposure of the eye to intense light ("photobleaching" of the visual pigment or simply "bleaching") is known to photo-isomerize almost all 11-cis-retinal in the retina. The recovery of 11-cis-retinal after bleaching can be used to estimate the activity of isomerase in vivo. Procedures were performed essentially as described by Golczak et al., *Proc. Natl. Acad. Sci. USA* 102:8162-67 (2005). See also Deigner et al., *Science*, 244: 968-71 (1989); Gollapalli et al., *Biochim Biophys Acta*. 1651: 93-101 (2003); Parish, et al., *Proc. Natl. Acad. Sci. USA*, 14609-13 (1998); Radu, et al., *Proc Natl Acad Sci USA* 101: 5928-33 (2004). The styrenyl compounds of the present invention are expected to inhibit an isomerase reaction resulting in production of 11-cis retinol, which reaction occurs in RPE, The expected ED50 value can be 1 mg/kg or less when measured 2 hours, 4 hours, 6 hours, 8 hours or longer aftering administering to the subject compounds a subject compound.

Six-week old dark-adapted CD-1 (albino) male mice were orally gavaged with compounds (0.1-25 mg/kg) dissolved in 100 µl corn oil containing 10% ethanol (five animals per group). Mice were gavaged with styrenyl derivative compounds, Compound 1 or Compound 25. Compound B was included as a positive control, and Compound A with low activity was also included. After 1-72 hours in the dark, the mice were exposed to photobleaching of 3,000 lux of white light for 10 minutes. The mice were allowed to recover 2 hours in the dark. The animals were then sacrificed by carbon dioxide inhalation. Retinoids were extracted from the eye and the regeneration of 11-cis-retinal was assessed at various time intervals.

Eye Retinoid Extraction

All steps were performed in darkness with minimal redlight illumination (low light darkroom lights and redfiltered flashlights for spot illumination as needed) (see, e.g., Maeda et al., *J. Neurochem* 85:944-956, 2003; Van Hooser et al., *J Biol Chem* 277:19173-82, 2002). After the mice were sacrificed, the eyes were immediately removed and placed in liquid nitrogen. The eyes were then homogenized in a glass/glass homogenizer (Kontes Glass Co., homogenizer & pestle 21) containing 1 ml retinoid analysis buffer (50 mM MOPS, 10 mM NH$_2$OH, 50% EtOH, pH 7.0 (stock buffer was stored in absence of ethanol)). The eyes were homogenized until no visible tissue remained (approximately 3 minutes). The samples were incubated 20 minutes at room temperature (including homogenizing) and then placed on ice. One ml cold EtOH was added to the homogenate to rinse the pestle, and the homogenate mixture was transferred to 7 ml glass screwtop tubes on ice. The homogenizer was rinsed with 7 ml hexane, which was added to the 7 ml tubes on ice.

The homogenate was mixed by vortexing at high speed for 1 minute. The phases were separated by centrifugation (5 minutes at 4000 rpm, 4° C.). The upper phase was collected and transferred to a clean glass test tube, taking care to avoid disturbing the interface by leaving approximately 0.2 ml of upper phase in the tube. The tubes with the collected upper phase were placed in a heating block at 25° C. and dried under a stream of Argon (~30 minutes). The lower phase was again extracted by adding 4 ml hexane, vortexing, and separating the phases by centrifugation. The upper phase was collected as described above and pooled into the drying tubes. The dried samples were solubilized in 300 µl Hexane (Fisher Optima grade) and vortexed lightly. The samples were transferred to clean 300 µl glass inserts in HPLC vials using glass pipette and the vials were crimped shut tightly.

The samples were analyzed by HPLC (HP 1100 series or Agilent 1100 series, Agilent Technologies) on a Beckman Ultraspere Si column (5µ particle diameter, 4.6 mm ID×25 cm length; Part #235341). Run parameters are as follows: flow: 1.4 ml/minute, 10% Ethylacetate+90% Hexane (clean with 50% ethylacetate for 20 minutes); volume per injection: 100 µl (blank sample of 300 µl was run first to equilibrate colum); detection at 360 nm (detecting 11-cis retinal oxime)). The area under the curve for 11-cis retinal oxime was calculated by Agilent Chemstation software and was recorded manually. Data processing was performed using Prizm software.

Positive control mice (no compound administered) were sacrificed fully dark-adapted and the eye retinoids analyzed. Light (bleached) control mice (no compound administered) were sacrificed and retinoids isolated and analyzed immediately after light treatment.

Figure 2:
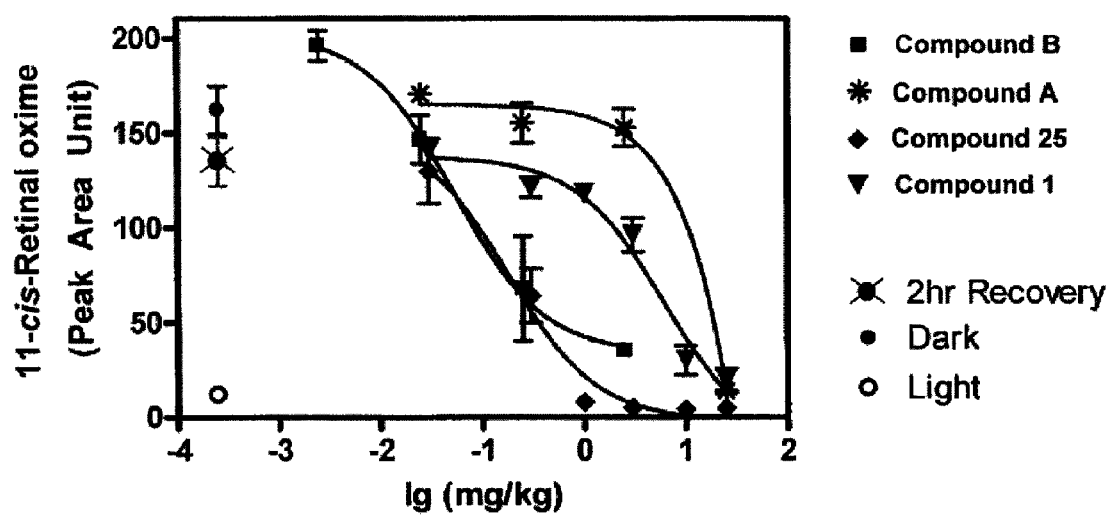
FIG. 2 shows concentration-dependent inhibition of isomerase activity by Compound A, Compound B, Compound 1 and Compound 25 in a mouse model.

The isomerase inhibitory activity of Compound A and Compound 1 over time is presented in FIG. 1. The maximum inhibitory effect was observed about 16 or 6 hours after gavage with Compound A or Compound 1, respectively. FIG. 2 presents the concentration dependent inhibition of isomerase activity by Compound 1, Compound 25, Compound A (prodrug ACU#3223), and Compound B (ACU#3222). The estimated $ED_{50}s$ (dose of compound that gives 50% inhibition of 11-cis retinal (oxime) recovery) calculated were 9.3, 4.3, 0.44 and 0.15 mg/kg for Compound A (prodrug ACU#3223), Compound 1 (ACU#3364), Compound 25 (ACU#4178) and Compound B (ACU#3222), respectively.

| | Inhibition (%) | | | | | | | |
|---|---|---|---|---|---|---|---|---|
| | 5 mg/kg | | | | 1 mg/Kg | | | |
| Example | 2 h | 4 h | 6 h | 24 h | 2 h | 4 h | 6 h | 24 h |
| 1 | | 57 | | 58 | 0 | | 0 | 0 |
| 25 | | | | | | 89 | | 96 |
| 43 | | 79 | | 54 | 0 | | 7 | 16 |
| 55 | | 75 | | 89 | 0 | | | |
| 56 | | | | | 26 | | 75 | 77 |
| 31 | | 53 | | 46 | 0 | | 2 | 0 |
| 59 | | 21 | | 7 | | 0 | 1 | |
| 61 | | 12 | | 0 | | 0 | 0 | |
| 49 | | 60 | | 84 | | 10 | | 0 |
| 74 | 83 | | 91 | 56 | 19 | | 40 | 9 |
| 75 | 81 | | 90 | 85 | 19 | | 20 | 13 |
| 79 | | 24 | | 0 | | | | |
| 83 | | 97 | | 3 | | 55 | | 0 |
| 111 | | 90 | | 0 | | | | |

| | 10 mg/kg | | | |
|---|---|---|---|---|
| Example | 2 h | 4 h | 6 h | 24 h |
| 26 | | 80 | | |
| 43 | | 94 | | |
| 27 | | 11 | | |
| 32 | | 52 | | |
| 68 | | 75 | | |
| 41 | | 76 | | |
| 40 | | 2 | | |
| 24 | | 16 | | |
| 23 | | 0 | | |
| 25 | | 100 | | |
| 22 | | 0 | | |
| 7 | | 36 | | 8 |
| 1 | | 80 | | |
| 21 | | 80 | | |

Negative numbers have been leveled to 0%. Some are quite low (~18%)
4231 have data at 0.1, 0.3 and 1 mg/kg
4230 have data at 10 and 25 mg/kg
4226 is 0 at 48 both doses
4203 is 44%, 5 mg/kg, 48 h 4195 is 80% 10 mg/kg, 4 h 4189 0 @ 48 h, 5 mg/kg also 94%, 4 h @ 10 mg/kg 4178 have lots of data 0.1, 0.3, 1 mg/kg at very extended timepoints 4128 8% 2 48 h, 10 mg/kg4110

3364 lots more data

Example 139

PREPARATION OF RETINAL NEURONAL CELL CULTURE SYSTEM

This Example describes methods for preparing a long-term culture of retinal neuronal cells.

All compounds and reagents are obtained from Sigma Aldrich Chemical Corporation (St. Louis, Mo.) except as noted.

Retinal Neuronal Cell Culture

Porcine eyes are obtained from Kapowsin Meats, Inc. (Graham, Wash.). Eyes are enucleated, and muscle and tissue are cleaned away from the orbit. Eyes are cut in half along their equator and the neural retina is dissected from the anterior part of the eye in buffered saline solution, according to standard methods known in the art. Briefly, the retina, ciliary body, and vitreous are dissected away from the anterior half of the eye in one piece, and the retina is gently detached from the clear vitreous. Each retina is dissociated with papain (Worthington Biochemical Corporation, Lakewood, N.J.), followed by inactivation with fetal bovine serum (FBS) and addition of 134 Kunitz units/ml of DNaseI. The enzymatically dissociated cells are triturated and collected by centrifugation, resuspended in Dulbecco's modified Eagle's medium (DMEM)/F12 medium (Gibco BRL, Invitrogen Life Technologies, Carlsbad, Calif.) containing 25 µg/ml of insulin, 100 µg/ml of transferrin, 60 µM putrescine, 30 nM selenium, 20 nM progesterone, 100 U/ml of penicillin, 100 µg/ml of streptomycin, 0.05 M Hepes, and 10% FBS. Dissociated primary retinal cells are plated onto Poly-D-lysine- and Matrigel-(BD, Franklin Lakes, N.J.) coated glass coverslips that are placed in 24-well tissue culture plates (Falcon Tissue Culture Plates, Fisher Scientific, Pittsburgh, Pa.). Cells are maintained in culture for 5 days to one month in 0.5 ml of media (as above, except with only 1% FBS) at 37° C. and 5% $CO_2$.

Immunocytochemistry Analysis

The retinal neuronal cells are cultured for 1, 3, 6, and 8 weeks, and the cells are analyzed by immunohistochemistry at each time point. Immunocytochemistry analysis is performed according to standard techniques known in the art. Rod photoreceptors are identified by labeling with a rhodopsin-specific antibody (mouse monoclonal, diluted 1:500; Chemicon, Temecula, Calif.). An antibody to mid-weight neurofilament (NFM rabbit polyclonal, diluted 1:10,000, Chemicon) is used to identify ganglion cells; an antibody to f33-tubulin (G7121 mouse monoclonal, diluted 1:1000, Promega, Madison, Wis.) is used to generally identify interneurons and ganglion cells, and antibodies to calbindin (AB1778 rabbit polyclonal, diluted 1:250, Chemicon) and calretinin (AB5054 rabbit polyclonal, diluted 1:5000, Chemicon) are used to identify subpopulations of calbindin- and calretinin-expressing interneurons in the inner nuclear layer. Briefly, the retinal cell cultures are fixed with 4% paraformaldehyde (Polysciences, Inc, Warrington, Pa.) and/or ethanol, rinsed in Dulbecco's phosphate buffered saline (DPBS), and incubated with primary antibody for 1 hour at 37° C. The cells are then rinsed with DPBS, incubated with a secondary antibody (Alexa 488- or Alexa 568-conjugated secondary antibodies (Molecular Probes, Eugene, Oreg.)), and rinsed with DPBS. Nuclei are stained with 4',6-diamidino-2-phenylindole (DAPI, Molecular Probes), and the cultures are rinsed with DPBS before removing the glass coverslips and mounting them with Fluoromount-G (Southern Biotech, Birmingham, Ala.) on glass slides for viewing and analysis.

Survival of mature retinal neurons after varying times in culture is indicated by the histochemical analyses. Photoreceptor cells are identified using a rhodopsin antibody; ganglion cells are identified using an NFM antibody; and amacrine and horizontal cells are identified by staining with an antibody specific for calretinin.

Cultures are analyzed by counting rhodopsin-labeled photoreceptors and NFM-labeled ganglion cells using an Olympus IX81 or CZX41 microscope (Olympus, Tokyo, Japan). Twenty fields of view are counted per coverslip with a 20× objective lens. Six coverslips are analyzed by this method for each condition in each experiment. Cells that are not exposed to any stressor are counted, and cells exposed to a stressor are normalized to the number of cells in the control.

Example 140

Effect of Styrenyl Derivative Compounds on Retinal Cell Survival

This Example describes the use of the mature retinal cell culture system that comprises a cell stressor for determining the effects of a styrenyl derivative compound on the viability of the retinal cells.

Retinal cell cultures are prepared as described in Example 112. A2E is added as a retinal cell stressor. After culturing the cells for 1 week, a chemical stress, A2E, is applied. A2E is diluted in ethanol and added to the retinal cell cultures at concentration of 0, 10 µM, 20 µM, and 40 µM. Cultures are treated for 24 and 48 hours. A2E is obtained from Dr. Koji Nakanishi (Columbia University, New York City, N.Y.) or is synthesized according to the method of Parish et al. (*Proc. Natl. Acad. Sci. USA* 95:14602-13 (1998)). A styrenyl derivative compound is then added to the culture. To other retinal cell cultures, a styrenyl derivative compound is added before application of the stressor or is added at the same time that A2E is added to the retinal cell culture. The cultures are maintained in tissue culture incubators for the duration of the stress at 37° C. and 5% $CO_2$. The cells are then analyzed by immunocytochemistry as described in Example 112.

Apoptosis Analysis

Retinal cell cultures are prepared as described in Example 1 and cultured for 2 weeks and then exposed to white light stress at 6000 lux for 24 hours followed by a 13-hour rest period. A device was built to uniformly deliver light of specified wavelengths to specified wells of the 24-well plates. The device contained a fluorescent cool white bulb (GE P/N FC12T9/CW) wired to an AC power supply. The bulb is mounted inside a standard tissue culture incubator. White light stress is applied by placing plates of cells directly underneath the fluorescent bulb. The $CO_2$ levels are maintained at 5%, and the temperature at the cell plate is maintained at 37° C. The temperature was monitored by using thin thermocouples. The light intensities for all devices were measured and adjusted using a light meter from Extech Instruments Corporation (P/N 401025; Waltham, Mass.). A styrenyl derivative compound is added to wells of the culture plates prior to exposure of the cells to white light and is added to other wells of the cultures after exposure to white light. To assess apoptosis, TUNEL is performed as described herein.

Apoptosis analysis is also performed after exposing retinal cells to blue light. Retinal cell cultures are cultured as described in Example 112. After culturing the cells for 1 week, a blue light stress is applied. Blue light is delivered by a custom-built light-source, which consists of two arrays of 24 (4×6) blue light-emitting diodes (Sunbrite LED P/N SSP-01TWB7UWB12), designed such that each LED is registered to a single well of a 24 well disposable plate. The first array is placed on top of a 24 well plate full of cells, while the second one is placed underneath the plate of cells, allowing both arrays to provide a light stress to the plate of cells simultaneously. The entire apparatus is placed inside a standard tissue culture incubator. The $CO_2$ levels are maintained at 5%, and the temperature at the cell plate is maintained at 37° C. The temperature is monitored with thin thermocouples. Current to each LED is controlled individually by a separate potentiometer, allowing a uniform light output for all LEDs. Cell plates are exposed to 2000 lux of blue light stress for either 2 hours or 48 hours, followed by a 14-hour rest period. A styrenyl derivative compound is added to wells of the culture plates prior to exposure of the cells to blue light and is added to other wells of the cultures after exposure to blue light. To assess apoptosis, TUNEL is performed as described herein.

To assess apoptosis, TUNEL is performed according to standard techniques practiced in the art and according to the manufacturer's instructions. Briefly, the retinal cell cultures are first fixed with 4% paraformaldehyde and then ethanol, and then rinsed in DPBS. The fixed cells are incubated with TdT enzyme (0.2 units/μl final concentration) in reaction buffer (Fermentas, Hanover, Md.) combined with Chroma-Tide Alexa568-5-dUTP (0.1 μM final concentration) (Molecular Probes) for 1 hour at 37° C. Cultures are rinsed with DPBS and incubated with primary antibody either overnight at 4° C. or for 1 hour at 37° C. The cells are then rinsed with DPBS, incubated with Alexa 488-conjugated secondary antibodies, and rinsed with DPBS. Nuclei are stained with DAPI, and the cultures are rinsed with DPBS before removing the glass coverslips and mounting them with Fluoromount-G on glass slides for viewing and analysis.

Cultures are analyzed by counting TUNEL-labeled nuclei using an Olympus IX81 or CZX41 microscope (Olympus, Tokyo, Japan). Twenty fields of view are counted per coverslip with a 20× objective lens. Six coverslips are analyzed by this method for each condition. Cells that are not exposed to a styrenyl derivative compound are counted, and cells exposed to the antibody are normalized to the number of cells in the control. Data are analyzed using the unpaired Student's t-test. One or more subject compounds are expected to reduce apoptosis of retinal cells.

Example 141

Level of Rhodopsin in Animals Treated with a Styrenyl Derivative Compound

This example describes determining the effect of a styrenyl derivative compound that is a visual cycle modulator on the level of rhodopsin in the eyes of mice after oral dosing of the animals with the compound. The level of rhodopsin in the eyes is determined 6 hours after administering the compound to the animals.

Groups of five eight-week old male mice (20-26 grams) (strain C57/Bl6, Balb/c, or CD1, Charles River Laboratories, Wilmington, Mass.) are housed at room temperature, 72±4° F., and relative humidity of approximately 25%. After an initial acclimation period with a 12-hour light/dark cycle, animals are housed in a 24-hour dark environment overnight before start of the in vivo phase of the study. Animals have free access to feed and drinking water and are checked for general health and well-being prior to use in the study. Body weights are determined for a representative sample of mice prior to initiation of dosing. The average weight determined from this sampling is used to establish the dose for all mice in the study.

Each test compound is dissolved in the control solvent (EtOH), and diluted 1:10 (vol/vol) in corn oil (Crisco Pure Corn Oil, J.M. Smucker Company, Orrville, Ohio) to the desired dose (mg/kg) in the desired volume (0.1 mL/animal). The control vehicle is ethanol:corn oil (1:10 (vol/vol)). The treatment designations and animal assignments are described in Table 14.

TABLE 14

| Group | Route | Treatment | Dose (mg/kg) | Animals |
|---|---|---|---|---|
| 1 | oral | Styrenyl Compound | 3 | 5 |
| 2 | oral | Styrenyl Compound | 1 | 5 |
| 3 | oral | Styrenyl Compound | 0.3 | 5 |
| 4 | oral | Styrenyl Compound | 0.1 | 5 |
| Control | oral | Vehicle | None | 5 |

Animals are dosed once orally by gavage, with the assigned vehicle control or test compounds under red safety light in the dark. The volume of the administered dose is not to exceed 10 mL/kg.

Four hours after dosing, the mice are exposed to 5000 Lux white light for 10 minutes to photobleach their visual pigment. The mice are returned to the dark and euthanized 2 hours after photobleach by administering carbon dioxide followed by cervical dislocation. Both eyes of each animal are removed, collected and frozen at −80° C. until processing and analysis. A record of dosing, photobleach, and harvest times is maintained.

Eye samples from the in vivo phase of the study are prepared for rhodopsin assays. The rhodopsin assay is conducted essentially as described by Yan et al. (*J. Biol. Chem.* 279: 48189-96 (2004)). All steps of the rhodopsin assay procedure are performed under dim red light. Typically, two mouse eyes are used per rhodopsin (Rho) measurement. Mouse eyes are enucleated and rinsed with distilled water. The lenses are removed, and the eyes are cut into 3-4 pieces and frozen immediately on a dry ice/EtOH bath. Rho is extracted with 0.9 ml of 20 mM BisTris propane (pH 7.5) containing 10 mM dodecyl-β-maltoside and 5 mM freshly neutralized $NH_2OH$. Each sample is homogenized with a Dounce tissue homogenizer and shaken for 5 min at room temperature (Eppendorf mixer 5432). The sample is then centrifuged at 14,000 rpm for 5 mM at room temperature (Eppendorf Centrifuge 5415R). The supernatant is collected, and the pellet extracted one more time. The combined supernatants are centrifuged at 50,000 rpm for 10 min (Beckman Optima centrifuge/50.2 Ti fixed angle rotor). The supernatant is collected and absorption spectra are recorded before and after exposing the supernatant to a 12-mM photobleach (60-watt incandescent bulb). The concentration of Rho is determined by the decrease in absorption at 500 nm when comparing absorption spectra recordings before and after the photobleach using the molar extinction coefficient ($\epsilon = 42,000$ $M^{-1}$ $cm^{-1}$). The total opsin protein level is assumed to be unchanged by the drug treatment and the amount of apo-rhodopsin is calculated based on the reduction of rhodopsin (Rho) following drug treatment when compared to the vehicle control group. It is expected that the rhodopsin level decreases and opsin/apo-rhodopsin level increases upon administering of one or more subject compounds to an animal under the conditions disclosed herein.

Animal procedures and data are recorded by group, interval and parameter. All data are recorded at the time observed. In vivo data and information are recorded manually. Statistical analysis is conducted using GraphPad Prism® 4 Software (Irvine, Calif.).

Example 142

Oxygenation of the Retina in an Animal Treated with a Styrenyl Derivative Compound This example describes determining the effect of a styrenyl derivative compound on the level of oxygen in the retina of animals after oral dosing of the animals with the compound. The retinal PO2 is measured 6 hours after dosing the cat with of a compound (doses range between 0.1 to 10 mg/kg) that inhibits isomerization of an all-trans retinyl ester or with vehicle by oral gavage, intra-venous injection, or intra-vitreal injection. Five cats are dosed with the compound and five cats receive vehicle alone.

The cat is initially given 0.4 mg/kg butorphanol (intramuscularly). Anesthesia is induced with an intravenous injection of 5% pentothal sodium (22 mg/kg) followed by additional pentothal as needed during surgery.

Intramuscular ketamine (25 mg/kg) is used when the cat is difficult to handle. Urethane (20%, 200 mg/kg loading dose followed by 20-40 mg/kg/h) is used to maintain long-term anesthesia. The cat is paralyzed by an intravenous injection of 2 mL 1% pancuronium bromide (Pavulon; Organon International, Roseland, N.J.) and is artificially ventilated. Body temperature is monitored by a rectal probe and is maintained at 39° C. At the end of the experiment, pentobarbital sodium or saturated KCl solution is injected intravenously to euthanize the cat.

Experimental methods are performed as described previously unless noted otherwise (Linsenmeier et al., *J. Gen. Physiol.* 99:177-97 (1992); Braun et al., *Invest. Ophthalmol. Vis. Sci.* 36:523-41 (1995)). The eye is stabilized by attaching the conjunctiva to an eye ring that is part of the microelectrode manipulator. Double-barreled oxygenmicroelectrodes (Linsenmeier et al., *J. Appl. Physiol.* 63:2554-57 (1987)) are inserted into the eye 6 mm behind the limbus through a guide needle. One barrel records a current that is proportional to the oxygen tension of the tissue, whereas the other barrel, filled with 0.9% saline, records local intraretinal ERGs. These electrodes are used to collect both PO2 as a function of distance across the retina (PO2 profiles) during electrode withdrawal and the electroretinograms (ERGs) during penetration. The photopigment of the eye is photobleached with white light and the oxygen profile is collected in the retina during dark adaptation. The microelectrode penetrates all the way to the choroid, signaled by the transepithelial potential (TEP) when the electrode crossed the retinal pigment epithelium (RPE).

A one-dimensional, three layer diffusion model (Linsenmeier et al., *J. Gen. Physiol.* 99:177-97 (1992); Haugh et al., *Ann. Biomed. Eng.* 18:19-36 (1990)) is fitted to the part of the oxygen profile in the avascular region of the retina to quantify photoreceptor oxygen consumption (Qav). The model assumes that only the layer corresponding to the inner segment consumes oxygen. This layer is the location of all the photoreceptor mitochondria, with the exception of those in the synapses. Diffusion is assumed to be the only mechanism for oxygen delivery to the photoreceptors from the choroid and from the retinal circulation, so the outer retina can be treated as a slab of tissue through which oxygen diffuses. The model equations for PO2 as a function of distance from the choroid has been described by Wang et al., *Invest. Ophthalmol. Vis. Sci.* 48:1335-41 (2007).

Animal procedures and data are recorded by animal, interval and parameter. All data are recorded at the time observed. Parameters derived from all profiles obtained under a given condition in each cat were averaged, and the results are reported as the mean±SD across cats. Paired t-tests are used to test for significant differences between any two conditions. The difference is considered significant if $P<0.05$. It is expected that the steady state oxygen concentration increases upon administering of one or more subject compounds to an animal under the conditions disclosed herein.

Example 143

Effect of a Strenyl Compound on Retinal Function in Oxygen-Induced Retinopathy

This example describes the effect of a styrenyl compound on rod function in the retinal. Oxygen-induced retinopathy is induced in 4 groups (six animals each) of Sprague-Dawley rat pups by exposing the pups to alternating periods of 50% and 10% oxygen beginning on the da of birth (Day 0) to Day 14. The light cycle is 12 hour light (10-30 lux) and 12 hours dark. The light to dark transition coincides with each oxygen alternation. Beginning at Day 7 and continuing for 15 days thereafter, within one hour of the light-to-dark transition, two of the four groups are administered 6 mg/kg of styrenyl compound intraperitoneally. Only vehicle is administered to the other two groups. When marked retinal vascular abnormality is generally observed, at Day 20-22, electroretinograms are recorded and receptor and post-receptor function are evaluated. The treatment effects are analyzed by ANOVA. (See, e.g., Liu et al., Invest. Ophthalmol. Vis. Sci. 47:5447-52 (2006); Akula et al., *Invest. Ophthalmol. Vis. Sci.* 48:4351-59 (2007); Liu et al., *Invest. Ophthalmol. Vis. Sci.* 47:2639-47 (2006)). It is expected that one or more subject compounds reduces oxygen-induced retinopathy when administered into a subject.

When ranges are used herein for physical properties, such as molecular weight, or chemical properties, such as chemical formulae, all combinations and subcombinations of ranges and specific embodiments therein are intended to be included.

The various embodiments described herein can be combined to provide further embodiments. All U.S. patents, U.S. patent application publications, U.S. patent applications, foreign patents, foreign patent applications, and non-patent publications referred to in this specification and/or listed in the Application Data Sheet, are incorporated herein by reference, in their entireties.

From the foregoing it will be appreciated that, although specific embodiments have been described herein for purposes of illustration, various modifications may be made. Those skilled in the art will recognize, or be able to ascertain, using no more than routine experimentation, many equivalents to the specific embodiments described herein. Such equivalents are intended to be encompassed by the following claims. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A compound, or the pharmaceutically acceptable salt thereof, having a structure of Formula (A):

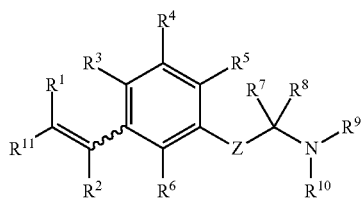

Formula (A)

wherein:
$R^1$ and $R^2$ are hydrogen;
$R^3$, $R^4$, $R^5$ and $R^6$ are each the same or different and independently hydrogen, halogen, —$OR^{12}$, alkyl or fluoroalkyl;
$R^7$ and $R^8$ are hydrogen;
$R^9$ is hydrogen;
$R^{10}$ is hydrogen;
$R^{11}$ is 5, 6-, or 7-member cycloalkyl;
each $R^{12}$ is independently selected from hydrogen or alkyl;
Z is W—Y, wherein
W is —$C(R^{14})(R^{15})$—;
Y is —$C(R^{16})(R^{17})$—;
$R^{14}$ and $R^{15}$ are each the same or different and independently hydrogen, halogen, alkyl, fluoroalkyl, —$OR^{12}$, or —$NR^{18}R^{19}$; or $R^{14}$ and $R^{15}$ together form an oxo;
$R^{16}$ and $R^{17}$ are each the same or different and independently hydrogen, halogen, alkyl, fluoroalkyl, —$OR^{12}$, or —$NR^{18}R^{19}$; or $R^{16}$ and $R^{17}$ together form an oxo; and
each $R^{18}$ and $R^{19}$ is independently selected from hydrogen or alkyl.

2. The compound of claim 1, or the pharmaceutically acceptable salt thereof, wherein $R^{11}$ is cyclohexyl.

3. The compound of claim 1, or the pharmaceutically acceptable salt thereof, wherein $R^{14}$, $R^{15}$, $R^{16}$ and $R^{17}$ are each independently hydrogen, halogen, alkyl, fluoroalkyl, —$OR^{12}$, or —$NR^{18}R^{19}$, wherein each $R^{12}$ is independently hydrogen or alkyl.

4. The compound of claim 1, or the pharmaceutically acceptable salt thereof, wherein $R^3$, $R^4$, $R^5$ and $R^6$ are each the same or different and independently hydrogen, halogen, —$OR^{12}$, or alkyl.

5. The compound of claim 1, or the pharmaceutically acceptable salt thereof, selected from:
(E)-3-(3-(2-cyclohexylvinyl)phenyl)propan-1-amine;
(E)-1-(3-(3-amino-1-hydroxypropyl)styryl)cyclohexanol;
(E)-1-(3-((1R,2R)-3-amino-1-hydroxy-2-methylpropyl)styryl)cyclohexanol;
(E)-1-(3-(3-amino-1-hydroxypropyl)-5-fluorostyryl)cyclohexanol;
(E)-1-(3-(3-amino-1-hydroxypropyl)-2-fluorostyryl)cyclohexanol;
(1S,2S)-3-amino-1-(3-((E)-2-(1-hydroxycyclohexyl)vinyl)phenyl)propane-1,2-diol;
(1R,2R)-3-amino-1-(3-((E)-2-(1-hydroxycyclohexyl)vinyl)phenyl)propane-1,2-diol;
(E)-1-(5-(3-amino-1-hydroxypropyl)-2-methoxystyryl)cyclohexanol;
(E)-1-(3-(3-amino-1-hydroxypropyl)-4-chlorostyryl)cyclohexanol;
(E)-1-(3-(3-amino-1-hydroxypropyl)-4-methylstyryl)cyclohexanol;
(E)-1-(3-(3-amino-1-hydroxypropyl)-5-methylstyryl)cyclohexanol;
(1S,2R)-3-amino-1-(3-((E)-2-(1-hydroxycyclohexyl)vinyl)phenyl)-propane-1,2-diol;
(E)-2-(3-(3-amino-1-hydroxypropyl)styryl)cyclohexanol;
(E)-1-(5-(3-amino-1-hydroxypropyl)-2-fluorostyryl)cyclohexanol;
(E)-1-(3-(3-amino-1-hydroxypropyl)-5-methoxystyryl)cyclohexanol;
(E)-1-(3-(3-amino-1-hydroxypropyl)-4-fluorostyryl)cyclohexanol;
(1R,2S)-3-amino-1-(3-((E)-2-(1-hydroxycyclohexyl)vinyl)phenyl)propane-1,2-diol;
(E)-1-(3-(3-amino-1-hydroxypropyl)-5-chlorostyryl)cyclohexanol; and
(E)-1-(3-(3-amino-1-hydroxypropyl)-2-methoxystyryl)cyclohexanol;
or the pharmaceutically acceptable salt thereof.

6. A compound selected from:
(E/Z)-3-(3-(2,6-dimethylstyryl)phenyl)prop-2-en-1-amine;
(E)-3-(3-(2-(2,6,6-trimethylcyclohex-1-enyl)vinyl)phenyl)prop-2-yn-1-amine; and
(E)-2-fluoro-3-(3-((E)-2-(2,6,6-trimethylcyclohex-1-enyl)vinyl)phenyl)prop-2-en-1-amine;
or the pharmaceutically acceptable salt thereof.

7. A compound having a structure described by
(E)-4-(3-(3-amino-1-hydroxypropyl)styryl)heptan-4-ol;
or the pharmaceutically acceptable salt thereof.

8. A pharmaceutical composition comprising a compound of Formula (A), or a pharmaceutically acceptable salt thereof, as described in claim 1, and a pharmaceutically acceptable excipient.

9. A pharmaceutical composition comprising a compound of claim 5, or a pharmaceutically acceptable salt thereof, and a pharmaceutically acceptable excipient.

10. A pharmaceutical composition comprising a compound of claim 6, or a pharmaceutically acceptable salt thereof, and a pharmaceutically acceptable excipient.

11. A pharmaceutical composition comprising a compound of claim 7, or a pharmaceutically acceptable salt thereof, and a pharmaceutically acceptable excipient.

* * * * *